US008008016B2

(12) United States Patent
Horanyi et al.

(10) Patent No.: US 8,008,016 B2
(45) Date of Patent: Aug. 30, 2011

(54) VECTORS AND METHODS FOR HIGH THROUGHPUT CO-EXPRESSIONS

(75) Inventors: Peter Horanyi, Athens, GA (US); James Griffith, Watkinsville, GA (US); Bi-Cheng Wang, Athens, GA (US); Francis E. Jenney, Jr., Hoschton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 89 days.

(21) Appl. No.: 12/501,666

(22) Filed: Jul. 13, 2009

(65) Prior Publication Data
US 2009/0311747 A1 Dec. 17, 2009

Related U.S. Application Data

(62) Division of application No. 11/327,200, filed on Jan. 6, 2006, now Pat. No. 7,582,475.

(60) Provisional application No. 60/756,028, filed on Jan. 4, 2006, provisional application No. 60/642,310, filed on Jan. 7, 2005, provisional application No. 60/642,309, filed on Jan. 7, 2005.

(51) Int. Cl.
*C12Q 1/68* (2006.01)
*C12P 19/34* (2006.01)
*C12N 15/00* (2006.01)
*C07H 21/02* (2006.01)
*C07H 21/04* (2006.01)

(52) U.S. Cl. ........ 435/6; 435/91.1; 435/91.31; 435/455; 435/462; 435/320.1; 435/252.3; 536/23.1; 536/23.7; 536/24.5

(58) Field of Classification Search .............. 435/6, 91.1, 435/320.1, 69.1; 536/23.1, 23.4, 23.5
See application file for complete search history.

(56) References Cited

U.S. PATENT DOCUMENTS

| | | | |
|---|---|---|---|
| 4,952,496 | A | 8/1990 | Studier et al. |
| 5,021,344 | A | 6/1991 | Armau et al. |
| 5,118,620 | A | 6/1992 | Armau et al. |
| 5,284,933 | A | 2/1994 | Döbeli et al. |
| 5,310,663 | A | 5/1994 | Döbeli et al. |
| 5,693,489 | A | 12/1997 | Studier et al. |
| 5,869,320 | A | 2/1999 | Studier et al. |
| 5,888,732 | A | 3/1999 | Hartley et al. |
| 6,143,557 | A | 11/2000 | Hartley et al. |
| 6,171,861 | B1 | 1/2001 | Hartley et al. |
| 6,270,969 | B1 | 8/2001 | Hartley et al. |
| 6,277,608 | B1 | 8/2001 | Hartley et al. |
| 6,720,140 | B1 | 4/2004 | Hartley et al. |
| 2005/0069929 | A1 | 3/2005 | Chestnut et al. |
| 2006/0183193 | A1 | 8/2006 | Horanyi et al. |
| 2007/0196838 | A1 | 8/2007 | Chestnut et al. |

FOREIGN PATENT DOCUMENTS
EP 282042 9/1988

OTHER PUBLICATIONS

Adams et al., "The Southeast Collaboratory for Structural Genomics: A High-Throughput Gene to Structure Factor," 2003 *Acc. Chem. Res.* 36:191-198.

Ambion, the RNA Company. "RNA Interference and Gene Silencing—History and Overview," Available online [retrieved on Jan. 6, 2006]. Retrieved from the Internet: <http://www.ambion.com/techlib/hottopics/rnai/rnai_may2002_print.html>; 8 pages.

Apfeld et al., "Cell Nonautonomy of *C. elegans* daf-2 Function in the Regulation of Diapause and Life Span," 1998 *Cell* 95:199-210.

Ausubel et al., eds, *Current Protocols in Molecular Biology*, Green Publishing Assoc., Inc., John Wiley & Sons, Inc., NY 1994 (12 pages).

Bass, B., "The Short Answer," 2001 *Nature* 411:428-429.

Benakis. "Artemisin and derivatives: recent progress in malaria treatment," Indian Medlars Centre. Laboratory of Drug Metabolism, Dept. of Pharm., Univ. Medical Centre, Geneva, Switzerland. Journal of Parasitic Diseases. 1996. 10(1):65. Available online [retrieved on Mar. 9, 2006]. Retrieved from the Internet: <http://medind.nic.in/imvw/imvw13236.html>; 1 page.

Bernard et al., "The F plasmid CcdB protein induces efficient ATP-dependent DNA cleavage by gyrase," 1993 *J. Mol. Biol.* 234:534-541.

Bernard et al., "The 41 Carboxy-terminal Residues of the Mini-F Plasmid CcdA Protein are sufficient to Antagonize the Killer Activity of the CcdB protein," 1991 *Mol. Gen. Genet.* 226:297-304.

Brenner, "Target Selection for Structural Genomics," 2000 *Nat. Struct. Biol.* 7 Suppl:967-969.

Brenner et al., "Expectations from Structural Genomics," 2000 *Protein Sci.* 9:197-200.

Burley, "An Overview of Structural Genomics," 2000 *Nat .Struct. Biol.* 7 Suppl:932-934.

Campbell et al., "A monomeric red fluorescent protein," 2002 *Proc. Natl. Acad. Sci. USA*, 99:7877-7882.

Celestino et al., "Update of microbial genome programs for bacteria and archaea," 2004. *Gen Mol.* Res. 3:421-431.

Chance et al., "Structural genomics: A pipeline for providing structures for the biologist," 2002 *Protein Science* 11:723-738.

Chayen, "Protein crystallization for genomics: throughput versus output," 2003 *J. Struct. Funct. Genomics* 4:115-120.

Cherry et al., "Genetic and physical maps of *Saccharomyces cerevisiae*," 1997 *Nature* 387(6632 Suppl):67-73.

Christendat et al., "Structural proteomics of an archaeon," 2000 *Nat. Struct. Biol.* 7:903-909.

CLONTECH. Innovative Tools to Accelerate Discovery. Living Colors® User Manual. PT2040-1 (PR1Y691). Published Nov. 26, 2001. 47 pages.

Collins et al., "A Vision for the Future of Genomics Research, A blueprint for the genomic era," 2003 *Nature* 422:835-847.

Cormack et al., "FACS—optimized mutants of the green fluorescent protein (GFP)," 1996 *Gene* 173:33-38.

Crabtree et al., "Facile and Gentle Method for Quantitative Lysis of *Escherichia coli* and *Salmonella typhimurium*," 1984 *J. Bact.* 158:354-356.

Cuff et al., "Jpred: a consensus secondary structure prediction server," 1998 *Bioinformatics Applications Note* 14:892-893.

(Continued)

*Primary Examiner* — Amy Bowman
(74) *Attorney, Agent, or Firm* — Mueting Raasch & Gebhardt, P.A.

(57) ABSTRACT

The present invention includes vectors and methods for high throughput co-expression.

7 Claims, 129 Drawing Sheets

OTHER PUBLICATIONS

Dolinski et al., "Changing perspectives in yeast research nearly a decade after the genome sequence," 2005 *Genome Research* 15(12):1611-1619.

Drocourt et al., "Cassettes of the *Streptoalloteichus hindustanus* ble gene for transformation of lower and higher eukaryotes to phleomycin resistance," 1990 *Nucleic Acids Res.* 18:4009.

Elshorst et al., "NMR solution structure of a complex of calmodulin with a binding peptide of the Ca2+ pump," 1999 *Biochemistry* 38(38):12320-12332.

Facts on Acts. Artemisinin-Based Combination Therapies. Jan. 2006 Update. World Health Organization. 4 pages.

Falconer et al., "Chemical Treatment of *Escherichia coli*: 1. Extraction of Intracellular Protein from Uninduced Cells," 1997 *Biotechnol. Bioengin.* 53:453-458.

Ferreira et al., "Distribution of Artemisinin in *Artemisia annua*," 1996. Distribution of artemisinin in Artemisia annua. p. 579-584. J. Janick (ed.), Progress in New Crops. ASHS Press, Arlington, VA. Available online [retrieved on Mar. 9, 2006]. Retrieved from the Internet: <http://www.hort.purdue.edu/newcrop/proceedings1996/v3-578.html>; 12 pages.

Fire et al., "Potent and specific genetic interference by double-stranded RNA in *Caenorhabditis elegans*," 1998 *Nature* 391:806-811.

Gateway Technology Manual, Version E, updated Sep. 22, 2003; available on the wordwide web at invitrogen.com/content/sfs/manuals/gatewayman.pdf.

Gonczy et al., "Functional genomic analysis of cell division in *C. elegans* using RNAi of genes on chromosome III," 2000 *Nature* 408(6810):331-336.

Hartley et al., "DNA Cloning Using In Vitro Site-Specific Recombination," 2000 *Genome Res.* 10:1788-1795.

Henricksen et al., "Recombinant Replication Protein A: Expression, Complex Formation, and Functional Characterization," 1994 *J. Biol. Chem.* 269:11121-11132.

Invitrogen life technologies. Letter to Global Life Science Research Community. Re: "Gateway® Clone Distribution Policy," Oct. 29, 2003. 4 pages.

Invitrogen life technologies. "Champion™ pET104 BioEase™ Gateway® Expression System, for Cloning and Expression of biotinylated fusion proteins in *E. coli*," Catalog No. K104-01, Version C, Mar. 15, 2004, 25-0472. 36 pages.

Invitrogen Catalog # 11828-029. "Gateway® Vector Conversion System with One Shot® ccdB Survival™ Competent Cells," Accessible at www.invitrogen.com/content/sfs/manuals/gatewayvectorconversion_ccdbsurvival_man.pdf Invitrogen Life Technologies Instruction Manual. Version A. Jun. 14, 2004.

Kamath et al., "Genome-wide RNAi screening in *Carnorhabditis elegans*," 2003 *Methods* 30:313-321.

Kessler et al., "Study of Calmodulin Binding to the Alternatively Spliced C-Terminal Domain of the Plasma Membrane $Ca^{2+}$ Pump," 1992 *Biochemistry* 31:11785-11792.

Landy, "Dynamic, Structural, and Regulatory Aspects of λ Site-Specific Recombination," 1989 *Ann. Rev. Biochem.* 58:913-949.

Lesley et al., "Structural genomics of the *Thermotoga maritima* proteome implemented in a high-throughput structure determination pipeline," 2002 *Proc. Natl. Acad. Sci. USA* 99:11664-11669.

Li et al., "Coexpression of nuclear receptor partners increses their solubility and biological activities," 1997 *Proc Natl Acad Sci, USA* 94:2278-2283.

Lindblad-Toh et al., "Genome sequence, comparative analysis and haplotype structure of the domestic dog," 2005 *Nature* 438:803-819.

Liu et al., "The high-throughput protein-to-structure pipeline at SECSG," 2005 *Acta Cryst.* 61:679-684.

Machalek, "From Genes to Proteins: NIGMS Catalogs the Shapes of Life,"NIH Record, Feb. 2001. Retrieved from the wordlwide web at nigms.nih.gov/psi/ and resb.org/pdb/strucgen.html#Wordwide.

Matz et al., "Fluorescent proteins from nonbioluminescent Anthozoa species," 1999 *Nat. Biotechnol.* 17:969-973.

Nagai et al., "A variant of yellow fluorescent protein with fast and efficient maturation for cell-biological applications," 2002 *Nat. Biotechnol.* 20:87-90.

National Human Genome Research Institute. News Release. "International Consortium Completes Human Genome Project," Apr. 14, 2003. Available online [retrieved on Dec. 14, 2005]. Retrieved from the Internet: <http://www.genome.gov.pfv.cfm?pageID=11006929>; 5 pages.

"The map-based sequence of the rice genome," 2005 *Nature* 436:793-800.

Novagen 2004/2005 Catalog. Title page, Table of Contents. Protein Expression, Prokaryotic Expression: Coexpression. p. 207.

Novina et al., "The RNAi revolution," 2004 *Nature* 430:161-164.

Norvell et al., "Structural genomics programs at the US National Institute of General Medical Sciences," 2000 *Nat. Struct. Biol.* 7 Suppl:931.

Rost, "Marrying structure and genomics," 1998 *Structure* 6:259-263.

Rual et al., "Toward improving *Caenorhabditis elegans* Phenome Mapping with an ORFeome-based RNAi Library," 2004 *Genome Res.* 14:2162-2168.

Rual et al., "ORFeome projects: gateway between genomics and omics," 2004 *Curr. Opin. Chem. Biol.* 8(1):20-5, 2004.

Salmon et al., "The antidote and autoregulatory functions of the F plasmid CcdA protein: a genetic and biochemical survey," 1994 *Mol. Gen. Genet.* 244:530-538.

Salwinski et al., "The Database of Interacting Proteins: 2004 update," 2004 *Nucleic Acids Research* vol. 32, Database Issue D449-D451.

Sambrook et al., *Molecular Cloning: A Laboratory Manual*, 2001. Cold Spring Harbor Laboratory Press, Cold Spring Harbor, NY( 22 pages).

Sasaki et al., "Evidence for high specificity and efficiency of multiple recombination signals in mixed DNA cloning by the multisite gateway system," 2004 *J. Biotechnol.* 107:233-243.

Sasaki et al., "Multi-gene gateway clone design for expression of multiple heterologous genes in living cells: Eukaryotic clones containing two and three ORF multigene cassettes expressed from a single promotoer," 2005 *J. Biotechnol.* doi:10.1016/j.jbiotec.2005.02.022.

Sharp., "RNA Interference—2001," 2001. *Genes Dev.* 15:485-490.

Shen et al., "Target selection of soluble protein complexes for structural proteomics studies," May 18, 2005 *Proteome Science* 3(1):3 (9 pages).

Silva et al., "RNA-interference-based functional genomics in mammalian cells: reverse genetics coming of age," 2004 *Oncogene* 23:8401-8409.

Sone et al., "Multi-gene gateway clone design for expression of multiple heterologous genes in living cells: Modular construction of multiple cDNA expression elements using recombinant cloning," 2005 *J. Biotechnol.* Jun. 24 (doi: 10,1016/jbiotec.2005.02.021).

Sorenson et al., "Advanced genetic strategies for recombinant protein expression in *Escherichia coli*," 2005 *J. Biotechnol.* 115(2):113-128.

Stevens et al., "Global Efforts in Structural Genomics," 2001 *Science* 294:89-92.

Terskikh et al., "Analysis of DsRed Mutants, Space around the fluorophore accelerates fluorescence development," 2002 *J. Biol. Chem.* 277:7633-7636.

Timmons et al., "Specific interference by ingested dsRNA," 1998 *Nature*. 395:854.

Tsien. "Rosy Dawn for Fluorescent Proteins," 1999 *Nature Biotech*. 17:956-957.

Uetsuki et al., "Isolation and characterization of the human chromosomal gene for polypeptide chain elongation factor-I alpha," 1989 *J. Biol. Chem.* 264:5791-5798.

Van Haaften et al.,"Genomic instability and cancer: scanning the *Caenorhabditis elegans* genome for tumor suppressors," 2004 *Oncogene*. 23:8366-8375.

Vincze et al., "NEBcutter: a program to cleave DNA with restriction enzymes," 2003 *Nucleic Acids Res.* 31:3688-3691.

Walhout et al., "Gateway recombinational cloning: application to the cloning of large numbers of open reading frames or ORFeomes," 2000 *Methods Enzymol.* 328:575-592.

Wang et al., "*Visualization of coupled protein folding and binding in bacteria and purification of the heterodimeric complex*," 2003 Proc. Natl. Acad. Sci., USA 100:478-483.

Wianny et al., "Specific interference with gene function by double-stranded RNA in early mouse development," 2000 *Nature Cell Biology* 2:70-75.

Willingham et al., "RNAi and HTS:exploring cancer by systematic loss-of-function," 2004 *Oncogene.* 23:8392-8400.

Yahata et al., "Multi-gene gateway clone design for expression of multiple heterologous genes in living cells: Conditional gene expression at near physiological levels," 2005 *J. Biotechnol.* 118(2):123-134. Doi:10.1016/j.jbiotec.2005.02.020.

Zhang et al., "Genetically encoded reporters of protein kinase A activity reveal impact of substrate tethering," 2001 *PNAS* 98:26:14997-15002.

Zhang et al., "An enhanced green fluroescent protein allows sensitive detection of gene transfer in mammalian cells," 1996 *Biochem. Biophys. Res. Commun.* 227:707-711.

Sun et al., "Heterologous Expression and Maturation of an NADP-Dependent [NiFe]-Hydrogenase: A Key Enzyme in Biofuel Production," 2010. *PloS ONE*, vol. 5, Issue 5, e10526. pp. 1-11.

| Reading Frame Cassette: | A (1711 bp) | B (1713bp) | C.1 (1714 bp) |
|---|---|---|---|
| attR1 site | 4-128 | 5-129 | 6-130 |
| Primer 1 | 163-185 | 164-186 | 165-187 |
| Chloramphenicol resistance gene | 237-896 | 238-897 | 239-919 |
| ccdB gene | 1238-1543 | 1239-1544 | 1239-1544 |
| Primer 2 | 1444-1466 | 1445-1467 | 1445-1467 |
| attR2 site | 1584-1708 | 1585-1709 | 1585-1709 |

Fig. 3 pDEST-C1 sequence

```
   1  GGGGAATTGT GAGCGGATAA CAATTCCCCT GTAGAAATAA TTTTGTTTAA CTTTAATAAG
      CCCCTTAACA CTCGCCTATT GTTAAGGGGA CATCTTTATT AAAACAAATT GAAATTATTC
                 NcoI
                 ~~~~~~~
  61  GAGATATACC ATGGCACATC ACCACCACCA TCACGTGGGT ACCGGTTCGA ATGATGACGA
      CTCTATATGG TACCGTGTAG TGGTGGTGGT AGTGCACCCA TGGCCAAGCT TACTACTGCT
 121  CGACAAATCA ACAAGTTTGT ACAAAAAAGC TGAACGAGAA ACGTAAAATG ATATAAATAT
      GCTGTTTAGT TGTTCAAACA TGTTTTTTCG ACTTGCTCTT TGCATTTTAC TATATTTATA
 181  CAATATATTA AATTAGATTT TGCATAAAAA ACAGACTACA TAATACTGTA AAACACAACA
      GTTATATAAT TTAATCTAAA ACGTATTTTT TGTCTGATGT ATTATGACAT TTTGTGTTGT
                                NotI
                                ~~~~~~~~~
 241  TATCCAGTCA TATTGGCGGC CGCATTAGGC ACCCCAGGCT TTACACTTTA TGCTTCCGGC
      ATAGGTCAGT ATAACCGCCG GCGTAATCCG TGGGGTCCGA AATGTGAAAT ACGAAGGCCG
                                         BamHI
                                         ~~~~~~~
 301  TCGTATAATG TGTGGATTTT GAGTTAGGAT CCGTCGAGAT TTTCAGGAGC TAAGGAAGCT
      AGCATATTAC ACACCTAAAA CTCAATCCTA GGCAGCTCTA AAAGTCCTCG ATTCCTTCGA
 361  AAAATGGAGA AAAAAATCAC TGGATATACC ACCGTTGATA TATCCCAATG GCATCGTAAA
      TTTTACCTCT TTTTTTAGTG ACCTATATGG TGGCAACTAT ATAGGGTTAC CGTAGCATTT
 421  GAACATTTTG AGGCATTTCA GTCAGTTGCT CAATGTACCT ATAACCAGAC CGTTCAGCTG
      CTTGTAAAAC TCCGTAAAGT CAGTCAACGA GTTACATGGA TATTGGTCTG GCAAGTCGAC
 481  GATATTACGG CCTTTTTAAA GACCGTAAAG AAAAATAAGC ACAAGTTTTA TCCGGCCTTT
      CTATAATGCC GGAAAAATTT CTGGCATTTC TTTTTATTCG TGTTCAAAAT AGGCCGGAAA
                                                  EcoRI
                                                  ~~~~~~~
 541  ATTCACATTC TTGCCCGCCT GATGAATGCT CATCCGGAAT TCCGTATGGC AATGAAAGAC
      TAAGTGTAAG AACGGGCGGA CTACTTACGA GTAGGCCTTA AGGCATACCG TTACTTTCTG
 601  GGTGAGCTGG TGATATGGGA TAGTGTTCAC CCTTGTTACA CCGTTTTCCA TGAGCAAACT
      CCACTCGACC ACTATACCCT ATCACAAGTG GGAACAATGT GGCAAAAGGT ACTCGTTTGA
 661  GAAACGTTTT CATCGCTCTG GAGTGAATAC CACGACGATT TCCGGCAGTT TCTACACATA
      CTTTGCAAAA GTAGCGAGAC CTCACTTATG GTGCTGCTAA AGGCCGTCAA AGATGTGTAT
 721  TATTCGCAAG ATGTGGCGTG TTACGGTGAA AACCTGGCCT ATTTCCCTAA AGGGTTTATT
      ATAAGCGTTC TACACCGCAC AATGCCACTT TTGGACCGGA TAAAGGGATT TCCCAAATAA
 781  GAGAATATGT TTTCGTCTC AGCCAATCCC TGGGTGAGTT TCACCAGTTT TGATTTAAAC
      CTCTTATACA AAAAGCAGAG TCGGTTAGGG ACCCACTCAA AGTGGTCAAA ACTAAATTTG
                                                        NcoI
                                                        ~~~~~~~
 841  GTGGCCAATA TGGACAACTT CTTCGCCCCC GTTTTCACCA TGGGCAAATA TTATACGCAA
      CACCGGTTAT ACCTGTTGAA GAAGCGGGGG CAAAAGTGGT ACCCGTTTAT AATATGCGTT
 901  GGCGACAAGG TGCTGATGCC GCTGGCGATT CAGGTTCATC ATGCCGTTTG TGATGGCTTC
      CCGCTGTTCC ACGACTACGG CGACCGCTAA GTCCAAGTAG TACGGCAAAC ACTACGAAGG
 961  CATGTCGGCA GAATGCTTAA TGAATTACAA CAGTACGTGCG ATGAGTGGCA GGGCGGGGCG
      GTACAGCCGT CTTACGAATT ACTTAATGTT GTCATGACGC TACTCACCGT CCCGCCCCGC
                 BamHI
                 ~~~~~~~
1021  TAAAGATCTG GATCCGGCTT ACTAAAAGCC AGATAACAGT ATGCGTATTT GCGCGCTGAT
      ATTTCTAGAC CTAGGCCGAA TGATTTTCGG TCTATTGTCA TACGCATAAA CGCGCGACTA
1081  TTTTGCGGTA TAAGAATATA TACTGATATG TATACCCGAA GTATGTCAAA AAGAGGTATG
      AAAACGCCAT ATTCTTATAT ATGACTATAC ATATGGGCTT CATACAGTTT TTCTCCATAC
1141  CTATGAAGCA GCGTATTACA GTGACAGTTG ACAGCGACAG CTATCAGTTG CTCAAGGCAT
      GATACTTCGT CGCATAATGT CACTGTCAAC TGTCGCTGTC GATAGTCAAC GAGTTCCGTA
1201  ATATGATGTC AATATCTCCG GTCTGGTAAG CACAACCATG CAGAATGAAG CCCGTCGTCT
      TATACTACAG TTATAGAGGC CAGACCATTC GTGTTGGTAC GTCTTACTTC GGGCAGCAGA
1261  GCGTGCCGAA CGCTGGAAAG CGGAAAATCA GGAAGGGATG GCTGAGGTCG CCCGGTTTAT
      CGCACGGCTT GCGACCTTTC GCCTTTTAGT CCTTCCCTAC CGACTCCAGC GGGCCAAATA
1321  TGAAATGAAC GGCTCTTTTG CTGACGAGAA CAGGGGCTGG TGAAATGCAG TTTAAGGTTT
      ACTTTACTTG CCGAGAAAAC GACTGCTCTT GTCCCCGACC ACTTTACGTC AAATTCCAAA
1381  ACACCTATAA AAGAGAGAGC CGTTATCGTC TGTTTGTGGA TGTACAGAGT GATATTATTG
      TGTGGATATT TTCTCTCTCG GCAATAGCAG ACAAACACCT ACATGTCTCA CTATAATAAC
                 SmaI
                 ~~~~~~~
                 XmaI
                 ~~~~~~~
                 AvaI                             ApaLI
                 ~~~~~~~                          ~~~~~~~
1441  ACACGCCCGG GCGACGGATG GTGATCCCCC TGGCCAGTGC ACGTCTGCTG TCAGATAAAG
```

Fig. 3₁

```
      TGTGCGGGCC CGCTGCCTAC CACTAGGGGG ACCGGTCACG TGCAGACGAC AGTCTATTTC
1501  TCTCCCGTGA ACTTTACCCG GTGGTGCATA TCGGGGATGA AAGCTGGCGC ATGATGACCA
      AGAGGGCACT TGAAATGGGC CACCACGTAT AGCCCCTACT TTCGACCGCG TACTACTGGT
1561  CCGATATGGC CAGTGTGCCG GTCTCCGTTA TCGGGGAAGA AGTGGCTGAT CTCAGCCACC
      GGCTATACCG GTCACACGGC CAGAGGCAAT AGCCCCTTCT TCACCGACTA GAGTCGGTGG
1621  GCGAAAATGA CATCAAAAAC GCCATTAACC TGATGTTCTG GGGAATATAA ATGTCAGGCT
      CGCTTTTACT GTAGTTTTTG CGGTAATTGG ACTACAAGAC CCCTTATATT TACAGTCCGA
                                   PstI
                                 ~~~~~~~
1681  CCCTTATACA CAGCCAGTCT GCAGGTCGAC CATAGTGACT GGATATGTTG TGTTTTACAG
      GGGAATATGT GTCGGTCAGA CGTCCAGCTG GTATCACTGA CCTATACAAC ACAAAATGTC
1741  TATTATGTAG TCTGTTTTTT ATGCAAAATC TAATTTAATA TATTGATATT TATATCATTT
      ATAATACATC AGACAAAAAA TACGTTTTAG ATTAAATTAT ATAACTATAA ATATAGTAAA
                                                BamHI           SacI
                                               ~~~~~~~          ~~
1801  TACGTTTCTC GTTCAGCTTT CTTGTACAAA GTGGTTGATG AGTCCGGATC CCAATTGGGA
      ATGCAAAGAG CAAGTCGAAA GAACATGTTT CACCAACTAC TCAGGCCTAG GGTTAACCCT
                                                     NotI
                                                  ~~~~~~~~~~
      SacI                PstI              HindIII       AvaI
      ~~~~              ~~~~~~~             ~~~~~~      ~~~~~~~
1861  GCTCGTGTAC ACGGCGCGCC TGCAGGTCGA CAAGCTTGCG GCCGCACTCG AGTCTGGTAA
      CGAGCACATG TGCCGCGCGG ACGTCCAGCT GTTCGAACGC CGGCGTGAGC TCAGACCATT
1921  AGAAACCGCT GCTGCGAAAT TTGAACGCTA GCACATGGAC TCGTCTACTA GCGCAGCTTA
      TCTTTGGCGA CGACGCTTTA AACTTGCGGT CGTGTACCTG AGCAGATGAT CGCGTCGAAT
1981  ATTAACCTAG GCTGCTGCCA CCGCTGAGCA ATAACTAGCA TAACCCCTTG GGGCCTCTAA
      TAATTGGATC CGACGACGGT GGCGACTCGT TATTGATCGT ATTGGGGAAC CCCGGAGATT
2041  ACGGGTCTTG AGGGGTTTTT TGCTGAAACC TCAGGCATTT GAGAAGCACA CGGTCACACT
      TGCCCAGAAC TCCCCAAAAA ACGACTTTGG AGTCCGTAAA CTCTTCGTGT GCCAGTGTGA
2101  GCTTCCGGTA GTCAATAAAC CGGTAAACCA GCAATAGACA TAAGCGGCTA TTTAACGACC
      CGAAGGCCAT CAGTTATTTG GCCATTTGGT CGTTATCTGT ATTCGCCGAT AAATTGCTGG
2161  CTGCCCTGAA CCGACGACCG GGTCATCGTG GCCGGATCTT GCGGCCCCTC GGCTTGAACG
      GACGGGACTT GGCTGCTGGC CCAGTAGCAC CGGCCTAGAA CGCCGGGGAG CCGAACTTGC
2221  AATTGTTAGA CATTATTTGC CGACTACCTT GGTGATCGTC CCTTTCACCT AGTGGACAAA
      TTAACAATCT GTAATAAACG GCTGATGGAA CCACTAGCAG GGAAAGTGCA TCACCTGTTT
2281  TTCTTCCAAC TGATCTGCGC GCGAGGCCAA GCGATCTTCT TCTTGTCCAA GATAAGCCTG
      AAGAAGGTTG ACTAGACGCG CGCTCCGGTT CGCTAGAAGA AGAACAGGTT CTATTCGGAC
2341  TCTAGCTTCA AGTATGACGG GCTGATACTG GGCCGGCAGG CGCTCCATTG CCCAGTCGGC
      AGATCGAAGT TCATACTGCC CGACTATGAC CCGGCCGTCC GCGAGGTAAC GGGTCAGCCG
2401  AGCGACATCC TTCGGCGCGA TTTTGCCGGT TACTGCCGTG TACCAAATGC GGGACAACGT
      TCGCTGTAGG AAGCCGCGCT AAAACGGCCA ATGACGCGAC ATGGTTTACG CCCTGTTGCA
2461  AAGCACTACA TTTCGCTCAT CGCCAGCCCA GTCGGGCGGC GAGTTCCATA GCGTTAAGGT
      TTCGTGATGT AAAGCGAGTA GCGGTCGGGT CAGCCCGCCG CTCAAGGTAT CGCAATTCCA
2521  TTCATTTAGC GCCCTCAAATA GATCCTGTTC AGGAACCGGA TCAAAGAGTT CCTCCGCCGC
      AAGTAAATCG CGGAGTTTTA CTAGGACAAG TCCTTGGCCT AGTTTCTCAA GGAGGCGGCG
2581  TGGACCTACC AAGGCAACGC TATGTTCTCT TGCTTTTGTC AGCAAGATAG CCAGATCAAT
      ACCTGGATGG TTCCGTTGCG ATACAAGAGA ACGAAAACAG TCGTTCTATC GGTCTAGTTA
2641  GTCGATCGTG GCTGGCTCGA AGATACCTGC AAGAATGTCA TTGCGCTGCC ATTCTCCAAA
      CAGCTAGCAC CGACCGAGCT TCTATGGACG TTCTTACAGT AACGCGACGG TAAGAGGTTT
                                                          ApaLI
                                                        ~~~~~~~
2701  TTGCAGTTCG CGCTTAGCTG GATAACGCCA CGGAATGATG TCGTCGTGCA CAACAATGGT
      AACGTCAAGC GCGAATCGAC CTATTGCGGT GCCTTACTAC AGCAGCACGT GTTGTTACCA
2761  GACTTCTACA GCGCGGAGAA TCTCGCTCTC TCCAGGGGAA GCCGAAGTTT CCAAAAGGTC
      CTGAAGATGT CGCGCCTCTT AGAGCGAGAG AGGTCCCCTT CGGCTTCAAA GGTTTTCCAG
2821  GTTGATCAAA GCTCGCCGCG TTGTTTCATC AAGCCTTACG GTCACCGTAA CCAGCAAATC
      CAACTAGTTT CGAGCGGCGC AACAAAGTAG TTCGGAATGC CAGTGGCATT GGTCGTTTAG
2881  AATATCACTG TGTGGCTTCA GGCCGCCATC CACTGCGGAG CCGTACAAAT GTACGGCCAG
      TTATAGTGAC ACACCGAAGT CCGGCGGTAG GTGACGCCTC GGCATGTTTA CATGCCGGTC
2941  CAACGTCGGT TCGAGATGGC GCTCGATGAC GCCAACTACC TCTGATAGTT GAGTCGATAC
      GTTGCAGCCA AGCTCTACCG CGAGCTACTG CGGTTGATGG AGACTATCAA CTCAGCTATG
3001  TTCGGCGATC ACCGCTTCCC TCATACTCTT CCTTTTTCAA TATTATTGCA GCATTTATCA
      AAGCCGCTAG TGGCGAAGGG AGTATGAGAA GGAAAAAGTT ATAATAACTT CGTAAATAGT
3061  GGGTTATTGT CTCATGAGCG GATACATATT TGAATGTATT AGAAAAATA AACAAATAGC
      CCCAATAACA GAGTACTCGC CTATGTATAA ACTTACATAA ATCTTTTTAT TTGTTTATCG
3121  TAGCTCACTC GGTCGCTACG CTCCGGGCGT GAGACTGCGG CGGGCGTGC GGACACATAC
      ATCGAGTGAG CCAGCGATGC GAGGCCCGCA CTCTGACGCC GCCCGCACG CCTGTGTATG
3181  AAAGTTACCC ACAGATTCCG TGGATAAGCA GGGGACTAAC ATGTGAGGCA AAACAGCAGG
      TTTCAATGGG TGTCTAAGGC ACCTATTCGT CCCCTGATTG TACACTCCGT TTTGTCGTCC
3241  GCCGCGCCGG TGGCGTTTTT CCATAGGCTC CGCCCTCCTG CCAGAGTTCA CATAAACAGA
      CGGCGCGGCC ACCGCAAAAA GGTATCCGAG GCGGGAGGAC GGTCTCAAGT GTATTTGTCT
```

Fig. 3₂

```
      GCGAAAAGGC CACGTAGACA CCCTCGGCAC TCCGAGTTGG TACTTAGACT GTCATGCCCG
3361  GAAACCCGAC AGGACTTAAA GATCCCCACC GTTTCGGCG  GGTCGCTCCC TCTTGCGCTC
      CTTTGGGCTG TCCTGAATTT CTAGGGGTGG CAAAGGCCGC CCAGCGAGGG AGAACGCGAG
3421  TCCTGTTCCG ACCCTGCCGT TTACCGGATA CCTGTTCCGC CTTTCTCCCT TACGGGAAGT
      AGGACAAGGC TGGGACGGCA AATGGCCTAT GGACAAGGCG GAAAGAGGGA ATGCCCTTCA
3481  GTGGCGCTTT CTCATAGCTC ACACACTGGT ATCTCGGCTC GGTGTAGGTC GTTCGCTCCA
      CACCGCGAAA GAGTATCGAG TGTGTGACCA TAGAGCCGAG CCACATCCAG CAAGCGAGGT
3541  AGCTGGGCTG TAAGCAAGAA CTCCCCGTTC AGCCCGACTG CTGCGCCTTA TCCGGTAACT
      TCGACCCGAC ATTCGTTCTT GAGGGGCAAG TCGGGCTGAC GACGCGGAAT AGGCCATTGA
3601  GTTCACTTGA GTCCAACCCG GAAAAGCACG GTAAAACGCC ACTGCGAGCA GCCATTGGTA
      CAAGTGAACT CAGGTTGGGC CTTTTCGTGC CATTTTGCGG TGACCGTCGT CGGTAACCAT
3661  ACTGGGAGTT CGCAGAGGAT TTGTTTAGCT AAACACGCGG TTGCTCTTGA AGTGTGCGCC
      TGACCCTCAA GCGTCTCCTA AACAAATCGA TTTGTGCGCC AACGAGAACT TCACACGCGG
3721  AAAGTCCGGC TACACTGGAA GGACAGATTT GGTTGCTGTG CTCTGCGAAA GCCAGTTACC
      TTTCAGGCCG ATGTGACCTT CCTGTCTAAA CCAACGACAC GAGACGCTTT CGGTCAATGG
3781  ACGGTTAAGC AGTTCCCAA  CTGACTTAAC CTTCGATCAA ACCACCTCCC CAGGTGGTTT
      TGCCAATTCG TCAAGGGGTT GACTGAATTG GAAGCTAGTT TGGTGGAGGG GTCCACCAAA
3841  TTTCGTTTAC AGGGCAAAAG ATTACGCGCA GAAAAAAGG  ATCTCAAGAA GATCCTTTGA
      AAAGCAAATG TCCCGTTTTC TAATGCGCGT CTTTTTTTCC TAGAGTTCTT CTAGGAAACT
3901  TCTTTTCTAC TGAACCGCTC TAGATTTCAG TGCAATTTAT CTCTTCAAAT GTAGCACCTG
      AGAAAAGATG ACTTGGCGAG ATCTAAAGTC ACGTTAAATA GAGAAGTTTA CATCGTGGAC
3961  AAGTCAGCCC CATACGATAT AAGTTGTAAT TCTCATGTTA GTCATGCCCC GCGCCCACCG
      TTCAGTCGGG GTATGCTATA TTCAACATTA AGAGTACAAT CAGTACGGGG CGCGGGTGGC
4021  GAAGGAGCTG ACTGGGTTGA AGGCTCTCAA GGGCATCGGT CGAGATCCCG GTGCCTAATG
      CTTCCTCGAC TGACCCAACT TCCGAGAGTT CCCGTAGCCA GCTCTAGGGC CACGGATTAC
4081  AGTGAGCTAA CTTACATTAA TTGCGTTGCG CTCACTGCCC GCTTTCCAGT CGGGAAACCT
      TCACTCGATT GAATGTAATT AACGCAACGC GAGTGACGGG CGAAAGGTCA GCCCTTTGGA
4141  GTCGTGCCAG CTGCATTAAT GAATCGGCCA ACGCGCGGGG AGAGGCGGTT TGCGTATTGG
      CAGCACGGTC GACGTAATTA CTTAGCCGGT TGCGCGCCCC TCTCCGCCAA ACGCATAACC
4201  GCGCCAGGGT GGTTTTTCTT TTCACCAGTG AGACGGGCAA CAGCTGATTG CCCTTCACCG
      CGCGGTCCCA CCAAAAAGAA AAGTGGTCAC TCTGCCCGTT GTCGACTAAC GGGAAGTGGC
4261  CCTGGCCCTG AGAGAGTTGC AGCAAGCGGT CCACGCTGGT TTGCCCCAGC AGGCGAAAAT
      GGACCGGGAC TCTCTCAACG TCGTTCGCCA GGTGCGACCA AACGGGGTCG TCCGCTTTTA
4321  CCTGTTTGAT GGTGGTTAAC GGCGGGATAT AACATGAGCT GTCTTCGGTA TCGTCGTATC
      GGACAAACTA CCACCAATTG CCGCCCTATA TTGTACTCGA CAGAAGCCAT AGCAGCATAG
4381  CCACTACCGA GATGTCCGCA CCAACGCGCA GCCCGGACTC GGTAATGGCG CGCATTGCGC
      GGTGATGGCT CTACAGGCGT GGTTGCGCGT CGGGCCTGAG CCATTACCGC GCGTAACGCG
4441  CCAGCGCCAT CTGATCGTTG GCAACCAGCA TCGCAGTGGG AACGATGCCC TCATTCAGCA
      GGTCGCGGTA GACTAGCAAC CGTTGGTCGT AGCGTCACCC TTGCTACGGG AGTAAGTCGT
4501  TTTGCATGGT TTGTTGAAAA CCGGACATGG CACTCCAGTC GCCTTCCCGT TCCGCTATCG
      AAACGTACCA AACAACTTTT GGCCTGTACC GTGAGGTCAG CGGAAGGGCA AGGCGATAGC
4561  GCTGAATTTG ATTGCGAGTG AGATATTTAT GCCAGCCAGC CAGACGCAGA CGCGCCGAGA
      CGACTTAAAC TAACGCTCAC TCTATAAATA CGGTCGTCG  GTCTGCGTCT GCGCGGCTCT
4621  CAGAACTTAA TGGGCCCGCT AACAGCGCGA TTTGCTGGTG ACCCAATGCG ACCAGATGCT
      GTCTTGAATT ACCCGGGCGA TTGTCGCGCT AAACGACCAC TGGGTTACGC TGGTCTACGA
4681  CCACGCCCAG TCGCGTACCG TCTTCATGGG AGAAATAAT  ACTGTTGATG GGTGTCTGGT
      GGTGCGGGTC AGCGCATGGC AGAAGTACCC TCTTTTATTA TGACAACTAC CCACAGACCA
4741  CAGAGACATC AAGAAATAAC GCCGGAACAT TAGTGCAGGC AGCTTCCACA GCAATGGCAT
      GTCTCTGTAG TTCTTTATTG CGGCCTTGTA ATCACGTCCG TCGAAGGTGT CGTTACCGTA
                                                                 ApaLI
                                                                 ~~
4801  CCTGGTCATC CAGCGGATAG TTAATGATCA GCCCACTGAC GCGTTGCGCG AGAAGATTGT
      GGACCAGTAG GTCGCCTATC AATTACTAGT CGGGTGACTG CGCAACGCGC TCTTCTAACA
      ApaLI
      ~~~~
4861  GCACCGCCGC TTTACAGGCT TCGACGCCGC TTCGTTCTAC CATCGACACC ACCACGCTGG
      CGTGGCGGCG AAATGTCCGA AGCTGCGGCG AAGCAAGATG GTAGCTGTGG TGGTGCGACC
4921  CACCCAGTTG ATCGGCGCGA GATTTAATCG CCGCGACAAT TTGCGACGGC GCGTGCAGGG
      GTGGGTCAAC TAGCCGCGCT CTAAATTAGC GGCGCTGTTA AACGCTGCCG CGCACGTCCC
4981  CCAGACTGGA GGTGGCAACG CCAATCAGCA ACGACTGTTT GCCCGCCAGT TGTTGTGCCA
      GGTCTGACCT CCACCGTTGC GGTTAGTCGT TGCTGACAAA CGGGCGGTCA ACAACACGGT
5041  CGCGGTTGGG AATGTAATTC AGCTCCGCCA TCGCCGCTTC CACTTTTTCC GCGTTTTCG
      GCGCCAACCC TTACATTAAG TCGAGGCGGT AGCGGCGAAG GTGAAAAAGG CGCAAAAGC
5101  CAGAAACGTG GCTGGCCTGG TTCACCACGC GGGAAACGGT CTGATAAGAG ACACCGGCAT
      GTCTTTTGCAC CGACCGGACC AAGTGGTGCG CCCTTTGCCA GACTATTCTC TGTGGCCGTA
5161  ACTCTGCGAC ATCGTATAAC GTTACTGGTT TCACATTCAC CACCCTGAAT TGACTCTCTT
      TGAGACGCTG TAGCATATTG CAATGACCAA AGTGTAAGTG GTGGGACTTA ACTGAGAGAA
5221  CCGGGCGCTA TCATGCCATA CCGCGAAAGG TTTTGCGCCA TTCGATGGTG TCCGGGATCT
      GGCCCGCGAT AGTACGGTAT GGCGCTTTCC AAAACGCGGT AAGCTACCAC AGGCCCTAGA
5281  CGACGCTCTC CCTTATGCGA CTCCTGCATT AGGAAATTAA TACGACTCAC TATA
      GCTGCGAGAG GGAATACGCT GAGGACGTAA TCCTTTAATT ATGCTGAGTG ATAT
```

Fig. 3₃

| Fig. 5$_1$ |
|---|
| Fig. 5$_2$ |
| Fig. 5$_3$ |

Fig. 5 pDEST-C2 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                NcoI
                ~~~~~~~
  61 GAGATATACC ATGGCACATC ACCACCACCA TCACGTGGGT ACCGGTTCGA ATGATGACGA
     CTCTATATGG TACCGTGTAG TGGTGGTGGT AGTGCACCCA TGGCCAAGCT TACTACTGCT
                SacI
                ~~~~~~~
 121 CGACAAGAGC TCGATCACAA GTTTGTACAA AAAAGCTGAA CGAGAAACGT AAAATGATAT
     GCTGTTCTCG AGCTAGTGTT CAAACATGTT TTTTCGACTT GCTCTTTGCA TTTTACTATA
 181 AAATATCAAT ATATTAAATT AGATTTTGCA TAAAAAACAG ACTACATAAT ACTGTAAAAC
     TTTATAGTTA TATAATTTAA TCTAAAACGT ATTTTTTGTC TGATGTATTA TGACATTTTG
 241 ACAACATATC CAGTCACTAT GGCGGCCGCC ACGTTAAGGG ATTTTGGTCA TGATCAGCAC
     TGTTGTATAG GTCAGTGATA CCGCCGGCGG TGCAATTCCC TAAAACCAGT ACTAGTCGTG
 301 GTGTTGACAA TTAATCATCG GCATAGTATA TCGGCATAGT ATAATACGAC AAGGTGAGGA
     CACAACTGTT AATTAGTAGC CGTATCATAT AGCCGTATCA TATTATGCTG TTCCACTCCT
                                                         NcoI
                                                         ~~~~~~~
 361 ACTAAACCAT GGCCAAGTTG ACCAGTGCCG TTCCGGTGCT CACCGCGCGC GACGTCGCCG
     TGATTTGGTA CCGGTTCAAC TGGTCACGGC AAGGCCACGA GTGGCGCGCG CTGCAGCGGC
                                                            SmaI
                                                            ~~~~~~~
                                                            XmaI
                                                            ~~~~~~~
                                                AvaI        AvaI
 421 GAGCGGTCGA GTTCTGGACC GACCGGCTCG GGTTCTCCCG GACTTCGTG GAGGACGACT
     CTCGCCAGCT CAAGACCTGG CTGGCCGAGC CCAAGAGGGC CCTGAAGCAC CTCCTGCTGA
 481 TCGCCGGTGT GGTCCGGGAC GACGTGACCC TGTTCATCAG CGCGGTCCAG GACCAGGTGG
     AGCGGCCACA CCAGGCCCTG CTGCACTGGG ACAAGTAGTC GCGCCAGGTC CTGGTCCACC
 541 TGCCGGACAA CACCCTGGCC TGGGTGTGGG TGCGCCGGCT GGACGAGCTG TACGCCGAGT
     ACGGCCTGTT GTGGGACCGG ACCCACACCC ACGCGCCGGA CCTGCTCGAC ATGCGGCTCA
 601 GGTCGGAGGT CGTGTCCACG AACTTCCGGG ACGCCTCCGG GCCGGCCATG ACCGAGATCG
     CCAGCCTCCA GCACAGGTGC TTGAAGGCCC TGCGGAGGCC CGGCCGGTAC TGGCTCTAGC
                                                                ApaLI
                                                                ~~~~~~
 661 GCGAGCAGCC GTGGGGGCGG GAGTTCGCCC TGCGCGACCC GGCCGGCAAC TGCGTGCACT
     CGCTCGTCGG CACCCCCGCC CTCAAGCGGG ACGCGCTGGG CCGGCCGTTG ACGCACGTGA
 721 TCGTGGCCGA GGAGCAGGAC TGATCATGAT GATATTATTT TATCTTGTGC AATGTAACAT
     AGCACCGGCT CCTCGTCCTG ACTAGTACTA CTATAATAAA ATAGAACACG TTACATTGTA
 781 CAGAGATTTT GAGACACGGG CCAGAGCTGC AGGAAACAG CTATGACCAT GTAATACGAC
     GTCTCTAAAA CTCTGTGCCC GGTCTCGACG GTCCTTTGTC GATACTGGTA CATTATGCTG
 841 TCACTATAGG GGATATCAGC TGGATGGCAA ATAATGATTT TATTTTGACT GATAGTGACC
     AGTGATATCC CCTATAGTCG ACCTACCGTT TATTACTAAA ATAAAACTGA CTATCACTGG
 901 TGTTCGTTGC AACACCGGTG CTAGCGTATA CCCGAAGTAT GTCAAAAAGA GGTGTGCTAT
     ACAAGCAACG TTGTGGCCAC GATCGCATAT GGGCTTCATA CAGTTTTTCT CCACACGATA
 961 GAAGCACGT ATTACAGTGA CAGTTGACAG CGACAGCTAT CAGTTGCTCA AGGCATATAT
     CTTCGTCGCA TAATGTCACT GTCAACTGTC GCTGTCGATA GTCAACGAGT TCCGTATATA
1021 GATGTCAATA TCTCCGGTCT GGTAAGCACA ACCATGCAGA ATGAAGCCCG TCGTCTGCGT
     CTACAGTTAT AGAGGCCAGA CCATTCGTGT TGGTACGTCT TACTTCGGGC AGCAGACGCA
1081 GCCGAACGCT GGAAAGCGGA AAATCAGGAA GGGATGGCTG AGGTCGCCCG GTTTATTGAA
     CGGCTTGCGA CCTTTCGCCT TTTAGTCCTT CCCTACCGAC TCCAGCGGGC CAAATAACTT
1141 ATGAACGGCT CTTTTGCTGA CGAGACAGG GACTGGTGAA ATGCAGTTTA AGGTTTACAC
     TACTTGCCGA GAAAACGACT GCTCTTGTCC CTGACCACTT TACGTCAAAT TCCAAATGTG
1201 CTATAAAAGA GAGAGCCGTT ATCGTCTGTT TGTGGATGTA CAGAGTGATA TTATTGACAC
     GATATTTTCT CTCTCGGCAA TAGCAGACAA ACACCTACAT GTCTCACTAT AATAACTGTG
         SmaI
         ~~~~~~
         XmaI
         ~~~~~~
         AvaI                                    ApaLI
         ~~~~~~                                  ~~~~~~
1261 GCCCGGGCGA CGGATGGTGA TCCCCCTGGC CAGTGCACGT CTGCTGTCAG ATAAAGTCTC
     CGGGCCCGCT GCCTACCACT AGGGGGACCG GTCACGTGCA GACGACAGTC TATTTCAGAG
1321 CCGTGAACTT TACCCGGTGG TGCATATCGG GGATGAAAGC TGGCGCATGA TGACCACCGA
     GGCACTTGAA ATGGGCCACC ACGTATAGCC CCTACTTTCG ACCGCGTACT ACTGGTGGCT
1381 TATGGCCAGT GTGCCGGTCT CCGTTATCGG GGAAGAAGTG GCTGATCTCA GCCGCCGCGA
     ATACCGGTCA CACGGCCAGA GGCAATAGCC CCTTCTTCAC CGACTAGAGT CGGCGGCGCT
1441 AAATGACATC AAAAACGCCA TTAACCTGAT GTTCTGGGGA ATATAAATGT CAGGCTCCCT
     TTTACTGTAG TTTTTGCGGT AATTGGACTA CAAGACCCCT TATATTTACA GTCCGAGGGA
```

Fig. 5₁

```
                    PstI
                   ~~~~~~~
1501 TATACACAGC CAGTCTGCAG GTCGACCATA GTGACTGGAT ATGTTGTGTT TTACAGTATT
     ATATGTGTCG GTCAGACGTC CAGCTGGTAT CACTGACCTA TACAACACAA AATGTCATAA
1561 ATGTAGTCTG TTTTTTATGC AAAATCTAAT TTAATATATT GATATTTATA TCATTTTACG
     TACATCAGAC AAAAAATACG TTTTAGATTA AATTATATAA CTATAAATAT AGTAAAATGC
1621 TTTCTCGTTC AGCTTTCTTG TACAAAGTGG TGATAATTAA TTAAGATCAG ATCCGGCTGC
     AAAGAGCAAG TCGAAAGAAC ATGTTTCACC ACTATTAATT AATTCTAGTC TAGGCCGACG
                                                              PstI
                                                             ~~~~~~~

HindIII    BamHI      SacI                                 HindIII
     ~~~~~~     ~~~~~~     ~~~~~~~                              ~
1681 TAAGCTTGAG TCCGGATCCC AATTGGGAGC TCGTGTACAC GGCGCGCCTG CAGGTCGACA
     ATTCGAACTC AGGCCTAGGG TTAACCCTCG AGCACATGTG CCGCGCGGAC GTCCAGCTGT
     HindIII    AvaI
     ~~~~~      ~~~~~~~
1741 AGCTTGCGGC CGCACTCGAG TCTGGTAAAG AAACCGCTGC TGCGAAATTT GAACGCCAGC
     TCGAACGCCG GCGTGAGCTC AGACCATTTC TTTGGCGACG ACGCTTTAAA CTTGCGGTCG
1801 ACATGGACTC GTCTACTAGC GCAGCTTAAT TAACCTAGGC TGCTGCCACC GCTGAGCAAT
     TGTACCTGAG CAGATGATCG CGTCGAATTA ATTGGATCCG ACGACGGTGG CGACTCGTTA
1861 AACTAGCATA ACCCCTTGGG GCCTCTAAAC GGGTCTTGAG GGGTTTTTTG CTGAAACCTC
     TTGATCGTAT TGGGGAACCC CGGAGATTTG CCCAGAACTC CCCAAAAAAC GACTTTGGAG
1921 AGGCATTTGA GAAGCACACG GTCACACTGC TTCCGGTAGT CAATAAACCG GTAAACCAGC
     TCCGTAAACT CTTCGTGTGC CAGTGTGACG AAGGCCATCA GTTATTTGGC CATTTGGTCG
1981 AATAGACATA AGCGGCTATT TAACGACCCT GCCCTGAACC GACGACAAGC TGACGACCGG
     TTATCTGTAT TCGCCGATAA ATTGCTGGGA CGGGACTTGG CTGCTGTTCG ACTGCTGGCC
2041 GTCTCCGCAA GTGGCACTTT TCGGGGAAAT GTGCGCGGAA CCCCTATTTG TTTATTTTTC
     CAGAGGCGTT CACCGTGAAA AGCCCCTTTA CACGCGCCTT GGGGATAAAC AAATAAAAAG
2101 TAAATACATT CAAATATGTA TCCGCTCATG AATTAATTCT TAGAAAAACT CATCGAGCAT
     ATTTATGTAA GTTTATACAT AGGCGAGTAC TTAATTAAGA ATCTTTTTGA GTAGCTCGTA
2161 CAAATGAAAC TGCAATTTAT TCATATCAGG ATTATCATAA CCATATTTTT GAAAAAGCCG
     GTTTACTTTG ACGTTAAATA AGTATAGTCC TAATAGTTAT GGTATAAAAA CTTTTTCGGC
2221 TTTCTGTAAT GAAGGAGAAA ACTCACCGAG GCAGTTCCAT AGGATGCAA GATCCTGGTA
     AAAGACATTA CTTCCTCTTT TGAGTGGCTC CGTCAAGGTA TCCTACCGTT CTAGGACCAT
2281 TCGGTCTGCG ATTCCGACTC GTCCAACATC AATACAACCT ATTAATTTCC CCTCGTCAAA
     AGCCAGACGC TAAGGCTGAG CAGGTTGTAG TTATGTTGGA TAATTAAAGG GGAGCAGTTT
2341 AATAAGGTTA TCAAGTGAGA AATCACCATG AGTGACGACT GAATCCGGTG AGAATGGCAA
     TTATTCCAAT AGTTCACTCT TTAGTGGTAC TCACTGCTGA CTTAGGCCAC TCTTACCGTT
2401 AAGTTTATGC ATTTCTTTCC AGACTTGTTC AACAGGCCAG CCATTACGCT CGTCATCAAA
     TTCAAATACG TAAAGAAAGG TCTGAACAAG TTGTCCGGTC GGTAATGCGA GCAGTAGTTT
2461 ATCACTCGCA TCAACCAAAC CGTTATTCAT TCGTGATTGC GCCTGAGCGA GACGAAATAC
     TAGTGAGCGT AGTTGGTTTG GCAATAAGTA AGCACTAACG CGGACTCGCT CTGCTTTATG
2521 GCGGTCGCTG TTAAAAGGAC AATTACAAAC AGGAATCGAA TGCAACCGGC GCAGGAACAC
     CGCCAGCGAC AATTTTCCTG TTAATGTTTG TCCTTAGCTT ACGTTGGCCG CGTCCTTGTG
2581 TGCCAGCGCA TCAACAATAT TTTCACCTGA ATCAGGATAT CTTCTAATA CCTGGAATGC
     ACGGTCGCGT AGTTGTTATA AAAGTGGACT TAGTCCTATA GAAGATTAT GGACCTTACG
              SmaI
              ~~~~~~~
              XmaI
              ~~~~~~~
              AvaI
              ~~~~~~~
2641 TGTTTTCCCG GGGATCGCAG TGGTGAGTAA CCATGCATCA TCAGGAGTAC GGATAAAATG
     ACAAAAGGGC CCCTAGCGTC ACCACTCATT GGTACGTAGT AGTCCTCATG CCTATTTTAC
2701 CTTGATGGTC GGAAGAGGCA TAAATTCCGT CAGCCAGTTT AGTCTGACCA TCTCATCTGT
     GAACTACCAG CCTTCTCCGT ATTTAAGGCA GTCGGTCAAA TCAGACTGGT AGAGTAGACA
2761 AACATCATTG GCAACGCTAC CTTTGCCATG TTTCAGAAAC AACTCTGGCG CATCGGGCTT
     TTGTAGTAAC CGTTGCGATG GAAACGGTAC AAAGTCTTTG TTGAGACCGC GTAGCCCGAA
              ClaI
              ~~~~~~~
2821 CCCATACAAT CGATAGATTG TCGCACCTGA TTGCCCGACA TTATCGCGAG CCCATTTATA
     GGGTATGTTA GCTATCTAAC AGCGTGGACT AACGGGCTGT AATAGCGCTC GGGTAAATAT
2881 CCCATATAAA TCAGCATCCA TGTTGGAATT TAATCGCGGC CTAGAGCAAG ACGTTTCCCG
     GGGTATATTT AGTCGTAGGT ACAACCTTAA ATTAGCGCCG GATCTCGTTC TGCAAAGGGC
2941 TTGAATATGG CTCATACTCT TCCTTTTTCA ATATTATTGA AGCATTTATC AGGGTTATTG
     AACTTATACC GAGTATGAGA AGGAAAAAGT TATAATAACT TCGTAAATAG TCCCAATAAC
3001 TCTCATGAGC GGATACATAT TTGAATGTAT TTAGAAAAAT AAACAAATAG GCATGCAGCG
     AGAGTACTCG CCTATGTATA AACTTACATA AATCTTTTTA TTTGTTTATC CGTACGTCGC
3061 CTCTTCCGCT TCCTCGCTCA CTGACTCGCT ACGCTCGGTC GTTCGACTGC GGCGAGCGGT
     GAGAAGGCGA AGGAGCGAGT GACTGAGCGA TGCGAGCCAG CAAGCTGACG CCGCTCGCCA
3121 GTCAGCTCAC TCAAAAGCGG TAATACGGTT ATCCACAGAA TCAGGGGATA AAGCCGGAAA
     CAGTCGAGTG AGTTTTCGCC ATTATGCCAA TAGGTGTCTT AGTCCCCTAT TTCGGCCTTT
3181 GAACATGTGA GCAAAAAGCA AAGCACCGGA AGAAGCCAAC GCCGCAGGCG TTTTTCCATA
```

Fig. 5₂

```
      CTTGTACACT CGTTTTTCGT TTCGTGGCCT TCTTCGGTTG CGGCGTCCGC AAAAAGGTAT
3241  GGCTCCGCCC CCCTGACGAG CATCACAAAA ATCGACGCTC AAGCCAGAGG TGGCGAAACC
      CCGAGGCGGG GGGACTGCTC GTAGTGTTTT TAGCTGCGAG TTCGGTCTCC ACCGCTTTGG
3301  CGACAGGACT ATAAAGATAC CAGGCGTTTC CCCCTGGAAG CTCCCTCGTG CGCTCTCCTG
      GCTGTCCTGA TATTTCTATG GTCCGCAAAG GGGGACCTTC GAGGGACCAC GCGAGAGGAC
3361  TTCCGACCCT GCCGCTTACC GGATACCTGT CCGCCTTTCT CCCTTCGGGA AGCGTGGCGC
      AAGGCTGGGA CGGCGAATGG CCTATGACA  GGCGGAAAGA GGGAAGCCCT TCGCACCGCG
3421  TTTCTCATAG CTCACGCTGT TGGTATCTCA GTTCGGTGTA GGTCGTTCGC TCCAAGCTGG
      AAAGAGTATC GAGTGCGACA ACCATAGAGT CAAGCCACAT CCAGCAAGCG AGGTTCGACC
          ApaLI
          ~~~~~~~
3481  GCTGTGTGCA CGAACCCCCC GTTCAGCCCG ACCGCTGCGC CTTATCCGGT AACTATCGTC
      CGACACACGT GCTTGGGGGG CAAGTCGGGC TGGCGACGCG GAATAGGCCA TTGATAGCAG
3541  TTGAGTCCAA CCCGGTAAGA CACGACTTAT CGCCACTGGC AGCAGCCATT GGTAACTGAT
      AACTCAGGTT GGGCCATTCT GTGCTGAATA GCGGTGACCG TCGTCGGTAA CCATTGACTA
3601  TTAGAGGACT TTGTCTTGAA GTTATGCACC TGTTAAGGCT AAACTGAAAG AACAGATTTT
      AATCTCCTGA AACAGAACTT CAATACGTGG ACAATTCCGA TTTGACTTTC TTGTCTAAAA
3661  GGTGAGTGCG GTCCTCCAAC CCACTTACCT TGGTTCAAAG AGTTGGTAGC TCAGCGAACC
      CCACTCACGC CAGGAGGTTG GGTGAATGGA ACCAAGTTTC TCAACCATCG AGTCGCTTGG
3721  TTGAGAAAAC CACCGTTGGT AGCGGTGGTT TTTCTTTATT TATGAGATGA TGAATCAATC
      AACTCTTTTG GTGGCAACCA TCGCCACCAA AAAGAAATAA ATACTCTACT ACTTAGTTAG
3781  GGTCTATCAA GTCAACGAAC AGCTATTCCG TTACTCTAGA TTTCAGTGCA ATTTATCTCT
      CCAGATAGTT CAGTTGCTTG TCGATAAGGC AATGAGATCT AAAGTCACGT TAAATAGAGA
3841  TCAAATGTAG CACCTGAAGT CAGCCCCATA CGATATAAGT TGTAATTCTC ATGTTAGTCA
      AGTTTACATC GTGGACTTCA GTCGGGGTAT GCTATATTCA ACATTAAGAG TACAATCAGT
3901  TGCCCCGCGC CCACCGGAAG GAGCTGACTG GGTTGAAGGC TCTCAAGGCG ATCGGTCGAG
      ACGGGGCGCG GGTGGCCTTC CTCGACTGAC CCAACTTCCG AGAGTTCCCG TAGCCAGCTC
3961  ATCCCGGTGC CTAATGAGTG AGCTAACTTA CATTAATTGC GTTGCGCTCA CTGCCCGCTT
      TAGGGCCACG GATTACTCAC TCGATTGAAT GTAATTAACG CAACGCGAGT GACGGGCGAA
4021  TCCAGTCGGG AAACCTGTCG TGCCAGCTGC ATTAATGAAT CGGCCAACGC GCGGGGAGAG
      AGGTCAGCCC TTTGGACAGC ACGGTCGACG TAATTACTTA GCCGGTTGCG CGCCCCTCTC
4081  GCGGTTTGCG TATTGGGCGC CAGGGTGGTT TTTCTTTTCA CCAGTGAGAC GGGCAACAGC
      CGCCAAACGC ATAACCCGCG GTCCCACCAA AAAGAAAAGT GGTCACTCTG CCCGTTGTCG
4141  TGATTGCCCT TCACCGCCTG GCCCTGAGAG AGTTGCAGCA AGCGGTCCAC GCTGGTTTGC
      ACTAACGGGA AGTGGCGGAC CGGGACTCTC TCAACGTCGT TCGCCAGGTG CGACCAAACG
4201  CCCAGCAGGC GAAAATCCTG TTTGATGGTG GTTAACGGCG GGATATAACA TGAGCTGTCT
      GGGTCGTCCG CTTTTAGGAC AAACTACCAC CAATTGCCGC CCTATATTGT ACTCGACAGA
4261  TCGGTATCGT CGTATCCCAC TACCGAGATG TCCGCACCAA CGCGCAGCCC GGACTCGGTA
      AGCCATAGCA GCATAGGGTG ATGGCTCTAC AGGCGTGGTT GCGCGTCGGG CCTGAGCCAT
4321  ATGGCGCGCA TTGCGCCCAG CGCCATCTGA TCGTTGGCAA CCAGCATCGC AGTGGGAACG
      TACCGCGCGT AACGCGGGTC GCGGTAGACT AGCAACCGTT GGTCGTAGCG TCACCCTTGC
4381  ATGCCCTCAT TCAGCATTTG CATGGTTTGT TGAAAACCGG ACATGGCACT CCAGTCGCCT
      TACGGGAGTA AGTCGTAAAC GTACCAAACA ACTTTTGGCC TGTACCGTGA GGTCAGCGGA
4441  TCCCGTTCCG CTATCGGCTG AATTTGATTG CGAGTGAGAT ATTTATGCCA GCCAGCCAGA
      AGGGCAAGGC GATAGCCGAC TTAAACTAAC GCTCACTCTA TAAATACGGT CGGTCGGTCT
4501  CGCAGACGCG CCGAGACAGA ACTTAATGGG CCCGCTAACA GCGCGATTTG CTGGTGACCC
      GCGTCTGCGC GGCTCTGTCT TGAATTACCC GGGCGATTGT CGCGCTAAAC GACCACTGGG
4561  AATGCGACCA GATGCTCCAC GCCCAGTCGC GTACCGTCTT CATGGGAGAA AATAATACTG
      TTACGCTGGT CTACGAGGTG CGGGTCAGCG CATGGCAGAA GTACCCTCTT TTATTATGAC
4621  TTGATGGGTG TCTGGTCAGA GACATCAAGA AATAACGCCG GAACATTAGT GCAGGCAGCT
      AACTACCCAC AGACCAGTCT CTGTAGTTCT TTATTGCGGC CTTGTAATCA CGTCCGTCGA
4681  TCCACAGCAA TGGCATCCTG GTCATCCAGC GGATAGTTAA TGATCAGCCC ACTGACGCGT
      AGGTGTCGTT ACCGTAGGAC CAGTAGGTCG CCTATCAATT ACTAGTCGGG TGACTGCGCA
          ApaLI
          ~~~~~~~
4741  TGCGCGAGAA GATTGTGCAC CGCCGCTTTA CAGGCTTCGA CGCCGCTTCG TTCTACCATC
      ACGCGCTCTT CTAACACGTG GCGGCGAAAT GTCCGAAGCT GCGGCGAAGC AAGATGGTAG
4801  GACACCACCA CGCTGGCACC CAGTTGATCG GCGCGAGATT TAATCGCCGC GACAATTTGC
      CTGTGGTGGT GCGACCGTGG GTCAACTAGC CGCGCTCTAA ATTAGCGGCG CTGTTAAACG
4861  GACGGCGCGT GCAGGGCCAG ACTGGAGGTG GCAACGCCAA TCAGCAACGA CTGTTTGCCC
      CTGCCGCGCA CGTCCCGGTC TGACCTCCAC CGTTGCGGTT AGTCGTTGCT GACAAACGGG
4921  GCCAGTTGTT GTGCCACGCG GTTGGGAATG TAATTCAGCT CCGCCATCGC CGCTTCCACT
      CGGTCAACAA CACGGTGCGC CAACCCTTAC ATTAAGTCGA GGCGGTAGCG GCGAAGGTGA
4981  TTTTCCCGCG TTTTCGCAGA AACGTGGCTG GCCTGGTTCA CCACGCGGGA AACGGTCTGA
      AAAAGGGCGC AAAAGCGTCT TTGCACCGAC CGGACCAAGT GGTGCGCCCT TTGCCAGACT
5041  TAAGAGACAC CGGCATACTC TGCGACATCG TATAACGTTA CTGGTTTCAC ATTCACCACC
      ATTCTCTGTG GCCGTATGAG ACGCTGTAGC ATATTGCAAT GACCAAAGTG TAAGTGGTGG
5101  CTGAATTGAC TCTCTTCCGG GCGCTATCAT GCCATACCGC GAAAGGTTTT GCGCCATTCG
      GACTTAACTG AGAGAAGGCC CGCGATAGTA CGGTATGGCG CTTTCCAAAA CGCGGTAAGC
5161  ATGGTGTCCG GGATCTCGAC GCTCTCCCTT ATGCGACTCC TGCATTAGGA AATTAATACG
      TACCACAGGC CCTAGAGCTG CGAGAGGGAA TACGCTGAGG ACGTAATCCT TTAATTATGC
5221  ACTCACTATA
      TGAGTGATAT
```

Fig. 5₃

| Fig. 7₁ |
|---|
| Fig. 7₂ |
| Fig. 7₃ |

Fig. 7 pDEST-C3 nucleotide

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                               EcoRI
                                                              ~~~~~~
             NcoI                                 BamHI        SacI
            ~~~~~~~                              ~~~~~~~        ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
      ~~~
 121 CTCGATCACA AGTTTGTACA AAAAAGCTGA ACGAGAAACG TAAAATGATA TAAATATCAA
     GAGCTAGTGT TCAAACATGT TTTTTCGACT TGCTCTTTGC ATTTTACTAT ATTTATAGTT
 181 TATATTAAAT TAGATTTTGC ATAAAAAACA GACTACATAA TACTGTAAAA CACAACATAT
     ATATAATTTA ATCTAAAACG TATTTTTTGT CTGATGTATT ATGACATTTT GTGTTGTATA
                    NotI
                  ~~~~~~~~~
 241 CCAGTCACTA TGGCGGCCGC CACGTTAAGG GATTTTGGTC ATGATCAGCA CGTGTTGACA
     GGTCAGTGAT ACCGCCGGCG GTGCAATTCC CTAAAACCAG TACTAGTCGT GCACAACTGT
                                                                 NcoI
                                                                  ~~~
 301 ATTAATCATC GGCATAGTAT ATCGGCATAG TATAATACGA CAAGGTGAGG AACTAAACCA
     TAATTAGTAG CCGTATCATA TAGCCGTATC ATATTATGCT GTTCCACTCC TTGATTTGGT
     NcoI
      ~~~
 361 TGGCCAAGTT GACCAGTGCC GTTCCGGTGC TCACCGCGCG CGACGTCGCC GGAGCGGTCG
     ACCGGTTCAA CTGGTCACGG CAAGGCCACG AGTGGCGCGC GCTGCAGCGG CCTCGCCAGC
 421 AGTTCTGGAC CGACCGGCTC GGGTTCTCCC GGGACTTCGT GGAGGACGAC TTCGCCGGTG
     TCAAGACCTG GCTGGCCGAG CCCAAGAGGG CCCTGAAGCA CCTCCTGCTG AAGCGGCCAC
 481 TGGTCCGGGA CGACGTGACC CTGTTCATCA GCGCGGTCCA GGACCAGGTG GTGCCGGACA
     ACCAGGCCCT GCTGCACTGG GACAAGTAGT CGCGCCAGGT CCTGGTCCAC CACGGCCTGT
 541 ACACCCTGGC CTGGGTGTGG GTGCGCGGCC TGGACGAGCT GTACGCCGAG TGGTCGGAGG
     TGTGGGACCG GACCCACACC CACGCGCCGG ACCTGCTCGA CATGCGGCTC ACCAGCCTCC
 601 TCGTGTCCAC GAACTTCCGG GACGCCTCCG GCCGGCCAT GACCGAGATC GGCGAGCAGC
     AGCACAGGTG CTTGAAGGCC CTGCGGAGGC CCGGCCGGTA CTGGCTCTAG CCGCTCGTCG
 661 CGTGGGGGCG GGAGTTCGCC CTGCGCGACC CGGCCGGCAA CTGCGTGCAC TTCGTGGCCG
     GCACCCCCGC CCTCAAGCGG GACGCGCTGG GCCGGCCGTT GACGCACGTG AAGCACCGGC
 721 AGGAGCAGGA CTGATCATGA TGATATTATT TTATCTTGTG CAATGTAACA TCAGAGATTT
     TCCTCGTCCT GACTAGTACT ACTATAATAA AATAGAACAC GTTACATTGT AGTCTCTAAA
 781 TGAGACACGG GCCAGAGCTG CCAGGAAACA GCTATGACCA TGTAATACGA CTCACTATAG
     ACTCTGTGCC CGGTCTCGAC GGTCCTTTGT CGATACTGGT ACATTATGCT GAGTGATATC
 841 GGGATATCAG CTGGATGGCA AATAATGATT TTATTTTGAC TGATAGTGAC CTGTTCGTTG
     CCCTATAGTC GACCTACCGT TTATTACTAA AATAAAACTG ACTATCACTG GACAAGCAAC
 901 CAACACCGGT GCTAGCGTAT ACCCGAAGTA TGTCAAAAAG AGGTGTGCTA TGAAGCAGCG
     GTTGTGGCCA CGATCGCATA TGGGCTTCAT ACAGTTTTTC TCCACACGAT ACTTCGTCGC
 961 TATTACAGTG ACAGTTGACA GCGACAGCTA TCAGTTGCTC AAGGCATATA TGATGTCAAT
     ATAATGTCAC TGTCAACTGT CGCTGTCGAT AGTCAACGAG TTCCGTATAT ACTACAGTTA
1021 ATCTCCGGTC TGGTAAGCAC AACCATGCAG AATGAAGCCC GTCGTCTGCG TGCCGAACGC
     TAGAGGCCAG ACCATTCGTG TTGGTACGTC TTACTTCGGG CAGCAGACGC ACGGCTTGCG
1081 TGGAAAGCGG AAAATCAGGA AGGGATGGCT GAGGTCGCCC GGTTTATTGA AATGAACGGC
     ACCTTTCGCC TTTTAGTCCT TCCCTACCGA CTCCAGCGGG CCAAATAACT TTACTTGCCG
1141 TCTTTTGCTG ACGAGAACAG GGACTGGTGA AATGCAGTTT AAGGTTTACA CCTATAAAAG
     AGAAAACGAC TGCTCTTGTC CCTGACCACT TTACGTCAAA TTCCAAATGT GGATATTTTC
1201 AGAGAGCCGT TATCGTCTGT TTGTGGATGT ACAGAGTGAT ATTATTGACA CGCCCGGGCG
     TCTCTCGGCA ATAGCAGACA AACACCTACA TGTCTCACTA TAATAACTGT GCGGGCCCGC
1261 ACGGATGGTG ATCCCCTGG CCAGTGCACG TCTGCTGTCA GATAAAGTCT CCCGTGAACT
     TGCCTACCAC TAGGGGGACC GGTCACGTGC AGACGACAGT CTATTTCAGA GGGCACTTGA
1321 TTACCCGGTG GTGCATATCG GGGATGAAAG CTGGCGCATG ATGACCACCG ATGCCAGGTC
     AATGGGCCAC CACGTATAGC CCCTACTTTC GACCGCGTAC TACTGGTGGC TATACCGGTC
1381 TGTGCCGGTC TCCGTTATCG GGAAGAAGT GGCTGATCTC AGCCGCCGCG AAAATGACAT
     ACACGGCCAG AGGCAATAGC CCCTTCTTCA CCGACTAGAG TCGGCGGCGC TTTTACTGTA
1441 CAAAAACGCC ATTAACCTGA TGTTCTGGGG AATATAAATG TCAGGCTCCC TTATACACAG
     GTTTTTGCGG TAATTGGACT ACAAGACCCC TTATATTTAC AGTCCGAGGG AATATGTGTC
                    PstI
                  ~~~~~~~
1501 CCAGTCTGCA GGTCGACCAT AGTGACTGGA TATGTTGTGT TTTACAGTAT TATGTAGTCT
     GGTCAGACGT CCAGCTGGTA TCACTGACCT ATACAACACA AAATGTCATA ATACATCAGA
1561 GTTTTTTATG CAAAATCTAA TTTAATATAT TGATATTTAT ATCATTTTAC GTTTCTCGTT
     CAAAAAATAC GTTTTAGATT AAATTATATA ACTATAAATA TAGTAAAATG CAAAGAGCAA
```

Fig. 7₁

```
                                                                          NotI
                                                                          ~~
                                                              HindIII
                                                              ~~~~~~
1621  CAGCTTTCTT GTACAAAGTG GTGATAATTA ATTAAGATCA GATCCGGCTG CTAAGCTTGC
      GTCGAAAGAA CATGTTTCAC CACTATTAAT TAATTCTAGT CTAGGCCGAC GATTCGAACG
        NotI
        ~~~~~~
1681  GGCCGCATAA TGCTTAAGTC GAACAGAAAG TAATCGTATT GTACACGGCC GCATAATCGA
      CCGGCGTATT ACGAATTCAG CTTGTCTTTC ATTAGCATAA CATGTGCCGG CGTATTAGCT
1741  AATTAATACG ACTCACTATA GGGGAATTGT GAGCGGATAA CAATTCCCCA TCTTAGTATA
      TTAATTATGC TGAGTGATAT CCCCTTAACA CTCGCCTATT GTTAAGGGGT AGAATCATAT
1801  TTAGTTAAGT ATAAGAAGGA GATATACATA TGGCTAGCTC CAATTGGATA TCGGCCGGCC
      AATCAATTCA TATTCTTCCT CTATATGTAT ACCGTCTAGA GTTAACCTAT AGCCGGCCGG
1861  ACGCGATCGC TGACGTCGGT ACCCTCGAGT CTGGTAAAGA AACCGCTGCT GCGAAATTTG
      TGCGCTAGCG ACTGCAGCCA TGGGAGCTCA GACCATTTCT TTGGCGACGA CGCTTTAAAC
1921  AACGCCAGCA CATGGACTCG TCTACTAGCG CAGCTTAATT AACCTAGGCT GCTGCCACCG
      TTGCGGTCGT GTACCTGAGC AGATGATCGC GTCGAATTAA TTGGATCCGA CGACGGTGGC
1981  CTGAGCAATA ACTAGCATAA CCCCTTGGGG CCTCTAAACG GGTCTTGAGG GGTTTTTTGC
      GACTCGTTAT TGATCGTATT GGGGAACCCC GGAGATTTGC CCAGAACTCC CCAAAAAACG
2041  TGAAACCTCA GGCATTTGAG AAGCACACGG TCACACTGCT TCCGGTAGTC AATAAACCGG
      ACTTTGGAGT CCGTAAACTC TTCGTGTGCC AGTGTGACGA AGGCCATCAG TTATTTGGCC
2101  TAAACCAGCA ATAGACATAA GCGGCTATTT AACGACCCTG CCCTGAACCG ACGACCGGGT
      ATTTGGTCGT TATCTGTATT CGCCGATAAA TTGCTGGGAC GGGACTTGGC TGCTGGCCCA
2161  CGAATTTGCT TTCGAATTTC TGCCATTCAT CCGCTTATTA TCACTTATTC AGGCGTAGCA
      GCTTAAACGA AAGCTTAAAG ACGGTAAGTA GGCGAATAAT AGTGAATAAG TCCGCATCGT
2221  CCAGGCGTTT AAGGGCACCA ATAACTGCCT TAAAAAAATT ACGCCCCGCC CTGCCACTCA
      GGTCCGCAAA TTCCCGTGGT TATTGACGGA ATTTTTTTAA TGCGGGGCGG GACGGTGAGT
2281  TCGCAGTACT GTTGTAATTC ATTAAGCATT CTGCCGACAT ACAGACGGCA
      AGCGTCATGA CAACATTAAG TAATTCGTAA GACGGCTGTA CCTTCGGTAG TGTCTGCCGT
2341  TGATGAACCT GAATCGCCAG CGGCATCAGC ACCTTGTCGC CTTGCGTATA ATATTTGCCC
      ACTACTTGGA CTTAGCGGTC GCCGTAGTCG TGGAACAGCG GAACGCATAT TATAAACGGG
2401  ATAGTGAAAA CGGGGGCGAA GAAGTTGTCC ATATTGGCCA CGTTTAAATC AAAAACTGGTG
      TATCACTTTT GCCCCCGCTT CTTCAACAGG TATAACCGGT GCAAATTTAG TTTTTGACCAC
2461  AAACTCACCC AGGGATTGGC TGAGACGAAA AACATATTCT CAATAAACCC TTTAGGGAAA
      TTTGAGTGGG TCCCTAACCG ACTCTGCTTT TTGTATAAGA GTTATTTGGG AAATCCCTTT
2521  TAGGCCAGGT TTTCACCGTA ACACGCCACA TCTTGCGAAT ATATGTGTAG AAACTGCCGG
      ATCCGGTCCA AAAGTGGCAT TGTGCGGTGT AGAACGCTTA TATACACATC TTTGACGGCC
2581  AAATCGTCGT GGTATTCACT CCAGAGCGAT GAAAACGTTT CAGTTTGCTC ATGGAAAACG
      TTTAGCAGCA CCATAAGTGA GGTCTCGCTA CTTTTGCAAA GTCAAACGAG TACCTTTTGC
2641  GTGTAACAAG GGTGAACACT ATCCCATATC ACCAGCTCAC CGTCTTTCAT TGCCATACGG
      CACATTGTTC CCACTTGTGA TAGGGTATAG TGGTCGAGTG GCAGAAAGTA ACGGTATGCC
2701  AACTCCGGAT GAGCATTCAT CAGGCGGGCA AGAATGTGAA TAAAGGCCGG ATAAAACTTG
      TTGAGGCCTA CTCGTAAGTA GTCCGCCCGT TCTTACACTT ATTTCCGGCC TATTTTGAAC
2761  TGCTTATTTT TCTTTACGGT CTTTAAAAAG GCCGTAATAT CCAGCTGAAC GGTCTGGTTA
      ACGAATAAAA AGAAATGCCA GAAATTTTTC CGGCATTATA GGTCGACTTG CCAGACCAAT
2821  TAGGTACATT GAGCAACTGA CTGAAATGCC TCAAATGTT CTTTACGATG CCATTGGGAT
      ATCCATGTAA CTCGTTGACT GACTTTACGG AGTTTTACAA GAAATGCTAC GGTAACCCTA
2881  ATATCAACGG TGGTATATCC AGTGATTTTT TTCTCCATTT TAGCTTCCTT AGCTCCTGAA
      TATAGTTGCC ACCATATAGG TCACTAAAAA AAGAGGTAAA TCGAAGGAA TCGAGGACTT
2941  AATCTCGATA ACTCAAAAAA TACGCCCGGT AGTGATCTTA TTTCATTATG TGAAAGTTG
      TTAGAGCTAT TGAGTTTTTT ATGCGGGCCA TCACTAGAAT AAAGTAATAC CACTTTCAAC
3001  GAACCTCTTA CGTGCCGATC AACGTCTCAT TTCGCCAAA AGTTGGCCCA GGGCTTCCCG
      CTTGGAGAAT GCACGGCTAG TTGCAGAGTA AAAGCGGTTT TCAACCGGGT CCCGAAGGGC
3061  GTATCAACAG GGACACCAGG ATTTATTTAT TCTGCGAAGT GATCTTCCGT CACAGGTATT
      CATAGTTGTC CCTGTGGTCC TAAATAAATA AGACGCTTCA CTAGAAGGCA GTGTCCATAA
3121  TATTCGGCGC AAAGTGCGTC GGGTGATGCT GCCAACTTAC TGATTTAGTG TATGATGGTG
      ATAAGCCGCG TTTCACGCAG CCCACTACGA CGGTTGAATG ACTAAATCAC ATACTACCAC
3181  TTTTTGAGGT GCTCCAGTGG CTTCTGTTTC TATCAGCTGT CCCTCCTGTT CAGCTACTGA
      AAAAACTCCA CGAGGTCACC GAAGACAAAG ATAGTCGACA GGGAGGACAA GTCGATGACT
3241  CGGGGTGGTG CGTAACGGCA AAAGCACCGC CGGACATCAG CGCTAGCGGA GTGTATACTG
      GCCCCACCAC GCATTGCCGT TTTCGTGGCG GCCTGTAGTC GCGATCGCCT CACATATGAC
3301  GCTTACTATG TTGGCACTGA TGAGGGTGTC AGTGAAGTGC TTCATGTGGC AGGAGAAAAA
      CGAATGATAC AACCGTGACT ACTCCCACAG TCACTTCACG AAGTACACCG TCCTCTTTTT
3361  AGGCTGCACC GGTGCGTCAG CAGAATATGT GATACAGGAT ATATTCCGCT TCCTCGCTCA
      TCCGACGTGG CCACGCAGTC GTCTTATACA CTATGTCCTA TATAAGGCGA AGGAGCGAGT
3421  CTGACTCGCT ACGCTCGGTC GTTCGACTGC GGCGAGCGGA ATGCTTAC GAACGGGCG
      GACTGAGCGA TGCGAGCCAG CAAGCTGACG CCGCTCGCCT TTACCGAATG CTTGCCCCGC
3481  GAGATTTCCT GGAAGATGCC AGGAAGATAC TTAACGGGA AGTGAGAGGG CCGCGGCAAA
      CTCTAAAGGA CCTTCTACGG TCCTTCTATG AATTGTCCCT TCACTCTCCC GGCGCCGTTT
3541  GCCGTTTTTC CATAGGCTCC GCCCCCTGA CAAGCATCAC GAAATCTGAC GCTCAAATCA
      CGGCAAAAAG GTATCCGAGG CGGGGGGACT GTTCGTAGTG CTTTAGACTG CGAGTTTAGT
3601  GTGGTGGCGA AACCCGACAG GACTATAAAG ATACCAGGCG TTTCCCCTGG CGGCTCCCTC
```

Fig. 7$_2$

```
          CACCACCGCT TTGGGCTGTC CTGATATTTC TATGGTCCGC AAAGGGGACC GCCGAGGGAG
     3661 GTGCGCTCTC CTGTTCCTGC CTTTCGGTTT ACCGGTGTCA TTCCGCTGTT ATGGCCGCGT
          CACGCGAGAG GACAAGGACG GAAAGCCAAA TGGCCACAGT AAGGCGACAA TACCGGCGCA
     3721 TTGTCTCATT CCACGCCTGA CACTCAGTTC CGGGTAGGCG GTTCGCTCCA AGCTGGACTG
          AACAGAGTAA GGTGCGGACT GTGAGTCAAG GCCCATCCGT CAAGCGAGGT TCGACCTGAC
     3781 TATGCACGAA CCCCCCGTTC AGTCCGACCG CTGCGCCTTA TCCGGTAACT ATCGTCTTGA
          ATACGTGCTT GGGGGGCAAG TCAGGCTGGC GACGCGGAAT AGGCCATTGA TAGCAGAACT
     3841 GTCCAACCCG GAAAGACATG CAAAAGCACC ACTGGCAGCA GCCACTGGTA ATTGATTTAG
          CAGGTTGGGC CTTTCTGTAC GTTTTCGTGG TGACCGTCGT CGGTGACCAT TAACTAAATC
     3901 AGGAGTTAGT CTTGAAGTCA TGCGCCGGTT AAGGCTAAAC TGAAAGGACA AGTTTTGGTG
          TCCTCAATCA GAACTTCAGT ACGCGGCCAA TTCCGATTTG ACTTTCCTGT TCAAAACCAC
     3961 ACTGCGCTCC TCCAAGCCAG TTACCTCGGT TCAAAGAGTT GGTAGCTCAG AGAACCTTCG
          TGACGCGAGG AGGTTCGGTC AATGGAGCCA AGTTTCTCAA CCATCGAGTC TCTTGGAAGC
     4021 AAAAACCGCC CTGCAAGGCG GTTTTTTCGT TTTCAGAGCA AGAGATTACG CGCAGACCAA
          TTTTTGGCGG GACGTTCCGC CAAAAAAGCA AAAGTCTCGT TCTCTAATGC GCGTCTGGTT
     4081 AACGATCTCA AGAAGATCAT CTTATTAATC AGATAAAATA TTTCTAGATT TCAGTGCAAT
          TTGCTAGAGT TCTTCTAGTA GAATAATTAG TCTATTTTAT AAAGATCTAA AGTCACGTTA
     4141 TTATCTCTTC AAATGTAGCA CCTGAAGTCA GCCCCATACG ATATAAGTTG TAATTCTCAT
          AATAGAGAAG TTTACATCGT GGACTTCAGT CGGGGTATGC TATATTCAAC ATTAAGAGTA
     4201 GTTAGTCATG CCCCGCGCCC ACCGGAAGGA GCTGACTGGG TTGAAGGCTC TCAAGGGCAT
          CAATCAGTAC GGGGCGCGGG TGGCCTTCCT CGACTGACCC AACTTCCGAG AGTTCCCGTA
     4261 CGGTCGAGAT CCCGGTGCCT AATGAGTGAG CTAACTTACA TTAATTGCGT TGCGCTCACT
          GCCAGCTCTA GGGCCACGGA TTACTCACTC GATTGAATGT AATTAACGCA ACGCGAGTGA
     4321 GCCCGCTTTC CAGTCGGGAA ACCTGTCGTG CCAGCTGCAT TAATGAATCG GCCAACGCGC
          CGGGCGAAAG GTCAGCCCTT TGGACAGCAC GGTCGACGTA ATTACTTAGC CGGTTGCGCG
     4381 GGGGAGAGGC GGTTTGCGTA TTGGGCGCCA GGGTGGTTTT TCTTTTCACC AGTGAGACGG
          CCCCTCTCCG CCAAACGCAT AACCCGCGGT CCCACCAAAA AGAAAAGTGG TCACTCTGCC
     4441 GCAACAGCTG ATTGCCCTTC ACCGCCTGGC CCTGAGAGAG TTGCAGCAAG CGGTCCACGC
          CGTTGTCGAC TAACGGGAAG TGGCGGACCG GGACTCTCTC AACGTCGTTC GCCAGGTGCG
     4501 TGGTTTGCCC CAGCAGGCGA AAATCCTGTT TGATGGTGGT TAACGGCGGG ATATAACATG
          ACCAAACGGG GTCGTCCGCT TTTAGGACAA ACTACCACCA ATTGCCGCCC TATATTGTAC
     4561 AGCTGTCTTC GGTATCGTCG TATCCCACTA CCGAGATGTC CGCACCAACG CGCAGCCCGG
          TCGACAGAAG CCATAGCAGC ATAGGGTGAT GGCTCTACAG GCGTGGTTGC GCGTCGGGCC
     4621 ACTCGGTAAT GGCGCGCATT GCGCCCAGCG CCATCTGATC GTTGGCAACC AGCATCGCAG
          TGAGCCATTA CCGCGCGTAA CGCGGGTCGC GGTAGACTAG CAACCGTTGG TCGTAGCGTC
     4681 TGGGAACGAT GCCCTCATTC AGCATTTGCA TGGTTTGTTG AAAACCGGAC ATGGCACTCC
          ACCCTTGCTA CGGGAGTAAG TCGTAAACGT ACCAAACAAC TTTTGGCCTG TACCGTGAGG
     4741 AGTCGCCTTC CCGTTCCGCT ATCGGCTGAA TTTGATTGCG AGTGAGATAT TTATGCCAGC
          TCAGCGGAAG GGCAAGGCGA TAGCCGACTT AAACTAACGC TCACTCTATA AATACGGTCG
     4801 CAGCCAGACG CAGACGCGCC GAGACAGAAC TTAATGGGCC CGCTAACAGC GCGATTTGCT
          GTCGGTCTGC GTCTGCGCGG CTCTGTCTTG AATTACCCGG GCGATTGTCG CGCTAAACGA
     4861 GGTGACCCAA TGCGACCAGA TGCTCCACGC CCAGTCGCGT ACCGTCTTCA TGGGAGAAAA
          CCACTGGGTT ACGCTGGTCT ACGAGGTGCG GGTCAGCGCA TGGCAGAAGT ACCCTCTTTT
     4921 TAATACTGTT GATGGGTGTC TGGTCAGAGA CATCAAGAAA TAACGCCGGA ACATTAGTGC
          ATTATGACAA CTACCCACAG ACCAGTCTCT GTAGTTCTTT ATTGCGGCCT TGTAATCACG
     4981 AGGCAGCTTC CACAGCAATG GCATCCTGGT CATCCAGCGG ATAGTTAATG ATCAGCCCAC
          TCCGTCGAAG GTGTCGTTAC CGTAGGACCA GTAGGTCGCC TATCAATTAC TAGTCGGGTG
     5041 TGACGCGTTG CGCGAGAAGA TTGTGCACCG CCGCTTTACA GGCTTCGACG CCGCTTCGTT
          ACTGCGCAAC GCGCTCTTCT AACACGTGGC GGCGAAATGT CCGAAGCTGC GGCGAAGCAA
     5101 CTACCATCGA CACCACCACG CTGGCACCCA GTTGATCGGC GCGAGATTTA ATCGCCGCGA
          GATGGTAGCT GTGGTGGTGC GACCGTGGGT CAACTAGCCG CGCTCTAAAT TAGCGGCGCT
     5161 CAATTTGCGA CGGCGCGTGC AGGGCCAGAC TGGAGGTGGC AACGCCAATC AGCAACGACT
          GTTAAACGCT GCCGCGCACG TCCCGGTCTG ACCTCCACCG TTGCGGTTAG TCGTTGCTGA
     5221 GTTTGCCCGC CAGTTGTTGT GCCACGCGGT TGGGAATGTA ATTCAGCTCC GCCATCGCCG
          CAAACGGGCG GTCAACAACA CGGTGCGCCA ACCCTTACAT TAAGTCGAGG CGGTAGCGGC
     5281 CTTCCACTTT TTCCCGCGTT TTCGCAGAAA CGTGGCTGGC CTGGTTCACC ACGCGGGAAA
          GAAGGTGAAA AAGGGCGCAA AAGCGTCTTT GCACCGACCG GACCAAGTGG TGCGCCCTTT
     5341 CGGTCTGATA AGAGACACCG GCATACTCTG CGACATCGTA TAACGTTACT GGTTTCACAT
          GCCAGACTAT TCTCTGTGGC CGTATGAGAC GCTGTAGCAT ATTGCAATGA CCAAAGTGTA
     5401 TCACCACCCT GAATTGACTC TCTTCCGGGC GCTATCATGC CATACCGCGA AAGGTTTTGC
          AGTGGTGGGA CTTAACTGAG AGAAGGCCCG CGATAGTACG GTATGGCGCT TTCCAAAACG
     5461 GCCATTCGAT GGTGTCCGGG ATCTCGACGC TCTCCCTTAT GCGACTCCTG CATTAGGAAA
          CGGTAAGCTA CCACAGGCCC TAGAGCTGCG AGAGGGAATA CGCTGAGGAC GTAATCCTTT
     5521 TTAATACGAC TCACTATA
          AATTATGCTG AGTGATAT
```

Fig. 7₃

G144704 Cassette

A.

B.

C.

D.

G144704 cassette
1561 bp

| Fig. 9₁ |
|---|
| Fig. 9₂ |

Fig. 9

G144704 sequence attR1 and attR2

```
           SacI
           ~~~~~~
    1  GAGCTCGATC ACAAGTTTGT ACAAAAAAGC TGAACGAGAA ACGTAAAATG ATATAAATAT
       CTCGAGCTAG TGTTCAAACA TGTTTTTTCG ACTTGCTCTT TGCATTTTAC TATATTTATA

61  CAATATATTA AATTAGATTT TGCATAAAAA ACAGACTACA TAATACTGTA AAACACAACA
       GTTATATAAT TTAATCTAAA ACGTATTTTT TGTCTGATGT ATTATGACAT TTTGTGTTGT
                                            NotI
                                       ~~~~~~~~~~
  121  TATCCAGTCA CTATGGCGGC CGCCACGTTA AGGGATTTTG GTCATGATCA GCACGTGTTG
       ATAGGTCAGT GATACCGCCG GCGGTGCAAT TCCCTAAAAC CAGTACTAGT CGTGCACAAC

181  ACAATTAATC ATCGGCATAG TATATCGGCA TAGTATAATA CGACAAGGTG AGGAACTAAA
       TGTTAATTAG TAGCCGTATC ATATAGCCGT ATCATATTAT GCTGTTCCAC TCCTTGATTT
        NcoI
       ~~~~~~
           MetAlaLys LeuThrSer AlaValProVal LeuThrAla ArgAspVal AlaGlyAlaVal·
  241  CCATGGCCAA GTTGACCAGT GCCGTTCCGG TGCTCACCGC GCGCGACGTC GCCGGAGCGG
       GGTACCGGTT CAACTGGTCA CGGCAAGGCC ACGAGTGGCG CGCGCTGCAG CGGCCTCGCC

·VGluPheTrp ThrAspArg LeuGlyPheSer ArgAspPhe ValGluAsp AspPheAlaGly·
  301  TCGAGTTCTG GACCGACCGG CTCGGGTTCT CCCGGGACTT CGTGGAGGAC GACTTCGCCG
       AGCTCAAGAC CTGGCTGGCC GAGCCCAAGA GGGCCCTGAA GCACCTCCTG CTGAAGCGGC

·GValValArg AspAspVal ThrLeuPheIle SerAlaVal GlnAspGln ValValProAsp·
  361  GTGTGGTCCG GGACGACGTG ACCCTGTTCA TCAGCGCGGT CCAGGACCAG GTGGTGCCGG
       CACACCAGGC CCTGCTGCAC TGGGACAAGT AGTCGCGCCA GGTCCTGGTC CACCACGGCC

·AAsnThrLeu AlaTrpVal TrpValArgGly LeuAspGlu LeuTyrAla GluTrpSerGlu·
  421  ACAACACCCT GGCCTGGGTG TGGGTGCGCG GCCTGGACGA GCTGTACGCC GAGTGGTCGG
       TGTTGTGGGA CCGGACCCAC ACCCACGCGC CGGACCTGCT CGACATGCGG CTCACCAGCC

·GValValSer ThrAsnPhe ArgAspAlaSer GlyProAla MetThrGlu IleGlyGluGln·
  481  AGGTCGTGTC CACGAACTTC CGGGACGCCT CCGGGCCGGC CATGACCGAG ATCGGCGAGC
       TCCAGCACAG GTGCTTGAAG GCCCTGCGGA GGCCCGGCCG GTACTGGCTC TAGCCGCTCG
           BglI                                              ApaLI
           ~~~~~~~~~~                                        ~~~~~~
       ·GProTrpGly ArgGluPhe AlaLeuArgAsp ProAlaGly AsnCysVal HisPheValAla·
  541  AGCCGTGGGG GCGGGAGTTC GCCCTGCGCG ACCCGGCCGG CAACTGCGTG CACTTCGTGG
       TCGGCACCCC CGCCCTCAAG CGGGACGCGC TGGGCCGGCC GTTGACGCAC GTGAAGCACC

·AGluGluGln Asp***
  601  CCGAGGAGCA GGACTGATCA TGATGATATT ATTTTATCTT GTGCAATGTA ACATCAGAGA
       GGCTCCTCGT CCTGACTAGT ACTACTATAA TAAAATAGAA CACGTTACAT TGTAGTCTCT

661  TTTTGAGACA CGGGCCAGAG CTGCCAGGAA ACAGCTATGA CCATGTAATA CGACTCACTA
       AAAACTCTGT GCCCGGTCTC GACGGTCCTT TGTCGATACT GGTACATTAT GCTGAGTGAT

721  TAGGGGATAT CAGCTGGATG GCAAATAATG ATTTTATTTT GACTGATAGT GACCTGTTCG
       ATCCCCTATA GTCGACCTAC CGTTTATTAC TAAAATAAAA CTGACTATCA CTGGACAAGC
                AgeI
                ~~~~~~~
  781  TTGCAACACC GGTGCTAGCG TATACCCGAA GTATGTCAAA AGAGGTGTG CTATGAAGCA
       AACGTTGTGG CCACGATCGC ATATGGGCTT CATACAGTTT TCTCCACAC GATACTTCGT

841  GCGTATTACA GTGACAGTTG ACAGCGACAG CTATCAGTTG CTCAAGGCAT ATATGATGTC
       CGCATAATGT CACTGTCAAC TGTCGCTGTC GATAGTCAAC GAGTTCCGTA TATACTACAG

901  AATATCTCCG GTCTGGTAAG CACAACCATG CAGAATGAAG CCCGTCGTCT GCGTGCCGAA
       TTATAGAGGC CAGACCATTC GTGTTGGTAC GTCTTACTTC GGGCAGCAGA CGCACGGCTT

961  CGCTGGAAAG CGGAAAATCA GGAAGGGATG GCTGAGGTCG CCCGGTTTAT TGAAATGAAC
       GCGACCTTTC GCCTTTTAGT CCTTCCCTAC CGACTCCAGC GGGCCAAATA ACTTTACTTG
```

Fig. 9₁

```
                                                         MetGln  PheLysValTyr ThrTyrLys·
1021  GGCTCTTTTG CTGACGAGAA CAGGGACTGG TGAAATGCAG TTTAAGGTTT ACACCTATAA
      CCGAGAAAAC GACTGCTCTT GTCCCTGACC ACTTTACGTC AAATTCCAAA TGTGGATATT

·ArgGluSer ArgTyrArgLeu PheValAsp  ValGlnSer  AspIleIleAsp ThrProGly·
1081  AAGAGAGAGC CGTTATCGTC  TGTTTGTGGA TGTACAGAGT GATATTATTG  ACACGCCCGG
      TTCTCTCTCG GCAATAGCAG  ACAAACACCT ACATGTCTCA CTATAATAAC  TGTGCGGGCC
                                                   ApaLI
                                                   ~~~~~~~
      ·ArgArgMet ValIleProLeu AlaSerAla  ArgLeuLeu  SerAspLysVal SerArgGlu·
1141  GCGACGGATG GTGATCCCCC  TGGCCAGTGC ACGTCTGCTG TCAGATAAAG  TCTCCCGTGA
      CGCTGCCTAC CACTAGGGGG  ACCGGTCACG TGCAGACGAC AGTCTATTTC  AGAGGGCACT

·LeuTyrPro ValValHisIle GlyAspGlu  SerTrpArg  MetMetThrThr AspMetAla·
1201  ACTTTACCCG GTGGTGCATA  TCGGGGATGA AAGCTGGCGC ATGATGACCA  CCGATATGGC
      TGAAATGGGC CACCACGTAT  AGCCCCTACT TTCGACCGCG TACTACTGGT  GGCTATACCG

·SerValPro ValSerValIle GlyGluGlu  ValAlaAsp  LeuSerArgArg GluAsnAsp·
1261  CAGTGTGCCG GTCTCCGTTA  TCGGGGAAGA AGTGGCTGAT CTCAGCCGCC  GCGAAAATGA
      GTCACACGGC CAGAGGCAAT  AGCCCCTTCT TCACCGACTA GAGTCGGCGG  CGCTTTTACT

·IleLysAsn AlaIleAsnLeu MetPheTrp  GlyIle***
1321  CATCAAAAAC GCCATTAACC  TGATGTTCTG GGGAATATAA ATGTCAGGCT CCCTTATACA
      GTAGTTTTTG CGGTAATTGG  ACTACAAGAC CCCTTATATT TACAGTCCGA GGGAATATGT
              PstI
              ~~~~~~~
1381  CAGCCAGTCT GCAGGTCGAC CATAGTGACT GGATATGTTG TGTTTACAG TATTATGTAG
      GTCGGTCAGA CGTCCAGCTG GTATCACTGA CCTATACAAC ACAAATGTC ATAATACATC

1441  TCTGTTTTTT ATGCAAAATC TAATTTAATA TATTGATATT TATATCATTT TACGTTTCTC
      AGACAAAAAA TACGTTTTAG ATTAAATTAT ATAACTATAA ATATAGTAAA ATGCAAAGAG
                                                                HindIII
                                                                ~~~~~
1501  GTTCAGCTTT CTTGTACAAA GTGGTGATAA TTAATTAAGA TCAGATCCGG CTGCTAAGCT
      CAAGTCGAAA GAACATGTTT CACCACTATT AATTAATTCT AGTCTAGGCC GACGATTCGA HindIII
      ~
1561  T
      A
```

Fig. 9$_2$

| Fig. 17₁ |
|---|
| Fig. 17₂ |
| Fig. 17₃ |

Fig. 17 pDEST-CM1 sequence

```
   1  GGGGAATTGT GAGCGGATAA CAATTCCCCT GTAGAAATAA TTTTGTTTAA CTTTAATAAG
      CCCCTTAACA CTCGCCTATT GTTAAGGGGA CATCTTTATT AAAACAAATT GAAATTATTC
                                                                 SacI
                                                                 ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGGACCAT GATTACGCCA AGCTATCAAC TTTGTATAGA AAAGTTGAAC GAGAAACGTA
      GAGCCTGGTA CTAATGCGGT TCGATAGTTG AAACATATCT TTTCAACTTG CTCTTTGCAT
 181  AAATGATATA AATATCAATA TATTAAATTA GATTTTGCAT AAAAAACAGA CTACATAATA
      TTTACTATAT TTATAGTTAT ATAATTTAAT CTAAAACGTA TTTTTTGTCT GATGTATTAT
                                                 PstI
                                                 ~~~~~~~
 241  CTGTAAAACA CAACATATCC AGTCACTATG GTCGACCTGC AGACTGGCTG TGTATAAGGG
      GACATTTTGT GTTGTATAGG TCAGTGATAC CAGCTGGACG TCTGACCGAC ACATATTCCC
 301  AGCCTGACAT TTATATTCCC CAGAACATCA GGTTAATGGC GTTTTTGATG TCATTTTCGC
      TCGGACTGTA AATATAAGGG GTCTTGTAGT CCAATTACCG CAAAAACTAC AGTAAAAGCG
 361  GGTGGCTGAG ATCAGCCACT TCTTCCCCGA TAACGGAGAC CGGCACACTG GCCATATCGG
      CCACCGACTC TAGTCGGTGA AGAAGGGGCT ATTGCCTCTG GCCGTGTGAC CGGTATAGCC
 421  TGGTCATCAT GCGCCAGCTT TCATCCCCGA TATGCACCAC CGGGTAAAGT TCACGGGGGA
      ACCAGTAGTA CGCGGTCGAA AGTAGGGGCT ATACGTGGTG GCCCATTTCA AGTGCCCCCT
                                                        XmaI
                                                        ~~~~~~~
                                                        SmaI
                                                        ~~~~~~~
 481  CTTTATCTGA CAGCAGACGT GCACTGGCCA GGGGGATCAC CATCCGTCGC CCGGGCGTGT
      GAAATAGACT GTCGTCTGCA CGTGACCGGT CCCCCTAGTG GTAGGCAGCG GGCCCGCACA
 541  CAATAATATC ACTCTGTACA TCCACAAACA GACGATAACG GCTCTCTCTT TTATAGGTGT
      GTTATTATAG TGAGACATGT AGGTGTTTGT CTGCTATTGC CGAGAGAGAA AATATCCACA
 601  AAACCTTAAA CTGCATTTCA CCAGCCCCTG TTCTCGTCGG CAAAAGAGCC GTTCATTTCA
      TTTGGAATTT GACGTAAAGT GGTCGGGGAC AAGAGCAGCC GTTTTCTCGG CAAGTAAAGT
 661  ATAAACCGGG CGACCTCAGC CATCCCTTCC TGATTTTCCG CTTTCCAGCG TTCGGCACGC
      TATTTGGCCC GCTGGAGTCG GTAGGGAAGG ACTAAAAGGC GAAAGGTCGC AAGCCGTGCG
 721  AGACGACGGG CTTCATTCTG CATGGTTGTG CTTACCGAAC CGGAGATATT GACATCTCAT
      TCTGCTGCCC GAAGTAAGAC GTACCAACAC GAATGGCTTG GCCTCTATAA CTGTAGTATA
 781  ATGCCTTGAG CAACTGATAG CTGTCGCTGT CAACTGTCAC TGTAATACGC TGCTTCATAG
      TACGGAACTC GTTGACTATC GACAGCGACA GTTGACAGTG ACATTATGCG ACGAAGTATC
 841  CATACCTCTT TTTGACATAC TTCGGGTATA CATATCAGTA TATATTCTTA TACCGCAAAA
      GTATGGAGAA AAACTGTATG AAGCCCATAT GTATAGTCAT ATATAAGAAT ATGGCGTTTT
 901  ATCAGCGCGC AAATACGCAT ACTGTTATCT GGCTTTTAGT AAGCCGGATC CTCTAGATTA
      TAGTCGCGCG TTTATGCGTA TGACAATAGA CCGAAAATCA TTCGGCCTAG GAGATCTAAT
 961  CGCCCCGCCC TGCCACTCAT CGCAGTACTG TTGTAATTCA TTAAGCATTC TGCCGACATG
      GCGGGGCGGG ACGGTGAGTA GCGTCATGAC AACATTAAGT AATTCGTAAG ACGGCTGTAC
1021  GAAGCCATCA CAAACGGCAT GATGAACCTG AATCGCCAGC GGCATCACCA CCTTGTCGCC
      CTTCGGTAGT GTTTGCCGTA CTACTTGGAC TTAGCGGTCG CCGTAGTCGT GGAACAGCGG
1081  TTGCGTATAA TATTTGCCCA TGGTGAAAAC GGGGGCGAAG AAGTTGTCCA TATTGGCCAC
      AACGCATATT ATAAACGGGT ACCACTTTTG CCCCCGCTTC TTCAACAGGT ATAACCGGTG
1141  GTTTAAATCA AAACTGGTGA AACTCACCCA GGGATTGGCT GAGACGAAAA ACATATTCTC
      CAAATTTAGT TTTGACCACT TTGAGTGGGT CCCTAACCGA CTCTGCTTTT TGTATAAGAG
1201  AATAAACCCT TTAGGGAAAT AGGCCAGGTT TTCACCGTAA CACGCCACAT CTTGCGAATA
      TTATTTGGGA AATCCCTTTA TCCGGTCCAA AAGTGGCATT GTGCGGTGTA GAACGCTTAT
1261  TATGTGTAGA AACTGCCGGA AATCGTCGTG GTATTCACTC CAGAGCGATG AAAACGTTTC
      ATACACATCT TTGACGGCCT TTAGCAGCAC CATAAGTGAG GTCTCGCTAC TTTTGCAAAG
1321  AGTTTGCTCA TGGAAAACGG TGTAACAAGG GTGAACACTA TCCCATATCA CCAGCTCACC
      TCAAACGAGT ACCTTTTGCC ACATTGTTCC CACTTGTGAT AGGGTATAGT GGTCGAGTGG
1381  GTCTTTCATT GCCATACGGA ATTCCGGATG AGCATTCATC AGGCGGGCAA GAATGTGAAT
      CAGAAAGTAA CGGTATGCCT TAAGGCCTAC TCGTAAGTAG TCCGCCCGTT CTTACACTTA
1441  AAAGGCCGGA TAAAACTTGT GCTTATTTTT CTTTACGGTC TTTAAAAAGG CCGTAATATC
      TTTCCGGCCT ATTTTGAACA CGAATAAAAA GAAATGCCAG AAATTTTTCC GGCATTATAG
1501  CAGCTGAACG GTCTGGTTAT AGGTACATTG AGCAACTGAC TGAAATGCCT CAAAATGTTC
      GTCGACTTGC CAGACCAATA TCCATGTAAC TCGTTGACTG ACTTTACGGA GTTTTACAAG
1561  TTTACGATGC CATTGGGATA TATCAACGGT GGTATATCCA GTGATTTTTT CTCCATTTTT
      AAATGCTACG GTAACCCTAT ATAGTTGCCA CCATATAGGT CACTAAAAAA GAGGTAAAA
1621  AGCTTCCTTA GCTCCTGAAA ATCTCGACGG ATCCTAACTC AAAATCCACA CATTATACGA
      TCGAAGGAAT CGAGGACTTT TAGAGCTGCC TAGGATTGAG TTTTAGGTGT GTAATATGCT
1681  GCCGGAAGCA TAAAGTGTAA AGCCTGGGGT GCCTAATGCG GCCGCCATA GTGACTGGAT
      CGGCCTTCGT ATTTCACATT TCGGACCCCC ACGGATTACG CCGGCGGTAT CACTGACCTA
```

Fig. 17₁

1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTTAGATTA AATTATATAA
1801 GATATTTATA TCATTTTACG TTTCTCGTTC AACTTTATTA TACATAGTTG ATAATTCACT
     CTATAAATAT AGTAAAATGC AAAGAGCAAG TTGAAATAAT ATGTATCAAC TATTAAGTGA
1861 GGCCGTCGTT TTACAACGTC GTGACTGGGA AAACCCTGGC GTTACCCAAC TTAATCGCCT
     CCGGCAGCAA AATGTTGCAG CACTGACCCT TTTGGGACCG CAATGGGTTG AATTAGCGGA
                 HindIII
                 ~~~~~~~
1921 TGCAGCACAA GCTTGCGGCC GCATAATGCT TAAGTCGAAC AGAAAGTAAT CGTATTGTAC
     ACGTCGTGTT CGAACGCCGG CGTATTACGA ATTCAGCTTG TCTTTCATTA GCATAACATG
1981 ACGGCCGCAT AATCGAAATT AATACGACTC ACTATAGGGG AATTGTGAGC GGATAACAAT
     TGCCGGCGTA TTAGCTTTAA TTATGCTGAG TGATATCCCC TTAACACTCG CCTATTGTTA
2041 TCCCCATCTT AGTATATTAG TTAAGTATAA GAAGGAGATA TACATATGGC AGATCTCAAT
     AGGGGTAGAA TCATATAATC AATTCATATT CTTCCTCTAT ATGTATACCG TCTAGAGTTA
2101 TGGATATCGG CCGGCCACGC GATCGCTGAC GTCGGTACCC TCGAGTCTGG TAAAGAAACC
     ACCTATAGCC GGCCGGTGCG CTAGCGACTG CAGCCATGGG AGCTCAGACC ATTTCTTTGG
                                                                    AvrII
                                                                    ~~
2161 GCTGCTGCGA AATTTGAACG CCAGCACATG GACTCGTCTA CTAGCGCAGC TTAATTAACC
     CGACGACGCT TTAAACTTGC GGTCGTGTAC CTGAGCAGAT GATCGCGTCG AATTAATTGG
     AvrII
     ~~~~
2221 TAGGCTGCTG CCACCGCTGA GCAATAACTA GCATAACCCC TTGGGGCCTC TAAACGGGTC
     ATCCGACGAC GGTGGCGACT CGTTATTGAT CGTATTGGGG AACCCCGGAG ATTTGCCCAG
2281 TTGAGGGGTT TTTTGCTGAA ACCTCAGGCA TTTGAGAAGC ACACGGTCAC ACTGCTTCCG
     AACTCCCCAA AAAACGACTT TGGAGTCCGT AAACTCTTCG TGTGCCAGTG TGACGAAGGC
2341 GTAGTCAATA AACCGGTAAA CCAGCAATAG ACATAAGCGG CTATTTAACG ACCCTGCCCT
     CATCAGTTAT TTGGCCATTT GGTCGTTATC TGTATTCGCC GATAAATTGC TGGGACGGGA
2401 GAACCGACGA CCGGGTCATC GTGGCCGGAT CTTGCGGCCC CTCGGCTTGA ACGAATTGTT
     CTTGGCTGCT GGCCCAGTAG CACCGGCCTA GAACGCCGGG GAGCCGAACT TGCTTAACAA
2461 AGACATTATT TGCCGACTAC CTTGGTGATC TCGCCTTTCA CGTAGTGGAC AAATTCTTCC
     TCTGTAATAA ACGGCTGATG GAACCACTAG AGCGGAAAGT GCATCACCTG TTTAAGAAGG
2521 AACTGATCTG CGCGCGAGGC CAAGCGATCT TCTTCTTGTC CAAGATAAGC CTGTCTAGCT
     TTGACTAGAC GCGCGCTCCG GTTCGCTAGA AGAAGAACAG GTTCTATTCG GACAGATCGA
2581 TCAAGTATGA CGGGCTGATA CTGGGCCGGC AGGCGCTCCA TTGCCCAGTC GGCAGCGACA
     AGTTCATACT GCCCGACTAT GACCCGGCCG TCCGCGAGGT AACGGGTCAG CCGTGCTGT
2641 TCCTTCGGCG CGATTTGCC GGTTACTGCG CTGTACCAAA TGCGGGACAA CGTAAGCACT
     AGGAAGCCGC GCTAAAACGG CCAATGACGC GACATGGTTT ACGCCCTGTT GCATTCGTGA
2701 ACATTTCGCT CATCGCCAGC CCAGTCGGGC GGCGAGTTCC ATAGCGTTAA GGTTTCATTT
     TGTAAAGCGA GTAGCGGTCG GGTCAGCCCG CCGCTCAAGG TATCGCAATT CCAAAGTAAA
2761 AGCGCCTCAA ATAGATCCTG TTCAGGAACC GGATCAAAGA GTTCCTCCGC CGCTGGACCT
     TCGCGGAGTT TATCTAGGAC AAGTCCTTGG CCTAGTTTCT CAAGGAGGCG GCGACCTGGA
2821 ACCAAGGCAA CGCTATGTTC TCTTGCTTTT GTCAGCAAGA TAGCCAGATC AATGTCGATC
     TGGTTCCGTT GCGATACAAG AGAACGAAAA CAGTCGTTCT ATCGGTCTAG TTACAGCTAG
2881 GTGGCTGGCT CGAAGATACC TGCAAGAATG TCATTGCGCT GCCATTCTCC AAAATTGCAGT
     CACCGACCGA GCTTCTATGG ACGTTCTTAC AGTAACGCGA CGGTAAGAGG TTTAACGTCA
2941 TCGCGCTTAG CTGGATAACG CCACGAACTA ATGTCGTCGT GCACACAAT GGTGACTTCT
     AGCGCGAATC GACCTATTGC GGTGCCTTAC TACAGCAGCA CGTGTTGTTA CCACTGAAGA
3001 ACAGCGCGGA GAATCTCGCT CTCTCCAGGG GAAGCCGAAG TTTCCAAAAG GTCGTTGATC
     TGTCGCGCCT CTTAGAGCGA GAGAGGTCCC CTTCGGCTTC AAAGGTTTTC CAGCAACTAG
3061 AAAGCTCGCC GCGTTGTTTC ATCAAGCTTT ACGGTCACCG TAACCAGCAA ATCAATATCA
     TTTCGAGCGG CGCAACAAAG TAGTTCGAAA TGCCAGTGGC ATTGGTCGTT TAGTTATAGT
3121 CTGTGTGGCT TCAGGCCGCC ATCCACTGCG GAGCCGTACA AATGTACGGC GCGACAACGTC
     GACACACCGA AGTCCGGCGG TAGGTGACGC CTCGGCATGT TTACATGCCG GTCGTTGCAG
3181 GGTTCGAGAT GGCGCTCGAT GACGCCAACT ACCTCTGATA GTTGAGTCGA TACTTCGGCG
     CCAAGCTCTA CCGCGAGCTA CTGCGGTTGA TGGAGACTAT CAACTCAGCT ATGAAGCCGC
3241 ATCACCGCTT CCCTCATACT CTTCCTTTTT CAATATTATT GAAGCATTTA TCAGGGTTAT
     TAGTGGCGAA GGGAGTATGA GAAGGAAAAA GTTATAATAA CTTCGTAAAT AGTCCCAATA
3301 TGTCTCATGA GCGGATACAT ATTTGAATGT ATTTAGAAAA ATAAACAAAT AGCTAGCTCA
     ACAGAGTACT CGCCTATGTA TAAACTTACA TAAATCTTTT TATTTGTTTA TCGATCGAGT
3361 CTCGGTCGCT ACGCTCCGGG CGTGAGACTG CGGCGGCGC TGCGGACACA TACAAAGTTA
     GAGCCAGCGA TGCGAGGCCC GCACTCTGAC GCCGCCCGC ACGCCTGTGT ATGTTTCAAT
3421 CCCACAGATT CCGTGGATAA GCAGGGGACT AACATGTGAG GCAAAACAGC AGGGCCGCGC
     GGGTGTCTAA GGCACCTATT CGTCCCCTGA TTGTACACTC CGTTTTGTCG TCCCGGCGCG
3481 CGGTGGCGTT TTTCCATAGG CTCCGCCCTC CTGCCAGAGT TCACATAAAC AGACGCTTTT
     GCCACCGCAA AAAGGTATCC GAGGCGGGAG GACGGTCTCA AGTGTATTTG TCTGCGAAAA
3541 CCGGTGCATC TGTGGGAGCC GTGAGGCTCA ACCATGAATC TGACAGTACG GCGAAACCC
     GGCCACGTAG ACACCCTCGG CACTCCGAGT TGGTACTTAG ACTGTCATGC CGCTTTGGG
3601 GACAGGACTT AAAGATCCCC ACCGTTTCCG GCGGGTCGCT CCCTCTTGCG CTCTCCTGTT
     CTGTCCTGAA TTTCTAGGGG TGGCAAAGGC CGCCCAGCGA GGGAGAACGC GAGAGGACAA
3661 CCGACCCTGC CGTTTACCGG ATACCTGTTC CGCCTTTCTC CCTTACGGGA AGTGTGGCGC

```
            GGCTGGGACG GCAAATGGCC TATGGACAAG GCGGAAAGAG GGAATGCCCT TCACACCGCG
3721   TTTCTCATAG CTCACACACT GGTATCTCGG CTCGGTGTAG GTCGTTCGCT CCAAGCTGGG
       AAAGAGTATC GAGTGTGTGA CCATAGAGCC GAGCCACATC CAGCAAGCGA GGTTCGACCC
3781   CTGTAAGCAA GAACTCCCCG TTCAGCCCGA CTGCTGCGCC TTATCCGGTA ACTGTTCACT
       GACATTCGTT CTTGAGGGGC AAGTCGGGCT GACGACGCGG AATAGGCCAT TGACAAGTGA
3841   TGAGTCCAAC CCGGAAAAGC ACGGTAAAAC GCCACTGGCA GCAGCCATTG GTAACTGGGA
       ACTCAGGTTG GGCCTTTTCG TGCCATTTTG CGGTGACCGT CGTCGGTAAC CATTGACCCT
3901   GTTCGCAGAG GATTTGTTTA GCTAAACACG CGGTTGCTCT TGAAGTGTGC GCCAAAGTCC
       CAAGCGTCTC CTAAACAAAT CGATTTGTGC GCCAACGAGA ACTTCACACG CGGTTTCAGG
3961   GGCTACACTG GAAGGACAGA TTTGGTTGCT GTGCTCTGCG AAAGCCAGTT ACCACGGTTA
       CCGATGTGAC CTTCCTGTCT AAACCAACGA CACGAGACGC TTTCGGTCAA TGGTGCCAAT
4021   AGCAGTTCCC CAACTGACTT AACCTTCGAT CAAACCACCT CCCCAGGTGG TTTTTTCGTT
       TCGTCAAGGG GTTGACTGAA TTGGAAGCTA GTTTGGTGGA GGGGTCCACC AAAAAAGCAA
4081   TACAGGGCAA AAGATTACGC GCAGAAAAAA AGGATCTCAA GAAGATCCTT TGATCTTTTC
       ATGTCCCGTT TTCTAATGCG CGTCTTTTTT TCCTAGAGTT CTTCTAGGAA ACTAGAAAAG
4141   TACTGAACCG CTCTAGATTT CAGTGCAATT TATCTCTTCA AATGTAGCAC CTGAAGTCAG
       ATGACTTGGC GAGATCTAAA GTCACGTTAA ATAGAGAAGT TTACATCGTG GACTTCAGTC
4201   CCCCATACGA TATAAGTTGT AATTCTCATG TTAGTCATGC CCCGCGCCCA CCGGAAGGAG
       GGGGTATGCT ATATTCAACA TTAAGAGTAC AATCAGTACG GGGCGCGGGT GGCCTTCCTC
4261   CTGACTGGGT TGAAGGCTCT CAAGGGCATC GGTCGAGATC CCGGTGCCTA ATGAGTGAGC
       GACTGACCCA ACTTCCGAGA GTTCCCGTAG CCAGCTCTAG GCCACGGAT TACTCACTCG
4321   TAACTTACAT TAATTGCGTT GCGCTCACTG CCCGCTTTCC AGTCGGGAAA CCTGTCGTGC
       ATTGAATGTA ATTAACGCAA CGCGAGTGAC GGGCGAAAGG TCAGCCCTTT GGACAGCACG
4381   CAGCTGCATT AATGAATCGG CCAACGCGCG GGGAGAGGCG GTTTGCGTAT TGGGCGCCAG
       GTCGACGTAA TTACTTAGCC GGTTGCGCGC CCCTCTCCGC CAAACGCATA ACCCGCGGTC
4441   GGTGGTTTTT CTTTTCACCA GTGAGACGGG CAACAGCTGA TTGCCCTTCA CCGCCTGGCC
       CCACCAAAAA GAAAAGTGGT CACTCTGCCC GTTGTCGACT AACGGGAAGT GGCGGACCGG
4501   CTGAGAGAGT TGCAGCAAGC GGTCCACGCT GGTTTGCCCC AGCAGGCGAA AATCCTGTTT
       GACTCTCTCA ACGTCGTTCG CCAGGTGCGA CCAAACGGGG TCGTCCGCTT TTAGGACAAA
4561   GATGGTGGTT AACGGCGGGA TATAACATGA GCTGTCTTCG GTATCGTCGT ATCCCACTAC
       CTACCACCAA TTGCCGCCCT ATATTGTACT CGACAGAAGC CATAGCAGCA TAGGGTGATG
4621   CGAGATGTCC GCACCAACGC GCAGCCCGGA CTCGGTAATG GCGCGCATTG CGCCCAGCGC
       GCTCTACAGG CGTGGTTGCG CGTCGGGCCT GAGCCATTAC CGCGCGTAAC GCGGGTCGCG
4681   CATCTGATCG TTGGCAACCA GCATCGCAGT GGGAACGATG CCCTCATTCA GCATTTGCAT
       GTAGACTAGC AACCGTTGGT CGTAGCGTCA CCCTTGCTAC GGGAGTAAGT CGTAAACGTA
4741   GGTTTGTTGA AAACCGGACA TGGCACTCCA GTCGCTTCC CGTTCCGCTA TCGGCTGAAT
       CCAAACAACT TTTGGCCTGT ACCGTGAGGT CAGCGGAAGG GCAAGGCGAT AGCCGACTTA
4801   TTGATTGCGA GTGAGATATT TATGCCAGCC AGCCAGACGC AGACGCGCCG AGACAGAACT
       AACTAACGCT CACTCTATAA ATACGGTCGG TCGGTCTGCG TCTGCGCGGC TCTGTCTTGA
4861   TAATGGGCCC GCTAACAGCG CGATTTGCTG GTGACCCAAT GCGACCAGAT GCTCCACGCC
       ATTACCCGGG CGATTGTCGC GCTAAACGAC CACTGGGTTA CGCTGGTCTA CGAGGTGCGG
4921   CAGTCGCGTA CCGTCTTCAT GGGAGAAAAT AATACTGTTG ATGGGTGTCT GGTCAGAGAC
       GTCAGCGCAT GGCAGAAGTA CCCTCTTTTA TTATGACAAC TACCCACAGA CCAGTCTCTG
4981   ATCAAGAAAT AACGCCGGAA CATTAGTGCA GGCAGCTTCC ACAGCAATGG CATCCTGGTC
       TAGTTCTTTA TTGCGGCCTT GTAATCACGT CCGTCGAAGG TGTCGTTACC GTAGGACCAG
5041   ATCCAGCGGA TAGTTAATGA TCAGCCCACT GACGCGTTGC GCGAGAAGAT TGTGCACCGC
       TAGGTCGCCT ATCAATTACT AGTCGGGTGA CTGCGCAACG CGCTCTTCTA ACACGTGGCG
5101   CGCTTTACAG GCTTCGACGC CGCTTCGTTC TACCATCGAC ACCACCACGC TGGCACCCAG
       GCGAAATGTC CGAAGCTGCG GCGAAGCAAG ATGGTAGCTG TGGTGGTGCG ACCGTGGGTC
5161   TTGATCGGCG CGAGATTTAA TCGCCGCGAC AATTTGCGAC GGCGCGTGCA GGGCCAGACT
       AACTAGCCGC GCTCTAAATT AGCGGCGCTG TTAAACGCTG CCGCGCACGT CCCGGTCTGA
5221   GGAGGTGGCA ACGCCAATCA GCAACGACTG TTTGCCCGCC AGTTGTTGTG CCACGCGGTT
       CCTCCACCGT TGCGGTTAGT CGTTGCTGAC AAACGGGCGG TCAACAACAC GGTGCGCCAA
5281   GGGAATGTAA TTCAGCTCCG CCATCGCCGC TTCCACTTTT TCCCGCGTTT TCGCAGAAAC
       CCCTTACATT AAGTCGAGGC GGTAGCGGCG AAGGTGAAAA AGGGCGCAAA AGCGTCTTTG
5341   GTGGCTGGCC TGGTTCACCA CGCGGGAAAC GGTCTGATAA GAGACACCGG CATACTCTGC
       CACCGACCGG ACCAAGTGGT GCGCCCTTTG CCAGACTATT CTCTGTGGCC GTATGAGACG
5401   GACATCGTAT AACGTTACTG GTTTCACATT CACCACCCTG AATTGACTCT CTTCCGGGCG
       CTGTAGCATA TTGCAATGAC CAAAGTGTAA GTGGTGGGAC TTAACTGAGA GAAGGCCCGC
5461   CTATCATGCC ATACCGCGAA AGGTTTTGCG CCATTCGATG GTGTCCGGGA TCTCGACGCT
       GATAGTACGG TATGGCGCTT TCCAAAACGC GGTAAGCTAC CACAGGCCCT AGAGCTGCGA
5521   CTCCCTTATG CGACTCCTGC ATTAGGAAAT TAATACGACT CACTATA
       GAGGGAATAC GCTGAGGACG TAATCCTTTA ATTATGCTGA GTGATAT
```

Fig. 17₃

| Fig. 19₁ |
|---|
| Fig. 19₂ |
| Fig. 19₃ |

Fig. 19 pDEST-CM2 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                              EcoRI
                                                              ~~~~~~
            NcoI                              BamHI        SacI
            ~~~~~~~                           ~~~~~~~      ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                             PstI
                                             ~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
                                                     XmaI
                                                     ~~~~~~~
                                                     SmaI
                                                     ~~~~~~~
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG CTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
                                                                BamHI
                                                                ~~~~~~~
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
                       NcoI
                       ~~~~~~~
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TAGGGAAAT AGGCAGGTT TCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
                                                      EcoRI
                                                      ~~~~~~~
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT CTCCATTTT
```

Fig. 19₁

```
                AAATGCTACG GTAACCCTAT ATAGTTGCCA CCATATAGGT CACTAAAAAA AGAGGTAAAA
                                                BamHI
                                                ~~~~~~~
         1621   AGCTTCCTTA GCTCCTGAAA ATCTCGACGG ATCCTAACTC AAAATCCACA CATTATACGA
                TCGAAGGAAT CGAGGACTTT TAGAGCTGCC TAGGATTGAG TTTTAGGTGT GTAATATGCT
         1681   GCCGGAAGCA TAAAGTGTAA AGCCTGGGGG TGCCTAATGC GGCCGCCATA GTGACTGGAT
                CGGCCTTCGT ATTTCACATT TCGGACCCCC ACGGATTACG CCGGCGGTAT CACTGACCTA
         1741   ATGTTGTGTT TTACAGTATT ATGTAGTCTG TTTTTTATGC AAAATCTAAT TTAATATATT
                TACAACACAA AATGTCATAA TACATCAGAC AAAAAATACG TTTTAGATTA AATTATATAA
         1801   GATATTTATA TCATTTTACG TTTCTCGTTC AACTTTATTA TACATAGTTG ATAATTCACT
                CTATAAATAT AGTAAAATGC AAAGAGCAAG TTGAAATAAT ATGTATCAAC TATTAAGTGA
         1861   GGCCGTCGTT TTACAACGTC GTGACTGGGA AAACCCTGGC GTTACCCAAC TTAATCGCCT
                CCGGCAGCAA AATGTTGCAG CACTGACCCT TTTGGGACCG CAATGGGTTG AATTAGCGGA
                         HindIII
                         ~~~~~~~
         1921   TGCAGCACAA GCTTGCGGCC GCATAATGCT TAAGTCGAAC AGAAAGTAAT CGTATTGTAC
                ACGTCGTGTT CGAACGCCGG CGTATTACGA ATTCAGCTTG TCTTTCATTA GCATAACATG
         1981   ACGGCCGCAT AATCGAAATT AATACGACTC ACTATAGGGG AATTGTGAGC GGATAACAAT
                TGCCGGCGTA TTAGCTTTAA TTATGCTGAG TGATATCCCC TTAACACTCG CCTATTGTTA
         2041   TCCCCATCTT AGTATATTAG TTAAGTATAA GAAGGAGATA TACATATGGC AGATCTCAAT
                AGGGGTAGAA TCATATAATC AATTCATATT CTTCCTCTAT ATGTATACCG TCTAGAGTTA
         2101   TGGATATCGG CCGGCCACGC GATCGCTGAC GTCGGTACCC TCGAGTCTGG TAAAGAAACC
                ACCTATAGCC GGCCGGTGCG CTAGCGACTG CAGCCATGGG AGCTCAGACC ATTTCTTTGG
         2161   GCTGCTGCGA AATTTGAACG CCAGCACATG GACTCGTCTA CTAGCGCAGC TTAATTAACC
                CGACGACGCT TTAAACTTGC GGTCGTGTAC CTGAGCAGAT GATCGCGTCG AATTAATTGG
         2221   TAGGCTGCTG CCACCGCTGA GCAATAACTA GCATAACCCC TTGGGGCCTC TAAACGGGTC
                ATCCGACGAC GGTGGCGACT CGTTATTGAT CGTATTGGGG AACCCCGGAG ATTTGCCCAG
         2281   TTGAGGGGTT TTTTGCTGAA ACCTCAGGCA TTTGAGAAGC ACACGGTCAC ACTGCTTCCG
                AACTCCCCAA AAAACGACTT GGAGTCCGT AAACTCTTCG TGTGCCAGTG TGACGAAGGC
         2341   GTAGTCAATA AACCGGTAAA CCAGCAATAG ACATAAGCGG CTATTTAACG ACCCTGCCCT
                CATCAGTTAT TTGGCCATTT GGTCGTTATC TGTATTCGCC GATAAATTGC TGGGACGGGA
         2401   GAACCGACGA CAAGCTGACG ACCGGGTCTC CGCAAGTGGC ACTTTTCGGG GAAATGTGCG
                CTTGGCTGCT GTTCGACTGC TGGCCCAGAG GCGTTCACCG TGAAAAGCCC CTTTACACGC
         2461   CGGAACCCCT ATTTGTTTAT TTTTCTAAAT ACATTCAAAT ATGTATCGC TCATGAATTA
                GCCTTGGGGA TAAACAAATA AAAAGATTTA TGTAAGTTTA TACATAGGCG AGTACTTAAT
         2521   ATTCTTAGAA AAACTCATCG AGCATCAAAT GAAACTGCAA TTTATTCATA TCAGGATTAT
                TAAGAATCTT TTTGAGTAGC TCGTAGTTTA CTTTGACGTT AAATAAGTAT AGTCCTAATA
         2581   CAATACCATA TTTTTGAAAA AGCCGTTTCT GTAATGAAGG AGAAAACTCA CCGAGGCAGT
                GTTATGGTAT AAAAACTTTT TCGGCAAAGA CATTACTTCC TCTTTTGAGT GGCTCCGTCA
         2641   TCCATAGGAT GGCAAGATCC TGGTATCGGT CTGCGATTCC GACTCGTCCA ACATCAATAC
                AGGTATCCTA CCGTTCTAGG ACCATAGCCA GACGCTAAGG CTGAGCAGGT TGTAGTTATG
         2701   AACCTATTAA TTTCCCCTCG TCAAAAATAA GGTTATCAAG TGAGAAATCA CCATGAGTGA
                TTGGATAATT AAAGGGGAGC AGTTTTTATT CCAATAGTTC ACTCTTTAGT GGTACTCACT
         2761   CGACTGAATC CGGTGAGAAT GGCAAAAGTT TATGCATTTC TTTCCAGACT TGTTCAACAG
                GCTGACTTAG GCCACTCTTA CCGTTTTCAA ATACGTAAAG AAAGGTCTGA ACAAGTTGTC
         2821   GCCAGCCATT ACGCTCGTCA TCAAAATCAC TCGCATCAAC CAAACCGTTA TTCATTCGTG
                CGGTCGGTAA TGCGAGCAGT AGTTTTAGTG AGCGTAGTTG GTTTGGCAAT AAGTAAGCAC
         2881   ATTGCGCCTG AGCGAGACGA AATACGCGGT CGCTGTTAAA AGGACAATTA CAAACAGGAA
                TAACGCGGAC TCGCTCTGCT TTATGCGCCA GCGACAATTT TCCTGTTAAT GTTTGTCCTT
         2941   TCGAATGCAA CCGGCGCAGG AACACTGCCA GCGCATCAAC AATATTTTCA CCTGAATCAG
                AGCTTACGTT GGCCGCGTCC TTGTGACGGT CGCGTAGTTG TTATAAAAGT GGACTTAGTC
                                                                          XmaI
                                                                        ~~~~~~
                                                                          SmaI
                                                                        ~~~~~~
         3001   GATATTCTTC TAATACCTGG AATGCTGTTT TCCCGGGGAT CGCAGTGGTG AGTAACCATG
                CTATAAGAAG ATTATGGACC TTACGACAAA AGGGCCCCTA GCGTCACCAC TCATTGGTAC
         3061   CATCATCAGG AGTACGGATA AAATGCTTGA TGGTCGGAAG AGGCATAAAT TCCGTCAGCC
                GTAGTAGTCC TCATGCCTAT TTTACGAACT ACCAGCCTTC TCCGTATTTA AGGCAGTCGG
         3121   AGTTTAGTCT GACCATCTCA TCTGTAACAT CATTGGCAAC GCTACCTTTG CCATGTTTCA
                TCAAATCAGA CTGGTAGAGT AGACATTGTA GTAACCGTTG CGATGGAAAC GGTACAAAGT
                                                                     ClaI
                                                                   ~~~~~~
         3181   GAAACAACTC TGGCGCATCG GGCTTCCCAT ACAATCGATA GATTGTCGCA CCTGATTGCC
                CTTTGTTGAG ACCGCGTAGC CCGAAGGGTA TGTTAGCTAT CTAACAGCGT GGACTAACGG
         3241   CGACATTATC GCGAGCCCAT TTATACCCAT ATAAATCAGC ATCCATGTTG GAATTTAATC
                GCTGTAATAG CGCTCGGGTA AATATGGGTA TATTTAGTCG TAGGTACAAC CTTAAATTAG
         3301   GCGGCCTAGA GCAAGACGTT TCCCGTTGAA TATGGCTCAT ACTCTTCCTT TTTCAATATT
                CGCCGGATCT CGTTCTGCAA AGGGCAACTT ATACCGAGTA TGAGAAGGAA AAAGTTATAA
         3361   ATTGAAGCAT TTATCAGGGT TATTGTCTCA TGAGCGGATA CATATTTGAA TGTATTTAGA
                TAACTTCGTA AATAGTCCCA ATAACAGAGT ACTCGCCTAT GTATAAACTT ACATAAATCT
         3421   AAAATAAACA AATAGGCATG CAGCGCTCTT CCGCTTCCTC GCTCACTGAC TCGCTACGCT
                TTTTATTTGT TTATCCGTAC GTCGCGAGAA GGCGAAGGAG CGAGTGACTG AGCGATGCGA
```

Fig. 19₂

```
3481  CGGTCGTTCG ACTGCGGCGA GCGGTGTCAG CTCACTCAAA AGCGGTAATA CGGTTATCCA
      GCCAGCAAGC TGACGCCGCT CGCCACAGTC GAGTGAGTTT TCGCCATTAT GCCAATAGGT
3541  CAGAATCAGG GGATAAAGCC GGAAAGAACA TGTGAGCAAA AAGCAAAGCA CCCGAAGAAG
      GTCTTAGTCC CCTATTTCGG CCTTTCTTGT ACACTCGTTT TTCGTTTCGT GGCCTTCTTC
3601  CCAACGCCGC AGGCGTTTTT CCATAGGCTC CGCCCCCCTG ACGAGCATCA CAAAAATCGA
      GGTTGCGGCG TCCGCAAAAA GGTATCCGAG GCGGGGGGAC TGCTCGTAGT GTTTTTAGCT
3661  CGCTCAAGCC AGAGGTGGCG AAACCCGACA GGACTATAAA GATACCAGGC GTTTCCCCCT
      GCGAGTTCGG TCTCCACCGC TTTGGGCTGT CCTGATATTT CTATGGTCCG CAAAGGGGGA
3721  GGAAGCTCCC TCGTGCGCTC TCCTGTTCCG ACCCTGCCGC TTACCGGATA CCTGTCCGCC
      CCTTCGAGGG AGCACGCGAG AGGACAAGGC TGGGACGGCG AATGGCCTAT GGACAGGCGG
3781  TTTCTCCCTT CGGGAAGCGT GGCGCTTTCT CATAGCTCAC GCTGTTGGTA TCTCAGTTCG
      AAAGAGGGAA GCCCTTCGCA CCGCGAAAGA GTATCGAGTG CGACAACCAT AGAGTCAAGC
3841  GTGTAGGTCG TTCGCTCCAA GCTGGGCTGT GTGCACGAAC CCCCCGTTCA GCCCGACCGC
      CACATCCAGC AAGCGAGGTT CGACCCGACA CACGTGCTTG GGGGCAAGT CGGGCTGGCG
3901  TGCGCCTTAT CCGGTAACTA TCGTCTTGAG TCCAACCCGG TAAGACACGA CTTATCGCCA
      ACGCGGAATA GGCCATTGAT AGCAGAACTC AGGTTGGGCC ATTCTGTGCT GAATAGCGGT
3961  CTGGCAGCAG CCATTGGTAA CTGATTTAGA GGACTTTGTC TTGAAGTTAT GCACCTGTTA
      GACCGTCGTC GGTAACCATT GACTAAATCT CCTGAAACAG AACTTCAATA CGTGGACAAT
4021  AGGCTAAACT GAAAGAACAG ATTTTGGTGA GTGCGGTCCT CCAACCCACT TACCTTGGTT
      TCCGATTTGA CTTTCTTGTC TAAAACCACT CACGCCAGGA GGTTGGGTGA ATGGAACCAA
4081  CAAAGAGTTG GTAGCTCAGC GAACCTTGAG AAAACCACCG TTGGTAGCGG TGGTTTTTCT
      GTTTCTCAAC CATCGAGTCG CTTGGAACTC TTTTGGTGGC AACCATCGCC ACCAAAAAGA
4141  TTATTTATGA GATGATGAAT CAATCGGTCT ATCAAGTCAA CGAACAGCTA TTCCGTTACT
      AATAAATACT CTACTACTTA GTTAGCCAGA TAGTTCAGTT GCTTGTCGAT AAGGCAATGA
4201  CTAGATTTCA GTGCAATTTA TCTCTTCAAA TGTAGCACCT GAAGTCAGCC CCATACGATA
      GATCTAAAGT CACGTTAAAT AGAGAAGTTT ACATCGTGGA CTTCAGTCGG GGTATGCTAT
4261  TAAGTTGTAA TTCTCATGTT AGTCATGCCC CGCGCCCACC GGAAGGAGCT GACTGGGTTG
      ATTCAACATT AAGAGTACAA TCAGTACGGG GCGCGGGTGG CCTTCCTCGA CTGACCCAAC
4321  AAGGCTCTCA AGGGCATCGG TCGAGATCCC GGTGCCTAAT GAGTGAGCTA ACTTACATTA
      TTCCGAGAGT TCCCGTAGCC AGCTCTAGGG CCACGGATTA CTCACTCGAT TGAATGTAAT
4381  ATTGCGTTGC GCTCACTGCC CGCTTTCCAG TCGGGAAACC TGTCGTGCCA GCTGCATTAA
      TAACGCAACG CGAGTGACGG GCGAAAGGTC AGCCCTTTGG ACAGCACGGT CGACGTAATT
4441  TGAATCGGCC AACGCGCGGG GAGAGGCGGT TTGCGTATTG GGCGCCAGGG TGGTTTTTCT
      ACTTAGCCGG TTGCGCGCCC CTCTCCGCCA AACGCATAAC CCGCGGTCCC ACCAAAAAGA
4501  TTTCACCAGT GAGACGGGCA ACAGCTGATT GCCCTTCACC GCCTGGCCCT GAGAGAGTTG
      AAAGTGGTCA CTCTGCCCGT TGTCGACTAA CGGGAAGTGG CGGACCGGGA CTCTCTCAAC
4561  CAGCAAGCGG TCCACGCTGG TTTGCCCCAG CAGGCGAAAA TCCTGTTTGA TGGTGGTTAA
      GTCGTTCGCC AGGTGCGACC AAACGGGGTC GTCCGCTTTT AGGACAAACT ACCACCAATT
4621  CGGCGGGATA TAACATGAGC TGTCTTCGGT ATCGTCGTAT CCCACTACCG AGATGTCCGC
      GCCGCCCTAT ATTGTACTCG ACAGAAGCCA TAGCAGCATA GGGTGATGGC TCTACAGGCG
4681  ACCAACGCGC AGCCCGGACT CGGTAATGGC GCGCATTGCG CCCAGCGCCA TCTGATCGTT
      TGGTTGCGCG TCGGGCCTGA GCCATTACCG CGCGTAACGC GGGTCGCGGT AGACTAGCAA
4741  GGCAACCAGC ATCGCAGTGG GAACGATGCC CTCATTCAGC ATTTGCATGG TTTGTTGAAA
      CCGTTGGTCG TAGCGTCACC CTTGCTACGG GAGTAAGTCG TAAACGTACC AAACAACTTT
4801  ACCGGACATG GCACTCCAGT CGCCTTCCCG TTCCGCTATC GGCTGAATTT GATTGCGAGT
      TGGCCTGTAC CGTGAGGTCA GCGGAAGGGC AAGGCGATAG CCGACTTAAA CTAACGCTCA
4861  GAGATATTTA TGCCAGCCAG CCAGACGCAG ACGCGCCGAG ACAGAACTTA ATGGGCCCGC
      CTCTATAAAT ACGGTCGGTC GGTCTGCGTC TGCGCGGCTC TGTCTTGAAT TACCCGGGCG
4921  TAACAGCGCG ATTTGCTGGT GACCCAATGC GACCAGATGC TCCACGCCCA GTCGCGTACC
      ATTGTCGCGC TAAACGACCA CTGGGTTACG CTGGTCTACG AGGTGCGGGT CAGCGCATGG
4981  GTCTTCATGG GAGAAAATAA TACTGTTGAT GGGTGTCTGG TCAGAGACAT CAAGAAATAA
      CAGAAGTACC CTCTTTTATT ATGACAACTA CCCACAGACC AGTCTCTGTA GTTCTTTATT
5041  CGCCGGAACA TTAGTGCAGG CAGCTTCCAC AGCAATGGCA TCCTGGTCAT CCAGCGGATA
      GCGGCCTTGT AATCACGTCC GTCGAAGGTG TCGTTACCGT AGGACCAGTA GGTCGCCTAT
5101  GTTAATGATC AGCCCACTGA CGCGTTGCGC GAGAAGATTG TGCACCGCCG CTTTACAGGC
      CAATTACTAG TCGGGTGACT GCGCAACGCG CTCTTCTAAC ACGTGGCGGC GAAATGTCCG
5161  TTCGACGCCG CTTCGTTCTA CCATCGACAC CACCACGCTG GCACCCAGTT GATCGGCGCG
      AAGCTGCGGC GAAGCAAGAT GGTAGCTGTG GTGGTGCGAC CGTGGGTCAA CTAGCCGCGC
5221  AGATTTAATC GCCGCGACAA TTTGCCACGG CGCGTGCAGG GCCAGACTGG AGGTGGCAAC
      TCTAAATTAG CGGCGCTGTT AAACGCTGCC GCGCACGTCC CGGTCTGACC TCCACCGTTG
5281  GCCAATCAGC AACGACTGTT TGCCCGCCAG TTGTTGTGCC ACGCGGTTGG GAATGTAATT
      CGGTTAGTCG TTGCTGACAA ACGGGCGGTC AACAACACGG TGCGCCAACC CTTACATTAA
5341  CAGCTCCGCC ATCGCCGCTT CCACTTTTTC CCGCGTTTTC GCAGAAACGT GGCTGGCCTG
      GTCGAGGCGG TAGCGGCGAA GGTGAAAAAG GGCGCAAAAG CGTCTTTGCA CCGACCGGAC
5401  GTTCACCACG CGGGAAACGG TCTGATAAGA GACACCGGCA TACTCTGCGA CATCGTATAA
      CAAGTGGTGC GCCCTTTGCC AGACTATTCT CTGTGGCCGT ATGAGACGCT GTAGCATATT
5461  CGTTACTGGT TTCACATTCA CCACCCTGAA TTGACTCTCT TCCGGGCGCT ATCATGCCAT
      GCAATGACCA AAGTGTAAGT GGTGGGACTT AACTGAGACA AGGCCCGCGA TAGTACGGTA
5521  ACCGCGAAAG GTTTTGCGCC ATTCGATGGT GTCCGGGATC TCGACGCTCT CCCTTATGCG
      TGGCGCTTTC CAAAACGCGG TAAGCTACCA CAGGCCCTAG AGCTGCGAGA GGGAATACGC
5581  ACTCCTGCAT TAGGAAATTA ATACGACTCA CTATA
      TGAGGACGTA ATCCTTTAAT TATGCTGAGT GATAT
```

Fig. 19$_3$

| Fig. 21₁ |
|---|
| Fig. 21₂ |

Fig. 21

Multisite TetR cassette sequence:

```
       SacI
1    GAGCTCGACC ATGATTACGC CAAGCTATCA ACTTTGTATA GAAAAGTTGA ACGAGAAACG
     CTCGAGCTGG TACTAATGCG GTTCGATAGT TGAAACATAT CTTTTCAACT TGCTCTTTGC
61   TAAAATGATA TAAATATCAA TATATTAAAT TAGATTTTGC ATAAAAAACA GACTACATAA
     ATTTTACTAT ATTTATAGTT ATATAATTTA ATCTAAAACG TATTTTTTGT CTGATGTATT
                                              PstI
121  TACTGTAAAA CACAACATAT CCAGTCACTA TGGTCGACCT GCAGACTGGC TGTGTATAAG
     ATGACATTTT GTGTTGTATA GGTCAGTGAT ACCAGCTGGA CGTCTGACCG ACACATATTC
181  GGAGCCTGAC ATTTATATTC CCCAGAACAT CAGGTTAATG GCGTTTTTGA TGTCATTTTC
     CCTCGGACTG TAAATATAAG GGGTCTTGTA GTCCAATTAC CGCAAAAACT ACAGTAAAAG
241  GCGGTGGCTG AGATCAGCCA CTTCTTCCCC GATAACGGAG ACCGGCACAC TGGCCATATC
     CGCCACCGAC TCTAGTCGGT GAAGAAGGGG CTATTGCCTC TGGCCGTGTG ACCGGTATAG
301  GGTGGTCATC ATGCGCCAGC TTTCATCCCC GATATGCACC ACCGGGTAAA GTTCACGGGG
     CCACCAGTAG TACGCGGTCG AAAGTAGGGG CTATACGTGG TGGCCCATTT CAAGTGCCCC
                                                         SmaI
                                                         ~~~~~~
                                                         XmaI
                                                         ~~~~~~
                     ApaLI                               AvaI
361  GACTTTATCT GACAGCAGAC GTGCACTGGC CAGGGGGATC ACCATCCGTC GCCCGGGCGT
     CTGAAATAGA CTGTCGTCTG CACGTGACCG GTCCCCCTAG TGGTAGGCAG CGGGCCCGCA
421  GTCAATAATA TCACTCTGTA CATCCACAAA CAGACGATAA CGGCTCTCTC TTTTATAGGT
     CAGTTATTAT AGTGAGACAT GTAGGTGTTT GTCTGCTATT GCCGAGAGAG AAAATATCCA
481  GTAAACCTTA AACTGCATTT CACCAGCCCC TGTTCTCGTC GGCAAAAGAG CCGTTCATTT
     CATTTGGAAT TTGACGTAAA GTGGTCGGGG ACAAGAGCAG CCGTTTTCTC GGCAAGTAAA
541  CAATAAACCG GGCGACCTCA GCCATCCCTT CCTGATTTTC CGCTTTCCAG CGTTCGGCAC
     GTTATTTGGC CCGCTGGAGT CGGTAGGGAA GGACTAAAAG GCGAAAGGTC GCAAGCCGTG
601  GCAGACGACG GGCTTCATTC TGCATGGTTG TGCTTACCGA ACCGGAGATA TTGACATCAT
     CGTCTGCTGC CCGAAGTAAG ACGTACCAAC ACGAATGGCT TGGCCTCTAT AACTGTAGTA
661  ATATGCCTTG AGCAACTGAT AGCTGTCGCT GTCAACTGTC ACTGTAATAC GCTGCTTCAT
     TATACGGAAC TCGTTGACTA TCGACAGCGA CAGTTGACAG TGACATTATG CGACGAAGTA
721  AGCATACCTC TTTTTGACAT ACTTCGGGTA TACATATCAG TATATATTCT TATACCGCAA
     TCGTATGGAG AAAAACTGTA TGAAGCCCAT ATGTATAGTC ATATATAAGA ATATGGCGTT
                                                            XbaI
                                                            ~~~~~~
                             BamHI
                             ~~~~~~~
781  AAATCAGCGC GCAAATACGC ATACTGTTAT CTGGCTTTTA GTAAGCCGGA TCCTCTAGAG
     TTTAGTCGCG CGTTTATGCG TATGACAATA GACCGAAAAT CATTCGGCCT AGGAGATCTC
841  ACGCGATGGA TATGTTCTGC CAAGGGTTGG TTTGCGCATT CACAGTTCTC CGCAAGAATT
     TGCGCTACCT ATACAAGACG GTTCCCAACC AAACGCGTAA GTGTCAAGAG GCGTTCTTAA
901  GATTGGCTCC AATTCTTGGA GTGGTGAATC CGTTAGCGAG GTGCCGCCGG CTTCCATTCA
     CTAACCGAGG TTAAGAACCT CACCACTTAG GCAATCGCTC CACGGCGGCC GAAGGTAAGT
961  GGTCGAGGTG GCCCGGCTCC ATGCACGCG ACGCAACGCG GGGAGGCAGA CAAGGTATAG
     CCAGCTCCAC CGGGCCGAGG TACGTGGCGC TGCGTTGCGC CCCTCCGTCT GTTCCATATC
1021 GGCGGCGCCT ACAATCCATG CCAACCCGTT CCATGTGCTC GCCGAGGCGG CATAAATCGC
     CCGCCGCGGA TGTTAGGTAC GGTTGGGCAA GGTACACGAG CGGCTCCGCC GTATTTAGCG
1081 CGTGACGATC AGCGGTCCAG TGATCGAAGT TAGGCTGGTA AGAGCCGCGA GGATCCTTG
     GCACTGCTAG TCGCCAGGTC ACTAGCTTCA ATCCGACCAT TCTCGGCGCT CGCTAGGAAC
1141 AAGCTGTCCC TGATGGTCGT CATCTACCTG CCTGGACAGC ATGGCCTGCA ACGCGGGCAT
     TTCGACAGGG ACTACCAGCA GTAGATGGAC GGACCTGTCG TACCGGACGT TGCGCCCGTA
1201 CCCGATGCCG CCGGAAGCGA AAGAATCAT AATGGGGAAG GCCATCCAGC CTCGCGTCGC
     GGGCTACGGC GGCCTTCGCT CTTCTTAGTA TTACCCCTTC CGGTAGGTCG GAGCGCAGCG
1261 GAACGCCAGC AAGACGTAGC CCAGCGCGTC GGCCGCCATG CCGGCGATAA TGGCCTGCTT
     CTTGCGGTCG TTCTGCATCG GGTCGCGCAG CCGGCGGTAC GGCCGCTATT ACCGGACGAA
1321 CTCGCCGAAA CGTTTGGTGG CGGGACCAGT GACGAAGGCT TGAGCGAGGG CGTGCAAGAT
     GAGCGGCTTT GCAAACCACC GCCCTGGTCA CTGCTTCCGA ACTCGCTCCC GCACGTTCTA
1381 TCCGAATACC GCAAGCGACA GGCCGATCAT CGTCGCGCTC CAGCGAAAGC GGTCCTCGCC
     AGGCTTATGG CGTTCGCTGT CCGGCTAGTA GCAGCGCGAG GTCGCTTTCG CCAGGAGCGG
1441 GAAAATGACC CAGAGCGCTG CCGGCACCTG TCCTACGAGT TGCATGATAA AGAAGACAGT
     CTTTTACTGG GTCTCGCGAC GGCCGTGGAC AGGATGCTCA ACGTACTATT TCTTCTGTCA
1501 CATAAGTGCG GCGACGATAG TCATGCCCCG CGCCCACCGG AAGGAGCTGA CTGGGTTGAA
     GTATTCACGC CGCTGCTATC AGTACGGGGC GCGGGTGGCC TTCCTCGACT GACCCAACTT
```

Fig. 21$_1$

```
                                                              EcoNI
                                                        ~~~~~~~~~~~
1561  GGCTCTCAAG GGCATCGGTC GACGCTCTCC CTTATGCGAC TCCTGCATTA GGAAGCAGCC
      CCGAGAGTTC CCGTAGCCAG CTGCGAGAGG GAATACGCTG AGGACGTAAT CCTTCGTCGG
1621  CAGTAGTAGG TTGAGGCCGT TGAGCACCGC CGCCGCAAGG AATGGTGCAT GCAAGGAGAT
      GTCATCATCC AACTCCGGCA ACTCGTGGCG GCGGCGTTCC TTACCACGTA CGTTCCTCTA
1681  GGCGCCCAAC AGTCCCCCGG CCACGGGGCC TGCCACCATA CCCACGCCGA AACAAGCGCT
      CCGCGGGTTG TCAGGGGGCC GGTGCCCCGG ACGGTGGTAT GGGTGCGGCT TTGTTCGCGA
1741  CATGAGCCCG AAGTGGCGAG CCCGATCTTC CCCATCGGTG ATGTCGGCGA TATAGGCGCC
      GTACTCGGGC TTCACCGCTC GGGCTAGAAG GGGTAGCCAC TACAGCCGCT ATATCCGCGG
                                                                BamHI
                                                               ~~~~~~
1801  AGCAACCGCA CCTGTGGCGC CGGTGATGCC GGCCACGATG CGTCCGGCGT AGAGGATCCA
      TCGTTGGCGT GGACACCGCG GCCACTACGG CCGGTGCTAC GCAGGCCGCA TCTCCTAGGT
1861  CAGGACGGGT GTGGTCGCCA TGATCGCGTA GTCGATAGTG GCTCCAAGTA GCGAAGCGAG
      GTCCTGCCCA CACCAGCGGT ACTAGCGCAT CAGCTATCAC CGAGGTTCAT CGCTTCGCTC
1921  CAGGACTGGG CGGCGGCCAA AGCGGTCGGA CAGTGCTCCG AGAACGGGTG CGCATAGAAA
      GTCCTGACCC GCCGCCGGTT TCGCCAGCCT GTCACGAGGC TCTTGCCCAC GCGTATCTTT
1981  TTGCATCAAC GCATATAGCG CTAGCAGCAC GCCATAGTGA CTGGCGATGC TGTCGGAATG
      AACGTAGTTG CGTATATCGC GATCGTCGTG CGGTATCACT GACCGCTACG ACAGCCTTAC
2041  GACGATATCC CGCAAGAGGC CCGGCAGTAC CGGCATAACC AAGCCTATGC CTACAGCATC
      CTGCTATAGG GCGTTCTCCG GGCCGTCATG GCCGTATTGG TTCGGATACG GATGTCGTAG
2101  CAGGGTGACG GTGCCGAGGA TGACGATGAG CGCATTGTTA GATTTCATAC ACGGTGCCTG
      GTCCCACTGC CACGGCTCCT ACTGCTACTC GCGTAACAAT CTAAAGTATG TGCCACGGAC
                                                    HindIII
                                                   ~~~~~~~
                                          ClaI
                                         ~~~~~~~
2161  ACTGCGTTAG CAATTTAACT GTGATAAACT ACCGCATTAA AGCTTATCGA TGATAAGCTG
      TGACGCAATC GTTAAATTGA CACTATTTGA TGGCGTAATT TCGAATAGCT ACTATTCGAC
                         NotI
                        ~~~~~~~~~
2221  TCAAACATGA GAAGCGGCCG CCATAGTGAC TGGATATGTT GTGTTTTACA GTATTATGTA
      AGTTTGTACT CTTCGCCGGC GGTATCACTG ACCTATACAA CACAAAATGT CATAATACAT
2281  GTCTGTTTTT TATGCAAAAT CTAATTTAAT ATATTGATAT TTATATCATT TTACGTTTCT
      CAGACAAAAA ATACGTTTTA GATTAAATTA TATAACTATA AATATAGTAA AATGCAAAGA
2341  CGTTCAACTT TATTATACAT AGTTGATAAT TCACTGGCCG TCGTTTTACA ACGTCGTGAC
      GCAAGTTGAA ATAATATGTA TCAACTATTA AGTGACCGGC AGCAAAATGT TGCAGCACTG
                                                              HindIII
                                                              ~~~~~~
2401  TGGGAAAACC CTGGCGTTAC CCAACTTAAT CGCCTTGCAG CACAAGCTT
      ACCCTTTTGG GACCGCAATG GGTTGAATTA GCGGAACGTC GTGTTCGAA
```

Fig. 21$_2$

| Fig. 23$_1$ |
|---|
| Fig. 23$_2$ |
| Fig. 23$_3$ |
| Fig. 23$_4$ |

Fig. 23 pDEST-CM3 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                              EcoRI
                                                              ~~~~~~
           NcoI                                   BamHI          SacI
           ~~~~~~                                 ~~~~~~         ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGACCATG ATTACGCCAA GCTATCAACT TTGTATAGAA AAGTTGAACG AGAAACGTAA
     GAGCTGGTAC TAATGCGGTT CGATAGTTGA AACATATCTT TTCAACTTGC TCTTTGCATT
 181 AATGATATAA ATATCAATAT ATTAAATTAG ATTTTGCATA AAAAACAGAC TACATAATAC
     TTACTATATT TATAGTTATA TAATTTAATC TAAAACGTAT TTTTTGTCTG ATGTATTATG
                                              PstI
                                              ~~~~~~~
 241 TGTAAAACAC AACATATCCA GTCACTATGG TCGACCTGCA GACTGGCTGT GTATAAGGGA
     ACATTTTGTG TTGTATAGGT CAGTGATACC AGCTGGACGT CTGACCGACA CATATTCCCT
 301 GCCTGACATT TATATTCCCC AGAACATCAG GTTAATGGCG TTTTTGATGT CATTTTCGCG
     CGGACTGTAA ATATAAGGGG TCTTGTAGTC CAATTACCGC AAAAACTACA GTAAAAGCGC
 361 GTGGCTGAGA TCAGCCACTT CTTCCCCGAT AACGGAGACC GGCACACTGG CCATATCGGT
     CACCGACTCT AGTCGGTGAA GAAGGGGCTA TTGCCTCTGG CCGTGTGACC GGTATAGCCA
 421 GGTCATCATG CGCCAGCTTT CATCCCCGAT ATGCACCACC GGGTAAAGTT CACGGGGGAC
     CCAGTAGTAC GCGGTCGAAA GTAGGGGCTA TACGTGGTGG CCCATTTCAA GTGCCCCCTG
 481 TTTATCTGAC AGCAGACGTG CACTGGCCAG GGGGATCACC ATCCGTCGCC CGGGCGTGTC
     AAATAGACTG TCGTCTGCAC GTGACCGGTC CCCCTAGTGG TAGGCAGCGG GCCCGCACAG
 541 AATAATATCA CTCTGTACAT CCACAAACAG ACGTAACGG CTCTCTCTTT TATAGGTGTA
     TTATTATAGT GAGACATGTA GGTGTTTGTC TGCTATTGCC GAGAGAGAAA ATATCCACAT
 601 AACCTTAAAC TGCATTTCAC CAGCCCCTGT TCTCGTCGGC AAAAGAGCCG TTCATTTCAA
     TTGGAATTTG ACGTAAAGTG GTCGGGGACA AGAGCAGCCG TTTTCTCGGC AAGTAAAGTT
 661 TAAACCGGGC GACCTCAGCC ATCCCTTCCT GATTTTCCGC TTTCCAGCGT TCGGCACGCA
     ATTTGGCCCG CTGGAGTCGG TAGGGAAGGA CTAAAAGGCG AAAGGTCGCA AGCCGTGCGT
 721 GACGACGGGC TTCATTCTGC ATGGTTGTGC TTACCGAACC GGAGATATTG ACATCATATA
     CTGCTGCCCG AAGTAAGACG TACCAACACG AATGGCTTGG CCTCTATAAC TGTAGTATAT
 781 TGCCTTGAGC AACTGATAGC TGTCGCTGTC AACTGTCACT GTAATACGCT GCTTCATAGC
     ACGGAACTCG TTGACTATCG ACAGCGACAG TTGACAGTGA CATTATGCGA CGAAGTATCG
 841 ATACCTCTTT TTGACATACT TCGGGTATAC ATATCAGTAT ATATTCTTAT ACCGCAAAAA
     TATGGAGAAA AACTGTATGA AGCCCATATG TATAGTCATA TATAAGAATA TGGCGTTTTT
                                                           BamHI
                                                           ~~~~~~~
 901 TCAGCGCGCA AATACGCATA CTGTTATCTG GCTTTTAGTA AGCCGGATCC TCTAGAGACG
     AGTCGCGCGT TTATGCGTAT GACAATAGAC CGAAAATCAT TCGGCCTAGG AGATCTCTGC
 961 CGATGGATAT GTTCTGCCAA GGGTTGGTTT GCGCATTCGA AGTTCTCCGC AAGAATTGAT
     GCTACCTATA CAAGACGGTT CCCAACCAAA CGCGTAAGCT TCAAGAGGCG TTCTTAACTA
1021 TGGCTCCAAT TCTTGGAGTG GTGAATCCGT TAGCGAGGTG CCGCCGGCTT CCATTCAGGT
     ACCGAGGTTA AGAACCTCAC CACTTAGGCA ATCGCTCCAC GGCGGCCGAA GGTAAGTCCA
1081 CGAGGTGGCC CGGCTCCATG CACCGCGACG CAACGCGGGG AGGCAGACAA GGTATAGGGC
     GCTCCACCGG GCCGAGGTAC GTGGCGCTGC GTTGCGCCCC TCCGTCTGTT CCATATCCCG
1141 GGCGCCTACA ATCCATGCCA ACCCGTTCCA TGTGCTCGCC GAGGCGGCAT AAATCGCCGT
     CCGCGGATGT TAGGTACGGT TGGGCAAGGT ACACGAGCGG CTCCGCCGTA TTTAGCGGCA
1201 GACGATCAGC GGTCCAGTGA TCGAAGTTAG CTGGTAAGA GCCGCGAGCG ATCCTTGAAG
     CTGCTAGTCG CCAGGTCACT AGCTTCAATC GACCATTCT CGGCGCTCGC TAGGAACTTC
1261 CTGTCCCTGA TGGTCGTCAT CTACCTGCCT GGACAGCATG GCCTGCAACG CGGGCATCCC
     GACAGGGACT ACCAGCAGTA GATGGACGGA CCTGTCGTAC CGGACGTTGC GCCCGTAGGG
1321 GATGCCGCCG GAAGCGAGAA GAATCATAAT GGGGAAGGCC ATCCAGCCTC GCGTCGCGAA
     CTACGGCGGC CTTCGCTCTT CTTAGTATTA CCCCTTCCGG TAGGTCGGAG CGCAGCGCTT
1381 CGCCAGCAAG ACGTAGCCCA GCGCGTCGGC CGCCATGCCG GCGATAATGG CCTGCTTCTC
     GCGGTCGTTC TGCATCGGGT CGCGCAGCCG GCGGTACGGC CGCTATTACC GGACGAAGAG
1441 GCCGAAACGT TTGGTGGCGG GACCAGTGAC GAAGGCTTGA GCGAGGGCGT GCAAGATTCC
     CGGCTTTGCA AACCACCGCC CTGGTCACTG CTTCCGAACT CGCTCCCGCA CGTTCTAAGG
1501 GAATACCGCA AGCGACAGGC CGATCATCGT CGCGCTCCAG CGAAAGCGGT CCTCGCCGAA
     CTTATGGCGT TCGCTGTCCG GCTAGTAGCA GCGCGAGGTC GCTTTCGCCA GGAGCGGCTT
1561 AATGACCCAG AGCGCTGCCG GCACCTGTCC TACGAGTTGC ATGATAAGA AGACAGTCAT
     TTACTGGGTC TCGCGACGGC CGTGGACAGG ATGCTCAACG TACTATTTCT TCTGTCAGTA
1621 AAGTGCGGCG ACGATAGTCA TGCCCCGCGC CCACCGGAAG GAGCTGACTG GGTTGAAGGC
     TTCACGCCGC TGCTATCAGT ACGGGGCGCG GGTGGCCTTC CTCGACTGAC CCAACTTCCG
                                                       EcoNI
                                                       ~~~~~~~
1681 TCTCAAGGGC ATCGGTCGAC GCTCTCCCTT ATGCGACTCC TGCATTAGGA AGCAGCCCAG
     AGAGTTCCCG TAGCCAGCTG CGAGAGGGAA TACGCTGAGG ACGTAATCCT TCGTCGGGTC
```

Fig. 23₁

```
1741 TAGTAGGTTG AGGCCGTTGA GCACCGCCGC CGCAAGGAAT GGTGCATGCA AGGAGATGGC
     ATCATCCAAC TCCGGCAACT CGTGGCGGCG GCGTTCCTTA CCACGTACGT TCCTCTACCG
1801 GCCCAACAGT CCCCCGGCCA CGGGGCCTGC CACCATACCC ACGCCGAAAC AAGCGCTCAT
     CGGGTTGTCA GGGGGCCGGT GCCCCGGACG GTGGTATGGG TGCGGCTTTG TTCGCGAGTA
1861 GAGCCCGAAG TGGCGAGCCC GATCTTCCCC ATCGGTGATG TCGGCGATAT AGGCGCCAGC
     CTCGGGCTTC ACCGCTCGGG CTAGAAGGGG TAGCCACTAC AGCCGCTATA TCCGCGGTCG
                                                            BamHI
                                                            ~~~~~~
1921 AACCGCACCT GTGGCGCCGG TGATGCCGGC CACGATGCGT CCGGCGTAGA GGATCCACAG
     TTGGCGTGGA CACCGCGGCC ACTACGGCCG GTGCTACGCA GGCCGCATCT CCTAGGTGTC
1981 GACGGGTGTG GTCGCCATGA TCGCGTAGTC GATAGTGGCT CCAAGTAGCG AAGCGAGCAG
     CTGCCCACAC CAGCGGTACT AGCGCATCAG CTATCACCGA GGTTCATCGC TTCGCTCGTC
2041 GACTGGGCGG CGGCCAAAGC GGTCGGACAG TGCTCCGAGA ACGGGTGCGC ATAGAAATTG
     CTGACCCGCC GCCGGTTTCG CCAGCCGTCA ACGAGGCTCT TGCCCACGCG TATCTTTAAC
2101 CATCAACGCA TATAGCGCTA GCAGCACGCA ATAGTGACTG GCGATGCTGT CGGAATGGAC
     GTAGTTGCGT ATATCGCGAT CGTCGTGCGT TATCACTGAC CGCTACGACA GCCTTACCTG
2161 GATATCCCGC AAGAGGCCCG GCAGTACCGG CATAACCAAG CCTATGCCTA CAGCATCCAG
     CTATAGGGCG TTCTCCGGGC CGTCATGGCC GTATTGGTTC GGATACGGAT GTCGTAGGTC
2221 GGTGACGGTG CCGAGGATGA CGATGAGCGC ATTGTTAGAT TTCATACACG GTGCCTGACT
     CCACTGCCAC GGCTCCTACT GCTACTCGCG TAACAATCTA AAGTATGTGC CACGGACTGA
                                                HindIII
                                                ~~~~~~~
2281 GCGTTAGCAA TTTAACTGTG ATAAACTACC GCATTAAAGC TTATCGATGA TAAGCTGTCA
     CGCAATCGTT AAATTGACAC TATTTGATGG CGTAATTTCG AATAGCTACT ATTCGACAGT
2341 AACATGAGAA GCGGCCGCCA TAGTGACTGG ATATGTTGTG TTTTACAGTA TTATGTAGTC
     TTGTACTCTT CGCCGGCGGT ATCACTGACC TATACAACAC AAAATGTCAT AATACATCAG
2401 TGTTTTTTAT GCAAAATCTA ATTTAATATA TTGATATTTA TATCATTTTA CGTTTCTCGT
     ACAAAAAATA CGTTTTAGAT TAAATTATAT AACTATAAAT ATAGTAAAAT GCAAAGAGCA
2461 TCAACTTTAT TATACATAGT TGATAATTCA CTGGCCGTCG TTTTACAACG TCGTGACTGG
     AGTTGAAATA ATATGTATCA ACTATTAAGT GACCGGCAGC AAAATGTTGC AGCACTGACC
                                                HindIII
                                                ~~~~~~~
2521 GAAAACCCTG GCGTTACCCA ACTTAATCGC CTTGCAGCAC AAGCTTGCGG CCGCATAATG
     CTTTTGGGAC CGCAATGGGT TGAATTAGCG GAACGTCGTG TTCGAACGCC GGCGTATTAC
2581 CTTAAGTCGA ACAGAAAGTA ATCGTATTGT ACACGGCCGC ATAATCGAAA TTAATACGAC
     GAATTCAGCT TGTCTTTCAT TAGCATAACA TGTGCCGGCG TATTAGCTTT AATTATGCTG
2641 TCACTATAGG GGAATTGTGA GCGGATAACA ATTCCCATC TTAGTATATT AGTTAAGTAT
     AGTGATATCC CCTTAACACT CGCCTATTGT TAAGGGGTAG AATCATATAA TCAATTCATA
2701 AAGAAGGAGA TATACATATG GCAGATCTCA ATTGGATATC GGCCGGCCAC GCGATCGCTG
     TTCTTCCTCT ATATGTATAC CGTCTAGAGT TAACCTATAG CCGGCCGGTG CGCTAGCGAC
2761 ACGTCGGTAC CCTCGAGTCT GGTAAAGAAA CCGCTGCTGC GAAATTTGAA CGCCAGCACA
     TGCAGCCATG GGAGCTCAGA CCATTTCTTT GGCGACGACG CTTTAAACTT GCGGTCGTGT
2821 TGGACTCGTC TACTAGCGCA GCTTAATTAA CCTAGGCTGC TGCCACCGCT GAGCAATAAC
     ACCTGAGCAG ATGATCGCGT CGAATTAATT GGATCCGACG ACGGTGGCGA CTCGTTATTG
2881 TAGCATAACC CCTTGGGGCC TCTAAACGGG TCTTGAGGGG TTTTTTGCTG AAACCTCAGG
     ATCGTATTGG GGAACCCCGG AGATTTGCCC AGAACTCCCC AAAAAACGAC TTTGGAGTCC
2941 CATTTGAGAA GCACACGGTC ACACTGCTTC CGGTAGTCAA TAAACCGGTA AACCAGCAAT
     GTAAACTCTT CGTGTGCCAG TGTGACGAAG GCCATCAGTT ATTTGGCCAT TTGGTCGTTA
3001 AGACATAAGC GGCTATTTAA CGACCCTGCC CTGAACCGAC GACCGGGTCG AATTTGCTTT
     TCTGTATTCG CCGATAAATT GCTGGGACGG GACTTGGCTG CTGGCCCAGC TTAAACGAAA
3061 CGAATTTCTG CCATTCATCC GCTTATTATC ACTTATTCAG GCGTAGCACC AGGCGTTTAA
     GCTTAAAGAC GGTAAGTAGG CGAATAATAG TGAATAAGTC CGCATCGTGG TCCGCAAATT
3121 GGGCACCAAT AACTGCCTTA AAAAAATTAC GCCCCGCCCT GCCACTCATC GCAGTACTGT
     CCCGTGGTTA TTGACGGAAT TTTTTTAATG CGGGGCGGGA CGGTGAGTAG CGTCATGACA
3181 TGTAATTCAT TAAGCATTCT GCCGACATGG AAGCCATCAC AGACGGCATG ATGAACCTGA
     ACATTAAGTA ATTCGTAAGA CGGCTGTACC TTCGGTAGTG TCTGCCGTAC TACTTGGACT
3241 ATCGCCAGCG GCATCAGCAC CTTGTCGCCT TGCGTATAAT ATTTGCCCAT AGTGAAAACG
     TAGCGGTCGC CGTAGTCGTG GAACAGCGGA ACGCATATTA TAAACGGGTA TCACTTTTGC
3301 GGGGCGAAGA AGTTGTCCAT ATTGGCCACG TTTAAATCAA AACTGGTGAA ACTCACCCAG
     CCCCGCTTCT TCAACAGGTA TAACCGGTGC AAATTTAGTT TTGACCACTT TGAGTGGGTC
3361 GGATTGGCTG AGACGAAAAA CATATTCTCA ATAAACCCTT TAGGGAAATA GGCCAGGTTT
     CCTAACCGAC TCTGCTTTTT GTATAAGAGT TATTTGGGAA ATCCCTTTAT CCGGTCCAAA
3421 TCACCGTAAC ACGCCACATC TTGCGAATAT ATGTGTAGAA ACTGCCGGAA ATCGTCGTGG
     AGTGGCATTG TGCGGTGTAG AACGCTTATA TACACATCTT TGACGGCCTT TAGCAGCACC
3481 TATTCACTCC AGAGCGATGA AAACGTTTCA GTTTGCTCAT GGAAAACGGT GTAACAAGGG
     ATAAGTGAGG TCTCGCTACT TTTGCAAAGT CAAACGAGTA CCTTTTGCCA CATTGTTCCC
3541 TGAACACTAT CCCATATCAC CAGCTCACCG TCTTTCATTG CCATACGGAA CTCCGGATGA
     ACTTGTGATA GGGTATAGTG GTCGAGTGGC AGAAAGTAAC GGTATGCCTT GAGGCCTACT
3601 GCATTCATCA GGCGGGCAAG AATGTGAATA AAGGCCGGAT AAAACTTGTG CTTATTTTTC
     CGTAAGTAGT CCGCCCGTTC TTACACTTAT TTCCGGCCTA TTTTGAACAC GAATAAAAAG
3661 TTTACGGTCT TAAAAAGGCC GTAATATCC AGCTGAACGG TCTGGTTATA GGTACATTGA
     AAATGCCAGA ATTTTTTCCG GCATTATAGG TCGACTTGCC AGACCAATAT CCATGTAACT
3721 GCAACTGACT GAAATGCCTC AAAATGTTCT TTACGATGCC ATTGGGATAT ATCAACGGTG
```

Fig. 23$_2$

```
      CGTTGACTGA CTTTACGGAG TTTTACAAGA AATGCTACGG TAACCCTATA TAGTTGCCAC
3781  GTATATCCAG TGATTTTTTT CTCCATTTTA GCTTCCTTAG CTCCTGAAAA TCTCGATAAC
      CATATAGGTC ACTAAAAAAA GAGGTAAAAT CGAAGGAATC GAGGACTTTT AGAGCTATTG
3841  TCAAAAAATA CGCCCGGTAG TGATCTTATT TCATTATGGT GAAAGTTGGA ACCTCTTACG
      AGTTTTTTAT GCGGGCCATC ACTAGAATAA AGTAATACCA CTTTCAACCT TGGAGAATGC
3901  TGCCGATCAA CGTCTCATTT TCGCCAAAAG TTGGCCCAGG GCTTCCCGGT ATCAACAGGG
      ACGGCTAGTT GCAGAGTAAA AGCGGTTTTC AACCGGGTCC CGAAGGGCCA TAGTTGTCCC
3961  ACACCAGGAT TTATTTATTC TGCGAAGTGA TCTTCCGTCA CAGGTATTTA TTCGGCGCAA
      TGTGGTCCTA AATAAATAAG ACGCTTCACT AGAAGGCAGT GTCCATAAAT AAGCCGCGTT
4021  AGTGCGTCGG GTGATGCTGC CAACTTACTG ATTTAGTGTA TGATGGTGTT TTTGAGGTGC
      TCACGCAGCC CACTACGACG GTTGAATGAC TAAATCACAT ACTACCACAA AAACTCCACG
4081  TCCAGTGGCT TCTGTTTCTA TCAGCTGTCC CTCCTGTTCA GCTACTGACG GGGTGGTGCG
      AGGTCACCGA AGACAAAGAT AGTCGACAGG GAGGACAAGT CGATGACTGC CCCACCACGC
4141  TAACGGCAAA AGCACCGCCG GACATCAGCG CTAGCGGAGT GTATACTGGC TTACTATGTT
      ATTGCCGTTT TCGTGGCGGC CTGTAGTCGC GATCGCCTCA CATATGACCG AATGATACAA
4201  GGCACTGATG AGGGTGTCAG TGAAGTGCTT CATGTGGCAG GAGAAAAAAG GCTGCACCGG
      CCGTGACTAC TCCCACAGTC ACTTCACGAA GTACACCGTC CTCTTTTTTC CGACGTGGCC
4261  TGCGTCAGCA GAATATGTGA TACAGGATAT ATTCCGCTTC CTCGCTCACT GACTCGCTAC
      ACGCAGTCGT CTTATACACT ATGTCCTATA TAAGGCGAAG GAGCGAGTGA CTGAGCGATG
4321  GCTCGGTCGT TCGACTGCGG CGAGCGGAAA TGGCTTACGA ACGGGGCGGA GATTTCCTGG
      CGAGCCAGCA AGCTGACGCC GCTCGCCTTT ACCGAATGCT TGCCCCGCCT CTAAAGGACC
4381  AAGATGCCAG GAAGATACTT AACAGGGAAG TGAGAGGGCC GCGGCAAAGC CGTTTTTCCA
      TTCTACGGTC CTTCTATGAA TTGTCCCTTC ACTCTCCCGG CGCCGTTTCG GCAAAAAGGT
4441  TAGGCTCCGC CCCCCTGACA AGCATCACGA AATCTGACGC TCAAATCAGT GGTGGCGAAA
      ATCCGAGGCG GGGGGACTGT TCGTAGTGCT TTAGACTGCG AGTTTAGTCA CCACCGCTTT
4501  CCCGACAGGA CTATAAAGAT ACCAGGCGTT TCCCCTGGCG GCTCCCTCGT GCGCTCTCCT
      GGGCTGTCCT GATATTTCTA TGGTCCGACA AGGGGACCGC CGAGGGAGCA CGCGAGAGGA
4561  GTTCCTGCCT TTCGGTTTAC CGGTGTCATT CCGCTGTTAT GGCCGCGTTT GTCTCATTCC
      CAAGGACGGA AAGCCAAATG GCCACAGTAA GGCGACAATA CCGGCGCAAA CAGAGTAAGG
4621  ACGCCTGACA CTCAGTTCCG GGTAGGCAGT TCGCTCCAAG CTGGACTGTA TGCACGAACC
      TGCGGACTGT GAGTCAAGGC CCATCCGTCA AGCGAGGTTC GACCTGACAT ACGTGCTTGG
4681  CCCCCTTCAG TCCGACCGCT GCGCCTTATC CGGTAACTAT CGTCTTGAGT CCAACCCGGA
      GGGGCAAGTC AGGCTGGCGA CGCGGAATAG GCCATTGATA GCAGAACTCA GGTTGGGCCT
4741  AAGACATGCA AAAGCACCAC TGGCAGCAGC CACTGGTAAT TGATTTAGAG GAGTTAGTCT
      TTCTGTACGT TTTCGTGGTG ACCGTCGTCG GTGACCATTA ACTAAATCTC CTCAATCAGA
4801  TGAAGTCATG CGCCGGTTAA GGCTAAACTG AAAGGACAAG TTTTGGTGAC TGCGCTCCTC
      ACTTCAGTAC GCGGCCAATT CCGATTTGAC TTTCCTGTTC AAAACCACTG ACGCGAGGAG
4861  CAAGCCAGTT ACCTCGGTTC AAAGAGTTGG TAGCTCAGAG AACCTTCGAA AAACCGCCCT
      GTTCGGTCAA TGGAGCCAAG TTTCTCAACC ATCGAGTCTC TTGGAAGCTT TTTGGCGGGA
4921  GCAAGGCGGT TTTTTCGTTT TCAGAGCAAG AGATTACGCG CAGACCAAAA CGATCTCAAG
      CGTTCCGCCA AAAAAGCAAA AGTCTCGTTC TCTAATGCGC GTCTGGTTTT GCTAGAGTTC
4981  AAGATCATCT TATTAATCAG ATAAAATATT TCTAGATTTC AGTGCAATTT ATCTCTTCAA
      TTCTAGTAGA ATAATTAGTC TATTTTATAA AGATCTAAAG TCACGTTAAA TAGAGAAGTT
5041  ATGTAGCACC TGAAGTCAGC CCCATACGAT ATAAGTTGTA ATTCTCATGT TAGTCATGCC
      TACATCGTGG ACTTCAGTCG GGGTATGCTA TATTCAACAT TAAGAGTACA ATCAGTACGG
5101  CCGCGCCCAC CGGAAGGAGC TGACTGGGTT GAAGGCTCTC AAGGGCATCG GTCGAGATCC
      GGCGCGGGTG GCCTTCCTCG ACTGACCCAA CTTCCGAGAG TTCCCGTAGC CAGCTCTAGG
5161  CGGTGCCTAA TGAGTGAGCT AACTTACATT AATTGCGTTG CGCTCACTGC CCGCTTTCCA
      GCCACGGATT ACTCACTCGA TTGAATGTAA TTAACGCAAC GCGAGTGACG GGCGAAAGGT
5221  GTCGGGAAAC CTGTCGTGCC AGCTGCATTA ATGAATCGGC CAACGCGCGG GGAGAGGCGG
      CAGCCCTTTG ACAGCACGG TCGACGTAAT TACTTAGCCG GTTGCGCGCC CCTCTCCGCC
5281  TTTGCGTATT GGGCGCCAGG GTGGTTTTTC TTTTCACCAG TGAGACGGGC AACAGCTGAT
      AAACGCATAA CCCGCGGTCC CACCAAAAAG AAAAGTGGTC ACTCTGCCCG TTGTCGACTA
5341  TGCCCTTCAC CGCCTGGCCC TGAGAGAGTT GCAGCAAGCG GTCCACGCTG GTTTGCCCCA
      ACGGGAAGTG GCGGACCGGG ACTCTCTCAA CGTCGTTCGC CAGGTGCGAC CAAACGGGGT
5401  GCAGGCGAAA ATCCTGTTTG ATGGTGGTTA ACGGCGGGAT ATAACATGAG CTGTCTTCGG
      CGTCCGCTTT TAGGACAAAC TACCACCAAT TGCCGCCCTA TATTGTACTC GACAGAAGCC
5461  TATCGTCGTA TCCCACTACC GAGATGTCCG CACCAACGCG CAGCCCGGAC TCGGTAATGG
      ATAGCAGCAT AGGGTGATGG CTCTACAGGC GTGGTTGCGC GTCGGGCCTG AGCCATTACC
5521  CGCGCATTGC GCCCAGCGCC ATCTGATCGT TGGCAACCAG CATCGCAGTG GGAACGATGC
      GCGCGTAACG CGGGTCGCGG TAGACTAGCA ACCGTTGGTC GTAGCGTCAC CCTTGCTACG
5581  CCTCATTCAG CATTTGCATG GTTTGTTGAA AACCGGACAT GGCACTCCAG TCGCCTTCCC
      GGAGTAAGTC GTAAACGTAC CAAACAACTT TTGGCCTGTA CCGTGAGGTC AGCGGAAGGG
5641  GTTCCGCTAT CGGCTGAATT TGATTGCGAG TGAGATATTT ATGCCAGCCA GCCAGACGCA
      CAAGGCGATA GCCGACTTAA ACTAACGCTC ACTCTATAAA TACGGTCGGT CGGTCTGCGT
5701  GACGCGCCGA GACAGAACTT AATGGGCCCG CTAACGCGGC GATTTGCTGG TGACCCAATG
      CTGCGCGGCT CTGTCTTGAA TTACCCGGGC GATTGTCGCG CTAAACGACC ACTGGGTTAC
5761  CGACCAGATG CTCCACGCCC AGTCGCGTAC CGTCTTCATG GGAGAAAATA ATACTGTTGA
      GCTGGTCTAC GAGGTGCGGG TCAGCGCATG CAGAAGTAC CCTCTTTTAT TATGACAACT
5821  TGGGTGTCTG GTCAGAGACA TCAAGAAATA ACGCCGGAAC ATTAGTGCAG GCAGCTTCCA
      ACCCACAGAC CAGTCTCTGT AGTTCTTTAT TGCGGCCTTG TAATCACGTC CGTCGAAGGT
5881  CAGCAATGGC ATCCTGGTCA TCCAGCGGAT AGTAATGAT CAGCCCACTG ACGCGTTGCG
      GTCGTTACCG TAGGACCAGT AGGTCGCCTA TCAATTACTA GTCGGGTGAC TGCGCAACGC
```

Fig. 23₃

```
5941  CGAGAAGATT GTGCACCGCC GCTTTACAGG CTTCGACGCC GCTTCGTTCT ACCATCGACA
      GCTCTTCTAA CACGTGGCGG CGAAATGTCC GAAGCTGCGG CGAAGCAAGA TGGTAGCTGT
6001  CCACCACGCT GGCACCCAGT TGATCGGCGC GAGATTTAAT CGCCGCGACA ATTTGCGACG
      GGTGGTGCGA CCGTGGGTCA ACTAGCCGCG CTCTAAATTA GCGGCGCTGT TAAACGCTGC
6061  GCGCGTGCAG GGCCAGACTG GAGGTGGCAA CGCCAATCAG CAACGACTGT TTGCCCGCCA
      CGCGCACGTC CCGGTCTGAC CTCCACCGTT GCGGTTAGTC GTTGCTGACA AACGGGCGGT
6121  GTTGTTGTGC CACGCGGTTG GGAATGTAAT TCAGCTCCGC CATCGCCGCT TCCACTTTTT
      CAACAACACG GTGCGCCAAC CCTTACATTA AGTCGAGGCG GTAGCGGCGA AGGTGAAAAA
6181  CCCGCGTTTT CGCAGAAACG TGGCTGGCCT GGTTCACCAC GCGGGAAACG GTCTGATAAG
      GGGCGCAAAA GCGTCTTTGC ACCGACCGGA CCAAGTGGTG CGCCCTTTGC CAGACTATTC
6241  AGACACCGGC ATACTCTGCG ACATCGTATA ACGTTACTGG TTTCACATTC ACCACCCTGA
      TCTGTGGCCG TATGAGACGC TGTAGCATAT TGCAATGACC AAAGTGTAAG TGGTGGGACT
6301  ATTGACTCTC TTCCGGGCGC TATCATGCCA TACCGCGAAA GGTTTTGCGC CATTCGATGG
      TAACTGAGAG AAGGCCCGCG ATAGTACGGT ATGGCGCTTT CCAAAACGCG GTAAGCTACC
                                                        EcoNI
                                                  ~~~~~~~~~~~~
6361  TGTCCGGGAT CTCGACGCTC TCCCTTATGC GACTCCTGCA TTAGGAAATT AATACGACTC
      ACAGGCCCTA GAGCTGCGAG AGGGAATACG CTGAGGACGT AATCCTTTAA TTATGCTGAG
6421  ACTATA
      TGATAT
```

Fig. 23₄

| Fig. 25₁ |
|---|
| Fig. 25₂ |
| Fig. 25₃ |
| Fig. 25₄ |

Fig. 25 pDEST-CM4 sequence

```
   1  GGGGAATTGT GAGCGGATAA CAATTCCCCT CTAGAAATAA TTTTGTTTAA CTTTAAGAAG
      CCCCTTAACA CTCGCCTATT GTTAAGGGGA GATCTTTATT AAAACAAATT GAAATTCTTC
                                                                SacI
                                                                ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGGACCAT GATTACGCCA AGCTATCAAC TTTGTATAGA AAAGTTGAAC GAGAAACGTA
      GAGCCTGGTA CTAATGCGGT TCGATAGTTG AAACATATCT TTTCAACTTG CTCTTTGCAT
 181  AAATGATATA AATATCAATA TATTAAATTA GATTTTGCAT AAAAAACAGA CTACATAATA
      TTTACTATAT TTATAGTTAT ATAATTTAAT CTAAAACGTA TTTTTTGTCT GATGTATTAT
                                                 PstI
                                                 ~~~~~~~
 241  CTGTAAAACA CAACATATCC AGTCACTATG GTCGACCTGC AGACTGGCTG TGTATAAGGG
      GACATTTTGT GTTGTATAGG TCAGTGATAC CAGCTGGACG TCTGACCGAC ACATATTCCC
 301  AGCCTGACAT TTATATTCCC CAGAACATCA GGTTAATGGC GTTTTTGATG TCATTTTCGC
      TCGGACTGTA AATATAAGGG GTCTTGTAGT CCAATTACCG CAAAAACTAC AGTAAAAGCG
 361  GGTGGCTGAG ATCAGCCACT TCTTCCCCGA TAACGGAGAC CGGCACACTG GCCATATCGG
      CCACCGACTC TAGTCGGTGA AGAAGGGGCT ATTGCCTCTG GCCGTGTGAC CGGTATAGCC
 421  TGGTCATCAT GCGCCAGCTT TCATCCCCGA TATGCACCAC CGGGTAAAGT TCACGGGGGA
      ACCAGTAGTA CGCGGTCGAA AGTAGGGGCT ATACGTGGTG GCCCATTTCA AGTGCCCCCT
 481  CTTTATCTGA CAGCAGACGT GCACTGGCCA GGGGGATCAC CATCCGTCGC CCGGGCGTGT
      GAAATAGACT GTCGTCTGCA CGTGACCGGT CCCCCTAGTG GTAGGCAGCG GGCCCGCACA
 541  CAATAATATC ACTCTGTACA TCCACAAACA GACGATAACG GCTCTCTCTT TTATAGGTGT
      GTTATTATAG TGAGACATGT AGGTGTTTGT CTGCTATTGC CGAGAGAGAA AATATCCACA
 601  AAACCTTAAA CTGCATTTCA CCAGCCCCTG TTCTCGTCGG CAAAAGAGCC GTTCATTTCA
      TTTGGAATTT GACGTAAAGT GGTCGGGGAC AAGAGCAGCC GTTTTCTCGG CAAGTAAAGT
 661  ATAAACCGGG CGACCTCAGC CATCCCTTCC TGATTTTCCG CTTTCCAGCC TTCGGCACGC
      TATTTGGCCC GCTGGAGTCG GTAGGGAAGG ACTAAAAGGC GAAAGGTCGC AAGCCGTGCG
 721  AGACGACGGG CTTCATTCTG CATGGTTGTG CTTACCGAAC CGGAGATATT GACATCATAT
      TCTGCTGCCC GAAGTAAGAC GTACCAACAC GAATGGCTTG GCCTCTATAA CTGTAGTATA
 781  ATGCCTTGAG CAACTGATAG CTGTCGCTGT CAACTGTCAC TGTAATACGC TGCTTCATAG
      TACGGAACTC GTTGACTATC GACAGCGACA GTTGACAGTG ACATTATGCG ACGAAGTATC
 841  CATACCTCTT TTTGACATAC TTCGGGTATA CATATCAGTA TATATTCTTA TACCGCAAAA
      GTATGGAGAA AAACTGTATG AAGCCCATAT GTATAGTCAT ATATAAGAAT ATGGCGTTTT
 901  ATCAGCGCGC AAATACGCAT ACTGTTATCT GGCTTTTAGT AAGCCGGATC CTCTAGATTA
      TAGTCGCGCG TTTATGCGTA TGACAATAGA CCGAAAATCA TTCGGCCTAG GAGATCTAAT
 961  CGCCCCGCCC TGCCACTCAT CGCAGTACTG TTGTAATTCA TTAAGCATTC TGCCGACATG
      GCGGGGCGGG ACGGTGAGTA GCGTCATGAC AACATTAAGT AATTCGTAAG ACGGCTGTAC
1021  GAAGCCATCA CAAACGGCAT GATGAACCTG AATCGCCAGC GGCATCAGCA CCTTGTCGCC
      CTTCGGTAGT GTTTGCCGTA CTACTTGGAC TTAGCGGTCG CCGTAGTCGT GGAACAGCGG
1081  TTGCGTATAA TATTTGCCCA TGGTGAAAAC GGGGGCGAAG AAGTTGTCCA TATTGGCCAC
      AACGCATATT ATAAACGGGT ACCACTTTTG CCCCCGCTTC TTCAACAGGT ATAACCGGTG
1141  GTTTAAATCA AAACTGGTGA AACTCACCCA GGGATTGGCT GAGACGAAAA ACATATTCTC
      CAAATTTAGT TTTGACCACT TTGAGTGGGT CCCTAACCGA CTCTGCTTTT TGTATAAGAG
1201  AATAAACCCT TTAGGGAAAT AGGCCAGGTT TCACCGTAA CACGCCACAT CTTGCGAATA
      TTATTTGGGA AATCCCTTTA TCCGGTCCAA AAGTGGCATT GTGCGGTGTA GAACGCTTAT
1261  TATGTGTAGA AACTGCCGGA AATCGTCGTG GTATTCACTC CAGAGCGATG AAAACGTTTC
      ATACACATCT TTGACGGCCT TTAGCAGCAC CATAAGTGAG GTCTCGCTAC TTTTGCAAAG
1321  AGTTTGCTCA TGGAAAACGG TGTAACAAGG GTGAACACTA TCCCATATCA CCAGCTCACC
      TCAAACGAGT ACCTTTTGCC ACATTGTTCC CACTTGTGAT AGGGTATAGT GGTCGAGTGG
1381  GTCTTTCATT GCCATACGGA ATTCCGGATG AGCATTCATC AGGCGGGCAA GAATGTGAAT
      CAGAAAGTAA CGGTATGCCT TAAGGCCTAC TCGTAAGTAG TCCGCCCGTT CTTACACTTA
1441  AAAGGCCGGA TAAAACTTGT GCTTATTTTT CTTTACGGTC TTTAAAAAGG CCGTAATATC
      TTTCCGGCCT ATTTTGAACA CGAATAAAAA GAAATGCCAG AAATTTTTCC GGCATTATAG
1501  CAGCTGAACG GTCTGGTTAT AGGTACATTG AGCAACTGAC TGAAATGCCT CAAAATGTTC
      GTCGACTTGC CAGACCAATA TCCATGTAAC TCGTTGACTG ACTTTACGGA GTTTTACAAG
1561  TTTACGATGC CATTGGGATA TATCAACGGT GGTATATCCA GTGATTTTTT CTCCATTTT
      AAATGCTACG GTAACCCTAT ATAGTTGCCA CCATATAGGT CACTAAAAAA GAGGTAAAA
1621  AGCTTCCTTA GCTCCTGAAA ATCTCGACGG ATCCTAACTC AAAATCCACA CATTATACGA
      TCGAAGGAAT CGAGGACTTT TAGAGCTGCC TAGGATTGAG TTTTAGGTGT GTAATATGCT
1681  GCCGGAAGCA TAAAGTGTAA AGCCTGGGGG TGCCTAATGC GGCCGCCATA GTGACTGGAT
      CGGCCTTCGT ATTTCACATT TCGGACCCCC ACGGATTACG CCGGCGGTAT CACTGACCTA
1741  ATGTTGTGTT TTACAGTATT ATGTAGTCTG TTTTTTATGC AAAATCTAAT TTAATATATT
      TACAACACAA AATGTCATAA TACATCAGAC AAAAAATACG TTTTAGATTA AATTATATAA
```

Fig. 25₁

```
1801  GATATTTATA TCATTTTACG TTTCTCGTTC AACTTTATTA TACATAGTTG ATAATTCACT
      CTATAAATAT AGTAAAATGC AAAGAGCAAG TTGAAATAAT ATGTATCAAC TATTAAGTGA
1861  GGCCGTCGTT TTACAACGTC GTGACTGGGA AAACCCTGGC GTTACCCAAC TTAATCGCCT
      CCGGCAGCAA AATGTTGCAG CACTGACCCT TTTGGGACCG CAATGGGTTG AATTAGCGGA
               HindIII
               ~~~~~~~
1921  TGCAGCACAA GCTTGCGGCC GCATAATGCT TAAGTCGAAC AGAAAGTAAT CGTATTGTAC
      ACGTCGTGTT CGAACGCCGG CGTATTACGA ATTCAGCTTG TCTTTCATTA GCATAACATG
1981  ACGGCCGCAT AATCGAAATT AATACGACTC ACTATAGGGG AATTGTGAGC GGATAACAAT
      TGCCGGCGTA TTAGCTTTAA TTATGCTGAG TGATATCCCC TTAACACTCG CCTATTGTTA
2041  TCCCCATCTT AGTATATTAG TTAAGTATAA GAAGGAGATA TACATATGGC AGATCTCAAT
      AGGGGTAGAA TCATATAATC AATTCATATT CTTCCTCTAT ATGTATACCG TCTAGAGTTA
2101  TGGATATCGG CCGGCCACGC GATCGCTGAC GTCGGTACCC TCGAGTCTGG TAAAGAAACC
      ACCTATAGCC GGCCGGTGCG CTAGCGACTG CAGCCATGGG AGCTCAGACC ATTTCTTTGG
                                                                  AvrII
                                                                  ~~
2161  GCTGCTGCGA AATTGAACG CCAGCACATG GACTCGTCTA CTAGCGCAGC TTAATTAACC
      CGACGACGCT TTAAACTTGC GGTCGTGTAC CTGAGCAGAT GATCGCGTCG AATTAATTGG
      AvrII
      ~~~~
2221  TAGGCTGCTG CCACCGCTGA GCAATAACTA GCATAACCCC TTGGGGCCTC TAAACGGGTC
      ATCCGACGAC GGTGGCGACT CGTTATTGAT CGTATTGGGG AACCCCGGAG ATTTGCCCAG
2281  TTGAGGGGTT TTTTGCTGAA AGGAGGAACT ATATCCGGAT TGGCGAATGG GACGCGCCCT
      AACTCCCCAA AAAACGACTT TCCTCCTTGA TATAGGCCTA ACCGCTTACC CTGCGCGGGA
2341  GTAGCGCGC ATTAAGCGCG GCGGGTGTGG TGGTTACGCG CAGCGTGACC GCTACACTTG
      CATCGCGCG TAATTCGCGC CGCCCACACC ACCAATGCGC GTCGCACTGG CGATGTGAAC
2401  CCAGCGCCCT AGCGCCCGCT CCTTTCGCTT TCTTCCCTTC CTTTCTCGCC ACGTTCGCCG
      GGTCGCGGGA TCGCGGGCGA GGAAAGCGAA AGAAGGGAAG GAAAGAGCGG TGCAAGCGGC
2461  GCTTTCCCCG TCAAGCTCTA AATCGGGGGC TCCCTTTAGG GTTCCGATTT AGTGCTTTAC
      CGAAAGGGGC AGTTCGAGAT TTAGCCCCCG AGGGAAATCC CAAGGCTAAA TCACGAAATG
2521  GGCACCTCGA CCCCAAAAAA CTTGATTAGG GTGATGGTTC ACGTAGTGGG CCATCGCCCT
      CCGTGGAGCT GGGGTTTTTT GAACTAATCC CACTACCAAG TGCATCACCC GGTAGCGGGA
2581  GATAGACGGT TTTTCGCCCT TTGACGTTGG AGTCCACGTT CTTTAATAGT GGACTCTTGT
      CTATCTGCCA AAAAGCGGGA AACTGCAACC TCAGGTGCAA GAAATTATCA CCTGAGAACA
2641  TCCAAACTGG AACAACACTC AACCCTATCT CGGTCTATTC TTTTGATTTA TAAGGGATTT
      AGGTTTGACC TTGTTGTGAG TTGGGATAGA GCCAGATAAG AAAACTAAAT ATTCCCTAAA
2701  TGCCGATTTC GGCCTATTGG TTAAAAAATG AGCTGATTTA ACAAAAATTT AACGCGAATT
      ACGGCTAAAG CCGGATAACC AATTTTTTAC TCGACTAAAT TGTTTTTAAA TTGCGCTTAA
2761  TTAACAAAAT ATTAACGTTT ACAATTTCTG GCGGCACGAT GGCATGAGAT TATCAAAAAG
      AATTGTTTTA TAATTGCAAA TGTTAAAGAC CGCCGTGCTA CCGTACTCTA ATAGTTTTTC
2821  GATCTTCACC TAGATCCTTT TAAATTAAAA ATGAAGTTTT AAATCAATCT AAAGTATATA
      CTAGAAGTGG ATCTAGGAAA ATTTAATTTT TACTTCAAAA TTTAGTTAGA TTTCATATAT
2881  TGAGTAAACT TGGTCTGACA GTTACCAATG CTTAATCAGT GAGGCACCTA TCTCAGCGAT
      ACTCATTTGA ACCAGACTGT CAATGGTTAC GAATTAGTCA CTCCGTGGAT AGAGTCGCTA
2941  CTGTCTATTT CGTTCATCCA TAGTTGCCTG ACTCCCCGTC GTGTAGATAA CTACGATACG
      GACAGATAAA GCAAGTAGGT ATCAACGGAC TGAGGGGCAG CACATCTATT GATGCTATGC
3001  GGAGGGCTTA CCATCTGGCC CCAGTGCTGC AATGATACCG CGAGACCCAC GCTCACCGGC
      CCTCCCGAAT GGTAGACCGG GGTCACGACG TTACTATGGC GCTCTGGGTG CGAGTGGCCG
3061  TCCAGATTTA TCAGCAATAA ACCAGCCAGC CGGAAGGGCC GAGCGCAGAA GTGGTCCTGC
      AGGTCTAAAT AGTCGTTATT TGGTCGGTCG GCCTTCCCGG CTCGCGTCTT CACCAGGACG
3121  AACTTTATCC GCCTCCATCC AGTCTATTAA TTGTTGCCGG GAAGCTAGAG TAAGTAGTTC
      TTGAAATAGG CGGAGGTAGG TCAGATAATT AACAACGGCC CTTCGATCTC ATTCATCAAG
3181  GCCAGTTAAT AGTTTGCGCA ACGTTGTTGC CATTGCTACA GGCATCGTGG TGTCACGCTC
      CGGTCAATTA TCAAACGCGT TGCAACAACG GTAACGATGT CCGTAGCACC ACAGTGCGAG
3241  GTCGTTTGGT ATGGCTTCAT TCAGCTCCGG TTCCCAACGA TCAAGGCGAG TTACATGATC
      CAGCAAACCA TACCGAAGTA AGTCGAGGCC AAGGGTTGCT AGTTCCGCTC AATGTACTAG
3301  CCCCATGTTG TGCAAAAAAG CGGTTAGCTC CTTCGGTCCT CCGATCGTTG TCAGAAGTAA
      GGGGTACAAC ACGTTTTTTC GCCAATCGAG GAAGCCAGGA GGCTAGCAAC AGTCTTCATT
3361  GTTGGCCGCA GTGTTATCAC TCATGGTTAT GGCAGCACTG CATAATTCTC TTACTGTCAT
      CAACCGGCGT CACAATAGTG AGTACCAATA CCGTCGTGAC GTATTAAGAG AATGACAGTA
3421  GCCATCCGTA AGATGCTTTT CTGTGACTGG TGAGTACTCA ACCAAGTCAT TCTGAGAATA
      CGGTAGGCAT TCTACGAAAA GACACTGACC ACTCATGAGT TGGTTCAGTA AGACTCTTAT
3481  GTGTATGCGG CGACCGAGTT GCTCTTGCCC GGCGTCAATA CGGGATAATA CCGCGCCACA
      CACATACGCC GCTGGCTCAA CGAGAACGGG CCGCAGTTAT GCCCTATTAT GGCGCGGTGT
3541  TAGCAGAACT TTAAAAGTGC TCATCATTGG AAAACGTTCT TCGGGGCGAA AACTCTCAAG
      ATCGTCTTGA AATTTTCACG AGTAGTAACC TTTTGCAAGA AGCCCCGCTT TTGAGAGTTC
3601  GATCTTACCG CTGTTGAGAT CCAGTTCGAT GTAACCCACT CGTGCACCCA ACTGATCTTC
      CTAGAATGGC GACAACTCTA GGTCAAGCTA CATTGGGTGA GCACGTGGGT TGACTAGAAG
3661  AGCATCTTTT ACTTTCACCA GCGTTTCTGG GTGAGCAAAA ACAGGAAGGC AAAATGCCGC
      TCGTAGAAAA TGAAAGTGGT CGCAAAGACC CACTCGTTTT TGTCCTTCCG TTTTACGGCG
3721  AAAAAGGGA ATAAGGGCGA CACGGAAATG TTGAATACTC ATACTCTTCC TTTTTCAATC
```

Fig. 25₂

```
      TTTTTTCCCT TATTCCCGCT GTGCCTTTAC AACTTATGAG TATGAGAAGG AAAAAGTTAG
3781  ATGATTGAAG CATTTATCAG GGTTATTGTC TCATGAGCGG ATACATATTT GAATGTATTT
      TACTAACTTC GTAAATAGTC CCAATAACAG AGTACTCGCC TATGTATAAA CTTACATAAA
3841  AGAAAAATAA ACAAATAGGT CATGACCAAA ATCCCTTAAC GTGAGTTTTC GTTCCACTGA
      TCTTTTTATT TGTTTATCCA GTACTGGTTT TAGGGAATTG CACTCAAAAG CAAGGTGACT
3901  GCGTCAGACC CCGTAGAAAA GATCAAAGGA TCTTCTTGAG ATCCTTTTTT TCTGCGCGTA
      CGCAGTCTGG GGCATCTTTT CTAGTTTCCT AGAAGAACTC TAGGAAAAAA AGACGCGCAT
3961  ATCTGCTGCT TGCAAACAAA AAAACCACCG CTACCAGCGG TGGTTTGTTT GCCGGATCAA
      TAGACGACGA ACGTTTGTTT TTTTGGTGGC GATGGTCGCC ACCAAACAAA CGGCCTAGTT
4021  GAGCTACCAA CTCTTTTTCC GAAGGTAACT GGCTTCAGCA GAGCGCAGAT ACCAAATACT
      CTCGATGGTT GAGAAAAAGG CTTCCATTGA CCGAAGTCGT CTCGCGTCTA TGGTTTATGA
4081  GTCCTTCTAG TGTAGCCGTA GTTAGGCCAC CACTTCAAGA ACTCTGTAGC ACCGCCTACA
      CAGGAAGATC ACATCGGCAT CAATCCGGTG GTGAAGTTCT TGAGACATCG TGGCGGATGT
4141  TACCTCGCTC TGCTAATCCT GTTACCAGTG GCTGCTGCCA GTGGCGATAA GTCGTGTCTT
      ATGGAGCGAG ACGATTAGGA CAATGGTCAC CGACGACGGT CACCGCTATT CAGCACAGAA
4201  ACCGGGTTGG ACTCAAGACG ATAGTTACCG GATAAGGCGC AGCGGTCGGG CTGAACGGGG
      TGGCCCAACC TGAGTTCTGC TATCAATGGC CTATTCCGCG TCGCCAGCCC GACTTGCCCC
4261  GGTTCGTGCA CACAGCCCAG CTTGGAGCGA ACGACCTACA CCGAACTGAG ATACCTACAG
      CCAAGCACGT GTGTCGGGTC GAACCTCGCT TGCTGGATGT GGCTTGACTC TATGGATGTC
4321  CGTGAGCTAT GAGAAAGCGC CACGCTTCCC GAAGGGAGAA AGGCGGACAG GTATCCGGTA
      GCACTCGATA CTCTTTCGCG GTGCGAAGGG CTTCCCTCTT TCCGCCTGTC CATAGGCCAT
4381  AGCGGCAGGG TCGGAACAGG AGAGCGCACG AGGGAGCTTC CAGGGGGAAA CGCCTGGTAT
      TCGCCGTCCC AGCCTTGTCC TCTCGCGTGC TCCCTCGAAG GTCCCCCTTT GCGGACCATA
4441  CTTTATAGTC CTGTCGGGTT TCGCCACCTC TGACTTGAGC GTCGATTTTT GTGATGCTCG
      GAAATATCAG GACAGCCCAA AGCGGTGGAG ACTGAACTCG CAGCTAAAAA CACTACGAGC
4501  TCAGGGGGGC GGAGCCTATG GAAAAACGCC AGCAACGCGG CCTTTTTACG GTTCCTGGCC
      AGTCCCCCCG CCTCGGATAC CTTTTTGCGG TCGTTGCGCC GGAAAAATGC CAAGGACCGG
4561  TTTTGCTGGC CTTTTGCTCA CATGTTCTTT CCTGCGTTAT CCCCTGATTC TGTGGATAAC
      AAAACGACCG GAAAACGAGT GTACAAGAAA GGACGCAATA GGGGACTAAG ACACCTATTG
4621  CGTATTACCG CCTTTGAGTG AGCTGATACC GCTCGCCGCA GCCGAACGAC CGAGCGCAGC
      GCATAATGGC GGAAACTCAC TCGACTATGG CGAGCGGCGT CGGCTTGCTG GCTCGCGTCG
4681  GAGTCAGTGA GCGAGGAAGC GGAAGAGCGC CTGATGCGGT ATTTTCTCCT TACGCATCTG
      CTCAGTCACT CGCTCCTTCG CCTTCTCGCG GACTACGCCA TAAAAGAGGA ATGCGTAGAC
4741  TGCGGTATTT CACACCGCAT ATATGGTGCA CTCTCAGTAC AATCTGCTCT GATGCCGCAT
      ACGCCATAAA GTGTGGCGTA TATACCACGT GAGAGTCATG TTAGACGAGA CTACGGCGTA
4801  AGTTAAGCCA GTATACACTC CGCTATCGCT ACGTGACTGG GTCATGGCTG CGCCCCGACA
      TCAATTCGGT CATATGTGAG GCGATAGCGA TGCACTGACC CAGTACCGAC GCGGGGCTGT
4861  CCCGCCAACA CCCGCTGACG CGCCCTGACG GGCTTGTCTG CTCCCGGCAT CCGCTTACAG
      GGGCGGTTGT GGGCGACTGC GCGGGACTGC CCGAACAGAC GAGGGCCGTA GGCGAATGTC
4921  ACAAGCTGTG ACCGTCTCCG GGAGCTGCAT GTGTCAGAGG TTTTCACCGT CATCACCGAA
      TGTTCGACAC TGGCAGAGGC CCTCGACGTA CACAGTCTCC AAAAGTGGCA GTAGTGGCTT
4981  ACGCGCGAGG CAGCTGCGGT AAAGCTCATC AGCGTGGTCG TGAAGCGATT CACAGATGTC
      TGCGCGCTCC GTCGACGCCA TTTCGAGTAG TCGCACCAGC ACTTCGCTAA GTGTCTACAG
5041  TGCCTGTTCA TCCGCGTCCA GCTCGTTGAG TTTCTCCAGA AGCGTTAATG TCTGGCTTCT
      ACGGACAAGT AGGCGCAGGT CGAGCAACTC AAAGGAGGTCT TCGCAATTAC AGACCGAAGA
5101  GATAAAGCGG GCCATGTTAA GGGCGGTTTT TTCCTGTTTG GTCACTGATG CCTCCGTGTA
      CTATTTCGCC CGGTACAATT CCCGCCAAAA AAGGACAAAC CAGTGACTAC GGAGGCACAT
5161  AGGGGGATTT CTGTTCATGG GGGTAATGAT ACCGATGAAA CGAGAGAGGA TGCTCACGAT
      TCCCCCTAAA GACAAGTACC CCCATTACTA TGGCTACTTT GCTCTCTCCT ACGAGTGCTA
5221  ACGGGTTACT GATGATGAAC ATGCCCGGTT ACTGGAACGT TGTGAGGGTA ACAACTGGC
      TGCCCAATGA CTACTACTTG TACGGGCCAA TGACCTTGCA ACACTCCCAT TTGTTGACCG
5281  GGTATGGATG CGGCGGGACC AGAGAAAAAT CACTCAGGGT CAATGCCAGC GCTTCGTTAA
      CCATACCTAC GCCGCCCTGG TCTCTTTTTA GTGAGTCCCA GTTACGGTCG CGAAGCAATT
5341  TACAGATGTA GGTGTTCCAC AGGGTAGCCA GCAGCATCCT GCGATGCAGA TCCGGAACAT
      ATGTCTACAT CCACAAGGTG TCCCATCGGT CGTCGTAGGA CGCTACGTCT AGGCCTTGTA
5401  AATGGTGCAG GCGCTGACT TCCGCGTTTC CAGACTTTAC GAAACACGGA AACCGAAGAC
      TTACCACGTC CCGCGACTGA AGGCGCAAAG GTCTGAAATG CTTTGTGCCT TTGGCTTCTG
5461  CATTCATGTT GTTGCTCAGG TCGCAGACGT TTTGCAGCAG CAGTCGCTTC ACGTTCGCTC
      GTAAGTACAA CAACGAGTCC AGCGTCTGCA AAACGTCGTC GTCAGCGAAG TGCAAGCGAG
5521  GCGTATCGGT GATTCATTCT GCTAACCAGT AAGGCAACCC CGCCAGCCTA GCCGGGTCCT
      CGCATAGCCA CTAAGTAAGA CGATTGGTCA TTCCGTTGGG GCGGTCGGAT CGGCCCAGGA
5581  CAACGACAGG AGCACGATCA TGCTAGTCAT GCCCCGCGCC CACCGGAAGG AGCTGACTGG
      GTTGCTGTCC TCGTGCTAGT ACGATCAGTA CGGGGCGCGG GTGGCCTTCC TCGACTGACC
5641  GTTGAAGCT CTCAAGGGCA TCGGTCGAGA TCCCGGTGCC TAATGGTGA GCTAACTTAC
      CAACTTCCGA GAGTTCCCGT AGCCAGCTCT AGGGCCACGG ATTACTCACT CGATTGAATG
5701  ATTAATTGCG TTGCGCTCAC TGCCCGCTTT CCAGTCGGGA AACCTGTCGT GCCAGCTGCA
      TAATTAACGC AACGCGAGTG ACGGGCGAAA GGTCAGCCCT TTGGACAGCA CGGTCGACGT
5761  TTAATGAATC GGCCAACGCG CGGGGAGAGG CGGTTTGCGT ATTGGGCGCC AGGGTGGTTT
      AATTACTTAG CCGGTTGCGC GCCCCTCTCC GCCAAACGCA TAACCCGCGG TCCCACCAAA
5821  TTCTTTTCAC CAGTGAGACG GGCAACAGCT GATTGCCCTT CACCGCCTGG CCCTGAGAGA
```

Fig. 25₃

```
        AAGAAAAGTG GTCACTCTGC CCGTTGTCGA CTAACGGGAA GTGGCGGACC GGGACTCTCT
5881    GTTGCAGCAA GCGGTCCACG CTGGTTTGCC CCAGCAGGCG AAAATCCTGT TTGATGGTGG
        CAACGTCGTT CGCCAGGTGC GACCAAACGG GGTCGTCCGC TTTTAGGACA AACTACCACC
5941    TTAACGGCGG GATATAACAT GAGCTGTCTT CGGTATCGTC GTATCCCACT ACCGAGATGT
        AATTGCCGCC CTATATTGTA CTCGACAGAA GCCATAGCAG CATAGGGTGA TGGCTCTACA
6001    CCGCACCAAC GCGCAGCCCG GACTCGGTAA TGGCGCGCAT GCGCCCAGC GCCATCTGAT
        GGCGTGGTTG CGCGTCGGGC CTGAGCCATT ACCGCGCGTA ACGCGGGTCG CGGTAGACTA
6061    CGTTGGCAAC CAGCATCGCA GTGGGAACGA TGCCCTCATT CAGCATTTGC ATGGTTTGTT
        GCAACCGTTG GTCGTAGCGT CACCCTTGCT ACGGGAGTAA GTCGTAAACG TACCAAACAA
6121    GAAAACCGGA CATGGCACTC CAGTCGCCTT CCCGTTCCGC TATCGGCTGA ATTTGATTGC
        CTTTTGGCCT GTACCGTGAG GTCAGCGGAA GGGCAAGGCG ATAGCCGACT TAAACTAACG
6181    GAGTGAGATA TTTATGCCAG CCAGCCAGAC GCAGACGCGC CGAGACAGAA CTTAATGGGC
        CTCACTCTAT AAATACGGTC GGTCGGTCTG CGTCTGCGCG GCTCTGTCTT GAATTACCCG
6241    CCGCTAACAG CGCGATTTGC TGGTGACCCA ATGCGACCAG ATGCTCCACG CCCAGTCGCG
        GGCGATTGTC GCGCTAAACG ACCACTGGGT TACGCTGGTC TACGAGGTGC GGGTCAGCGC
6301    TACCGTCTTC ATGGAGAAA ATAATACTGT TGATGGGTGT CTGGTCAGAG ACATCAAGAA
        ATGGCAGAAG TACCCTCTTT TATTATGACA ACTACCCACA GACCAGTCTC TGTAGTTCTT
6361    ATAACGCCGG AACATTAGTG CAGGCAGCTT CCACAGCAAT GGCATCCTGG TCATCCAGCG
        TATTGCGGCC TTGTAATCAC GTCCGTCGAA GGTGTCGTTA CCGTAGGACC AGTAGGTCGC
6421    GATAGTTAAT GATCAGCCCA CTGACGCGTT GCGCGAGAAG ATTGTGCACC GCCGCTTTAC
        CTATCAATTA CTAGTCGGGT GACTGCGCAA CGCGCTCTTC TAACACGTGG CGGCGAAATG
6481    AGGCTTCGAC GCCGCTTCGT TCTACCATCG ACACCACCAC GCTGGCACCC AGTTGATCGG
        TCCGAAGCTG CGGCGAAGCA AGATGGTAGC TGTGGTGGTG CGACCGTGGG TCAACTAGCC
6541    CGCGAGATTT AATCGCCGCG ACAATTTGCG ACGGCGCGTG CAGGGCCAGA CTGGAGGTGG
        GCGCTCTAAA TTAGCGGCGC TGTTAAACGC TGCCGCGCAC GTCCCGGTCT GACCTCCACC
6601    CAACGCCAAT CAGCAACGAC TGTTTGCCCG CCAGTTGTTG TGCCACGCGG TTGGGAATGT
        GTTGCGGTTA GTCGTTGCTG ACAAACGGGC GGTCAACAAC ACGGTGCGCC AACCCTTACA
6661    AATTCAGCTC CGCCATCGCC GCTTCCACTT TTTCCCGCGT TTTCGCAGAA ACGTGGCTGG
        TTAAGTCGAG GCGGTAGCGG CGAAGGTGAA AAAGGGCGCA AAAGCGTCTT TGCACCGACC
6721    CCTGGTTCAC CACGCGGGAA ACGGTCTGAT AAGAGACACC GGCATACTCT GCGACATCGT
        GGACCAAGTG GTGCGCCCTT TGCCAGACTA TTCTCTGTGG CCGTATGAGA CGCTGTAGCA
6781    ATAACGTTAC TGGTTTCACA TTCACCACCC TGAATTGACT CTCTTCCGGG CGCTATCATG
        TATTGCAATG ACCAAAGTGT AAGTGGTGGG ACTTAACTGA GAGAAGGCCC GCGATAGTAC
6841    CCATACCGCG AAAGGTTTTG CGCCATTCGA TGGTGTCCGG GATCTCGACG CTCTCCCTTA
        GGTATGGCGC TTTCCAAAAC GCGGTAAGCT ACCACAGGCC CTAGAGCTGC GAGAGGGAAT
6901    TGCGACTCCT GCATTAGGAA GCAGCCCAGT AGTAGGTTGA GGCCGTTGAG CACCGCCGCC
        ACGCTGAGGA CGTAATCCTT CGTCGGGTCA TCATCCAACT CCGGCAACTC GTGGCGGCGG
6961    GCAAGGAATG GTGCATGCAA GGAGATGGCG CCCAACAGTC CCCCGGCCAC GGGGCCTGCC
        CGTTCCTTAC CACGTACGTT CCTCTACCGC GGGTTGTCAG GGGGCCGGTG CCCCGGACGG
7021    ACCATACCCA CGCCGAAACA AGCGCTCATG AGCCCGAAGT GGCGAGCCCG ATCTTCCCCA
        TGGTATGGGT GCGGCTTTGT TCGCGAGTAC TCGGGCTTCA CCGCTCGGGC TAGAAGGGGT
7081    TCGGTGATGT CGGCGATATA GGCGCCAGCA ACCGCACCTG TGGCGCCGGT GATGCCGGCC
        AGCCACTACA GCCGCTATAT CCGCGGTCGT TGGCGTGGAC ACCGCGGCCA CTACGGCCGG
                                                      ClaI
                                                      ~~~~~~~
7141    ACGATGCGTC CGGCGTAGAG GATCGAGATC GATCTCGATC CCGCGAAATT AATACGACTC
        TGCTACGCAG GCCGCATCTC CTAGCTCTAG CTAGAGCTAG GGCGCTTTAA TTATGCTGAG
7201    ACTATA
        TGATAT
```

Fig. 25₄

| Fig. 28₁ |
|---|
| Fig. 28₂ |
| Fig. 28₃ |

Fig. 28

```
  1  GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                               EcoRI
                                                              ~~~~~~
              NcoI                              BamHI       SacI
             ~~~~~~~                           ~~~~~~       ~~~
 61  GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
121  CTCGATCACA AGTTTGTACA AAAAAGCTGA ACGAGAAACG TAAAATGATA TAAATATCAA
     GAGCTAGTGT TCAAACATGT TTTTTCGACT TGCTCTTTGC ATTTTACTAT ATTTATAGTT
181  TATATTAAAT TAGATTTTGC ATAAAAAACA GACTACATAA TACTGTAAAA CACAACATAT
     ATATAATTTA ATCTAAAACG TATTTTTTGT CTGATGTATT ATGACATTTT GTGTTGTATA
                         NotI
                    ~~~~~~~~~
241  CCAGTCACTA TGGCGGCCGC CACGTTAAGG GATTTTGGTC ATGATCAGCA CGTGTTGACA
     GGTCAGTGAT ACCGCCGGCG GTGCAATTCC CTAAAACCAG TACTAGTCGT GCACAACTGT
                                                                  NcoI
                                                                  ~~~
301  ATTAATCATC GGCATAGTAT ATCGGCATAG TATAATACGA CAAGGTGAGG AACTAAACCA
     TAATTAGTAG CCGTATCATA TAGCCGTATC ATATTATGCT GTTCCACTCC TTGATTTGGT
     NcoI
     ~~~
361  TGGCCAAGTT GACCAGTGCC GTTCCGGTGC TCACCGCGCG CGACGTCGCC GGAGCGGTCG
     ACCGGTTCAA CTGGTCACGG CAAGGCCACG AGTGGCGCGC GCTGCAGCGG CCTCGCCAGC
421  AGTTCTGGAC CGACCGGCTC GGGTTCTCCC GGGACTTCGT GGAGGACGAC TTCGCCGGTG
     TCAAGACCTG GCTGGCCGAG CCCAAGAGGG CCCTGAAGCA CCTCCTGCTG AAGCGGCCAC
481  TGGTCCGGGA CGACGTGACC CTGTTCATCA GCGCGGTCCA GGACCAGGTG GTGCCGGACA
     ACCAGGCCCT GCTGCACTGG GACAAGTAGT CGCGCCAGGT CCTGGTCCAC CACGGCCTGT
541  ACACCCTGGC CTGGGTGTGG GTGCGCGGCC TGGACGAGCT GTACGCCGAG TGGTCGGAGG
     TGTGGGACCG GACCCACACC CACGCGCCGG ACCTGCTCGA CATGCGGCTC ACCAGCCTCC
601  TCGTGTCCAC GAACTTCCGG GACGCCTCCG GGCCGGCCAT GACCGAGATC GGCGAGCAGC
     AGCACAGGTG CTTGAAGGCC CTGCGGAGGC CCGGCCGGTA CTGGCTCTAG CCGCTCGTCG
661  CGTGGGGCCG GGAGTTCGCC CTGCGCGACC CGGCCGGCAA CTGCGTGCAC TTCGTGGCCG
     GCACCCCGGC CCTCAAGCGG GACGCGCTGG GCCGGCCGTT GACGCACGTG AAGCACCGGC
721  AGGAGCAGGA CTGATCATGA TGATATTATT TTATCTTGTG CAATGTAACA TCAGAGATTT
     TCCTCGTCCT GACTAGTACT ACTATAATAA AATAGAACAC GTTACATTGT AGTCTCTAAA
781  TGAGACACGG GCCAGAGCTG CCAGGAAACA GCTATGACCA TGTAATACGA CTCACTATAG
     ACTCTGTGCC CGGTCTCGAC GGTCCTTTGT CGATACTGGT ACATTATGCT GAGTGATATC
841  GGGATATCAG CTGGATGGCA ATAATGATT  TTATTTTGAC TGATAGTGAC CTGTTCGTTG
     CCCTATAGTC GACCTACCGT TTATTACTAA AATAAAACTG ACTATCACTG GACAAGCAAC
901  CAACACCGGT GCTAGCGTAT ACCCGAAGTA TGTCAAAAAG AGGTGTGCTA TGAAGCAGCG
     GTTGTGGCCA CGATCGCATA TGGGCTTCAT ACAGTTTTTC TCCACACGAT ACTTCGTCGC
961  TATTACAGTG ACAGTTGACA GCGACAGCTA TCAGTTGCTC AAGGCATATA TGATGTCAAT
     ATAATGTCAC TGTCAACTGT CGCTGTCGAT AGTCAACGAG TTCCGTATAT ACTACAGTTA
1021 ATCTCCGGTC TGGTAAGCAC AACCATGCAG AATGAAGCCC GTCGTCTGCG TGCCGAACGC
     TAGAGGCCAG ACCATTCGTG TTGGTACGTC TTACTTCGGG CAGCAGACGC ACGGCTTGCG
1081 TGGAAAGCGG AAAATCAGGA AGGGATGGCT GAGGTCGCCC GGTTTATTGA AATGAACGGC
     ACCTTTCGCC TTTTAGTCCT TCCCTACCGA CTCCAGCGGG CCAAATAACT TTACTTGCCG
1141 TCTTTTGCTG ACGAGAACAG GGACTGGTGA AATGCAGTTT AAGGTTTACA CCTATAAAAG
     AGAAAACGAC TGCTCTTGTC CCTGACCACT TTACGTCAAA TTCCAAATGT GGATATTTTC
1201 AGAGAGCCGT TATCGTCGT  TTGTGGATGT ACAGAGTGAT ATTATTGACA CGCCCGGGCG
     TCTCTCGGCA ATAGCAGACA AACACCTACA TGTCTCACTA TAATAACTGT GCGGGCCCGC
1261 ACGGATGGTG ATCCCCCTGG CCAGTGCACG TCTGCTGTCA GATAAAGTCT CCCGTGAACT
     TGCCTACCAC TAGGGGGACC GGTCACGTGC AGACGACAGT CTATTTCAGA GGGCACTTGA
1321 TTACCCGGTG GTGCATATCG GGGATGAAAG CTGGCGCATG ATGACCACCG ATATGGCCAG
     AATGGGCCAC CACGTATAGC CCCTACTTTC GACCGCGTAC TACTGGTGGC TATACCGGTC
1381 TGTGCCGGTC TCCGTTATCG GGGAAGAAGT GGCTGATCTC AGCCGCCGCG AAAATGACAT
     ACACGGCCAG AGGCAATAGC CCCTTCTTCA CCGACTAGAG TCGGCGGCGC TTTTACTGTA
1441 CAAAAACGCC ATTAACCTGA TGTTCTGGGG AATATAAATG TCAGGCTCCC TTATACACAG
     GTTTTTGCGG TAATTGGACT ACAAGACCCC TTATATTTAC AGTCCGAGGG AATATGTGTC
                 PstI
                 ~~~~~~~
1501 CCAGTCTGCA GGTCGACCAT AGTGACTGGA TATGTTGTGT TTTACAGTAT TATGTAGTCT
     GGTCAGACGT CCAGCTGGTA TCACTGACCT ATACAACACA AAATGTCATA ATACATCAGA
```

Fig. 28₁

1561 GTTTTTTATG CAAAATCTAA TTTAATATAT TGATATTTAT ATCATTTTAC GTTTCTCGTT
     CAAAAAATAC GTTTTAGATT AAATTATATA ACTATAAATA TAGTAAAATG CAAAGAGCAA
                                                                 HindIII
                                                                 ~~~~~~
1621 CAGCTTTCTT GTACAAAGTG GTGATAATTA ATTAAGATCA GATCCGGCTG CTAAGCTTGG
     GTCGAAAGAA CATGTTTCAC CACTATTAAT TAATTCTAGT CTAGGCCGAC GATTCGAACC
                                                          AvrII
                                                          ~~~~~~
1681 AATTGTTATC CGCTCACAAT TCCTATAGTG AGTCGTATTA CCTAGGCTGC TGCCACCGCT
     TTAACAATAG GCGAGTGTTA AGGATATCAC TCAGCATAAT GGATCCGACG ACGGTGGCGA
1741 GAGCAATAAC TAGCATAACC CCTTGGGGCC TCTAAACGGG TCTTGAGGGG TTTTTTGCTG
     CTCGTTATTG ATCGTATTGG GGAACCCCGG AGATTTGCCC AGAACTCCCC AAAAAACGAC
1801 AAACCTCAGG CATTTGAGAA GCACACGGTC ACACTGCTTC CGGTAGTCAA TAAACCGGTA
     TTTGGAGTCC GTAAACTCTT CGTGTGCCAG TGTGACGAAG GCCATCAGTT ATTTGGCCAT
1861 AACCAGCAAT AGACATAAGC GGCTATTTAA CGACCCTGCC CTGAACCGAC GACCGGGTCG
     TTGGTCGTTA TCTGTATTCG CCGATAAATT GCTGGGACGG GACTTGGCTG CTGGCCCAGC
1921 AATTTGCTTT CGAATTTCTG CCATTCATCC GCTTATTATC ACTTATTCAG GCGTAGCACC
     TTAAACGAAA GCTTAAAGAC GGTAAGTAGG CGAATAATAG TGAATAAGTC CGCATCGTGG
1981 AGGCGTTTAA GGGCACCAAT AACTGCCTTA AAAAAATTAC GCCCCGCCCT GCCACTCATC
     TCCGCAAATT CCCGTGGTTA TTGACGGAAT TTTTTTAATG CGGGGCGGGA CGGTGAGTAG
2041 GCAGTACTGT TGTAATTCAT TAAGCATTCT GCCGACATGG AAGCCATCAC AGACGGCATG
     CGTCATGACA ACATTAAGTA ATTCGTAAGA CGGCTGTACC TTCGGTAGTG TCTGCCGTAC
2101 ATGAACCTGA ATCGCCAGCG GCATCAGCAC CTTGTCGCCT TGCGTATAAT ATTTGCCCAT
     TACTTGGACT TAGCGGTCGC CGTAGTCGTG GAACAGCGGA ACGCATATTA TAAACGGGTA
2161 AGTGAAAACG GGGGCGAAGA AGTTGTCCAT ATTGGCCACG TTTAAATCAA AACTGGTGAA
     TCACTTTTGC CCCCGCTTCT TCAACAGGTA TAACCGGTGC AAATTTAGTT TTGACCACTT
2221 ACTCACCCAG GGATTGGCTG AGACGAAAAA CATATTCTCA ATAAACCCTT TAGGGAAATA
     TGAGTGGGTC CCTAACCGAC TCTGCTTTTT GTATAAGAGT TATTTGGGAA ATCCCTTTAT
2281 GGCCAGGTTT TCACCGTAAC ACGCCACATC TTGCGAATAT ATGTGTAGAA ACTGCCGGAA
     CCGGTCCAAA AGTGGCATTG TGCGGTGTAG AACGCTTATA TACACATCTT TGACGGCCTT
2341 ATCGTCGTGG TATTCACTCC AGAGCGATGA AAACGTTTCA GTTTGCTCAT GGAAAACGGT
     TAGCAGCACC ATAAGTGAGG TCTCGCTACT TTTGCAAAGT CAAACGAGTA CCTTTTGCCA
2401 GTAACAGGGG TGAACACTAT CCCATATCAC CAGCTCACCG TCTTTCATTG CCATACGGAA
     CATTGTTCCC ACTTGTGATA GGGTATAGTG GTCGAGTGGC AGAAAGTAAC GGTATGCCTT
2461 CTCCGGATGA GCATTCATCA GGCGGGCAAG AATGTGAATA AAGGCCGGAT AAAACTTGTG
     GAGGCCTACT CGTAAGTAGT CCGCCCGTTC TTACACTTAT TTCCGGCCTA TTTTGAACAC
2521 CTTATTTTTC TTTACGGTCT TTAAAAAGGC CGTAATATCC AGCTGAACGG TCTGGTTATA
     GAATAAAAAG AAATGCCAGA AATTTTTCCG GCATTATAGG TCGACTTGCC AGACCAATAT
2581 GGTACATTGA GCAACTGACT GAAATGCCTC AAAATGTTCT TTACGATGCC ATTGGGATAT
     CCATGTAACT CGTTGACTGA CTTTACGGAG TTTTACAAGA AATGCTACGG TAACCCTATA
2641 ATCAACGGTG GTATATCCAG TGATTTTTTT CTCCATTTTA GCTTCCTTAG CTCCTGAAAA
     TAGTTGCCAC CATATAGGTC ACTAAAAAAA GAGGTAAAAT CGAAGGAATC GAGGACTTTT
2701 TCTCGATAAC TCAAAAAATA CGCCCGGTAG TGATCTTATT TCATTATGGT GAAAGTTGGA
     AGAGCTATTG AGTTTTTTAT GCGGGCCATC ACTAGAATAA AGTAATACCA CTTTCAACCT
2761 ACCTCTTACG TGCCGATCAA CGTCTCATTT TCGCCAAAAG TTGGCCCAGG GCTTCCCGGT
     TGGAGAATGC ACGGCTAGTT GCAGAGTAAA AGCGGTTTTC AACCGGGTCC CGAAGGGCCA
2821 ATCAACAGGG ACACCAGGAT TTATTTATTC TGCGAAGTGA TCTTCCGTCA CAGGTATTTA
     TAGTTGTCCC TGTGGTCCTA AATAAATAAG ACGCTTCACT AGAAGGCAGT GTCCATAAAT
2881 TTCGGCGCAA AGTGCGTCGG GTGATGCTGC CAACTTACTG ATTTAGTGTA TGATGGTGTT
     AAGCCGCGTT TCACGCAGCC CACTACGACG GTTGAATGAC TAAATCACAT ACTACCACAA
2941 TTTGAGGTGC TCCAGTGGCT TCTGTTTCTA TCAGCTGTCC CTCCTGTTCA GCTACTGACG
     AAACTCCACG AGGTCACCGA AGACAAAGAT AGTCGACAGG GAGGACAAGT CGATGACTGC
3001 GGGTGGTGCG TAACGGCAAA AGCACCGCCG GACATCAGCG CTAGCGGAGT GTATACTGGC
     CCCACCACGC ATTGCCGTTT TCGTGGCGGC CTGTAGTCGC GATCGCCTCA CATATGACCG
3061 TTACTATGTT GGCACTGATG AGGGTGTCAG TGAAGTGCTT CATGTGGCAG GAGAAAAAAG
     AATGATACAA CCGTGACTAC TCCCACAGTC ACTTCACGAA GTACACCGTC CTCTTTTTTC
3121 GCTGCACCGG TGCGTCAGCA GAATATGTGA TACAGGATAT ATTCCGCTTC CTCGCTCACT
     CGACGTGGCC ACGCAGTCGT CTTATACACT ATGTCCTATA TAAGGCGAAG GAGCGAGTGA
3181 GACTCGCTAC GCTCGGTCGT TCGACTGCGG CGAGCGGAAA TGGCTTACGA ACGGGGCGGA
     CTGAGCGATG CGAGCCAGCA AGCTGACGCC GCTCGCCTTT ACCGAATGCT TGCCCCGCCT
3241 GATTTCCTGG AAGATGCCAG GAAGATACTT AACAGGGAAG TGAGAGGGCC GCGGCAAAGC
     CTAAAGGACC TTCTACGGTC CTTCTATGAA TTGTCCCTTC ACTCTCCCGG CGCCGTTTCG
3301 CGTTTTTCCA TAGGCTCCGC CCCCCTGACA AGCATCACGA AATCTGACGC TCAAATCAGT
     GCAAAAAGGT ATCCGAGGCG GGGGGACTGT TCGTAGTGCT TTAGACTGCG AGTTTAGTCA
3361 GGTGGCGAAA CCCGACAGGA CTATAAAGAT ACCAGGCGTT TCCCCTGCGG GCTCCCTCGT
     CCACCGCTTT GGGCTGTCCT GATATTTCTA TGGTCCGCAA AGGGGACGCC CGAGGGAGCA
3421 GCGCTCTCCT GTTCCTGCCT TTCGGTTTAC CGGTGTCATT CCGCTGTTAT GGCCGCGTTT
     CGCGAGAGGA CAAGGACGGA AAGCCAAATG GCCACAGTAA GGCGACAATA CCGGCGCAAA
3481 GTCTCATTCC ACGCCTGACA CTCAGTTCCG GGTAGGCAGT TCGCTCCAAG CTGGACTGTA
     CAGAGTAAGG TGCGGACTGT GAGTCAAGGC CCATCCGTCA AGCGAGGTTC GACCTGACAT
3541 TGCACGAACC CCCCGTTCAG TCCGACCGCT GCGCCTTATC CGGTAACTAT CGTCTTGAGT

Fig. 28₂

```
            ACGTGCTTGG GGGGCAAGTC AGGCTGGCGA CGCGGAATAG GCCATTGATA GCAGAACTCA
 3601  CCAACCCGGA AAGACATGCA AAAGCACCAC TGGCAGCAGC CACTGGTAAT TGATTTAGAG
            GGTTGGGCCT TTCTGTACGT TTTCGTGGTG ACCGTCGTCG GTGACCATTA ACTAAATCTC
 3661  GAGTTAGTCT TGAAGTCATG CGCCGGTTAA GGCTAAACTG AAAGGACAAG TTTTGGTGAC
            CTCAATCAGA ACTTCAGTAC GCGGCCAATT CCGATTTGAC TTTCCTGTTC AAAACCACTG
 3721  TGCGCTCCTC CAAGCCAGTT ACCTCGGTTC AAAGAGTTGG TAGCTCAGAG AACCTTCGAA
            ACGCGAGGAG GTTCGGTCAA TGGAGCCAAG TTTCTCAACC ATCGAGTCTC TTGGAAGCTT
 3781  AAACCGCCCT GCAAGGCGGT TTTTTCGTTT TCAGAGCAAG AGATTACGCG CAGACCAAAA
            TTTGGCGGGA CGTTCCGCCA AAAAGCAAA AGTCTCGTTC TCTAATGCGC GTCTGGTTTT
 3841  CGATCTCAAG AAGATCATCT TATTAATCAG ATAAATATT TCTAGATTTC AGTGCAATTT
            GCTAGAGTTC TTCTAGTAGA ATAATTAGTC TATTTTATAA AGATCTAAAG TCACGTTAAA
 3901  ATCTCTTCAA ATGTAGCACC TGAAGTCAGC CCCATACGAT ATAAGTTGTA ATTCTCATGT
            TAGAGAAGTT TACATCGTGG ACTTCAGTCG GGGTATGCTA TATTCAACAT TAAGAGTACA
 3961  TAGTCATGCC CCGCGCCCAC CGGAAGGAGC TGACTGGGTT GAAGGCTCTC AAGGGCATCG
            ATCAGTACGG GGCGCGGGTG GCCTTCCTCG ACTGACCCAA CTTCCGAGAG TTCCCGTAGC
 4021  GTCGAGATCC CGGTGCCTAA TGAGTGAGCT AACTTACATT AATTGCGTTG CGCTCACTGC
            CAGCTCTAGG GCCACGGATT ACTCACTCGA TTGAATGTAA TTAACGCAAC GCGAGTGACG
 4081  CCGCTTTCCA GTCGGGAAAC CTGTCGTGCC AGCTGCATTA ATGAATCGGC CAACGCGCGG
            GGCGAAAGGT CAGCCCTTTG GACAGCACGG TCGACGTAAT TACTTAGCCG GTTGCGCGCC
 4141  GGAGAGGCGG TTTGCGTATT GGGCGCCAGG GTGGTTTTTC TTTTCACCAG TGAGACGGGC
            CCTCTCCGCC AAACGCATAA CCCGCGGTCC CACCAAAAAG AAAAGTGGTC ACTCTGCCCG
 4201  AACAGCTGAT TGCCCTTCAC CGCCTGGCCC TGAGAGAGTT GCAGCAAGCG GTCCACGCTG
            TTGTCGACTA ACGGGAAGTG GCGGACCGGG ACTCTCTCAA CGTCGTTCGC CAGGTGCGAC
 4261  GTTTGCCCCA GCAGGCGAAA ATCCTGTTTG ATGGTGGTTA ACGGCGGGAT ATAACATGAG
            CAAACGGGGT CGTCCGCTTT TAGGACAAAC TACCACCAAT GCCGCCCTA TATTGTACTC
 4321  CTGTCTTCGG TATCGTCGTA TCCCACTACC GAGATGTCCG CACCAACGCG CAGCCCGGAC
            GACAGAAGCC ATAGCAGCAT AGGGTGATGG CTCTACAGGC GTGGTTGCGC GTCGGGCCTG
 4381  TCGGTAATGG CGCGCATTGC GCCCAGCGCC ATCTGATCGT TGGCAACCAG CATCGCAGTG
            AGCCATTACC GCGCGTAACG CGGGTCGCGG TAGACTAGCA ACCGTTGGTC GTAGCGTCAC
 4441  GGAACGATGC CCTCATTCAG CATTTGCATG GTTTGTTGAA ACCGGACAT GGCACTCCAG
            CCTTGCTACG GGAGTAAGTC GTAAACGTAC CAAACAACTT TTGGCCTGTA CCGTGAGGTC
 4501  TCGCCTTCCC GTTCCGCTAT CGGCTGAATT TGATTGCGAG TGAGATATTT ATGCCAGCCA
            AGCGGAAGGG CAAGGCGATA GCCGACTTAA ACTAACGCTC ACTCTATAAA TACGGTCGGT
 4561  GCCAGACGCA GACGCGCCGA GACAGAACTT AATGGGCCCG CTAACAGCGC GATTTGCTGG
            CGGTCTGCGT CTGCGCGGCT CTGTCTTGAA TTACCCGGGC GATTGTCGCG CTAAACGACC
 4621  TGACCCAATG CGACCAGATG CTCCACGCCC AGTCGCGTAC CGTCTTCATG GGAGAAAATA
            ACTGGGTTAC GCTGGTCTAC GAGGTGCGGG TCAGCGCATG GCAGAAGTAC CCTCTTTTAT
 4681  ATACTGTTGA TGGGTGTCTG GTCAGAGACA TCAAGAAATA ACGCCGGAAC ATTAGTGCAG
            TATGACAACT ACCCACAGAC CAGTCTCTGT AGTTCTTTAT TGCGGCCTTG TAATCACGTC
 4741  GCAGCTTCCA CAGCAATGGC ATCCTGGTCA TCCAGCGGAT AGTTAATGAT CAGCCCACTG
            CGTCGAAGGT GTCGTTACCG TAGGACCAGT AGGTCGCCTA TCAATTACTA GTCGGGTGAC
 4801  ACGCGTTGCG CGAGAAGATT GTGCACCGCC GCTTTACAGG CTTCGACGCC GCTTCGTTCT
            TGCGCAACGC GCTCTTCTAA CACGTGGCGG CGAAATGTCC GAAGCTGCGG CGAAGCAAGA
 4861  ACCATCGACA CCACCACGCT GGCACCCAGT TGATCGGCGC GAGATTTAAT CGCCGCGACA
            TGGTAGCTGT GGTGGTGCGA CCGTGGGTCA ACTAGCCGCG CTCTAAATTA GCGGCGCTGT
 4921  ATTTGCGACG GCGCGTGCAG GGCCAGACTG GAGGTGGCAA CGCCAATCAG CAACGACTGT
            TAAACGCTGC CGCGCACGTC CCGGTCTGAC CTCCACCGTT GCGGTTAGTC GTTGCTGACA
 4981  TTGCCCGCCA GTTGTTGTGC CACGCGGTTG GGAATGTAAT TCAGCTCCGC CATCGCCGCT
            AACGGGCGGT CAACAACACG GTGCGCCAAC CCTTACATTA AGTCGAGGCG GTAGCGGCGA
 5041  TCCACTTTTT CCCGCGTTTT CGCAGAAACG TGGCTGGCCT GGTTCACCAC GCGGGAAACG
            AGGTGAAAAA GGGCGCAAAA GCGTCTTTGC ACCGACCGGA CCAAGTGGTG CGCCCTTTGC
 5101  GTCTGATAAG AGACACCGGC ATACTCTGCG ACATCGTATA ACGTTACTGG TTTCACATTC
            CAGACTATTC TCTGTGGCCG TATGAGACGC TGTAGCATAT TGCAATGACC AAAGTGTAAG
 5161  ACCACCCTGA ATTGACTCTC TTCCGGGCGC TATCATGCCA TACCGCGAAA GGTTTTGCGC
            TGGTGGGACT TAACTGAGAG AAGGCCCGCG ATAGTACGGT ATGGCGCTTT CCAAAACGCG
 5221  CATTCGATGG TGTCCGGGAT CTCGACGCTC TCCCTTATGC GACTCCTGCA TTAGGAAATT
            GTAAGCTACC ACAGGCCCTA GAGCTGCGAG AGGGAATACG CTGAGGACGT AATCCTTTAA
 5281  AATACGACTC ACTATA
            TTATGCTGAG TGATAT
```

Fig. 28₃

| Fig. 30$_1$ |
| --- |
| Fig. 30$_2$ |
| Fig. 30$_3$ |

Fig. 30

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                           EcoRI
                                                           ~~~~~~
                                                BamHI            SacI
                                                ~~~~~~           ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGATCACA AGTTTGTACA AAAAAGCTGA ACGAGAAACG TAAAATGATA TAAATATCAA
     GAGCTAGTGT TCAAACATGT TTTTTCGACT TGCTCTTTGC ATTTTACTAT ATTTATAGTT
 181 TATATTAAAT TAGATTTTGC ATAAAAAACA GACTACATAA TACTGTAAAA CACAACATAT
     ATATAATTTA ATCTAAAACG TATTTTTTGT CTGATGTATT ATGACATTTT GTGTTGTATA
 241 CCAGTCACTA TGGCGGCCGC CACGTTAAGG GATTTTGGTC ATGATCAGCA CGTGTTGACA
     GGTCAGTGAT ACCGCCGGCG GTGCAATTCC CTAAAACCAG TACTAGTCGT GCACAACTGT
 301 ATTAATCATC GGCATAGTAT ATCGGCATAG TATAATACGA CAAGGTGAGG AACTAAACCA
     TAATTAGTAG CCGTATCATA TAGCCGTATC ATATTATGCT GTTCCACTCG TTGATTTGGT
 361 TGGCCAAGTT GACCAGTGCC GTTCCGGTGC TCACCGCGCG CGACGTCGCC GGAGCGGTCG
     ACCGGTTCAA CTGGTCACGG CAAGGCCACG AGTGGCGCGC GCTGCAGCGG CCTCGCCAGC
 421 AGTTCTGGAC CGACCGGCTC GGGTTCTCCC GGGACTTCGT GGAGGACGAC TTCGCCGGTG
     TCAAGACCTG GCTGGCCGAG CCCAAGAGGG CCCTGAAGCA CCTCCTGCTG AAGCGGCCAC
 481 TGGTCCGGGA CGACGTGACC CTGTTCATCA GCGCGGTCCA GGACCAGGTG GTGCCGGACA
     ACCAGGCCCT GCTGCACTGG GACAAGTAGT CGCGCCAGGT CCTGGTCCAC CACGGCCTGT
 541 ACACCCTGGC CTGGGTGTGG GTGCGCGGCC TGGACGAGCT GTACGCCGAG TGGTCGGAGG
     TGTGGGACCG GACCCACACC CACGCGCCGG ACCTGCTCGA CATGCGGCTC ACCAGCCTCC
 601 TCGTGTCCAC GAACTTCCGG GACGCCTCCG GGCCGGCCAT GACCGAGATC GGCGAGCAGC
     AGCACAGGTG CTTGAAGGCC CTGCGGAGGC CCGGCCGGTA CTGGCTCTAG CCGCTCGTCG
 661 CGTGGGGGCG GGAGTTCGCC CTGCGCGACC CGGCCGGCAA CTGCGTGCAC TTCGTGGCCG
     GCACCCCCGC CCTCAAGCGG GACGCGCTGG GCCGGCCGTT GACGCACGTG AAGCACCGGC
 721 AGGAGCAGGA CTGATCATGA TGATATTATT TTATCTTGTG CAATGTAACA TCAGAGATTT
     TCCTCGTCCT GACTAGTACT ACTATAATAA AATAGAACAC GTTACATTGT AGTCTCTAAA
 781 TGAGACACGG GCCAGAGCTG CCAGGAAACA GCTATGACCA TGTAATACGA CTCACTATAG
     ACTCTGTGCC CGGTCTCGAC GGTCCTTTGT CGATACTGGT ACATTATGCT GAGTGATATC
 841 GGGATATCAG CTGGATGGCA AATAATGATT TTATTTTGAC TGATAGTGAC CTGTTCGTTG
     CCCTATAGTC GACCTACCGT TTATTACTAA AATAAAACTG ACTATCACTG GACAAGCAAC
 901 CAACACCGGT GCTAGCGTAT ACCCGAAGTA TGTCAAAAAG AGGTGTGCTA TGAAGCAGCG
     GTTGTGGCCA CGATCGCATA TGGGCTTCAT ACAGTTTTTC TCCACACGAT ACTTCGTCGC
 961 TATTACAGTG ACAGTTGACA GCGACAGCTA TCAGTTGCTC AAGGCATATA TGATGTCAAT
     ATAATGTCAC TGTCAACTGT CGCTGTCGAT AGTCAACGAG TTCCGTATAT ACTACAGTTA
1021 ATCTCCGGTC TGGTAAGCAC AACCATGCAG AATGAAGCCC GTCGTCTGCG TGCCGAACGC
     TAGAGGCCAG ACCATTCGTG TTGGTACGTC TTACTTCGGG CAGCAGACGC ACGGCTTGCG
1081 TGGAAAGCGG AAAATCAGGA AGGGATGGCT GAGGTCGCCC GGTTTATTGA AATGAACGGC
     ACCTTTCGCC TTTTAGTCCT TCCCTACCGA CTCCAGCGGG CCAAATAACT TTACTTGCCG
1141 TCTTTTGCTG ACGAGAACGG GGACTGGTGA ATGCAGTTT AAGGTTTACA CCTATAAAAG
     AGAAAACGAC TGCTCTTGTC CCTGACCACT TTACGTCAAA TTCCAAATGT GGATATTTTC
1201 AGAGAGCCGT TATCGTCTGT TTGTGGATGT ACAGAGTGAT ATTATTGACA CGCCCGGGCG
     TCTCTCGGCA ATAGCAGACA AACACCTACA TGTCTCACTA TAATAACTGT GCGGGCCCGC
1261 ACGGATGGTG ATCCCCCTGG CCAGTGCACG TCTGCTGTCA GATAAAGTCT CCCGTGAACT
     TGCCTACCAC TAGGGGGACC GGTCACGTGC AGACGACAGT CTATTCGAGA GGGCACTTGA
1321 TTACCCGGTG GTGCATATCG GGGATGAAAG CTGGCGCATG ATGACCACCG ATATGGCCAG
     AATGGGCCAC CACGTATAGC CCCTACTTTC GACCGCGTAC TACTGGTGGC TATACCGGTC
1381 TGTGCCGGTC TCCGTTATCG GGGAAGAAGT GGCTGATCTC AGCCGCCGCG AAAATGACAT
     ACACGGCCAG AGGCAATAGC CCCTTCTTCA CCGACTAGAG TCGGCGGCGC TTTTACTGTA
1441 CAAAAACGCC ATTAACCTGA TGTTCTGGGG AATATAAATG TCAGGCTCCC TTATACACAG
     GTTTTTGCGG TAATTGGACT ACAAGACCCC TTATATTTAC AGTCCGAGGG AATATGTGTC
     PstI
     ~~~~~~
1501 CCAGTCTGCA GGTCGACCAT AGTGACTGGA TATGTTGTGT TTTACAGTAT TATGTAGTCT
     GGTCAGACGT CCAGCTGGTA TCACTGACCT ATACAACACA AAATGTCATA ATACATCAGA
1561 GTTTTTTATG CAAAATCTAA TTTAATATAT TGATATTTAT ATCATTTTAC GTTTCTCGTT
     CAAAAAATAC GTTTTAGATT AAATTATATA ACTATAAATA TAGTAAAATG CAAAGAGCAA
                                                           HindIII
                                                           ~~~~~~
1621 CAGCTTTCTT GTACAAAGTG GTGATAATTA ATTAAGATCA GATCCGGCTG CTAAGCTTGG
     GTCGAAAGAA CATGTTTCAC CACTATTAAT TAATTCTAGT CTAGGCCGAC GATTCGAACC
                                                           AvrII
                                                           ~~~~~~
1681 AATTGTTATC CGCTCACAAT TCCTATAGTG AGTCGTATTA CCTAGGCTGC TGCCACCGCT
     TTAACAATAG GCGAGTGTTA AGGATATCAC TCAGCATAAT GGATCCGACG ACGGTGGCGA
```

Fig. 30₁

```
1741  GAGCAATAAC TAGCATAACC CCTTGGGGCC TCTAAACGGG TCTTGAGGGG TTTTTTGCTG
      CTCGTTATTG ATCGTATTGG GGAACCCCGG AGATTTGCCC AGAACTCCCC AAAAAACGAC
1801  AAACCTCAGG CATTTGAGAA GCACACGGTC ACACTGCTTC CGGTAGTCAA TAAACCGGTA
      TTTGGAGTCC GTAAACTCTT CGTGTGCCAG TGTGACGAAG GCCATCAGTT ATTTGGCCAT
1861  AACCAGCAAT AGACATAAGC GGCTATTTAA CGACCCTGCC CTGAACCGAC GACCGGGTCA
      TTGGTCGTTA TCTGTATTCG CCGATAAATT GCTGGGACGG GACTTGGCTG CTGGCCCAGT
1921  TCGTGGCCGG ATCTTGCGGC CCCTCGGCTT GAACGAATTG TTAGACATTA TTTGCCGACT
      AGCACCGGCC TAGAACGCCG GGGAGCCGAA CTTGCTTAAC AATCTGTAAT AAACGGCTGA
1981  ACCTTGTGA TCTCGCCTTT CACGTAGTGG ACAAATTCTT CCAACTGATC TGCGCGCGAG
      TGGAACCACT AGAGCGGAAA GTGCATCACC TGTTTAAGAA GGTTGACTAG ACGCGCGCTC
2041  GCCAAGCGAT CTTCTTCTTG TCCAAGATAA GCCTGTCTAG CTTCAAGTAT GACGGGCTGA
      CGGTTCGCTA GAAGAAGAAC AGGTTCTATT CGGACAGATC GAAGTTCATA CTGCCCGACT
2101  TACTGGGCCG GCAGGCGCTC CATTGCCCAG TCGGCAGCGA CATCCTTCGG CGCGATTTTG
      ATGACCCGGC CGTCCGCGAG GTAACGGGTC AGCCGTCGCT GTAGGAAGCC GCGCTAAAAC
2161  CCGGTTACTG CGCTGTACCA AATGCGGGAC AACGTAAGCA CTACATTTCG CTCATCGCCA
      GGCCAATGAC GCGACATGGT TTACGCCCTG TTGCATTCGT GATGTAAAGC GAGTAGCGGT
2221  GCCCAGTCGG GCGGCGAGTT CCATAGCGTT AAGGTTTCAT TTAGCGCCTC AAATAGATCC
      CGGGTCAGCC CGCCGCTCAA GGTATCGCAA TTCCAAAGTA AATCGCGGAG TTTATCTAGG
2281  TGTTCAGGAA CCGGATCAAA GAGTTCCTCC GCCGCTGGAC CTACCAAGGC AACGCTATGT
      ACAAGTCCTT GGCCTAGTTT CTCAAGGAGG CGGCGACCTG GATGGTTCCG TTGCGATACA
2341  TCTCTTGCTT TTGTCAGCAA GATAGCCAGA TCAATGCTGA TCGTGGCTGG CTCGAAGATA
      AGAGAACGAA AACAGTCGTT CTATCGGTCT AGTTACAGCT AGCACCGACC GAGCTTCTAT
2401  CCTGCAAGAA TGTCATTGCG CTGCCATTCT CCAAATTGCA GTTCGCGCTT AGCTGGATAA
      GGACGTTCTT ACAGTAACGC GACGGTAAGA GGTTTAACGT CAAGCGCGAA TCGACCTATT
2461  CGCCACGAA TGATGTCGTC GTGCACAACA ATGGTGACTT CTACAGCGCG GAGAATCTCG
      GCGGTGCCTT ACTACAGCAG CACGTGTTGT TACCACTGAA GATGTCGCGC CTCTTAGAGC
2521  CTCTCTCCAG GGGAAGCCGA AGTTTCCAAA AGGTCGTTGA TCAAAGCTCG CCGGCGTTGTT
      GAGAGAGGTC CCCTTCGGCT TCAAAGGTTT TCCAGCAACT AGTTTCGAGC GGCGCAACAA
2581  TCATCAAGCC TTACGGTCAC CGTAACCAGC AAATCAATAT CACTGTGTGG CTTCAGGCCG
      AGTAGTTCGG AATGCCAGTG GCATTGGTCG TTAGTTATA GTGACACACC GAAGTCCGGC
2641  CCATCCACTG CGGGAGCCGTA CAAATGTACG GCCAGCAACG TCGGTTCGAG ATGGCGCTCG
      GGTAGGTGAC GCCTCGGCAT GTTTACATGC CGGTCGTTGC AGCCAAGCTC TACCGCGAGC
2701  ATGACGCCAA CTACCTCTGA TAGTTGAGTC GATACTTCGG CGATCACCGC TTCCCTCATA
      TACTGCGGTT GATGGAGACT ATCAACTCAG CTATGAAGCC GCTAGTGGCG AAGGGAGTAT
2761  CTCTTCCTTT TCAATATTA TTGAAGCATT TATCAGGGTT ATTGTCTCAT GAGCGGATAC
      GAGAAGGAAA AAGTTATAAT AACTTCGTAA ATAGTCCCAA TAACAGAGTA CTCGCCTATG
2821  ATATTTGAAT GTATTTAGAA AAATAAACAA ATAGCTAGCT CACTCGGTCG CTACGCTCCG
      TATAAACTTA CATAAATCTT TTATTTGTT TATCGATCGA GTGAGCCAGC GATGCGAGGC
2881  GGCGTGAGAC TGCGGCGGGC GCTGCGGACA CATACAAAGT TACCCACAGA TTCCGTGGAT
      CCGCACTCTG ACGCCGCCCG CGACGCCTGT GTATGTTTCA ATGGGTGTCT AAGGCACCTA
2941  AAGCAGGGGA CTAACATGTG AGGCAAAACA GCAGGGCCGC GCCGGTGGCG TTTTTCCATA
      TTCGTCCCCT GATTGTACAC TCCGTTTTGT CGTCCCGGCG CGGCCACCGC AAAAAGGTAT
3001  GGCTCCGCCC TCCTGCCAGA GTTCACATAA ACAGACGCTT TTCCGGTGCA TCTGTGGGAG
      CCGAGGCGGG AGGACGGTCT CAAGTGTATT TGTCTGCGAA AAGGCCACGT AGACACCCTC
3061  CCGTGAGGCT CAACCATGAA TCTGACAGTA CGGGCGAAAC CCGACAGGAC TTAAAGATCC
      GGCACTCCGA GTTGGTACTT AGACTGTCAT GCCCGCTTTG GGCTGTCCTG AATTTCTAGG
3121  CCACCGTTTC CGGCGGGTCG CTCCCTCTTG CGCTCTCCTG TTCCGACCCT GCCGTTTACC
      GGTGGCAAAG GCCGCCCAGC GAGGGAGAAC GCGAGAGGAC AAGGCTGGGA CGGCAAATGG
3181  GGATACCTGT TCCGCCTTTC TCCCTTACGG GAAGTGTGGC GCTTTCTCAT AGCTCACACA
      CCTATGGACA AGGCGGAAAG AGGGAATGCC CTTCACCG CGAAAGAGTA TCGAGTGTGT
3241  CTGGTATCTC GGCTCGGTGT AGGTCGTTCG CTCCAAGCTG GGCTGTAAGC AAGAACTCCC
      GACCATAGAG CCGAGCCACA TCCAGCAAGC GAGGTTCGAC CCGACATTCG TTCTTGAGGG
3301  CGTTCAGCCC GACTGCTGCG CCTTATCCGG TAACTGTTCA CTTGAGTCCA ACCCGGAAAA
      GCAAGTCGGG CTGACGACGC GGAATAGGCC ATTGACAAGT GAACTCAGGT TGGGCCTTTT
3361  GCACGGTAAA ACGCCACTGG CAGCAGCCAT TGGTAACTGG GAGTTCGCAG AGGATTTGTT
      CGTGCCATTT TGCGGTGACC GTCGTCGGTA ACCATTGACC CTCAAGCGTC TCCTAAACAA
3421  TAGCTAAACA CGCGGTTGCT CTTGAAGTGT GCGCCAAAGT CCGGCTACAC TGGAAGGACA
      ATCGATTTGT GCGCCAACGA GAACTTCACA CGCGGTTTCA GGCCGATGTG ACCTTCCTGT
3481  GATTTGGTTG CTGTGCTCTG CGAAAGCCAG TTACCACGGT TAAGCAGTTC CCCAACTGAC
      CTAAACCAAC GACACGAGAC GCTTTCGGTC AATGGTGCCA ATTCGTCAAG GGGTTGACTG
3541  TTAACCTTCG ATCAAACCAC CTCCCCAGGT GGTTTTTTCG TTTACAGGGC AAAAGATTAC
      AATTGGAAGC TAGTTTGGTG GAGGGGTCCA CCAAAAAGC AAATGTCCCG TTTTCTAATG
3601  GCGCAGAAAA AAAGGATCTC AAGAAGATCC TTTGATCTTT TCTACTGAAC CGCTCTAGAT
      CGCGTCTTTT TTTCCTAGAG TTCTTCTAGG AAACTAGAAA AGATGACTTG GCGAGATCTA
3661  TTCAGTGCAA TTTATCTCTT CAAATGTAGC ACCTGAAGTC AGCCCCATAC GATATAAGTT
      AAGTCACGTT AAATAGAGAA GTTTACATCG TGGACTTCAG TCGGGGTATG CTATATTCAA
3721  GTAATTCTCA TGTTAGTCAT GCCCCGCGCC CACCGGAAGG AGCTGACTGG GTTGAAGGCT
      CATTAAGAGT ACAATCAGTA CGGGGCGCGG GTGGCCTTCC TCGACTGACC CAACTTCCGA
3781  CTCAAGGGCA TCGGTCGAGA TCCCGGTGCC TAATGAGTGA GCTAACTTAC ATTAATTGCG
```

Fig. 30₂

```
      GAGTTCCCGT AGCCAGCTCT AGGGCCACGG ATTACTCACT CGATTGAATG TAATTAACGC
3841  TTGCGCTCAC TGCCCGCTTT CCAGTCGGGA AACCTGTCGT GCCAGCTGCA TTAATGAATC
      AACGCGAGTG ACGGGCGAAA GGTCAGCCCT TTGGACAGCA CGGTCGACGT AATTACTTAG
3901  GGCCAACGCG CGGGGAGAGG CGGTTTGCGT ATTGGGCGCC AGGGTGGTTT TTCTTTTCAC
      CCGGTTGCGC GCCCCTCTCC GCCAAACGCA TAACCCGCGG TCCCACCAAA AAGAAAAGTG
3961  CAGTGAGACG GGCAACAGCT GATTGCCCTT CACCGCCTGG CCCTGAGAGA GTTGCAGCAA
      GTCACTCTGC CCGTTGTCGA CTAACGGGAA GTGGCGGACC GGGACTCTCT CAACGTCGTT
4021  GCGGTCCACG CTGGTTTGCC CCAGCAGGCG AAAATCCTGT TTGATGGTGG TTAACGGCGG
      CGCCAGGTGC GACCAAACGG GGTCGTCCGC TTTTAGGACA AACTACCACC AATTGCCGCC
4081  GATATAACAT GAGCTGTCTT CGGTATCGTC GTATCCCACT ACCGAGATGT CCGCACCAAC
      CTATATTGTA CTCGACAGAA GCCATAGCAG CATAGGGTGA TGGCTCTACA GGCGTGGTTG
4141  GCGCAGCCCG GACTCGGTAA TGGCGCGCAT TGCGCCCAGC GCCATCTGAT CGTTGGCAAC
      CGCGTCGGGC CTGAGCCATT ACCGCGCGTA ACGCGGGTCG CGGTAGACTA GCAACCGTTG
4201  CAGCATCGCA GTGGGAACGA TGCCCTCATT CAGCATTTGC ATGGTTTGTT GAAAACCGGA
      GTCGTAGCGT CACCCTTGCT ACGGGAGTAA GTCGTAAACG TACCAAACAA CTTTTGGCCT
4261  CATGGCACTC CAGTCGCCTT CCCGTTCCGC TATCGGCTGA ATTTGATTGC GAGTGAGATA
      GTACCGTGAG GTCAGCGGAA GGGCAAGGCG ATAGCCGACT TAAACTAACG CTCACTCTAT
4321  TTTATGCCAG CCAGCCAGAC GCAGACGCGC CGAGACAGAA CTTAATGGGC CCGCTAACAG
      AAATACGGTC GGTCGGTCTG CGTCTGCGCG GCTCTGTCTT GAATTACCCG GGCGATTGTC
4381  CGCGATTTGC TGGTGACCCA ATGCGACCAG ATGCTCCACG CCCAGTCGCG TACCGTCTTC
      GCGCTAAACG ACCACTGGGT TACGCTGGTC TACGAGGTGC GGGTCAGCGC ATGGCAGAAG
4441  ATGGGAGAAA ATAATACTGT TGATGGGTGT CTGGTCAGAG ACATCAAGAA ATAACGCCGG
      TACCCTCTTT TATTATGACA ACTACCCACA GACCAGTCTC TGTAGTTCTT TATTGCGGCC
4501  AACATTAGTG CAGGCAGCTT CCACAGCAAT GGCATCCTGG TCATCCAGCG GATAGTTAAT
      TTGTAATCAC GTCCGTCGAA GGTGTCGTTA CCGTAGGACC AGTAGGTCGC CTATCAATTA
4561  GATCAGCCCA CTGACGCGTT GCGCGAGAAG ATTGTGCACC GCCGCTTTAC AGGCTTCGAC
      CTAGTCGGGT GACTGCGCAA CGCGCTCTTC TAACACGTGG CGGCGAAATG TCCGAAGCTG
4621  GCCGCTTCGT TCTACCATCG ACACCACCAC GCTGGCACCC AGTTGATCGG CGCGAGATTT
      CGGCGAAGCA AGATGGTAGC TGTGGTGGTG CGACCGTGGG TCAACTAGCC GCGCTCTAAA
4681  AATCGCCGCG ACAATTTGCG ACGGCGCGTG CAGGGCCAGA CTGGAGGTGG CAACGCCAAT
      TTAGCGGCGC TGTTAAACGC TGCCGCGCAC GTCCCGGTCT GACCTCCACC GTTGCGGTTA
4741  CAGCAACGAC TGTTTGCCCG CCAGTTGTTG TGCCACGCGG TTGGGAATGT AATTCAGCTC
      GTCGTTGCTG ACAAACGGGC GGTCAACAAC ACGGTGCGCC AACCCTTACA TTAAGTCGAG
4801  CGCTCACGCC GCTTCCACTT TTTCCCGCGT TTTCGCAGAA ACGTGGCTGG CCTGGTTCAC
      GCGGTAGCGG CGAAGGTGAA AAAGGGCGCA AAAGCGTCTT TGCACCGACC GGACCAAGTG
4861  CACGCGGGAA ACGGTCTGAT AAGAGACACC GGCATACTCT GCGACATCGT ATAACGTTAC
      GTGCGCCCTT TGCCAGACTA TTCTCTGTGG CCGTATGAGA CGCTGTAGCA TATTGCAATG
4921  TGGTTTCACA TTCACCACCC TGAATTGACT CTCTTCCGGG CGCTATCATG CCATACCGCG
      ACCAAAGTGT AAGTGGTGGG ACTTAACTGA GAGAAGGCCC GCGATAGTAC GGTATGGCGC
4981  AAAGGTTTTG CGCCATTCGA TGGTGTCCGG GATCTCGACG CTCTCCCTTA TGCGACTCCT
      TTTCCAAAAC GCGGTAAGCT ACCACAGGCC CTAGAGCTGC GAGAGGGAAT ACGCTGAGGA
5041  GCATTAGGAA ATTAATACGA CTCACTATA
      CGTAATCCTT TAATTATGCT GAGTGATAT
```

Fig. 30₃

| Fig. 32$_1$ |
|---|
| Fig. 32$_2$ |
| Fig. 32$_3$ |

Fig. 32

```
  1 GGGGAATTGT GAGCGGATAA CAATTCCCCT GTAGAAATAA TTTTGTTTAA CTTTAATAAG
    CCCCTTAACA CTCGCCTATT GTTAAGGGGA CATCTTTATT AAAACAAATT GAAATTATTC
                                                            EcoRI
                                                            ~~~~~~
             NcoI                                BamHI          SacI
             ~~~~~~~                             ~~~~~~~        ~~~
 61 GAGATATACC ATGGGCAGCA GCCATCACCA TCATCACCAC AGCCAGGATC CGAATTCGAG
    CTCTATATGG TACCCGTCGT CGGTAGTGGT AGTAGTGGTG TCGGTCCTAG GCTTAAGCTC
    SacI
    ~~~
121 CTCGATCACA AGTTTGTACA AAAAAGCTGA ACGAGAAACG TAAAATGATA TAAATATCAA
    GAGCTAGTGT TCAAACATGT TTTTTCGACT TGCTCTTTGC ATTTTACTAT ATTTATAGTT
181 TATATTAAAT TAGATTTTGC ATAAAAAACA GACTACATAA TACTGTAAAA CACAACATAT
    ATATAATTTA ATCTAAAACG TATTTTTTGT CTGATGTATT ATGACATTTT GTGTTGTATA
241 CCAGTCACTA TGGCGGCCGC CACGTTAAGG GATTTTGGTC ATGATCAGCA CGTGTTGACA
    GGTCAGTGAT ACCGCCGGCG GTGCAATTCC CTAAAACCAG TACTAGTCGT GCACAACTGT
                                                                NcoI
                                                                ~~~
301 ATTAATCATC GGCATAGTAT ATCGGCATAG TATAATACGA CAAGGTGAGG AACTAAACCA
    TAATTAGTAG CCGTATCATA TAGCCGTATC ATATTATGCT GTTCCACTCC TTGATTTGGT
    NcoI
    ~~~
361 TGGCCAAGTT GACCAGTGCC GTTCCGGTGC TCACCGCGCG CGACGTCGCC GGAGCGGTCG
    ACCGGTTCAA CTGGTCACGG CAAGGCCACG AGTGGCGCGC GCTGCAGCGG CCTCGCCAGC
421 AGTTCTGGAC CGACCGGCTC GGGTTCTCCC GGGACTTCGT GGAGGACGAC TTCGCCGGTG
    TCAAGACCTG GCTGGCCGAG CCCAAGAGGG CCCTGAAGCA CCTCCTGCTG AAGCGGCCAC
481 TGGTCCGGGA CGACGTGACC CTGTTCATCA GCGCGGTCCA GGACCAGGTG GTGCCGGACA
    ACCAGGCCCT GCTGCACTGG GACAAGTAGT CGCGCCAGGT CCTGGTCCAC CACGGCCTGT
541 ACACCCTGGC CTGGGTGTGG GTGCGCGGCC TGGACGAGCT GTACGCCGAG TGGTCGGAGG
    TGTGGGACCG GACCCACACC CACGCGCCGG ACCTGCTCGA CATGCGGCTC ACCAGCCTCC
601 TCGTGTCCAC GAACTTCCGG GACGCCTCCG GGCCGGCCAT GACCGAGATC GGCGAGCAGC
    AGCACAGGTG CTTGAAGGCC CTGCGGAGGC CCGGCCGGTA CTGGCTCTAG CCGCTCGTCG
661 CGTGGGGGCG GGAGTTCGCC CTGCGCGACC CGGCCGGCAA CTGCGTGCAC TTCGTGGCCG
    GCACCCCCGC CCTCAAGCGG GACGCGCTGG GCCGGCCGTT GACGCACGTG AAGCACCGGC
721 AGGAGCAGGA CTGATCATGA TGATATTATT TTATCTTGTG CAATGTAACA TCAGAGATTT
    TCCTCGTCCT GACTAGTACT ACTATAATAA AATAGAACAC GTTACATTGT AGTCTCTAAA
781 TGAGACACGG GCCAGAGCTG CCAGGAAACA GCTATGACCA TGTAATACGA CTCACTATAG
    ACTCTGTGCC CGGTCTCGAC GGTCCTTTGT CGATACTGGT ACATTATGCT GAGTGATATC
841 GGGATATCAG CTGGATGGCA ATAATGATT TTATTTTGAC TGATAGTGAC CTGTTCGTTG
    CCCTATAGTC GACCTACCGT TATTACTAA AATAAAACTG ACTATCACTG GACAAGCAAC
901 CAACACCGGT GCTAGCGTAT ACCCGAAGTA TGTCAAAAAG AGGTGTGCTA TGAAGCAGCG
    GTTGTGGCCA CGATCGCATA TGGGCTTCAT ACAGTTTTTC TCCACACGAT ACTTCGTCGC
961 TATTACAGTG ACAGTTGACA GCGACAGCTA TCAGTTGCTC AAGGCATATA TGATGTCAAT
    ATAATGTCAC TGTCAACTGT CGCTGTCGAT AGTCAACGAG TTCCGTATAT ACTACAGTTA
1021 ATCTCCGGTC TGGTAAGCAC AACCATGCAG AATGAAGCCC GTCGTCTGCA TGCCGAACGC
     TAGAGGCCAG ACCATTCGTG TTGGTACGTC TTACTTCGGG CAGCAGACGC ACGGCTTGCG
1081 TGGAAAGCGG AAAATCAGGA AGGGATGGCT GAGGTCGCCC GGTTTATTGA ATGAACGGC
     ACCTTTCGCC TTTTAGTCCT TCCCTACCGA CTCCAGCGGG CCAAATAACT TTACTTGCCG
1141 TCTTTTGCTG ACGAGAACAG GGACTGGTGA AATGCAGTTT AAGGTTTACA CCTATAAAAG
     AGAAAACGAC TGCTCTTGTC CCTGACCACT TTACGTCAAA TTCCAAATGT GGATATTTTC
1201 AGAGAGCCGT TATCGTCTGT TTGTGGATGT ACAGATTGAT ATTATTGACA CGCCCGGGCG
     TCTCTCGGCA ATAGCAGACA AACACCTACA TGTCTCACTA TAATAACTGT GCGGGCCCGC
1261 ACGGATGGTG ATCCCCCTGG CCAGTGCACG TCTGCTGTCA GATAAAGTCT CCCGTGAACT
     TGCCTACCAC TAGGGGGACC GGTCACGTGC AGACGACAGT CTATTTCAGA GGGCACTTGA
1321 TTACCCGGTG GTGCATATCG GGGATGAAAG CTGGCGCATG ATGACCACCG ATATGGCCAG
     AATGGGCCAC CACGTATAGC CCCTACTTTC GACCGCGTAC TACTGGTGGC TATACCGGTC
1381 TGTGCCGGTC TCCGTTATCG GGAAGAAGT GGCTGATCTC AGCCGCCGCG AAAATGACAT
     ACACGGCCAG AGGCAATAGC CCCTTCTTCA CCGACTAGAG TCGGCGGCGC TTTTACTGTA
1441 CAAAAACGCC ATTAACCTGA TGTTCTGGGG AATATAAATG TCAGGCTCCC TTATACACAG
     GTTTTTGCGG TAATTGGACT ACAAGACCCC TTATATTTAC AGTCCGAGGG AATATGTGTC
             PstI
             ~~~~~~~
1501 CCAGTCTGCA GGTCGACCAT AGTGACTGGA TATGTTGTGT TTTACAGTAT TATGTAGTCT
     GGTCAGACGT CCAGCTGGTA TCACTGACCT ATACAACACA AAATGTCATA ATACATCAGA
1561 GTTTTTTATG CAAAATCTAA TTTAATATAT TGATATTTAT ATCATTTTAC GTTTCTCGTT
     CAAAAAATAC GTTTTAGATT AAATTATATA ACTATAAATA TAGTAAAATG CAAAGAGCAA
```

Fig. 32₁

```
                                                              HindIII
                                                              ~~~~~~
1621  CAGCTTTCTT GTACAAAGTG GTGATAATTA ATTAAGATCA GATCCGGCTG CTAAGCTTGG
      GTCGAAAGAA CATGTTTCAC CACTATTAAT TAATTCTAGT CTAGGCCGAC GATTCGAACC
                                                  AvrII
                                                  ~~~~~
1681  AATTGTTATC CGCTCACAAT TCCTATAGTG AGTCGTATTA CCTAGGCTGC TGCCACCGCT
      TTAACAATAG GCGAGTGTTA AGGATATCAC TCAGCATAAT GGATCCGACG ACGGTGGCGA
1741  GAGCAATAAC TAGCATAACC CCTTGGGGCC TCTAAACGGG TCTTGAGGGG TTTTTTGCTG
      CTCGTTATTG ATCGTATTGG GGAACCCCGG AGATTTGCCC AGAACTCCCC AAAAAACGAC
1801  AAACCTCAGG CATTTGAGAA GCACACGGTC ACACTGCTTC CGGTAGTCAA TAAACCGGTA
      TTTGGAGTCC GTAAACTCTT CGTGTGCCAG TGTGACGAAG GCCATCAGTT ATTTGGCCAT
1861  AACCAGCAAT AGACATAAGC GGCTATTTAA CGACCCTGCC CTGAACCGAC GACAAGCTGA
      TTGGTCGTTA TCTGTATTCG CCGATAAATT GCTGGGACGG GACTTGGCTG CTGTTCGACT
1921  CGACCGGGTC TCCGCAAGTG GCACTTTTCG GGGAAATGTG CGCGGAACCC CTATTTGTTT
      GCTGGCCCAG AGGCGTTCAC CGTGAAAAGC CCCTTTACAC GCGCCTTGGG GATAAACAAA
1981  ATTTTTCTAA ATACATTCAA ATATGTATCC GCTCATGAAT TAATTCTTAG AAAAACTCAT
      TAAAAAGATT TATGTAAGTT TATACATAGG CGAGTACTTA ATTAAGAATC TTTTTGAGTA
2041  CGAGCATCAA ATGAAACTGC AATTTATTCA TATCAGGATT ATCAATACCA TATTTTTGAA
      GCTCGTAGTT TACTTTGACG TTAAATAAGT ATAGTCCTAA TAGTTATGGT ATAAAAACTT
2101  AAAGCCGTTT CTGTAATGAA GGAGAAAACT CACCGAGGCA GTTCCATAGG ATGGCAAGAT
      TTTCGGCAAA GACATTACTT CCTCTTTTGA GTGGCTCCGT CAAGGTATCC TACCGTTCTA
2161  CCTGGTATCG GTCTGCGATT CCGACTCGTC CAACATCAAT ACAACCTATT AATTTCCCCT
      GGACCATAGC CAGACGCTAA GGCTGAGCAG GTTGTAGTTA TGTTGGATAA TTAAAGGGGA
2221  CGTCAAAAAT AAGGTTATCA AGTGAGAAAT CACCATGAGT GACGACTGAA TCCGGTGAGA
      GCAGTTTTTA TTCCAATAGT TCACTCTTTA GTGGTACTCA CTGCTGACTT AGGCCACTCT
2281  ATGGCAAAAG TTTATGCATT TCTTTCCAGA CTTGTTCAAC AGGCCAGCCA TTACGCTCGT
      TACCGTTTTC AAATACGTAA AGAAAGGTCT GAACAAGTTG TCCGGTCGGT AATGCGAGCA
2341  CATCAAAATC ACTCGCATCA ACCAAACCGT TATTCATTCG TGATTGCGCC TGAGCGAGAC
      GTAGTTTTAG TGAGCGTAGT TGGTTTGGCA ATAAGTAAGC ACTAACGCGG ACTCGCTCTG
2401  GAAATACGCG GTCGCTGTTA AAAGGACAAT TACAAACAGG AATCGAATGC AACCGGCGCA
      CTTTATGCGC CAGCGACAAT TTTCCTGTTA ATGTTTGTCC TTAGCTTACG TTGGCCGCGT
2461  GGAACACTGC CAGCGCATCA ACAATATTTT CACCTGAATC AGGATATTCT TCTAATACCT
      CCTTGTGACG GTCGCGTAGT TGTTATAAAA GTGGACTTAG TCCTATAAGA AGATTATGGA
2521  GGAATGCTGT TTTCCCGGGG ATCGCAGTGG TGAGTAACCA TGCATCATCA GGAGTACGGA
      CCTTACGACA AAAGGGCCCC TAGCGTCACC ACTCATTGGT ACGTAGTAGT CCTCATGCCT
2581  TAAAATGCTT GATGGTCGGA AGAGGCATAA ATTCCGTCAG CCAGTTTAGT CTGACCATCT
      ATTTTACGAA CTACCAGCCT TCTCCGTATT TAAGGCAGTC GGTCAAATCA GACTGGTAGA
2641  CATCTGTAAC ATCATTGGCA ACGCTACCTT TGCCATGTTT CAGAAACAAC TCTGGCGCAT
      GTAGACATTG TAGTAACCGT TGCGATGGAA ACGGTACAAA GTCTTTGTTG AGACCGCGTA
                        ClaI
                        ~~~~~~
2701  CGGGCTTCCC ATACAATCGA TAGATTGTCG CACCTGATTG CCCGACATTA TCGCGAGCCC
      GCCCGAAGGG TATGTTAGCT ATCTAACAGC GTGGACTAAC GGGCTGTAAT AGCGCTCGGG
2761  ATTTATACCC ATATAAATCA GCATCCATGT TGGAATTTAA TCGCGGCCTA GAGCAAGACG
      TAAATATGGG TATATTTAGT CGTAGGTACA ACCTTAAATT AGCGCCGGAT CTCGTTCTGC
2821  TTTCCGTTG AATATGGCTC ATACTCTTCC TTTTTCAATA TTATTGAAGC ATTTATCAGG
      AAAGGGCAAC TTATACCGAG TATGAGAAGG AAAAAGTTAT AATAACTTCG TAAATAGTCC
2881  GTTATTGTCT CATGAGCGGA TACATATTTG AATGTATTTA GAAAAATAAA CAAATAGGCA
      CAATAACAGA GTACTCGCCT ATGTATAAAC TTACATAAAT CTTTTTATTT GTTTATCCGT
2941  TGCAGCGCTC TTCCGCTTCC TCGCTCACTG ACTCGCTACG CTCGGTCGTT CGACTGCGGC
      ACGTCGCGAG AAGGCGAAGG AGCGAGTGAC TGAGCGATGC GAGCCAGCAA GCTGACGCCG
3001  GAGCGGTGTC AGCTCACTCA AAAGCGGTAA TACGGTTATC CACAGAATCA GGGGATAAAG
      CTCGCCACAG TCGAGTGAGT TTTCGCCATT ATGCCAATAG GTGTCTTAGT CCCCTATTTC
3061  CCGGAAAGAA CATGTGAGCA AAAAGCAAAG CACCGGAAGA AGCCAACGCC GCAGGCGTTT
      GGCCTTTCTT GTACACTCGT TTTTCGTTTC GTGGCCTTCT TCGGTTGCGG CGTCCGCAAA
3121  TTCCATAGGC TCCGCCCCCC TGACGAGCAT CACAAAAATC GACGCTCAAG CCAGAGGTGG
      AAGGTATCCG AGGCGGGGGG ACTGCTCGTA GTGTTTTTAG CTGCGAGTTC GGTCTCCACC
3181  CGAAACCCGA CAGGACTATA AAGATACCAG GCGTTTCCCC CTGGAAGCTC CCTCGTGCGC
      GCTTTGGGCT GTCCTGATAT TTCTATGGTC CGCAAAGGGG GACCTTCGAG GGAGCACGCG
3241  TCTCCTGTTC CGACCCTGCC GCTTACCGGA TACCTGTCCG CCTTTCTCCC TTCGGGAAGC
      AGAGGACAAG GCTGGGACGG CGAATGGCCT ATGGACAGGC GGAAAGAGGG AAGCCCTTCG
3301  GTGGCGCTTT CTCATAGCTC ACGCTGTTGG TATCTCAGTT CGGTGTAGGT CGTTCGCTCC
      CACCGCGAAA GAGTATCGAG TGCGACAACC ATAGAGTCAA GCCACATCCA GCAAGCGAGG
3361  AAGCTGGGCT GTGTGCACGA ACCCCCCGTT CAGCCCGACC GCTGCGCCTT ATCCGGTAAC
      TTCGACCCGA CACACGTGCT TGGGGGGCAA GTCGGGCTGG CGACGCGGAA TAGGCCATTG
3421  TATCGTCTTG AGTCCAACCC GGTAAGACAC GACTTATCGC CACTGGCAGC AGCCATTGGT
      ATAGCAGAAC TCAGGTTGGG CCATTCTGTG CTGAATAGCG GTGACCGTCG TCGGTAACCA
```

Fig. 32$_2$

```
3481  AACTGATTTA  GAGGACTTTG  TCTTGAAGTT  ATGCACCTGT  TAAGGCTAAA  CTGAAAGAAC
      TTGACTAAAT  CTCCTGAAAC  AGAACTTCAA  TACGTGGACA  ATTCCGATTT  GACTTTCTTG
3541  AGATTTTGGT  GAGTGCGGTC  CTCCAACCCA  CTTACCTTGG  TTCAAAGAGT  TGGTAGCTCA
      TCTAAAACCA  CTCACGCCAG  GAGGTTGGGT  GAATGGAACC  AAGTTTCTCA  ACCATCGAGT
3601  GCGAACCTTG  AGAAAACCAC  CGTTGGTAGC  GGTGGTTTTT  CTTTATTTAT  GAGATGATGA
      CGCTTGGAAC  TCTTTTGGTG  GCAACCATCG  CCACCAAAAA  GAAATAAATA  CTCTACTACT
3661  ATCAATCGGT  CTATCAAGTC  AACGAACAGC  TATTCCGTTA  CTCTAGATTT  CAGTGCAATT
      TAGTTAGCCA  GATAGTTCAG  TTGCTTGTCG  ATAAGGCAAT  GAGATCTAAA  GTCACGTTAA
3721  TATCTCTTCA  AATGTAGCAC  CTGAAGTCAG  CCCCATACGA  TATAAGTTGT  AATTCTCATG
      ATAGAGAAGT  TTACATCGTG  GACTTCAGTC  GGGGTATGCT  ATATTCAACA  TTAAGAGTAC
3781  TTAGTCATGC  CCCGCGCCCA  CCGGAAGGAG  CTGACTGGGT  TGAAGGCTCT  CAAGGGCATC
      AATCAGTACG  GGGCGCGGGT  GGCCTTCCTC  GACTGACCCA  ACTTCCGAGA  GTTCCCGTAG
3841  GGTCGAGATC  CCGGTGCCTA  ATGAGTGAGC  TAACTTACAT  TAATTGCGTT  GCGCTCACTG
      CCAGCTCTAG  GGCCACGGAT  TACTCACTCG  ATTGAATGTA  ATTAACGCAA  CGCGAGTGAC
3901  CCCGCTTTCC  AGTCGGGAAA  CCTGTCGTGC  CAGCTGCATT  AATGAATCGG  CCAACGCGCG
      GGGCGAAAGG  TCAGCCCTTT  GGACAGCACG  GTCGACGTAA  TTACTTAGCC  GGTTGCGCGC
3961  GGGAGAGGCG  GTTTGCGTAT  TGGGCGCCAG  GGTGGTTTTT  CTTTTCACCA  GTGAGACGGG
      CCCTCTCCGC  CAAACGCATA  ACCCGCGGTC  CCACCAAAAA  GAAAAGTGGT  CACTCTGCCC
4021  CAACAGCTGA  TTGCCCTTCA  CCGCCTGGCC  CTGAGAGAGT  TGCAGCAAGC  GGTCCACGCT
      GTTGTCGACT  AACGGGAAGT  GGCGGACCGG  GACTCTCTCA  ACGTCGTTCG  CCAGGTGCGA
4081  GGTTTGCCCC  AGCAGGCGAA  AATCCGTTT  GATGGTGGTT  AACGGCGGGA  TATAACATGA
      CCAAACGGGG  TCGTCCGCTT  TTAGGACAAA  CTACCACCAA  TTGCCGCCCT  ATATTGTACT
4141  GCTGTCTTCG  GTATCGTCGT  ATCCCACTAC  CGAGATGTCC  GCACCAACGC  GCAGCCCGGA
      CGACAGAAGC  CATAGCAGCA  TAGGGTGATG  GCTCTACAGG  CGTGGTTGCG  CGTCGGGCCT
4201  CTCGGTAATG  GCGCGCATTG  CGCCCAGCGC  CATCTGATCG  TTGGCAACCA  GCATCGCAGT
      GAGCCATTAC  CGCGCGTAAC  GCGGGTCGCG  GTAGACTAGC  AACCGTTGGT  CGTAGCGTCA
4261  GGGAACGATG  CCCTCATTCA  GCATTTGCAT  GGTTTGTTGA  AAACCGGACA  TGGCACTCCA
      CCCTTGCTAC  GGGAGTAAGT  CGTAAACGTA  CCAAACAACT  TTTGGCCTGT  ACCGTGAGGT
4321  GTCGCCTTCC  CGTTCCGCTA  TCGGCTGAAT  TTGATTGCGA  GTGAGATATT  TATGCCAGCC
      CAGCGGAAGG  GCAAGGCGAT  AGCCGACTTA  AACTAACGCT  CACTCTATAA  ATACGGTCGG
4381  AGCCAGACGC  AGACGCGCCG  AGACAGAACT  TAATGGGCCC  GCTAACAGCG  CGATTTGCTG
      TCGGTCTGCG  TCTGCGCGGC  TCTGTCTTGA  ATTACCCGGG  CGATTGTCGC  GCTAAACGAC
4441  GTGACCCAAT  GCGACCAGAT  GCTCCACGCC  CAGTCGCGTA  CCGTCTTCAT  GGGAGAAAAT
      CACTGGGTTA  CGCTGGTCTA  CGAGGTGCGG  GTCAGCGCAT  GGCAGAAGTA  CCCTCTTTTA
4501  AATACTGTTG  ATGGGTGTCT  GGTCAGAGAC  ATCAAGAAAT  AACGCCGGAA  CATTAGTGCA
      TTATGACAAC  TACCCACAGA  CCAGTCTCTG  TAGTTCTTTA  TTGCGGCCTT  GTAATCACGT
4561  GGCAGCTTCC  ACAGCAATGG  CATCCTGGTC  ATCCAGCGGA  TAGTTAATGA  TCAGCCCACT
      CCGTCGAAGG  TGTCGTTACC  GTAGGACCAG  TAGGTCGCCT  ATCAATTACT  AGTCGGGTGA
4621  GACGCGTTGC  GCGAGAAGAT  TGTGCACCGC  CGCTTTACAG  GCTTCGACGC  CGCTTCGTTC
      CTGCGCAACG  CGCTCTTCTA  ACACGTGGCG  GCGAAATGTC  CGAAGCTGCG  GCGAAGCAAG
4681  TACCATCGAC  ACCACCACGC  TGGCACCCAG  TTGATCGGCG  CGAGATTTAA  TCGCCGCGAC
      ATGGTAGCTG  TGGTGGTGCG  ACCGTGGGTC  AACTAGCCGC  GCTCTAAATT  AGCGGCGCTG
4741  AATTTGCGAC  GGCGCGTGCA  GGGCCAGACT  GGAGGTGGCA  ACGCCAATCA  GCAACGACTG
      TTAAACGCTG  CCGCGCACGT  CCCGGTCTGA  CCTCCACCGT  TGCGGTTAGT  CGTTGCTGAC
4801  TTTGCCCGCC  AGTTGTTGTG  CCACGCGGTT  GGGAATGTAA  TTCAGCTCCG  CCATCGCCGC
      AAACGGGCGG  TCAACAACAC  GGTGCGCCAA  CCCTTACATT  AAGTCGAGGC  GGTAGCGGCG
4861  TTCCACTTTT  TCCCGCGTTT  TCGCAGAAAC  GTGGCTGGCC  TGGTTCACCA  CGCGGGAAAC
      AAGGTGAAAA  AGGGCGCAAA  AGCGTCTTTG  CACCGACCGG  ACCAAGTGGT  GCGCCCTTTG
4921  GGTCTGATAA  GAGACACCGG  CATACTCTGC  GACATCGTAT  AACGTTACTG  GTTTCACATT
      CCAGACTATT  CTCTGTGGCC  GTATGAGACG  CTGTAGCATA  TTGCAATGAC  CAAAGTGTAA
4981  CACCACCCTG  AATTGACTCT  CTTCCGGGCG  CTATCATGCC  ATACCGCGAA  AGGTTTTGCG
      GTGGTGGGAC  TTAACTGAGA  GAAGGCCCGC  GATAGTACGG  TATGGCGCTT  TCCAAAACGC
5041  CCATTCGATG  GTGTCCGGGA  TCTCGACGCT  CTCCCTTATG  CGACTCCTGC  ATTAGGAAAT
      GGTAAGCTAC  CACAGGCCCT  AGAGCTGCGA  GAGGGAATAC  GCTGAGGACG  TAATCCTTTA
5101  TAATACGACT  CACTATA
      ATTATGCTGA  GTGATAT
```

```
   1    GGGGAATTGT GAGCGGATAA CAATTCCCCT CTAGAAATAA TTTTGTTTAA CTTTAAGAAG
        CCCCTTAACA CTCGCCTATT GTTAAGGGGA GATCTTTATT AAAACAAATT GAAATTCTTC
                                                                 EcoRI
                                                                 ~~~~~~
                NcoI                                  BamHI        SacI
                ~~~~~~                                ~~~~~~       ~~~
  61    GAGATATACC ATGGGCAGCA GCCATCACCA TCATCACCAC AGCCAGGATC CGAATTCGAG
        CTCTATATGG TACCCGTCGT CGGTAGTGGT AGTAGTGGTG TCGGTCCTAG GCTTAAGCTC
        SacI
        ~~~
 121    CTCGATCACA AGTTTGTACA AAAAAGCTGA ACGAGAAACG TAAAATGATA TAAATATCAA
        GAGCTAGTGT TCAAACATGT TTTTTCGACT TGCTCTTTGC ATTTTACTAT ATTTATAGTT
 181    TATATTAAAT TAGATTTTGC ATAAAAAACA GACTACATAA TACTGTAAAA CACAACATAT
        ATATAATTTA ATCTAAAACG TATTTTTTGT CTGATGTATT ATGACATTTT GTGTTGTATA
 241    CCAGTCACTA TGGCGGCCGC CACGTTAAGG GATTTTGGTC ATGATCAGCA CGTGTTGACA
        GGTCAGTGAT ACCGCCGGCG GTGCAATTCC CTAAAACCAG TACTAGTCGT GCACAACTGT
                                                                   NcoI
                                                                   ~~~
 301    ATTAATCATC GGCATAGTAT ATCGGCATAG TATAATACGA CAAGGTGAGG AACTAAACCA
        TAATTAGTAG CCGTATCATA TAGCCGTATC ATATTATGCT GTTCCACTCC TTGATTTGGT
        NcoI
        ~~~
 361    TGGCCAAGTT GACCAGTGCC GTTCCGGTGC TCACCGCGCG CGACGTCGCC GGAGCGGTCG
        ACCGGTTCAA CTGGTCACGG CAAGGCCACG AGTGGCGCGC GCTGCAGCGG CCTCGCCAGC
 421    AGTTCTGGAC CGACCGGCTC GGGTTCTCCC GGGACTTCGT GGAGGACGAC TTCGCCGGTG
        TCAAGACCTG GCTGGCCGAG CCCAAGAGGG CCCTGAAGCA CCTCCTGCTG AAGCGGCCAC
 481    TGGTCCGGGA CGACGTGACC CTGTTCATCA GCGCGGTCCA GGACCAGGTG GTGCCGGACA
        ACCAGGCCCT GCTGCACTGG GACAAGTAGT CGCGCCAGGT CCTGGTCCAC CACGGCCTGT
 541    ACACCCTGGC CTGGGTGTGG GTGCGCGGCC TGGACGAGCT GTACGCCGAG TGGTCGGAGG
        TGTGGGACCG GACCCACACC CACGCGCCGG ACCTGCTCGA CATGCGGCTC ACCAGCCTCC
 601    TCGTGTCCAC GAACTTCCGG GACGCTCCG GGCCGGCCAT GACCGAGATC GGCGAGCAGC
        AGCACAGGTG CTTGAAGGCC CTGCGGAGGC CCGGCCGGTA CTGGCTCTAG CCGCTCGTCG
 661    CGTGGGGCG GGAGTTCGCC CTGCGCGACC CGGCCGGCAA CTGCCGTGCAC TTCGTGGCCG
        GCACCCCCGC CCTCAAGCGG GACGCGCTGG GCCGGCCGTT GACGCACGTG AAGCACCGGC
 721    AGGAGCAGGA CTGATCATGA TGATATTATT TTATCTTGTG CAATGTAACA TCAGAGATTT
        TCCTCGTCCT GACTAGTACT ACTATAATAA AATAGAACAC GTTACATTGT AGTCTCTAAA
 781    TGAGACACGG GCCAGAGCTG CCAGGAAACA GCTATGACCA TGTAATACGA CTCACTATAG
        ACTCTGTGCC CGGTCTCGAC GGTCCTTTGT CGATACTGGT ACATTATGCT GAGTGATATC
 841    GGGATATCAG CTGGATGGCA ATAATGATT TTATTTTGAC TGATAGTGAC CTGTTCGTTG
        CCCTATAGTC GACCTACCGT TTATTACTAA AATAAAACTG ACTATCACTG GACAAGCAAC
 901    CAACACCGGT GCTAGCGTAT ACCCGAAGTA TGTCAAAAAG AGGTGTGCTA TGAAGCAGCG
        GTTGTGGCCA CGATCGCATA TGGGCTTCAT ACAGTTTTTC TCCACACGAT ACTTCGTCGC
 961    TATTACAGTG ACAGTTGACA GCGACAGCTA TCAGTTGCTC AAGGCATATA TGATGTCAAT
        ATAATGTCAC TGTCAACTGT CGCTGTCGAT AGTCAACGAG TTCCGTATAT ACTACAGTTA
1021    ATCTCCGGTC TGGTAAGCAC AACCATGCAG AATGAAGCCC GTCGTCTGCG TGCCGAACGC
        TAGAGGCCAG ACCATTCGTG TTGGTACGTC TTACTTCGGG CAGCAGACGC ACGGCTTGCG
1081    TGGAAAGCGG AAAATCAGGA AGGGATGGCT GAGGTCGCCC GGTTTATTGA AATGAACGGC
        ACCTTTCGCC TTTTAGTCCT TCCCTACCGA CTCCAGCGGG CCAAATAACT TTACTTGCCG
1141    TCTTTTGCTG ACGAGAACAG GGACTGGTGA AATGCAGTTT AAGGTTTACA CCTATAAAAG
        AGAAAACGAC TGCTCTTGTC CCTGACCACT TTACGTCAAA TTCCAAATGT GGATATTTTC
1201    AGAGAGCCGT ATCGTCTGT TTGTGGATGT ACAGAGTGAT ATTATTGACA CGCCCGGGCG
        TCTCTCGGCA ATAGCAGACA AACACCTACA TGTCTCACTA TAATAACTGT GCGGGCCCGC
1261    ACGGATGGTG ATCCCCCTGG CCAGTGCACG TCTGCTGTCA GATAAAGTCT CCCGTGAACT
        TGCCTACCAC TAGGGGGACC GGTCACGTGC AGACGACAGT CTATTTCAGA GGGCACTTGA
1321    TTACCCGGTG GTGCATATCG GGGATGAAAG CTGGCGCATG ATGACCACCG ATATGGCCAG
        AATGGGCCAC CACGTATAGC CCCTACTTTC GACCGCGTAC TACTGGTGGC TATACCGGTC
1381    TGTGCCGGTC TCCGTTATCG GGGAAGAAGT GGCTGATCTC AGCCGCCGCG AAAATGACAT
        ACACGGCCAG AGGCAATAGC CCCTTCTTCA CCGACTAGAG TCGGCGGCGC TTTTACTGTA
1441    CAAAAACGCC ATTAACCTGA TGTTCTGGGG AATATAAATG TCAGGCTCCC TTATACACAG
        GTTTTTGCGG TAATTGGACT ACAAGACCCC TTATATTTAC AGTCCGAGGG AATATGTGTC
            PstI
            ~~~~~~
1501    CCAGTCTGCA GGTCGACCAT AGTGACTGGA TATGTTGTGT TTTACAGTAT TATGTAGTCT
        GGTCAGACGT CCAGCTGGTA TCACTGACCT ATACAACACA AAATGTCATA ATACATCAGA
1561    GTTTTTTATG CAAAATCTAA TTTAATATAT TGATATTTAT ATCATTTTAC GTTTCTCGTT
        CAAAAAATAC GTTTTAGATT AAATTATATA ACTATAAATA TAGTAAAATG CAAAGAGCAA
                                                                  HindIII
                                                                  ~~~~~~
1621    CAGCTTTCTT GTACAAAGTG GTGATAATTA ATTAAGATCA GATCCGGCTG CTAAGCTTGG
```

Fig. 34₁

```
                GTCGAAAGAA CATGTTTCAC CACTATTAAT TAATTCTAGT CTAGGCCGAC GATTCGAACC
                                                                    AvrII
                                                                    ~~~~~~
        1681    AATTGTTATC CGCTCACAAT TCCTATAGTG AGTCGTATTA CCTAGGCTGC TGCCACCGCT
                TTAACAATAG GCGAGTGTTA AGGATATCAC TCAGCATAAT GGATCCGACG ACGGTGGCGA
        1741    GAGCAATAAC TAGCATAACC CCTTGGGGCC TCTAAACGGG TCTTGAGGGG TTTTTTGCTG
                CTCGTTATTG ATCGTATTGG GGAACCCCGG AGATTTGCCC AGAACTCCCC AAAAAACGAC
        1801    AAAGGAGGAA CTATATCCGG ATTGGCGAAT GGGACGCGCC CTGTAGCGGC GCATTAAGCG
                TTTCCTCCTT GATATAGGCC TAACCGCTTA CCCTGCGCGG GACATCGCCG CGTAATTCGC
        1861    CGGCGGGTGT GGTGGTTACG CGCAGCGTGA CCGCTACACT TGCCAGCGCC CTAGCGCCCG
                GCCGCCCACA CCACCAATGC GCGTCGCACT GGCGATGTGA ACGGTCGCGG GATCGCGGGC
        1921    CTCCTTTCGC TTTCTTCCCT TCCTTTCTCG CCACGTTCGC CGGCTTTCCC CGTCAAGCTC
                GAGGAAAGCG AAAGAAGGGA AGGAAAGAGC GGTGCAAGCG GCCGAAAGGG GCAGTTCGAG
        1981    TAAATCGGGG GCTCCCTTTA GGGTTCCGAT TTAGTGCTTT ACGGCACCTC GACCCCAAAA
                ATTTAGCCCC CGAGGGAAAT CCCAAGGCTA AATCAGCAAA TGCCGTGGAG CTGGGGTTTT
        2041    AACTTGATTA GGGTGATGGT TCACGTAGTG GGCCATCGCC CTGATAGACG GTTTTTCGCC
                TTGAACTAAT CCCACTACCA AGTGCATCAC CCGGTAGCGG GACTATCTGC CAAAAAGCGG
        2101    CTTTGACGTT GGAGTCCACG TTCTTTAATA GTGGACTCTT GTTCCAAACT GGAACAACAC
                GAAACTGCAA CCTCAGGTGC AAGAAATTAT CACCTGAGAA CAAGGTTTGA CCTTGTTGTG
        2161    TCAACCCTAT CTCGGTCTAT TCTTTTGATT TATAAGGGAT TTTGCCGATT TCGGCCTATT
                AGTTGGGATA GAGCCAGATA AGAAAACTAA ATATTCCCTA AAACGGCTAA AGCCGGATAA
        2221    GGTTAAAAAA TGAGCTGATT TAACAAAAAT TTAACGCGAA TTTTAACAAA ATATTAACGT
                CCAATTTTTT ACTCGACTAA ATTGTTTTTA AATTGCGCTT AAAATTGTTT TATAATTGCA
        2281    TTACAATTTC TGGCGGCACG ATGGCATGAG ATTATCAAAA AGGATCTTCA CCTAGATCCT
                AATGTTAAAG ACCGCCGTGC TACCGTACTC TAATAGTTTT TCCTAGAAGT GGATCTAGGA
        2341    TTTAAATTAA AAATGAAGTT TTAAATCAAT CTAAAGTATA TATGAGTAAA CTTGGTCTGA
                AAATTTAATT TTTACTTCAA AATTTAGTTA GATTTCATAT ATACTCATTT GAACCAGACT
        2401    CAGTTACCAA TGCTTAATCA GTGAGGCACC TATCTCAGCG ATCTGTCTAT TTCGTTCATC
                GTCAATGGTT ACGAATTAGT CACTCCGTGG ATAGAGTCGC TAGACAGATA AAGCAAGTAG
        2461    CATAGTTGCC TGACTCCCCG TCGTGTAGAT AACTACGATA CGGGAGGGCT TACCATCTGG
                GTATCAACGG ACTGAGGGGC AGCACATCTA TTGATGCTAT GCCCTCCCGA ATGGTAGACC
        2521    CCCCAGTGCT GCAATGATAC CGCGAGACCC ACGCTCACCG GCTCCAGATT TATCAGCAAT
                GGGGTCACGA CGTTACTATG GCGCTCTGGG TGCGAGTGGC CGAGGTCTAA ATAGTCGTTA
        2581    AAACCAGCCA GCCGGAAGGG CCGAGCGCAG AAGTGGTCCT GCAACTTTAT CCGCCTCCAT
                TTTGGTCGGT CGGCCTTCCC GGCTCGCGTC TTCACCAGGA CGTTGAAATA GGCGGAGGTA
        2641    CCAGTCTATT AATTGTTGCC GGGAAGCTAG AGTAAGTAGT TCGCCAGTTA ATAGTTTGCG
                GGTCAGATAA TTAACAACGG CCCTTCGATC TCATTCATCA AGCGGTCAAT TATCAAACGC
        2701    CAACGTTGTT GCCATTGCTA CAGGCATCGT GGTGTCACGC TCGTCGTTTG GTATGGCTTC
                GTTGCAACAA CGGTAACGAT GTCCGTAGCA CCACAGTGCG AGCAGCAAAC CATACCGAAG
        2761    ATTCAGCTCC GGTTCCCAAC GATCAAGGCG AGTTACATGA TCCCCCATGT TGTGCAAAAA
                TAAGTCGAGG CCAAGGGTTG CTAGTTCCGC TCAATGATCT AGGGGGTACA ACACGTTTTT
        2821    AGCGGTTAGC TCCTTCGGTC CTCCGATCGT TGTCAGAAGT AAGTTGGCCG CAGTGTTATC
                TCGCCAATCG AGGAAGCCAG GAGGCTAGCA ACAGTCTTCA TTCAACCGGC GTCACAATAG
        2881    ACTCATGGTT ATGGCAGCAC TGCATAATTC TCTTACTGTC ATGCCATCCG TAAGATGCTT
                TGAGTACCAA TACCGTCGTG ACGTATTAAG AGAATGACAG TACGGTAGGC ATTCTACGAA
        2941    TTCTGTGACT GGTGAGTACT CAACCAAGTC ATTCTGAGAA TAGTGTATGC GGCGACCGAG
                AAGACACTGA CCACTCATGA GTTGGTTCAG TAAGACTCTT ATCACATACG CCGCTGGCTC
        3001    TTGCTCTTGC CCGGCGTCAA TACGGGATAA TACCGCGCCA CATAGCAGAA CTTTAAAAGT
                AACGAGAACG GGCCGCAGTT ATGCCCTATT ATGGCGCGGT GTATCGTCTT GAAATTTTCA
        3061    GCTCATCATT GGAAAACGTT CTTCGGGGCG AAAACTCTCA AGGATCTTAC CGCTGTTGAG
                CGAGTAGTAA CCTTTTGCAA GAAGCCCCGC TTTTGAGAGT TCCTAGAATG GCGACAACTC
        3121    ATCCAGTTCG ATGTAACCCA CTCGTGCACC CAACTGATCT TCAGCATCTT TTACTTTCAC
                TAGGTCAAGC TACATTGGGT GAGCACGTGG GTTGACTAGA AGTCGTAGAA AATGAAAGTG
        3181    CAGCGTTTCT GGGTGAGCAA AAACAGGAAG GCAAAATGCC GCAAAAAAGG GAATAAGGGC
                GTCGCAAAGA CCCACTCGTT TTTGTCCTTC CGTTTTACGG CGTTTTTTCC CTTATTCCCG
        3241    GACACGGAAA TGTTGAATAC TCATGATTCT CCTTTTTCAA TCATGATTGA AGCATTTATC
                CTGTGCCTTT ACAACTTATG AGTATGAGAA GGAAAAAGTT AGTACTAACT TCGTAAATAG
        3301    AGGGTTATTG TCTCATGAGC GGATACATAT TTGAATGTAT TTAGAAAAAT AAACAAATAG
                TCCCAATAAC AGAGTACTCG CCTATGTATA AACTTACATA AATCTTTTTA TTTGTTTATC
        3361    GTCATGACCA AAATCCCTTA ACGTGAGTTT TCGTTCCACT GAGCGTCAGA CCCCGTAGAA
                CAGTACTGGT TTTAGGGAAT TGCACTCAAA AGCAAGGTGA CTCGCAGTCT GGGGCATCTT
        3421    AAGATCAAAG GATCTTCTTG AGATCCTTTT TTTCTGCGCG TAATCTGCTG CTTGCAAACA
                TTCTAGTTTC CTAGAAGAAC TCTAGGAAAA AAAGACGCGC ATTAGACGAC GAACGTTTGT
        3481    AAAAAACCAC CGCTACCAGC GGTGGTTTGT TTGCCGGATC AAGAGCTACC AACTCTTTTT
                TTTTTTGGTG GCGATGGTCG CCACCAAACA AACGGCCTAG TTCTCGATGG TTGAGAAAAA
        3541    CCGAAGGTAA CTGGCTTCAG CAGAGCGCAG ATACCAAATA CTGTCCTTCT AGTGTAGCCG
                GGCTTCCATT GACCGAAGTC GTCTCGCGTC TATGGTTTAT GACAGGAAGA TCACATCGGC
        3601    TAGTTAGGCC ACCACTTCAA GAACTCTGTA GCACCGCCTA CATACCTCGC TCTGCTAATC
                ATCAATCCGG TGGTGAAGTT CTTGAGACAT CGTGGCGGAT GTATGGAGCG AGACGATTAG
        3661    CTGTTACCAG TGGCTGCTGC CAGTGGCGAT AAGTCGTGTC TTACCGGGTT GGACTCAAGA
                GACAATGGTC ACCGACGACG GTCACCGCTA TTCAGCACAG AATGGCCCAA CCTGAGTTCT
        3721    CGATAGTTAC CGGATAAGGC GCAGCGGTCG GGCTGAACGG GGGGTTCGTG CACACAGCCC
```

Fig. 34$_2$

```
          GCTATCAATG GCCTATTCCG CGTCGCCAGC CCGACTTGCC CCCCAAGCAC GTGTGTCGGG
3781 AGCTTGGAGC GAACGACCTA CACCGAACTG AGATACCTAC AGCGTGAGCT ATGAGAAAGC
     TCGAACCTCG CTTGCTGGAT GTGGCTTGAC TCTATGGATG TCGCACTCGA TACTCTTTCG
3841 GCCACGCTTC CCGAAGGGAG AAAGGCGGAC AGGTATCCGG TAAGCGGCAG GGTCGGAACA
     CGGTGCGAAG GGCTTCCCTC TTTCCGCCTG TCCATAGGCC ATTCGCCGTC CCAGCCTTGT
3901 GGAGAGCGCA CGAGGGAGCT TCCAGGGGGA AACGCCTGGT ATCTTTATAG TCCTGTCGGG
     CCTCTCGCGT GCTCCCTCGA AGGTCCCCCT TTGCGGACCA TAGAAATATC AGGACAGCCC
3961 TTTCGCCACC TCTGACTTGA GCGTCGATTT TTGTGATGCT CGTCAGGGGG GCGGAGCCTA
     AAAGCGGTGG AGACTGAACT CGCAGCTAAA AACACTACGA GCAGTCCCCC CGCCTCGGAT
4021 TGGAAAAACG CCAGCAACGC GGCCTTTTTA CGGTTCCTGG CCTTTTGCTG GCCTTTTGCT
     ACCTTTTTGC GGTCGTTGCG CCGGAAAAAT GCCAAGGACC GGAAAACGAC CGGAAAACGA
4081 CACATGTTCT TTCCTGCGTT ATCCCCTGAT TCTGTGGATA ACCGTATTAC CGCCTTTGAG
     GTGTACAAGA AAGGACGCAA TAGGGGACTA AGACACCTAT TGGCATAATG GCGGAAACTC
4141 TGAGCTGATA CCGCTCGCCG CAGCCGAACG ACCGAGCGCA GCGAGTCAGT GAGCGAGGAA
     ACTCGACTAT GGCGAGCGGC GTCGGCTTGC TGGCTCGCGT CGCTCAGTCA CTCGCTCCTT
4201 GCGGAAGAGC GCCTGATGCG GTATTTTCTC CTTACGCATC TGTCGGGTAT TTCACACCGC
     CGCCTTCTCG CGGACTACGC CATAAAAGAG GAATGCGTAG ACACGCCATA AAGTGTGGCG
4261 ATATATGGTG CACTCTCAGT ACAATCTGCT CTGATGCCGC ATAGTTAAGC CAGTATACAC
     TATATACCAC GTGAGAGTCA TGTTAGACGA GACTACGGCG TATCAATTCG GTCATATGTG
4321 TCCGCTATCG CTACGTGACT GGGTCATGGC TGCGCCCCGA CACCCGCCAA CACCCGCTGA
     AGGCGATAGC GATGCACTGA CCCAGTACCG ACGCGGGGCT GTGGGCGGTT GTGGGCGACT
4381 CGCGCCCTGA CGGGCTTGTC TGCTCCCGGC ATCCGCTTAC AGACAAGCTG TGACCGTCTC
     GCGCGGGACT GCCCGAACAG ACGAGGGCCG TAGGCGAATG TCTGTTCGAC ACTGGCAGAG
4441 CGGGAGCTGC ATGTGTCAGA GGTTTTCACC GTCATCACCG AAACGCGCGA GGCAGCTGCG
     GCCCTCGACG TACACAGTCT CCAAAAGTGG CAGTAGTGGC TTTGCGCGCT CCGTCGACGC
4501 GTAAAGCTCA TCAGCGGTGG TCGTGAAGCGA TTCACAGATG TCTGCCTGTT CATCCGCGTC
     CATTTCGAGT AGTCGCACCA GCACTTCGCT AAGTGTCTAC AGACGGACAA GTAGGCGCAG
4561 CAGCTCGTTG AGTTTCTCCA GAAGCGTTAA TGTCTGGCTT CTGATAAAGC GGGCCATGTT
     GTCGAGCAAC TCAAAGAGGT CTTCGCAATT ACAGACCGAA GACTATTTCG CCCGGTACAA
4621 AAGGGCGGTT TTTTCCTGTT TGGTCACTGA TGCCTCCGTG TAAGGGGGAT TTCTGTTCAT
     TTCCCGCCAA AAAAGGACAA ACCAGTGACT ACGGAGGCAC ATTCCCCCTA AAGACAAGTA
4681 GGGGGTAATG ATACCGATGA AACGAGAGAG GATGCTCACG ATACGGGTTA TCGATCGATGA
     CCCCCATTAC TATGGCTACT TTGCTCTCTC CTACGAGTGC TATGCCCAAT GACTACTACT
4741 ACATGCCCGG TTACTGGAAC GTTGTGAGGG TAAACAACTG GCGGTATGGA TGCGGCGGGA
     TGTACGGGCC AATGACCTTG CAACACTCCC ATTTGTTGAC CGCCATACCT ACGCCGCCCT
4801 CCAGAGAAAA ATCACTCAGG GTCAATGCCA GCGCTTCGTT AATACAGATG TAGGTGTTCC
     GGTCTCTTTT TAGTGAGTCC CAGTTACGGT CGCGAAGCAA TTATGTCTAC ATCCACAAGG
4861 ACAGGGTAGC CAGCAGCATC CTGCGATGCA GATCCGGAAC ATAATGGTGC AGGGCGCTGA
     TGTCCCATCG GTCGTCGTAG GACGCTACGT CTAGGCCTTG TATTACCACG TCCCGCGACT
4921 CTTCCGCGTT TCCAGACTTT ACGAAACACG GAAACCGAAG ACCATTCATG TTGTTGCTCA
     GAAGGCGCAA AGGTCTGAAA TGCTTTGTGC CTTTGGCTTC TGGTAAGTAC AACAACGAGT
4981 GGTCGCAGAC GTTTTGCAGC AGCAGTCGCT TCACGTTCGC TCGCGTATCG GTGATTCATT
     CCAGCGTCTG CAAAACGTCG TCGTCAGCGA AGTGCAAGCG AGCGCATAGC CACTAAGTAA
5041 CTGCTAACCA GTAAGGCAAC CCCGCCAGCC TAGCCGGGTC CTCAACGACA GGAGCACGAT
     GACGATTGGT CATTCCGTTG GGGCGGTCGG ATCGGCCCAG GAGTTGCTGT CCTCGTGCTA
5101 CATGCTAGTC ATGCCCCGCG CCCACCGGAA GGAGCTGACT GGGTTGAAGG CTCTCAAGGG
     GTACGATCAG TACGGGGCGC GGGTGGCCTT CCTCGACTGA CCCAACTTCC GAGAGTTCCC
5161 CATCGGTCGA GATCCCGGTG CCTAATGAGT GAGCTAACTT ACATTAATTG CGTTGCGCTC
     GTAGCCAGCT CTAGGGCCAC GGATTACTCA CTCGATTGAA TGTAATTAAC GCAACGCGAG
5221 ACTGCCCGCT TTCCAGTCGG GAAACCTGTC GTGCCAGCTG CATTAATGAA TCGGCCAACG
     TGACGGGCGA AAGGTCAGCC CTTTGGACAG CACGGTCGAC GTAATTACTT AGCCGGTTGC
5281 CGCGGGGAGA GGCGGTTTGC GTATTGGGCG CCAGGGTGGT TTTTCTTTTC ACCAGTGAGA
     GCGCCCCTCT CCGCCAAACG CATAACCCGC GGTCCCACCA AAAGAAAAG TGGTCACTCT
5341 CGGGCAACAG CTGATTGCCC TTCACCGCCT GGCCCTGAGA GAGTTGCAGC AAGCGGTCCA
     GCCCGTTGTC GACTAACGGG AAGTGGCGGA CCGGGACTCT CTCAACGTCG TTCGCCAGGT
5401 CGCTGGTTTG CCCCAGCAGG CGAAAATCCT GTTTGATGGT GGTTAACGGC GGGATATAAC
     GCGACCAAAC GGGGTCGTCC GCTTTTAGGA CAAACTACCA CCAATTGCCG CCCTATATTG
5461 ATGAGCTGTC TTCGGTATCG TCGTATCCCA CTACCGAGAT GTCCGCACCA ACGCGCAGCC
     TACTCGACAG AAGCCATAGC AGCATAGGGT GATGGCTCTA CAGGCGTGGT TGCGCGTCGG
5521 CGGACTCGGT AATGGCGCGC ATTGCGCCCA GCGCCATCTG ATCGTTGGCA ACCAGCATCG
     GCCTGAGCCA TTACCGCGCG TAACGCGGGT CGCGGTAGAC TAGCAACCGT TGGTCGTAGC
5581 CAGTGGGAAC GATGCCCTCA TTCAGCATTT GCATGGTTTG TTGAAAACCG GACATGGCAC
     GTCACCCTTG CTACGGGAGT AAGTCGTAAA CGTACCAAAC AACTTTTGGC CTGTACCGTG
5641 TCCAGTCGCC TTCCCGTTCC GCTATCGGCT GAATTTGATT GCGAGTGAGA TATTTATGCC
     AGGTCAGCGG AAGGGCAAGG CGATAGCCGA CTTAAACTAA CGCTCACTCT ATAAATACGG
5701 AGCCAGCCAG ACGCAGACGC GCCGAGACAA AACTTAATGG GCCCGCTAAC AGCGCGATTT
     TCGGTCGGTC TGCGTCTGCG CGGCTCTGTC TTGAATTACC CGGGCGATTG TCGCGCTAAA
5761 GCTGGTGACC CAATGCGACC AGATGCTCCA CGCCCAGTCG CGTACCGTCT TCATGGGAGA
     CGACCACTGG GTTACGCTGG TCTACGAGGT GCGGGTCAGC GCATGCGACA AGTACCCTCT
```

Fig. 34₃

```
5821  AAATAATACT GTTGATGGGT GTCTGGTCAG AGACATCAAG AAATAACGCC GGAACATTAG
      TTTATTATGA CAACTACCCA CAGACCAGTC TCTGTAGTTC TTTATTGCGG CCTTGTAATC
5881  TGCAGGCAGC TTCCACAGCA ATGGCATCCT GGTCATCCAG CGGATAGTTA ATGATCAGCC
      ACGTCCGTCG AAGGTGTCGT TACCGTAGGA CCAGTAGGTC GCCTATCAAT TACTAGTCGG
5941  CACTGACGCG TTGCGCGAGA AGATTGTGCA CCGCCGCTTT ACAGGCTTCG ACGCCGCTTC
      GTGACTGCGC AACGCGCTCT TCTAACACGT GGCGGCGAAA TGTCCGAAGC TGCGGCGAAG
6001  GTTCTACCAT CGACACCACC ACGCTGGCAC CCAGTTGATC GGCGCGAGAT TTAATCGCCG
      CAAGATGGTA GCTGTGGTGG TGCGACCGTG GGTCAACTAG CCGCGCTCTA AATTAGCGGC
6061  CGACAATTTG CGACGGCGCG TGCAGGGCCA GACTGGAGGT GGCAACGCCA ATCAGCAACG
      GCTGTTAAAC GCTGCCGCGC ACGTCCCGGT CTGACCTCCA CCGTTGCGGT TAGTCGTTGC
6121  ACTGTTTGCC CGCCAGTTGT TGTGCCACGC GGTTGGGAAT GTAATTCAGC TCCGCCATCG
      TGACAAACGG GCGGTCAACA ACACGGTGCG CCAACCCTTA CATTAAGTCG AGGCGGTAGC
6181  CCGCTTCCAC TTTTTCCCGC GTTTTCGCAG AAACGTGGCT GGCCTGGTTC ACCACGCGGG
      GGCGAAGGTG AAAAAGGGCG CAAAAGCGTC TTTGCACCGA CCGGACCAAG TGGTGCGCCC
6241  AAACGGTCTG ATAAGAGACA CCGGCATACT CTGCGACATC GTATAACGTT ACTGGTTTCA
      TTTGCCGAC TATTCTCTGT GGCCGTATGA GACGCTGTAG CATATTGCAA TGACCAAAGT
6301  CATTCACCAC CCTGAATTGA CTCTCTTCCG GGCGCTATCA TGCCATACCG CGAAAGGTTT
      GTAAGTGGTG GGACTTAACT GAGAGAAGGC CCGCGATAGT ACGGTATGGC GCTTTCCAAA
6361  TGCGCCATTC GATGGTGTCC GGGATCTCGA CGCTCTCCCT TATGCGACTC CTGCATTAGG
      ACGCGGTAAG CTACCACAGG CCCTAGAGCT GCGAGAGGGA ATACGCTGAG GACGTAATCC
6421  AAGCAGCCCA GTAGTAGGTT GAGGCCGTTG AGCACCGCCG CCGCAAGGAA TGGTGCATGC
      TTCGTCGGGT CATCATCCAA CTCCGGCAAC TCGTGGCGGC GGCGTTCCTT ACCACGTACG
6481  AAGGAGATGG CGCCCAACAG TCCCCGGCC ACGGGGCCTG CCACCATACC CACGCCGAAA
      TTCCTCTACC GCGGGTTGTC AGGGGGCCGG TGCCCCGGAC GGTGGTATGG GTGCGGCTTT
6541  CAAGCGCTCA TGAGCCCGAA GTGGCGAGCC CGATCTTCCC CATCGGTGAT GTCGGCGATA
      GTTCGCGAGT ACTCGGGCTT CACCGCTCGG GCTAGAAGGG GTAGCCACTA CAGCCGCTAT
6601  TAGGCGCCAG CAACCGCACC TGTGGCGCCG GTGATGCCGG CCACGATGCG TCCGGCGTAG
      ATCCGCGGTC GTTGGCGTGG ACACCGCGG CACTACGGCC GGTGCTACGC AGGCCGCATC
                  ClaI
                  ~~~~~~~
6661  AGGATCGAGA TCGATCTCGA TCCCGCGAAA TTAATACGAC TCACTATA
      TCCTAGCTCT AGCTAGAGCT AGGGCGCTTT AATTATGCTG AGTGATAT
```

Fig. 34₄

| Fig. 36$_1$ |
|---|
| Fig. 36$_2$ |
| Fig. 36$_3$ |

Fig. 36

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                SacI
                                                                ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                                PstI
                                                ~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
                                                              XmaI
                                                              ~~~~~~~
                                                              SmaI
                                                              ~~~~~~~
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT TCTCCATTTT
     AAATGCTACG GTAACCCTAT ATAGTTGCCA CCATATAGGT CACTAAAAAA AGAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
     CGGCCTTCGT ATTTCACATT TCGGACCCCC ACGGATTACG CCGGCGGTAT CACTGACCTA
1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTAGATTA AATTATATAA
```

Fig. 36₁

```
1801 GATATTTATA TCATTTTACG TTTCTCGTTC AACTTTATTA TACATAGTTG ATAATTCACT
     CTATAAATAT AGTAAAATGC AAAGAGCAAG TTGAAATAAT ATGTATCAAC TATTAAGTGA
1861 GGCCGTCGTT TTACAACGTC GTGACTGGGA AAACCCTGGC GTTACCCAAC TTAATCGCCT
     CCGGCAGCAA AATGTTGCAG CACTGACCCT TTTGGGACCG CAATGGGTTG AATTAGCGGA
            HindIII                                                     AvrII
            ~~~~~~~                                                      ~~~~
1921 TGCAGCACAA GCTTGGAATT GTTATCCGCT CACAATTCCT ATAGTGAGTC GTATTACCTA
     ACGTCGTGTT CGAACCTTAA CAATAGGCGA GTGTTAAGGA TATCACTCAG CATAATGGAT
     AvrII
     ~~
1981 GGCTGCTGCC ACCGCTGAGC AATAACTAGC ATAACCCCTT GGGGCCTCTA AACGGGTCTT
     CCGACGACGG TGGCGACTCG TTATTGATCG TATTGGGGAA CCCCGGAGAT TTGCCCAGAA
2041 GAGGGGTTTT TTGCTGAAAC CTCAGGCATT TGAGAAGCAC ACGGTCACAC TGCTTCCGGT
     CTCCCCAAAA AACGACTTTG GAGTCCGTAA ACTCTTCGTG TGCCAGTGTG ACGAAGGCCA
2101 AGTCAATAAA CCGGTAAACC AGCAATAGAC ATAAGCGGCT ATTTAACGAC CCTGCCCTGA
     TCAGTTATTT GGCCATTTGG TCGTTATCTG TATTCGCCGA TAAATTGCTG GGACGGGACT
2161 ACCGACGACC GGGTCATCGT GGCCGGATCT TGCCGCCCCT CGGCTTGAAC GAATTGTTAG
     TGGCTGCTGG CCCAGTAGCA CCGGCCTAGA ACGCCGGGGA GCCGAACTTG CTTAACAATC
2221 ACATTATTTG CCGACTACCT TGGTGATCTC GCCTTTCACG TAGTGGACAA ATTCTTCCAA
     TGTAATAAAC GGCTGATGGA ACCACTAGAG CGGAAAGTGC ATCACCTGTT TAAGAAGGTT
2281 CTGATCTGCG CGCGAGGCCA AGCGATCTTC TTCTTGTCCA AGATAAGCCT GTCTAGCTTC
     GACTAGACGC GCGCTCCGGT TCGCTAGAAG AAGAACAGGT TCTATTCGGA CAGATCGAAG
2341 AAGTATGACG GGCTGATACT GGGCCGGCAG GCGCTCCATT GCCCAGTCGG CAGCGACATC
     TTCATACTGC CCGACTATGA CCCGGCCGTC CGCGAGGTAA CGGGTCAGCC GTCGCTGTAG
2401 CTTCGGCGCG ATTTTGCCGG TTACTGCGCT GTACCAAATG CGGGACAACG TAAGCACTAC
     GAAGCCGCGC TAAAACGGCC AATGACGCGA CATGGTTTAC GCCCTGTTGC ATTCGTGATG
2461 ATTTCGCTCA TCGCCAGCCC AGTCGGGCGG CGAGTTCCAT AGCGTTAAGG TTTCATTTAG
     TAAAGCGAGT AGCGGTCGGG TCAGCCCGCC GCTCAAGGTA TCGCAATTCC AAAGTAAATC
2521 CGCCTCAAAT AGATCCTGTT CAGGAACCGG ATCAAAGAGT TCCTCCGCCG CTGGACCTAC
     GCGGAGTTTA TCTAGGACAA GTCCTTGGCC TAGTTTCTCA AGGAGGCGGC GACCTGGATG
2581 CAAGGCAACG CTATGTTCTC TTGCTTTTGT CAGCAAGATA GCCAGATCAA TGTCGATCGT
     GTTCCGTTGC GATACAAGAG AACGAAAACA GTCGTTCTAT CGGTCTAGTT ACAGCTAGCA
2641 GGCTGGCTCG AAGATACCTG CAAGAATGTC ATTGCGCTGC CATTCTCCAA ATTGCAGTTC
     CCGACCGAGC TTCTATGGAC GTTCTTACAG TAACGCGACG GTAAGAGGTT TAACGTCAAG
2701 GCGCTTAGCT GGATAACGCC ACGGAATGAT GTCGTCGTGC ACAACAATGG TGACTTCTAC
     CGCGAATCGA CCTATTGCGG TGCCTTACTA CAGCAGCACG TGTTGTTACC ACTGAAGATG
2761 AGCGCGGAGA ATCTCGCTCT CTCCAGGGGA AGCCGAAGTT TCCAAAAGGT CGTTGATCAA
     TCGCGCCTCT TAGAGCGAGA GAGGTCCCCT TCGGCTTCAA AGGTTTTCCA GCAACTAGTT
2821 AGCTCGCCGC GTTGTTTCAT CAAGCCTTAC GGTCACCGTA ACCAGCAAAT CAATATCACT
     TCGAGCGGCG CAACAAAGTA GTTCGGAATG CCAGTGGCAT TGGTCGTTTA GTTATAGTGA
2881 GTGTGGCTTC AGGCCGCCAT CCACTGCGGA GCCGTACAAA TGTACGGCCA GCAACGTCGG
     CACACCGAAG TCCGGCGGTA GGTGACGCCT CGGCATGTTT ACATGCCGGT CGTTGCAGCC
2941 TTCGAGATGG CGCTCGATGA CGCCAACTAC CTCTGATAGT TGAGTCGATA CTTCGGCGAT
     AAGCTCTACC GCGAGCTACT GCGGTTGATG GAGACTATCA ACTCAGCTAT GAAGCCGCTA
3001 CACCGCTTCC CTCATACTCT TCCTTTTTCA ATATTATTGA AGCATTTATC AGGGTTATTG
     GTGGCGAAGG GAGTATGAGA AGGAAAAAGT TATAATAACT TCGTAAATAG TCCCAATAAC
3061 TCTCATGAGC GGATACATAT TTGAATGTAT TTAGAAAAAT AAACAAATAG CTAGCTCACT
     AGAGTACTCG CCTATGTATA AACTTACATA AATCTTTTTA TTTGTTTATC GATCGAGTGA
3121 CGGTCGCTAC GCTCCGGGCG TGAGACTGCG GCGGGCGCTG CGGACACATA CAAAGTTACC
     GCCAGCGATG CGAGGCCCGC ACTCTGACGC CGCCCGCGAC GCCTGTGTAT GTTTCAATGG
3181 CACAGATTCC GTGGATAAGC AGGGGACTAA CATGTGAGGC AAAACAGCAG GGCCGCGCCG
     GTGTCTAAGG CACCTATTCG TCCCCTGATT GTACACTCCG TTTTGTCGTC CCGGCGCGGC
3241 GTGGCGTTTT TCCATAGGCT CCGCCCTCCT GCCAGAGTTC ACATAAACAG ACGCTTTTCC
     CACCGCAAAA AGGTATCCGA GGCGGGAGGA CGGTCTCAAG TGTATTTGTC TGCGAAAAGG
3301 GGTGCATCTG TGGGAGCCGT GAGGCTCAAC CATGAATCTG ACAGTACGGG CGAAACCCGA
     CCACGTAGAC ACCCTCGGCA CTCCGAGTTG GTACTTAGAC TGTCATGCCC GCTTTGGGCT
3361 CAGGACTTAA AGATCCCCAC CGTTTCCGGC GGGTCGCTCC CTCTTGCGCT CTCCTGTTCC
     GTCCTGAATT TCTAGGGGTG GCAAAGGCCG CCCAGCGAGG GAGAACGCGA GAGGACAAGG
3421 GACCCTGCCG TTTACCGGAT ACCTGTTCCG CCTTTCTCCC TTACGGGAAG TGTGGCGCTT
     CTGGGACGGC AAATGGCCTA TGGACAAGGC GGAAAGAGGG AATGCCCTTC ACACCGCGAA
3481 TCTCATAGCT CACACACTGG TATCTCGGCT CGGTCTAGGT CGTTCGCTCC AAGCTGGGCT
     AGAGTATCGA GTGTGTGACC ATAGAGCCGA GCCAGATCCA GCAAGCGAGG TTCGACCCGA
3541 GTAAGCAAGA ACTCCCCGTT CAGCCCGACT GCTGCGCCTT ATCCGGTAAC TGTTCACTTG
     CATTCGTTCT TGAGGGGCAA GTCGGGCTGA CGACGCGGAA TAGGCCATTG ACAAGTGAAC
3601 AGTCCAACCC GGAAAAGCAC GGTAAAACGC CACTGGCAGC AGCCATTGGT AACTGGGAGT
     TCAGGTTGGG CCTTTTCGTG CCATTTTGCG GTGACCGTCG TCGGTAACCA TTGACCCTCA
3661 TCGCAGAGGA TTTGTTTAGC TAAACACGCG GTTGCTCTTG AAGTGTGCGC CAAAGTCCGG
     AGCGTCTCCT AAACAAATCG ATTTGTGCGC CAACGAGAAC TTCACACGCG GTTTCAGGCC
3721 CTACACTGGA AGGACAGATT TGGTTGCTGT GCTCTGCGAA AGCCAGTTAC CACGGTTAAG
```

Fig. 36₂

```
      GATGTGACCT TCCTGTCTAA ACCAACGACA CGAGACGCTT TCGGTCAATG GTGCCAATTC
3781  CAGTTCCCCA ACTGACTTAA CCTTCGATCA AACCACCTCC CCAGGTGGTT TTTTCGTTTA
      GTCAAGGGGT TGACTGAATT GGAAGCTAGT TTGGTGGAGG GGTCCACCAA AAAAGCAAAT
3841  CAGGGCAAAA GATTACGCGC AGAAAAAAAG GATCTCAAGA AGATCCTTTG ATCTTTTCTA
      GTCCCGTTTT CTAATGCGCG TCTTTTTTTC CTAGAGTTCT TCTAGGAAAC TAGAAAAGAT
3901  CTGAACCGCT CTAGATTTCA GTGCAATTTA TCTCTTCAAA TGTAGCACCT GAAGTCAGCC
      GACTTGGCGA GATCTAAAGT CACGTTAAAT AGAGAAGTTT ACATCGTGGA CTTCAGTCGG
3961  CCATACGATA TAAGTTGTAA TTCTCATGTT AGTCATGCCC CGCGCCCACC GGAAGGAGCT
      GGTATGCTAT ATTCAACATT AAGAGTACAA TCAGTACGGG GCGCGGGTGG CCTTCCTCGA
4021  GACTGGGTTG AAGGCTCTCA AGGGCATCGG TCGAGATCCC GGTGCCTAAT GAGTGAGCTA
      CTGACCCAAC TTCCGAGAGT TCCCGTAGCC AGCTCTAGGG CCACGGATTA CTCACTCGAT
4081  ACTTACATTA ATTGCGTTGC GCTCACTGCC CGCTTTCCAG TCGGGAAACC TGTCGTGCCA
      TGAATGTAAT TAACGCAACG CGAGTGACGG GCGAAAGGTC AGCCCTTTGG ACAGCACGGT
4141  GCTGCATTAA TGAATCGGCC AACGCGCGGG GAGAGGCGGT TTGCGTATTG GGCGCCAGGG
      CGACGTAATT ACTTAGCCGG TTGCGCGCCC CTCTCCGCCA AACGCATAAC CCGCGGTCCC
4201  TGGTTTTTCT TTTCACCAGT GAGACGGGCA ACAGCTGATT GCCCTTCACC GCCTGGCCCT
      ACCAAAAAGA AAAGTGGTCA CTCTGCCCGT TGTCGACTAA CGGGAAGTGG CGGACCGGGA
4261  GAGAGAGTTG CAGCAAGCGG TCCACGCTGG TTTGCCCCAG CAGGCGAAAA TCCTGTTTGA
      CTCTCTCAAC GTCGTTCGCC AGGTGCGACC AAACGGGGTC GTCCGCTTTT AGGACAAACT
4321  TGGTGGTTAA CGGCGGGATA TAACATGAGC TGTCTTCGGT ATCGTCGTAT CCCACTACCG
      ACCACCAATT GCCGCCCTAT ATTGTACTCG ACAGAAGCCA TAGCAGCATA GGGTGATGGC
4381  AGATGTCCGC ACCAACGCGC AGCCCGGACT CGGTAATGGC GCGCATTGCG CCCAGCGCCA
      TCTACAGGCG TGGTTGCGCG TCGGGCCTGA GCCATTACCG CGCGTAACGC GGGTCGCGGT
4441  TCTGATCGTT GGCAACCAGC ATCGCAGTGG AACGATGCC CTCATTCAGC ATTTGCATGG
      AGACTAGCAA CCGTTGGTCG TAGCGTCACC TTGCTACGG GAGTAAGTCG TAAACGTACC
4501  TTTGTTGAAA ACCGGACATG GCACTCCAGT CGCCTTCCCG TTCCGCTATC GGCTGAATTT
      AAACAACTTT TGGCCTGTAC CGTGAGGTCA GCGGAAGGGC AAGGCGATAG CCGACTTAAA
4561  GATTGCGAGT GAGATATTTA TGCCAGCCAG CCAGACGCAG ACGCGCCGAG ACAGAACTTA
      CTAACGCTCA CTCTATAAAT ACGGTCGGTC GGTCTGCGTC TGCGCGGCTC TGTCTTGAAT
4621  ATGGGCCCGC TAACAGCGCG ATTTGCTGGT GACCCAATGC GACCAGATGC TCCACGCCCA
      TACCCGGGCG ATTGTCGCGC TAAACGACCA CTGGGTTACG CTGGTCTACG AGGTGCGGGT
4681  GTCGCGTACC GTCTTCATGG GAGAAAATAA TACTGTTGAT GGGTGTCTGG TCAGAGACAT
      CAGCGCATGG CAGAAGTACC CTCTTTTATT ATGACAACTA CCCACAGACC AGTCTCTGTA
4741  CAAGAAATAA CGCCGGAACA TTAGTGCAGG CAGCTTCCAC AGCAATGGCA TCCTGGTCAT
      GTTCTTTATT GCGGCCTTGT AATCACGTCC GTCGAAGGTG TCGTTACCGT AGGACCAGTA
4801  CCAGCGGATA GTTAATGATC AGCCCACTGA CGCGTTGCGC GAGAAGATTG TGCACCGCCG
      GGTCGCCTAT CAATTACTAG TCGGGTGACT GCGCAACGCG CTCTTCTAAC ACGTGGCGGC
4861  CTTTACAGGC TTCGACGCCG CTTCGTTCTA CCATCGACAC CACCACGCTG GCACCCAGTT
      GAAATGTCCG AAGCTGCGGC GAAGCAAGAT GGTAGCTGTG GTGGTGCGAC CGTGGGTCAA
4921  GATCGGCGCG AGATTTAATC GCCGCGACAA TTTGCGACGG CGCGTGCAGG GCCAGACTGG
      CTAGCCGCGC TCTAAATTAG CGGCGCTGTT AAACGCTGCC GCGCACGTCC CGGTCTGACC
4981  AGGTGGCAAC GCCAATCAGC AACGACTGTT TGCCCGCCAG TTGTTGTGCC ACGCGGTTGG
      TCCACCGTTG CGGTTAGTCG TTGCTGACAA ACGGGCGGTC AACAACACGG TGCGCCAACC
5041  GAATGTAATT CAGCTCCGCC ATCGCCGCTT CCACTTTTTC CCGCGTTTTC GCAGAAACGT
      CTTACATTAA GTCGAGGCGG TAGCGGCGAA GGTGAAAAAG GGCGCAAAAG CGTCTTTGCA
5101  GGCTGGCCTG GTTCACCACG CGGGAAACGG TCTGATAAGA GACACCGGCA TACTCTGCGA
      CCGACCGGAC CAAGTGGTGC GCCCTTTGCC AGACTATTCT CTGTGGCCGT ATGAGACGCT
5161  CATCGTATAA CGTTACTGGT TTCACATTCA CCACCCTGAA TTGACTCTCT TCCGGCGCT
      GTAGCATATT GCAATGACCA AAGTGTAAGT GGTGGGACTT AACTGAGAGA AGGCCGCGA
5221  ATCATGCCAT ACCGCGAAAG GTTTTGCGCC ATTCGATGGT GTCCGGGATC TCGACGCTCT
      TAGTACGGTA TGGCGCTTTC CAAAACGCGG TAAGCTACCA CAGGCCCTAG AGCTGCGAGA
5281  CCCTTATGCG ACTCCTGCAT TAGGAAATTA ATACGACTCA CTATA
      GGGAATACGC TGAGGACGTA ATCCTTTAAT TATGCTGAGT GATAT
```

Fig. 36₃

| Fig. 38$_1$ |
|---|
| Fig. 38$_2$ |
| Fig. 38$_3$ |

Fig. 38

```
  1  GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                SacI
                                                                ~~~
              NcoI                                     EcoRI
              ~~~~~~~                                  ~~~~~~
 61  GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
121  CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
181  AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                                PstI
                                                ~~~~~~~
241  CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
301  AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
361  GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
421  TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
481  CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
541  CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
601  AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
661  ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
721  AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
781  ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
841  CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
901  ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
961  CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTGCTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
                     NcoI
                     ~~~~~~~
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
                                EcoRI
                                ~~~~~~~
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAACTTGT GCTTATTTTT CTTTACGGTC TTTAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT TCTCCATTTT
     AAATGCTACG GTAACCCTAT ATAGTTGCCA CCATATAAAA AGAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
```

Fig. 38₁

```
      CGGCCTTCGT ATTTCACATT TCGGACCCCC ACGGATTACG CCGGCGGTAT CACTGACCTA
1741  ATGTTGTGTT TTACAGTATT ATGTAGTCTG TTTTTTATGC AAAATCTAAT TTAATATATT
      TACAACACAA AATGTCATAA TACATCAGAC AAAAAATACG TTTTAGATTA AATTATATAA
1801  GATATTTATA TCATTTTACG TTTCTCGTTC AACTTTATTA TACATAGTTG ATAATTCACT
      CTATAAATAT AGTAAAATGC AAAGAGCAAG TTGAAATAAT ATGTATCAAC TATTAAGTGA
1861  GGCCGTCGTT TTACAACGTC GTGACTGGGA AAACCCTGGC GTTACCCAAC TTAATCGCCT
      CCGGCAGCAA AATGTTGCAG CACTGACCCT TTTGGGACCG CAATGGGTTG AATTAGCGGA
               HindIII                                            AvrII
               ~~~~~~~                                            ~~~~
1921  TGCAGCACAA GCTTGGAATT GTTATCCGCT CACAATTCCT ATAGTGAGTC GTATTACCTA
      ACGTCGTGTT CGAACCTTAA CAATAGGCGA GTGTTAAGGA TATCACTCAG CATAATGGAT
      AvrII
      ~~
1981  GGCTGCTGCC ACCGCTGAGC AATAACTAGC ATAACCCCTT GGGGCCTCTA AACGGGTCTT
      CCGACGACGG TGGCGACTCG TTATTGATCG TATTGGGGAA CCCCGGAGAT TTGCCCAGAA
2041  GAGGGGTTTT TTGCTGAAAC CTCAGGCATT TGAGAAGCAC ACGGTCACAC TGCTTCCGGT
      CTCCCCAAAA AACGACTTTG GAGTCCGTAA ACTCTTCGTG TGCCAGTGTG ACGAAGGCCA
2101  AGTCAATAAA CCGGTAAACC AGCAATAGAC ATAAGCGGCT ATTTAACGAC CCTGCCCTGA
      TCAGTTATTT GGCCATTTGG TCGTTATCTG TATTCGCCGA TAAATTGCTG GGACGGGACT
2161  ACCGACGACA AGCTGACGAC CGGGTCTCCG CAAGTGGCAC TTTTCGGGGA AATGTGCGCG
      TGGCTGCTGT TCGACTGCTG GCCCAGAGGC GTTCACCGTG AAAAGCCCCT TTACACGCGC
2221  GAACCCCTAT TTGTTTATTT TTCTAAATAC ATTCAAAATAT GTATCCGCTC ATGAATTAAT
      CTTGGGGATA AACAAATAAA AAGATTTATG TAAGTTTATA CATAGGCGAG TACTTAATTA
2281  TCTTAGAAAA ACTCATCGAG CATCAAATGA AACTGCAATT TATTCATATC AGGATTATCA
      AGAATCTTTT TGAGTAGCTC GTAGTTTACT TTGACGTTAA ATAAGTATAG TCCTAATAGT
2341  ATACCATATT TTTGAAAAAG CCGTTTCTGT AATGAAGGAG AAAACTCACC GAGGCAGTTC
      TATGGTATAA AAACTTTTTC GGCAAAGACA TTACTTCCTC TTTTGAGTGG CTCCGTCAAG
2401  CATAGGATGG CAAGATCCTG GTATCGGTCT GCGATTCCGA CTCGTCCAAC ATCAATACAA
      GTATCCTACC GTTCTAGGAC CATAGCCAGA CGCTAAGGCT GAGCAGGTTG TAGTTATGTT
2461  CCTATTAATT TCCCCTCGTC AAAAATAAGG TTATCAAGTG AGAAATCACC ATGAGTGACG
      GGATAATTAA AGGGGAGCAG TTTTTATTCC AATAGTTCAC TCTTTAGTGG TACTCACTGC
2521  ACTGAATCCG GTGAGAATGG CAAAAGTTTA TGCATTTCTT TCCAGACTTG TTCAACAGGC
      TGACTTAGGC CACTCTTACC GTTTTCAAAT ACGTAAAGAA AGGTCTGAAC AAGTTGTCCG
2581  CAGCCATTAC GCTCGTCATC AAAATCACTC GCATCAACCA AACCGTTATT CATTCGTGAT
      GTCGGTAATG CGAGCAGTAG TTTTAGTGAG CGTAGTTGGT TTGGCAATAA GTAAGCACTA
2641  TGCGCCTGAG CGAGACGAAA TACGCGGTCG CTGTTAAAAG GACAATTACA AACAGGAATC
      ACGCGGACTC GCTCTGCTTT ATGCGCCAGC GACAATTTTC CTGTTAATGT TTGTCCTTAG
2701  GAATGCAACC GGCGCAGGAA CACTGCCAGC GCATCAACAA TATTTTCACC TGAATCAGGA
      CTTACGTTGG CCGCGTCCTT GTGACGGTCG CGTAGTTGTT ATAAAAGTGG ACTTAGTCCT
2761  TATTCTTCTA ATACCTGGAA TGCTGTTTTC CCGGGGATCG CAGTGGTGAG TAACCATGCA
      ATAAGAAGAT TATGGACCTT ACGACAAAAG GGCCCCTAGC GTCACCACTC ATTGGTACGT
2821  TCATCAGGAG TACGGATAAA ATGCTTGATG GTCGGAAGAG GCATAAATTC CGTCAGCCAG
      AGTAGTCCTC ATGCCTATTT TACGAACTAC CAGCCTTCTC CGTATTTAAG GCAGTCGGTC
2881  TTTAGTCTGA CCATCTCATC TGTAACATCA TTGGCAACGC TACCTTTGCC ATGTTTCAGA
      AAATCAGACT GGTAGAGTAG ACATTGTAGT AACCGTTGCG ATGGAAACGG TACAAAGTCT
                                                        ClaI
                                                        ~~~~~~
2941  AACAACTCTG GCGCATCGGG CTTCCCATAC AATCGATAGA TTGTCGCACC TGATTGCCCG
      TTGTTGAGAC CGCGTAGCCC GAAGGGTATG TTAGCTATCT AACAGCGTGG ACTAACGGGC
3001  ACATTATCGC GAGCCCATTT ATACCCATAT AAATCAGCAT CCATGTTGGA ATTTAATCGC
      TGTAATAGCG CTCGGGTAAA TATGGGTATA TTTAGTCGTA GGTACAACCT TAAATTAGCG
3061  GGCCTAGAGC AAGACGTTTC CCGTTGAATA TGGCTCATAC TCTTCCTTTT TCAATATTAT
      CCGGATCTCG TTCTGCAAAG GGCAACTTAT ACCGAGTATG AGAAGGAAAA AGTTATAATA
3121  TGAAGCATTT ATCAGGGTTA TTGTCTCATG AGCGGATACA TATTTGAATG TATTTAGAAA
      ACTTCGTAAA TAGTCCCAAT AACAGAGTAC TCGCCTATGT ATAAACTTAC ATAAATCTTT
3181  AATAAACAAA TAGGCATGCA GCGCTCTTCC GCTTCCTCGC TCACTGACTC GCTACGCTCG
      TTATTTGTTT ATCCGTACGT CGCGAGAAGG CGAAGGAGCG AGTGACTGAG CGATGCGAGC
3241  GTCGTTCGAC TGCGGCGAGC GGTGTCAGCT CACTCAAAAG CGGTAATACG GTTATCCACA
      CAGCAAGCTG ACGCCGCTCG CCACATTCGA GTGAGTTTTC GCCATTATGC CAATAGGTGT
3301  GAATCAGGGG ATAAAGCCGG AAAGAACATG TGAGCAAAAA GCAAAGCACC GGAAGAAGCC
      CTTAGTCCCC TATTTCGGCC TTTCTTGTAC ACTCGTTTTT CGTTTCGTGG CCTTCTTCGG
3361  AACGCCGCAG CGTTTTTCC ATAGGCTCCG CCCCCCTGAC GAGCATCACA AAAATCGACG
      TTGCGGCGTC GCAAAAAGG TATCCGAGGC GGGGGGACTG CTCGTAGTGT TTTTAGCTGC
3421  CTCAAGCCAG AGGTGGCGAA ACCCGACAGG ACTATAAAGA TACCAGGCGT TTCCCCCTGG
      GAGTTCGGTC TCCACCGCTT TGGGCTGTCC TGATATTTCT ATGGTCCGCA AAGGGGGACC
3481  AAGCTCCCTC GTGCGCTCTC CTGTTCCGAC CCTGCCGCTT ACCGGATACC TGTCCGCCTT
      TTCGAGGGAG CACGCGAGAG GACAAGGCTG GGACGGCGAA TGGCCTATGG ACAGGCGGAA
3541  TCTCCCTTCG GGAAGCGTGG CGCTTTCTCA TAGCTCACGC TGTTGGTATC TCAGTTCGGT
      AGAGGGAAGC CCTTCGCACC GCGAAAGAGT ATCGAGTGCG ACAACCATAG AGTCAAGCCA
```

Fig. 38$_2$

```
3601  GTAGGTCGTT CGCTCCAAGC TGGGCTGTGT GCACGAACCC CCCGTTCAGC CCGACCGCTG
      CATCCAGCAA GCGAGGTTCG ACCCGACACA CGTGCTTGGG GGGCAAGTCG GGCTGGCGAC
3661  CGCCTTATCC GGTAACTATC GTCTTGAGTC CAACCCGGTA AGACACGACT TATCGCCACT
      GCGGAATAGG CCATTGATAG CAGAACTCAG GTTGGGCCAT TCTGTGCTGA ATAGCGGTGA
3721  GGCAGCAGCC ATTGGTAACT GATTTAGAGG ACTTTGTCTT GAAGTTATGC ACCTGTTAAG
      CCGTCGTCGG TAACCATTGA CTAAATCTCC TGAAACAGAA CTTCAATACG TGGACAATTC
3781  GCTAAACTGA AAGAACAGAT TTTGGTGAGT GCGGTCCTCC AACCCACTTA CCTTGGTTCA
      CGATTTGACT TTCTTGTCTA AAACCACTCA CGCCAGGAGG TTGGGTGAAT GGAACCAAGT
3841  AAGAGTTGGT AGCTCAGCGA ACCTTGAGAA AACCACCGTT GGTAGCGGTG GTTTTTCTTT
      TTCTCAACCA TCGAGTCGCT TGGAACTCTT TTGGTGGCAA CCATCGCCAC CAAAAAGAAA
3901  ATTTATGAGA TGATGAATCA ATCGGTCTAT CAAGTCAACG AACAGCTATT CCGTTACTCT
      TAAATACTCT ACTACTTAGT TAGCCAGATA GTTCAGTTGC TTGTCGATAA GGCAATGAGA
3961  AGATTTCAGT GCAATTTATC TCTTCAAATG TAGCACCTGA AGTCAGCCCC ATACGATATA
      TCTAAAGTCA CGTTAAATAG AGAAGTTTAC ATCGTGGACT TCAGTCGGGG TATGCTATAT
4021  AGTTGTAATT CTCATGTTAG TCATGCCCCG CGCCCACCGG AAGGAGCTGA CTGGGTTGAA
      TCAACATTAA GAGTACAATC AGTACGGGGC GCGGGTGGCC TTCCTCGACT GACCCAACTT
4081  GGCTCTCAAG GGCATCGGTC GAGATCCCGG TGCCTAATGA GTGAGCTAAC TTACATTAAT
      CCGAGAGTTC CCGTAGCCAG CTCTAGGGCC ACGGATTACT CACTCGATTG AATGTAATTA
4141  TGCGTTGCGC TCACTGCCCG CTTTCCAGTC GGGAAACCTG TCGTGCCAGC TGCATTAATG
      ACGCAACGCG AGTGACGGGC GAAAGGTCAG CCCTTTGGAC AGCACGGTCG ACGTAATTAC
4201  AATCGGCCAA CGCGCGGGGA GAGGCGGTTT GCGTATTGGG CGCCAGGGTG GTTTTTCTTT
      TTAGCCGGTT GCGCGCCCCT CTCCGCCAAA CGCATAACCC GCGGTCCCAC CAAAAAGAAA
4261  TCACCAGTGA GACGGGCAAC AGCTGATTGC CCTTCACCGC CTGGCCCTGA GAGAGTTGCA
      AGTGGTCACT CTGCCCGTTG TCGACTAACG GGAAGTGGCG GACCGGGACT CTCTCAACGT
4321  GCAAGCGGTC CACGCTGGTT TGCCCCAGCA GGCGAAAATC CTGTTTGATG GTGGTTAACG
      CGTTCGCCAG GTGCGACCAA ACGGGGTCGT CCGCTTTTAG GACAAACTAC CACCAATTGC
4381  GCGGGATATA ACATGAGCTG TCTTCGGTAT CGTCGTATCC CACTACCGAG ATGTCCGCAC
      CGCCCTATAT TGTACTCGAC AGAAGCCATA GCAGCATAGG GTGATGGCTC TACAGGCGTG
4441  CAACGCGCAG CCCGGACTCG GTAATGGCGC GCATTGCGCC CAGCGCCATC TGATCGTTGG
      GTTGCGCGTC GGGCCTGAGC CATTACCGCG CGTAACGCGG GTCGCGGTAG ACTAGCAACC
4501  CAACCAGCAT CGCAGTGGGA ACGATGCCCT CATTCAGCAT TTGCATGGTT TGTTGAAAAC
      GTTGGTCGTA GCGTCACCCT TGCTACGGGA GTAAGTCGTA AACGTACCAA ACAACTTTTG
4561  CGGACATGGC ACTCCAGTCG CCTTCCCGTT CCGCTATCGG CTGAATTTGA TTGCGAGTGA
      GCCTGTACCG TGAGGTCAGC GGAAGGGCAA GGCGATAGCC GACTTAAACT AACGCTCACT
4621  GATATTTATG CCAGCCAGCC AGACGCAGAC GCGCCGAGAC AGAACTTAAT GGGCCCGCTA
      CTATAAATAC GGTCGGTCGG TCTGCGTCTG CGCGGCTCTG TCTTGAATTA CCCGGGCGAT
4681  ACAGCGCGAT TTGCTGGTGA CCCAATGCGA CCAGATGCTC CACGCCCAGT CGCGTACCGT
      TGTCGCGCTA AACGACCACT GGGTTACGCT GGTCTACGAG GTGCGGGTCA GCGCATGGCA
4741  CTTCATGGGA GAAAATAATA CTGTTGATGG GTGTCTGGTC AGAGACATCA AGAAATAACG
      GAAGTACCCT CTTTTATTAT GACAACTACC CACAGACCAG TCTCTGTAGT TCTTTATTGC
4801  CCGGAACATT AGTGCAGGCA GCTTCCACAG CAATGGCATC CTGGTCATCC AGCGGATAGT
      GGCCTTGTAA TCACGTCCGT CGAAGGTGTC GTTACCGTAG GACCAGTAGG TCGCCTATCA
4861  TAATGATCAG CCCACTGACG CGTTGCGCGA GAAGATTGTG CACCGCCGCT TTACAGGCTT
      ATTACTAGTC GGGTGACTGC GCAACGCGCT CTTCTAACAC GTGGCGGCGA AATGTCCGAA
4921  CGACGCCGCT TCGTTCTACC ATCGACACCA CCACGCTGGC ACCCAGTTGA TCGGCGCGAG
      GCTGCGGCGA AGCAAGATGG TAGCTGTGGT GGTGCGACCG TGGGTCAACT AGCCGCGCTC
4981  ATTTAATCGC CGCGACAATT TGCGACGGCG CGTGCAGGGC CAGACTGGAG GTGGCAACGC
      TAAATTAGCG GCGCTGTTAA ACGCTGCCGC GCACGTCCCG GTCTGACCTC CACCGTTGCG
5041  CAATCAGCAA CGACTGTTTG CCCGCCAGTT GTTGTGCCAC GCGGTTGGGA ATGTAATTCA
      GTTAGTCGTT GCTGACAAAC GGGCGGTCAA CAACACGGTG CGCCAACCCT TACATTAAGT
5101  GCTCCGCCAT CGCCGCTTCC ACTTTTCCC GCGTTTTCGC AGAAACGTGG CTGGCCTGGT
      CGAGGCGGTA GCGGCGAAGG TGAAAAAGGG CGCAAAAGCG TCTTTGCACC GACCGGACCA
5161  TCACCACGCG GGAAACGGTC TGATAAGAGA CACCGGCATA CTCTGCGACA TCGTATAACG
      AGTGGTGCGC CCTTTGCCAG ACTATTCTCT GTGGCCGTAT GAGACGCTGT AGCATATTGC
5221  TTACTGGTTT CACATTCACC ACCCTGAATT GACTCTCTTC CGGGCGCTAT CATGCCATAC
      AATGACCAAA GTGTAAGTGG TGGGACTTAA CTGAGAGAAG GCCCGCGATA GTACGGTATG
5281  CGCGAAAGGT TTTGCGCCAT TCGATGGTGT CCGGGATCTC GACGCTCTCC CTTATGCGAC
      GCGCTTTCCA AAACGCGGTA AGCTACCACA GGCCCTAGAG CTGCGAGAGG GAATACGCTG
5341  TCCTGCATTA GGAAATTAAT ACGACTCACT ATA
      AGGACGTAAT CCTTTAATTA TGCTGAGTGA TAT
```

Fig. 38₃

| Fig. $40_1$ |
|---|
| Fig. $40_2$ |
| Fig. $40_3$ |
| Fig. $40_4$ |

Fig. 40

```
   1  GGGGAATTGT GAGCGGATAA CAATTCCCCT CTAGAAATAA TTTTGTTTAA CTTTAAGAAG
      CCCCTTAACA CTCGCCTATT GTTAAGGGGA GATCTTTATT AAAACAAATT GAAATTCTTC
                                                                SacI
                                                                ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGGACCAT GATTACGCCA AGCTATCAAC TTTGTATAGA AAGTTGAAC GAGAAACGTA
      GAGCCTGGTA CTAATGCGGT TCGATAGTTG AAACATATCT TTTCAACTTG CTCTTTGCAT
 181  AAATGATATA AATATCAATA TATTAAATTA GATTTTGCAT AAAAAACAGA CTACATAATA
      TTTACTATAT TTATAGTTAT ATAATTTAAT CTAAAACGTA TTTTTTGTCT GATGTATTAT
                                                 PstI
                                                 ~~~~~~~
 241  CTGTAAAACA CAACATATCC AGTCACTATG GTCGACCTGC AGACTGGCTG TGTATAAGGG
      GACATTTTGT GTTGTATAGG TCAGTGATAC CAGCTGGACG TCTGACCGAC ACATATTCCC
 301  AGCCTGACAT TTATATTCCC CAGAACATCA GGTTAATGGC GTTTTTGATG TCATTTTCGC
      TCGGACTGTA AATATAAGGG GTCTTGTAGT CCAATTACCG CAAAAACTAC AGTAAAGCG
 361  GGTGGCTGAG ATCAGCCACT TCTTCCCCGA TAACGGAGAC CGGCACACTG GCCATATCGG
      CCACCGACTC TAGTCGGTGA AGAAGGGGCT ATTGCCTCTG GCCGTGTGAC CGGTATAGCC
 421  TGGTCATCAT GCGCCAGCTT TCATCCCCGA TATGCACCAC CGGGTAAAGT TCACGGGGGA
      ACCAGTAGTA CGCGGTCGAA AGTAGGGGCT ATACGTGGTG GCCCATTTCA AGTGCCCCCT
 481  CTTTATCTGA CAGCAGACGT GCACTGGCCA GGGGGATCAC CATCCGTCGC CCGGGCGTGT
      GAAATAGACT GTCGTCTGCA CGTGACCGGT CCCCCTAGTG GTAGGCAGCG GGCCCGCACA
 541  CAATAATATC ACTCTGTACA TCCACAAACA GACGATAACG GCTCTCTCTT TTATAGGTGT
      GTTATTATAG TGAGACATGT AGGTGTTTGT CTGCTATTGC CGAGAGAGAA AATATCCACA
 601  AAACCTTAAA CTGCATTTCA CCAGCCCCTG TTCTCGTCGG CAAAAGAGCC GTTCATTTCA
      TTTGGAATTT GACGTAAAGT GGTCGGGGAC AAGAGCAGCC GTTTTCTCGG CAAGTAAAGT
 661  ATAAACCGGG CGACCTCAGC CATCCCTTCC TGATTTTCCG CTTTCCAGCG TTCGGCACGC
      TATTTGGCCC GCTGGAGTCG GTAGGGAAGG ACTAAAAGGC GAAAGGTCGC AAGCCGTGCG
 721  AGACGACGGG CTTCATTCTG CATGGTTGTG CTTACCGAAC CGGAGATATT GACATCATAT
      TCTGCTGCCC GAAGTAAGAC GTACCAACAC GAATGGCTTG GCCTCTATAA CTGTAGTATA
 781  ATGCCTTGAG CAACTGATAG CTGTCGCTGT CAACTGTCAC TGTAATACGC TGCTTCATAG
      TACGGAACTC GTTGACTATC GACAGCGACA GTTGACAGTG ACATTATGCG ACGAAGTATC
 841  CATACCTCTT TTTGACATAC TTCGGGTATA CATATCAGTA TATATTCTTA TACCGCAAAA
      GTATGGAGAA AAACTGTATG AAGCCCATAT GTATAGTCAT ATATAAGAAT ATGGCGTTTT
 901  ATCAGCGCGC AAATACGCAT ACTGTTATCT GGCTTTTAGT AAGCCGGATC CTCTAGATTA
      TAGTCGCGCG TTTATGCGTA TGACAATAGA CCGAAAATCA TTCGGCCTAG GAGATCTAAT
 961  CGCCCCGCCC TGCCACTCAT CGCAGTACTG TTGTAATTCA TTAAGCATTC TGCCGACATG
      GCGGGGCGGG ACGGTGAGTA GCGTCATGAC AACATTAAGT AATTCGTAAG ACGGCTGTAC
1021  GAAGCCATCA CAAACGGCAT GATGAACCTG AATCGCCAGC GGCATCAGCA CCTTGTCGCC
      CTTCGGTAGT GTTTGCCGTA CTACTTGGAC TTAGCGGTCG CCGTAGTCGT GGAACAGCGG
1081  TTGCGTATAA TATTTGCCCA TGGTGAAAAC GGGGGCGAAG AAGTTGTCCA TATTGGCCAC
      AACGCATATT ATAAACGGGT ACCACTTTTG CCCCCGCTTC TTCAACAGGT ATAACCGGTG
1141  GTTTAAATCA AAACTGGTGA AACTCACCCA GGGATTGGCT GAGACGAAAA ACATATTCTC
      CAAATTTAGT TTTGACCACT TTGAGTGGGT CCCTAACCGA CTCTGCTTTT TGTATAAGAG
1201  AATAAACCCT TTAGGGAAAT AGGCCAGGTT TTCACCGTAA CACGCCACAT CTTGCGAATA
      TTATTTGGGA AATCCCTTTA TCCGGTCCAA AAGTGGCATT GTGCGGTGTA GAACGCTTAT
1261  TATGTGTAGA AACTGCCGGA AATCGTCGTG GTATTCACTC CAGAGCGATG AAAACGTTTC
      ATACACATCT TTGACGGCCT TTAGCAGCAC CATAAGTGAG GTCTCGCTAC TTTTTGCAAAG
1321  AGTTTGCTCA TGGAAAACGG TGTAACAAGG GTGAACACTA TCCCATATCA CCAGCTCACC
      TCAAACGAGT ACCTTTTGCC ACATTGTTCC CACTTGTGAT AGGGTATAGT GGTCGAGTGG
1381  GTCTTTCATT GCCATACGGA ATTCCGGATG AGCATTCATC AGGCGGGCAA GAATGTGAAT
      CAGAAAGTAA CGGTATGCCT TAAGGCCTAC TCGTAAGTAG TCCGCCCGTT CTTACACTTA
1441  AAAGGCCGGA TAAAACTTGT GCTTATTTTT CTTTACGGTC TTTAAAAGG CCGTAATATC
      TTTCCGGCCT ATTTTGAACA CGAATATAAA GAAATGCCAG AAATTTTTCC GGCATTATAG
1501  CAGCTGAACG GTCTGGTTAT AGGTACATTG AGCAACTGAC TGAAATGCCT CAAAATGTTC
      GTCGACTTGC CAGACCAATA TCCATGTAAC TCGTTGACTG ACTTTACGGA GTTTTACAAG
1561  TTTACGATGC CATTGGGATA TATCAACGGT GGTATATCCA GTGATTTTTT CTCCATTTT
      AAATGCTACG GTAACCCTAT ATAGTTGCCA CCATATAGGT CACTAAAAAA AGAGGTAAAA
1621  AGCTTCCTTA GCTCCTGAAA ATCTCGACGG ATCCTAACTC AAAATCCACA CATTATACGA
      TCGAAGGAAT CGAGGACTTT TAGAGCTGCC TAGGATTGAG TTTTAGGTGT GTAATATGCT
1681  GCCGGAAGCA TAAAGTGTAA AGCCTGGGGG TGCCTAATGC GGCCGCCATA GTGACTGGAT
      CGGCCTTCGT ATTTCACATT TCGGACCCCC ACGGATTACG CCGGCGGTAT CACTGACCTA
1741  ATGTTGTGTT TTACAGTATT ATGTAGTCTG TTTTTTATGC AAAATCTAAT TTAATATATT
      TACAACACAA AATGTCATAA TACATCAGAC AAAAAATACG TTTTAGATTA AATTATATAA
1801  GATATTTATA TCATTTTACG TTTCTCGTTC AACTTTATTA TACATAGTTG ATAATTCACT
      CTATAAATAT AGTAAAATGC AAAGAGCAAG TTGAAATAAT ATGTATCAAC TATTAAGTGA
```

Fig. 40$_1$

```
1861  GGCCGTCGTT TTACAACGTC GTGACTGGGA AAACCCTGGC GTTACCCAAC TTAATCGCCT
      CCGGCAGCAA AATGTTGCAG CACTGACCCT TTTGGGACCG CAATGGGTTG AATTAGCGGA
                 HindIII                                           AvrII
                 ~~~~~~~                                           ~~~~
1921  TGCAGCACAA GCTTGGAATT GTTATCCGCT CACAATTCCT ATAGTGAGTC GTATTACCTA
      ACGTCGTGTT CGAACCTTAA CAATAGGCGA GTGTTAAGGA TATCACTCAG CATAATGGAT
      AvrII
      ~~
1981  GGCTGCTGCC ACCGCTGAGC AATAACTAGC ATAACCCCTT GGGGCCTCTA AACGGGTCTT
      CCGACGACGG TGGCGACTCG TTATTGATCG TATTGGGGAA CCCCGGAGAT TTGCCCAGAA
2041  GAGGGGTTTT TTGCTGAAAG GAGGAACTAT ATCCGGATTG GCGAATGGGA CGCGCCCTGT
      CTCCCCAAAA AACGACTTTC CTCCTTGATA TAGGCCTAAC CGCTTACCCT GCGCGGGACA
2101  AGCGGCGCAT TAAGCGCGGC GGGTGTGGTG GTTACGCGCA GCGTGACCGC TACACTTGCC
      TCGCCGCGTA ATTCGCGCCG CCCACACCAC CAATGCGCGT CGCACTGGCG ATGTGAACGG
2161  AGCGCCCTAG CGCCCGCTCC TTTCGCTTTC TTCCCTTCCT TTCTCGCCAC GTTCGCCGGC
      TCGCGGGATC GCGGGCGAGG AAAGCGAAAG AAGGGAAGGA AAGAGCGGTG CAAGCGGCCG
2221  TTTCCCCGTC AAGCTCTAAA TCGGGGCTCC CTTTAGGGT TCCGATTTAG TGCTTTACGG
      AAAGGGGCAG TTCGAGATTT AGCCCCCGAG GGAAATCCCA AGGCTAAATC ACGAAATGCC
2281  CACCTCGACC CCAAAAAACT TGATTAGGGT GATGGTTCAC GTAGTGGGCC ATCGCCCTGA
      GTGGAGCTGG GGTTTTTTGA ACTAATCCCA CTACCAAGTG CATCACCCGG TAGCGGGACT
2341  TAGACGGTTT TTCGCCCTTT GACGTTGGAG TCCACGTTCT TTAATAGTGG ACTCTTGTTC
      ATCTGCCAAA AGCGGGAAA CTGCAACCTC AGGTGCAAGA AATTATCACC TGAGAACAAG
2401  CAAACTGGAA CAACACTCAA CCCTATCTCG GTCTATTCTT TTGATTTATA AGGGATTTTG
      GTTTGACCTT GTTGTGAGTT GGGATAGAGC CAGATAAGAA AACTAAATAT TCCCTAAAAC
2461  CCGATTTCGG CCTATTGGTT AAAAAATGAG CTGATTTAAC AAAAATTTAA CGCGAATTTT
      GGCTAAAGCC GGATAACCAA TTTTTTACTC GACTAAATTG TTTTTAAATT GCGCTTAAAA
2521  AACAAAATAT TAACGTTTAC AATTTCTGGC GGCACGATGG CATGAGATTA TCAAAAAGGA
      TTGTTTTATA ATTGCAAATG TTAAAGACCG CCGTGCTACC GTACTCTAAT AGTTTTTCCT
2581  TCTTCACCTA GATCCTTTTA AATTAAAAAT GAAGTTTTAA ATCAATCTAA AGTATATATG
      AGAAGTGGAT CTAGGAAAAT TTAATTTTTA CTTCAAATT TAGTTAGATT TCATATATAC
2641  AGTAAACTTG GTCTGACAGT TACCAATGCT TAATCAGTGA GGCACCTATC TCAGCGATCT
      TCATTTGAAC CAGACTGTCA ATGGTTACGA ATTAGTCACT CCGTGGATAG AGTCGCTAGA
2701  GTCTATTTCG TTCATCCATA GTTGCCTGAC TCCCCGTCGT GTAGATAACT ACGATACGGG
      CAGATAAAGC AAGTAGGTAT CAACGGACTG AGGGGCAGCA CATCTATTGA TGCTATGCCC
2761  AGGGCTTACC ATCTGGCCCC AGTGCTGCAA TGATACCGCG AGACCCACGC TCACCGGCTC
      TCCCGAATGG TAGACCGGGG TCACGACGTT ACTATGGCGC TCTGGGTGCG AGTGGCCGAG
2821  CAGATTTATC AGCAATAAAC CAGCCAGCCG GAAGGGCCGA GCGCAGAAGT GGTCCTGCAA
      GTCTAAATAG TCGTTATTTG GTCGGTCGGC CTTCCCGGCT CGCGTCTTCA CCAGGACGTT
2881  CTTTATCCGC CTCCATCCAG TCTATTAATT GTTGCCGGGA AGCTAGAGTA AGTAGTTCGC
      GAAATAGGCG GAGGTAGGTC AGATAATTAA CAACGGCCCT TCGATCTCAT TCATCAAGCG
2941  CAGTTAATAG TTTGCGCAAC GTTGTTGCCA TTGCTACAGG CATCGTGGTG TCACGCTCGT
      GTCAATTATC AAACGCGTTG CAACAACGGT AACGATGTCC GTAGCACCAC AGTGCGAGCA
3001  CGTTTGGTAT GGCTTCATTC AGCTCCGGTT CCCAACGATC AAGGCGAGTT ACATGATCCC
      GCAAACCATA CCGAAGTAAG TCGAGGCCAA GGGTTGCTAG TTCCGCTCAA TGTACTAGGG
3061  CCATGTTGTG CAAAAAAGCG GTTAGCTCCT TCGGTCCTCC GATCGTTGTC AGAAGTAAGT
      GGTACAACAC GTTTTTTCGC CAATCGAGGA AGCCAGGAGG CTAGCAACAG TCTTCATTCA
3121  TGGCCGCAGT GTTATCACTC ATGGTTATGG CAGCACTGCA TAATTCTCTT ACTGTCATGC
      ACCGGCGTCA CAATAGTGAG TACCAATACC GTCGTGACGT ATTAAGAGAA TGACAGTACG
3181  CATCCGTAAG ATGCTTTTCT GTGACTGGTG AGTACTCAAC CAAGTCATTC TGAGAATAGT
      GTAGGCATTC TACGAAAAGA CACTGACCAC TCATGAGTTG GTTCAGTAAG ACTCTTATCA
3241  GTATGCGCGC ACCGAGTTGC TCTTCCCCGG CGTCAATACG GGATAATACC GCGCCACATA
      CATACGCGCG TGGCTCAACG AGAAGGGGCC GCAGTTATGC CCTATTATGG CGCGGTGTAT
3301  GCAGAACTTT AAAAGTGCTC ATCATTGGAA AACGTTCTTC GGGGCGAAAA CTCTCAAGGA
      CGTCTTGAAA TTTTCACGAG TAGTAACCTT TTGCAAGAAG CCCCGCTTTT GAGAGTTCCT
3361  TCTTACCGCT GTTGAGATCC AGTTCGATGT AACCCACTCG TGCACCCAAC TGATCTTCAG
      AGAATGGCGA CAACTCTAGG TCAAGCTACA TTGGGTGAGC ACGTGGGTTG ACTAGAAGTC
3421  CATCTTTTAC TTTCACCAGC GTTTCTGGGT GAGCAAAAAC AGGAAGGCAA AATGCCGCAA
      GTAGAAAATG AAAGTGGTCG CAAAGACCCA CTCGTTTTTG TCCTTCCGTT TTACGGCGTT
3481  AAAAGGGAAT AAGGGCGACA CGGAAATGTT GAATACTCAT ACTCTTCCTT TTTCAATCAT
      TTTTCCCTTA TTCCCGCTGT GCCTTTACAA CTTATGAGTA TGAGAAGGAA AAAGTTAGTA
3541  GATTGAAGCA TTTATCAGGG TTATTGTCTC ATGAGCGGAT ACATATTTGA ATGTATTTAG
      CTAACTTCGT AAATAGTCCC AATAACAGAG TACTCGCCTA TGTATAAACT TACATAAATC
3601  AAAAATAAAC AAATAGGTCA TGACCAAAAT CCCTTAACGT GAGTTTTCGT TCCACTGAGC
      TTTTTATTTG TTTATCCAGT ACTGGTTTTA GGGAATTGCA CTCAAAAGCA AGGTGACTCG
3661  GTCAGACCCC GTAGAAAAGA TCAAAGGATC TTCTTGAGAT CCTTTTTTTC TGCGCGTAAT
      CAGTCTGGGG CATCTTTTCT AGTTTCCTAG AAGAACTCTA GGAAAAAAAG ACGCGCATTA
3721  CTGCTGCTTG CAAACAAAAA AACCACCGCT ACCAGCGGTG GTTTGTTTGC CGGATCAAGA
      GACGACGAAC GTTTGTTTTT TTGGTGGCGA TGGTCGCCAC CAAACAAACG GCCTAGTTCT
3781  GCTACCAACT CTTTTTCCGA AGGTAACTGG CTTCAGCAGA GCGCAGATAC CAAATACTGT
      CGATGGTTGA GAAAAAGGCT TCCATTGACC GAAGTCGTCT CGCGTCTATG GTTTATGACA
3841  CCTTCTAGTG TAGCCGTAGT TAGGCCACCA CTTCAAGAAC TCTGTAGCAC CGCCTACATA
```

Fig. 40$_2$

```
      GGAAGATCAC ATCGGCATCA ATCCGGTGGT GAAGTTCTTG AGACATCGTG GCGGATGTAT
3901  CCTCGCTCTG CTAATCCTGT TACCAGTGGC TGCTGCCAGT GGCGATAAGT CGTGTCTTAC
      GGAGCGAGAC GATTAGGACA ATGGTCACCG ACGACGGTCA CCGCTATTCA GCACAGAATG
3961  CGGGTTGGAC TCAAGACGAT AGTTACCGGA TAAGGCGCAG CGGTCGGGCT GAACGGGGGG
      GCCCAACCTG AGTTCTGCTA TCAATGGCCT ATTCCGCGTC GCCAGCCCGA CTTGCCCCCC
4021  TTCGTGCACA CAGCCCAGCT GGAGCGAAC GACCTACACC GAACTGAGAT ACCTACAGCG
      AAGCACGTGT GTCGGGTCGA ACCTCGCTTG CTGGATGTGG CTTGACTCTA TGGATGTCGC
4081  TGAGCTATGA GAAAGCGCCA CGCTTCCCGA AGGGAGAAAG GCGGACAGGT ATCCGGTAAG
      ACTCGATACT CTTTCGCGGT GCGAAGGGCT TCCCTCTTTC CGCCTGTCCA TAGGCCATTC
4141  CGGCAGGGTC GGAACAGGAG AGCGCACGAG GGAGCTTCCA GGGGGAAACG CCTGGTATCT
      GCCGTCCCAG CCTTGTCCTC TCGCGTGCTC CCTCGAAGGT CCCCCTTTGC GGACCATAGA
4201  TTATAGTCCT GTCGGGTTTC GCCACCTCTG ACTTGAGCGT CGATTTTTGT GATGCTCGTC
      AATATCAGGA CAGCCCAAAG CGGTGGAGAC TGAACTCGCA GCTAAAAACA CTACGAGCAG
4261  AGGGGGGCGG AGCCTATGGA AAAACGCCAG CAACGCGGCC TTTTTACGGT TCCTGGCCTT
      TCCCCCCGCC TCGGATACCT TTTTGCGGTC GTTGCGCCGG AAAAATGCCA AGGACCGGAA
4321  TTGCTGGCCT TTTGCTCACA TGTTCTTTCC TGCGTTATCC CCTGATTCTG TGGATAACCG
      AACGACCGGA AAACGAGTGT ACAAGAAAGG ACGCAATAGG GGACTAAGAC ACCTATTGGC
4381  TATTACCGCC TTTGAGTGAG CTGATACCGC TCGCCGCAGC CGAACGACCG AGCGCAGCGA
      ATAATGGCGG AAACTCACTC GACTATGGCG AGCGGCGTCG GCTTGCTGGC TCGCGTCGCT
4441  GTCAGTGAGC GAGGAAGCGG AAGAGCGCCT GATGCGGTAT TTTCTCCTTA CGCATCTGTG
      CAGTCACTCG CTCCTTCGCC TTCTCGCGGA CTACGCCATA AAAGAGGAAT GCGTAGACAC
4501  CGGTATTTCA CACCGCATAT ATGGTGCACT CTCAGTACAA TCTGCTCTGA TGCCGCATAG
      GCCATAAAGT GTGGCGTATA TACCACGTGA GAGTCATGTT AGACGAGACT ACGGCGTATC
4561  TTAAGCCAGT ATACACTCCG CTATCGCTAC GTGACTGGGT CATGGCTGCG CCCCGACACC
      AATTCGGTCA TATGTGAGGC GATAGCGATG CACTGACCCA GTACCGACGC GGGGCTGTGG
4621  CGCCAACACC CGCTGACGCG CCCTGACGGG CTTGTCTGCT CCCGGCATCC GCTTACAGAC
      GCGGTTGTGG GCGACTGCGC GGGACTGCCC GAACAGACGA GGGCCGTAGG CGAATGTCTG
4681  AAGCTGTGAC CGTCTCCGGG AGCTGCATGT GTCAGAGGTT TTCACCGTCA TCACCGAAAC
      TTCGACACTG GCAGAGGCCC TCGACGTACA CAGTCTCCAA AAGTGGCAGT AGTGGCTTTG
4741  GCGCGAGGCA GCTGCGGTAA AGCTCATCAG CGTGGTCGTG AAGCGATTCA CAGATGTCTG
      CGCGCTCCGT CGACGCCATT TCGAGTAGTC GCACCAGCAC TTCGCTAAGT GTCTACAGAC
4801  CCTGTTCATC CGCGTCCAGC TCGTTGAGTT TCTCCAGAAG CGTTAATGTC TGGCTTCTGA
      GGACAAGTAG GCGCAGGTCG AGCAACTCAA AGAGGTCTTC GCAATTACAG ACCGAAGACT
4861  TAAAGCGGGC CATGTTAAGG GCGGTTTTTT CCTGTTTGGT CACTGATGCC TCCGTGTAAG
      ATTTCGCCCG GTACAATTCC CGCCAAAAAA GGACAAACCA GTGACTACGG AGGCACATTC
4921  GGGGATTTCT GTTCATGGGG GTAATGATAC CGATGAAACG AGAGAGGATG CTCACGATAC
      CCCCTAAAGA CAAGTACCCC CATTACTATG GCTACTTTGC TCTCTCCTAC GAGTGCTATG
4981  GGGTTACTGA TGATGAACAT GCCCGGTTAC TGGAACGTTG TGAGGGTAAA CAACTGGCGG
      CCCAATGACT ACTACTTGTA CGGGCCAATG ACCTTGCAAC ACTCCCATTT GTTGACCGCC
5041  TATGGATGCG GCGGGACCAG AGAAAAATCA CTCAGGGTCA ATGCCAGCGC TTCGTTAATA
      ATACCTACGC CGCCCTGGTC TCTTTTTAGT GAGTCCCAGT TACGGTCGCG AAGCAATTAT
5101  CAGATGTAGG TGTTCCACAG GGTAGCCAGC AGCATCCTGC GATGCAGATC CGGAACATAA
      GTCTACATCC ACAAGGTGTC CCATCGGTCG TCGTAGGACG CTACGTCTAG GCCTTGTATT
5161  TGGTGCAGGG CGCTGACTTC CGCGTTTCCA GACTTTACGA AACACGGAAA CCGAAGACCA
      ACCACGTCCC GCGACTGAAG GCGCAAAGGT CTGAAATGCT TTGTGCCTTT GGCTTCTGGT
5221  TTCATGTTGT TGCTCAGGTC GCAGACGTTT TGCAGCAGCA GTCGCTTCAC GTTCGCTCGC
      AAGTACAACA ACGAGTCCAG CGTCTGCAAA ACGTCGTCGT CAGCGAAGTG CAAGCGAGCG
5281  GTATCGGTGA TTCATTCTGC TAACCAGTAA GGCAACCCCG CCAGCCTAGC CGGGTCCTCA
      CATAGCCACT AAGTAAGACG ATTGGTCATT CCGTTGGGGC GGTCGGATCG GCCCAGGAGT
5341  ACGACAGGAG CACGATCATG CTAGTCATGC CCCGCGCCCA CCGGAAGGAG CTGACTGGGT
      TGCTGTCCTC GTGCTAGTAC GATCAGTACG GGGCGCGGGT GGCCTTCCTC GACTGACCCA
5401  TGAAGGCTCT CAAGGGCATC GGTCAGATCC CCGGTGCCTA ATGAGTGAGC TAACTTACAT
      ACTTCCGAGA GTTCCCGTAG CCAGCTCTAG GGCCACGGAT TACTCACTCG ATTGAATGTA
5461  TAATTGCGTT GCGCTCACTG CCCGCTTTCC AGTCGGGAAA CCTGTCGTGC CAGCTGCATT
      ATTAACGCAA CGCGAGTGAC GGGCGAAAGG TCAGCCCTTT GGACAGCACG GTCGACGTAA
5521  AATGAATCGG CCAACGCGCG GGGAGAGGCG GTTTGCGTAT TGGGCGCCAG GGTGGTTTTT
      TTACTTAGCC GGTTGCGCGC CCCTCTCCGC CAAACGCATA ACCCGCGGTC CCACCAAAAA
5581  CTTTTCACCA GTGAGACGGG CAACAGCTGA TTGCCCTTCA CCGCCTGGCC CTGAGAGAGT
      GAAAAGTGGT CACTCTGCCC GTTGTCGACT AACGGGAAGT GGCGGACCGG GACTCTCTCA
5641  TGCAGCAAGC GGTCCACGCT GGTTTGCCCC AGCAGGCGAA AATCCTGTTT GATGGTGGTT
      ACGTCGTTCG CCAGGTGCGA CCAAACGGGG TCGTCCGCTT TTAGGACAAA CTACCACCAA
5701  AACGGCGGGA TATAACATGA GCTGTCTTCG GTATCGTCGT ATCCCACTAC CGAGATGTCC
      TTGCCGCCCT ATATTGTACT CGACAGAAGC CATAGCAGCA TAGGGTGATG GCTCTACAGG
5761  GCACCAACGC GCAGCCCGGA CTCGGTAATG GCGCGCATTG CGCCCAGCGC CATCTGATCG
      CGTGGTTGCG CGTCGGGCCT GAGCCATTAC CGCGCGTAAC GCGGGTCGCG GTAGACTAGC
5821  TTGCAACCA GCATCGCAGT GGGAACGATG CCCTCATTCA GCATTTGCAT GGTTTGTTGA
      AACCGTTGGT CGTAGCGTCA CCCTTGCTAC GGGAGTAAGT CGTAAACGTA CCAAACAACT
```

Fig. 40₃

```
5881  AAACCGGACA TGGCACTCCA GTCGCCTTCC CGTTCCGCTA TCGGCTGAAT TTGATTGCGA
      TTTGGCCTGT ACCGTGAGGT CAGCGGAAGG GCAAGGCGAT AGCCGACTTA AACTAACGCT
5941  GTGAGATATT TATGCCAGCC AGCCAGACGC AGACGCGCCG AGACAGAACT TAATGGGCCC
      CACTCTATAA ATACGGTCGG TCGGTCTGCG TCTGCGCGGC TCTGTCTTGA ATTACCCGGG
6001  GCTAACAGCG CGATTTGCTG GTGACCCAAT GCGACCAGAT GCTCCACGCC CAGTCGCGTA
      CGATTGTCGC GCTAAACGAC CACTGGGTTA CGCTGGTCTA CGAGGTGCGG GTCAGCGCAT
6061  CCGTCTTCAT GGGAGAAAAT AATACTGTTG ATGGGTGTCT GGTCAGAGAC ATCAAGAAAT
      GGCAGAAGTA CCCTCTTTTA TTATGACAAC TACCCACAGA CCAGTCTCTG TAGTTCTTTA
6121  AACGCCGGAA CATTAGTGCA GGCAGCTTCC ACAGCAATGG CATCCTGGTC ATCCAGCGGA
      TTGCGGCCTT GTAATCACGT CCGTCGAAGG TGTCGTTACC GTAGGACCAG TAGGTCGCCT
6181  TAGTTAATGA TCAGCCCACT GACGCGTTGC GCGAGAAGAT TGTGCACCGC CGCTTTACAG
      ATCAATTACT AGTCGGGTGA CTGCGCAACG CGCTCTTCTA ACACGTGGCG GCGAAATGTC
6241  GCTTCGACGC CGCTTCGTTC TACCATCGAC ACCACCACGC TGGCACCCAG TTGATCGGCG
      CGAAGCTGCG GCGAAGCAAG ATGGTAGCTG TGGTGGTGCG ACCGTGGGTC AACTAGCCGC
6301  CGAGATTTAA TCGCCGCGAC AATTTGCGAC GGCGCGTGCA GGGCCAGACT GGAGGTGGCA
      GCTCTAAATT AGCGGCGCTG TTAAACGCTG CCGCGCACGT CCCGGTCTGA CCTCCACCGT
6361  ACGCCAATCA GCAACGACTG TTTGCCCGCC AGTTGTTGTG CCACGCGGTT GGGAATGTAA
      TGCGGTTAGT CGTTGCTGAC AAACGGGCGG TCAACAACAC GGTGCGCCAA CCCTTACATT
6421  TTCAGCTCCG CCATCGCCGC TTCCACTTTT TCCCGCGTTT TCGCAGAAAC GTGGCTGGCC
      AAGTCGAGGC GGTAGCGGCG AAGGTGAAAA AGGGCGCAAA AGCGTCTTTG CACCGACCGG
6481  TGGTTCACCA CGCGGGAAAC GGTCTGATAA GAGACACCGG CATACTCTGC GACATCGTAT
      ACCAAGTGGT GCGCCCTTTG CCAGACTATT CTCTGTGGCC GTATGAGACG CTGTAGCATA
6541  AACGTTACTG GTTTCACATT CACCACCCTG AATTGACTCT CTTCCGGGCG CTATCATGCC
      TTGCAATGAC CAAAGTGTAA GTGGTGGGAC TTAACTGAGA GAAGGCCCGC GATAGTACGG
6601  ATACCGCGAA AGGTTTTGCG CCATTCGATG GTGTCCGGGA TCTCGACGCT CTCCCTTATG
      TATGGCGCTT TCCAAAACGC GGTAAGCTAC CACAGGCCCT AGAGCTGCGA GAGGGAATAC
6661  CGACTCCTGC ATTAGGAAGC AGCCCAGTAG TAGGTTGAGG CCGTTGAGCA CCGCCGCCGC
      GCTGAGGACG TAATCCTTCG TCGGGTCATC ATCCAACTCC GGCAACTCGT GGCGGCGGCG
6721  AAGGAATGGT GCATGCAAGG AGATGGCGCC CAACAGTCCC CCGGCCACGG GGCCTGCCAC
      TTCCTTACCA CGTACGTTCC TCTACCGCGG GTTGTCAGGG GGCCGGTGCC CCGGACGGTG
6781  CATACCCACG CCGAAACAAG CGCTCATGAG CCCGGCTTAC CGCAGCCGAT CTTCCCCATC
      GTATGGGTGC GGCTTTGTTC GCGAGTACTC GGGCTTACC GCTCGGGCTA GAAGGGGTAG
6841  GGTGATGTCG GCGATATAGG CGCCAGCAAC CGCACCTGTG GCGCCGGTGA TGCCGGCCAC
      CCACTACAGC CGCTATATCC GCGGTCGTTG GCGTGGACAC CGCGGCCACT ACGGCCGGTG
                                                ClaI
                                                ~~~~~~~
6901  GATGCGTCCG GCGTAGAGGA TCGAGATCGA TCTCGATCCC GCGAAATTAA TACGACTCAC
      CTACGCAGGC CGCATCTCCT AGCTCTAGCT AGAGCTAGGG CGCTTTAATT ATGCTGAGTG
6961  TATA
      ATAT
```

Fig. 40₄

| Fig. 42$_1$ |
|---|
| Fig. 42$_2$ |
| Fig. 42$_3$ |
| Fig. 42$_4$ |

Fig. 42

```
   1 ATCCGGATAT AGTTCCTCCT TTCAGCAAAA AACCCCTCAA GACCCGTTTA GAGGCCCCAA
     TAGGCCTATA TCAAGGAGGA AAGTCGTTTT TTGGGGAGTT CTGGGCAAAT CTCCGGGGTT
  61 GGGGTTATGC TAGTTATTGC TCAGCGGTGG CAGCAGCCAA CTCAGCTTCC TTTCGGGCTT
     CCCCAATACG ATCAATAACG AGTCGCCACC GTCGTCGGTT GAGTCGAAGG AAAGCCCGAA
                                                                HindIII
                                                                ~~~~~~
 121 TGTTAGCAGC CGGATCTCAG TGGTGGTGGT GGTGGTGCTC GAGTGCGGCC GCAAGCTTAG
     ACAATCGTCG GCCTAGAGTC ACCACCACCA CCACCACGAG CTCACGCCGG CGTTCGAATC
                          ~~~~~~~~~~~~~~~~~~                   ~~~
                                  His tag
 181 CAGCCGGATC TGATCTTAAT TAATTATCAC CACTTTGTAC AAGAAAGCTG AACGAGAAAC
     GTCGGCCTAG ACTAGAATTA ATTAATAGTG GTGAAACATG TTCTTTCGAC TTGCTCTTTG
 241 GTAAAATGAT ATAAATATCA ATATATTAAA TTAGATTTTG CATAAAAAAC AGACTACATA
     CATTTTACTA TATTTATAGT TATATAATTT AATCTAAAAC GTATTTTTTG TCTGATGTAT
                                                    PstI
                                                    ~~~~~~
 301 ATACTGTAAA ACACAACATA TCCAGTCACT ATGGTCGACC TGCAGACTGG CTGTGTATAA
     TATGACATTT TGTGTTGTAT AGGTCAGTGA TACCAGCTGG ACGTCTGACC GACACATATT
 361 GGGAGCCTGA CATTTATATT CCCCAGAACA TCAGGTTAAT GGCGTTTTTG ATGTCATTTT
     CCCTCGGACT GTAAATATAA GGGGTCTTGT AGTCCAATTA CCGCAAAAAC TACAGTAAAA
 421 CGCGGCGGCT GAGATCAGCC ACTTCTTCCC CGATAACGGA GACCGGCACA CTGGCCATAT
     GCGCCGCCGA CTCTAGTCGG TGAAGAAGGG GCTATTGCCT CTGGCCGTGT GACCGGTATA
 481 CGGTGGTCAT CATGCGCCAG CTTTCATCCC CGATATGCAC CACCGGGTAA AGTTCACGGG
     GCCACCAGTA GTACGCGGTC GAAAGTAGGG GCTATACGTG GTGGCCCATT TCAAGTGCCC
                                                             XmaI
                                                             ~~~~~~
                                                              SmaI
                                                              ~~~~~~
 541 AGACTTTATC TGACAGCAGA CGTGCACTGG CCAGGGGGAT CACCATCCGT CGCCCGGGCG
     TCTGAAATAG ACTGTCGTCT GCACGTGACC GGTCCCCCTA GTGGTAGGCA GCGGGCCCGC
 601 TGTCAATAAT ATCACTCTGT ACATCCACAA ACAGACGATA ACGGCTCTCT CTTTTATAGG
     ACAGTTATTA TAGTGAGACA TGTAGGTGTT TGTCTGCTAT TGCCGAGAGA GAAAATATCC
 661 TGTAAACCTT AAACTGCATT TCACCAGTCC CTGTTCTCGT CAGCAAAAGA GCCGTTCATT
     ACATTTGGAA TTTGACGTAA AGTGGTCAGG GACAAGAGCA GTCGTTTTCT CGGCAAGTAA
 721 TCAATAAACC GGGCGACCTC AGCCATCCCT TCCTGATTTT CCGCTTTCCA GCGTTCGGCA
     AGTTATTTGG CCCGCTGGAG TCGGTAGGGA AGGACTAAAA GGCGAAAGGT CGCAAGCCGT
 781 CGCAGACGAC GGGCTTCATT CTGCATGGTT GTGCTTACCA GACCGGAGAT ATTGACATCA
     GCGTCTGCTG CCCGAAGTAA GACGTACCAA CACGAATGGT CTGGCCTCTA TAACTGTAGT
 841 TATATGCCTT GAGCAACTGA TAGCTGTCGC TGTCAACTGT CACTGTAATA CGCTGCTTCA
     ATATACGGAA CTCGTTGACT ATCGACAGCG ACAGTTGACA GTGACATTAT GCGACGAAGT
 901 TAGCACACCT CTTTTTGACA TACTTCGGGT ATACGCTAGC ACCGGTGTTG CAACGAACAG
     ATCGTGTGGA GAAAACTGT ATGAAGCCCA TATGCGATCG TGGCCACAAC GTTGCTTGTC
 961 GTCACTATCA GTCAAAATAA AATCATTATT TGCCATCCAG CTGATATCCC CTATAGTGAG
     CAGTGATAGT CAGTTTTATT TTAGTAATAA ACGGTAGGTC GACTATAGGG GATATCACTC
1021 TCGTATTACA TGGTCATAGC TGTTTCCTGG CAGCTCTGGC CCGTGTCTCA AAATCTCTGA
     AGCATAATGT ACCAGTATCG ACAAAGGACC GTCGAGACCG GGCACAGAGT TTTAGAGACT
1081 TGTTACATTG CACAAGATAA AATAATATCA TCATGATCAG TCCTGCTCCT CGGCCACGAA
     ACAATGTAAC GTGTTCTATT TTATTATAGT AGTACTAGTC AGGACGAGGA GCCGGTGCTT
1141 GTGCACGCAG TTGCCGGCCG GGTCGCGCAG GGCGAACTCC CGCCCCCACG GCTGCTCGCC
     CACGTGCGTC AACGGCCGGC CCAGCGCGTC CCGCTTGAGG GCGGGGGTGC CGACGAGCGG
1201 GATCTCGGTC ATGGCCGGCC CGGAGGCGTC CCGGAAGTTC GTGGACACGA CCTCCGACCA
     CTAGAGCCAG TACCGGCCGG GCCTCCGCAG GGCCTTCAAG CACCTGTGCT GGAGGCTGGT
1261 CTCGGCGTAC AGCTCGTCCA GGCCGCGCAC CCACACCCAG GCCAGGGTGT TGTCCGGCAC
     GAGCCGCATG TCGAGCAGGT CCGGCGCGTG GGTGTGGGTC CGGTCCCACA ACAGGCCGTG
1321 CACCTGGTCC TGGACCGCGC TGATGAACAG GGTCACGTCG TCCCGGACCA CACCGGCGAA
     GTGGACCAGG ACCTGGCGCG ACTACTTGTC CCAGTGCAGC AGGGCCTGGT GTGGCCGCTT
                           XmaI
                           ~~~~~~
                            SmaI
                            ~~~~~~
1381 GTCGTCCTCC ACGAAGTCCC GGGAGAACCC GAGCCGGTCG GTCCAGAACT CGACCGCTCC
     CAGCAGGAGG TGCTTCAGGG CCCTCTTGGG CTCGGCCAGC CAGGTCTTGA GCTGGCGAGG
                                                                NcoI
                                                                ~~~~~~
1441 GGCGACGTCG CGCGCGGTGA GCACCGGAAC GGCACTGGTC AACTTGGCCA TGGTTTAGTT
     CCGCTGCAGC GCGCGCCACT CGTGGCCTTG CCGTGACCAG TTGAACCGGT ACCAAATCAA
1501 CCTCACCTTG TCGTATTATA CTATGCCGAT ATACTATGCC GATGATTAAT TGTCAACACG
     GGAGTGGAAC AGCATAATAT GATACGGCTA TATGATACGG CTACTAATTA ACAGTTGTGC
1561 TGCTGATCAT GACCAAAATC CCTTAACGTG GCGGCCGCCA TAGTGACTGG ATATGTTGTG
     ACGACTAGTA CTGGTTTTAG GGAATTGCAC CGCCGGCGGT ATCACTGACC TATACAACAC
```

Fig. 42$_1$

```
1621  TTTTACAGTA TTATGTAGTC TGTTTTTTAT GCAAAATCTA ATTTAATATA TTGATATTTA
      AAAATGTCAT AATACATCAG ACAAAAAATA CGTTTTAGAT TAAATTATAT AACTATAAAT
                                                    EcoRI
                                                    ~~~~~~
                                        SacI                 BamHI
                                        ~~~~~~~              ~
1681  TATCATTTTA CGTTTCTCGT TCAGCTTTTT TGTACAAACT TGTGATCGAG CTCGAATTCG
      ATAGTAAAAT GCAAAGAGCA AGTCGAAAAA ACATGTTTGA ACACTAGCTC GAGCTTAAGC
      BamHI                NcoI
      ~~~~~                ~~~~~~
1741  GATCCGAATT AATTCCGATA TCCATGGCCA TCGCCGGCTG GGCAGCGAGG AGCAGCAGAC
      CTAGGCTTAA TTAAGGCTAT AGGTACCGGT AGCGGCCGAC CCGTCGCTCC TCGTCGTCTG
1801  CAGCAGCAGC GGTCGGCAGC AGGTATTTCA TATGTATATC TCCTTCTTAA AGTTAAACAA
      GTCGTCGTCG CCAGCCGTCG TCCATAAAGT ATACATATAG AGGAAGAATT TCAATTTGTT
1861  AATTATTTCT AGAGGGGAAT TGTTATCCGC TCACAATTCC CCTATAGTGA GTCGTATTAA
      TTAATAAAGA TCTCCCCTTA ACAATAGGCG AGTGTTAAGG GGATATCACT CAGCATAATT
1921  TTTCGCGGGA TCGAGATCTC GATCCTCTAC GCCGGACGCA TCGTGGCCGG CATCACCGGC
      AAAGCGCCCT AGCTCTAGAG CTAGGAGATG CGGCCTGCGT AGCACCGGCC GTAGTGGCCG
1981  GCCACAGGTG CGGTTGCTGG CGCCTATATC GCCGACATCA CCGATGGGGA AGATCGGGCT
      CGGTGTCCAC GCCAACGACC GCGGATATAG CGGCTGTAGT GGCTACCCCT TCTAGCCCGA
2041  CGCCACTTCG GGCTCATGAG CGCTTGTTTC GGCGTGGGTA TGGTGGCAGG CCCCGTGGCC
      GCGGTGAAGC CCGAGTACTC GCGAACAAAG CCGCACCCAT ACCACCGTCC GGGGCACCGG
2101  GGGGGACTGT TGGGCGCCAT CTCCTTGCAT GCACCATTCC TTGCGGCGGC GGTGCTCAAC
      CCCCCTGACA ACCCGCGGTA GAGGAACGTA CGTGGTAAGG AACGCCGCCG CCACGAGTTG
                                              EcoNI
                                              ~~~~~~~~~~~~
2161  GGCCTCAACC TACTACTGGG CTGCTTCCTA ATGCAGGAGT CGCATAAGGG AGAGCGTCGA
      CCGGAGTTGG ATGATGACCC GACGAAGGAT TACGTCCTCA GCGTATTCCC TCTCGCAGCT
2221  GATCCCGGAC ACCATCGAAT GGCGCAAAAC CTTTCGCGGT ATGGCATGAT AGCGCCCGGA
      CTAGGGCCTG TGGTAGCTTA CCGCGTTTTG GAAAGCGCCA TACCGTACTA TCGCGGGCCT
2281  AGAGAGTCAA TTCAGGGTGG TGAATGTGAA ACCAGTAACG TTATACGATG TCGCAGAGTA
      TCTCTCAGTT AAGTCCCACC ACTTACACTT TGGTCATTGC AATATGCTAC AGCGTCTCAT
2341  TGCCGGTGTC TCTTATCAGA CCGTTTCCCG CGTGGTGAAC CAGGCCAGCC ACGTTTCTGC
      ACGGCCACAG AGAATAGTCT GGCAAAGGGC GCACCACTTG GTCCGGTCGG TGCAAAGACG
2401  GAAAACGCGG GAAAAGTGG AAGCGGCGAT GCGGAGCTG AATTACATTC CCAACCGCGT
      CTTTTGCGCC CTTTTTCACC TTCGCCGCTA CCGCCTCGAC TTAATGTAAG GGTTGGCGCA
2461  GGCACAACAA CTGGCGGGCA AACAGTCGTT GCTGATTGGC GTTGCCACCT CCAGTCTGGC
      CCGTGTTGTT GACCGCCCGT TTGTCAGCAA CGACTAACCG CAACGGTGGA GGTCAGACCG
2521  CCTGCACGCG CCGTCGCAAA TTGTCGCGGC GATTAAATCT CGCGCCGATC AACTGGGTGC
      GGACGTGCGC GGCAGCGTTT AACAGCGCCG CTAATTTAGA GCGCGGCTAG TTGACCCACG
2581  CAGCGTGGTG GTGTCGATGG TAGAACGAAG CGGCGTCGAA GCCTGTAAAG CGGCGGTGCA
      GTCGCACCAC CACAGCTACC ATCTTGCTTC GCCGCAGCTT CGGACATTTC GCCGCCACGT
2641  CAATCTTCTC GCGCAACGCG TCAGTGGGCT GATCATTAAC TATCCGCTGG ATGACCAGGA
      GTTAGAAGAG CGCGTTGCGC AGTCACCCGA CTAGTAATTG ATAGGCGACC TACTGGTCCT
2701  TGCCATTGCT GTGGAAGCTG CCTGCACTAA TGTTCCGGCG TTATTTCTTG ATGTCTCTGA
      ACGGTAACGA CACCTTCGAC GGACGTGATT ACAAGGCCGC AATAAAGAAC TACAGAGACT
2761  CCAGACACCC ATCAACAGTA TTATTTTCTC CCATGAAGAC GGTACGCGAC TGGGCGTGGA
      GGTCTGTGGG TAGTTGTCAT AATAAAAGAG GGTACTTCTG CCATGCGCTG ACCCGCACCT
2821  GCATCTGGTC GCATTGGGTC ACCAGCAAAT CGCGCTGTTA GCGGGCCCAT TAAGTTCTGT
      CGTAGACCAG CGTAACCCAG TGGTCGTTTA GCGCGACAAT CGCCCGGGTA ATTCAAGACA
2881  CTCGGCGCGT CTGCGTCTGG CTGGCTGGCA TAAATATCTC ACTCGCAATC AAATTCAGCC
      GAGCCGCGCA GACGCAGACC GACCGACCGT ATTTATAGAG TGAGCGTTAG TTTAAGTCGG
2941  GATAGCGGAA CGGGAAGGCG ACTGGAGTGC CATGTCCGGT TTTCAACAAA CCATGCAAAT
      CTATCGCCTT GCCCTTCCGC TGACCTCACG GTACAGGCCA AAAGTTGTTT GGTACGTTTA
3001  GCTGAATGAG GGCATCGTTC CCACTGCTGA GCTGGTTGCC AACGATCAGA TGGCGCTGGG
      CGACTTACTC CCGTAGCAAG GGTGACGACT CGACCAACGG TTGCTAGTCT ACCGCGACCC
3061  CGCAATGCGC GCCATTACCG AGTCCGGGCT GCGCGTTGGT GCGGATATCT CGGTAGTGGG
      GCGTTACGCG CGGTAATGGC TCAGGCCCGA CGCGCAACCA CGCCTATAGA GCCATCACCC
3121  ATACGACGAT ACCGAAGACA GCTCATGTTA TATCCCGCCG TTAACCACCA TCAAACAGGA
      TATGCTGCTA TGGCTTCTGT CGAGTACAAT ATAGGGCGGC AATTGGTGGT AGTTTGTCCT
3181  TTTTCGCCTG CTGGGGCAAA CCAGCGTGGA CCGCTTGCTG CAACTCTCTC AGGGCCAGGC
      AAAAGCGGAC GACCCCGTTT GGTCGCACCT GGCGAACGAC GTTGAGAGAG TCCCGGTCCG
3241  GGTGAAGGGC AATCAGCTGT TGCCCGTCTC ACTGGTGAAA AGAAAAACCA CCCTGGCGCC
      CCACTTCCCG TTAGTCGACA ACGGGCAGAG TGACCACTTT TCTTTTTGGT GGGACCGCGG
3301  CAATACGCAA ACCGCCTCTC CCCGCGCGTT GGCCGATTCA TTAATGCAGC TGGCACGACA
      GTTATGCGTT TGGCGGAGAG GGGCGCGCAA CCGGCTAAGT AATTACGTCG ACCGTGCTGT
3361  GGTTTCCCGA CTGGAAAGCG GGCAGTGAGC GCAACGCAAT TAATGTAAGT TAGCTCACTC
      CCAAAGGGCT GACCTTTCGC CCGTCACTCG CGTTGCGTTA ATTACATTCA ATCGAGTGAG
3421  ATTAGGCACC GGGATCTCGA CCGATGCCCT TGAGAGCCTT CAACCCAGTC AGCTCCTTCC
```

Fig. 42₂

```
      TAATCCGTGG CCCTAGAGCT GGCTACGGGA ACTCTCGGAA GTTGGGTCAG TCGAGGAAGG
3481  GGTGGGCGCG GGGCATGACT ATCGTCGCCG CACTTATGAC TGTCTTCTTT ATCATGCAAC
      CCACCCGCGC CCCGTACTGA TAGCAGCGGC GTGAATACTG ACAGAAGAAA TAGTACGTTG
3541  TCGTAGGACA GGTGCCGGCA GCGCTCTGGG TCATTTTCGG CGAGGACCGC TTTCGCTGGA
      AGCATCCTGT CCACGGCCGT CGCGAGACCC AGTAAAAGCC GCTCCTGGCG AAAGCGACCT
3601  GCGCGACGAT GATCGGCCTG TCGCTTGCGG TATTCGGAAT CTTGCACGCC CTCGCTCAAG
      CGCGCTGCTA CTAGCCGGAC AGCGAACGCC ATAAGCCTTA GAACGTGCGG GAGCGAGTTC
3661  CCTTCGTCAC TGGTCCCGCC ACCAAACGTT TCGGCGAGAA GCAGGCCATT ATCGCCGGCA
      GGAAGCAGTG ACCAGGGCGG TGGTTTGCAA AGCCGCTCTT CGTCCGGTAA TAGCGGCCGT
3721  TGGCGGCCCC ACGGGTGCGC ATGATCGTGC TCCTGTCGTT GAGGACCCGG CTAGGCTGGC
      ACCGCCGGGG TGCCCACGCG TACTAGCACG AGGACAGCAA CTCCTGGGCC GATCCGACCG
3781  GGGGTTGCCT TACTGGTTAG CAGAATGAAT CACCGATACG CGAGCGAACG TGAAGCGACT
      CCCCAACGGA ATGACCAATC GTCTTACTTA GTGGCTATGC GCTCGCTTGC ACTTCGCTGA
3841  GCTGCTGCAA AACGTCTGCG ACCTGAGCAA CAACATGAAT GGTCTTCGGT TTCCGTGTTT
      CGACGACGTT TTGCAGACGC TGGACTCGTT GTTGTACTTA CCAGAAGCCA AAGGCACAAA
3901  CGTAAAGTCT GGAAACGCGG AAGTCAGCGC CCTGCACCAT TATGTTCCGG ATCTGCATCG
      GCATTTCAGA CCTTTGCGCC TTCAGTCGCG GGACGTGGTA ATACAAGGCC TAGACGTAGC
3961  CAGGATGCTG CTGGCTACCC TGTGAACAAG CTACATCTGT ATTAACGAAG CGCTGGCATT
      GTCCTACGAC GACCGATGGG ACACCTTGTG GATGTAGACA TAATTGCTTC GCGACCGTAA
4021  GACCCTGAGT GATTTTTCTC TGGTCCCGCC GCATCCATAC CGCCAGTTGT TTACCCTCAC
      CTGGGACTCA CTAAAAAGAG ACCAGGGCGG CGTAGGTATG GCGGTCAACA AATGGGAGTG
4081  AACGTTCCAG TAACCGGGCA TGTTCATCAT CAGTAACCCG TATCGTGAGC ATCCTCTCTC
      TTGCAAGGTC ATTGGCCCGT ACAAGTAGTA GTCATTGGGC ATAGCACTCG TAGGAGAGAG
4141  GTTTCATCGG TATCATTACC CCCATGAACA GAAATCCCCC TTACACGGAG GCATCAGTGA
      CAAAGTAGCC ATAGTAATGG GGGTACTTGT CTTTAGGGGG AATGTGCCTC CGTAGTCACT
4201  CCAAACAGGA AAAAACCGCC CTTAACATGG CCCGCTTTAT CAGAAGCCAG ACATTAACGC
      GGTTTGTCCT TTTTTGGCGG GAATTGTACC GGGCGAAATA GTCTTCGGTC TGTAATTGCG
4261  TTCTGGAGAA ACTCAACGAG CTGGACGCGG ATGAACAGGC AGACATCTGT GAATCGCTTC
      AAGACCTCTT TGAGTTGCTC GACCTGCGCC TACTTGTCCG TCTGTAGACA CTTAGCGAAG
4321  ACGACCGCGC TGATGAGCTT TACCGCAGCT GCCTCGCGCG TTTCGGTGAT GACGGTGAAA
      TGCTGGTGCG ACTACTCGAA ATGGCGTCGA CGGAGCGCGC AAAGCCACTA CTGCCACTTT
4381  ACCTCTGACA CATGCAGCTC CCGGAGACGG TCACAGCTTG TCTGTAAGCG GATGCCGGGA
      TGGAGACTGT GTACGTCGAG GGCCTCTGCC AGTGTCGAAC AGACATTCGC CTACGGCCCT
4441  GCAGACAAGC CCGTCAGGGC GCGTCAGCGG GTGTTGGCGG GTGTCGGGGC GCAGCCATGA
      CGTCTGTTCG GGCAGTCCCG CGCAGTCGCC CACAACCGCC CACAGCCCCG CGTCGGTACT
4501  CCCAGTCACG TAGCGATAGC GGAGTGTATA CTGGCTTAAC TATGCGGCAT CAGAGCAGAT
      GGGTCAGTGC ATCGCTATCG CCTCACATAT GACCGAATTG ATACGCCGTA GTCTCGTCTA
4561  TGTACTGAGA GTGCACCATA TATGCGGTGT GAAATACCGC ACAGATGCGT AAGGAGAAAA
      ACATGACTCT CACGTGGTAT ATACGCCACA CTTTATGGCG TGTCTACGCA TTCCTCTTTT
4621  TACCGCATCA GGCGCTCTTC CGCTTCCTCG CTCACTGACT CGCTGCGCTC GGTCGTTCGG
      ATGGCGTAGT CCGCGAGAAG GCGAAGGAGC GAGTGACTGA GCGACGCGAG CCAGCAAGCC
4681  CTGCGGCGAG CGGTATCAGC TCACTCAAAG GCGGTAATAC GGTTATCCAC AGAATCAGGG
      GACGCCGCTC GCCATAGTCG AGTGAGTTTC CGCCATTATG CCAATAGGTG TCTTAGTCCC
4741  GATAACGCAG GAAAGAACAT GTGAGCAAAA GGCCAGCAAA AGGCCAGGAA CCGTAAAAAG
      CTATTGCGTC CTTTCTTGTA CACTCGTTTT CCGGTCGTTT TCCGGTCCTT GGCATTTTTC
4801  GCCGCGTTGC TGGCGTTTTT CCATAGGCTC CGCCCCCCTG ACGAGCATCA CAAAAATCGA
      CGGCGCAACG ACCGCAAAAA GGTATCCGAG GCGGGGGGAC TGCTCGTAGT GTTTTTAGCT
4861  CGCTCAAGTC AGAGGTGGCG AAACCCGACA GGACTATAAA GATACCAGGC GTTTCCCCCT
      GCGAGTTCAG TCTCCACCGC TTTGGGCTGT CCTGATATTT CTATGGTCCG CAAAGGGGGA
4921  GGAAGCTCCC TCGTGCGCTC TCCTGTTCCG ACCCTGCCGC TTACGGATA CCTGTCCGCC
      CCTTCGAGGG AGCACGCGAG AGGACAAGGC TGGGACGGCG AATGCCTAT GGACAGGCGG
4981  TTTCTCCCTT CGGGAAGCGT GGCGCTTTCT CATAGCTCAC GCTGTAGGTA TCTCAGTTCG
      AAAGAGGGAA GCCCTTCGCA CCGCGAAAGA GTATCGAGTG CGACATCCAT AGAGTCAAGC
5041  GTGTAGGTCG TTCGCTCCAA GCTGGGCTGT GTGCACGAAC CCCCCGTTCA GCCCGACCGC
      CACATCCAGC AAGCGAGGTT CGACCCGACA CACGTGCTTG GGGGGCAAGT CGGGCTGGCG
5101  TGCGCCTTAT CCGGTAACTA TCGTCTTGAG TCCAACCCGG TAAGACACGA CTTATCGCCA
      ACGCGGAATA GGCCATTGAT AGCAGAACTC AGGTTGGGCC ATTCTGTGCT GAATAGCGGT
5161  CTGGCAGCAG CCACTGGTAA CAGGATTAGC AGAGCGAGGT ATGTAGGCGG TGCTACAGAG
      GACCGTCGTC GGTGACCATT GTCCTAATCG TCTCGCTCCA TACATCCGCC ACGATGTCTC
5221  TTCTTGAAGT GGTGGCCTAA CTACGGCTAC ACTAGAAGGA CAGTATTTGG TATCTGCGCT
      AAGAACTTCA CCACCGGATT GATGCCGATG TGATCTTCCT GTCATAAACC ATAGACGCGA
5281  CTGCTGAAGC CAGTTACCTT CGGAAAAAGA GTTGGTAGCT CTTGATCCGG CAAACAAACC
      GACGACTTCG GTCAATGGAA GCCTTTTTCT CAACCATCGA GAACTAGGCC GTTTGTTTGG
5341  ACCGCTGGTA GCGGTGGTTT TTTTGTTTGC AAGCAGCAGA TTACGCGCAG AAAAAAAGGA
      TGGCGACCAT CGCCACCAAA AAAACAAACG TTCGTCGTCT AATGCGCGTC TTTTTTTCCT
5401  TCTCAAGAAG ATCCTTTGAT CTTTTCTACG GGGTCTGACG CTCAGTGGAA CGAAAACTCA
      AGAGTTCTTC TAGGAAACTA GAAAAGATGC CCCAGACTGC GAGTCACCTT GCTTTTGAGT
5461  CGTTAAGGGA TTTTGGTCAT GAACAATAAA ACTGTCTGCT TACATAAACA GTAATACAAG
      GCAATTCCCT AAAACCAGTA CTTGTTATTT TGACAGACGA ATGTATTTGT CATTATGTTC
```

Fig. 42₃

```
5521  GGGTGTTATG AGCCATATTC AACGGGAAAC GTCTTGCTCT AGGCCGCGAT TAAATTCCAA
      CCCACAATAC TCGGTATAAG TTGCCCTTTG CAGAACGAGA TCCGGCGCTA ATTTAAGGTT
5581  CATGGATGCT GATTTATATG GGTATAAATG GGCTCGCGAT AATGTCGGGC AATCAGGTGC
      GTACCTACGA CTAAATATAC CCATATTTAC CCGAGCGCTA TTACAGCCCG TTAGTCCACG
                           ClaI
                           ~~~~~~
5641  GACAATCTAT CGATTGTATG GGAAGCCCGA TGCGCCAGAG TTGTTTCTGA ACATGGCAA
      CTGTTAGATA GCTAACATAC CCTTCGGGCT ACGCGGTCTC AACAAAGACT TGTACCGTT
5701  AGGTAGCGTT GCCAATGATG TTACAGATGA GATGGTCAGA CTAAACTGGC TGACGGAATT
      TCCATCGCAA CGGTTACTAC AATGTCTACT CTACCAGTCT GATTTGACCG ACTGCCTTAA
5761  TATGCCTCTT CCGACCATCA AGCATTTTAT CCGTACTCCT GATGATGCAT GGTTACTCAC
      ATACGGAGAA GGCTGGTAGT TCGTAAAATA GGCATGAGGA CTACTACGTA CCAATGAGTG
                   XmaI
                   ~~~~~~
              SmaI                                        EcoNI
              ~~~~~~                                 ~~~~~~~~~~~~
5821  CACTGCGATC CCCGGGAAAA CAGCATTCCA GGTATTAGAA GAATATCCTG ATTCAGGTGA
      GTGACGCTAG GGGCCCTTTT GTCGTAAGGT CCATAATCTT CTTATAGGAC TAAGTCCACT
5881  AAATATTGTT GATGCGCTGG CAGTGTTCCT GCGCCGGTTG CATTCGATTC CTGTTTGTAA
      TTTATAACAA CTACGCGACC GTCACAAGGA CGCGGCCAAC GTAAGCTAAG GACAAACATT
5941  TTGTCCTTTT AACAGCGATC GCGTATTTCG TCTCGCTCAG GCGCAATCAC GAATGAATAA
      AACAGGAAAA TTGTCGCTAG CGCATAAAGC AGAGCGAGTC CGCGTTAGTG CTTACTTATT
6001  CGGTTTGGTT GATGCGAGTG ATTTTGATGA CGAGCGTAAT GGCTGGCCTG TTGAACAAGT
      GCCAAACCAA CTACGCTCAC TAAAACTACT GCTCGCATTA CCGACCGGAC AACTTGTTCA
6061  CTGGAAAGAA ATGCATAAAC TTTTGCCATT CTCACCGGAT TCAGTCGTCA CTCATGGTGA
      GACCTTTCTT TACGTATTTG AAAACGGTAA GAGTGGCCTA AGTCAGCAGT GAGTACCACT
6121  TTTCTCACTT GATAACCTTA TTTTTGACGA GGGGAAATTA ATAGGTTGTA TTGATGTTGG
      AAAGAGTGAA CTATTGGAAT AAAAACTGCT CCCCTTTAAT TATCCAACAT AACTACAACC
6181  ACGAGTCGGA ATCGCAGACC GATACCAGGA TCTTGCCATC CTATGGAACT GCCTCGGTGA
      TGCTCAGCCT TAGCGTCTGG CTATGGTCCT AGAACGGTAG GATACCTTGA CGGAGCCACT
6241  GTTTTCTCCT TCATTACAGA AACGGCTTTT TCAAAAATAT GGTATTGATA ATCCTGATAT
      CAAAAGAGGA AGTAATGTCT TTGCCGAAAA AGTTTTTATA CCATAACTAT TAGGACTATA

6301  GAATAAATTG CAGTTTCATT TGATGCTCGA TGAGTTTTTC TAAGAATTAA TTCATGAGCG
      CTTATTTAAC GTCAAAGTAA ACTACGAGCT ACTCAAAAAG ATTCTTAATT AAGTACTCGC
6361  GATACATATT TGAATGTATT TAGAAAAATA AACAAATAGG GGTTCCGCGC ACATTTCCCC
      CTATGTATAA ACTTACATAA ATCTTTTTAT TTGTTTATCC CCAAGGCGCG TGTAAAGGGG
6421  GAAAAGTGCC ACCTGAAATT GTAAACGTTA ATATTTTGTT AAAATTCGCG TTAAATTTTT
      CTTTTCACGG TGGACTTTAA CATTTGCAAT TATAAAACAA TTTTAAGCGC AATTTAAAAA
6481  GTTAAATCAG CTCATTTTTT AACCAATAGG CCGAAATCGG CAAAATCCCT TATAAATCAA
      CAATTTAGTC GAGTAAAAAA TTGGTTATCC GGCTTTAGCC GTTTTAGGGA ATATTTAGTT
6541  AAGAATAGAC CGAGATAGGG TTGAGTGTTG TTCCAGTTTG GAACAAGAGT CCACTATTAA
      TTCTTATCTG GCTCTATCCC AACTCACAAC AAGGTCAAAC CTTGTTCTCA GGTGATAATT
6601  AGAACGTGGA CTCCAACGTC AAAGGGCGAA AAACCGTCTA TCAGGGCGAT GGCCCACTAC
      TCTTGCACCT GAGGTTGCAG TTTCCCGCTT TTTGGCAGAT AGTCCCGCTA CCGGGTGATG
6661  GTGAACCATC ACCCTAATCA AGTTTTTTGG GGTCGAGGTG CCGTAAAGCA CTAAATCGGA
      CACTTGGTAG TGGGATTAGT TCAAAAAACC CCAGCTCCAC GGCATTTCGT GATTTAGCCT
6721  ACCCTAAAGG GAGCCCCCGA TTTAGAGCTT GACGGGGAAA GCCGGCGAAC GTGGCGAGAA
      TGGGATTTCC CTCGGGGGCT AAATCTCGAA CTGCCCCTTT CGGCCGCTTG CACCGCTCTT
6781  AGGAAGGGAA GAAAGCGAAA GGAGCGGGCG CTAGGGCGCT GGCAAGTGTA GCGGTCACGC
      TCCTTCCCTT CTTTCGCTTT CCTCGCCCGC GATCCCGCGA CCGTTCACAT CGCCAGTGCG
6841  TGCGCGTAAC CACCACACCC GCCGCGCTTA ATGCGCCGCT ACAGGGCGCG TCCCATTCGC
      ACGCGCATTG GTGGTGTGGG CGGCGCGAAT TACGCGGCGA TGTCCCGCGC AGGGTAAGCG
6901  CA
      GT
```

```
        EcoNI
        ~~~~~~~~~~~
   1 CCTGCATTAG GAAGCAGCCC AGTAGTAGGT TGAGGCCGTT GAGCACCGCC GCCGCAAGGA
     GGACGTAATC CTTCGTCGGG TCATCATCCA ACTCCGGCAA CTCGTGGCGG CGGCGTTCCT
  61 ATGGTGCATG CAAGGAGATG GCGCCCAACA GTCCCCCGGC CACGGGGCCT GCCACCATAC
     TACCACGTAC GTTCCTCTAC CGCGGGTTGT CAGGGGGCCG GTGCCCCGGA CGGTGGTATG
 121 CCACGCCGAA ACAAGCGCTC ATGAGCCCGA GTGGCGAGCC CCGATCTTCC CCATCGGTGA
     GGTGCGGCTT TGTTCGCGAG TACTCGGGCT TCACCGCTCG GGCTAGAAGG GGTAGCCACT
 181 TGTCGGCGAT ATAGGCGCCA GCAACCGCAC CTGTGGCGCC GGTGATGCCG CCACGATGC
     ACAGCCGCTA TATCCGCGGT CGTTGGCGTG GACACCGCGG CCACTACGGC CGGTGCTACG
 241 GTCCGGCGTA GAGGATCGAG ATCTCGATCC CGCGAAATTA ATACGACTCA CTATAGGGGA
     CAGGCCGCAT CTCCTAGCTC TAGAGCTAGG GCGCTTTAAT TATGCTGAGT GATATCCCCT
 301 ATTGTGAGCG GATAACAATT CCCCTCTAGA AATAATTTTG TTTAACTTTA AGAAGGAGAT
     TAACACTCGC CTATTGTTAA GGGGAGATCT TTATTAAAAC AAATTGAAAT TCTTCCTCTA
 361 ATACATATGA AATACCTGCT GCCGACCGCT GCTGCTGGTC TGCTGCTCCT CGCTGCCCAG
     TATGTATACT TTATGGACGA CGGCTGGCGA CGACGACCAG ACGACGAGGA GCGACGGGTC
                                                      EcoRI
                                                      ~~~~~~~
        NcoI                       BamHI       SacI
        ~~~~~~                     ~~~~~~      ~~~~~~~
 421 CCGGCGATGG CCATGGATAT CGGAATTAAT TCGGATCCGA ATTCGAGCTC GATCACAAGT
     GGCCGCTACC GGTACCTATA GCCTTAATTA AGCCTAGGCT TAAGCTCGAG CTAGTGTTCA
 481 TTGTACAAAA AAGCTGAACG AGAAACGTAA AATGATATAA ATATCAATAT ATTAAATTAG
     AACATGTTTT TTCGACTTGC TCTTTGCATT TTACTATATT TATAGTTATA TAATTTAATC
 541 ATTTTGCATA AAAAACAGAC TACATAATAC TGTAAAACAC AACATATCCA GTCACTATGG
     TAAAACGTAT TTTTTGTCTG ATGTATTATG ACATTTTGTG TTGTATAGGT CAGTGATACC
 601 CGGCCGCCAC GTTAAGGGAT TTTGGTCATG ATCAGCACGT GTTGACAATT AATCATCGGC
     GCCGGCGGTG CAATTCCCTA AAACCAGTAC TAGTCGTGCA CAACTGTTAA TTAGTAGCCG
                                                      NcoI
                                                      ~~~~~~~
 661 ATAGTATATC GGCATAGTAT AATACGACAA GGTGAGGAAC TAAACCATGG CCAAGTTGAC
     TATCATATAG CCGTATCATA TTATGCTGTT CCACTCCTTG ATTTGGTACC GGTTCAACTG
 721 CAGTGCCGTT CCGGTGCTCA CCGCGCGCGA CGTCGCCGGA GCGGTCGAGT TCTGGACCGA
     GTCACGGCAA GGCCACGAGT GGCGCGCGCT GCAGCGGCCT CGCCAGCTCA AGACCTGGCT
 781 CCGGCTCGGG TTCTCCCGGG ACTTCGTGGA GGACGACTTC GCCGGTGTGG TCCGGGACGA
     GGCCGAGCCC AAGAGGGCCC TGAAGCACCT CCTGCTGAAG CGGCCACACC AGGCCCTGCT
 841 CGTGACCCTG TTCATCAGCG CGGTCCAGGA CCAGGTGGTG CCGGACAACA CCCTGGCCTG
     GCACTGGGAC AAGTAGTCGC GCCAGGTCCT GGTCCACCAC GGCCTGTTGT GGGACCGGAC
 901 GGTGTGGGTG CGCGGCCTGG ACGAGCTGTA CGCCGAGTGG TCGGAGGTCG TGTCCACGAA
     CCACACCCAC GCGCCGGACC TGCTCGACAT GCGGCTCACC AGCCTCCAGC ACAGGTGCTT
 961 CTTCCGGGAC GCCTCCGGGC CGGCCATGAC CGAGATCGGC GAGCAGCCGT GGGGGCGGGA
     GAAGGCCCTG CGGAGGCCCG GCCGGTACTG GCTCTAGCCG CTCGTCGGCA CCCCCGCCCT
1021 GTTCGCCCTG CGCGACCCGG CCGGCAACTG CGTGCACTTC GTGGCCGAGG AGCAGGACTG
     CAAGCGGGAC GCGCTGGGCC GGCCGTTGAC GCACGTGAAG CACCGGCTCC TCGTCCTGAC
1081 ATCATGATGA TATTATTTTA TCTTGTGCAA TGTAACATCA GAGATTTTGA GACACGGGCC
     TAGTACTACT ATAATAAAAT AGAACACGTT ACATTGTAGT CTCTAAAACT CTGTGCCCGG
1141 AGAGCTGCCA GGAAACAGCT ATGACCATGT AATACGACTC ACTATAGGGG ATATCAGCTG
     TCTCGACGGT CCTTTGTCGA TACTGGTACA TTATGCTGAG TGATATCCCC TATAGTCGAC
1201 GATGGCAAAT AATGATTTTA TTTTGACTGA TAGTGACCTG TTCGTTGCAA CACCGGTGCT
     CTACCGTTTA TTACTAAAAT AAAACTGACT ATCACTGGAC AAGCAACGTT GTGGCCACGA
1261 AGCGTATACC CGAAGTATGT CAAAAAGAGG TGTGCTATGA AGCAGCGTAT TACAGTGACA
     TCGCATATGG GCTTCATACA GTTTTTCTCC ACACGATACT TCGTCGCATA ATGTCACTGT
1321 GTTGACAGCG ACAGCTATCA GTTGCTCAAG GCATATATGA TGTCAATATC TCCGGTCTGG
     CAACTGTCGC TGTCGATAGT CAACGAGTTC CGTATATACT ACAGTTATAG AGGCCAGACC
1381 TAAGCACAAC CATGCAGAAT GAAGCCCGTC GTCTGCGTGC CGAACGCTGG AAAGCGGAAA
     ATTCGTGTTG GTACGTCTTA CTTCGGGCAG CAGACGCACG GCTTGCGACC TTTCGCCTTT
1441 ATCAGGAAGG GATGGCTGAG GTCGCCCGGT TTATTGAAAT GAACGGCTCT TTTGCTGACG
     TAGTCCTTCC CTACCGACTC CAGCGGGCCA AATAAGTTTA CTTGCCGAGA AAACGACTGC
1501 AGAACAGGGA CTGGTGAAAT GCAGTTTAAG GTTTACACCT ATAAAAGAGA GAGCCGTTAT
     TCTTGTCCCT GACCACTTTA CGTCAAATTC CAAATGTGGA TATTTTCTCT CTCGGCAATA
1561 CGTCTGTTTG TGGATGTACA GAGTGATATT ATTGACACGC CGGGCGACGG ATGGTGATC
     GCAGACAAAC ACCTACATGT CTCACTATAA TAACTGTGCG GGCCCGCTGC CTACCACTAG
1621 CCCCTGGCCA GTGCACGTCT GCTGTCAGAT AAAGTCTCCC GTGAACTTTA CCCGGTGGTG
     GGGGACCGGT CACGTGCAGA CGACAGTCTA TTTCAGAGGG CACTTGAAAT GGGCCACCAC
1681 CATATCGGGG ATGAAAGCTG ACCATGATGT ACCATGATGT TGGCAGTGT GCCGGTCTCC
     GTATAGCCCC TACTTTCGAC CGCGTACTAC TGGTGGCTAT ACCGGTCACA CGGCCAGAGG
1741 GTTATCGGGG AAGAAGTGGC TGATCTCAGC CGCCGCGAAA ATGACATCAA AAACGCCATT
     CAATAGCCCC TTCTTCACCG ACTAGAGTCG GCGGCGCTTT TACTGTAGTT TTTGCGGTAA
```

Fig. 44₁

```
                                                        PstI
                                                      ~~~~~~
1801  AACCTGATGT TCTGGGGAAT ATAAATGTCA GGCTCCCTTA TACACAGCCA GTCTGCAGGT
      TTGGACTACA AGACCCCTTA TATTTACAGT CCGAGGGAAT ATGTGTCGGT CAGACGTCCA
1861  CGACCATAGT GACTGGATAT GTTGTGTTTT ACAGTATTAT GTAGTCTGTT TTTTATGCAA
      GCTGGTATCA CTGACCTATA CAACACAAAA TGTCATAATA CATCAGACAA AAAATACGTT
1921  AATCTAATTT AATATATTGA TATTTATATC ATTTTACGTT TCTCGTTCAG CTTTCTTGTA
      TTAGATTAAA TTATATAACT ATAAATATAG TAAAATGCAA AGAGCAAGTC GAAAGAACAT
                                              HindIII
                                              ~~~~~~~
1981  CAAAGTGGTG ATAATTAATT AAGATCAGAT CCGGCTGCTA AGCTTGCGGC CGCATAATGC
      GTTTCACCAC TATTAATTAA TTCTAGTCTA GGCCGACGAT TCGAACGCCG GCGTATTACG
2041  TTAAGTCGAA CAGAAAGTAA TCGTATTGTA CACGGCCGCA TAATCGAAAT TAATACGACT
      AATTCAGCTT GTCTTTCATT AGCATAACAT GTGCCGGCGT ATTAGCTTTA ATTATGCTGA
2101  CACTATAGGG GAATTGTGAG CGGATAACAA TTCCCCATCT TAGTATATTA GTTAAGTATA
      GTGATATCCC CTTAACACTC GCCTATTGTT AAGGGGTAGA ATCATATAAT CAATTCATAT
2161  AGAAGGAGAT ATACATATGG CAGATCTCAA TTGGATATCG GCCGGCCACG CGATCGCTGA
      TCTTCCTCTA TATGTATACC GTCTAGAGTT AACCTATAGC CGGCCGGTGC GCTAGCGACT
2221  CGTCGGTACC CTCGAGTCTG GTAAAGAAAC CGCTGCTGCG AAATTTGAAC GCCAGCACAT
      GCAGCCATGG GAGCTCAGAC CATTTCTTTG GCGACGACGC TTTAAACTTG CGGTCGTGTA
                                   AvrII
                                   ~~~~~~~
2281  GGACTCGTCT ACTAGCGCAG CTTAATTAAC CTAGGCTGCT GCCACCGCTG AGCAATAACT
      CCTGAGCAGA TGATCGCGTC GAATTAATTG GATCCGACGA CGGTGGCGAC TCGTTATTGA
2341  AGCATAACCC CTTGGGGCCT CTAAACGGGT CTTGAGGGGT TTTTTGCTGA AACCTCAGGC
      TCGTATTGGG GAACCCCGGA GATTTGCCCA GAACTCCCCA AAAAACGACT TTGGAGTCCG
2401  ATTTGAGAAG CACACGGTCA CACTGCTTCC GGTAGTCAAT AAACCGGTAA ACCAGCAATA
      TAAACTCTTC GTGTGCCAGT GTGACGAAGG CCATCAGTTA TTTGGCCATT TGGTCGTTAT
2461  GACATAAGCG GCTATTTAAC GACCCTGCCC TGAACCGACG ACCGGGTCAT CGTGGCCGGA
      CTGTATTCGC CGATAAATTG CTGGGACGGG ACTTGGCTGC TGGCCCAGTA GCACCGGCCT
2521  TCTTGCGGCC CCTCGGCTTG AACGAATTGT TAGACATTAT TTGCCGACTA CCTTGGTGAT
      AGAACGCCGG GGAGCCGAAC TTGCTTAACA ATCTGTAATA AACGGCTGAT GGAACCACTA
2581  CTCGCCTTTC ACGTAGTGGA CAAATTCTTC CAACTGATCT GCGCGCGAGG CCAAGCGATC
      GAGCGGAAAG TGCATCACCT GTTTAAGAAG GTTGACTAGA CGCGCGCTCC GGTTCGCTAG
2641  TTCTTCTTGT CCAAGATAAG CCTGTCTAGC TTCAAGTATG ACGGGCTGAT ACTGGGCCGG
      AAGAAGAACA GGTTCTATTC GGACAGATCG AAGTTCATAC TGCCCGACTA TGACCCGGCC
2701  CAGGCGCTCC ATTGCCCAGT CGGCAGCGAC ATCCTTCGGC GCGATTTTGC CGGTTACTGC
      GTCCGCGAGG TAACGGGTCA GCCGTCGCTG TAGGAAGCCG CGCTAAAACG GCCAATGACG
2761  GCTGTACCAA ATGCGGGACA ACGTAAGCAC TACATTTCGC TCATCGCCAG CCCAGTCGGG
      CGACATGGTT TACGCCCTGT TGCATTCGTG ATGTAAAGCG AGTAGCGGTC GGGTCAGCCC
2821  CGGCGAGTTC CATAGCGTTA AGGTTTCATT TAGCGCCTCA AATAGATCCT GTTCAGGAAC
      GCCGCTCAAG GTATCGCAAT TCCAAAGTAA ATCGCGGAGT TTATCTAGGA CAAGTCCTTG
2881  CGGATCAAAG AGTTCCTCCG CCGCTGGACC TACCAAGGCA ACGCTATGTT CTCTTGCTTT
      GCCTAGTTTC TCAAGGAGGC GGCGACCTGG ATGGTTCCGT TGCGATACAA GAGAACGAAA
2941  TGTCAGCAAG ATAGCCAGAT CAATGTCGAT CGTGGCTGGC TCGAAGATAC CTGCAAGAAT
      ACAGTCGTTC TATCGGTCTA GTTACAGCTA GCACCGACCG AGCTTCTATG GACGTTCTTA
3001  GTCATTGCGC TGCCATTCTC CAAATTGCAG TTCGCGCTTA GCTGGATAAC GCCACGGAAT
      CAGTAACGCG ACGGTAAGAG GTTTAACGTC AAGCGCGAAT CGACCTATTG CGGTGCCTTA
3061  GATGTCGTCG TGCACAACAG TGGTGACTTC TACAGCGCGG AGAATCTGCC TCTCTCCAGG
      CTACAGCAGC ACGTGTTGTT ACCACTGAAG ATGTCGCGCC TCTTAGAGCG AGAGAGGTCC
3121  GGAAGCCGAA GTTCCAAAAA GGTCGTTGAT CAAAGCTCGC CGCGTTGTTT CATCAAGCCT
      CCTTCGGCTT CAAGGTTTTT CCAGCAACTA GTTTCGAGCG GCGCAACAAA GTAGTTCGGA
3181  TACGGTCACC GTAACCAGCA AATCAATATC ACTGTGTGGC TTCAGGCCGC CATCCACTGC
      ATGCCAGTGG CATTGGTCGT TTAGTTATAG TGACACACCG AAGTCCGGCG GTAGGTGACG
3241  GGAGCCGTAC AAATGTACGG CCAGCAACGT CGGTTCGAGA TGGCGCTCGA TGACGCCAAC
      CCTCGGCATG TTTACATGCC GGTCGTTGCA GCCAAGCTCT ACCGCGAGCT ACTGCGGTTG
3301  TACCTCTGAT AGTTGAGTCG ATACTTCGGC GATCACCGCT TCCCTCATAC TCTTCCTTTT
      ATGGAGACTA TCAACTCAGC TATGAAGCCG CTAGTGGCGA AGGGAGTATG AGAAGGAAAA
3361  TCAATATTAT TGAAGCATTT ATCAGGGTTA TTGTCTCATG AGCGGATACA TATTTGAATG
      AGTTATAATA ACTTCGTAAA TAGTCCCAAT AACAGAGTAC TCGCCTATGT ATAAACTTAC
3421  TATTTAGAAA AATAAACAAA TAGCTAGCTC ACTCGGTCGC TACGCTCCGG GCGTGAGACT
      ATAAATCTTT TATTTGTTT ATCGATCGAG TGAGCCAGCG ATGCGAGGCC CGCACTCTGA
3481  GCGGCGGCG CTGCGGACAC ATACAAAGTT ACCCACAGAT TCCGTGGATA AGCAGGGGAC
      CGCCGCCCGC GACGCCTGTG TATGTTTCAA TGGGTGTCTA AGGCACCTAT TCGTCCCCTG
3541  TAACATGTGA GGCAAAACAG CAGGGCCGCG CCGGTGGCGT TTTTCCATAG GCTCCGCCCT
      ATTGTACACT CCGTTTTGTC GTCCCGGCGC GGCCACCGCA AAAAGGTATC CGAGGCGGGA
3601  CCTGCCAGAG TTCACATAAA CAGACGCTTT TCCGGTGCAT CTGTGGGAGC CGTGAGGCTC
      GGACGGTCTC AAGTGTATTT GTCTGCGAAA AGGCCACGTA GACACCCTCG GCACTCCGAG
3661  AACCATGAAT CTGACAGTAC GGGCGAAACC CGACAGGACT TAAAGATCCC CACCGTTTCC
      TTGGTACTTA GACTGTCATG CCCGCTTTGG GCTGTCCTGA ATTTCTAGGG GTGGCAAAGG
```

Fig. 44$_2$

```
3721  GGCGGGTCGC TCCCTCTTGC GCTCTCCTGT TCCGACCCTG CCGTTTACCG GATACCTGTT
      CCGCCCAGCG AGGGAGAACG CGAGAGGACA AGGCTGGGAC GGCAAATGGC CTATGGACAA
3781  CCGCCTTTCT CCCTTACGGG AAGTGTGGCG CTTTCTCATA GCTCACACAC TGGTATCTCG
      GGCGGAAAGA GGGAATGCCC TTCACACCGC GAAAGAGTAT CGAGTGTGTG ACCATAGAGC
3841  GCTCGGTGTA GGTCGTTCGC TCCAAGCTGG GCTGTAAGCA AGAACTCCCC GTTCAGCCCG
      CGAGCCACAT CCAGCAAGCG AGGTTCGACC CGACATTCGT TCTTGAGGGG CAAGTCGGGC
3901  ACTGCTGCGC CTTATCCGGT AACTGTTCAC TTGAGTCCAA CCCGGAAAAG CACGGTAAAA
      TGACGACGCG GAATAGGCCA TTGACAAGTG AACTCAGGTT GGGCCTTTTC GTGCCATTTT
3961  CGCCACTGGC AGCAGCCATT GGTAACTGGG AGTTCGCAGA GGATTTGTTT AGCTAAACAC
      GCGGTGACCG TCGTCGGTAA CCATTGACCC TCAAGCGTCT CCTAAACAAA TCGATTTGTG
4021  GCGGTTGCTC TTGAAGTGTG CGCCAAAGTC CGGCTACACT GGAAGGACAG ATTTGGTTGC
      CGCCAACGAG AACTTCACAC GCGGTTTCAG GCCGATGTGA CCTTCCTGTC TAAACCAACG
4081  TGTGCTCTGC GAAAGCCAGT TACCACGGTT AAGCAGTTCC CCAACTGACT TAACCTTCGA
      ACACGAGACG CTTTCGGTCA ATGGTGCCAA TTCGTCAAGG GGTTGACTGA ATTGGAAGCT
4141  TCAAACCACC TCCCCAGGTG GTTTTTTCGT TTACAGGGCA AAAGATTACG CGCAGAAAAA
      AGTTTGGTGG AGGGGTCCAC CAAAAAAGCA AATGTCCCGT TTTCTAATGC GCGTCTTTTT
4201  AAGGATCTCA AGAAGATCCT TTGATCTTTT CTACTGAACC GCTCTAGATT TCAGTGCAAT
      TTCCTAGAGT TCTTCTAGGA AACTAGAAAA GATGACTTGG CGAGATCTAA AGTCACGTTA
4261  TTATCTCTTC AAATGTAGCA CCTGAAGTCA GCCCCATACG ATATAAGTTG TAATTCTCAT
      AATAGAGAAG TTTACATCGT GGACTTCAGT CGGGGTATGC TATATTCAAC ATTAAGAGTA
4321  GTTAGTCATG CCCCGCGCCC ACCGGAAGGA GCTGACTGGG TTGAAGGCTC TCAAGGGCAT
      CAATCAGTAC GGGGCGCGGG TGGCCTTCCT CGACTGACCC AACTTCCGAG AGTTCCCGTA
4381  CGGTCGAGAT CCCGGTGCCT AATGAGTGAG CTAACTTACA TTAATTGCGT TGCGCTCACT
      GCCAGCTCTA GGGCCACGGA TTACTCACTC GATTGAATGT AATTAACGCA ACGCGAGTGA
4441  GCCCGCTTTC CAGTCGGGAA ACCTGTCGTG CCAGCTGCAT TAATGAATCG GCCAACGCGC
      CGGGCGAAAG GTCAGCCCTT TGGACAGCAC GGTCGACGTA ATTACTTAGC CGGTTGCGCG
4501  GGGGAGAGGC GGTTTGCGTA TTGGGCGCCA GGGTGGTTTT TCTTTTCACC AGTGAGACGG
      CCCCTCTCCG CCAAACGCAT AACCCGCGGT CCCACCAAAA AGAAAAGTGG TCACTCTGCC
4561  GCAACAGCTG ATTGCCCTTC ACCGCCTGGC CCTGAGAGAG TTGCAGCAAG CGGTCCACGC
      CGTTGTCGAC TAACGGGAAG TGGCGGACCG GGACTCTCTC AACGTCGTTC GCCAGGTGCG
4621  TGGTTTGCCC CAGCAGGCGA AAATCCTGTT TGATGGTGGT TAACGGCGGG ATATAACATG
      ACCAAACGGG GTCGTCCGCT TTTAGGACAA ACTACCACCA ATTGCCGCCC TATATTGTAC
4681  AGCTGTCTTC GGTATCGTCG TATCCCACTA CCGAGATGTC CGCACCAACG CGCAGCCCGG
      TCGACAGAAG CCATAGCAGC ATAGGGTGAT GGCTCTACAG GCGTGGTTGC GCGTCGGGCC
4741  ACTCGGTAAT GGCGCGCATT GCGCCCAGCG CCATCTGATC GTTGGCAACC AGCATCGCAG
      TGAGCCATTA CCGCGCGTAA CGCGGGTCGC GGTAGACTAG CAACCGTTGG TCGTAGCGTC
4801  TGGGAACGAT GCCCTCATTC AGCATTTGCA TGGTTTGTTG AAAACCGGAC ATGGCACTCC
      ACCCTTGCTA CGGGAGTAAG TCGTAAACGT ACCAAACAAC TTTTGGCCTG TACCGTGAGG
4861  AGTCGCTTTC CCGTTCCGCT ATCGGCTGAA TTTGATTGCG AGTGAGATAT TTATGCCAGC
      TCAGCGGAAG GGCAAGGCGA TAGCCGACTT AAACTAACGC TCACTCTATA AATACGGTCG
4921  CAGCCAGACG CAGACGCGCC GAGACAGAAC TTAATGGCC CGCTAACAGC GCGATTTGCT
      GTCGGTCTGC GTCTGCGCGG CTCTGTCTTG AATTACCCGG GCGATTGTCG CGCTAAACGA
4981  GGTGACCCAA TGCGACCAGA TGCTCCACGC CCAGTCGCGT ACCGTCTTCA TGGGAGAAAA
      CCACTGGGTT ACGCTGGTCT ACGAGGTGCG GGTCAGCGCA TGGCAGAAGT ACCCTCTTTT
5041  TAATACTGTT GATGGGTGTC TGGTCAGAGA CATCAAGAAA TAACGCCGGA ACATTAGTGC
      ATTATGACAA CTACCCACAG ACCAGTCTCT GTAGTTCTTT ATTGCGGCCT TGTAATCACG
5101  AGGCAGCTTC CACAGCAATG GCATCCTGGT CATCCAGCGG ATAGTTAATG ATCAGCCCAC
      TCCGTCGAAG GTGTCGTTAC CGTAGGACCA GTAGGTCGCC TATCAATTAC TAGTCGGGTG
5161  TGACGCGTTG CGCGAGAAGA TTGTGCACCG CCGCTTTACA GGCTTCGACG CCGCTTCGTT
      ACTGCGCAAC GCGCTCTTCT AACACGTGGC GGCGAAATGT CCGAAGCTGC GGCGAAGCAA
5221  CTACCATCGA CACCACCACG CTGGCACCCA GTTGATCGGC GCGAGATTTA ATCGCCGCGA
      GATGGTAGCT GTGGTGGTGC GACCGTGGGT CAACTAGCCG CGCTCTAAAT TAGCGGCGCT
5281  CAATTTGCGA CGGCGCGTGC AGGGCCAGAC TGGAGGTGGC AACGCCAATC AGCAACGACT
      GTTAAACGCT GCCGCGCACG TCCCGGTCTG ACCTCCACCG TTGCGGTTAG TCGTTGCTGA
5341  GTTTGCCCGC CAGTTGTTGT GCCACGCGGT TGGGAATGTA ATTCAGCTCC GCCATCGCCG
      CAAACGGGCG GTCAACAACA CGGTGCGCCA ACCCTTACAT TAAGTCGAGG CGGTAGCGGC
5401  CTTCCACTTT TTCCCGCGTT TTCGCAGAAA CGTGGCTGGC CTGGTTCACC ACGCGGGAAA
      GAAGGTGAAA AAGGGCGCAA AAGCGTCTTT GCACCGACCG GACCAAGTGG TGCGCCCTTT
5461  CGGTCTGATA AGAGACACCG GCATACTCTG CGACATCGTA TAACGTTACT GGTTTCACAT
      GCCAGACTAT TCTCTGTGGC CGTATGAGAC GCTGTAGCAT ATTGCAATGA CCAAAGTGTA
5521  TCACCACCCT GAATTGACTC TCTTCCGGGC GCTATCATGC CATACCGCGA AAGGTTTTGC
      AGTGGTGGGA CTTAACTGAG AGAAGGCCCG CGATAGTACG GTATGGCGCT TTCCAAAACG
5581  GCCATTCGAT GGTGTCCGGG ATCTCGACGC TCTCCCTTAT GCGACT
      CGGTAAGCTA CCACAGGCCC TAGAGCTGCG AGAGGGAATA CGCTGA
```

Fig. 44₃

| Fig. 46$_1$ |
|---|
| Fig. 46$_2$ |
| Fig. 46$_3$ |

Fig. 46

```
             EcoNI
             ~~~~~~~~~~~
   1    CCTGCATTAG GAAGCAGCCC AGTAGTAGGT TGAGGCCGTT GAGCACCGCC GCCGCAAGGA
        GGACGTAATC CTTCGTCGGG TCATCATCCA ACTCCGGCAA CTCGTGGCGG CGGCGTTCCT
  61    ATGGTGCATG CAAGGAGATG GCGCCCAACA GTCCCCCGGC CACGGGGCCT GCCACCATAC
        TACCACGTAC GTTCCTCTAC CGCGGGTTGT CAGGGGGCCG GTGCCCCGGA CGGTGGTATG
 121    CCACGCCGAA ACAAGCGCTC ATGAGCCCGA AGTGGCGAGC CCGATCTTCC CCATCGGTGA
        GGTGCGGCTT TGTTCGCGAG TACTCGGGCT TCACCGCTCG GGCTAGAAGG GGTAGCCACT
 181    TGTCGGCGAT ATAGGCGCCA GCAACCGCAC CTGTGCGCC GGTGATGCCG GCCACGATGC
        ACAGCCGCTA TATCCGCGGT CGTTGGCGTG GACACCGCGG CCACTACGGC CGGTGCTACG
 241    GTCCGGCGTA GAGGATCGAG ATCTCGATCC CGCGAAATTA ATACGACTCA CTATAGGGGA
        CAGGCCGCAT CTCCTAGCTC TAGAGCTAGG GCGCTTTAAT TATGCTGAGT GATATCCCCT
 301    ATTGTGAGCG GATAACAATT CCCCTCTAGA AATAATTTTG TTTAACTTTA AGAAGGAGAT
        TAACACTCGC CTATTGTTAA GGGGAGATCT TTATTAAAAC AAATTGAAAT TCTTCCTCTA
 361    ATACATATGA AATACCTGCT GCCGACCGCT GCTGCTGGTC TGCTGCTCCT CGCTGCCCAG
        TATGTATACT TTATGGACGA CGGCTGGCGA CGACGACCAG ACGACGAGGA GCGACGGGTC
                                                           EcoRI
                                                           ~~~~~~~
             NcoI                   BamHI
             ~~~~~~                 ~~~~~~
 421    CCGGCGATGG CCATGGATAT CGGAATTAAT TCGGATCCGA ATTCGAGCTC GATCACAAGT
        GGCCGCTACC GGTACCTATA GCCTTAATTA AGCCTAGGCT TAAGCTCGAG CTAGTGTTCA
 481    TTGTACAAAA AAGCTGAACG AGAAACGTAA AATGATATAA ATATCAATAT ATTAAATTAG
        AACATGTTTT TTCGACTTGC TCTTTGCATT TTACTATATT TATAGTTATA TAATTTAATC
 541    ATTTTGCATA AAAAACAGAC TACATAACAC TGTAAAACAC AACATATCCA GTCACTATGG
        TAAAACGTAT TTTTTGTCTG ATGTATTATG ACATTTTGTG TTGTATAGGT CAGTGATACC
 601    CGGCCGCCAC GTTAAGGGAT TTTGGTCATG ATCAGCACGT GTTGACAATT AATCATCGGC
        GCCGGCGGTG CAATTCCCTA AAACCAGTAC TAGTCGTGCA CAACTGTTAA TTAGTAGCCG
                                                              NcoI
                                                              ~~~~~~~
 661    ATAGTATATC GGCATAGTAT AATACGACAA GGTGAGGAAC TAAACCATGG CCAAGTTGAC
        TATCATATAG CCGTATCATA TTATGCTGTT CCACTCCTTG ATTTGGTACC GGTTCAACTG
 721    CAGTGCCGTT CCGGTGCTCA CCGCGCGCGA CGTCGCCGGA GCGGTCGAGT TCTGGACCGA
        GTCACGGCAA GGCCACGAGT GGCGCGCGCT GCAGCGGCCT CGCCAGCTCA AGACCTGGCT
             XmaI
             ~~~~~~~
             SmaI
             ~~~~~~~
 781    CCGGCTCGGG TTCTCCCGGG ACTTCGTGGA GGACGACTTC GCCGGTGTGG TCCGGGACGA
        GGCCGAGCCC AAGAGGGCCC TGAAGCACCT CCTGCTGAAG CGGCCACACC AGGCCCTGCT
 841    CGTGACCCTG TTCATCAGCG CGGTCCAGGA CCAGGTGGTG CCGGACAACA CCCTGGCCTG
        GCACTGGGAC AAGTAGTCGC GCCAGGTCCT GGTCCACCAC GGCCTGTTGT GGGACCGGAC
 901    GGTGTGGGTG CGCGGCCTGG ACGAGCTGTA CGCCGAGTGG TCGGAGGTCG TGTCCACGAA
        CCACACCCAC GCGCCGGACC TGCTCGACAT GCGGCTCACC AGCCTCCAGC ACAGGTGCTT
 961    CTTCCGGGAC GCCTCCGGGC CGGCCATGAC CGAGATCGGC GAGCAGCCGT GGGGGCGGGA
        GAAGGCCCTG CGGAGGCCCG GCCGGTACTG GCTCTAGCCG CTCGTCGGCA CCCCCGCCCT
1021    GTTCGCCCTG CGCGACCCGG CCGGCAACTG CGTGCACTTC GTGGCCGAGG AGCAGGACTG
        CAAGCGGGAC GCGCTGGGCC GGCCGTTGAC GCACGTGAAG CACCGGCTCC TCGTCCTGAC
1081    ATCGATGATGA TATTATTTTA TCTTGTGCAA TGTAACATCA GAGATTTTGA GACACGGGCC
        TAGTACTACT ATATAAAAT AGAACACGTT ACATTGTAGT CTCTAAAACT CTGTGCCCGG
1141    AGAGCTGCCA GGAAACAGCT ATGACCATGT AATACGACTC ACTATAGGGG ATATCAGCTG
        TCTCGACGGT CCTTTGTCGA TACTGGTACA TTATGCTGAG TGATATCCCC TATAGTCGAC
1201    GATGGCAAAT AATGATTTTA TTTTGACTGA TAGTGACCTG TTCGTTGCAA CACCGGTGCT
        CTACCGTTTA TTACTAAAAT AAAACTGACT ATCACTGGAC AAGCAACGTT GTGGCCACGA
1261    AGCGTATACC CGAAGTATGT CAAAAAGAGG TGTGCTATGA AGCAGCGTAT TACAGTGACA
        TCGCATATGG GCTTCATACA GTTTTTCTCC ACACGATACT TCGTCGCATA ATGTCACTGT
1321    GTTGACAGCG ACAGCTATCA GTTGCTCAAG GCATATATGA TGTCAATATC TCCGGTCTGG
        CAACTGTCGC TGTCGATAGT CAACGAGTTC CGTATATACT ACAGTTATAG AGGCCAGACC
1381    TAAGCACAAC CATGCAGAAT GAAGCCCGTC GTCTGCGTGC CGAACGCTGG AAAGCGGAAA
        ATTCGTGTTG GTACGTCTTA CTTCGGGCAG CAGACGCACG GCTTGCGACC TTTCGCCTTT
1441    ATCAGGAAGG GATGGCTGAG GTCGCCCGGT TTATTGAAAT GAACGGCTCT TTTGCTGACG
        TAGTCCTTCC CTACCGACTC CAGCGGGCCA AATAACTTTA CTTGCCGAGA AAACGACTGC
1501    AGAACAGGGA CTGGTGAAAT GCAGTTTAAG GTTACACCTA TAAAAGAGA GAGCCGTTAT
        TCTTGTCCCT GACCACTTTA CGTCAAATTC CAAATGTGGA TATTTTCTCT CTCGGCAATA
                                                              XmaI
                                                              ~~~~~~~
                                                              SmaI
                                                              ~~~~~~~
1561    CGTCTGTTTG TGGATGTACA GAGTGATATT ATTGACACGC CCGGGCGACG GATGGTGATC
        GCAGACAAAC ACCTACATGT CTCACTATAA TAACTGTGCG GGCCCGCTGC CTACCACTAG
1621    CCCCTGGCCA GTGCACGTCT GCTGTCAGAT AAAGTCTCCC GTGAACTTTA CCCGGTGGTG
        GGGGACCGGT CACGTGCAGA CGACAGTCTA TTTCAGAGGG CACTTGAAAT GGGCCACCAC
1681    CATATCGGGG ATGAAAGCTG GCGCATGATG ACCACCGATA TGGCCAGTGT GCCGGTCTCC
```

Fig. 46₁

```
      GTATAGCCCC TACTTTCGAC CGCGTACTAC TGGTGGCTAT ACCGGTCACA CGGCCAGAGG
 1741 GTTATCGGGG AAGAAGTGGC TGATCTCAGC CGCCGCGAAA ATGACATCAA AAACGCCATT
      CAATAGCCCC TTCTTCACCG ACTAGAGTCG GCGGCGCTTT TACTGTAGTT TTTGCGGTAA
                                                           PstI
                                                           ~~~~~~
 1801 AACCTGATGT TCTGGGGAAT ATAAATGTCA GGCTCCCTTA TACACAGCCA GTCTGCAGGT
      TTGGACTACA AGACCCCTTA TATTTACAGT CCGAGGGAAT ATGTGTCGGT CAGACGTCCA
 1861 CGACCATAGT GACTGGATAT GTTGTGTTTT ACAGTATTAT GTAGTCTGTT TTTTATGCAA
      GCTGGTATCA CTGACCTATA CAACACAAAA TGTCATAATA CATCAGACAA AAAATACGTT
 1921 AATCTAATTT AATATATTGA TATTTATATC ATTTTACGTT TCTCGTTCAG CTTTCTTGTA
      TTAGATTAAA TTATATAACT ATAAATATAG TAAAATGCAA AGAGCAAGTC GAAAGAACAT
                                                          HindIII
                                                          ~~~~~~~
 1981 CAAAGTGGTG ATAATTAATT AAGATCAGAT CCGGCTGCTA AGCTTGCGGC CGCATAATGC
      GTTTCACCAC TATTAATTAA TTCTAGTCTA GGCCGACGAT TCGAACGCCG GCGTATTACG
 2041 TTAAGTCGAA CAGAAATAA CACGGCCGCA TAATCGAAAT TAATACGACT
      AATTCAGCTT GTCTTTCATT AGCATAACAT GTGCCGGCGT ATTAGCTTTA ATTATGCTGA
 2101 CACTATAGGG GAATTGTGAG CGGATAACAA TTCCCCATCT TAGTATATTA GTTAAGTATA
      GTGATATCCC CTTAACACTC GCCTATTGTT AAGGGGTAGA ATCATATAAT CAATTCATAT
 2161 AGAAGGAGAT ATACATATGG CAGATCTCAA TTGGATATCG GCCGGCCACG CGATCGCTGA
      TCTTCCTCTA TATGTATACC GTCTAGAGTT AACCTATAGC CGGCCGGTGC GCTAGCGACT
 2221 CGTCGGTACC CTCGAGTCTG GTAAAGAAAC CGCTGCTGCG AAATTTGAAC GCCAGCACAT
      GCAGCCATGG GAGCTCAGAC CATTTCTTTG GCGACGACGC TTTAAACTTG CGGTCGTGTA
 2281 GGACTCGTCT ACTAGCGCAG CTTAATTAAC CTAGGCTGCT GCCACCGCTG AGCAATAACT
      CCTGAGCAGA TGATCGCGTC GAATTAATTG GATCCGACGA CGGTGGCGAC TCGTTATTGA
 2341 AGCATAACCC CTTGGGGCCT CTAAACGGGT CTTGAGGGGT TTTTTGCTGA AACCTCAGGC
      TCGTATTGGG GAACCCCGGA GATTTGCCCA GAACTCCCCA AAAAACGACT TTGGAGTCCG
 2401 ATTTGAGAAG CACACGGTCA CACTGCTTCC GGTAGTCAAT AAACCGGTAA ACCAGCAATA
      TAAACTCTTC GTGTGCCAGT GTGACGAAGG CCATCAGTTA TTTGGCCATT TGGTCGTTAT
 2461 GACATAAGCG GCTATTAAC GACCCTGCCC TGAACCGACG ACAAGCTGAC GACCGGGTCT
      CTGTATTCGC CGATAAATTG CTGGGACGGG ACTTGGCTGC TGTTCGACTG CTGGCCCAGA
 2521 CCGCAAGTGG CACTTTTCGG GGAAATGTGC GCGGAACCCC TATTTGTTTA TTTTTCTAAA
      GGCGTTCACC GTGAAAAGCC CCTTTACACG CGCCTTGGGG ATAAACAAAT AAAAAGATTT
 2581 TACATTCAAA TATGTATCCG CTCATGAATT AATTCTTAGA AAAACTCATC GAGCATCAAA
      ATGTAAGTTT ATACATAGGC GAGTACTTAA TTAAGAATCT TTTTGAGTAG CTCGTAGTTT
 2641 TGAAACTGCA ATTTATTCAT ATCAGGATTA TCAATACCAT ATTTTTGAAA AAGCCGTTTC
      ACTTTGACGT TAAATAAGTA TAGTCCTAAT AGTTATGGTA TAAAACTTT TTCGGCAAAG
 2701 TGTAATGAAG GAGAAAACTC ACCGAGGCAG TTCCATAGGA TGGCAAGATC CTGGTATCGG
      ACATTACTTC CTCTTTTGAG TGGCTCCGTC AAGGTATCCT ACCGTTCTAG GACCATAGCC
 2761 TCTGCGATTC CGACTCGTCC AACATCAATA CAACCTATTA ATTTCCCCTC GTCAAAAATA
      AGACGCTAAG GCTGAGCAGG TTGTAGTTAT GTTGGATAAT TAAAGGGGAG CAGTTTTTAT
 2821 AGGTTATCAA GTGAGAAATC ACCATGAGTG ACGACTGAAT CCGGTGAGAA TGGCAAAAGT
      TCCAATAGTT CACTCTTTAG TGGTACTCAC TGCTGACTTA GGCCACTCTT ACCGTTTTCA
 2881 TTATGCATTT CTTTCCAGAC TTGTTCAACA GGCCAGCCAT TACGCTCGTC ATCAAAATCA
      AATACGTAAA GAAAGGTCTG AACAAGTTGT CCGGTCGGTA ATGCGAGCAG TAGTTTTAGT
 2941 CTCGCATCAA CCAAACCGTT ATTCATTCGT GATTGCGCCT GAGCGAGACG AAATACGCGG
      GAGCGTAGTT GGTTTGGCAA TAAGTAAGCA CTAACGCGGA CTCGCTCTGC TTTATGCGCC
 3001 TCGCTGTTAA AAGGACAATT ACAAACAGGA ATCGAATGCA ACCGGCGCAG GAACACTGCC
      AGCGACAATT TTCCTGTTAA TGTTTGTCCT TAGCTTACGT TGGCCGCGTC CTTGTGACGG
                                      EcoNI
                                      ~~~~~~~~~~~
 3061 AGCGCATCAA CAATATTTTC ACCTGAATCA GGATATTCTT CTAATACCTG GAATGCTGTT
      TCGCGTAGTT GTTATAAAAG TGGACTTAGT CCTATAAGAA GATTATGGAC CTTACGACAA
      XmaI
      ~~~~~~
      SmaI
      ~~~~~~
 3121 TTCCCGGGGA TCGCAGTGGT GAGTAACCAT GCATCATCAG GAGTACGGAT AAAATGCTTG
      AAGGGCCCCT AGCGTCACCA CTCATTGGTA CGTAGTAGTC CTCATGCCTA TTTTACGAAC
 3181 ATGGTCGGAA GAGGCATAAA TTCCGTCAGC CAGTTTAGTC TGACCATCTC ATCTGTAACA
      TACCAGCCTT CTCCGTATTT AAGGCAGTCG GTCAAATCAG ACTGGTAGAG TAGACATTGT 3241 TCATTGGCAA CGCTACCTTT GCCATGTTTC AGAAACAACT CTGGCGCATC GGGCTTCCCA
      AGTAACCGTT GCGATGGAAA CGGTACAAAG TCTTTGTTGA GACCGCGTAG CCCGAAGGGT
      ClaI
      ~~~~~~
 3301 TACAATCGAT AGATTGTCGC ACCTGATTGC CGACATTAT CGCGAGCCCA TTTATACCCA
      ATGTTAGCTA TCTAACAGCG TGGACTAACG GCTGTAATA GCGCTCGGGT AAATATGGGT
 3361 TATAAATCAG CATCCATGTT GGAATTTAAT CGCGGCCTAG AGCAAGACGT TTCCCGTTGA
      ATATTTAGTC GTAGGTACAA CCTTAAATTA GCGCCGGATC TCGTTCTGCA AAGGGCAACT
 3421 ATATGGCTCA TACTCTTCCT TTTTCAATAT TATTGAAGCA TTTATCAGGG TTATTGTCTC
      TATACCGAGT ATGAGAAGGA AAAAGTTATA ATAACTTCGT AAATAGTCCC AATAACAGAG
 3481 ATGAGCGGAT ACATATTTGA ATGTATTTAG AAAAATAAAC AAATAGGCAT GCAGCGCTCT
```

Fig. 46$_2$

```
        TACTCGCCTA TGTATAAACT TACATAAATC TTTTTATTTG TTTATCCGTA CGTCGCGAGA
3541    TCCGCTTCCT CGCTCACTGA CTCGCTACGC TCGGTCGTTC GACTGCGGCG AGCGGTGTCA
        AGGCGAAGGA GCGAGTGACT GAGCGATGCG AGCCAGCAAG CTGACGCCGC TCGCCACAGT
3601    GCTCACTCAA AAGCGGTAAT ACGGTTATCC ACAGAATCAG GGGATAAAGC CGGAAAGAAC
        CGAGTGAGTT TTCGCCATTA TGCCAATAGG TGTCTTAGTC CCCTATTTCG GCCTTTCTTG
3661    ATGTGAGCAA AAAGCAAAGC ACCGGAAGAA GCCAACGCCG CAGGCGTTTT TCCATAGGCT
        TACACTCGTT TTTCGTTTCG TGGCCTTCTT CGGTTGCGGC GTCCGCAAAA AGGTATCCGA
3721    CCGCCCCCCT GACGAGCATC ACAAAAATCG ACGCTCAAGC CAGAGGTGGC GAAACCCGAC
        GGCGGGGGGA CTGCTCGTAG TGTTTTTAGC TGCGAGTTCG GTCTCCACCG CTTTGGGCTG
3781    AGGACTATAA AGATACCAGG CGTTTCCCCC TGGAAGCTCC CTCGTGCGCT CTCCTGTTCC
        TCCTGATATT TCTATGGTCC GCAAAGGGGG ACCTTCGAGG GAGCACGCGA GAGGACAAGG
3841    GACCCTGCCG CTTACCGGAT ACCTGTCCGC CTTTCTCCCT TCGGGAAGCG TGGCGCTTTC
        CTGGGACGGC GAATGGCCTA TGGACAGGCG GAAAGAGGGA AGCCCTTCGC ACCGCGAAAG
3901    TCATAGCTCA CGCTGTTGGT ATCTCAGTTC GGTGTAGGTC GTTCGCTCCA AGCTGGGCTG
        AGTATCGAGT GCGACAACCA TAGAGTCAAG CCACATCCAG CAAGCGAGGT TCGACCCGAC
3961    TGTGCACGAA CCCCCCGTTC AGCCCGACCG CTGCGCCTTA TCCGGTAACT ATCGTCTTGA
        ACACGTGCTT GGGGGGCAAG TCGGGCTGGC GACGCGGAAT AGGCCATTGA TAGCAGAACT
4021    GTCCAACCCG GTAAGACACG ACTTATCGCC ACTGGCAGCA GCCATTGGTA ACTGATTTAG
        CAGGTTGGGC CATTCTGTGC TGAATAGCGG TGACCGTCGT CGGTAACCAT TGACTAAATC
4081    AGGACTTTGT CTTGAAGTTA TGCACCTGTT AAGGCTAAAC TGAAAGAACA GATTTTGGTG
        TCCTGAAACA GAACTTCAAT ACGTGGACAA TTCCGATTTG ACTTTCTTGT CTAAAACCAC
4141    AGTGCGGTCC TCCAACCCAC TTACCTTGGT TCAAAGAGTT GGTAGCTCAG CGAACCTTGA
        TCACGCCAGG AGGTTGGGTG AATGGAACCA AGTTTCTCAA CCATCGAGTC GCTTGGAACT
4201    GAAAACCACC GTTGGTAGCG GTGGTTTTTC TTTATTTATG AGATGATGAA TCAATCGGTC
        CTTTTGGTGG CAACCATCGC CACCAAAAAG AAATAAATAC TCTACTACTT AGTTAGCCAG
4261    TATCAAGTCA ACGAACAGCT ATTCCGTTAC TCTAGATTTC AGTGCAATTT ATCTCTTCAA
        ATAGTTCAGT TGCTTGTCGA TAAGGCAATG AGATCTAAAG TCACGTTAAA TAGAGAAGTT
4321    ATGTAGCACC TGAAGTCAGC CCCATACGAT ATAAGTTGTA ATTCTCATGT TAGTCATGCC
        TACATCGTGG ACTTCAGTCG GGGTATGCTA TATTCAACAT TAAGAGTACA ATCAGTACGG
4381    CCGCGCCCAC CGGAAGGAGC TGACTGGGTT GAAGGCTCTC AAGGGCATCG GTCGAGATCC
        GGCGCGGGTG GCCTTCCTCG ACTGACCCAA CTTCCGAGAG TTCCCGTAGC CAGCTCTAGG
4441    CGGTGCCTAA TGAGTGAGCT AACTTACATT AATTGCGTTG CGCTCACTGC CCGCTTTCCA
        GCCACGGATT ACTCACTCGA TTGAATGTAA TTAACGCAAC GCGAGTGACG GGCGAAAGGT
4501    GTCGGGAAAC CTGTCGTGCC AGCTGCATTA ATGAATCGGC CAACGCGCGG GGAGAGGCGG
        CAGCCCTTTG GACAGCACGG TCGACGTAAT TACTTAGCCG GTTGCGCGCC CCTCTCCGCC
4561    TTTGCGTATT GGGCGCCAGG GTGGTTTTTC TTTTCACCAG TGAGACGGGC AACAGCTGAT
        AAACGCATAA CCCGCGGTCC CACCAAAAAG AAAAGTGGTC ACTCTGCCCG TTGTCGACTA
4621    TGCCCTTCAC CGCCTGGCCC TGAGAGAGTT GCAGCAAGCG GTCCACGCTG GTTTGCCCCA
        ACGGGAAGTG GCGGACCGGG ACTCTCTCAA CGTCGTTCGC CAGGTGCGAC CAAACGGGGT
4681    GCAGGCGAAA ATCCTGTTTG ATGGTGGTTA ACGGCGGGAT ATAACATGAG CTGTCTTCGG
        CGTCCGCTTT TAGGACAAAC TACCACCAAT TGCCGCCCTA TATTGTACTC GACAGAAGCC
4741    TATCGTCGTA TCCCACTACC GAGATGTCCG CACCAACGCG CAGCCCGGAC TCGGTAATGG
        ATAGCAGCAT AGGGTGATGG CTCTACAGGC GTGGTTGCGC GTCGGGCCTG AGCCATTACC
4801    CGCGCATTGC GCCCAGCGCC ATCTGATCGT TGGCAACCAG CATCGCAGTG GGAACGATGC
        GCGCGTAACG CGGGTCGCGG TAGACTAGCA ACCGTTGGTC GTAGCGTCAC CCTTGCTACG
4861    CCTCATTCAG CATTTGCATG GTTTGTTGAA AACCGGACAT GGCACTCCAG TCGCCTTCCC
        GGAGTAAGTC GTAAACGTAC CAAACAACTT TTGGCCTGTA CCGTGAGGTC AGCGGAAGGG
4921    GTTCCGCTAT CGGCTGAATT TGATTGCGAG TGAGATATTT ATGCCAGCCA GCCAGACGCA
        CAAGGCGATA GCCGACTTAA ACTAACGCTC ACTCTATAAA TACGGTCGGT CGGTCTGCGT
4981    GACGCGCCGA GACAGAACTT AATGGGCCCG CTAACAGCGC GATTTGCTGG TGACCCAATG
        CTGCGCGGCT CTGTCTTGAA TTACCCGGGC GATTGTCGCG CTAAACGACC ACTGGGTTAC
5041    CGACCAGATG CTCCACGCCC AGTCGCGTAC CGTCTTCATG GGAGAAAATA ATACTGTTGA
        GCTGGTCTAC GAGGTGCGGG TCAGCGCATG GCAGAAGTAC CCTCTTTTAT TATGACAACT
5101    TGGGTGTCTG GTCAGAGACA TCAAGAAATA ACGCCGGAAC ATTAGTGCAG GCAGCTTCCA
        ACCCACAGAC CAGTCTCTGT AGTTCTTTAT TGCGGCCTTG TAATCACGTC CGTCGAAGGT
5161    CAGCAATGGC ATCCTGGTCA TCCAGCGGAT AGTTAATGAT CAGCCCACTG ACGCGTTGCG
        GTCGTTACCG TAGGACCAGT AGGTCGCCTA TCAATTACTA GTCGGGTGAC TGCGCAACGC
5221    CGAGAAGATT GTGCACCGCC GCTTTACAGG CTTCGACGCC GCTTCGTTCT ACCATCGACA
        GCTCTTCTAA CACGTGGCGG CGAAATGTCC GAAGCTGCGG CGAAGCAAGA TGGTAGCTGT
5281    CCACCACGCT GGCACCCAGT TGATCGGCGC GAGATTTAAT CGCCGCGACA ATTTGCGACG
        GGTGGTGCGA CCGTGGGTCA ACTAGCCGCG CTCTAAATTA GCGGCGCTGT TAAACGCTGC
5341    GCGCGTGCAG GGCCAGACTG GAGGTGGCAA CGCCAATCAG CAACGACTGT TTGCCCGCCA
        CGCGCACGTC CCGGTCTGAC CTCCACCGTT GCGGTTAGTC GTTGCTGACA AACGGGCGGT
5401    GTTGTTGTGC CACGCGGTTG GGAATGTAAT TCAGCTCCGC CATCGCCGCT TCCACTTTTT
        CAACACACG GTGCGCCAAC CCTTACATTA AGTCGAGGCG GTAGCGGCGA AGGTGAAAAA
5461    CCCGCGTTTT CGCAGAAACG TGGCTGGCCT GGTTCACCAC GCGGGAAACG GTCTGATAAG
        GGGCGCAAAA GCGTCTTTGC ACCGACCGGA CCAAGTGGTG CGCCCTTTGC CAGACTATTC
5521    AGACACCGGC ATACTCTGCG ACATCGTATA ACGTTACTGG TTTCACATTC ACCACCCTGA
        TCTGTGGCCG TATGAGACGC TGTAGCATAT TGCAATGACC AAAGTGTAAG TGGTGGGACT
5581    ATTGACTCTC TTCCGGGCGC TATCATGCCA TACCGCGAAA GGTTTTGCGC CATTCGATGG
        TAACTGAGAG AAGGCCCGCG ATAGTACGGT ATGCGCTTT CCAAAACGCG GTAAGCTACC
5641    TGTCCGGGAT CTCGACGCTC TCCCTTATGC GACT
        ACAGGCCCTA GAGCTGCGAG AGGGAATACG CTGA
```

Fig. 46₃

| Fig. 48₁ |
|---|
| Fig. 48₂ |
| Fig. 48₃ |

Fig. 48

```
   1 CCTGCATTAG GAAGCAGCCC AGTAGTAGGT TGAGGCCGTT GAGCACCGCC GCCGCAAGGA
     GGACGTAATC CTTCGTCGGG TCATCATCCA ACTCGTGGCG CGGCGTTCCT
  61 ATGGTGCATG CAAGGAGATG GCGCCCAACA GTCCCCCGGC CACGGGGCCT GCCACCATAC
     TACCACGTAC GTTCCTCTAC CGCGGGTTGT CAGGGGGCCG GTGCCCCGGA CGGTGGTATG
 121 CCACGCCGAA ACAAGCGCTC ATGAGCCCGA AGTGGCGAGC CGATCTTCC CCATCGGTGA
     GGTGCGGCTT TGTTCGCGAG TACTCGGGCT TCACCGCTCG GCTAGAAGG GGTAGCCACT
 181 TGTCGGCGAT ATAGGCGCCA GCAACCGCAC CTGTGGCGCC GGTGATGCCG GCCACGATGC
     ACAGCCGCTA TATCCGCGGT CGTTGGCGTG GACACCGCGG CCACTACGGC CGGTGCTACG
 241 GTCCGGCGTA GAGGATCGAG ATCTCGATCC CGCGAAATTA ATACGACTCA CTATAGGGGA
     CAGGCCGCAT CTCCTAGCTC TAGAGCTAGG GCGCTTTAAT TATGCTGAGT GATATCCCCT
 301 ATTGTGAGCG GATAACAATT CCCCTCTAGA AATAATTTTG TTTAACTTTA AGAAGGAGAT
     TAACACTCGC CTATTGTTAA GGGGAGATCT TTATTAAAAC AAATTGAAAT TCTTCCTCTA
 361 ATACATATGA ATACCTGCT GCCGACCGCT GCTGCTGGTC TGCTGCTCCT CGCTGCCCAG
     TATGTATACT TTATGGACGA CGGCTGGCGA CGACGACCAG ACGACGAGGA GCGACGGGTC
                                                EcoRI
                                                ~~~~~~
                NcoI                   BamHI          SacI
                ~~~~~~                 ~~~~~~         ~~~~~~
 421 CCGGCGATGG CCATGGATAT CGGAATTAAT TCGGATCCGA ATTCGAGCTC GATCACAAGT
     GGCCGCTACC GGTACCTATA GCCTTAATTA AGCCTAGGCT TAAGCTCGAG CTAGTGTTCA

481 TTGTACAAAA AAGCTGAACG AGAAACGTAA AATGATATAA ATATCAATAT ATTAAATTAG
     AACATGTTTT TTCGACTTGC TCTTTGCATT TTACTATATT TATAGTTATA TAATTTAATC
 541 ATTTTGCATA AAAACAGAC TACATAATAC TGTAAAACAC AACATATCCA GTCACTATGG
     TAAAACGTAT TTTTTGTCTG ATGTATTATG ACATTTTGTG TTGTATAGGT CAGTGATACC
 601 CGGCCGCCAC GTTAAGGGAT TTTGGTCATG ATCAGCACGT GTTGACAATT AATCATCGGC
     GCCGGCGGTG CAATTCCCTA AAACCAGTAC TAGTCGTGCA CAACTGTTAA TTAGTAGCCG
                                                             NcoI
                                                             ~~~~~~
 661 ATAGTATATC GGCATAGTAT AATACGACAA GGTGAGGAAC TAAACCATGG CCAAGTTGAC
     TATCATATAG CCGTATCATA TTATGCTGTT CCACTCCTTG ATTTGGTACC GGTTCAACTG
 721 CAGTGCCGTT CCGGTGCTCA CCGCGCGCGA CGTCGCCGGA GCGGTCGAGT TCTGGACCGA
     GTCACGGCAA GGCCACGAGT GGCGCGCGCT GCAGCGGCCT CGCCAGCTCA AGACCTGGCT
 781 CCGGCTCGGG TTCTCCCGGG ACTTCGTGGA GGACGACTTC GCCGGTGTGG TCCGGGACGA
     GGCCGAGCCC AAGAGGGCCC TGAAGCACCT CCTGCTGAAG CGGCCACACC AGGCCCTGCT
 841 CGTGACCCTG TTCATCAGCG CGGTCCAGGA CCAGGTGGTG CCGGACAACA CCCTGGCCTG
     GCACTGGGAC AAGTAGTCGC GCCAGGTCCT GGTCCACCAC GGCCTGTTGT GGGACCGGAC
 901 GGTGTGGGTG CGCGGCCTGG ACGAGCTGTA CGCCGAGTGG TCGGAGGTCG TGTCCACGAA
     CCACACCCAC GCGCCGGACC TGCTCGACAT GCGGCTCACC AGCCTCCAGC ACAGGTGCTT
 961 CTTCCGGGAC GCCTCCGGGC CGGCCATGAC CGAGATCGGC GAGCAGCCGT GGGGGCGGGA
     GAAGGCCCTG CGGAGGCCCG GCCGGTACTG GCTCTAGCCG CTCGTCGGCA CCCCCGCCCT
1021 GTTCGCCCTG CGCGACCCGG CCGGCAACTG CGTTGACTTC GTGGCCGAGG AGCAGGACTG
     CAAGCGGGAC GCGCTGGGCC GGCCGTTGAC GCACGTGAAG CACCGGCTCC TCGTCCTGAC
1081 ATCATGATGA TATTATTTTA TCTTGTGCAA TGTAACATCA GAGATTTTGA GACACGGGCC
     TAGTACTACT ATAATAAAAT AGAACACGTT ACATTGTAGT CTCTAAAACT CTGTGCCCGG
1141 AGAGCTGCCA GGAAACAGCT ATGACCATGT AATACGACTC ACTATAGGGG ATATCAGCTG
     TCTCGACGGT CCTTTGTCGA TACTGGTACA TTATGCTGAG TGATATCCCC TATAGTCGAC
1201 GATGGCAAAT AATGATTTTA TTTTGACTGA TAGTGACCTG TTCGTTGCAA CACCGGTGCT
     CTACCGTTTA TTACTAAAAT AAAACTGACT ATCACTGGAC AAGCAACGTT GTGGCCACGA
1261 AGCGTATACC CGAAGTATGT CAAAAAGAGG TGTGCTATGA AGCAGCGTAT TACAGTGACA
     TCGCATATGG GCTTCATACA GTTTTTCTCC ACACGATACT TCGTCGCATA ATGTCACTGT
1321 GTTGACAGCG CACAGCTATCA GTTGCTCAAG GCATATATGA TGTCAATATC TCCGGTCTGG
     CAACTGTCGC GTGTCGATAGT CAACGAGTTC CGTATATACT ACAGTTATAG AGGCCAGACC
1381 TAAGCACAAC CATGCAGAAT GAAGCCCGTC GTCTGCGTGC CGAACGCTGG AAAGCGGAAA
     ATTCGTGTTG GTACGTCTTA CTTCGGGCAG CAGACGCACG GCTTGCGACC TTTCGCCTTT
1441 ATCAGGAAGG GATGGCTGAG GTCGCCCGGT TTATTGAAAT GAACGGCTCT TTTGCTGACG
     TAGTCCTTCC CTACCGACTC CAGCGGGCCA AATAACTTTA CTTGCCGAGA AAACGACTGC
1501 AGAACAGGGA CTGGTGAAAT GCAGTTTAAG GTTTACACCT ATAAAAGAGA GAGCCGTTAT
     TCTTGTCCCT GACCACTTTA CGTCAAATTC CAAATGTGGA TATTTTCTCT CTCGGCAATA
1561 CGTCTGTTTG TGGATGTACA GAGTGATATT ATTGACACGG CCGGGCCAG GATGGTGATC
     GCAGACAAAC ACCTACATGT CTCACTATAA TAACTGTGCG GGCCCGGCTGC CTACCACTAG
1621 CCCCTGGCCA GTGCACGTCT GCTGTCAGAT AAAGTCTCCC GTGAACTTTA CCCGGTGGTG
     GGGGACCGGT CACGTGCAGA CGACAGTCTA TTTCAGAGGG CACTTGAAAT GGGCCACCAC
1681 CATATCGGGG ATGAAAGCTG GCGCATGATG ACCACCGATA TGGCCAGTGT GCCGGTCTCC
     GTATAGCCCC TACTTTCGAC CGCGTACTAC TGGTGGCTAT ACCGGTCACA CGGCCAGAGG
1741 GTTATCGGGG AAGAAGTGGC TGATCTCAGC CGCCGCGAAA ATGACATCAA AAACGCCATT
     CAATAGCCCC TTCTTCACCG ACTAGAGTCG GCGGCGCTTT TACTGTAGTT TTTGCGGTAA
                                                              PstI
                                                              ~~~~~~
1801 AACCTGATGT TCTGGGGAAT ATAAATGTCA GGCTCCCTTA TACACAGCCA GTCTGCAGGT
     TTGGACTACA AGACCCCTTA TATTTACAGT CCGAGGGAAT ATGTGTCGGT CAGACGTCCA
```

Fig. 48₁

1861 CGACCATAGT GACTGGATAT GTTGTGTTTT ACAGTATTAT GTAGTCTGTT TTTTATGCAA
     GCTGGTATCA CTGACCTATA CAACACAAAA TGTCATAATA CATCAGACAA AAAATACGTT
1921 AATCTAATTT AATATATTGA TATTTATATC ATTTTACGTT TCTCGTTCAG CTTTCTTGTA
     TTAGATTAAA TTATATAACT ATAAATATAG TAAAATGCAA AGAGCAAGTC GAAAGAACAT
                                                           HindIII
                                                           ~~~~~~~
1981 CAAAGTGGTG ATAATTAATT AAGATCAGAT CCGGCTGCTA AGCTTGCGGC CGCATAATGC
     GTTTCACCAC TATTAATTAA TTCTAGTCTA GGCCGACGAT TCGAACGCCG GCGTATTACG
2041 TTAAGTCGAA CAGAAAGTAA TCGTATTGTA CACGGCCGCA TAATCGAAAT TAATACGACT
     AATTCAGCTT GTCTTTCATT AGCATAACAT GTGCCGGCGT ATTAGCTTTA ATTATGCTGA
2101 CACTATAGGG GAATTGTGAG CGGATAACAA TTCCCCATCT TAGTATATTA GTTAAGTATA
     GTGATATCCC CTTAACACTC GCCTATTGTT AAGGGGTAGA ATCATATAAT CAATTCATAT
2161 AGAAGGAGAT ATACATATGG CAGATCTCAA TTGGATATCG GCCGGCCACG CGATCGCTGA
     TCTTCCTCTA TATGTATACC GTCTAGAGTT AACCTATAGC CGGCCGGTGC GCTAGCGACT
2221 CGTCGGTACC CTCGAGTCTG GTAAAGAAAC CGCTGCTGCG AAATTTGAAC GCCAGCACAT
     GCAGCCATGG GAGCTCAGAC CATTTCTTTG GCGACGACGC TTTAAACTTG CGGTCGTGTA
2281 GGACTGCTCT ACTAGCGCAG CTTAATTAAC CTAGGCTGCT GCCACCGCTG AGCAATAACT
     CCTGACGAGA TGATCGCGTC GAATTAATTG GATCCGACGA CGGTGGCGAC TCGTTATTGA
2341 AGCATAACCC CTTGGGGCCT CTAAACGGGT CTTGAGGGGT TTTTTGCTGA AACCTCAGGC
     TCGTATTGGG GAACCCCGGA GATTTGCCCA GAACTCCCCA AAAAACGACT TTGGAGTCCG
2401 ATTTGAGAAG CACACGGTCA CACTGCTTCC GGTAGTCAAT AAACCGGTAA ACCAGCAATA
     TAAACTCTTC GTGTGCCAGT GTGACGAAGG CCATCAGTTA TTTGGCCATT TGGTCGTTAT
2461 GACATAAGCG GCTATTTAAC GACCCTGCCC TGAACCGACG ACCGGGTCGA ATTTGCTTTC
     CTGTATTCGC CGATAAATTG CTGGGACGGG ACTTGGCTGC TGGCCCAGCT TAAACGAAAG
2521 GAATTTCTGC CATTCATCCG CTTATTATCA CTTATTCAGG CGTAGCACCA GGCGTTTAAG
     CTTAAAGACG GTAAGTAGGC GAATAATAGT GAATAAGTCC GCATCGTGGT CCGCAAATTC
2581 GGCACCAATA ACTGCCTTAA AAAATTACGC CCCGCCCTG CCACTCATCG CAGTACTGTT
     CCGTGGTTAT TGACGGAATT TTTTTAATGC GGGGCGGGAC GGTGAGTAGC GTCATGACAA
2641 GTAATTCATT AAGCATTCTG CCGACATGGA AGCCATCACA GACGGCATGA TGAACCTGAA
     CATTAAGTAA TTCGTAAGAC GGCTGTACCT TCGGTAGTGT CTGCCGTACT ACTTGGACTT
2701 TCGCCAGCGG CATCAGCACC TTGTCGCCTT GCGTATAATA TTTGCCCATA GTGAAAACGG
     AGCGGTCGCC GTAGTCGTGG AACAGCGGAA CGCATATTAT AAACGGGTAT CACTTTTGCC
2761 GGGCGAAGAA GTTGTCCATA TTGGCCACGT TTAAATCAAA ACTGGTGAAA CTCACCCAGG
     CCCGCTTCTT CAACAGGTAT AACCGGTGCA AATTTAGTTT TGACCACTTT GAGTGGGTCC
2821 GATTGGCTGA GACGAAAAAC ATATTCTCAA TAAACCCTTT AGGGAAATAG GCCAGGTTTT
     CTAACCGACT CTGCTTTTTG TATAAGAGTT ATTTGGGAAA TCCCTTTATC CGGTCCAAAA
2881 CACCGTAACA CGCCACATCT TGCGAATATA TGTGTAGAAA CTGCCGGAAA TCGTCGTGGT
     GTGGCATTGT GCGGTGTAGA ACGCTTATAT ACACATCTTT GACGGCCTTT AGCAGCACCA
2941 ATTCACTCCA GAGCGATGAA AACGTTTCAG TTTGCTCATG GAAAACGGTG TAACAAGGGT
     TAAGTGAGGT CTCGCTACTT TTGCAAAGTC AAACGAGTAC CTTTTGCCAC ATTGTTCCCA
3001 GAACACTATC CCATATCACC AGCTCACCGT CTTTCATTGC CATACGGAAC TCCGGATGAG
     CTTGTGATAG GGTATAGTGG TCGAGTGGCA GAAAGTAACG GTATGCCTTG AGGCCTACTC
3061 CATTCATCAG GCGGGCAAGA ATGTGAATAA AGGCCGGATA AACTTGTGC TTATTTTTCT
     GTAAGTAGTC CGCCCGTTCT TACACTTATT TCCGGCCTAT TTTGAACACG AATAAAAAGA
3121 TTACGGTCTT TAAAAAGGCC GTAATATCCA GCTGAACGGT CTGGTTATAG GTACATTGAG
     AATGCCAGAA ATTTTTCCGG CATTATAGGT CGACTTGCCA GACCAATATC CATGTAACTC
3181 CAACTGACTG AAATGCCTCA AAATGTTCTT TACGATGCCA TTGGGATATA TCAACGGTGG
     GTTGACTGAC TTTACGGAGT TTTACAAGAA ATGCTACGGT AACCCTATAT AGTTGCCACC
3241 TATATCCAGT GATTTTTTTC TCCATTTTAG CTTCCTTAGC TCCTGAAAAT CTCGATAACT
     ATATAGGTCA CTAAAAAAAG AGGTAAAATC GAAGGAATCG AGGACTTTTA GAGCTATTGA
3301 CAAAAAATAC GCCCGGTAGT GATCTTATTT CATTATGGTG AAAGTTGGAA CCTCTTACGT
     GTTTTTTATG CGGGCCATCA CTAGAATAAA GTAATACCAC TTTCAACCTT GGAGAATGCA
3361 GCCGATCAAC GTCTCATTTT CGCCAAAAGT TGGCCCAGGG CTTCCCGGTA TCAACAGGGA
     CGGCTAGTTG CAGAGTAAAA GCGGTTTTCA ACCGGGTCCC GAAGGGCCAT AGTTGTCCCT
3421 CACCAGGATT TATTTATTCT GCGAAGTGAT CTTCCGTCAC AGGTATTTAT TCGGCGCAAA
     GTGGTCCTAA ATAATAAGA CGCTTCACTA GAAGGCAGTG TCCATAAATA AGCCGCGTTT
3481 GTGCGTCGGG TGATGCTGCC AACTTACTGA TTTAGTGTAT GATGGTGTTT TTGAGGTGCT
     CACGCAGCCC ACTACGACGG TTGAATGACT AAATCACATA CTACCACAAA AACTCCACGA
3541 CCAGTGGCTT CTGTTTCTAT CAGCTGTCCC TCCTGTTCAG CTACTGACGG GGTGGTGCGT
     GGTCACCGAA GACAAAGATA GTCGACAGGG AGGACAAGTC GATGACTGCC CCACCACGCA
3601 AACGGCAAAA GCACCGCCGG ACATCAGCGC TAGCGGAGTG TATACTGGCT TACTATGTTG
     TTGCCGTTTT CGTGGCGGCC TGTAGTCGCG ATCGCCTCAC ATATGACCGA ATGATACAAC
3661 GCACTGATGA GGGTGTCAGT GAAGTGCTTC ATGTGGCAGG AGAAAAAAGG CTGCACCGGT
     CGTGACTACT CCCACAGTCA CTTCACGAAG TACACCGTCC TCTTTTTTCC GACGTGGCCA
3721 GCGTCAGCAG AATATGTGAT ACAGGATATA TTCCGCTTCC TCGCTCACTG ACTCGCTACG
     CGCAGTCGTC TTATACACTA TGTCCTATAT AAGGCGAAGG AGCGAGTGAC TGAGCGATGC
3781 CTCGGTCGTT CGACTGCGGC GAGCGGAAAT GGCTTACGAA CGGGGCGGAG ATTTCCTGGA
     GAGCCAGCAA GCTGACGCCG CTCGCCTTTA CCGAATGCTT GCCCCGCCTC TAAAGGACCT
3841 AGATGCCAGG AAGATACTTA ACAGGGAAGT GAGAGGGCCG CGGCAAAGCC GTTTTTCCAT

Fig. 48$_2$

```
           TCTACGGTCC TTCTATGAAT TGTCCCTTCA CTCTCCCGGC GCCGTTTCGG CAAAAAGGTA
     3901  AGGCTCCGCC CCCCTGACAA GCATCACGAA ATCTGACGCT CAAATCAGTG GTGGCGAAAC
           TCCGAGGCGG GGGGACTGTT CGTAGTGCTT TAGACTGCGA GTTTAGTCAC CACCGCTTTG
     3961  CCGACAGGAC TATAAAGATA CCAGGCGTTT CCCCTGGCGG CTCCCTCGTG CGCTCTCCTG
           GGCTGTCCTG ATATTTCTAT GGTCCGCAAA GGGGACCGCC GAGGGAGCAC GCGAGAGGAC
     4021  TTCCTGCCTT TCGGTTTACC GGTGTCATTC CGCTGTTATG GCCGCGTTTG TCTCATTCCA
           AAGGACGGAA AGCCAAATGG CCACAGTAAG GCGACAATAC CGGCGCAAAC AGAGTAAGGT
     4081  CGCCTGACAC TCAGTTCCGG GTAGGCAGTT CGCTCCAAGC TGGACTGTAT GCACGAACCC
           GCGGACTGTG AGTCAAGGCC CATCCGTCAA GCGAGGTTCG ACCTGACATA CGTGCTTGGG
     4141  CCCGTTCAGT CCGACCGCTG CGCCTTATCC GGTAACTATC GTCTTGAGTC CAACCCGGAA
           GGGCAAGTCA GGCTGGCGAC GCGGAATAGG CCATTGATAG CAGAACTCAG GTTGGGCCTT
     4201  AGACATGCAA AAGCACCACT GGCAGCAGCC ACTGGTAATT GATTTAGAGG AGTTAGTCTT
           TCTGTACGTT TTCGTGGTGA CCGTCGTCGG TGACCATTAA CTAAATCTCC TCAATCAGAA
     4261  GAAGTCATGC GCCGGTTAAG GCTAAACTGA AAGGACAAGT TTTGGTGACT GCGCTCCTCC
           CTTCAGTACG CGGCCAATTC CGATTTGACT TTCCTGTTCA AAACCACTGA CGCGAGGAGG
     4321  AAGCCAGTTA CCTCGGTTCA AAGAGTTGGT AGCTCAGAGA ACCTTCGAAA AACCGCCCTG
           TTCGGTCAAT GGAGCCAAGT TTCTCAACCA TCGAGTCTCT TGGAAGCTTT TTGGCGGGAC
     4381  CAAGGCGGTT TTTTCGTTTT CAGAGCAAGA GATTACGCGC AGACCAAAAC GATCTCAAGA
           GTTCCGCCAA AAAAGCAAAA GTCTCGTTCT CTAATGCGCG TCTGGTTTTG CTAGAGTTCT
     4441  AGATCATCTT ATTAATCAGA TAAAATATTT CTAGATTTCA GTGCAATTTA TCTCTTCAAA
           TCTAGTAGAA TAATTAGTCT ATTTTATAAA GATCTAAAGT CACGTTAAAT AGAGAAGTTT
     4501  TGTAGCACCT GAAGTCAGCC CCATACGATA TAAGTTGTAA TTCTCATGTT AGTCATGCCC
           ACATCGTGGA CTTCAGTCGG GGTATGCTAT ATTCAACATT AAGAGTACAA TCAGTACGGG
     4561  CGCGCCCACC GGAAGGAGCT GACTGGGTTG AAGGCTCTCA AGGGCATCGG TCGAGATCCC
           GCGCGGGTGG CCTTCCTCGA CTGACCCAAC TTCCGAGAGT TCCCGTAGCC AGCTCTAGGG
     4621  GGTGCCTAAT GAGTGAGCTA ACTTACATTA ATTGCGTTGC GCTCACTGCC CGCTTTCCAG
           CCACGGATTA CTCACTCGAT TGAATGTAAT TAACGCAACG CGAGTGACGG GCGAAAGGTC
     4681  TCGGGAAACC TGTCGTGCCA GCTGCATTAA TGAATCGGCC AACGCGCGGG GAGAGGCGGT
           AGCCCTTTGG ACAGCACGGT CGACGTAATT ACTTAGCCGG TTGCGCGCCC CTCTCCGCCA
     4741  TTGCGTATTG GGCGCCAGGG TGGTTTTTCT TTTCACCAGT GAGACGGGCA ACAGCTGATT
           AACGCATAAC CCGCGGTCCC ACCAAAAAGA AAAGTGGTCA CTCTGCCCGT TGTCGACTAA
     4801  GCCCTTCACC GCCTGGCCCT GAGAGAGTTG CAGCAAGCGG TCCACGCTGG TTTGCCCCAG
           CGGGAAGTGG CGGACCGGGA CTCTCTCAAC GTCGTTCGCC AGGTGCGACC AAACGGGGTC
     4861  CAGGCGAAAA TCCTGTTTGA TGGTGGTTAA CGGCGGGATA TAACATGAGC TGTCTTCGGT
           GTCCGCTTTT AGGACAAACT ACCACCAATT GCCGCCCTAT ATTGTACTCG ACAGAAGCCA
     4921  ATCGTCGTAT CCCACTACCG AGATGTCCGC ACCAACGCGC AGCCCGGACT CGGTAATGGC
           TAGCAGCATA GGGTGATGGC TCTACAGGCG TGGTTGCGCG TCGGGCCTGA GCCATTACCG
     4981  GCGCATTGCG CCCAGCGCCA TCTGATCGTT GGCAACCAGC ATCGCAGTGG GAACGATGCC
           CGCGTAACGC GGGTCGCGGT AGACTAGCAA CCGTTGGTCG TAGCGTCACC CTTGCTACGG
     5041  CTCATTCAGC ATTTGCATGG TTTGTTGAAA ACCGGACATG GCACTCCAGT CGCCTTCCCG
           GAGTAAGTCG TAAACGTACC AAACAACTTT TGGCCTGTAC CGTGAGGTCA GCGGAAGGGC
     5101  TTCCGCTATC GGCTGAATTT GATTGCAGTG GAGATATTTA TGCCAGCCAG CCAGACGCAG
           AAGGCGATAG CCGACTTAAA CTAACGCTCA CTCTATAAAT ACGGTCGGTC GGTCTGCGTC
     5161  ACGCGCCGAG ACAGAACTTA ATGGGCCCGC TAACAGCGCG ATTTGCTGGT GACCCAATGC
           TGCGCGGCTC TGTCTTGAAT TACCCGGGCG ATTGTCGCGC TAAACGACCA CTGGGTTACG
     5221  GACCAGATGC TCCACGCCCA GTCGCGTACC GTCTTCATGG GAGAAAATAA TACTGTTGAT
           CTGGTCTACG AGGTGCGGGT CAGCGCATGG CAGAAGTACC CTCTTTTATT ATGACAACTA
     5281  GGGTGTCTGG TCAGAGACAT CAAGAAATAA CGCCGGAACA TTAGTGCAGG CAGCTTCCAC
           CCCACAGACC AGTCTCTGTA GTTCTTTATT GCGGCCTTGT AATCACGTCC GTCGAAGGTG
     5341  AGCAATGGCA TCCTGGTCAT CCAGCGGATA GTTAATGATC AGCCCACTGA CGCGTTGCGC
           TCGTTACCGT AGGACCAGTA GGTCGCCTAT CAATTACTAG TCGGGTGACT GCGCAACGCG
     5401  GAGAAGATTG TGCACCGCCG CTTTACAGGC TTCGACGCCG CTTCGTTCTA CCATCGACAC
           CTCTTCTAAC ACGTGGCGGC GAAATGTCCG AAGCTGCGGC GAAGCAAGAT GGTAGCTGTG
     5461  CACCACGCTG GCACCCAGTT GATCGGCGCG AGATTTAATC GCCGCGACAA TTTGCGACGG
           GTGGTGCGAC CGTGGGTCAA CTAGCCGCGC TCTAAATTAG CGGCGCTGTT AAACGCTGCC
     5521  CGCGTGCAGG GCCAGACTGG AGGTGGCAAC GCCAATCAGC AACGACTGTT TGCCCGCCAG
           GCGCACGTCC CGGTCTGACC TCCACCGTTG CGGTTAGTCG TTGCTGACAA ACGGGCGGTC
     5581  TTGTTGTGCC ACGCGGTTGG GAATGTAATT CAGCTCCGCC ATCGCCGCTT CCACTTTTTC
           AACAACACGG TGCGCCAACC CTTACATTAA GTCGAGGCGG TAGCGGCGAA GGTGAAAAAG
     5641  CCGCGTTTTC GCAGAAACGT GGCTGGCCTG GTTCACCACG CGGGAAACGG TCTGATAAGA
           GGCGCAAAAG CGTCTTTGCA CCGACCGGAC CAAGTGGTGC GCCCTTTGCC AGACTATTCT
     5701  GACACCGGCA TACTCTGCGA CATCGTATAA CGTTACTGGT TTCACATTCA CCACCCTGAA
           CTGTGGCCGT ATGAGACGCT GTAGCATATT GCAATGACCA AAGTGTAAGT GGTGGGACTT
     5761  TTGACTCTCT TCCGGGCGCT ATCATGCCAT ACCGCGAAAG GTTTTGCGCC ATTCGATGGT
           AACTGAGAGA AGGCCCGCGA TAGTACGGTA TGGCGCTTTC CAAAACGCGG TAAGCTACCA
     5821  GTCCGGGATC TCGACGCTCT CCCTTATGCG ACT
           CAGGCCCTAG AGCTGCGAGA GGGAATACGC TGA
```

Fig. 48₃

| Fig. $50_1$ |
|---|
| Fig. $50_2$ |
| Fig. $50_3$ |
| Fig. $50_4$ |

Fig. 50

```
         EcoNI
       ~~~~~~~~~~~~
   1   CCTGCATTAG GAAGCAGCCC AGTAGTAGGT TGAGGCCGTT GAGCACCGCC GCCGCAAGGA
       GGACGTAATC CTTCGTCGGG TCATCATCCA ACTCCGGCAA CTCGTGGCGG CGGCGTTCCT
  61   ATGGTGCATG CAAGGAGATG GCGCCCAACA GTCCCCCGGC CACGGGCCT GCCACCATAC
       TACCACGTAC GTTCCTCTAC CGCGGGTTGT CAGGGGGCCG GTGCCCCGGA CGGTGGTATG
 121   CCACGCCGAA ACAAGCGCTC ATGAGCCCGA AGTGGCGAGC CCGATCTTCC CCATCGGTGA
       GGTGCGGCTT TGTTCGCGAG TACTCGGGCT TCACCGCTCG GGCTAGAAGG GGTAGCCACT
 181   TGTCGGCGAT ATAGGCGCCA GCAACCGCAC CTGTGGCGCC GGTGATGCCG GCCACGATGC
       ACAGCCGCTA TATCCGCGGT CGTTGGCGTG GACACCGCGG CCACTACGGC CGGTGCTACG
 241   GTCCGGCGTA GAGGATCGAG ATCTCGATCC CGCGAAATTA ATACGACTCA CTATAGGGGA
       CAGGCCGCAT CTCCTAGCTC TAGAGCTAGG GCGCTTTAAT TATGCTGAGT GATATCCCCT
 301   ATTGTGAGCG GATAACAATT CCCCTCTAGA AATAATTTTG TTTAACTTTA AGAAGGAGAT
       TAACACTCGC CTATTGTTAA GGGGAGATCT TTATTAAAAC AAATTGAAAT TCTTCCTCTA
 361   ATACATATGA AATACCTGCT GCCGACCGCT GCTGCTGGTC TGCTGCTCCT CGCTGCCCAG
       TATGTATACT TTATGGACGA CGGCTGGCGA CGACGACCAG ACGACGAGGA GCGACGGGTC
                                                EcoRI
                                              ~~~~~~~
            NcoI                    BamHI    SacI
           ~~~~~~                  ~~~~~~   ~~~~~~~
 421   CCGGCGATGG CCATGGATAT CGGAATTAAT TCGGATCCGA ATTCGAGCTC GATCACAAGT
       GGCCGCTACC GGTACCTATA GCCTTAATTA AGCCTAGGCT TAAGCTCGAG CTAGTGTTCA
 481   TTGTACAAAA AAGCTGAACG AGAAACGTAA AATGATATAA ATATCAATAT ATTAAATTAG
       AACATGTTTT TTCGACTTGC TCTTTGCATT TTACTATATT TATAGTTATA TAATTTAATC
 541   ATTTTGCATA AAAAACAGAC TACATAATAC TGTAAAACAC AACATATCCA GTCACTATGG
       TAAAACGTAT TTTTTGTCTG ATGTATTATG ACATTTTGTG TTGTATAGGT CAGTGATACC
 601   CGGCCGCCAC GTTAAGGGAT TTTGGTCATG ATCAGCACGT GTTGACAATT AATCATCGGC
       GCCGGCGGTG CAATTCCCTA AAACCAGTAC TAGTCGTGCA CAACTGTTAA TTAGTAGCCG
                                                                 NcoI
                                                                ~~~~~~
 661   ATAGTATATC GGCATAGTAT AATACGACAA GGTGAGGAAC TAAACCATGG CCAAGTTGAC
       TATCATATAG CCGTATCATA TTATGCTGTT CCACTCCTTG ATTTGGTACC GGTTCAACTG
 721   CAGTGCCGTT CCGGTGCTCA CCGCGCGCGA CGTCGCCGGA GCGGTCGAGT TCTGGACCGA
       GTCACGGCAA GGCCACGAGT GGCGCGCGCT GCAGCGGCCT CGCCAGCTCA AGACCTGGCT
            AvaI       AvaI
           ~~~~~~~    ~~~~~~~
 781   CCGGCTCGGG TTCTCCCGGG ACTTCGTGGA GGACGACTTC GCCGGTGTGG TCCGGGACGA
       GGCCGAGCCC AAGAGGGCCC TGAAGCACCT CCTGCTGAAG CGGCCACACC AGGCCCTGCT
 841   CGTGACCCTG TTCATCAGCG CGGTCCAGGA CCAGGTGGTG CCGGACAACA CCCTGGCCTG
       GCACTGGGAC AAGTAGTCGC GCCAGGTCCT GGTCCACCAC GGCCTGTTGT GGGACCGGAC
 901   GGTGTGGGTG CGCGGCCTGG ACGAGCTGTA CGCCGAGTGG TCGGAGGTCG TGTCCACGAA
       CCACACCCAC GCGCCGGACC TGCTCGACAT GCGGCTCACC AGCCTCCAGC ACAGGTGCTT
 961   CTTCCGGGAC GCCTCCGGGC CGGCCATGAC CGAGATCGGC GAGCAGCCGT GGGGGCGGGA
       GAAGGCCCTG CGGAGGCCCG GCCGGTACTG GCTCTAGCCG CTCGTCGGCA CCCCCGCCCT
1021   GTTCGCCCTG CGCGACCCGG CCGGCAACTG CGTCGACTTC GTGGCCGAGG AGCAGGACTG
       CAAGCGGGAC GCGCTGGGCC GGCCGTTGAC GCACGTGAAG CACCGGCTCC TCGTCCTGAC
1081   ATCATGATGA TATTATTTTA TCTTGTGCAA TGTAACATCA GAGATTTTGA GACACGGGCC
       TAGTACTACT ATAATAAAAT AGAACACGTT ACATTGTAGT CTCTAAAACT CTGTGCCCGG
1141   AGAGCTGCCA GGAAACAGCT ATGACCATGT AATACGACTC ACTATAGGGG ATATCAGCTG
       TCTCGACGGT CCTTTGTCGA TACTGGTACA TTATGCTGAG TGATATCCCC TATAGTCGAC
1201   GATGGCAAAT AATGTTTTTA TTTTGACTGA TAGTGACCTG TTCGTTGCAA CACCGGTGCT
       CTACCGTTTA TTACTAAAAT AAAACTGACT ATCACTGGAC AAGCAACGTT GTGGCCACGA
1261   AGCGTATACC CGAAGTATGT CAAAAGAGG TGTGCTATGA AGCAGCGTAT TACAGTGACA
       TCGCATATGG GCTTCATACA GTTTTTCTCC ACACGATACT TCGTCGCATA ATGTCACTGT
1321   GTTGACAGCG ACAGCTATCA GTTGCTCAAG GCATATATGA TGTCAATATC TCCGGTCTGG
       CAACTGTCGC TGTCGATAGT CAACGAGTTC CGTATATACT ACAGTTATAG AGGCCAGACC
1381   TAAGCACAAC CATGCAGAAT GAAGCCCGTC GTCTGCGTGC CGAACGCTGG AAAGCGGAAA
       ATTCGTGTTG GTACGTCTTA CTTCGGGCAG CAGACGCACG GCTTGCGACC TTTCGCCTTT
1441   ATCAGGAAGG GATGGCTGAG GTCGCCCGGT TTATTGAAAT GACGGCTCT TTTGCTGACG
       TAGTCCTTCC CTACCGACTC CAGCGGGCCA AATAACTTTA CTGCCGAGA AAACGACTGC
1501   AGAACAGGGA CTGGTGAAAT GCAGTTTAAG GTTTACACCT ATAAAAGAGA GAGCCGTTAT
       TCTTGTCCCT GACCACTTTA CGTCAAATTC CAAATGTGGA TATTTTCTCT CTCGGCAATA
                                                            AvaI
                                                           ~~~~~~~
1561   CGTCTGTTTG TGGATGTACA GAGTGATATT ATTGACACGC CGGGCGACG  GATGGTGATC
       GCAGACAAAC ACCTACATGT CTCACTATAA TAACTGTGCG GCCCGCTGC  CTACCACTAG
1621   CCCCTGGCCA GTGCACGTCT GCTGTCAGAT AAAGTCTCCC GTGAACTTTA CCCGGTGGTG
       GGGGACCGGT CACGTGCAGA CGACAGTCTA TTTCAGAGGG CACTTGAAAT GGGCCACCAC
1681   CATATCGGGA TGAAAGCTG CGCATGATG ACCACCGATA TGGCCAGTGT GCCGGTCTCC
       GTATAGCCCC TACTTTCGAC CGCGTACTAC TGGTGGCTAT ACCGGTCACA CGGCCAGAGG
1741   GTTATCGGGG AAGAAGTGGC TGATCTCAGC CGCCGCGAAA ATGACATCAA AAACGCCATT
```

Fig. 50₁

```
                CAATAGCCCC TTCTTCACCG ACTAGAGTCG GCGGCGCTTT TACTGTAGTT TTTGCGGTAA
                                                                          PstI
                                                                        ~~~~~~
      1801 AACCTGATGT TCTGGGGAAT ATAAATGTCA GGCTCCCTTA TACACAGCCA GTCTGCAGGT
           TTGGACTACA AGACCCCTTA TATTTACAGT CCGAGGGAAT ATGTGTCGGT CAGACGTCCA
      1861 CGACCATAGT GACTGGATAT GTTGTGTTTT ACAGTATTAT GTAGTCTGTT TTTTATGCAA
           GCTGGTATCA CTGACCTATA CAACACAAAA TGTCATAATA CATCAGACAA AAAATACGTT
      1921 AATCTAATTT AATATATTGA TATTTATATC ATTTTACGTT TCTCGTTCAG CTTTCTTGTA
           TTAGATTAAA TTATATAACT ATAAATATAG TAAAATGCAA AGAGCAAGTC GAAAGAACAT
                                                                HindIII
                                                                ~~~~~~~
      1981 CAAAGTGGTG ATAATTAATT AAGATCAGAT CCGGCTGCTA AGCTTGCGGC CGCATAATGC
           GTTTCACCAC TATTAATTAA TTCTAGTCTA GGCCGACGAT TCGAACGCCG GCGTATTACG
      2041 TTAAGTCGAA CAGAAAGTAA TCGTATTGTA CACGGCCGCA TAATCGAAAT TAATACGACT
           AATTCAGCTT GTCTTTCATT AGCATAACAT GTGCCGGCGT ATTAGCTTTA ATTATGCTGA
      2101 CACTATAGGG GAATTGTGAG CGGATAACAA TTCCCCATCT TAGTATATTA GTTAAGTATA
           GTGATATCCC CTTAACACTC GCCTATTGTT AAGGGGTAGA ATCATATAAT CAATTCATAT
      2161 AGAAGGAGAT ATACATATGG CAGATCTCAA TTGGATATCG GCCGGCCACG CGATCGCTGA
           TCTTCCTCTA TATGTATACC GTCTAGAGTT AACCTATAGC CGGCCGGTGC GCTAGCGACT
                        AvaI
                        ~~~~~~
      2221 CGTCGGTACC CTCGAGTCTG GTAAAGAAAC CGCTGCTGCG AAATTTGAAC GCCAGCACAT
           GCAGCCATGG GAGCTCAGAC CATTTCTTTG GCGACGACGC TTTAAACTTG CGGTCGTGTA
                                         AvrII
                                         ~~~~~~~
      2281 GGACTCGTCT ACTAGCGCAG CTTAATTAAC CTAGGCTGCT GCCACCGCTG AGCAATAACT
           CCTGAGCAGA TGATCGCGTC GAATTAATTG GATCCGACGA CGGTGGCGAC TCGTTATTGA
      2341 AGCATAACCC CTTGGGGCCT CTAAACGGGT CTTGGGGGT TTTTTGCTGA AAGGAGGAAC
           TCGTATTGGG GAACCCCGGA GATTTGCCCA GAACTCCCCA AAAAACGACT TTCCTCCTTG
      2401 TATATCCGGA TTGGCGAATG GGACGCGCCC TGTAGCGGCG CATTAAGCGC GGCGGGTGTG
           ATATAGGCCT AACCGCTTAC CCTGCGCGGG ACATCGCCGC GTAATTCGCG CCGCCCACAC
      2461 GTGGTTACGC GCAGCGTGAC CGCTACACTT GCCAGCGCCC TAGCGCCCGC TCCTTTCGCT
           CACCAATGCG CGTCGCACTG GCGATGTGAA CGGTCGCGGG ATCGCGGGCG AGGAAGCGA
      2521 TTCTTCCCTT CCTTTCTCGC CACGTTCGCC GGCTTTCCCC GTCAAGCTCT AAATCGGGGG
           AAGAAGGGAA GGAAAGAGCG GTGCAAGCGG CCGAAAGGGG CAGTTCGAGA TTTAGCCCCC
      2581 CTCCCTTTAG GGTTCGATTT TAGTGCTTTA CGGCACCTCG ACCCCAAAAA ACTTGATTAG
           GAGGGAAATC CCAAGGCTAA ATCACGAAAT GCCGTGGAGC TGGGGTTTTT TGAACTAATC
      2641 GGTGATGGTT CACGTAGTGG GCCATCGCCC TGATAGACGG TTTTTCGCCC TTTGACGTTG
           CCACTACCAA GTGCATCACC CGGTAGCGGG ACTATCTGCC AAAAAGCGGG AAACTGCAAC
      2701 GAGTCCACGT TCTTTAATAG TGGACTCTTG TTCCAAACTG GAACAACACT CAACCCTATC
           CTCAGGTGCA AGAAATTATC ACCTGAGAAC AAGGTTTGAC CTTGTTGTGA GTTGGGATAG
      2761 TCGGTCTATT CTTTTGATTT ATAAGGGATT TTGCCGATTT CGGCCTATTG GTTAAAAAAT
           AGCCAGATAA GAAAACTAAA TATTCCCTAA AACGGCTAAA GCCGGATAAC CAATTTTTTA
      2821 GAGCTGATTT AACAAAAATT TAACGCGAAT TTTAACAAAA TATTAACGTT TACAATTTCT
           CTCGACTAAA TTGTTTTTAA ATTGCGCTTA AAATTGTTTT ATAATTGCAA ATGTTAAAGA
      2881 GGCGGCACGA TGGCATGAGA TTATCAAAAA GGATCTTCAC CTAGATCCTT TTAAATTAAA
           CCGCCGTGCT ACCGTACTCT AATAGTTTTT CCTAGAAGTG GATCTAGGAA AATTTAATTT
      2941 AATGAAGTTT TAAATCAATC TAAAGTATAT ATGAGTAAAC TTGGTCTGAC AGTTACCAAT
           TTACTTCAAA ATTTAGTTAG ATTTCATATA TACTCATTTG AACCAGACTG TCAATGGTTA
      3001 GCTTAATCAG TGAGGCACCT ATCTCAGCGA TCTGTCTATT TCGTTCATCC ATAGTTGCCT
           CGAATTAGTC ACTCCGTGGA TAGAGTCGCT AGACAGATAA AGCAAGTAGG TATCAACGGA
      3061 GACTCCCCGT CGTGTAGATA ACTACGATAC GGGAGGGCTT ACCATCTGGC CCCAGTGCTG
           CTGAGGGGCA GCACATCTAT TGATGCTATG CCCTCCCGAA TGGTAGACCG GGGTCACGAC
      3121 CAATGATACC GCGAGACCCA CGCTCACCGG CTCCAGATTT ATCAGCAATA AACCAGCCAG
           GTTACTATGG CGCTCTGGGT GCGAGTGGCC GAGGTCTAAA TAGTCGTTAT TTGGTCGGTC
      3181 CCGGAAGGGC CGAGCGCAGA AGTGGTCCTG CAACTTTATC CGCCTCCATC CAGTCTATTA
           GGCCTTCCCG GCTCGCGTCT TCACCAGGAC GTTGAAATAG GCGGAGGTAG GTCAGATAAT
      3241 ATTGTTGCCG GGAAGCTAGA GTAAGTAGTT CGCCAGTTAA TAGTTTGCGC AACGTTGTTG
           TAACAACGGC CCTTCGATCT CATTCATCAA GCGGTCAATT ATCAAACGCG TTGCAACAAC
      3301 CCATTGCTAC AGGCATCGTG GTGTCACGCT CGTCGTTTGG TATGGCTTCA TTCAGCTCCG
           GGTAACGATG TCCGTAGCAC CACAGTGCGA GCAGCAAACC ATACGAAGT AAGTCGAGGC
      3361 GTTCCCAACG ATCAAGGCGA GTTACATGAT CCCCCATGTT GTGCAAAAAA GCGGTTAGCT
           CAAGGGTTGC TAGTTCCGCT CAATGTACTA GGGGGTACAA CACGTTTTTT CGCCAATCGA
      3421 CCTTCGGTCC TCCGATCGTT GTCAGAAGTA AGTTGGCCGC AGTGTTATCA CTCATGGTTA
           GGAAGCCAGG AGGCTAGCAA CAGTCTTCAT TCAACCGGCG TCACAATAGT GAGTACCAAT
      3481 TGGCAGCACT GCATAATTCT CTTACTGTCA TGCCATCCGT AAGATGCTTT TCTGTGACTG
           ACCGTCGTGA CGTATTAAGA GAATGACAGT ACGGTAGGCA TTCTACGAAA AGACACTGAC
      3541 GTGAGTACTC AACCAAGTCA TTCTGAGAAT AGTGTATGCG GCGACCGAGT TGCTCTTGCC
           CACTCATGAG TTGGTTCAGT AAGACTCTTA TCACATACGC CGCTGGCTCA ACGAGAACGG
      3601 CGGCGTCAAT ACGGGATAAT ACCGCGCCAC ATAGCAGAAC TTTAAAGTG CTCATCATTG
           GCCGCAGTTA TGCCCTATTA TGGCGCGGTG TATCGTCTTG AAATTTCAC GAGTAGTAAC
```

Fig. 50₂

```
3661  GAAAACGTTC TTCGGGGCGA AAACTCTCAA GGATCTTACC GCTGTTGAGA TCCAGTTCGA
      CTTTTGCAAG AAGCCCCGCT TTTGAGAGTT CCTAGAATGG CGACAACTCT AGGTCAAGCT
3721  TGTAACCCAC TCGTGCACCC AACTGATCTT CAGCATCTTT TACTTTCACC AGCGTTTCTG
      ACATTGGGTG AGCACGTGGG TTGACTAGAA GTCGTAGAAA ATGAAAGTGG TCGCAAAGAC
3781  GGTGAGCAAA AACAGGAAGG CAAAATGCCG CAAAAAGGG AATAAGGGCG ACACGGAAAT
      CCACTCGTTT TTGTCCTTCC GTTTTACGGC GTTTTTTCCC TTATTCCCGC TGTGCCTTTA
3841  GTTGAATACT CATACTCTTC CTTTTTCAAT CATGATTGAA GCATTTATCA GGGTTATTGT
      CAACTTATGA GTATGAGAAG GAAAAGTTA GTACTAACTT CGTAAATAGT CCCAATAACA
3901  CTCATGAGCG GATACATATT TGAATGTATT TAGAAAAATA AACAAATAGG TCATGACCAA
      GAGTACTCGC CTATGTATAA ACTTACATAA ATCTTTTTAT TTGTTTATCC AGTACTGGTT
3961  AATCCCTTAA CGTGAGTTTT CGTTCCACTG AGCGTCAGAC CCCGTAGAAA AGATCAAAGG
      TTAGGGAATT GCACTCAAAA GCAAGGTGAC TCGCAGTCTG GGGCATCTTT TCTAGTTTCC
4021  ATCTTCTTGA GATCCTTTTT TTCTGCGCGT AATCTGCTGC TTGCAAACAA AAAAACCACC
      TAGAAGAACT CTAGGAAAAA AAGACGCGCA TTAGACGACG AACGTTTGTT TTTTTGGTGG
4081  GCTACCAGCG GTGGTTTGTT TGCCGGATCA AGAGCTACCA ACTCTTTTTC CGAAGGTAAC
      CGATGGTCGC CACCAAACAA ACGGCCTAGT TCTCGATGGT TGAGAAAAAG GCTTCCATTG
4141  TGGCTTCAGC AGAGCGCAGA TACCAAATAC TGTCCTTCTA GTGTAGCCGT AGTTAGGCCA
      ACCGAAGTCG TCTCGCGTCT ATGGTTTATG ACAGGAAGAT CACATCGGCA TCAATCCGGT
4201  CCACTTCAAG AACTCTGTAG CACCGCCTAC ATACCTCGCT CTGCTAATCC TGTTACCAGT
      GGTGAAGTTC TTGAGACATC GTGGCGGATG TATGGAGCGA GACGATTAGG ACAATGGTCA
4261  GGCTGCTGCC AGTGGCGATA AGTCGTGTCT TACCGGGTTG GACTCAAGAC GATAGTTACC
      CCGACGACGG TCACCGCTAT TCAGCACAGA ATGGCCCAAC CTGAGTTCTG CTATCAATGG
4321  GGATAAGGCG CAGCGGTCGG GCTGAACGGG GGGTTCGTGC ACACAGCCCA GCTTGGAGCG
      CCTATTCCGC GTCGCCAGCC CGACTTGCCC CCCAAGCACG TGTGTCGGGT CGAACCTCGC
4381  AACGACCTAC ACCGAACTGA GATACCTACA GCGTGAGCTA TGAGAAAGCG CCACGCTTCC
      TTGCTGGATG TGGCTTGACT CTATGGATGT CGCACTCGAT ACTCTTTCGC GGTGCGAAGG
4441  CGAAGGGAGA AAGGCGGACA GGTATCCGGT AAGCGGCAGG GTCGGAACAG GAGAGCGCAC
      GCTTCCCTCT TTCCGCCTGT CCATAGGCCA TTCGCCGTCC CAGCCTTGTC CTCTCGCGTG
4501  GAGGGAGCTT CCAGGGGGAA ACGCCTGGTA TCTTTATAGT CCTGTCGGGT TTCGCCACCT
      CTCCCTCGAA GGTCCCCCTT TGCGGACCAT AGAAATATCA GGACAGCCCA AAGCGGTGGA
4561  CTGACTTGAG CGTCGATTTT TGTGATGCTC GTCAGGGGGG CGGAGCCTAT GGAAAAACGC
      GACTGAACTC GCAGCTAAAA ACACTACGAG CAGTCCCCCC GCCTCAGGATA CCTTTTTGCG
4621  CAGCAACGCG GCCTTTTTAC GGTTCCTGGC CTTTTGCTGG CCTTTTGCTC ACATGTTCTT
      GTCGTTGCGC CGGAAAAATG CCAAGGACCG GAAAACGACC GGAAAACGAG TGTACAAGAA
4681  TCCTGCGTTA TCCCCTGATT CTGTGGATAA CCGTATTACC GCCTTTGAGT GAGCTGATAC
      AGGACGCAAT AGGGGACTAA GACACCTATT GGCATAATGG CGGAAACTCA CTCGACTATG
4741  CGCTCGCCGC AGCCGAACGA CCGAGCGCAG CGAGTCAGTG AGCGAGGAAG CGGAAGAGCG
      GCGAGCGGCG TCGGCTTGCT GGCTCGCGTC GCTCAGTCAC TCGCTCCTTC GCCTTCTCGC
4801  CCTGATGCGG TATTTTCTCC TTACGCATCT GTGCGGTATT TCACACCGCA TATATGGTGC
      GGACTACGCC ATAAAAGAGG AATGCGTAGA CACGCCATAA AGTGTGGCGT ATATACCACG
4861  ACTCTCAGTA CAATCTGCTC TGATGCCGCA TAGTTAAGCC AGTATACACT CCGCTATCGC
      TGAGAGTCAT GTTAGACGAG ACTACGGCGT ATCAATTCGG TCATATGTGA GGCGATAGCG
4921  TACGTGACTG GGTCATGGCT GCGCCCCGAC ACCCGCCAAC ACCCGCTGAC GCGCCCTGAC
      ATGCACTGAC CCAGTACCGA CGCGGGGCTG TGGGCGGTTG TGGGCGACTG CGCGGGACTG
4981  GGGCTTGTCT GCTCCCGGCA TCCGCTTACA GACAAGCTGT GACCGTCTCC GGGAGCTGCA
      CCCGAACAGA CGAGGGCCGT AGGCGAATGT CTGTTCGACA CTGGCAGAGG CCCTCGACGT
5041  TGTGTCAGAG GTTTTCACCG TCATCACCGA AACGCGCGAG GCAGCTGCGG TAAAGCTCAT
      ACACAGTCTC CAAAAGTGGC AGTAGTGGCT TTGCGCGCTC CGTCGACGCC ATTTCGAGTA
5101  CAGCGTGGTC GTGAAGCGAT TCACAGATGT CTGCCTGTTC ATCCGCGTCC AGCTCGTTGA
      GTCGCACCAG CACTTCGCTA AGTGTCTACA GACGGACAAG TAGGCGCAGG TCGAGCAACT
5161  GTTTCTCCAG AAGCGTTAAT GTCTGGCTTC TGATAAAGCG GGCCATGTTA AGGGCGGTTT
      CAAAGAGGTC TTCGCAATTA CAGACCGAAG ACTATTTCGC CCGGTACAAT TCCCGCCAAA
5221  TTTCCTGTTT GGTCACTGAT GCCTCCGTGT AAGGGGGATT TCTGTTCATG GGGGTAATGA
      AAAGGACAAA CCAGTGACTA CGGAGGCACA TTCCCCCTAA AGACAAGTAC CCCCATTACT
5281  TACCGATGAA ACGAGAGAGG ATGCTCACGA TACGGGTTAC TGATGATGAA CATGCCCGGT
      ATGGCTACTT TGCTCTCTCC TACGAGTGCT ATGCCCAATG ACTACTACTT GTACGGGCCA
5341  TACTGGAACG TTGTGAGGGT AAACAACTGG CGGTATGGAT GCGGCGGGAC CAGAGAAAAA
      ATGACCTTGC AACACTCCCA TTTGTTGACC GCCATACCTA CGCCGCCCTG GTCTCTTTTT
5401  TCACTCAGGG TCAATGCCAG CGCTTCGTTA ATACAGATGT AGGTGTTCCA CAGGGTAGCC
      AGTGAGTCCC AGTTACGGTC GCGAAGCAAT TATGTCTACA TCCACAAGGT GTCCCATCGG
5461  AGCAGCATCC TGCGATGCAG ATCCGGAACA TAATGGTGCA GGGCGCTGAC TTCCGCGTTT
      TCGTCGTAGG ACGCTACGTC TAGGCCTTGT ATTACCACGT CCCGCGACTG AAGGCGCAAA
5521  CCAGACTTTA CGAAACACGG AAACCGAAGA CCATTCATGT TGTTGCTCAG GTCGCAGACG
      GGTCTGAAAT GCTTTGTGCC TTTGGCTTCT GGTAAGTACA ACAACGAGTC CAGCGTCTGC
5581  TTTTGCAGCA GCAGTCGCTT CACGTTCGCT CGCGTATCGG TGATTCATTC TGCTAACCAG
      AAAACGTCGT CGTCAGCGAA GTGCAAGCGA GCGCATAGCC ACTAAGTAAG ACGATTGGTC
5641  TAAGGCAACC CCGCCAGCCT AGCCGGGTCC TCAACGACAG GAGCACGATC ATGTAGTCA
      ATTCCGTTGG GGCGGTCGGA TCGGCCCAGG AGTTGCTGTC CTCGTGCTAG TACGATCAGT
```

Fig. 50₃

```
5701  TGCCCCGCGC CCACCGGAAG GAGCTGACTG GGTTGAAGGC TCTCAAGGGC ATCGGTCGAG
      ACGGGGCGCG GGTGGCCTTC CTCGACTGAC CCAACTTCCG AGAGTTCCCG TAGCCAGCTC
5761  ATCCCGGTGC CTAATGAGTG AGCTAACTTA CATTAATTGC GTTGCGCTCA CTGCCCGCTT
      TAGGGCCACG GATTACTCAC TCGATTGAAT GTAATTAACG CAACGCGAGT GACGGGCGAA
5821  TCCAGTCGGG AAACCTGTCG TGCCAGCTGC ATTAATGAAT CGGCCAACGC GCGGGGAGAG
      AGGTCAGCCC TTTGGACAGC ACGGTCGACG TAATTACTTA GCCGGTTGCG CGCCCCTCTC
5881  GCGGTTTGCG TATTGGGCGC CAGGGTGGTT TTTCTTTTCA CCAGTGAGAC GGGCAACAGC
      CGCCAAACGC ATAACCCGCG GTCCCACCAA AAAGAAAAGT GGTCACTCTG CCCGTTGTCG
5941  TGATTGCCCT TCACCGCCTG GCCCTGAGAG AGTTGCAGCA AGCGGTCCAC GCTGGTTTGC
      ACTAACGGGA AGTGGCGGAC CGGGACTCTC TCAACGTCGT TCGCCAGGTG CGACCAAACG
6001  CCCAGCAGGC GAAAATCCTG TTTGATGGTG GTTAACGGCG GGATATAACA TGAGCTGTCT
      GGGTCGTCCG CTTTTAGGAC AAACTACCAC CAATTGCCGC CCTATATTGT ACTCGACAGA
6061  TCGGTATCGT CGTATCCCAC TACCGAGATG TCCGCACCAA CGCGCAGCCC GGACTCGGTA
      AGCCATAGCA GCATAGGGTG ATGGCTCTAC AGGCGTGGTT GCGCGTCGGG CCTGAGCCAT
6121  ATGGCGCGCA TTGCGCCCAG CGCCATCTGA TCGTTGGCAA CCAGCATCGC AGTGGGAACG
      TACCGCGCGT AACGCGGGTC GCGGTAGACT AGCAACCGTT GGTCGTAGCG TCACCCTTGC
6181  ATGCCCTCAT TCAGCATTTG CATGGTTTGT TGAAAACCGG ACATGGCACT CCAGTCGCCT
      TACGGGAGTA AGTCGTAAAC GTACCAAACA ACTTTTGGCC TGTACCGTGA GGTCAGCGGA
6241  TCCCGTTCCG CTATCGGCTG AATTTGATTG CGAGTGAGAT ATTTATGCCA GCCAGCCAGA
      AGGGCAAGGC GATAGCCGAC TTAAACTAAC GCTCACTCTA TAAATACGGT CGGTCGGTCT
6301  CGCAGACGCG CCGAGACAGA ACTTAATGGG CCCGCTAACA GCGCGATTTG CTGGTGACCC
      GCGTCTGCGC GGCTCTGTCT TGAATTACCC GGGCGATTGT CGCGCTAAAC GACCACTGGG
6361  AATGCGACCA GATGCTCCAC GCCCAGTCGC GTACCGTCTT CATGGGAGAA AATAATACTG
      TTACGCTGGT CTACGAGGTG CGGGTCAGCG CATGGCAGAA GTACCCTCTT TTATTATGAC
6421  TTGATGGGTG TCTGGTCAGA GACATCAAGA AATAACGCCG GAACATTAGT GCAGGCAGCT
      AACTACCCAC AGACCAGTCT CTGTAGTTCT TTATTGCGGC CTTGTAATCA CGTCCGTCGA
6481  TCCACAGCAA TGGCATCCTG GTCATCCAGC GGATAGTTAA TGATCAGCCC ACTGACGCGT
      AGGTGTCGTT ACCGTAGGAC CAGTAGGTCG CCTATCAATT ACTAGTCGGG TGACTGCGCA
6541  TGCGCGAGAA GATTGTGCAC CGCCGCTTTA CAGGCTTCGA CGCCGCTTCG TTCTACCATC
      ACGCGCTCTT CTAACACGTG GCGGCGAAAT GTCCGAAGCT GCGGCGAAGC AAGATGGTAG
6601  GACACCACCA CGCTGGCACC CAGTTGATCG GCGCGAGATT TAATCGCCGC GACAATTTGC
      CTGTGGTGGT GCGACCGTGG GTCAACTAGC CGCGCTCTAA ATTAGCGGCG CTGTTAAACG
6661  GACGGCGCGT GCAGGGCCAG ACTGGAGGTG GCAACGCCAA TCAGCAACGA CTGTTTGCCC
      CTGCCGCGCA CGTCCCGGTC TGACCTCCAC CGTTGCGGTT AGTCGTTGCT GACAAACGGG
6721  GCCAGTTGTT GTGCCACGCG GTTGGGAATG TAATTCAGCT CCGCCATCGC CGCTTCCACT
      CGGTCAACAA CACGGTGCGC CAACCCTTAC ATTAAGTCGA GGCGGTAGCG GCGAAGGTGA
6781  TTTTCCCGCG TTTTCGCAGA AACGTGGCTG GCCTGGTTCA CCACGCGGGA AACGGTCTGA
      AAAAGGGCGC AAAAGCGTCT TTGCACCGAC CGGACCAAGT GGTGCGCCCT TTGCCAGACT
6841  TAAGAGACAC CGGCATACTC TGCGACATCG TATAACGTTA CTGGTTTCAC ATTCACCACC
      ATTCTCTGTG GCCGTATGAG ACGCTGTAGC ATATTGCAAT GACCAAAGTG TAAGTGGTGG
6901  CTGAATTGAC TCTCTTCCGG GCGCTATCAT GCCATACCGC GAAAGGTTTT GCGCCATTCG
      GACTTAACTG AGAGAAGGCC CGCGATAGTA CGGTATGGCG CTTTCCAAAA CGCGGTAAGC
6961  ATGGTGTCCG GGATCTCGAC GCTCTCCCTT ATGCGACT
      TACCACAGGC CCTAGAGCTG CGAGAGGGAA TACGCTGA
```

Fig. 50$_4$

| Fig. 52$_1$ |
|---|
| Fig. 52$_2$ |
| Fig. 52$_3$ |
| Fig. 52$_4$ |

Fig. 52 pDEST-CMZ1 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                SacI
                                                                ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCACGG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT CTCCATTTT
     AAATGCTACG GTAACCCTAT ATAGTTGCCA CCATATAGGT CACTAAAAAA AGAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
     CGGCCTTCGT ATTTCACATT TCGGACCCCC ACGGATTACG CCGGCGGTAT CACTGACCTA
1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTTAGATTA AATTATATAA
1801 GATATTTATA TCATTTTACG TTTCTCGTTC AACTTTATTA TACATAGTTG ATAATTCACT
     CTATAAATAT AGTAAAATGC AAAGAGCAAG TTGAAATAAT ATGTATCAAC TATTAAGTGA
1861 GGCCGTCGTT TTACAACGTC GTGACTGGGA AAACCCTGGC GTTACCCAAC TTAATCGCCT
```

Fig. 52₁

```
            CCGGCAGCAA AATGTTGCAG CACTGACCCT TTTGGGACCG CAATGGGTTG AATTAGCGGA
                      HindIII
                      ~~~~~~~
      1921  TGCAGCACAA GCTTGCGGCC GCATAATGCT TAAGTCGAAC AGAAAGTAAT CGTATTGTAC
            ACGTCGTGTT CGAACGCCGG CGTATTACGA ATTCAGCTTG TCTTTCATTA GCATAACATG
      1981  ACGGCCGCAT AATCGAAATT AATACGACTC ACTATAGGGG AATTGTGAGC GGATAACAAT
            TGCCGGCGTA TTAGCTTTAA TTATGCTGAG TGATATCCCC TTAACACTCG CCTATTGTTA
                                                                      NdeI
                                                                     ~~~~~~
      2041  TCCCCATCTT AGTATATTAG TTAAGTATAA GAAGGAGATA TACATATGGA TCACAAGTTT
            AGGGGTAGAA TCATATAATC AATTCATATT CTTCCTCTAT ATGTATACCT AGTGTTCAAA
      2101  GTACAAAAAA GCTGAACAGA AAACGTAAAA TGATATAAAT ATCAATATAT TAAATTAGAT
            CATGTTTTTT CGACTTGCTC TTTGCATTTT ACTATATTTA TAGTTATATA ATTTAATCTA
      2161  TTTGCATAAA AAACAGACTA CATAATACTG TAAAACACAA CATATCCAGT CACTATGGCG
            AAACGTATTT TTTGTCTGAT GTATTATGAC ATTTTGTGTT GTATAGGTCA GTGATACCGC
      2221  GCCGCCACGT TAAGGGATTT TGGTCATGAT CAGCACGTGT TGACAATTAA TCATCGGCAT
            CGGCGGTGCA ATTCCCTAAA ACCAGTACTA GTCGTGCACA ACTGTTAATT AGTAGCCGTA
      2281  AGTATATCGG CATAGTATAA TACGACAAGG TGAGGAACTA AACCATGGCC AAGTTGACCA
            TCATATAGCC GTATCATATT ATGCTGTTCC ACTCCTTGAT TTGGTACCGG TTCAACTGGT
      2341  GTGCCGTTCC GGTGCTCACC GGGCGCGACG TCGCCGGAGC GGTCGAGTTC GGACCGACC
            CACGGCAAGG CCACGAGTGG CGCGCGCTGC AGCGGCCTCG CCAGTCAAG ACCTGGCTGG
      2401  GGCTCGGGTT CTCCCGGGAC TTCGTGGAGG ACGACTTCGC CGGTGTGGTC CGGGACGACG
            CCGAGCCCAA GAGGGCCCTG AAGCACCTCC TGCTGAAGCG GCCACACCAG GCCCTGCTGC
      2461  TGACCCTGTT CATCAGCGCG GTCCAGGACC AGGTGGTGCC GGACAACACC CTGGCCTGGG
            ACTGGGACAA GTAGTCGCGC CAGGTCCTGG TCCACCACGG CCTGTTGTGG GACCGGACCC
      2521  TGTGGTGCG CGGCCTGGAC GAGCTGTACG CCGAGTGGTC GGAGGTGTACTG TCCACGAACT
            ACACCCACGC GCCGGACCTG CTCGACATGC GGCTCACCAG CCTCCAGCAC AGGTGCTTGA
      2581  TCCGGGACGC CTCCGGGCCG GCCATGACCG AGATCGGCGA GCAGCCGTGG GGGCGGGAGT
            AGGCCCTGCG GAGGCCCGGC CGGTACTGGC TCTAGCCGCT CGTCGGCACC CCCGCCCTCA
      2641  TCGCCCTGCG CGACCCGGCC GGCAACTGCG TGCACTTCGT GGCCGAGGAG CAGGACTGAT
            AGCGGGACGC GCTGGGCCGG CCGTTGACGC ACGTGAAGCA CCGGCTCCTC GTCCTGACTA
      2701  CATGATGATA TTATTTTATC TTGTGCAATG TAACATCAGA GATTTTGAGA CACGGGCCAG
            GTACTACTAT AATAAAATAG AACACGTTAC ATTGTAGTCT CTAAAACTCT GTGCCCGGTC
      2761  AGCTGCCAGG AAACAGCTAT GACCATGTAA TACGACTCAC TATAGGGGAT ATCAGCTGGA
            TCGACGGTCC TTTGTCGATA CTGGTACATT ATGCTGAGTG ATATCCCCTA TAGTCGACCT
      2821  TGGCAAATAA TGATTTTATT TTGACTGATA GTGACCTGTT CGTTGCAACA CCGGTGCTAG
            ACCGTTTATT ACTAAAATAA AACTGACTAT CACTGGACAA GCAACGTTGT GGCCACGATC
      2881  CGTATACCCG AAGTATGTCA AAAAGAGGTG TGCTATGAAG CAGCGTATTA CAGTGACAGT
            GCATATGGGC TTCATACAGT TTTTCTCCAC ACGATACTTC GTCGCATAAT GTCACTGTCA
      2941  TGACAGCGAC AGCTATCAGT TGCTCAAGGC ATATATGATG TCAATATCTC CGGTCTGGTA
            ACTGTCGCTG TCGATAGTCA ACGAGTTCCG TATATACTAC AGTTATAGAG GCCAGACCAT
      3001  AGCACAACCA TGCAGAATGA AGCCCGTCGT CTGCGTGCCG AACGCTGGAA AGCGGAAAAT
            TCGTGTTGGT ACGTCTTACT TCGGGCAGCA GACGCACGGC TTGCGACCTT TCGCCTTTTA
      3061  CAGGAAGGGA TGGCTCAGGT CGCCCGGTTT ATTGAAATGA ACGGCTCTTT TGCTGACGAG
            GTCCTTCCCT ACCGACTCCA GCGGGCCAAA TAACTTTACT TGCCGAGAAA ACGACTGCTC
      3121  AACAGGGACT GGTGAAATGC AGTTTAAGGT TTACACCTAT AAAAGAGAGA GCCGTTATCG
            TTGTCCCTGA CCACTTTACG TCAAATTCCT AATGTGGATA TTTTCTCTCT CGGCAATAGC
      3181  TCTGTTTGTG GATGTACAGA GTGATATTAT TGACACGCCC GGGCGACGGA TGGTGATCCC
            AGACAAACAC CTACATGTCT CACTATAATA ACTGTGCGGG CCCGCTGCCT ACCACTAGGG
      3241  CCTGGCCAGT GCACGTCTGC TGTCAGATAA AGTCTCCCGT GAACTTTACC CGGTGGTGCA
            GGACCGGTCA CGTGCAGACG ACAGTCTATT TCAGAGGGCA CTTGAAATGG GCCACCACGT
      3301  TATCGGGGAT GAAAGCTGGC GCATGATGAC CACCGATATG GCCAGTGTCG CGGTCTCCGT
            ATAGCCCCTA CTTTCGACCG CGTACTACTG GTGGCTATAC CGGTCACACG GCCAGAGGCA
      3361  TATCGGGGAA GAAGTGGCTG ATCTCAGCCG CCGCGAAAAT GACATCAAAA ACGCCATTAA
            ATAGCCCCTT CTTCACCGAC TAGAGTCGGC GGCGCTTTTA CTGTAGTTTT GCGGTAATT
      3421  CCTGATGTTC TGGGGAATAT AAATGTCAGG CTCCCTTATA CACAGCCAGT CTGCAGGTCG
            GGACTACAAG ACCCCTTATA TTTACAGTCC GAGGGAATAT GTGTCGGTCA GACGTCCAGC
      3481  ACCATAGTGA CTGGATATGT TGTCTTTTAC AGTATTATGT AGTCTGTTTT TTATGCAAAA
            TGGTATCACT GACCTATACA ACAGAAAATG TCATAATACA TCAGACAAAA AATACGTTTT
      3541  TCTAATTTAA TATATTGATA TTTATATCAT TTTACGTTTC TCGTTCAGCT TTCTTGTACA
            AGATTAAATT ATATAACTAT AAATATAGTA AAATGCAAAG AGCAAGTCGA AGAACATGT
                                                              KpnI
                                                             ~~~~~~~
      3601  AAGTGGTGAT AATTAATTAA GATCAGATCC GGCTGCTGGT ACCCTCGAGT CTGGTAAAGA
            TTCACCACTA TTAATTAATT CTAGTCTAGG CCGACGACCA TGGGAGCTCA GACCATTTCT
      3661  AACCGCTGCT GCGAAATTTG AACGCCAGCA CATGGACTCG TCTACTAGCG CAGCTTAATT
            TTGGCGACGA CGCTTTAAAC TTGCGGTCGT GTACCTGAGC AGATGATCGC GTCGAATTAA
            AvrII
            ~~~~~
      3721  AACCTAGGCT GCTGCCACCG CTGAGCAATA ACTAGCATAA CCCCTTGGGG CCTCTAAACG
            TTGGATCCGA CGACGGTGGC GACTCGTTAT TGATCGTATT GGGGAACCCC GGAGATTTGC
      3781  GGTCTTGAGG GGTTTTTTGC TGAAACCTCA GGCATTTGAG AAGCACACGG TCACACTGCT
```

Fig. 52₂

```
        CCAGAACTCC CCAAAAAACG ACTTTGGAGT CCGTAAACTC TTCGTGTGCC AGTGTGACGA
3841    TCCGGTAGTC AATAAACCGG TAAACCAGCA ATAGACATAA GCGGCTATTT AACGACCCTG
        AGGCCATCAG TTATTTGGCC ATTTGGTCGT TATCTGTATT CGCCGATAAA TTGCTGGGAC
3901    CCCTGAACCG ACGACCGGGT CATCGTGGCC GGATCTTGCG GCCCCTCGGC TTGAACGAAT
        GGGACTTGGC TGCTGGCCCA GTAGCACCGG CCTAGAACGC CGGGGAGCCG AACTTGCTTA
3961    TGTTAGACAT TATTTGCCGA CTACCTTGGT GATCTCGCCT TTCACGTAGT GGACAAATTC
        ACAATCTGTA ATAAACGGCT GATGGAACCA CTAGAGCGGA AAGTGCATCA CCTGTTTAAG
4021    TTCCAACTGA TCTGCGCGCG AGGCCAAGCG ATCTTCTTCT TGTCCAAGAT AAGCCTGTCT
        AAGGTTGACT AGACGCGCGC TCCGGTTCGC TAGAAGAAGA ACAGGTTCTA TTCGGACAGA
4081    AGCTTCAAGT ATGACGGGCT GATCATGGGC CGGCAGGCGC TCCATTGCCC AGTCGGCAGC
        TCGAAGTTCA TACTGCCCGA CTATGACCCG GCCGTCCGCG AGGTAACGGG TCAGCCGTCG
4141    GACATCCTTC GGCGCGATTT TGCCGGTTAC TGCGCTGTAC CAAATGCGGG ACAACGTAAG
        CTGTAGGAAG CCGCGCTAAA ACGGCCAATG ACGCGACATG GTTTACGCCC TGTTGCATTC
4201    CACTACATTT CGCTCATCGC CAGCCCAGTC GGGCGGCGAG TTCCATAGCG TTAAGGTTTC
        GTGATGTAAA GCGAGTAGCG GTCGGGTCAG CCCGCCGCTC AAGGTATCGC AATTCCAAAG
4261    ATTTAGCGCC TCAAATAGAT CCTGTTCAGG AACCGGATCA AAGAGTTCCT CCGCCGCTGG
        TAAATCGCGG AGTTTATCTA GGACAAGTCC TTGGCCTAGT TTCTCAAGGA GGCGGCGACC
4321    ACCTACCAAG GCAACGCTAT GTTCTCTTGC TTTTGTCAGC AAGATAGCCA GATCAATGTC
        TGGATGGTTC CGTTGCGATA CAAGAGAACG AAAACAGTCG TTCTATCGGT CTAGTTACAG
4381    GATCGTGGCT GGCTCGAAGA TACCTGCAAG AATGTCATTG CGCTGCCATT CTCCAAATTG
        CTAGCACCGA CCGAGCTTCT ATGGACGTTC TTACAGTAAC GCGACGGTAA GAGGTTTAAC
4441    CAGTTCGCGC TTAGCTGGAT AACGCCACGG AATGATGTCG TCGTGCACAA CAATGGTGAC
        GTCAAGCGCG AATCGACCTA TTGCGGTGCC TTACTACAGC AGCACGTGTT GTTACCACTG
4501    TTCTACAGCG CGGAGAATCT CGCTCTCTCC AGGGGAAGCC GAAGTTTCCA AAAGGTCGTT
        AAGATGTCGC GCCTCTTAGA GCGAGAGAGG TCCCCTTCGG CTTCAAAGGT TTTCCAGCAA
4561    GATCAAAGCT CGCCGCGTTG TTTCATCAAG CCTTACGGTC ACCGTAACCA GCAAATCAAT
        CTAGTTTCGA GCGGCGCAAC AAAGTAGTTC GGAATGCCAG TGGCATTGGT CGTTTAGTTA
4621    ATCACTGTGT GGCTTCAGGC CGCCATCCAC TGCGGAGCCG TACAAATGTA CGGCCAGCAA
        TAGTGACACA CCGAAGTCCG GCGGTAGGTG ACGCCTCGGC ATGTTTACAT GCCGGTCGTT
4681    CGTCGGTTCG AGATGCGCT CGATGACGCC AACTACCTCT GATAGTTGAG TCGATACTTC
        GCAGCCAAGC TCTACCGCGA GCTACTGCGG TTGATGGAGA CTATCAACTC AGCTATGAAG
4741    GGCGATCACC GCTTCCCTCA TACTCTTCCT TTTTCAATAT TATTGAAGCA TTTATCAGGG
        CCGCTAGTGG CGAAGGAGT ATGAGAAGGA AAAAGTTATA ATAACTTCGT AAATAGTCCC
4801    TTATTGTCTC ATGAGCGGAT ACATATTTGA ATGTATTTAG AAAAATAAAC AAATAGCTAG
        AATAACAGAG TACTCGCCTA TGTATAAACT TACATAAATC TTTTTATTTG TTTATCGATC
4861    CTCACTCGGT CGCTACGCTC CGGGCGTGAG ACTGCGGCGG GCGCTGCGGA CACATACAAA
        GAGTGAGCCA GCGATGCGAG GCCCGCACTC TGACGCCGCC CGCGACGCCT GTGTATGTTT
4921    GTTACCCACA GATTCCGTGG ATAAGCAGGG GACTAACATG TGAGGCAAAA CAGCAGGGCC
        CAATGGGTGT CTAAGGCACC TATTCGTCCC CTGATTGTAC ACTCCGTTTT GTCGTCCCGG
4981    GCGCCGGTGG CGTTTTTCCA TAGGCTCCGC CCTCCTGCCA GAGTTCACAT AAACAGACGC
        CGCGGCCACC GCAAAAAGGT ATCCGAGGCG GGAGGACGGT CTCAAGTGTA TTTGTCTGCG
5041    TTTTCCGGTG CATCTGTGGG AGCCGTGAGG CTCAACCATG AATCTGACAG TACGGGCGAA
        AAAAGGCCAC GTAGACACCC TCGGCACTCC GAGTTGGTAC TTAGACGTC ATGCCCGCTT
5101    ACCCGACAGG ACTTAAAGAT CCCCACCGTT TCCGGCGGGT CGCTCCCTCT TGCGCTCTCC
        TGGGCTGTCC TGAATTTCTA GGGGTGGCAA AGGCCGCCCA GCGAGGGAGA ACGCGAGAGG
5161    TGTTCCGACC CTGCCGTTTA CCGGATACCT GTTCCGCCTT TCTCCCTTAC GGGAAGTGTG
        ACAAGGCTGG GACGGCAAAT GGCCTATGGA CAAGGCGGAA AGAGGGAATG CCCTTCACAC
5221    GCGCTTTCTC ATAGCTCACA CACTGGTATC TCGGCTCGGT GTAGGTCGTT CGCTCCAAGC
        CGCGAAAGAG TATCGAGTGT GTGACCATAG AGCCGAGCCA CATCCAGCAA GCGAGGTTCG
5281    TGGGCTGTAA GCAAGAACTC CCCGTTCACG CCGACTGCTG CGCCTTATCC GGTAACTGTT
        ACCCGACATT CGTTCTTGAG GGGCAAGTCG GCTGACGAC GCGGAATAGG CCATTGACAA
5341    CACTTGAGTC CAACCCGGAA AAGCACGGTA AACGCCACT GGCAGCAGCC ATTGGTAACT
        GTGAACTCAG GTTGGGCCTT TCGTGCCAT TTGCGGTGA CCGTCGTCGG TAACCATTGA
5401    GGGAGTTCGC AGAGGATTTG TTTAGCTAAA CACGCGGTTG CTCTTGAAGT GTGCGCCAAA
        CCCTCAAGCG TCTCCTAAAC AAATCGATTT GTGCGCCAAC GAGAACTTCA CACGCGGTTT
5461    GTCCGGCTAC ACTGGAAGGA CAGATTTGGT TGCTGTGCTC TGCGAAAGCC AGTTACCACG
        CAGGCCGATG TGACCTTCCT GTCTAAACCA ACGACGACGAG ACGCTTTCGG TCAATGGTGC
5521    GTTAAGCAGT TCCCCAACTG ACTTAACCTT CGATCAAACC ACCTCCCCAG GTGGTTTTTT
        CAATTCGTCA AGGGGTTGAC TGAATTGGAA GCTAGTTTGG TGAGGGGTC CACCAAAAAA
5581    CGTTTACAGG GCAAAGATT ACGCGCAGAA AAAAGGATC TCAAGAAGAT CCTTTGATCT
        GCAAATGTCC CGTTTTCTAA TGCGCGTCTT TTTTCCTAG AGTTCTTCTA GGAAACTAGA
5641    TTTCTACTGA ACCGCTCTAG ATTTCAGTGC AATTTATCTC TTCAAATGTA GCACCTGAAG
        AAAGATGACT TGGCAGAGATC TAAAGTCACG TTAAATAGAG AAGTTTACAT CGTGGACTTC
5701    TCAGCCCCAT ACGATATAAG TTGTAATTCT CATGTTAGTC ATGCCCCGCG CCCACCGGAA
        AGTCGGGGTA TGCTATATTC AACATTAAGA GTACAATCAG TACGGGGCGC GGGTGGCCTT
5761    GGAGCTGACT GGGTTGAAGG CTCTCAAGGG CATCGGTCGA GATCCCGGTG CCTAATGAGT
        CCTCGACTGA CCCAACTTCC GAGAGTTCCC GTAGCCAGCT CTAGGGCCAC GGATTACTCA
```

Fig. 52₃

```
5821  GAGCTAACTT ACATTAATTG CGTTGCGCTC ACTGCCCGCT TTCCAGTCGG GAAACCTGTC
      CTCGATTGAA TGTAATTAAC GCAACGCGAG TGACGGGCGA AAGGTCAGCC CTTTGGACAG
5881  GTGCCAGCTG CATTAATGAA TCGGCCAACG CGCGGGGAGA GGCGGTTTGC GTATTGGGCG
      CACGGTCGAC GTAATTACTT AGCCGGTTGC GCGCCCCTCT CCGCCAAACG CATAACCCGC
5941  CCAGGGTGGT TTTTCTTTTC ACCAGTGAGA CGGGCAACAG CTGATTGCCC TTCACCGCCT
      GGTCCCACCA AAAAGAAAAG TGGTCACTCT GCCCGTTGTC GACTAACGGG AAGTGGCGGA
6001  GGCCCTGAGA GAGTTGCAGC AAGCGGTCCA CGCTGGTTTG CCCCAGCAGG CGAAAATCCT
      CCGGGACTCT CTCAACGTCG TTCGCCAGGT GCGACCAAAC GGGGTCGTCC GCTTTTAGGA
6061  GTTTGATGGT GGTTAACGGC GGGATATAAC ATGAGCTGTC TTCGGTATCG TCGTATCCCA
      CAAACTACCA CCAATTGCCG CCCTATATTG TACTCGACAG AAGCCATAGC AGCATAGGGT
6121  CTACCGAGAT GTCCGCACCA ACGCGCAGCC CGGACTCGGT AATGGCGCGC ATTGCGCCCA
      GATGGCTCTA CAGGCGTGGT TGCGCGTCGG GCCTGAGCCA TTACCGCGCG TAACGCGGGT
6181  GCGCCATCTG ATCGTTGGCA ACCAGCATCG CAGTGGGAAC GATGCCCTCA TTCAGCATTT
      CGCGGTAGAC TAGCAACCGT TGGTCGTAGC GTCACCCTTG CTACGGGAGT AAGTCGTAAA
6241  GCATGGTTTG TTGAAAACCG GACATGGCAC TCCAGTCGCC TTCCCGTTCC GCTATCGGCT
      CGTACCAAAC AACTTTTGGC CTGTACCGTG AGGTCAGCGG AAGGGCAAGG CGATAGCCGA
6301  GAATTTGATT GCGAGTGAGA TATTTATGCG AGCCAGCCAC ACGCAGACGC GCCGAGACAG
      CTTAAACTAA CGCTCACTCT ATAAATACGC TCGGTCGGTC TGCGTCTGCG CGGCTCTGTC
6361  AACTTAATGG GCCCGCTAAC AGCGCGATTT GCTGGTGACC CAATGCGACC AGATGCTCCA
      TTGAATTACC CGGGCGATTG TCGCGCTAAA CGACCACTGG GTTACGCTGG TCTACGAGGT
6421  CGCCCAGTCG CGTACCGTCT TCATGGGAGA AAATAATACT GTTGATGGGT GTCTGGTCAG
      GCGGGTCAGC GCATGGCAGA AGTACCCTCT TTTATTATGA CAACTACCCA CAGACCAGTC
6481  AGACATCAAG AAATAACGCC GGAACATTAG TGCAGGCAGC TTCCACAGCA ATGGCATCCT
      TCTGTAGTTC TTTATTGCGG CCTTGTAATC ACGTCCGTCG AAGGTGTCGT TACCGTAGGA
6541  GGTCATCCAG CGGATAGTTA ATGATCAGCC CACTGACGCG TTGCGCGAGA AGATTGTGCA
      CCAGTAGGTC GCCTATCAAT TACTAGTCGG GTGACTGCGC AACGCGCTCT TCTAACACGT
6601  CCGCCGCTTT ACAGGCTTCG ACGCCGCTTC GTTCTACCAT CGACACCACC ACGCTGGCAC
      GGCGGCGAAA TGTCCGAAGC TGCGGCGAAG CAAGATGGTA GCTGTGGTGG TGCGACCGTG
6661  CCAGTTGATC GGCGCGAGAT TTAATCGCCG CGACAATTTG CGACGGCGCG TGCAGGGCCA
      GGTCAACTAG CCGCGCTCTA AATTAGCGGC GCTGTTAAAC GCTGCCGCGC ACGTCCCGGT
6721  GACTGGAGGT GGCAACGCCA ATCAGCAACG ACTGTTTGCC CGCCAGTTGT TGTGCCACGC
      CTGACCTCCA CCGTTGCGGT TAGTCGTTGC TGACAAACGG GCGGTCAACA ACACGGTGCG
6781  GGTTGGGAAT GTAATTCAGC TCCGCCATCG CCGCTTCCAC TTTTTCCCGC GTTTTCGCAG
      CCAACCCTTA CATTAAGTCG AGGCGGTAGC GGCGAAGGTG AAAAAGGGCG CAAAAGCGTC
6841  AAACGTGGCT GGCCTGGTTC ACCACGCGGG AAACGGTCTG ATAAGAGACA CCGGCATACT
      TTTGCACCGA CCGGACCAAG TGGTGCGCCC TTTGCCAGAC TATTCTCTGT GGCCGTATGA
6901  CTGCGACATC GTATAACGTT ACTGGTTTCA CATTCACCAC CCTGAATTGA CTCTCTTCCG
      GACGCTGTAG CATATTGCAA TGACCAAAGT GTAAGTGGTG GGACTTAACT GAGAGAAGGC
6961  GGCGCTATCA TGCCATACCG CGAAAGGTTT TGCGCCATTC GATGGTGTCC GGGATCTCGA
      CCGCGATAGT ACGGTATGGC GCTTTCCAAA ACGCGGTAAG CTACCACAGG CCCTAGAGCT
7021  CGCTCTCCCT TATGCGACTC CTGCATTAGG AAATTAATAC GACTCACTAT A
      GCGAGAGGGA ATACGCTGAG GACGTAATCC TTTAATTATG CTGAGTGATA T
```

Fig. 52₄

| Fig. $54_1$ |
|---|
| Fig. $54_2$ |
| Fig. $54_3$ |
| Fig. $54_4$ |
| Fig. $54_5$ |

Fig. 54

Sequence for pDEST-CMZc1

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                              SacI
                                                              ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
                                                              SacI
                                                              ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
                                                              SphI
                                                              ~~~~~~~
 961 GCATGCCTAC AGGAACAGGT GGTGGCGGCC CTCGGTGCGC TCGTACTGCT CCACGATGGT
     CGTACGGATG TCCTTGTCCA CCACCGCCGG GAGCCACGCG AGCATGACGA GGTGCTACCA
1021 GTAGTCCTCG TTGTGGGAGG TGATGTCCAG CTTGGCGTCC ACGTAGTAGT AGCCGGGCAG
     CATCAGGAGC AACACCCTCC ACTACAGGTC GAACCGCAGG TGCATCATCA TCGGCCCGTC
1081 CTGCACGGGC TTCTTGGCCA TGTAGATGGA CTTGAACTCC ACCAGGTAGT GGCCGCCGTC
     GACGTGCCCG AAGAACCGGT ACATCTACCT GAACTTGAGG TGGTCCATCA CCGGCGGCAG
1141 CTTCAGCTTC AGGGCCTTGT GGGTCTCGCC CTTCAGCACG CCGTCGCGGG GGTACAGGCG
     GAAGTCGAAG TCCCGGAACA CCCAGAGCGG GAAGTCGTGC GGCAGCGCCC CCATGTCCGC
1201 CTCGGTGGAG GCCTCCCAGC CCATGGTCTT CTTCTGCATC ACGGGGCCGT CGGAGGGGAA
     GAGCCACCTC CGGAGGGTCG GGTACCAGAA GAAGACGTAG TGCCCCGGCA GCCTCCCCTT
1261 GTTCACGCCG ATGAACTTCA CCTTGTAGAT GAAGCAGCCG TCCTGCAGGG AGGAGTCCTG
     CAAGTGCGGC TACTTGAAGT GGAACATCTA CTTCGTCGGC AGGACGTCCC TCCTCAGGAC
1321 GGTCCGGTC GCCACGCCGC CGTCCTCGAA GTTCATCACG CGCTCCCACT TGAAGCCCTC
     CCAGTGCCAG CGGTGCGGCG GCAGGAGCTT CAAGTAGTGC GCGAGGGTGA ACTTCGGGAG
1381 GGGGAAGGAC AGCTTCTTGT AGTCGGGGAT GTCGGCGGGG TGCTTCACGT ACACCTTGGA
     CCCCTTCCTG TCGAAGAACA TCAGCCCCTA CAGCCGCCCC ACGAAGTGCA TGTGGAACCT
1441 GCCGTACTGG AACTGGGGGG ACAGGATGTC CCAGGCGAAG GCAGGGGGC CGCCCTTGGT
     CGGCATGACC TTGACCCCCC TGTCCTACAG GGTCCGCTTC CGTCCCCCG GCGGGAACCA
1501 CACCTTCAGC TTCACGGTGT TGTGGCCCCT GTAGGGGCGG CCCTCGCCCT CGCCCTCGAT
     GTGGAAGTCG AAGTGCCACA ACACCGGGAG CATCCCCGCC GGGAGCGGGA GCGGGAGCTA
1561 CTCGAACTCG TGGCCGTTCA CGGTGCCCTC CATGCGCACC TTGAAGCGCA TGAACTCGGT
     GAGCTTGAGC ACCGGCAAGT GCCACGGGAG GTACGCGTGG AACTTCGCGT ACTTGAGCCA
                                           SpeI
                                           ~~~~~~~
1621 GATGACGTTC TCGGAGGAGG CCATACTAGT CGCCCCGCCC TGCCACTCAT CGCAGTACTG
     CTACTGCAAG AGCCTCCTCC GGTATGATCA GCGGGGCGGG ACGGTGAGTA GCGTCATGAC
1681 TTGTAATTCA TTAAGCATTC TGCCGACATG GAAGCCATCA CAAACGGCAT GATGAACCTG
     AACATTAAGT AATTCGTAAG ACGGCTGTAC CTTCGGTAGT GTTTGCCGTA CTACTTGGAC
1741 AATCGCCAGC GGCATCAGCA CCTTGTCGCC TTGCGTATAA TATTTGCCCA TGGTGAAAAC
```

Fig. 54₁

```
      TTAGCGGTCG CCGTAGTCGT GGAACAGCGG AACGCATATT ATAAACGGGT ACCACTTTTG
1801  GGGGGCGAAG AAGTTGTCCA TATTGGCCAC GTTTAAATCA AAACTGGTGA AACTCACCCA
      CCCCCGCTTC TTCAACAGGT ATAACCGGTG CAAATTTAGT TTTGACCACT TTGAGTGGGT
1861  GGGATTGGCT GAGACGAAAA ACATATTCTC AATAAACCCT TTAGGGAAAT AGGCCAGGTT
      CCCTAACCGA CTCTGCTTTT TGTATAAGAG TTATTTGGGA AATCCCTTTA TCCGGTCCAA
1921  TTCACCGTAA CACGCCACAT CTTGCGAATA TATGTGTAGA AACTGCCGGA AATCGTCGTG
      AAGTGGCATT GTGCGGTGTA GAACGCTTAT ATACACATCT TTGACGGCCT TTAGCAGCAC
1981  GTATTCACTC CAGAGCGATG AAAACGTTTC AGTTTGCTCA TGGAAAACGG TGTAACAAGG
      CATAAGTGAG GTCTCGCTAC TTTTGCAAAG TCAAACGAGT ACCTTTTGCC ACATTGTTCC
2041  GTGAACACTA TCCCATATCA CCAGCTCACC GTCTTTCATT GCCATACGGA ATTCCGGATG
      CACTTGTGAT AGGGTATAGT GGTCGAGTGG CAGAAAGTAA CGGTATGCCT TAAGGCCTAC
2101  AGCATTCATC AGGCGGGCAA GAATGTGAAT AAAGGCCGGA TAAAACTTGT GCTTATTTTT
      TCGTAAGTAG TCCGCCCGTT CTTACACTTA TTTCCGGCCT ATTTTGAACA CGAATAAAAA
2161  CTTTACGGTC TTTAAAAAGG CCGTAATATC CAGCTGAACG GTCTGGTTAT AGGTACATTG
      GAAATGCCAG AAATTTTTCC GGCATTATAG GTCGACTTGC CAGACCAATA TCCATGTAAC
2221  AGCAACTGAC TGAAATGCCT CAAAATGTTC TTTACGATGC CATTGGGATA TATCAACGGT
      TCGTTGACTG ACTTTACGGA GTTTTACAAG AAATGCTACG GTAACCCTAT ATAGTTGCCA
2281  GGTATATCCA GTGATTTTTT TCTCCATTTT AGCTTCCTTA GCTCCTGAAA ATCTCGACGG
      CCATATAGGT CACTAAAAAA AGAGGTAAAA TCGAAGGAAT CGAGGACTTT TAGAGCTGCC
2341  ATCCTAACTC AAAATCCACA CATTATACGA GCCGGAAGCA TAAAGTGTAA AGCCTGGGGG
      TAGGATTGAG TTTTAGGTGT GTAATATGCT CGGCCTTCGT ATTTCACATT TCGGACCCCC
2401  TGCCTAATGC GGCCGCCATA GTGACTGGAT ATGTTGTGTT TTACAGTATT ATGTAGTCTG
      ACGGATTACG CCGGCGGTAT CACTGACCTA TACAACACAA AATGTCATAA TACATCAGAC
2461  TTTTTTATGC AAAATCTAAT TTAATATATT GATATTTATA TCATTTTACG TTTCTCGTTC
      AAAAAAATACG TTTTAGATTA AATTATATAA CTATAAATAT AGTAAAATGC AAAGAGCAAG
2521  AACTTTATTA TACATAGTTG ATAATTCACT GGCCGTCGTT TTACAACGTC GTGACTGGGA
      TTGAAATAAT ATGTATCAAC TATTAAGTGA CCGGCAGCAA AATGTTGCAG CACTGACCCT
                                                      HindIII
                                                      ~~~~~~~
2581  AAACCCTGGC GTTACCCAAC TTAATCGCCT TGCAGCACAA GCTTGCGGCC GCATAATGCT
      TTTGGGACCG CAATGGGTTG AATTAGCGGA ACGTCGTGTT CGAACGCCGG CGTATTACGA
2641  TAAGTCGAAC AGAAAGTAAT CGTATTGTAC ACGGCCGCAT AATCGAAATT AATACGACTC
      ATTCAGCTTG TCTTTCATTA GCATAACATG TGCCGGCGTA TTAGCTTTAA TTATGCTGAG
2701  ACTATAGGGA AATTGTGAGC GGATAACAAT TCCCCATCTT AGTATATTAG TTAAGTATAA
      TGATATCCCC TTAACACTCG CCTATTGTTA AGGGGTAGAA TCATATAATC AATTCATATT
               NdeI
               ~~~~
2761  GAAGGAGATA TACATATGGA TCACAAGTTT GTACAAAAAA GCTGAACGAG AAACGTAAAA
      CTTCCTCTAT ATGTATACCT AGTGTTCAAA CATGTTTTTT CGACTTGCTC TTTGCATTTT
2821  TGATATAAAT ATCAATATAT TAAATTAGAT TTTGCATAAA AACAGACTA CATATACTG
      ACTATATTTA TAGTTATATA ATTTAATCTA AAACGTATTT TTGTCTGAT GTATTATGAC
2881  TAAAACACAA CATATCCAGT CACTATGGCG GCCGCCACGT TAAGGGATTT TGGTCATGAT
      ATTTTGTGTT GTATAGGTCA GTGATACCGC CGGCGGTGCA ATTCCCTAAA ACCAGTACTA
2941  CAGCACGTGT TGACAATTAA TCATCGGCAT AGTATATCGG CATAGTATAA TACGACAAGG
      GTCGTGCACA ACTGTTAATT AGTAGCCGTA TCATATAGCC GTATCATATT ATGCTGTTCC
3001  TGAGGACTA AACCATGGCC AAGTTGACCA GTGCCGTTCC GGTGCTCACC GCGCGCGACG
      ACTCCTTGAT TTGGTACCGG TTCAACTGGT CACGGCAAGG CCACGAGTGG CGCGCGCTGC
3061  TCGCCGGAGC GGTCGAGTTC TGGACCGACC GGCTCGGGTT CTCCCGGGAC TTCGTGGAGG
      AGCGGCCTCG CCAGCTCAAG ACCTGGCTGG CCGAGCCCAA GAGGGCCCTG AAGCACCTCC
3121  ACGACTTCGC CGGTGTGGTC CGGGACGACG TGACCCTGTT CATCAGCGCG GTCCAGGACC
      TGCTGAAGCG GCCACACCAG GCCCTGCTGC ACTGGGACAA GTAGTCGCGC CAGGTCCTGG
3181  AGGTGGTGCC GGACAACACC CTGGCCTGGG TGTGGGTGCG CGGCCTGGAC GAGCTGTACG
      TCCACCACGG CCTGTTGTGG GACCGGACCC ACACCCACGC GCCGGACCTG CTCGACATGC
3241  CCGAGTGGTC GGAGGTCGTG TCCACGAACT TCCGGGACGC CTCCGGGCCG GCCATGACCG
      GGCTCACCAG CCTCCAGCAC AGGTGCTTGA AGGCCCTGCG GAGGCCCGGC CGGTACTGGC
3301  AGATCGGCGA GCAGCCGTGG GGGCGGGAGT TCGCCCTGCG CGACCCCGCC GGCAACTGCG
      TCTAGCCGCT CGTCGGCACC CCCGCCCTCA AGCGGGACGC GCTGGGCCGG CCGTTGACGC
                                                SpeI
                                                ~~~~~~~
3361  TGCACTTCGT GGCCGAGGAG CAGGACACTA GTATGAGTAA AGGAGAAGAA CTTTTCACTG
      ACGTGAAGCA CCGGCTCCTC GTCCTGTGAT CATACTCATT TCCTCTTCTT GAAAAGTGAC
3421  GAGTTGTCCC AATTCTTGTT GAATTAGATG GTGATGTTAA TGGGCACAAA TTTTCTGTCA
      CTCAACAGGG TTAAGAACAA CTTAATCTAC CACTACAATT ACCCGTGTTT AAAAGACAGT
3481  GTGGAGAGGG TGAAGGTGAT GCAACATACG GAAAACTTAC CCTTAAATTT ATTTGCACTA
      CACCTCTCCC ACTTCCACTA CGTTGTATGC CTTTTGAATG GGAATTTAAA TAAACGTGAT
3541  CTGGAAAACT ACCTGTTCCA TGGCCAACAC TTGTCACTAC TTTCTCTTAT GGTGTTCAAT
      GACCTTTTGA TGGACAAGGT ACCGGTTGTG AACAGTGATG AAAGAGAATA CCACAAGTTA
                                                NdeI
                                                ~~~~
3601  GCTTTTCCCG TTATCCGGAT CATATGAAAC GGCATGACTT TTCAAGAGT GCCATGCCCG
      CGAAAAGGGC AATAGGCCTA GTATACTTTG CCGTACTGAA AAGTTCTCA CGGTACGGGC
```

Fig. 54₂

```
3661  AAGGTTATGT ACAGGAACGC ACTATATCTT TCAAAGATGA CGGGAACTAC AAGACGCGTG
      TTCCAATACA TGTCCTTGCG TGATATAGAA AGTTTCTACT GCCCTTGATG TTCTGCGCAC
3721  CTGAAGTCAA GTTTGAAGGT GATACCCTTG TTAATCGTAT CGAGTTAAAA GGTATTGATT
      GACTTCAGTT CAAACTTCCA CTATGGGAAC AATTAGCATA GCTCAATTTT CCATAACTAA
3781  TTAAAGAAGA TGGAAACATT CTCGGACACA AACTCGAGTA CAACTATAAC TCACACAATG
      AATTTCTTCT ACCTTTGTAA GAGCCTGTGT TTGAGCTCAT GTTGATATTG AGTGTGTTAC
3841  TATACATCAC GGCAGACAAA CAAAAGAATG GAATCAAAGC TAACTTCAAA ATTCGCCACA
      ATATGTAGTG CCGTCTGTTT GTTTTCTTAC CTTAGTTTCG ATTGAAGTTT TAAGCGGTGT
3901  ACATTGAAGA TGGATCCGTT CAACTAGCAG ACCATTATCA ACAAAATACT CCAATTGGCG
      TGTAACTTCT ACCTAGGCAA GTTGATCGTC TGGTAATAGT TGTTTTATGA GGTTAACCGC
3961  ATGGCCCTGT CCTTTTACCA GACAACCATT ACCTGTCGAC ACAATCTGCC CTTTCGAAAG
      TACCGGGACA GGAAAATGGT CTGTTGGTAA TGGACAGCTG TGTTAGACGG GAAAGCTTTC
4021  ATCCCAACGA AAAGCGTGAC CACATGGTCC TTCTTGAGTT TGTAACTGCT GCTGGGATTA
      TAGGGTTGCT TTTCGCACTG GTGTACCAGG AAGAACTCAA ACATTGACGA CGACCCTAAT
                                SacI             SphI
                                ~~~~~~           ~~~~~~
4081  CACATGGCAT GGATGAGCTC TACAAATAAG CATGCTGATC ATGATGATAT TATTTTATCT
      GTGTACCGTA CCTACTCGAG ATGTTTATTC GTACGACTAG TACTACTATA ATAAAATAGA
4141  TGTGCAATGT AACATCAGAG ATTTTGAGAC ACGGGCCAGA GCTGCCAGGA AACAGCTATG
      ACACGTTACA TTGTAGTCTC TAAAACTCTG TGCCCGGTCT CGACGGTCCT TTGTCGATAC
4201  ACCATGTAAT ACGACTCACT ATAGGGGATA TCAGCTGGAT GGCAAATAAT GATTTTATTT
      TGGTACATTA TGCTGAGTGA TATCCCCTAT AGTCGACCTA CCGTTTATTA CTAAAATAAA
4261  TGACTGATAG TGACCTGTTC GTTGCAACAC CGGTGCTAGC GTATACCCGA AGTATGTCAA
      ACTGACTATC ACTGGACAAG CAACGTTGTG GCCACGATCG CATATGGGCT TCATACAGTT
4321  AAAGAGGTGT GCTATGAAGC AGCGTATTAC AGTGACAGTT GACAGCGACA GCTATCAGTT
      TTTCTCCACA CGATACTTCG TCGCATAATG TCACTGTCAA CTGTCGCTGT CGATAGTCAA
4381  GCTCAAGGCA TATATGATGT CAATATCTCC GGTCTGGTAA GCACAACCAT GCAGAATGAA
      CGAGTTCCGT ATATACTACA GTTATAGAGG CCAGACCATT CGTGTTGGTA CGTCTTACTT
4441  GCCCGTCGTC TGCGTGCCGA ACGCTGGAAA GCGGAAAATC AGGAAGGGAT GGCTGAGGTC
      CGGGCAGCAG ACGCACGGCT TGCGACCTTT CGCCTTTTAG TCCTTCCCTA CCGACTCCAG
4501  GCCGGGTTTA TTGAAATGAA CGGCTCTTTT GCTGACGAGA ACAGGGACTG GTGAAATGCA
      CGGGCCAAAT AACTTTACTT GCCGAGAAAA CGACTGCTCT TGTCCCTGAC CACTTTACGT
4561  GTTTAAGGTT TACACCTATA AAAGAGAGAG CCGTTATCGT CTGTTTGTGG ATGTACAGAG
      CAAATTCCAA ATGTGGATAT TTTCTCTCTC GGCAATAGCA GACAAACACC TACATGTCTC
4621  TGATATTATT GACACGCCCG GGCGACGGAT GGTGATCCCC CTGGCCAGTG CACGTCTGCT
      ACTATAATAA CTGTGCGGGC CCGCTGCCTA CCACTAGGGG GACCGGTCAC GTGCAGACGA
4681  GTCAGATAAA GTCTCCCGTG AACTTTACCC GGTGGTGCAT ATCGGGGATG AAAGCTGGCG
      CAGTCTATTT CAGAGGGCAC TTGAAATGGG CCACCACGTA TAGCCCCTAC TTTCGACCGC
4741  CATGATGACC ACCGATATGG CCAGTGTGCC GGTCTCCGTT ATCGGGGAAG AAGTGGCTGA
      GTACTACTGG TGGCTATACC GGTCACACGG CCAGAGGCAA TAGCCCCTTC TTCACCGACT
4801  TCTCAGCCGC CGCGAAAATG ACATCAAAAA CGCCATTAAC CTGATGTTCT GGGGAATATA
      AGAGTCGGCG GCGCTTTTAC TGTAGTTTTT GCGGTAATTG GACTACAAGA CCCCTTATAT
4861  AATGTCAGGC TCCCTTATAC ACAGCCAGTC TGCAGGTCGA CCATAGTGAC TGGATATGTT
      TTACAGTCCG AGGGAATATG TGTCGGTCAG ACGTCCAGCT GGTATCACTG ACCTATACAA
4921  GTGTTTTACA GTATTATGTA GTCTGTTTTT TATGCAAAAT CTAATTTAAT ATATTGATAT
      CACAAAATGT CATAATACAT CAGACAAAAA ATACGTTTTA GATTAAATTA TATAACTATA
4981  TTATATCATT TTACGTTTCT CGTTCAGCTT TCTTGTACAA AGTGGTGATA ATTAATTAAG
      AATATAGTAA AATGCAAAGA GCAAGTCGAA AGAACATGTT TCACCACTAT TAATTAATTC
                                     KpnI
                                     ~~~~~~
5041  ATCAGATCCG GCTGCTGGTA CCCTCGAGTC TGGTAAAGAA ACCGCTGCTG CGAAATTTGA
      TAGTCTAGGC CGACGACCAT GGGAGCTCAG ACCATTTCTT TGGCGACGAC GCTTTAAACT
                                              AvrII
                                              ~~~~~~
5101  ACGCCAGCAC ATGGACTCGT CTACTAGCGC AGCTTAATTA ACCTAGGCTG CTGCCACCGC
      TGCGGTCGTG TACCTGAGCA GATGATCGCG TCGAATTAAT TGGATCCGAC GACGGTGGCG
5161  TGAGCAATAA CTAGCATAAC CCCTTGGGGC CTCTAAACGG TCTTGAGGG GTTTTTTGCT
      ACTCGTTATT GATCGTATTG GGGAACCCCG GAGATTTGCC CAGAACTCCC CAAAAAACGA
5221  GAAACCTCAG GCATTTGAGA AGCACACGGT CACACTGCTT CCGGTAGTCA ATAAACCGGT
      CTTTGGAGTC CGTAAACTCT TCGTGTGCCA GTGTGACGAA GGCCATCAGT TATTTGGCCA
5281  AAACCAGCAA TAGACATAAG CGGCTATTTA ACGACCCTGC CCTGAACCGA CGACCGGGTC
      TTTGGTCGTT ATCTGTATTC GCCGATAAAT TGCTGGGACG GGACTTGGCT GCTGGCCCAG
5341  ATCGTGGCCG GATCTTGCGG CCCCTCGGCT TGAACGAATT GTTAGACATT ATTTGCCGAC
      TAGCACCGGC CTAGAACGCC GGGGAGCCGA ACTTGCTTAA CAATCTGTAA TAAACGGCTG
5401  TACCTTGGTG ATCTCGCCTT TCACGTAGTG GACAAATTCT TCCAACTGAT CTGCGCGCGA
      ATGGAACCAC TAGAGCGGAA AGTGCATCAC CTGTTTAAGA AGGTTGACTA GACGCGCGCT
5461  GGCCAAGCGA TCTTCTTCTT GTCCAAGATA AGCCTGTCTA GCTTCAAGTA TGACGGGCTG
      CCGGTTCGCT AGAAGAAGAA CAGGTTCTAT TCGGACAGAT CGAAGTTCAT ACTGCCCGAC
5521  ATACTGGGCC GGCAGGCGCT CCATTGCCCA GTCGGCAGCG ACATCTTCG GCGCGATTTT
      TATGACCCGG CCGTCCGCGA GGTAACGGGT CAGCCGTCGC TGTAGGAAGC CGCGCTAAAA
```

Fig. 54₃

```
5581  GCCGGTTACT GCGCTGTACC AAATGCGGGA CAACGTAAGC ACTACATTTC GCTCATCGCC
      CGGCCAATGA CGCGACATGG TTTACGCCCT GTTGCATTCG TGATGTAAAG CGAGTAGCGG
5641  AGCCCAGTCG GGCGGCGAGT TCCATAGCGT TAAGGTTTCA TTTAGCGCCT CAAATAGATC
      TCGGGTCAGC CCGCCGCTCA AGGTATCGCA ATTCCAAAGT AAATCGCGGA GTTTATCTAG
5701  CTGTTCAGGA ACCGGATCAA AGAGTTCCTC CGCCGCTGGA CCTACCAAGG CAACGCTATG
      GACAAGTCCT TGGCCTAGTT TCTCAAGGAG GCGGCGACCT GGATGGTTCC GTTGCGATAC
5761  TTCTCTTGCT TTTGTCAGCA AGATAGCCAG ATCAATGTCG ATCGTGGCTG GCTCGAAGAT
      AAGAGAACGA AAACAGTCGT TCTATCGGTC TAGTTACAGC TAGCACCGAC CGAGCTTCTA
5821  ACCTGCAAGA ATGTCATTGC GCTGCCATTC TCCAAATTGC AGTTCGCGCT TAGCTGGATA
      TGGACGTTCT TACAGTAACG CGACGGTAAG AGGTTTAACG TCAAGCGCGA ATCGACCTAT
5881  ACGCCACGGA ATGATGTCGT CGTGCACAAC AATGGTGACT TCTACAGCGC GGAGAATCTC
      TGCGGTGCCT TACTACAGCA GCACGTGTTG TTACCACTGA AGATGTCGCG CCTCTTAGAG
5941  GCTCTCTCCA GGGGAAGCCG AAGTTCCAA AAGGTCGTTG ATCAAAGCTC GCCGCGTTGT
      CGAGAGAGGT CCCCTTCGGC TTCAAAGGTT TTCCAGCAAC TAGTTTCGAG CGGCGCAACA
6001  TTCATCAAGC CTTACGGTCA CCGTAACCAG CAAATAATTA TCACTGTGTG GCTTCAGGCC
      AAGTAGTTCG GAATGCCAGT GGCATTGGTC GTTTAGTTAT AGTGACACAC CGAAGTCCGG
6061  GCCATCCACT GCGGAGCCGT ACAAATGTAC GGCCAGCAAC GTCGGTTCGA GATGGCGCTC
      CGGTAGGTGA CGCCTCGGCA TGTTTACATG CCGGTCGTTG CAGCCAAGCT CTACCGCGAG
6121  GATGACGCCA ACTACCTCTG ATAGTTGAGT CGATACTTCG GCGATCACCG CTTCCCTCAT
      CTACTGCGGT TGATGGAGAC TATCAACTCA GCTATGAAGC CGCTAGTGGC GAAGGGAGTA
6181  ACTCTTCCTT TTTCAATATT ATTGAAGCAT TTATCAGGGT TATTGTCTCA TGAGCGGATA
      TGAGAAGGAA AAAGTTATAA TAACTTCGTA AATAGTCCCA ATAACAGAGT ACTCGCCTAT
6241  CATATTTGAA TGTATTTAGA AAAATAAACA AATAGCTAGC TCACTCGGTC GCTACGCTCC
      GTATAAACTT ACATAAATCT TTTTATTTGT TTATCGATCG AGTGAGCCAG CGATGCGAGG
6301  GGGCGTGAGA CTGCGGCGGG CGCTGCGGAC ACATACAAAG TTACCCACGA ATTCCGTGGA
      CCCGCACTCT GACGCCGCCC GCGACGCCTG TGTATGTTTC AATGGGTGCT TAAGGCACCT
6361  TAAGCAGGGG ACTAACATGT GAGGCAAAAC AGCAGGGCCG CGCCGGTGGC GTTTTTCCAT
      ATTCGTCCCC TGATTGTACA CTCCGTTTTG TCGTCCCGGC GCGGCCACCG CAAAAAGGTA
6421  AGGCTCCGCC CTCCTGCCAG AGTTCACATA AACAGACGCT TTTCCGGTGC ATCTGTGGGA
      TCCGAGGCGG GAGGACGGTC TCAAGTGTAT TTGTCTGCGA AAAGGCCACG TAGACACCCT
6481  GCCGTGAGGC TCAACCATGA ATCTGACAGT ACGGGCGAAA CCCGACAGGA CTTAAAGATC
      CGGCACTCCG AGTTGGTACT TAGACTGTCA TGCCCGCTTT GGGCTGTCCT GAATTTCTAG
6541  CCCACCGTTT CCGGCGGGTC GCTCCCTCTT GCGCTCTCCT GTTCCGACCC TGCCGTTTAC
      GGGTGGCAAA GGCCGCCCAG CGAGGGAGAA CGCGAGAGGA CAAGGCTGGG ACGGCAAATG
6601  CGGATACCTG TTCCGCCTTT CTCCCTTACG GGAAGTGTGG CGCTTTCTCA TAGCTCACAC
      GCCTATGGAC AAGGCGGAAA GAGGGAATGC CCTTCACACC GCGAAAGAGT ATCGAGTGTG
6661  ACTGGTATCT CGGCTCGGTG TAGGTCGTTC GCTCCAAGCT GGGCTGTAAG CAAGAACTCC
      TGACCATAGA GCCGAGCCAC ATCCAGCAAG CGAGGTTCGA CCCGACATTC GTTCTTGAGG
6721  CCGTTCAGCC CGACTGCTGC GCCTTATCCG GTAACTGTTC ACTTGAGTCC AACCCGGAAA
      GGCAAGTCGG GCTGACGACG CGGAATAGGC CATTGACAAG TGAACTCAGG TTGGGCCTTT
6781  AGCACGGTAA AACGCCACTG GCAGCAGCCA TTGGTAACTG GGAGTTCGCA GAGGATTTGT
      TCGTGCCATT TTGCGGTGAC CGTCGTCGGT AACCATTGAC CCTCAAGCGT CTCCTAAACA
6841  TTAGCTAAAC ACGCGGTTGC TCTTGAAGTG TGCGCCAAAG TCCGGCTACA CTGGAAGGAC
      AATCGATTTG TGCGCCAACG AGAACTTCAC ACGCGGTTTC AGGCCGATGT GACCTTCCTG
6901  AGATTTGGTT GCTGTGCTCT GCGAAAGCCA GTTACCACGG TTAAGCAGTT CCCCAACTGA
      TCTAAACCAA CGACACGAGA CGCTTTCGGT CAATGGTGCC AATTCGTCAA GGGGTTGACT
6961  CTTAACCTTC GATCAAACCA CCTCCCCAGG TGGTTTTTTC GTTTACAGGG CAAAAGATTA
      GAATTGGAAG CTAGTTTGGT GGAGGGGTCC ACCAAAAAAG CAAATGTCCC GTTTTCTAAT
7021  CGCGCAGAAA AAAAGGATCT CAAGAAGATC CTTTGATCTT TTCTACTGAA CCGCTCTAGA
      GCGCGTCTTT TTTTCCTAGA GTTCTTCTAG GAAACTAGAA AAGATGACTT GGCGAGATCT
7081  TTTCAGTGCA ATTTATCTCT TCAAATGTAG CACCTGAAGT CAGCCCCATA CGATATAAGT
      AAAGTCACGT TAAATAGAGA AGTTTACATC GTGGACTTCA GTCGGGGTAT GCTATATTCA
7141  TGTAATTCTC ATGTTAGTCA TGCCCCGCGC CCACCGGAAG GAGCTGACTG GGTTGAAGGC
      ACATTAAGAG TACAATCAGT ACGGGGCGCG GGTGGCCTTC CTCGACTGAC CCAACTTCCG
7201  TCTCAAGGGC ATCGGTCGAG ATCCCGGTGC CTAATGAGTG AGCTAACTTA CATTAATTGC
      AGAGTTCCCG TAGCCAGCTC TAGGGCCACG GATTACTCAC TCGATTGAAT GTAATTAACG
7261  GTTGCGCTCA CTGCCCGCTT TCCAGTCGGG AAACCTGTCG TGCCAGCTGC ATTAATGAAT
      CAACGCGAGT GACGGGCGAA AGGTCAGCCC TTTGGACAGC ACGGTCGACG TAATTACTTA
7321  CGGCCAACGC GCGGGGAGAG GCGGTTTGCG TATTGGGCGC CAGGGTGGTT TTTCTTTTCA
      GCCGGTTGCG CGCCCCTCTC CGCCAAACGC ATAACCCGCG GTCCCACCAA AAAGAAAAGT
7381  CCAGTGAGAC GGGCAACAGC TGATTGCCCT TCACCGCCTG GCCCTGAGAG AGTTGCAGCA
      GGTCACTCTG CCCGTTGTCG ACTAACGGGA AGTGGCGGAC CGGGACTCTC TCAACGTCGT
7441  AGCGGTCCAC GCTGGTTTGC CCCAGCAGGC GAAAATCCTG TTTGATGGTG GTTAACGGCG
      TCGCCAGGTG CGACCAAACG GGGTCGTCCG CTTTTAGGAC AAACTACCAC CAATTGCCGC
7501  GGATATAACA TGAGCTGTCT TCGGTATCGT CGTATCCCAC TACCGAGATG TCCGCACCAA
      CCTATATTGT ACTCGACAGA AGCCATAGCA GCATAGGGTG ATGGCTCTAC AGGCGTGGTT
7561  CGCGCAGCCC GGACTCGGTA ATGGCGCGCA TTGCGCCCAG CGCCATCTGA TCGTTGGCAA
      GCGCGTCGGG CCTGAGCCAT TACCGCGCGT AACGCGGGTC GCGGTAGCTA GCAACCGTT
7621  CCAGCATCGC AGTGGGAACG ATGCCCTCAT TCAGCATTTG CATGGTTTGT TGAAAACCGG
      GGTCGTAGCG TCACCCTTGC TACGGGAGTA AGTCGTAAAC GTACCAAACA ACTTTTGGCC
7681  ACATGGCACT CCAGTCGCCT TCCCGTTCCG CTATCGGCTG AATTTGATTG CGAGTGAGAT
```

Fig. 54₄

```
            TGTACCGTGA GGTCAGCGGA AGGGCAAGGC GATAGCCGAC TTAAACTAAC GCTCACTCTA
7741 ATTTATGCCA GCCAGCCAGA CGCAGACGCG CCGAGACAGA ACTTAATGGG CCCGCTAACA
     TAAATACGGT CGGTCGGTCT GCGTCTGCGC GGCTCTGTCT TGAATTACCC GGGCGATTGT
7801 GCGCGATTTG CTGGTGACCC AATGCGACCA GATGCTCCAC GCCCAGTCGC GTACCGTCTT
     CGCGCTAAAC GACCACTGGG TTACGCTGGT CTACGAGGTG CGGGTCAGCG CATGGCAGAA
7861 CATGGGAGAA AATAATACTG TTGATGGGTG TCTGGTCAGA GACATCAAGA AATAACGCCG
     GTACCCTCTT TTATTATGAC AACTACCCAC AGACCAGTCT CTGTAGTTCT TTATTGCGGC
7921 GAACATTAGT GCAGGCAGCT TCCACAGCAA TGGCATCCTG GTCATCCAGC GGATAGTTAA
     CTTGTAATCA CGTCCGTCGA AGGTGTCGTT ACCGTAGGAC CAGTAGGTCG CCTATCAATT
7981 TGATCAGCCC ACTGACGCGT TGCGCGAGAA GATTGTGCAC CGCCGCTTTA CAGGCTTCGA
     ACTAGTCGGG TGACTGCGCA ACGCGCTCTT CTAACACGTG GCGGCGAAAT GTCCGAAGCT
8041 CGCCGCTTCG TTCTACCATC GACACCACCA CGCTGGCACC CAGTTGATCG GCGCGAGATT
     GCGGCGAAGC AAGATGGTAG CTGTGGTGGT GCGACCGTGG GTCAACTAGC CGCGCTCTAA
8101 TAATCGCCGC GACAATTTGC GACGGCGCGT GCAGGGCCAG ACTGGAGGTG GCAACGCCAA
     ATTAGCGGCG CTGTTAAACG CTGCCGCGCA CGTCCCGGTC TGACCTCCAC CGTTGCGGTT
8161 TCAGCAACGA CTGTTTGCCC GCCAGTTGTT GTGCCACGCG GTTGGGAATG TAATTCAGCT
     AGTCGTTGCT GACAAACGGG CGGTCAACAA CACGGTGCGC CAACCCTTAC ATTAAGTCGA
8221 CCGCCATCGC CGCTTCCACT TTTTCCCGCG TTTTCGCAGA AACGTGGCTG GCCTGGTTCA
     GGCGGTAGCG GCGAAGGTGA AAAAGGGCGC AAAAGCGTCT TTGCACCGAC CGGACCAAGT
8281 CCACGCGGGA AACGGTCTGA TAAGAGACAC CGGCATACTC TGCGACATCG TATAACGTTA
     GGTGCGCCCT TTGCCAGACT ATTCTCTGTG GCCGTATGAG ACGCTGTAGC ATATTGCAAT
8341 CTGGTTTCAC ATTCACCACC CTGAATTGAC TCTCTTCCGG GCGCTATCAT GCCATACCGC
     GACCAAAGTG TAAGTGGTGG GACTTAACTG AGAGAAGGCC CGCGATAGTA CGGTATGGCG
8401 GAAAGGTTTT GCGCCATTCG ATGGTGTCCG GGATCTCGAC GCTCTCCCTT ATGCGACTCC
     CTTTCCAAAA CGCGGTAAGC TACCACAGGC CCTAGAGCTG CGAGAGGGAA TACGCTGAGG
8461 TGCATTAGGA AATTAATACG ACTCACTATA
     ACGTAATCCT TTAATTATGC TGAGTGATAT
```

Fig. 54₅

SEQUENCE LISTING

```
<160> NUMBER OF SEQ ID NOS: 45

<210> SEQ ID NO 1
<211> LENGTH: 5334
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 1
ggggaattgt gagcggataa caattcccct gtagaaataa ttttgtttaa ctttaataag      60
gagatatacc atggcacatc accaccacca tcacgtgggt accggttcga atgatgacga     120
cgacaaatca acaagtttgt acaaaaaagc tgaacgagaa acgtaaaatg atataaatat     180
caatatatta aattagattt tgcataaaaa acagactaca taatactgta aaacacaaca     240
tatccagtca tattggcggc cgcattaggc accccaggct ttacactta tgcttccggc      300 tcgtataatg tgtggatttt gagttaggat ccgtcgagat tttcaggagc taaggaagct     360
aaaatggaga aaaaaatcac tggatatacc accgttgata tatcccaatg gcatcgtaaa     420
gaacattttg aggcatttca gtcagttgct caatgtacct ataaccagac cgttcagctg     480
gatattacgg cctttttaaa gaccgtaaag aaaaataagc acaagtttta tccggccttt     540
attcacattc ttgcccgcct gatgaatgct catccggaat tccgtatggc aatgaaagac     600
ggtgagctgg tgatatggga tagtgttcac ccttgttaca ccgttttcca tgagcaaact     660
gaaacgtttt catcgctctg gagtgaatac cacgacgatt tccggcagtt tctacacata     720
tattcgcaag atgtggcgtg ttacggtgaa aacctggcct atttccctaa agggtttatt     780
gagaatatgt tttttcgtctc agccaatccc tgggtgagtt tcaccagttt tgatttaaac     840
gtggccaata tggacaactt cttcgccccc gttttcacca tgggcaaata ttatacgcaa     900
ggcgacaagg tgctgatgcc gctggcgatt caggttcatc atgccgtttg tgatggcttc     960
catgtcggca gaatgcttaa tgaattacaa cagtactgcg atgagtggca gggcggggcg    1020
taaagatctg gatccggctt actaaaagcc agataacagt atgcgtattt gcgcgctgat    1080
ttttgcggta taagaatata tactgatatg tatacccgaa gtatgtcaaa aagaggtatg    1140
ctatgaagca gcgtattaca gtgacagttg acagcgacag ctatcagttg ctcaaggcat    1200
atatgatgtc aatatctccg gtctggtaag cacaaccatg cagaatgaag cccgtcgtct    1260
gcgtgccgaa cgctggaaag cggaaaatca ggaagggatg gctgaggtcg cccggtttat    1320
tgaaatgaac ggctcttttg ctgacgagaa caggggctgg tgaaatgcag tttaaggttt    1380
acacctataa aagagagagc cgttatcgtc tgtttgtgga tgtacagagt gatattattg    1440
acacgcccgg gcgacggatg gtgatccccc tggccagtgc acgtctgctg tcagataaag    1500
tctcccgtga actttacccg gtggtgcata tcggggatga agctggcgc atgatgacca    1560
```

```
ccgatatggc cagtgtgccg gtctccgtta tcggggaaga agtggctgat ctcagccacc    1620
gcgaaaatga catcaaaaac gccattaacc tgatgttctg gggaatataa atgtcaggct    1680
cccttataca cagccagtct gcaggtcgac catagtgact ggatatgttg tgttttacag    1740
tattatgtag tctgtttttt atgcaaaatc taatttaata tattgatatt tatatcattt    1800
tacgtttctc gttcagcttt cttgtacaaa gtggttgatg agtccggatc ccaattggga    1860
gctcgtgtac acggcgcgcc tgcaggtcga caagcttgcg gccgcactcg agtctggtaa    1920
agaaaccgct gctgcgaaat tgaacgcca gcacatggac tcgtctacta gcgcagctta    1980
attaacctag gctgctgcca ccgctgagca ataactagca taaccccttg ggcctctaa    2040 acgggtcttg aggggttttt tgctgaaacc tcaggcattt gagaagcaca cggtcacact    2100
gcttccggta gtcaataaac cggtaaacca gcaatagaca taagcggcta tttaacgacc    2160
ctgccctgaa ccgacgaccg ggtcatcgtg gccggatctt gcggcccctc ggcttgaacg    2220
aattgttaga cattatttgc cgactacctt ggtgatctcg cctttcacgt agtggacaaa    2280
ttcttccaac tgatctgcgc gcgaggccaa gcgatcttct tcttgtccaa gataagcctg    2340
tctagcttca agtatgacgg gctgatactg ggccggcagg cgctccattg cccagtcggc    2400
agcgacatcc ttcggcgcga ttttgccggt tactgcgctg taccaaatgc gggacaacgt    2460
aagcactaca tttcgctcat cgccagccca gtcgggcggc gagttccata gcgttaaggt    2520
ttcatttagc gcctcaaata gatcctgttc aggaaccgga tcaaagagtt cctccgccgc    2580
tggacctacc aaggcaacgc tatgttctct tgcttttgtc agcaagatag ccagatcaat    2640
gtcgatcgtg gctggctcga agatacctgc aagaatgtca ttgcgctgcc attctccaaa    2700
ttgcagttcg cgcttagctg gataacgcca cggaatgatg tcgtcgtgca acaatggt     2760 gacttctaca gcgcggagaa tctcgctctc tccagggga gccgaagttt ccaaaaggtc    2820
gttgatcaaa gctcgccgcg ttgtttcatc aagccttacg gtcaccgtaa ccagcaaatc    2880
aatatcactg tgtggcttca ggccgccatc cactgcggag ccgtacaaat gtacggccag    2940
caacgtcggt tcgagatggc gctcgatgac gccaactacc tctgatagtt gagtcgatac    3000
ttcggcgatc accgcttccc tcatactctt cctttttcaa tattattgaa gcatttatca    3060
gggttattgt ctcatgagcg gatacatatt tgaatgtatt tagaaaaata aacaaatagc    3120
tagctcactc ggtcgctacg ctccgggcgt gagactgcgg cgggcgctgc ggacacatac    3180
aaagttaccc acagattccg tggataagca ggggactaac atgtgaggca aaacagcagg    3240
gccgcgccgg tggcgttttt ccataggctc cgccctcctg ccagagttca cataaacaga    3300
cgcttttccg gtgcatctgt gggagccgtg aggctcaacc atgaatctga cagtacgggc    3360
gaaacccgac aggacttaaa gatccccacc gtttccggcg gtcgctccc tcttgcgctc    3420 tcctgttccg accctgccgt ttaccggata cctgttccgc cttctcccct acgggaagt    3480 gtggcgcttt ctcatagctc acacactggt atctcggctc ggtgtaggtc gttcgctcca    3540
agctgggctg taagcaagaa ctccccgttc agcccgactg ctgcgcctta tccggtaact    3600
gttcacttga gtccaacccg gaaaagcacg gtaaaacgcc actggcagca gccattggta    3660
actgggagtt cgcagaggat tgtttagct aaacacgcgg ttgctcttga agtgtgcgcc    3720
aaagtccggc tacactggaa ggacagattt ggttgctgtg ctctgcgaaa gccagttacc    3780
acggttaagc agttccccaa ctgacttaac cttcgatcaa accacctccc caggtggttt    3840
tttcgtttac agggcaaaag attacgcgca gaaaaaagg atctcaagaa gatcctttga    3900 tctttttctac tgaaccgctc tagatttcag tgcaatttat ctcttcaaat gtagcacctg    3960
```

```
aagtcagccc catacgatat aagttgtaat tctcatgtta gtcatgcccc gcgcccaccg    4020
gaaggagctg actgggttga aggctctcaa gggcatcggt cgagatcccg gtgcctaatg    4080
agtgagctaa cttacattaa ttgcgttgcg ctcactgccc gctttccagt cgggaaacct    4140
gtcgtgccag ctgcattaat gaatcggcca acgcgcgggg agaggcggtt tgcgtattgg    4200
gcgccagggt ggttttctt ttcaccagtg agacgggcaa cagctgattg cccttcaccg     4260
cctggccctg agagagttgc agcaagcggt ccacgctggt ttgccccagc aggcgaaaat    4320
cctgtttgat ggtggttaac ggcgggatat aacatgagct gtcttcggta tcgtcgtatc    4380
ccactaccga gatgtccgca ccaacgcgca gcccggactc ggtaatggcg cgcattgcgc    4440
ccagcgccat ctgatcgttg gcaaccagca tcgcagtggg aacgatgccc tcattcagca    4500
tttgcatggt ttgttgaaaa ccggacatgg cactccagtc gccttccgt tccgctatcg     4560 gctgaatttg attgcgagtg agatatttat gccagccagc cagacgcaga cgcgccgaga    4620
cagaacttaa tgggcccgct aacagcgcga tttgctggtg acccaatgcg accagatgct    4680
ccacgcccag tcgcgtaccg tcttcatggg agaaataat actgttgatg ggtgtctggt      4740
cagagacatc aagaaataac gccggaacat tagtgcaggc agcttccaca gcaatggcat    4800
cctggtcatc cagcggatag ttaatgatca gcccactgac gcgttgcgcg agaagattgt    4860
gcaccgccgc tttacaggct tcgacgccgc ttcgttctac catcgacacc accacgctgg    4920
cacccagttg atcggcgcga gatttaatcg ccgcgacaat ttgcgacggc gcgtgcaggg    4980
ccagactgga ggtggcaacg ccaatcagca acgactgttt gcccgccagt tgttgtgcca    5040
cgcggttggg aatgtaattc agctccgcca tcgccgcttc cacttttcc cgcgttttcg      5100 cagaaacgtg gctggcctgg ttcaccacgc gggaaacggt ctgataagag acaccggcat    5160
actctgcgac atcgtataac gttactggtt tcacattcac caccctgaat tgactctctt    5220
ccgggcgcta tcatgccata ccgcgaaagg ttttgcgcca ttcgatggtg tccgggatct    5280
cgacgctctc ccttatgcga ctcctgcatt aggaaattaa tacgactcac tata           5334
```

<210> SEQ ID NO 2  
<211> LENGTH: 5230  
<212> TYPE: DNA  
<213> ORGANISM: Artificial Sequence  
<220> FEATURE:  
<223> OTHER INFORMATION: Description of Artificial Sequence: Synthetic vector nucleotide sequence

<400> SEQUENCE: 2

```
ggggaattgt gagcggataa caattcccct gtagaaataa ttttgtttaa ctttaataag      60
gagatatacc atggcacatc accaccacca tcacgtgggt accggttcga atgatgacga    120
cgacaagagc tcgatcacaa gtttgtacaa aaaagctgaa cgagaaacgt aaaatgatat    180
aaatatcaat atattaaatt agattttgca taaaaaacag actacataat actgtaaaac    240
acaacatatc cagtcactat ggcggccgcc acgttaaggg attttggtca tgatcagcac    300
gtgttgacaa ttaatcatcg gcatagtata tcggcatagt ataatacgac aaggtgagga    360
actaaaccat ggccaagttg accagtgccg ttccggtgct caccgcgcgc gacgtcgccg    420
gagcggtcga gttctggacc gaccggctcg gttctcccg ggacttcgtg gaggacgact     480
tcgccggtgt ggtccgggac gacgtgaccc tgttcatcag cgcggtccag gaccaggtgg    540
tgccggacaa caccctggcc tgggtgtggg tgcgcggcct ggacgagctg tacgccgagt    600
ggtcggaggt cgtgtccacg aacttccggg acgcctccgg gccggccatg accgagatcg    660
```

```
gcgagcagcc gtgggggcgg gagttcgccc tgcgcgaccc ggccggcaac tgcgtgcact    720
tcgtggccga ggagcaggac tgatcatgat gatattattt tatcttgtgc aatgtaacat    780
cagagatttt gagacacggg ccagagctgc aggaaacag ctatgaccat gtaatacgac    840
tcactatagg ggatatcagc tggatggcaa ataatgattt tattttgact gatagtgacc    900
tgttcgttgc aacaccggtg ctagcgtata cccgaagtat gtcaaaaaga ggtgtgctat    960
gaagcagcgt attacagtga cagttgacag cgacagctat cagttgctca aggcatatat   1020
gatgtcaata tctccggtct ggtaagcaca accatgcaga atgaagcccg tcgtctgcgt   1080
gccgaacgct ggaaagcgga aaatcaggaa gggatggctg aggtcgcccg gtttattgaa   1140
atgaacggct cttttgctga cgagaacagg gactggtgaa atgcagttta aggtttacac   1200
ctataaaaga gagagccgtt atcgtctgtt tgtggatgta cagagtgata ttattgacac   1260
gcccgggcga cggatggtga tcccctggc cagtgcacgt ctgctgtcag ataaagtctc   1320
ccgtgaactt acccggtgg tgcatatcgg ggatgaaagc tggcgcatga tgaccaccga   1380
tatggccagt gtgccggtct ccgttatcgg ggaagaagtg gctgatctca gccgccgcga   1440
aaatgacatc aaaaacgcca ttaacctgat gttctgggga atataaatgt caggctccct   1500
tatacacagc cagtctgcag gtcgaccata gtgactggat atgttgtgtt ttacagtatt   1560
atgtagtctg tttttatgc aaaatctaat ttaatatatt gatatttata tcattttacg   1620
tttctcgttc agctttcttg tacaaagtgg tgataattaa ttaagatcag atccggctgc   1680
taagcttgag tccggatccc aattgggagc tcgtgtacac ggcgcgcctg caggtcgaca   1740
agcttgcggc cgcactcgag tctggtaaag aaaccgctgc tgcgaaattt gaacgccagc   1800
acatggactc gtctactagc gcagcttaat taacctaggc tgctgccacc gctgagcaat   1860
aactagcata accccttggg gcctctaaac gggtcttgag gggttttttg ctgaaacctc   1920
aggcatttga gaagcacacg gtcacactgc ttccggtagt caataaaccg gtaaaccagc   1980
aatagacata agcggctatt taacgaccct gccctgaacc gacgacaagc tgacgaccgg   2040
gtctccgcaa gtggcacttt tcggggaaat gtgcgcggaa cccctatttg tttattttc   2100 taaatacatt caaatatgta tccgctcatg aattaattct tagaaaaact catcgagcat   2160
caaatgaaac tgcaatttat tcatatcagg attatcaata ccatattttt gaaaagccg   2220 tttctgtaat gaaggagaaa actcaccgag gcagttccat aggatggcaa gatcctggta   2280
tcggtctgcg attccgactc gtccaacatc aatacaacct attaatttcc cctcgtcaaa   2340
aataaggtta tcaagtgaga atcaccatg agtgacgact gaatccggtg agaatggcaa   2400
aagtttatgc atttctttcc agacttgttc aacaggccag ccattacgct cgtcatcaaa   2460
atcactcgca tcaaccaaac cgttattcat tcgtgattgc gcctgagcga gacgaaatac   2520
gcggtcgctg ttaaaaggac aattacaaac aggaatcgaa tgcaaccggc gcaggaacac   2580
tgccagcgca tcaacaatat tttcacctga atcaggatat tcttctaata cctggaatgc   2640
tgttttcccg gggatcgcag tggtgagtaa ccatgcatca tcaggagtac ggataaaatg   2700
cttgatggtc ggaagaggca taaattccgt cagccagttt agtctgacca tctcatctgt   2760
aacatcattg gcaacgctac cttttgccatg tttcagaaac aactctggcg catcgggctt   2820
cccatacaat cgatagattg tcgcacctga ttgcccgaca ttatcgcgag cccatttata   2880
cccatataaa tcagcatcca tgttggaatt taatcgcggc ctagagcaag acgtttcccg   2940
ttgaatatgg ctcatactct tcctttttca atattattga agcatttatc agggttattg   3000
tctcatgagc ggatacatat ttgaatgtat ttagaaaaat aaacaaatag gcatgcagcg   3060
```

-continued

```
ctcttccgct tcctcgctca ctgactcgct acgctcggtc gttcgactgc ggcgagcggt    3120
gtcagctcac tcaaaagcgg taatacggtt atccacagaa tcaggggata aagccggaaa    3180
gaacatgtga gcaaaaagca agcaccgga agaagccaac gccgcaggcg ttttccata     3240 ggctccgccc cctgacgag catcacaaaa atcgacgctc aagccagagg tggcgaaacc    3300
cgacaggact ataaagatac caggcgtttc cccctggaag ctccctcgtg cgctctcctg    3360
ttccgaccct gccgcttacc ggatacctgt ccgcctttct cccttcggga agcgtggcgc    3420
tttctcatag ctcacgctgt tggtatctca gttcggtgta ggtcgttcgc tccaagctgg    3480
gctgtgtgca cgaaccccc gttcagcccg accgctgcgc cttatccggt aactatcgtc    3540
ttgagtccaa cccggtaaga cacgacttat cgccactggc agcagccatt ggtaactgat    3600
ttagaggact ttgtcttgaa gttatgcacc tgttaaggct aaactgaaag aacagatttt    3660
ggtgagtgcg gtcctccaac ccacttacct tggttcaaag agttggtagc tcagcgaacc    3720
ttgagaaaac caccgttggt agcggtggtt tttctttatt tatgagatga tgaatcaatc    3780
ggtctatcaa gtcaacgaac agctattccg ttactctaga tttcagtgca atttatctct    3840
tcaaatgtag cacctgaagt cagccccata cgatataagt tgtaattctc atgttagtca    3900
tgccccgcgc ccaccggaag gagctgactg ggttgaaggc tctcaagggc atcggtcgag    3960
atcccggtgc ctaatgagtg agctaactta cattaattgc gttgcgctca ctgcccgctt    4020
tccagtcggg aaacctgtcg tgccagctgc attaatgaat cggccaacgc gcggggagag    4080
gcggtttgcg tattgggcgc cagggtggtt tttcttttca ccagtgagac gggcaacagc    4140
tgattgccct tcaccgcctg gccctgagag agttgcagca agcggtccac gctggtttgc    4200
cccagcaggc gaaaatcctg tttgatggtg gttaacggcg ggatataaca tgagctgtct    4260
tcggtatcgt cgtatcccac taccgagatg tccgcaccaa cgcgcagccc ggactcggta    4320
atggcgcgca ttgcgcccag cgccatctga tcgttggcaa ccagcatcgc agtgggaacg    4380
atgccctcat tcagcatttg catggtttgt tgaaaaccgg acatggcact ccagtcgcct    4440
tcccgttccg ctatcggctg aatttgattg cgagtgagat attttatgcca gccagccaga    4500 cgcagacgcg ccgagacaga acttaatggg cccgctaaca gcgcgatttg ctggtgaccc    4560
aatgcgacca gatgctccac gcccagtcgc gtaccgtctt catgggagaa aataatactg    4620
ttgatgggtg tctggtcaga gacatcaaga ataacgccg gaacattagt gcaggcagct    4680
tccacagcaa tggcatcctg gtcatccagc ggatagttaa tgatcagccc actgacgcgt    4740
tgcgcgagaa gattgtgcac cgccgcttta caggcttcga cgccgcttcg ttctaccatc    4800
gacaccacca cgctggcacc cagttgatcg cgcgagatt taatcgccgc gacaatttgc    4860
gacggcgcgt gcagggccag actggaggtg caacgccaa tcagcaacga ctgtttgccc    4920
gccagttgtt gtgccacgcg gttgggaatg taattcagct ccgccatcgc cgcttccact    4980
ttttcccgcg ttttcgcaga aacgtggctg gcctggttca ccacgcggga aacggtctga    5040
taagagacac cggcatactc tgcgacatcg tataacgtta ctggtttcac attcaccacc    5100
ctgaattgac tctcttccgg cgctatcat gccataccgc gaaaggtttt gcgccattcg    5160
atggtgtccg ggatctcgac gctctccctt atgcgactcc tgcattagga aattaatacg    5220
actcactata                                                         5230
```

<210> SEQ ID NO 3
<211> LENGTH: 5538
<212> TYPE: DNA
<213> ORGANISM: Artificial Sequence
<220> FEATURE:

<223> OTHER INFORMATION: Description of Artificial Sequence: Synthetic vector nucleotide sequence

<400> SEQUENCE: 3

```
ggggaattgt gagcggataa caattcccct gtagaaataa ttttgtttaa ctttaataag      60
gagatatacc atgggcagca gccatcacca tcatcaccac agccaggatc cgaattcgag     120
ctcgatcaca agtttgtaca aaaaagctga acgagaaacg taaaatgata taaatatcaa     180
tatattaaat tagattttgc ataaaaaaca gactacataa tactgtaaaa cacaacatat     240
ccagtcacta tggcggccgc cacgttaagg gattttggtc atgatcagca cgtgttgaca     300
attaatcatc ggcatagtat atcggcatag tataatacga caaggtgagg aactaaacca     360
tggccaagtt gaccagtgcc gttccggtgc tcaccgcgcg cgacgtcgcc ggagcggtcg     420
agttctggac cgaccggctc gggttctccc gggacttcgt ggaggacgac ttcgccggtg     480
tggtccggga cgacgtgacc ctgttcatca gcgcggtcca ggaccaggtg gtgccggaca     540
acaccctggc ctgggtgtgg gtgcgcgcc tggacgagct gtacgccgag tggtcggagg     600
tcgtgtccac gaacttccgg gacgcctccg ggccggccat gaccgagatc ggcgagcagc     660
cgtgggggcg ggagttcgcc ctgcgcgacc cggccggcaa ctgcgtgcac ttcgtggccg     720
aggagcagga ctgatcatga tgatattatt ttatcttgtg caatgtaaca tcagagattt     780
tgagacacgg gccagagctg ccaggaaaca gctatgacca tgtaatacga ctcactatag     840
gggatatcag ctggatggca ataatgatt ttattttgac tgatagtgac ctgttcgttg     900
caacaccggt gctagcgtat acccgaagta tgtcaaaaag aggtgtgcta tgaagcagcg     960
tattacagtg acagttgaca gcgacagcta tcagttgctc aaggcatata tgatgtcaat    1020
atctccggtc tggtaagcac aaccatgcag aatgaagccc gtcgtctgcg tgccgaacgc    1080
tggaaagcgg aaaatcagga agggatggct gaggtcgccc ggtttattga aatgaacggc    1140
tcttttgctg acgagaacag ggactggtga atgcagttt aaggtttaca cctataaaag    1200
agagagccgt tatcgtctgt ttgtggatgt acagagtgat attattgaca cgcccgggcg    1260
acggatggta atcccctgg ccagtgcacg tctgctgtca gataaagtct cccgtgaact    1320
taccccggtg gtgcatatcg gggatgaaag ctggcgcatg atgaccaccg atatggccag    1380
tgtgccggtc tccgttatcg gggaagaagt ggctgatctc agccgccgcg aaaatgacat    1440
caaaaacgcc attaacctga tgttctgggg aatataaatg tcaggctccc ttatacacag    1500
ccagtctgca ggtcgaccat agtgactgga tatgttgtgt tttacagtat tatgtagtct    1560
gttttttatg caaaatctaa tttaatatat tgatatttat atcatttac gtttctcgtt    1620
cagctttctt gtacaaagtg gtgataatta attaagatca gatccggctg ctaagcttgc    1680
ggccgcataa tgcttaagtc gaacagaaag taatcgtatt gtacacggcc gcataatcga    1740
aattaatacg actcactata ggggaattgt gagcggataa caattcccca tcttagtata    1800
ttagttaagt ataagaagga gatatacata tggcagatct caattggata tcggccggcc    1860
acgcgatcgc tgacgtcggt accctcgagt ctggtaaaga accgctgct gcgaatttg    1920
aacgccagca catggactcg tctactagcg cagcttaatt aacctaggct gctgccaccg    1980
ctgagcaata actagcataa cccttgggg cctctaaacg ggtcttgagg gttttttgc    2040
tgaaacctca ggcatttgag aagcacacgg tcacactgct tccggtagtc aataaaccgg    2100
taaaccagca atagacataa gcggctattt aacgaccctg ccctgaaccg acgaccgggt    2160
cgaatttgct ttcgaatttc tgccattcat ccgcttatta tcacttattc aggcgtagca    2220
ccaggcgttt aagggcacca ataactgcct taaaaaaatt acgccccgcc ctgccactca    2280
```

```
tcgcagtact gttgtaattc attaagcatt ctgccgacat ggaagccatc acagacggca    2340
tgatgaacct gaatcgccag cggcatcagc accttgtcgc cttgcgtata atatttgccc    2400
atagtgaaaa cggggggcgaa gaagttgtcc atattggcca cgtttaaatc aaaactggtg   2460
aaactcaccc agggattggc tgagacgaaa aacatattct caataaaccc tttagggaaa    2520
taggccaggt tttcaccgta acacgccaca tcttgcgaat atatgtgtag aaactgccgg    2580
aaatcgtcgt ggtattcact ccagagcgat gaaaacgttt cagtttgctc atggaaaacg    2640
gtgtaacaag ggtgaacact atcccatatc accagctcac cgtctttcat tgccatacgg    2700
aactccggat gagcattcat caggcgggca agaatgtgaa taaaggccgg ataaaacttg    2760
tgcttatttt tctttacggt ctttaaaaag gccgtaatat ccagctgaac ggtctggtta    2820
taggtacatt gagcaactga ctgaaatgcc tcaaaatgtt ctttacgatg ccattgggat    2880
atatcaacgg tggtatatcc agtgattttt ttctccattt tagcttcctt agctcctgaa    2940
aatctcgata actcaaaaaa tacgcccggt agtgatctta tttcattatg gtgaaagttg    3000
gaacctctta cgtgccgatc aacgtctcat tttcgccaaa agttggccca gggcttcccg    3060
gtatcaacag gacaccagg atttatttat tctgcgaagt gatcttccgt cacaggtatt    3120
tattcggcgc aaagtgcgtc gggtgatgct gccaacttac tgatttagtg tatgatggtg    3180
tttttgaggt gctccagtgg cttctgtttc tatcagctgt ccctcctgtt cagctactga    3240
cggggtggtg cgtaacggca aaagcaccgc cggacatcag cgctagcgga gtgtatactg    3300
gcttactatg ttggcactga tgagggtgtc agtgaagtgc ttcatgtggc aggagaaaaa    3360
aggctgcacc ggtgcgtcag cagaatatgt gatacaggat atattccgct tcctcgctca    3420
ctgactcgct acgctcggtc gttcgactgc ggcgagcgga atggcttac gaacggggcg    3480 gagatttcct ggaagatgcc aggaagatac ttaacaggga agtgagaggg ccgcggcaaa    3540 gccgttttc cataggctcc gccccctga caagcatcac gaaatctgac gctcaaatca    3600
gtggtggcga aacccgacag gactataaag ataccaggcg tttccctgg cggctccctc     3660 gtgcgctctc ctgttcctgc ctttcggttt accggtgtca ttccgctgtt atggccgcgt    3720
ttgtctcatt ccacgcctga cactcagttc cgggtaggca gttcgctcca agctggactg    3780
tatgcacgaa ccccccgttc agtccgaccg ctgcgcctta tccggtaact atcgtcttga    3840
gtccaacccg gaaagacatg caaaagcacc actggcagca gccactggta attgatttag    3900
aggagttagt cttgaagtca tgcgccggtt aaggctaaac tgaaaggaca gttttggtg    3960 actgcgctcc tccaagccag ttacctcggt tcaaagagtt ggtagctcag agaaccttcg    4020
aaaaaccgcc ctgcaaggcg gttttttcgt tttcagagca agagattacg cgcagaccaa    4080
aacgatctca agaagatcat cttattaatc agataaaata tttctagatt tcagtgcaat    4140
ttatctcttc aaatgtagca cctgaagtca gccccatacg atataagttg taattctcat    4200
gttagtcatg ccccgcgccc accggaagga gctgactggg ttgaaggctc tcaagggcat    4260
cggtcgagat cccggtgcct aatgagtgag ctaacttaca ttaattgcgt tgcgctcact    4320
gcccgctttc cagtcgggaa acctgtcgtg ccagctgcat taatgaatcg ccaacgcgc    4380 ggggagaggc ggtttgcgta ttgggcgcca gggtggtttt tcttttcacc agtgagacgg    4440
gcaacagctg attgcccttc accgcctggc cctgagagag ttgcagcaag cggtccacgc    4500
tggtttgccc cagcaggcga aaatcctgtt tgatggtggt taacggcggg atataacatg    4560
agctgtcttc ggtatcgtcg tatcccacta ccgagatgtc cgcaccaacg cgcagcccgg    4620
actcggtaat ggcgcgcatt gcgcccagcg ccatctgatc gttggcaacc agcatcgcag    4680
```

```
tgggaacgat gccctcattc agcatttgca tggtttgttg aaaaccggac atggcactcc    4740
agtcgccttc ccgttccgct atcggctgaa tttgattgcg agtgagatat ttatgccagc    4800
cagccagacg cagacgcgcc gagacagaac ttaatgggcc cgctaacagc gcgatttgct    4860
ggtgacccaa tgcgaccaga tgctccacgc ccagtcgcgt accgtcttca tgggagaaaa    4920
taatactgtt gatgggtgtc tggtcagaga catcaagaaa taacgccgga acattagtgc    4980
aggcagcttc cacagcaatg gcatcctggt catccagcgg atagttaatg atcagcccac    5040
tgacgcgttg cgcgagaaga ttgtgcaccc ccgctttaca ggcttcgacg ccgcttcgtt    5100
ctaccatcga caccaccacg ctggcaccca gttgatcggc gcgagattta atcgccgcga    5160
caatttgcga cggcgcgtgc agggccgact ggaggtggc aacgccaatc agcaacgact    5220
gtttgcccgc cagttgttgt gccacgcggt tgggaatgta attcagctcc gccatcgccg    5280
cttccacttt ttcccgcgtt ttcgcagaaa cgtggctggc ctggttcacc acgcgggaaa    5340
cggtctgata agagacaccg gcatactctg cgacatcgta taacgttact ggtttcacat    5400
tcaccaccct gaattgactc tcttccgggc gctatcatgc cataccgcga aaggttttgc    5460
gccattcgat ggtgtccggg atctcgacgc tctcccttat gcgactcctg cattaggaaa    5520
ttaatacgac tcactata                                                 5538

<210> SEQ ID NO 4
<211> LENGTH: 1561
<212> TYPE: DNA
<213> ORGANISM: Artificial Sequence
<220> FEATURE:
<223> OTHER INFORMATION: Description of Artificial Sequence: Synthetic
      vector nucleotide sequence
<220> FEATURE:
<221> NAME/KEY: CDS
<222> LOCATION: (243)..(614)

<400> SEQUENCE: 4
gagctcgatc acaagtttgt acaaaaaagc tgaacgagaa acgtaaaatg atataaatat    60
caatatatta aattagattt tgcataaaaa acagactaca taatactgta aaacacaaca   120
tatccagtca ctatggcggc cgccacgtta agggattttg gtcatgatca gcacgtgttg   180
acaattaatc atcggcatag tatatcggca tagtataata cgacaaggtg aggaactaaa   240 cc atg gcc aag ttg acc agt gcc gtt ccg gtg ctc acc gcg cgc gac       287
   Met Ala Lys Leu Thr Ser Ala Val Pro Val Leu Thr Ala Arg Asp
   1               5                   10                  15 gtc gcc gga gcg gtc gag ttc tgg acc gac cgg ctc ggg ttc tcc cgg      335
Val Ala Gly Ala Val Glu Phe Trp Thr Asp Arg Leu Gly Phe Ser Arg
                20                  25                  30 gac ttc gtg gag gac gac ttc gcc ggt gtg gtc cgg gac gac gtg acc      383
Asp Phe Val Glu Asp Asp Phe Ala Gly Val Val Arg Asp Asp Val Thr
            35                  40                  45 ctg ttc atc agc gcg gtc cag gac cag gtg gtg ccg gac aac acc ctg      431
Leu Phe Ile Ser Ala Val Gln Asp Gln Val Val Pro Asp Asn Thr Leu
        50                  55                  60 gcc tgg gtg tgg gtg cgc ggc ctg gac gag ctg tac gcc gag tgg tcg      479
Ala Trp Val Trp Val Arg Gly Leu Asp Glu Leu Tyr Ala Glu Trp Ser
    65                  70                  75 gag gtc gtg tcc acg aac ttc cgg gac gcc tcc ggg ccg gcc atg acc      527
Glu Val Val Ser Thr Asn Phe Arg Asp Ala Ser Gly Pro Ala Met Thr
80                  85                  90                  95 gag atc ggc gag cag ccg tgg ggg cgg gag ttc gcc ctg cgc gac ccg      575
Glu Ile Gly Glu Gln Pro Trp Gly Arg Glu Phe Ala Leu Arg Asp Pro
                100                 105                 110
```

```
gcc ggc aac tgc gtg cac ttc gtg gcc gag gag cag gac tgatcatgat       624
Ala Gly Asn Cys Val His Phe Val Ala Glu Glu Gln Asp
            115                 120
gatattattt tatcttgtgc aatgtaacat cagagatttt gagacacggg ccagagctgc    684
caggaaacag ctatgaccat gtaatacgac tcactatagg ggatatcagc tggatggcaa    744
ataatgattt tattttgact gatagtgacc tgttcgttgc aacaccggtg ctagcgtata    804
cccgaagtat gtcaaaaaga ggtgtgctat gaagcagcgt attacagtga cagttgacag    864
cgacagctat cagttgctca aggcatatat gatgtcaata tctccggtct ggtaagcaca    924
accatgcaga atgaagcccg tcgtctgcgt gccgaacgct ggaaagcgga aaatcaggaa    984
gggatggctg aggtcgcccg gtttattgaa atgaacggct cttttgctga cgagaacagg   1044
gactggtgaa atgcagttta aggtttacac ctataaaaga gagagccgtt atcgtctgtt   1104
tgtggatgta cagagtgata ttattgacac gcccgggcga cggatggtga tccccctggc   1164
cagtgcacgt ctgctgtcag ataaagtctc ccgtgaactt tacccggtgg tgcatatcgg   1224
ggatgaaagc tggcgcatga tgaccaccga tatggccagt gtgccggtct ccgttatcgg   1284
ggaagaagtg gctgatctca gccgccgcga aaatgacatc aaaaacgcca ttaacctgat   1344
gttctgggga atataaatgt caggctccct tatacacagc cagtctgcag gtcgaccata   1404
gtgactggat atgttgtgtt ttacagtatt atgtagtctg tttttttatgc aaaatctaat   1464
ttaatatatt gatatttata tcattttacg tttctcgttc agctttcttg tacaaagtgg   1524
tgataattaa ttaagatcag atccggctgc taagctt                            1561

<210> SEQ ID NO 5
<211> LENGTH: 5567
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 5
ggggaattgt gagcggataa caattcccct gtagaaataa ttttgtttaa ctttaataag     60
gagatatacc atgggcagca gccatcacca tcatcaccac agccaggatc cgaattcgag    120
ctcggaccat gattacgcca agctatcaac tttgtataga aaagttgaac gagaaacgta    180
aaatgatata aatatcaata tattaaatta gattttgcat aaaaaacaga ctacataata    240
ctgtaaaaca caacatatcc agtcactatg gtcgacctgc agactggctg tgtataaggg    300
agcctgacat ttatattccc cagaacatca ggttaatggc gtttttgatg tcattttcgc    360
ggtggctgag atcagccact tcttccccga taacggagac cggcacactg gccatatcgg    420
tggtcatcat gcgccagctt tcatccccga tatgcaccac cgggtaaagt tcacggggga    480
ctttatctga cagcagacgt gcactggcca gggggatcac catccgtcgc ccgggcgtgt    540
caataatatc actctgtaca tccacaaaca gacgataacg gctctctctt ttataggtgt    600
aaaccttaaa ctgcatttca ccagcccctg ttctcgtcgg caaaagagcc gttcatttca    660
ataaaccggg cgacctcagc catcccttcc tgattttccg ctttccagcg ttcggcacgc    720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc ctctagatta    960
```

```
cgccccgccc tgccactcat cgcagtactg ttgtaattca ttaagcattc tgccgacatg   1020
gaagccatca caaacggcat gatgaacctg aatcgccagc ggcatcagca ccttgtcgcc   1080
ttgcgtataa tatttgccca tggtgaaaac ggggggcgaag aagttgtcca tattggccac  1140
gtttaaatca aaactggtga aactcaccca gggattggct gagacgaaaa acatattctc   1200
aataaaccct ttagggaaat aggccaggtt ttcaccgtaa cacgccacat cttgcgaata   1260
tatgtgtaga aactgccgga aatcgtcgtg gtattcactc cagagcgatg aaaacgtttc   1320
agtttgctca tggaaaacgg tgtaacaagg gtgaacacta tcccatatca ccagctcacc   1380
gtctttcatt gccatacgga attccggatg agcattcatc aggcgggcaa gaatgtgaat   1440
aaaggccgga taaaacttgt gcttattttt ctttacggtc tttaaaaagg ccgtaatatc   1500
cagctgaacg gtctggttat aggtacattg agcaactgac tgaaatgcct caaaatgttc   1560
tttacgatgc cattgggata tatcaacggt ggtatatcca gtgatttttt tctccatttt   1620
agcttcctta gctcctgaaa atctcgacgg atcctaactc aaaatccaca cattatacga   1680
gccggaagca taaagtgtaa agcctggggg tgcctaatgc ggccgccata gtgactggat   1740
atgttgtgtt ttacagtatt atgtagtctg tttttttatgc aaaatctaat ttaatatatt   1800
gatatttata tcattttacg tttctcgttc aactttatta tacatagttg ataattcact   1860
ggccgtcgtt ttacaacgtc gtgactggga aaaccctggc gttacccaac ttaatcgcct   1920
tgcagcacaa gcttgcggcc gcataatgct taagtcgaac agaaagtaat cgtattgtac   1980
acggccgcat aatcgaaatt aatacgactc actataggg aattgtgagc ggataacaat   2040
tccccatctt agtatattag ttaagtataa gaaggagata tacatatggc agatctcaat   2100
tggatatcgg ccggccacgc gatcgctgac gtcggtaccc tcgagtctgg taaagaaacc   2160
gctgctgcga atttgaacg ccagcacatg gactcgtcta ctagcgcagc ttaattaacc   2220
taggctgctg ccaccgctga gcaataacta gcataacccc ttggggcctc taaacgggtc   2280
ttgaggggtt ttttgctgaa acctcaggca tttgagaagc acacggtcac actgcttccg   2340
gtagtcaata aaccggtaaa ccagcaatag acataagcgg ctatttaacg accctgccct   2400
gaaccgacga ccgggtcatc gtggccggat cttgcggccc ctcggcttga acgaattgtt   2460
agacattatt tgccgactac cttggtgatc tcgcctttca cgtagtggac aaattcttcc   2520
aactgatctg cgcgcgaggc caagcgatct tcttcttgtc caagataagc ctgtctagct   2580
tcaagtatga cgggctgata ctgggccggc aggcgctcca ttgcccagtc ggcagcgaca   2640
tccttcggcg cgattttgcc ggttactgcg ctgtaccaaa tgcgggacaa cgtaagcact   2700
acatttcgct catcgccagc ccagtcgggc ggcgagttcc atagcgttaa ggtttcattt   2760
agcgcctcaa atagatcctg ttcaggaacc ggatcaaaga gttcctccgc cgctggacct   2820
accaaggcaa cgctatgttc tcttgctttt gtcagcaaga tagccagatc aatgtcgatc   2880
gtggctggct cgaagatacc tgcaagaatg tcattgcgct gccattctcc aaattgcagt   2940
tcgcgcttag ctggataacg ccacggaatg atgtcgtcgt gcacaacaat ggtgacttct   3000
acagcgcgga gaatctcgct ctctccaggg gaagccgaag tttccaaaag gtcgttgatc   3060
aaagctcgcc gcgttgtttc atcaagcctt acggtcaccg taaccagcaa atcaatatca   3120
ctgtgtggct tcaggccgcc atccactgcg gagccgtaca aatgtacggc cagcaacgtc   3180
ggttcgagat ggcgctcgat gacgccaact acctctgata gttgagtcga tacttcggcg   3240
atcaccgctt ccctcatact cttcctttt caatattatt gaagcattta tcagggttat   3300
tgtctcatga gcggatacat atttgaatgt atttagaaaa ataaacaaat agctagctca   3360
```

```
ctcggtcgct acgctccggg cgtgagactg cggcgggcgc tgcggacaca tacaaagtta    3420
cccacagatt ccgtggataa gcaggggact aacatgtgag gcaaaacagc agggccgcgc    3480
cggtggcgtt tttccatagg ctccgccctc ctgccagagt tcacataaac agacgctttt    3540
ccggtgcatc tgtgggagcc gtgaggctca accatgaatc tgacagtacg ggcgaaaccc    3600
gacaggactt aaagatcccc accgtttccg gcgggtcgct ccctcttgcg ctctcctgtt    3660
ccgaccctgc cgtttaccgg atacctgttc cgcctttctc ccttacggga agtgtggcgc    3720
tttctcatag ctcacacact ggtatctcgg ctcggtgtag gtcgttcgct ccaagctggg    3780
ctgtaagcaa gaactcccg ttcagcccga ctgctgcgcc ttatccggta actgttcact    3840
tgagtccaac ccggaaaagc acggtaaaac gccactggca gcagccattg gtaactggga    3900
gttcgcagag gatttgttta gctaaacacg cggttgctct tgaagtgtgc gccaaagtcc    3960
ggctacactg gaaggacaga tttggttgct gtgctctgcg aaagccagtt accacggtta    4020
agcagttccc caactgactt aaccttcgat caaaccacct ccccaggtgg ttttttcgtt    4080
tacagggcaa aagattacgc gcagaaaaaa aggatctcaa gaagatcctt tgatcttttc    4140
tactgaaccg ctctagattt cagtgcaatt tatctcttca aatgtagcac ctgaagtcag    4200
ccccatacga tataagttgt aattctcatg ttagtcatgc cccgcgccca ccggaaggag    4260
ctgactgggt tgaaggctct caagggcatc ggtcgagatc ccggtgccta atgagtgagc    4320
taacttacat taattgcgtt gcgctcactg cccgctttcc agtcgggaaa cctgtcgtgc    4380
cagctgcatt aatgaatcgg ccaacgcgcg gggagaggcg gtttgcgtat tgggcgccag    4440
ggtggttttt cttttcacca gtgagacggg caacagctga ttgcccttca ccgcctggcc    4500
ctgagagagt tgcagcaagc ggtccacgct ggtttgcccc agcaggcgaa aatcctgttt    4560
gatggtggtt aacggcggga tataacatga gctgtcttcg gtatcgtcgt atcccactac    4620
cgagatgtcc gcaccaacgc gcagcccgga ctcggtaatg gcgcgcattg cgcccagcgc    4680
catctgatcg ttggcaacca gcatcgcagt gggaacgatg ccctcattca gcatttgcat    4740
ggtttgttga aaaccggaca tggcactcca gtcgccttcc cgttccgcta tcggctgaat    4800
ttgattgcga gtgagatatt tatgccagcc agccagacgc agacgcgccg agacagaact    4860
taatgggccc gctaacagcg cgatttgctg gtgacccaat gcgaccagat gctccacgcc    4920
cagtcgcgta ccgtcttcat gggagaaaat aatactgttg atgggtgtct ggtcagagac    4980
atcaagaaat aacgccggaa cattagtgca ggcagcttcc acagcaatgg catcctggtc    5040
atccagcgga tagttaatga tcagcccact gacgcgttgc gcgagaagat tgtgcaccgc    5100
cgctttacag gcttcgacgc cgcttcgttc taccatcgac accaccacgc tggcacccag    5160
ttgatcggcg cgagatttaa tcgccgcgac aatttgcgac ggcgcgtgca gggccagact    5220
ggaggtggca acgccaatca gcaacgactg tttgcccgcc agttgttgtg ccacgcggtt    5280
gggaatgtaa ttcagctccg ccatcgccgc ttccactttt tcccgcgttt tcgcagaaac    5340
gtggctggcc tggttcacca cgcgggaaac ggtctgataa gagacaccgg catactctgc    5400
gacatcgtat aacgttactg gtttcacatt caccaccctg aattgactct cttccgggcg    5460
ctatcatgcc ataccgcgaa aggttttgcg ccattcgatg gtgtccggga tctcgacgct    5520
ctcccttatg cgactcctgc attaggaaat taatacgact cactata              5567
```

<210> SEQ ID NO 6
<211> LENGTH: 5615
<212> TYPE: DNA
<213> ORGANISM: Artificial Sequence
<220> FEATURE:

<223> OTHER INFORMATION: Description of Artificial Sequence: Synthetic vector nucleotide sequence

<400> SEQUENCE: 6

```
ggggaattgt gagcggataa caattcccct gtagaaataa ttttgtttaa ctttaataag      60
gagatatacc atgggcagca gccatcacca tcatcaccac agccaggatc cgaattcgag     120
ctcggaccat gattacgcca agctatcaac tttgtataga aaagttgaac gagaaacgta     180
aaatgatata aatatcaata tattaaatta gattttgcat aaaaaacaga ctacataata     240
ctgtaaaaca caacatatcc agtcactatg gtcgacctgc agactggctg tgtataaggg     300
agcctgacat ttatattccc cagaacatca ggttaatggc gttttttgatg tcattttcgc    360
ggtggctgag atcagccact tcttccccga taacggagac cggcacactg gccatatcgg    420
tggtcatcat gcgccagctt tcatcccccga tatgcaccac cgggtaaagt tcacggggga   480
ctttatctga cagcagacgt gcactggcca ggggggatcac catccgtcgc ccgggcgtgt    540
caataatatc actctgtaca tccacaaaca gacgataacg gctctctctt ttataggtgt    600
aaaccttaaa ctgcatttca ccagcccctg ttctcgtcgg caaaagagcc gttcatttca    660
ataaaccggg cgacctcagc catcccttcc tgattttccg ctttccagcg ttcggcacgc    720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc tctagatta    960
cgccccgccc tgccactcat cgcagtactg ttgtaattca ttaagcattc tgccgacatg   1020
gaagccatca caaacggcat gatgaacctg aatcgccagc ggcatcagca ccttgtcgcc   1080
ttgcgtataa tatttgccca tggtgaaaac gggggcgaag aagttgtcca tattggccac   1140
gtttaaatca aaactggtga aactcaccca gggattggct gagacgaaaa acatattctc   1200
aataaaccct ttagggaaat aggccaggtt ttcaccgtaa cacgccacat cttgcgaata   1260
tatgtgtaga aactgccgga atcgtcgtg gtattcactc cagagcgatg aaaacgtttc   1320
agtttgctca tggaaaacgg tgtaacaagg gtgaacacta tcccatatca ccagctcacc   1380
gtctttcatt gccatacgga attccggatg agcattcatc aggcgggcaa gaatgtgaat   1440
aaaggccgga taaaacttgt gcttattttt ctttacggtc tttaaaaagg ccgtaatatc   1500
cagctgaacg gtctggttat aggtacattg agcaactgac tgaaatgcct caaaatgttc   1560
tttacgatgc cattgggata tatcaacggt ggtatatcca gtgatttttt tctccatttt   1620
agcttcctta gctcctgaaa atctcgacgg atcctaactc aaaatccaca cattatacga   1680
gccggaagca taaagtgtaa agcctggggg tgcctaatgc ggccgccata gtgactggat   1740
atgttgtgtt ttacagtatt atgtagtctg tttttatgc aaaatctaat ttaatatatt   1800
gatatttata tcattttacg tttctcgttc aactttatta tacatagttg ataattcact   1860
ggccgtcgtt ttacaacgtc gtgactggga aaaccctggc gttacccaac ttaatcgcct   1920
tgcagcacaa gcttgcggcc gcataatgct taagtcgaac agaaagtaat cgtattgtac   1980
acggccgcat aatcgaaatt aatacgactc actatagggg aattgtgagc ggataacaat   2040
tcccatcatt agtatattag ttaagtataa gaaggagata tacatatggc agatctcaat   2100
tggatatcgg ccggccacgc gatcgctgac gtcggtaccc tcgagtctgg taaagaaacc   2160
gctgctgcga aatttgaacg ccagcacatg gactcgtcta ctagcgcagc ttaattaacc   2220
taggctgctg ccaccgctga gcaataacta gcataacccc ttggggcctc taaacgggtc   2280
```

```
ttgaggggtt ttttgctgaa acctcaggca tttgagaagc acacggtcac actgcttccg    2340
gtagtcaata aaccggtaaa ccagcaatag acataagcgg ctatttaacg accctgccct    2400
gaaccgacga caagctgacg accgggtctc cgcaagtggc acttttcggg gaaatgtgcg    2460
cggaacccct atttgtttat ttttctaaat acattcaaat atgtatccgc tcatgaatta    2520
attcttagaa aaactcatcg agcatcaaat gaaactgcaa tttattcata tcaggattat    2580
caataccata ttttgaaaa agccgtttct gtaatgaagg agaaaactca ccgaggcagt     2640
tccataggat ggcaagatcc tggtatcggt ctgcgattcc gactcgtcca acatcaatac    2700
aacctattaa tttccctcg tcaaaaataa ggttatcaag tgagaaatca ccatgagtga     2760
cgactgaatc cggtgagaat ggcaaaagtt tatgcatttc tttccagact tgttcaacag    2820
gccagccatt acgctcgtca tcaaaatcac tcgcatcaac caaaccgtta ttcattcgtg    2880
attgcgcctg agcgagacga atacgcggt cgctgttaaa aggacaatta caaacaggaa     2940
tcgaatgcaa ccgcgcagg aacactgcca gcgcatcaac aatattttca cctgaatcag     3000
gatattcttc taatacctgg aatgctgttt tcccggggat cgcagtggtg agtaaccatg    3060
catcatcagg agtacggata aaatgcttga tggtcggaag aggcataaat tccgtcagcc    3120
agtttagtct gaccatctca tctgtaacat cattggcaac gctacctttg ccatgtttca    3180
gaaacaactc tggcgcatcg ggcttcccat acaatcgata gattgtcgca cctgattgcc    3240
cgacattatc gcgagcccat ttatacccat ataaatcagc atccatgttg gaatttaatc    3300
gcggcctaga gcaagacgtt tcccgttgaa tatggctcat actcttcctt tttcaatatt    3360
attgaagcat ttatcagggt tattgtctca tgagcggata catatttgaa tgtatttaga    3420
aaaataaaca aataggcatg cagcgctctt ccgcttcctc gctcactgac tcgctacgct    3480
cggtcgttcg actgcggcga gcggtgtcag ctcactcaaa gcggtaata cggttatcca     3540 cagaatcagg ggataaagcc ggaaagaaca tgtgagcaaa aagcaaagca ccggaagaag    3600
ccaacgccgc aggcgttttt ccataggctc cgccccctg acgagcatca caaaaatcga     3660
cgctcaagcc agaggtggcg aaacccgaca ggactataaa gataccaggc gtttccccct    3720
ggaagctccc tcgtgcgctc tcctgttccg accctgccgc ttaccggata cctgtccgcc    3780
tttctccctt cgggaagcgt ggcgctttct catagctcac gctgttggta tctcagttcg    3840
gtgtaggtcg ttcgctccaa gctgggctgt gtgcacgaac cccccgttca gcccgaccgc    3900
tgcgccttat ccggtaacta tcgtcttgag tccaacccgg taagacacga cttatcgcca    3960
ctggcagcag ccattggtaa ctgatttaga ggactttgtc ttgaagttat gcacctgtta    4020
aggctaaact gaaagaacag attttggtga gtgcggtcct ccaacccact taccttggtt    4080
caaagagttg gtagctcagc gaaccttgag aaaaccaccg ttggtagcgg tggttttct    4140 ttatttatga gatgatgaat caatcggtct atcaagtcaa cgaacagcta ttccgttact    4200
ctagatttca gtgcaattta tctcttcaaa tgtagcacct gaagtcagcc ccatacgata    4260
taagttgtaa ttctcatgtt agtcatgccc cgcgcccacc ggaaggagct gactgggttg    4320
aaggctctca agggcatcgg tcgagatccc ggtgcctaat gagtgagcta acttacatta    4380
attgcgttgc gctcactgcc cgcttttcag tcgggaaacc tgtcgtgcca gctgcattaa    4440
tgaatcggcc aacgcgcggg gagaggcggt ttgcgtattg ggcgccaggg tggtttttct    4500
tttcaccagt gagacgggca acagctgatt gcccttcacc gcctggccct gagagagttg    4560
cagcaagcgg tccacgctgg tttgccccag caggcgaaaa tcctgtttga tggtggttaa    4620
cggcgggata taacatgagc tgtcttcggt atcgtcgtat cccactaccg agatgtccgc    4680
```

| | |
|---|---:|
| accaacgcgc agcccggact cggtaatggc gcgcattgcg cccagcgcca tctgatcgtt | 4740 |
| ggcaaccagc atcgcagtgg gaacgatgcc ctcattcagc atttgcatgg tttgttgaaa | 4800 |
| accggacatg gcactccagt cgccttcccg ttccgctatc ggctgaattt gattgcgagt | 4860 |
| gagatattta tgccagccag ccagacgcag acgcgccgag acagaactta atgggcccgc | 4920 |
| taacagcgcg atttgctggt gacccaatgc gaccagatgc tccacgccca gtcgcgtacc | 4980 |
| gtcttcatgg gagaaaataa tactgttgat gggtgtctgg tcagagacat caagaaataa | 5040 |
| cgccggaaca ttagtgcagg cagcttccac agcaatggca tcctggtcat ccagcggata | 5100 |
| gttaatgatc agcccactga cgcgttgcgc gagaagattg tgcaccgccg ctttacaggc | 5160 |
| ttcgacgccg cttcgttcta ccatcgacac caccacgctg gcacccagtt gatcggcgcg | 5220 |
| agatttaatc gccgcgacaa tttgcgacgg cgcgtgcagg gccagactgg aggtggcaac | 5280 |
| gccaatcagc aacgactgtt tgcccgccag ttgttgtgcc acgcggttgg gaatgtaatt | 5340 |
| cagctccgcc atcgccgctt ccactttttc ccgcgttttc gcagaaacgt ggctggcctg | 5400 |
| gttcaccacg cgggaaacgg tctgataaga gacaccggca tactctgcga catcgtataa | 5460 |
| cgttactggt ttcacattca ccaccctgaa ttgactctct tccgggcgct atcatgccat | 5520 |
| accgcgaaag gttttgcgcc attcgatggt gtccgggatc tcgacgctct cccttatgcg | 5580 |
| actcctgcat taggaaatta atacgactca ctata | 5615 |

<210> SEQ ID NO 7
<211> LENGTH: 2449
<212> TYPE: DNA
<213> ORGANISM: Artificial Sequence
<220> FEATURE:
<223> OTHER INFORMATION: Description of Artificial Sequence: Synthetic
    vector nucleotide sequence

<400> SEQUENCE: 7

| | |
|---|---:|
| gagctcgacc atgattacgc caagctatca actttgtata gaaaagttga acgagaaacg | 60 |
| taaaatgata taaatatcaa tatattaaat tagattttgc ataaaaaaca gactacataa | 120 |
| tactgtaaaa cacaacatat ccagtcacta tggtcgacct gcagactggc tgtgtataag | 180 |
| ggagcctgac atttatattc cccagaacat caggttaatg gcgttttga tgtcattttc | 240 |
| gcggtggctg agatcagcca cttcttcccc gataacggag accggcacac tggccatatc | 300 |
| ggtggtcatc atgcgccagc tttcatcccc gatatgcacc accgggtaaa gttcacgggg | 360 |
| gactttatct gacagcagac gtgcactggc caggggatc accatccgtc gcccgggcgt | 420 |
| gtcaataata tcactctgta catccacaaa cagacgataa cggctctctc ttttataggt | 480 |
| gtaaacctta aactgcattt caccagcccc tgttctcgtc ggcaaaagag ccgttcattt | 540 |
| caataaaccg ggcgacctca gccatccctt cctgattttc cgctttccag cgttcggcac | 600 |
| gcagacgacg gcttcattc tgcatggttg tgcttaccga accggagata ttgacatcat | 660 |
| atatgccttg agcaactgat agctgtcgct gtcaactgtc actgtaatac gctgcttcat | 720 |
| agcataccte tttttgacat acttcgggta tacatatcag tatatattct tataccgcaa | 780 |
| aaatcagcgc gcaaatacgc atactgttat ctggctttta gtaagccgga tcctctagag | 840 |
| acgcgatgga tatgttctgc caagggttgg tttgcgcatt cacagttctc cgcaagaatt | 900 |
| gattggctcc aattcttgga gtggtgaatc cgttagcgag gtgccgccgg cttccattca | 960 |
| ggtcgaggtg gcccggctcc atgcaccgcg acgcaacgcg gggaggcaga caaggtatag | 1020 |
| ggcggcgcct acaatccatg ccaacccgtt ccatgtgctc gccgaggcgg cataaatcgc | 1080 |

| | |
|---|---:|
| cgtgacgatc agcggtccag tgatcgaagt taggctggta agagccgcga gcgatccttg | 1140 |
| aagctgtccc tgatggtcgt catctacctg cctggacagc atggcctgca acgcgggcat | 1200 |
| cccgatgccg ccggaagcga gaagaatcat aatggggaag ccatccagcc tcgcgtcgc | 1260 |
| gaacgccagc aagacgtagc ccagcgcgtc ggccgccatg ccggcgataa tggcctgctt | 1320 |
| ctcgccgaaa cgtttggtgg cgggaccagt gacgaaggct tgagcgaggg cgtgcaagat | 1380 |
| tccgaatacc gcaagcgaca ggccgatcat cgtcgcgctc cagcgaaagc ggtcctcgcc | 1440 |
| gaaaatgacc cagagcgctg ccggcacctg tcctacgagt tgcatgataa agaagacagt | 1500 |
| cataagtgcg cgcgacgatag tcatgccccg cgcccaccgg aaggagctga ctgggttgaa | 1560 |
| ggctctcaag ggcatcggtc gacgctctcc cttatgcgac tcctgcatta ggaagcagcc | 1620 |
| cagtagtagg ttgaggccgt tgagcaccgc cgccgcaagg aatggtgcat gcaaggagat | 1680 |
| ggcgcccaac agtcccccgg ccacggggcc tgccaccata cccacgccga acaagcgct | 1740 |
| catgagcccg aagtggcgag cccgatcttc cccatcggtg atgtcggcga tataggcgcc | 1800 |
| agcaaccgca cctgtggcgc cggtgatgcc ggccacgatg cgtccggcgt agaggatcca | 1860 |
| caggacgggt gtggtcgcca tgatcgcgta gtcgatagtg gctccaagta gcgaagcgag | 1920 |
| caggactggg cggcggccaa agcggtcgga cagtgctccg agaacgggtg cgcatagaaa | 1980 |
| ttgcatcaac gcatatagcg ctagcagcac gccatagtga ctggcgatgc tgtcggaatg | 2040 |
| gacgatatcc cgcaagaggc ccggcagtac cggcataacc aagcctatgc ctacagcatc | 2100 |
| cagggtgacg gtgccgagga tgacgatgag cgcattgtta gatttcatac acggtgcctg | 2160 |
| actgcgttag caatttaact gtgataaact accgcattaa agcttatcga tgataagctg | 2220 |
| tcaaacatga gaagcggccg ccatagtgac tggatatgtt gtgttttaca gtattatgta | 2280 |
| gtctgttttt tatgcaaaat ctaatttaat atattgatat ttatatcatt ttacgtttct | 2340 |
| cgttcaactt tattatacat agttgataat tcactggccg tcgttttaca acgtcgtgac | 2400 |
| tgggaaaacc ctggcgttac ccaacttaat cgccttgcag cacaagctt | 2449 |

<210> SEQ ID NO 8
<211> LENGTH: 6426
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 8

| | |
|---|---:|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcgaccatg attacgccaa gctatcaact ttgtatagaa aagttgaacg agaaacgtaa | 180 |
| aatgatataa atatcaatat attaaattag attttgcata aaaaacagac tacataatac | 240 |
| tgtaaaacac aacatatcca gtcactatgg tcgacctgca gactggctgt gtataaggga | 300 |
| gcctgacatt tatattcccc agaacatcag gttaatggcg ttttttgatgt cattttcgcg | 360 |
| gtggctgaga tcagccactt cttccccgat aacggagacc ggcacactgg ccatatcggt | 420 |
| ggtcatcatg cgccagcttt catccccgat atgcaccacc gggtaaagtt cacggggac | 480 |
| tttatctgac agcagacgtg cactggccag ggggatcacc atccgtcgcc cgggcgtgtc | 540 |
| aataatatca ctctgtacat ccacaaacag acgataacgg ctctctcttt tataggtgta | 600 |
| aaccttaaac tgcatttcac cagcccctgt tctcgtcggc aaaagagccg ttcatttcaa | 660 |
| taaaccgggc gacctcagcc atcccttcct gattttccgc tttccagcgt tcggcacgca | 720 |

```
gacgacgggc ttcattctgc atggttgtgc ttaccgaacc ggagatattg acatcatata    780
tgccttgagc aactgatagc tgtcgctgtc aactgtcact gtaatacgct gcttcatagc    840
atacctcttt ttgacatact tcgggtatac atatcagtat atattcttat accgcaaaaa    900
tcagcgcgca aatacgcata ctgttatctg gcttttagta agccggatcc tctagagacg    960
cgatggatat gttctgccaa gggttggttt gcgcattcac agttctccgc aagaattgat   1020
tggctccaat tcttggagtg gtgaatccgt tagcgaggtg ccgccggctt ccattcaggt   1080
cgaggtggcc cggctccatg caccgcgacg caacgcgggg aggcagacaa ggtatagggc   1140
ggcgcctaca atccatgcca acccgttcca tgtgctcgcc gaggcggcat aaatcgccgt   1200
gacgatcagc ggtccagtga tcgaagttag gctggtaaga gccgcgagcg atccttgaag   1260
ctgtccctga tggtcgtcat ctacctgcct ggacagcatg gcctgcaacg cgggcatccc   1320
gatgccgccg gaagcgagaa gaatcataat ggggaaggcc atccagcctc gcgtcgcgaa   1380
cgccagcaag acgtagccca gcgcgtcggc cgccatgccg gcgataatgg cctgcttctc   1440
gccgaaacgt ttggtggcgg gaccagtgac gaaggcttga gcgagggcgt gcaagattcc   1500
gaataccgca agcgacaggc cgatcatcgt cgcgctccag cgaaagcggt cctcgccgaa   1560
aatgacccag agcgctgccg gcacctgtcc tacgagttgc atgataaaga agacagtcat   1620
aagtgcggcg acgatagtca tgccccgcgc ccaccggaag gagctgactg ggttgaaggc   1680
tctcaagggc atcggtcgac gctctcccgtt atgcgactcc tgcattagga agcagcccag   1740
tagtaggttg aggccgttga gcaccgccgc cgcaaggaat ggtgcatgca aggagatggc   1800
gcccaacagt cccccggcca cggggcctgc caccatacccc acgccgaaac aagcgctcat   1860
gagcccgaag tggcgagccc gatcttcccc atcggtgatg tcggcgatat aggcgccagc   1920
aaccgcacct gtggcgccgg tgatgccggc cacgatgcgt ccggcgtaga ggatccacag   1980
gacgggtgtg gtcgccatga tcgcgtagtc gatagtggct ccaagtagcg aagcgagcag   2040
gactgggcgg cggccaaagc ggtcggacag tgctccgaga acgggtgcgc atagaaattg   2100
catcaacgca tatagcgcta gcagcacgcc atagtgactg gcgatgctgt cggaatggac   2160
gatatcccgc aagaggcccg gcagtaccgg cataaccaag cctatgccta cagcatccag   2220
ggtgacggtg ccgaggatga cgatgagcgc attgttagat tcatacacg gtgcctgact   2280
gcgttagcaa tttaactgtg ataaactacc gcattaaagc ttatcgatga taagctgtca   2340
aacatgagaa gcggccgcca tagtgactgg atatgttgtg ttttacagta ttatgtagtc   2400
tgttttttat gcaaaatcta atttaatata ttgatattta tatcatttta cgtttctcgt   2460
tcaactttat tatacatagt tgataattca ctggccgtcg ttttacaacg tcgtgactgg   2520
gaaaaccctg gcgttaccca acttaatcgc cttgcagcac aagcttgcgg ccgcataatg   2580
cttaagtcga acagaaagta atcgtattgt acacggccgc ataatcgaaa ttaatacgac   2640
tcactatagg gaattgtga gcggataaca attcccccatc ttagtatatt agttaagtat   2700
aagaaggaga tatacatatg gcagatctca attggatatc ggccggccac gcgatcgctg   2760
acgtcggtac cctcgagtct ggtaaagaaa ccgctgctgc gaaatttgaa cgccagcaca   2820
tggactcgtc tactagcgca gcttaattaa cctaggctgc tgccaccgct gagcaataac   2880
tagcataacc ccttggggcc tctaaacggg tcttgagggg ttttttgctg aaacctcagg   2940
catttgagaa gcacacggtc acactgcttc cggtagtcaa taaaccggta aaccagcaat   3000
agacataagc ggctatttaa cgaccctgcc ctgaaccgac gaccgggtcg aatttgcttt   3060
cgaatttctg ccattcatcc gcttattatc acttattcag gcgtagcacc aggcgtttaa   3120
```

```
gggcaccaat aactgcctta aaaaaattac gccccgccct gccactcatc gcagtactgt   3180
tgtaattcat taagcattct gccgacatgg aagccatcac agacggcatg atgaacctga   3240
atcgccagcg gcatcagcac cttgtcgcct tgcgtataat atttgcccat agtgaaaacg   3300
ggggcgaaga agttgtccat attggccacg tttaaatcaa aactggtgaa actcacccag   3360
ggattggctg agacgaaaaa catattctca ataaaccctt tagggaaata ggccaggttt   3420
tcaccgtaac acgccacatc ttgcgaatat atgtgtagaa actgccggaa atcgtcgtgg   3480
tattcactcc agagcgatga aaacgtttca gtttgctcat ggaaaacggt gtaacaaggg   3540
tgaacactat cccatatcac cagctcaccg tctttcattg ccatacggaa ctccggatga   3600
gcattcatca ggcgggcaag aatgtgaata aggccggata aaacttgtg cttattttc    3660
tttacggtct ttaaaaaggc cgtaatatcc agctgaacgg tctggttata ggtacattga   3720
gcaactgact gaaatgcctc aaaatgttct ttacgatgcc attgggatat atcaacggtg   3780
gtatatccag tgattttttt ctccattta gcttccttag ctcctgaaaa tctcgataac    3840
tcaaaaaata cgcccggtag tgatcttatt tcattatggt gaaagttgga acctcttacg   3900
tgccgatcaa cgtctcattt tcgccaaaag ttggcccagg gcttcccggt atcaacaggg   3960
acaccaggat ttatttattc tgcgaagtga tcttccgtca caggtattta ttcggcgcaa   4020
agtgcgtcgg gtgatgctgc caacttactg atttagtgta tgatggtgtt tttgaggtgc   4080
tccagtggct tctgtttcta tcagctgtcc ctcctgttca gctactgacg gggtggtgcg   4140
taacggcaaa agcaccgccg gacatcagcg ctagcgagt gtatactggc ttactatgtt    4200
ggcactgatg agggtgtcag tgaagtgctt catgtggcag gagaaaaaag gctgcaccgg   4260
tgcgtcagca gaatatgtga tacaggatat attccgcttc ctcgctcact gactcgctac   4320
gctcggtcgt tcgactgcgg cgagcggaaa tggcttacga acggggcgga gatttcctgg   4380
aagatgccag gaagatactt aacagggaag tgagagggcc gcggcaaagc cgttttccca   4440
taggctccgc ccccctgaca agcatcacga atctgacgc tcaaatcagt ggtggcgaaa    4500
cccgacagga ctataaagat accaggcgtt cccctggcg ctccctcgt gcgctctcct     4560
gttcctgcct ttcggtttac cggtgtcatt ccgctgttat ggccgcgttt gtctcattcc   4620
acgcctgaca ctcagttccg ggtaggcagt tcgctccaag ctggactgta tgcacgaacc   4680
ccccgttcag tccgaccgct gcgccttatc cggtaactat cgtcttgagt ccaacccgga   4740
aagacatgca aaagcaccac tggcagcagc cactggtaat tgatttagag gagttagtct   4800
tgaagtcatg cgccggttaa ggctaaactg aaaggacaag ttttggtgac tgcgctcctc   4860
caagccagtt acctcggttc aaagagttgg tagctcagag aaccttcgaa aaaccgccct   4920
gcaaggcggt ttttcgttt tcagagcaag agattacgcg cagaccaaaa cgatctcaag    4980
aagatcatct tattaatcag ataaaatatt tctagatttc agtgcaattt atctcttcaa   5040
atgtagcacc tgaagtcagc cccatacgat ataagttgta attctcatgt tagtcatgcc   5100
ccgcgcccac cggaaggagc tgactggggt gaaggctctc aagggcatcg gtcgagatcc   5160
cggtgcctaa tgagtgagct aacttacatt aattgcgttg cgctcactgc ccgctttcca   5220
gtcgggaaac ctgtcgtgcc agctgcatta atgaatcggc caacgcgcgg ggagaggcgg   5280
tttgcgtatt gggcgccagg gtggtttttc ttttcaccag tgagacgggc aacagctgat   5340
tgcccttcac cgcctggccc tgagagagtt gcagcaagcg gtccacgctg gtttgcccca   5400
gcaggcgaaa atcctgtttg atggtggtta acggcgggat ataacatgag ctgtcttcgg   5460
tatcgtcgta tcccactacc gagatgtccg caccaacgcg cagcccggac tcggtaatgg   5520
```

```
cgcgcattgc gcccagcgcc atctgatcgt tggcaaccag catcgcagtg ggaacgatgc   5580
cctcattcag catttgcatg gtttgttgaa aaccggacat ggcactccag tcgccttccc   5640
gttccgctat cggctgaatt tgattgcgag tgagatattt atgccagcca gccagacgca   5700
gacgcgccga gacagaactt aatgggcccg ctaacagcgc gatttgctgg tgacccaatg   5760
cgaccagatg ctccacgccc agtcgcgtac cgtcttcatg ggagaaaata atactgttga   5820
tgggtgtctg gtcagagaca tcaagaaata acgccggaac attagtgcag gcagcttcca   5880
cagcaatggc atcctggtca tccagcggat agttaatgat cagcccactg acgcgttgcg   5940
cgagaagatt gtgcaccgcc gctttacagg cttcgacgcc gcttcgttct accatcgaca   6000
ccaccacgct ggcacccagt tgatcggcgc gagatttaat cgccgcgaca atttgcgacg   6060
gcgcgtgcag ggccagactg gaggtggcaa cgccaatcag caacgactgt ttgcccgcca   6120
gttgttgtgc cacgcggttg ggaatgtaat tcagctccgc catcgccgct tccactttt   6180 cccgcgtttt cgcagaaacg tggctggcct ggttcaccac gcgggaaacg gtctgataag   6240
agacaccggc atactctgcg acatcgtata acgttactgg tttcacattc accaccctga   6300
attgactctc ttccgggcgc tatcatgcca taccgcgaaa ggttttgcgc cattcgatgg   6360
tgtccgggat ctcgacgctc tcccttatgc gactcctgca ttaggaaatt aatacgactc   6420
actata                                                              6426
```

<210> SEQ ID NO 9
<211> LENGTH: 7206
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 9

```
ggggaattgt gagcggataa caattcccct ctagaaataa ttttgtttaa ctttaagaag     60
gagatatacc atgggcagca gccatcacca tcatcaccac agccaggatc cgaattcgag    120
ctcggaccat gattacgcca agctatcaac tttgtataga aaagttgaac gagaaacgta    180
aaatgatata aatatcaata tattaaatta gattttgcat aaaaaacaga ctacataata    240
ctgtaaaaca acatatatcc agtcactatg gtcgacctgc agactggctg tgtataaggg    300
agcctgacat ttatattccc cagaacatca ggttaatggc gttttttgatg tcattttcgc    360 ggtggctgag atcagccact tcttccccga taacggagac cggcacactg gccatatcgg    420
tggtcatcat gcgccagctt tcatccccga tatgcaccac cgggtaaagt tcacggggga    480 cttttatctga cagcagacgt gcactggcca ggggggatcac catccgtcgc ccgggcgtgt    540
caataatatc actctgtaca tccacaaaca gacgataacg gctctctctt ttataggtgt    600
aaaccttaaa ctgcatttca ccagccccttg ttctcgtcgg caaagagcc gttcattttca    660 ataaaccggg cgacctcagc catcccttcc tgattttccg ctttccagcg ttcggcacgc    720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc tctagatta    960 cgcccgccc tgccactcat cgcagtactg ttgtaattca ttaagcattc tgccgacatg   1020
gaagccatca caaacggcat gatgaacctg aatcgccagc ggcatcagca ccttgtcgcc   1080
```

```
ttgcgtataa tatttgccca tggtgaaaac gggggcgaag aagttgtcca tattggccac    1140
gtttaaatca aaactggtga aactcaccca gggattggct gagacgaaaa acatattctc    1200
aataaaccct ttagggaaat aggccaggtt ttcaccgtaa cacgccacat cttgcgaata    1260
tatgtgtaga aactgccgga aatcgtcgtg gtattcactc cagagcgatg aaaacgtttc    1320
agtttgctca tggaaaacgg tgtaacaagg gtgaacacta tcccatatca ccagctcacc    1380
gtctttcatt gccatacgga attccggatg agcattcatc aggcgggcaa gaatgtgaat    1440
aaaggccgga taaaacttgt gcttattttt ctttacggtc tttaaaaagg ccgtaatatc    1500
cagctgaacg gtctggttat aggtacattg agcaactgac tgaaatgcct caaaatgttc    1560
tttacgatgc cattgggata tatcaacggt ggtatatcca gtgattttttt ctccatttt     1620 agcttcctta gctcctgaaa atctcgacgg atcctaactc aaaatccaca cattatacga    1680
gccggaagca taaagtgtaa agcctggggg tgcctaatgc ggccgccata gtgactggat    1740
atgttgtgtt ttacagtatt atgtagtctg tttttatgc aaaatctaat ttaatatatt      1800
gatatttata tcattttacg tttctcgttc aactttatta tacatagttg ataattcact    1860
ggccgtcgtt ttacaacgtc gtgactggga aaaccctggc gttacccaac ttaatcgcct    1920
tgcagcacaa gcttgcggcc gcataatgct taagtcgaac agaaagtaat cgtattgtac    1980
acggccgcat aatcgaaatt aatacgactc actataggggg aattgtgagc ggataacaat    2040
tccccatctt agtatattag ttaagtataa gaaggagata tacatatggc agatctcaat    2100
tggatatcgg ccggccacgc gatcgctgac gtcggtaccc tcgagtctgg taaagaaacc    2160
gctgctgcga atttgaacg ccagcacatg gactcgtcta ctagcgcagc ttaattaacc      2220
taggctgctg ccaccgctga gcaataacta gcataacccc ttggggcctc taaacgggtc    2280 ttgagggggtt ttttgctgaa aggaggaact atatccggat tggcgaatgg gacgcgccct    2340
gtagcggcgc attaagcgcg gcgggtgtgg tggttacgcg cagcgtgacc gctacacttg    2400
ccagcgccct agcgcccgct cctttcgctt tcttcccttc ctttctcgcc acgttcgccg    2460
gctttccccg tcaagctcta aatcgggggc tccctttagg gttccgattt agtgctttac    2520
ggcacctcga ccccaaaaaa cttgattagg gtgatggttc acgtagtggg ccatcgccct    2580
gatagacggt ttttcgccct ttgacgttgg agtccacgtt ctttaatagt ggactcttgt    2640
tccaaactgg aacaacactc aaccctatct cggtctattc ttttgattta agggattt        2700 tgccgatttc ggcctattgg ttaaaaaatg agctgattta acaaaaattt aacgcgaatt    2760
ttaacaaaat attaacgttt acaatttctg gcggcacgat ggcatgagat tatcaaaaag    2820
gatcttcacc tagatccttt taaattaaaa atgaagtttt aaatcaatct aaagtatata    2880
tgagtaaact tggtctgaca gttaccaatg cttaatcagt gaggcaccta tctcagcgat    2940
ctgtctattt cgttcatcca tagttgcctg actccccgtc gtgtagataa ctacgatacg    3000
ggagggctta ccatctggcc ccagtgctgc aatgataccg cgagacccac gctcaccggc    3060
tccagattta tcagcaataa accagccagc cggaagggcc gagcgcagaa gtggtcctgc    3120
aactttatcc gcctccatcc agtctattaa ttgttgccgg gaagctagag taagtagttc    3180
gccagttaat agtttgcgca acgttgttgc cattgctaca ggcatcgtgg tgtcacgctc    3240
gtcgtttggt atggcttcat tcagctccgg ttcccaacga tcaaggcgag ttacatgatc    3300
ccccatgttg tgcaaaaaag cggttagctc cttcggtcct ccgatcgttg tcagaagtaa    3360
gttggccgca gtgttatcac tcatggttat ggcagcactg cataattctc ttactgtcat    3420
gccatccgta agatgctttt ctgtgactgg tgagtactca accaagtcat tctgagaata    3480
```

-continued

```
gtgtatgcgg cgaccgagtt gctcttgccc ggcgtcaata cgggataata ccgcgccaca   3540
tagcagaact ttaaaagtgc tcatcattgg aaaacgttct cggggcgaaa actctcaag    3600 gatcttaccg ctgttgagat ccagttcgat gtaacccact cgtgcaccca actgatcttc   3660
agcatctttt actttcacca gcgtttctgg gtgagcaaaa acaggaaggc aaaatgccgc   3720
aaaaaaggga taagggcga cacggaaatg ttgaatactc atactcttcc ttttcaatc    3780 atgattgaag catttatcag ggttattgtc tcatgagcgg atacatattt gaatgtattt   3840
agaaaaataa acaaataggt catgaccaaa atcccttaac gtgagttttc gttccactga   3900
gcgtcagacc ccgtagaaaa gatcaaagga tcttcttgag atcctttttt tctgcgcgta   3960
atctgctgct tgcaaacaaa aaaccaccg ctaccagcgg tggtttgttt gccggatcaa    4020
gagctaccaa ctcttttcc gaaggtaact ggcttcagca gagcgcagat accaaatact    4080
gtccttctag tgtagccgta gttaggccac cacttcaaga actctgtagc accgcctaca   4140
tacctcgctc tgctaatcct gttaccagtg gctgctgcca gtggcgataa gtcgtgtctt   4200
accgggttgg actcaagacg atagttaccg gataaggcgc agcggtcggg ctgaacgggg   4260
ggttcgtgca cacagcccag cttggagcga acgacctaca ccgaactgag atacctacag   4320
cgtgagctat gagaaagcgc cacgcttccc gaagggagaa aggcggacag gtatccggta   4380
agcggcaggg tcggaacagg agagcgcacg agggagcttc caggggggaaa cgcctggtat   4440 ctttatagtc ctgtcgggtt tcgccacctc tgacttgagc gtcgattttt gtgatgctcg   4500 tcagggggc ggagcctatg gaaaaacgcc agcaacgcgg cctttttacg gttcctggcc    4560
ttttgctggc cttttgctca catgttcttt cctgcgttat cccctgattc tgtggataac   4620
cgtattaccg cctttgagtg agctgatacc gctcgccgca gccgaacgac cgagcgcagc   4680
gagtcagtga gcgaggaagc ggaagagcgc ctgatgcggt attttctcct tacgcatctg   4740
tgcggtattt cacaccgcat atatggtgca ctctcagtac aatctgctct gatgccgcat   4800
agttaagcca gtatacactc cgctatcgct acgtgactgg gtcatggctg cgccccgaca   4860
cccgccaaca cccgctgacg cgccctgacg ggcttgtctg ctcccggcat ccgcttacag   4920
acaagctgtg accgtctccg ggagctgcat gtgtcagagg ttttcaccgt catcaccgaa   4980
acgcgcgagg cagctgcggt aaagctcatc agcgtggtcg tgaagcgatt cacagatgtc   5040
tgcctgttca tccgcgtcca gctcgttgag tttctccaga agcgttaatg tctggcttct   5100
gataaagcgg gccatgttaa gggcggtttt ttcctgtttg gtcactgatg cctccgtgta   5160
agggggattt ctgttcatgg gggtaatgat accgatgaaa cgagagagga tgctcacgat   5220
acgggttact gatgatgaac atgcccggtt actggaacgt tgtgagggta acaactggc    5280 ggtatggatg cggcgggacc agagaaaaat cactcagggt caatgccagc gcttcgttaa   5340
tacagatgta ggtgttccac agggtagcca gcagcatcct gcgatgcaga tccggaacat   5400
aatggtgcag gcgctgact tccgcgtttc cagactttac gaaacacgga aaccgaagac    5460
cattcatgtt gttgctcagg tcgcagacgt tttgcagcag cagtcgcttc acgttcgctc   5520
gcgtatcggt gattcattct gctaaccagt aaggcaaccc cgccagccta gccgggtcct   5580
caacgacagg agcacgatca tgctagtcat gccccgcgcc caccggaagg agctgactgg   5640
gttgaaggct ctcaagggca tcggtcgaga tcccggtgcc taatgagtga gctaacttac   5700
attaattgcg ttgcgctcac tgcccgcttt ccagtcggga aacctgtcgt gccagctgca   5760
ttaatgaatc ggccaacgcg cggggagagg cggtttgcgt attgggcgcc agggtggttt   5820
ttcttttcac cagtgagacg ggcaacagct gattgccctt caccgcctgg ccctgagaga   5880
```

| | |
|---|---:|
| gttgcagcaa gcggtccacg ctggtttgcc ccagcaggcg aaaatcctgt tgatggtgg | 5940 |
| ttaacggcgg gatataacat gagctgtctt cggtatcgtc gtatcccact accgagatgt | 6000 |
| ccgcaccaac gcgcagcccg gactcggtaa tggcgcgcat tgcgcccagc gccatctgat | 6060 |
| cgttggcaac cagcatcgca gtgggaacga tgccctcatt cagcatttgc atggtttgtt | 6120 |
| gaaaaccgga catggcactc cagtcgcctt cccgttccgc tatcggctga atttgattgc | 6180 |
| gagtgagata tttatgccag ccagccagac gcagacgcgc cgagacgaaa cttaatgggc | 6240 |
| ccgctaacag cgcgatttgc tggtgaccca atgcgaccag atgctccacg cccagtcgcg | 6300 |
| taccgtcttc atgggagaaa ataatactgt tgatgggtgt ctggtcagag acatcaagaa | 6360 |
| ataacgccgg aacattagtg caggcagctt ccacagcaat ggcatcctgg tcatccagcg | 6420 |
| gatagttaat gatcagccca ctgacgcgtt gcgcgagaag attgtgcacc gccgctttac | 6480 |
| aggcttcgac gccgcttcgt tctaccatcg acaccaccac gctggcaccc agttgatcgg | 6540 |
| cgcgagattt aatcgccgcg acaatttgcg acggcgcgtg cagggccaga ctggaggtgg | 6600 |
| caacgccaat cagcaacgac tgtttgcccg ccagttgttg tgccacgcgg ttgggaatgt | 6660 |
| aattcagctc cgccatcgcc gcttccactt tttcccgcgt tttcgcagaa acgtggctgg | 6720 |
| cctggttcac cacgcgggaa acggtctgat aagagacacc ggcatactct gcgacatcgt | 6780 |
| ataacgttac tggtttcaca ttcaccaccc tgaattgact ctcttccggg cgctatcatg | 6840 |
| ccataccgcg aaaggttttg cgccattcga tggtgtccgg gatctcgacg ctctccctta | 6900 |
| tgcgactcct gcattaggaa gcagcccagt agtaggttga ggccgttgag caccgccgcc | 6960 |
| gcaaggaatg gtgcatgcaa ggagatggcg cccaacagtc ccccggccac ggggcctgcc | 7020 |
| accatacccca cgccgaaaca agcgctcatg agcccgaagt ggcgagcccg atcttcccca | 7080 |
| tcggtgatgt cggcgatata ggcgccagca accgcacctg tggcgccggt gatgccggcc | 7140 |
| acgatgcgtc cggcgtagag gatcgagatc gatctcgatc ccgcgaaatt aatacgactc | 7200 |
| actata | 7206 |

<210> SEQ ID NO 10
<211> LENGTH: 5296
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 10

| | |
|---|---:|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcgatcaca agtttgtaca aaaaagctga acgagaaacg taaaatgata taaatatcaa | 180 |
| tatattaaat tagattttgc ataaaaaaca gactacataa tactgtaaaa cacaacatat | 240 |
| ccagtcacta tggcggccgc cacgttaagg gattttggtc atgatcagca cgtgttgaca | 300 |
| attaatcatc ggcatagtat atcggcatag tataatacga caaggtgagg aactaaacca | 360 |
| tggccaagtt gaccagtgcc gttccggtgc tcaccgcgcg cgacgtcgcc ggagcggtcg | 420 |
| agttctggac cgaccggctc gggttctccc gggacttcgt ggaggacgac ttcgccggtg | 480 |
| tggtccggga cgacgtgacc ctgttcatca gcgcggtcca ggaccaggtg gtgccggaca | 540 |
| acaccctggc ctgggtgtgg gtgcgcggcc tggacgagct gtacgccgag tggtcggagg | 600 |
| tcgtgtccac gaacttccgg gacgcctccg gccggccat gaccgagatc ggcgagcagc | 660 |
| cgtgggggcg ggagttcgcc ctgcgcgacc cggccggcaa ctgcgtgcac ttcgtggccg | 720 |

```
aggagcagga ctgatcatga tgatattatt ttatcttgtg caatgtaaca tcagagattt      780
tgagacacgg gccagagctg ccaggaaaca gctatgacca tgtaatacga ctcactatag      840
gggatatcag ctggatggca aataatgatt ttattttgac tgatagtgac ctgttcgttg      900
caacaccggt gctagcgtat acccgaagta tgtcaaaaag aggtgtgcta tgaagcagcg      960
tattacagtg acagttgaca gcgacagcta tcagttgctc aaggcatata tgatgtcaat     1020
atctccggtc tggtaagcac aaccatgcag aatgaagccc gtcgtctgcg tgccgaacgc     1080
tggaaagcgg aaaatcagga agggatggct gaggtcgccc ggtttattga aatgaacggc     1140
tcttttgctg acgagaacag ggactggtga aatgcagttt aaggtttaca cctataaaag     1200
agagagccgt tatcgtctgt ttgtggatgt acagagtgat attattgaca cgcccgggcg     1260
acggatggta atcccctgg ccagtgcacg tctgctgtca gataaagtct cccgtgaact      1320
ttacccggtg gtgcatatcg gggatgaaag ctggcgcatg atgaccaccg atatggccag     1380
tgtgccggtc tccgttatcg gggaagaagt ggctgatctc agccgccgcg aaaatgacat     1440
caaaaacgcc attaacctga tgttctgggg aatataaatg tcaggctccc ttatacacag     1500
ccagtctgca ggtcgaccat agtgactgga tatgttgtgt tttacagtat tatgtagtct     1560
gttttttatg caaaatctaa tttaatatat tgatatttat atcattttac gtttctcgtt     1620
cagctttctt gtacaaagtg gtgataatta attaagatca gatccggctg ctaagcttgg     1680
aattgttatc cgctcacaat tcctatagtg agtcgtatta cctaggctgc tgccaccgct     1740
gagcaataac tagcataacc ccttggggcc tctaaacggg tcttgagggg ttttttgctg     1800
aaacctcagg catttgagaa gcacacggtc acactgcttc cggtagtcaa taaaccggta     1860
aaccagcaat agacataagc ggctatttaa cgaccctgcc ctgaaccgac gacccgggtcg     1920 aatttgcttt cgaatttctg ccattcatcc gcttattatc acttattcag gcgtagcacc     1980
aggcgtttaa gggcaccaat aactgcctta aaaaaattac gccccgccct gccactcatc     2040
gcagtactgt tgtaattcat taagcattct gccgacatgg aagccatcac agacggcatg     2100
atgaacctga atcgccagcg gcatcagcac cttgtcgcct tgcgtataat atttgcccat     2160
agtgaaaacg ggggcgaaga agttgtccat attggccacg tttaaatcaa aactggtgaa     2220
actcacccag ggattggctg agacgaaaaa catattctca ataaaccctt tagggaaata     2280
ggccaggttt tcaccgtaac acgccacatc ttgcgaatat atgtgtagaa actgccggaa     2340
atcgtcgtgg tattcactcc agagcgatga aaacgtttca gtttgctcat ggaaaacggt     2400
gtaacaaggg tgaacactat cccatatcac cagctcaccg tctttcattg ccatacggaa     2460
ctccggatga gcattcatca ggcgggcaag aatgtgaata aaggccggat aaaacttgtg     2520
cttatttttc tttacggtct ttaaaaaggc cgtaatatcc agctgaacgg tctggttata     2580
ggtacattga gcaactgact gaaatgcctc aaaatgttct ttacgatgcc attgggatat     2640
atcaacggtg gtatatccag tgatttttt ctccatttta gcttccttag ctcctgaaaa     2700
tctcgataac tcaaaaaata cgcccggtag tgatcttatt tcattatggt gaaagttgga     2760
acctcttacg tgccgatcaa cgtctcattt tcgccaaaag ttgggccagg cttcccggt     2820 atcaacaggg acaccaggat ttatttattc tgcgaagtga tcttccgtca caggtattta     2880
ttcggcgcaa agtgcgtcgg gtgatgctgc caacttactg atttagtgta tgatggtgtt     2940
tttgaggtgc tccagtggct tctgtttcta tcagctgtcc ctcctgttca gctactgacg     3000
gggtggtgcg taacggcaaa agcaccgccg gacatcagcg ctagcggagt gtatactggc     3060
ttactatgtt ggcactgatg agggtgtcag tgaagtgctt catgtggcag gagaaaaaag     3120
```

```
gctgcaccgg tgcgtcagca gaatatgtga tacaggatat attccgcttc ctcgctcact    3180
gactcgctac gctcggtcgt tcgactgcgg cgagcggaaa tggcttacga acggggcgga    3240
gatttcctgg aagatgccag gaagatactt aacaggaag tgagagggcc gcggcaaagc     3300
cgttttcca taggctccgc cccctgaca agcatcacga aatctgacgc tcaaatcagt      3360
ggtggcgaaa cccgacagga ctataaagat accaggcgtt tccctggcg gctccctcgt     3420
gcgctctcct gttcctgcct ttcggtttac cggtgtcatt ccgctgttat ggccgcgttt    3480
gtctcattcc acgcctgaca ctcagttccg gtaggcagt tcgctccaag ctggactgta    3540
tgcacgaacc ccccgttcag tccgaccgct gcgccttatc cggtaactat cgtcttgagt    3600
ccaacccgga aagacatgca aaagcaccac tggcagcagc cactggtaat tgatttagag    3660
gagttagtct tgaagtcatg cgccggttaa ggctaaactg aaaggacaag ttttggtgac    3720
tgcgctcctc caagccagtt acctcggttc aaagagttgg tagctcagag aaccttcgaa    3780
aaaccgccct gcaaggcggt ttttcgttt tcagagcaag agattacgcg cagaccaaaa     3840
cgatctcaag aagatcatct tattaatcag ataaaatatt tctagatttc agtgcaattt    3900
atctcttcaa atgtagcacc tgaagtcagc cccatacgat ataagttgta attctcatgt    3960
tagtcatgcc ccgcgcccac cggaaggagc tgactgggtt gaaggctctc aagggcatcg    4020
gtcgagatcc cggtgcctaa tgagtgagct aacttacatt aattgcgttg cgctcactgc    4080
ccgctttcca gtcgggaaac ctgtcgtgcc agctgcatta atgaatcggc caacgcgcgg    4140
ggagaggcgg tttgcgtatt gggcgccagg gtggtttttc ttttcaccag tgagacgggc    4200
aacagctgat tgcccttcac cgcctggccc tgagagagtt gcagcaagcg gtccacgctg    4260
gtttgcccca gcaggcgaaa atcctgtttg atggtggtta acggcgggat ataacatgag    4320
ctgtcttcgg tatcgtcgta tcccactacc gagatgtccg caccaacgcg cagcccggac    4380
tcggtaatgg cgcgcattgc gcccagcgcc atctgatcgt tggcaaccag catcgcagtg    4440
ggaacgatgc cctcattcag catttgcatg gtttgttgaa aaccggacat ggcactccag    4500
tcgccttccc gttccgctat cggctgaatt tgattgcgag tgagatattt atgccagcca    4560
gccagacgca gacgcgccga gacagaactt aatgggcccg ctaacagcgc gatttgctgg    4620
tgacccaatg cgaccagatg ctccacgccc agtcgcgtac cgtcttcatg ggagaaaata    4680
atactgttga tgggtgtctg gtcagagaca tcaagaaata cgccggaac attagtgcag     4740
gcagcttcca cagcaatggc atcctggtca tccagcggat agttaatgat cagcccactg    4800
acgcgttgcg cgagaagatt gtgcaccgcc gctttacagg cttcgacgcc gcttcgttct    4860
accatcgaca ccaccacgct ggcacccagt tgatcggcgc gagatttaat cgccgcgaca    4920
atttgcgacg gcgcgtgcag ggccagactg gaggtggcaa cgccaatcag caacgactgt    4980
ttgcccgcca gttgttgtgc cacgcggttg ggaatgtaat tcagctccgc catcgccgct    5040
tccactttt cccgcgtttt cgcagaaacg tggctggcct ggttcaccac gcgggaaacg    5100
gtctgataag agacaccggc atactctgcg acatcgtata acgttactgg tttcacattc    5160
accaccctga attgactctc ttccgggcgc tatcatgcca taccgcgaaa ggttttgcgc    5220
cattcgatgg tgtccgggat ctcgacgctc tcccttatgc gactcctgca ttaggaaatt    5280
aatacgactc actata                                                    5296
```

<210> SEQ ID NO 11
<211> LENGTH: 5069
<212> TYPE: DNA
<213> ORGANISM: Artificial Sequence
<220> FEATURE:
<223> OTHER INFORMATION: Description of Artificial Sequence: Synthetic vector nucleotide sequence

<400> SEQUENCE: 11

| | | | | | |
|---|---|---|---|---|---|
| ggggaattgt | gagcggataa | caattcccct | gtagaaataa | ttttgtttaa | ctttaataag | 60 |
| gagatatacc | atgggcagca | gccatcacca | tcatcaccac | agccaggatc | cgaattcgag | 120 |
| ctcgatcaca | agtttgtaca | aaaaagctga | acgagaaacg | taaatgata | taatatcaa | 180 |
| tatattaaat | tagattttgc | ataaaaaaca | gactacataa | tactgtaaaa | cacaacatat | 240 |
| ccagtcacta | tggcggccgc | cacgttaagg | gattttggtc | atgatcagca | cgtgttgaca | 300 |
| attaatcatc | ggcatagtat | atcggcatag | tataatacga | caaggtgagg | aactaaacca | 360 |
| tggccaagtt | gaccagtgcc | gttccggtgc | tcaccgcgcg | cgacgtcgcc | ggagcggtcg | 420 |
| agttctggac | cgaccggctc | gggttctccc | gggacttcgt | ggaggacgac | ttcgccggtg | 480 |
| tggtccggga | cgacgtgacc | ctgttcatca | gcgcggtcca | ggaccaggtg | gtgccggaca | 540 |
| acaccctggc | ctgggtgtgg | gtgcgcggcc | tggacgagct | gtacgccgag | tggtcggagg | 600 |
| tcgtgtccac | gaacttccgg | gacgcctccg | ggcggccat | gaccgagatc | ggcgagcagc | 660 |
| cgtgggggcg | ggagttcgcc | ctgcgcgacc | cggccggcaa | ctgcgtgcac | ttcgtggccg | 720 |
| aggagcagga | ctgatcatga | tgatattatt | ttatcttgtg | caatgtaaca | tcagagattt | 780 |
| tgagacacgg | gccagagctg | ccaggaaaca | gctatgacca | tgtaatacga | ctcactatag | 840 |
| gggatatcag | ctggatggca | aataatgatt | ttattttgac | tgatagtgac | ctgttcgttg | 900 |
| caacaccggt | gctagcgtat | acccgaagta | tgtcaaaaag | aggtgtgcta | tgaagcagcg | 960 |
| tattacagtg | acagttgaca | gcgacagcta | tcagttgctc | aaggcatata | tgatgtcaat | 1020 |
| atctccggtc | tggtaagcac | aaccatgcag | aatgaagccc | gtcgtctgcg | tgccgaacgc | 1080 |
| tggaaagcgg | aaaatcagga | agggatggct | gaggtcgccc | ggtttattga | aatgaacggc | 1140 |
| tcttttgctg | acgagaacag | ggactggtga | aatgcagttt | aaggtttaca | cctataaaag | 1200 |
| agagagccgt | tatcgtctgt | ttgtggatgt | acagagtgat | attattgaca | cgcccgggcg | 1260 |
| acggatggta | atccccctgg | ccagtgcacg | tctgctgtca | gataaagtct | cccgtgaact | 1320 |
| ttacccggtg | gtgcatatcg | gggatgaaag | ctggcgcatg | atgaccaccg | atatggccag | 1380 |
| tgtgccggtc | tccgttatcg | gggaagaagt | ggctgatctc | agccgccgcg | aaaatgacat | 1440 |
| caaaaacgcc | attaacctga | tgttctgggg | aatataaatg | tcaggctccc | ttatacacag | 1500 |
| ccagtctgca | ggtcgaccat | agtgactgga | tatgttgtgt | tttacagtat | tatgtagtct | 1560 |
| gttttttatg | caaaatctaa | tttaatatat | tgatatttat | atcattttac | gtttctcgtt | 1620 |
| cagctttctt | gtacaaagtg | gtgataatta | attaagatca | gatccggctg | ctaagcttgg | 1680 |
| aattgttatc | cgctcacaat | tcctatagtg | agtcgtatta | cctaggctgc | tgccaccgct | 1740 |
| gagcaataac | tagcataacc | ccttggggcc | tctaaacggg | tcttgagggg | ttttttgctg | 1800 |
| aaacctcagg | catttgagaa | gcacacggtc | acactgcttc | cggtagtcaa | taaaccggta | 1860 |
| aaccagcaat | agacataagc | ggctatttaa | cgaccctgcc | ctgaaccgac | gacgggtca | 1920 |
| tcgtggccgg | atcttgcggc | ccctcggctt | gaacgaattg | ttagacatta | tttgccgact | 1980 |
| accttggtga | tctcgccttt | cacgtagtgg | acaaattctt | ccaactgatc | tgcgcgcgag | 2040 |
| gccaagcgat | cttcttcttg | tccaagataa | gcctgtctag | cttcaagtat | gacgggctga | 2100 |
| tactgggccg | gcaggcgctc | cattgcccag | tcggcagcga | catccttcgg | cgcgattttg | 2160 |
| ccggttactg | cgctgtacca | aatgcgggac | aacgtaagca | ctacatttcg | ctcatcgcca | 2220 |

-continued

| | |
|---|---|
| gcccagtcgg gcggcgagtt ccatagcgtt aaggtttcat ttagcgcctc aaatagatcc | 2280 |
| tgttcaggaa ccggatcaaa gagttcctcc gccgctggac ctaccaaggc aacgctatgt | 2340 |
| tctcttgctt ttgtcagcaa gatagccaga tcaatgtcga tcgtggctgg ctcgaagata | 2400 |
| cctgcaagaa tgtcattgcg ctgccattct ccaaattgca gttcgcgctt agctggataa | 2460 |
| cgccacggaa tgatgtcgtc gtgcacaaca atggtgactt ctacagcgcg gagaatctcg | 2520 |
| ctctctccag gggaagccga agtttccaaa aggtcgttga tcaaagctcg ccgcgttgtt | 2580 |
| tcatcaagcc ttacggtcac cgtaaccagc aaatcaatat cactgtgtgg cttcaggccg | 2640 |
| ccatccactg cggagccgta caaatgtacg gccagcaacg tcggttcgag atggcgctcg | 2700 |
| atgacgccaa ctacctctga tagttgagtc gatacttcgg cgatcaccgc ttccctcata | 2760 |
| ctcttccttt ttcaatatta ttgaagcatt tatcagggtt attgtctcat gagcggatac | 2820 |
| atatttgaat gtatttagaa aaataaacaa atagctagct cactcggtcg ctacgctccg | 2880 |
| ggcgtgagac tgcggcgggc gctgcggaca catacaaagt tacccacaga ttccgtggat | 2940 |
| aagcagggga ctaacatgtg aggcaaaaca gcagggccgc gccggtggcg ttttccata | 3000 |
| ggctccgccc tcctgccaga gttcataa acagacgctt ttccggtgca tctgtgggag | 3060 |
| ccgtgaggct caaccatgaa tctgacagta cgggcgaaac ccgacaggac ttaaagatcc | 3120 |
| ccaccgtttc cggcgggtcg ctccctcttg cgctctcctg ttccgaccct gccgtttacc | 3180 |
| ggatacctgt tccgcctttc tcccttacgg gaagtgtggc gctttctcat agctcacaca | 3240 |
| ctggtatctc ggctcggtgt aggtcgttcg ctccaagctg ggctgtaagc aagaactccc | 3300 |
| cgttcagccc gactgctgcg ccttatccgg taactgttca cttgagtcca acccggaaaa | 3360 |
| gcacggtaaa acgccactgg cagcagccat tggtaactgg gagttcgcag aggatttgtt | 3420 |
| tagctaaaca cgcggttgct cttgaagtgt gcgccaaagt ccggctacac tggaaggaca | 3480 |
| gatttggttg ctgtgctctg cgaaagccag ttaccacggt taagcagttc cccaactgac | 3540 |
| ttaaccttcg atcaaaccac ctccccaggt ggttttttcg tttacagggc aaaagattac | 3600 |
| gcgcagaaaa aaaggatctc aagaagatcc tttgatcttt tctactgaac cgctctagat | 3660 |
| ttcagtgcaa tttatctctt caaatgtagc acctgaagtc agccccatac gatataagtt | 3720 |
| gtaattctca tgttagtcat gccccgcgcc caccggaagg agctgactgg gttgaaggct | 3780 |
| ctcaagggca tcggtcgaga tcccggtgcc taatgagtga gctaacttac attaattgcg | 3840 |
| ttgcgctcac tgcccgcttt ccagtcggga aacctgtcgt gccagctgca ttaatgaatc | 3900 |
| ggccaacgcg cggggagagg cggtttgcgt attgggcgcc agggtggttt tcttttcac | 3960 |
| cagtgagacg ggcaacagct gattgccctt caccgcctgg ccctgagaga gttgcagcaa | 4020 |
| gcggtccacg ctggtttgcc ccagcaggcg aaaatcctgt ttgatggtgg ttaacggcgg | 4080 |
| gatataacat gagctgtctt cggtatcgtc gtatcccact accgagatgt ccgcaccaac | 4140 |
| gcgcagcccg gactcggtaa tggcgcgcat tgcgcccagc gccatctgat cgttggcaac | 4200 |
| cagcatcgca gtgggaacga tgccctcatt cagcatttgc atggtttgtt gaaaaccgga | 4260 |
| catggcactc cagtcgcctt cccgttccgc tatcggctga atttgattgc gagtgagata | 4320 |
| tttatgccag ccagccagac gcagacgcgc cgagacagaa cttaatgggc ccgctaacag | 4380 |
| cgcgatttgc tggtgaccca atgcgaccag atgctccacg cccagtcgcg taccgtcttc | 4440 |
| atgggagaaa ataatactgt tgatgggtgt ctggtcagag acatcaagaa ataacgccgg | 4500 |
| aacattagtg caggcagctt ccacagcaat ggcatcctgg tcatccagcg gatagttaat | 4560 |
| gatcagccca ctgacgcgtt gcgcgagaag attgtgcacc gccgctttac aggcttcgac | 4620 |

```
gccgcttcgt tctaccatcg acaccaccac gctggcaccc agttgatcgg cgcgagattt    4680
aatcgccgcg acaatttgcg acggcgcgtg cagggccaga ctggaggtgg caacgccaat    4740
cagcaacgac tgtttgcccg ccagttgttg tgccacgcgg ttgggaatgt aattcagctc    4800
cgccatcgcc gcttccactt tttcccgcgt tttcgcagaa acgtggctgg cctggttcac    4860
cacgcgggaa acggtctgat aagagacacc ggcatactct gcgacatcgt ataacgttac    4920
tggtttcaca ttcaccaccc tgaattgact ctcttccggg cgctatcatg ccataccgcg    4980
aaaggttttg cgccattcga tggtgtccgg gatctcgacg ctctccctta tgcgactcct    5040
gcattaggaa attaatacga ctcactata                                       5069

<210> SEQ ID NO 12
<211> LENGTH: 5117
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 12
ggggaattgt gagcggataa caattcccct gtagaaataa ttttgtttaa ctttaataag     60
gagatatacc atgggcagca gccatcacca tcatcaccac agccaggatc cgaattcgag    120
ctcgatcaca agtttgtaca aaaaagctga acgagaaacg taaatgata taatatcaa     180 tatattaaat tagattttgc ataaaaaaca gactacataa tactgtaaaa cacaacatat    240
ccagtcacta tggcggccgc cacgttaagg gattttggtc atgatcagca cgtgttgaca    300
attaatcatc ggcatagtat atcggcatag tataatacga caaggtgagg aactaaacca    360
tggccaagtt gaccagtgcc gttccggtgc tcaccgcgcg cgacgtcgcc ggagcggtcg    420
agttctggac cgaccggctc gggttctccc gggacttcgt ggaggacgac ttcgccggtg    480
tggtccggga cgacgtgacc ctgttcatca gcgcggtcca ggaccaggtg gtgccggaca    540
acaccctggc ctgggtgtgg gtgcgcggcc tggacgagct gtacgccgag tggtcggagg    600
tcgtgtccac gaacttccgg gacgcctccg gccggccat gaccgagatc ggcgagcagc    660
cgtgggggcg ggagttcgcc ctgcgcgacc cggccggcaa ctgcgtgcac ttcgtggccg    720
aggagcagga ctgatcatga tgatattatt ttatcttgtg caatgtaaca tcagagattt    780
tgagacacgg gccagagctg ccaggaaaca gctatgacca tgtaatacga ctcactatag    840
gggatatcag ctggatggca ataatgatt ttatttttgac tgatagtgac ctgttcgttg    900
caacaccggt gctagcgtat acccgaagta tgtcaaaaag aggtgtgcta tgaagcagcg    960
tattacagtg acagttgaca gcgacagcta tcagttgctc aaggcatata tgatgtcaat   1020
atctccggtc tggtaagcac aaccatgcag aatgaagccc gtcgtctgcg tgccgaacgc   1080
tggaaagcgg aaaatcagga agggatggct gaggtcgccc ggtttattga atgaacggc    1140 tcttttgctg acgagaacag ggactggtga atgcagttt aaggtttaca cctataaaag    1200
agagagccgt tatcgtctgt tgtggatgt acagagtgat attattgaca cgcccgggcg    1260
acggatggta atcccctgg ccagtgcacg tctgctgtca gataaagtct cccgtgaact   1320
ttacccggtg gtgcatatcg gggatgaaag ctggcgcatg atgaccaccg atatggccag    1380
tgtgccggtc tccgttatcg gggaagaagt ggctgatctc agccgccgcg aaaatgacat    1440
caaaaacgcc attaacctga tgttctgggg aatataaatg tcaggctccc ttatacacag    1500
ccagtctgca ggtcgaccat agtgactgga tatgttgtgt tttacagtat tatgtagtct    1560
gttttttatg caaaatctaa tttaatatat tgatatttat atcattttac gtttctcgtt   1620
```

```
cagctttctt gtacaaagtg gtgataatta attaagatca gatccggctg ctaagcttgg    1680
aattgttatc cgctcacaat tcctatagtg agtcgtatta cctaggctgc tgccaccgct    1740
gagcaataac tagcataacc ccttggggcc tctaaacggg tcttgagggg ttttttgctg    1800
aaacctcagg catttgagaa gcacacggtc acactgcttc cggtagtcaa taaaccggta    1860
aaccagcaat agacataagc ggctatttaa cgaccctgcc ctgaaccgac gacaagctga    1920
cgaccgggtc tccgcaagtg gcacttttcg gggaaatgtg cgcggaaccc ctatttgttt    1980 attttttctaa atacattcaa atatgtatcc gctcatgaat taattcttag aaaaactcat    2040
cgagcatcaa atgaaactgc aatttattca tatcaggatt atcaatacca tatttttgaa    2100
aaagccgttt ctgtaatgaa ggagaaaact caccgaggca gttccatagg atggcaagat    2160
cctggtatcg gtctgcgatt ccgactcgtc aacatcaat acaacctatt aatttcccct     2220
cgtcaaaaat aaggttatca agtgagaaat caccatgagt gacgactgaa tccggtgaga    2280
atggcaaaag tttatgcatt tctttccaga cttgttcaac aggccagcca ttacgctcgt    2340
catcaaaatc actcgcatca accaaaccgt tattcattcg tgattgcgcc tgagcgagac    2400
gaaatacgcg gtcgctgtta aaaggacaat acaaacagg aatcgaatgc aaccggcgca     2460
ggaacactgc cagcgcatca acaatatttt cacctgaatc aggatattct tctaatacct    2520
ggaatgctgt tttcccgggg atcgcagtgg tgagtaacca tgcatcatca ggagtacgga    2580
taaaatgctt gatggtcgga agaggcataa attccgtcag ccagtttagt ctgaccatct    2640
catctgtaac atcattggca acgctacctt tgccatgttt cagaaacaac tctggcgcat    2700
cgggcttccc atacaatcga tagattgtcg cacctgattg cccgacatta tcgcgagccc    2760
atttataccc atataaatca gcatccatgt tggaatttaa tcgcggccta gagcaagacg    2820
tttcccgttg aatatggctc atactcttcc ttttttcaata ttattgaagc atttatcagg    2880
gttattgtct catgagcgga tacatatttg aatgtattta gaaaaataaa caaataggca    2940
tgcagcgctc ttccgcttcc tcgctcactg actcgctacg ctcggtcgtt cgactgcggc    3000
gagcggtgtc agctcactca aaagcggtaa tacggttatc cacagaatca ggggataaag    3060
ccggaaagaa catgtgagca aaaagcaaag caccggaaga agccaacgcc gcaggcgttt    3120
ttccataggc tccgcccccc tgacgagcat cacaaaaatc gacgctcaag ccagaggtgg    3180
cgaaacccga caggactata agataccag gcgtttcccc ctggaagctc cctcgtgcgc     3240
tctcctgttc cgaccctgcc gcttaccgga tacctgtccg cctttctccc ttcgggaagc    3300
gtggcgcttt ctcatagctc acgctgttgg tatctcagtt cggtgtaggt cgttcgctcc    3360
aagctgggct gtgtgcacga accccccgtt cagcccgacc gctgcgcctt atccggtaac    3420
tatcgtcttg agtccaaccc ggtaagacac gacttatcgc cactggcagc agccattggt    3480
aactgattta gaggactttg tcttgaagtt atgcacctgt taaggctaaa ctgaaagaac    3540
agattttggt gagtgcggtc ctccaaccca cttaccttgg ttcaaagagt tggtagctca    3600
gcgaaccttg agaaaaccac cgttggtagc ggtggttttt ctttatttat gagatgatga    3660
atcaatcggt ctatcaagtc aacgaacagc tattccgtta ctctagattt cagtgcaatt    3720
tatctcttca aatgtagcac ctgaagtcag ccccatacga tataagttgt aattctcatg    3780
ttagtcatgc cccgcgccca ccggaaggag ctgactgggt tgaaggctct caagggcatc    3840
ggtcgagatc ccggtgccta atgagtgagc taacttacat taattgcgtt gcgctcactg    3900
cccgctttcc agtcgggaaa cctgtcgtgc cagctgcatt aatgaatcgg ccaacgcgcg    3960
gggagaggcg gtttgcgtat tgggcgccag ggtggttttt cttttcacca gtgagacggg    4020
```

```
caacagctga ttgcccttca ccgcctggcc ctgagagagt tgcagcaagc ggtccacgct    4080
ggtttgcccc agcaggcgaa atcctgtttt gatggtggtt aacggcggga tataacatga    4140
gctgtcttcg gtatcgtcgt atcccactac cgagatgtcc gcaccaacgc gcagcccgga    4200
ctcggtaatg gcgcgcattg cgcccagcgc catctgatcg ttggcaacca gcatcgcagt    4260
gggaacgatg ccctcattca gcatttgcat ggtttgttga aaaccggaca tggcactcca    4320
gtcgccttcc cgttccgcta tcggctgaat ttgattgcga gtgagatatt tatgccagcc    4380
agccagacgc agacgcgccg agacagaact taatgggccc gctaacagcg cgatttgctg    4440
gtgacccaat gcgaccagat gctccacgcc cagtcgcgta ccgtcttcat gggagaaaat    4500
aatactgttg atgggtgtct ggtcagagac atcaagaaat aacgccggaa cattagtgca    4560
ggcagcttcc acagcaatgg catcctggtc atccagcgga tagttaatga tcagcccact    4620
gacgcgttgc gcgagaagat tgtgcaccgc cgctttacag gcttcgacgc cgcttcgttc    4680
taccatcgac accaccacgc tggcacccag ttgatcggcg cgagatttaa tcgccgcgac    4740
aatttgcgac ggcgcgtgca gggccagact ggaggtggca acgccaatca gcaacgactg    4800
tttgcccgcc agttgttgtg ccacgcggtt gggaatgtaa ttcagctccg ccatcgccgc    4860
ttccactttt tcccgcgttt tcgcagaaac gtggctggcc tggttcacca cgcgggaaac    4920
ggtctgataa gagacaccgg catactctgc gacatcgtat aacgttactg gtttcacatt    4980
caccaccctg aattgactct cttccgggcg ctatcatgcc ataccgcgaa aggttttgcg    5040
ccattcgatg gtgtccggga tctcgacgct ctcccttatg cgactcctgc attaggaaat    5100
taatacgact cactata                                                  5117

<210> SEQ ID NO 13
<211> LENGTH: 6707
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 13
ggggaattgt gagcggataa caattcccct ctagaaataa ttttgtttaa ctttaagaag      60
gagatatacc atgggcagca gccatcacca tcatcaccac agccaggatc cgaattcgag     120
ctcgatcaca gtttgtaca aaaaagctga acgagaaacg taaaatgata taaatatcaa     180
tatattaaat tagattttgc ataaaaaaca gactacataa tactgtaaaa cacaacatat     240
ccagtcacta tggcggccgc cacgttaagg gattttggtc atgatcagca cgtgttgaca     300
attaatcatc ggcatagtat atcggcatag tataatacga caaggtgagg aactaaacca     360
tggccaagtt gaccagtgcc gttccggtgc tcaccgcgcg cgacgtcgcc ggagcggtcg     420
agttctggac cgaccggctc gggttctccc ggacttcgt ggaggacgac ttcgccggtg     480
tggtccggga cgacgtgacc ctgttcatca gcgcggtcca ggaccaggtg gtgccggaca     540
acaccctggc ctgggtgtgg gtgcgcgcc tggacgagct gtacgccgag tggtcggagg     600
tcgtgtccac gaacttccgg gacgcctccg gccggccat gaccgagatc ggcgagcagc     660
cgtgggggcg ggagttcgcc ctgcgcgacc cggccggcaa ctgcgtgcac ttcgtggccg     720
aggagcagga ctgatcatga tgatattatt ttatcttgtg caatgtaaca tcagagattt     780
tgagacacgg gccagagctg ccaggaaaca gctatgacca tgtaaatcga ctcactatag     840
gggatatcag ctggatggca aataatgatt ttattttgac tgatagtgac ctgttcgttg     900
```

```
cacaccggtg ctagcgtata cccgaagtat gtcaaaaaga ggtgtgctat gaagcagcgt    960
attacagtga cagttgacag cgacagctat cagttgctca aggcatatat gatgtcaata   1020
tctccggtct ggtaagcaca accatgcaga atgaagcccg tcgtctgcgt gccgaacgct   1080
ggaaagcgga aaatcaggaa gggatggctg aggtcgcccg gtttattgaa atgaacggct   1140
cttttgctga cgagaacagg gactggtgaa atgcagttta aggtttacac ctataaaaga   1200
gagagccgtt atcgtctgtt tgtggatgta cagagtgata ttattgacac gcccgggcga   1260
cggatggtga tcccctggc cagtgcacgt ctgctgtcag ataaagtctc ccgtgaactt    1320
tacccggtgg tgcatatcgg ggatgaaagc tggcgcatga tgaccaccga tatggccagt   1380
gtgccggtct ccgttatcgg ggaagaagtg gctgatctca gccgccgcga aaatgacatc   1440
aaaaacgcca ttaacctgat gttctgggga atataaatgt caggctccct tatacacagc   1500
cagtctgcag gtcgaccata gtgactggat atgttgtgtt ttacagtatt atgtagtctg   1560
tttttttatgc aaaatctaat ttaatatatt gatatttata tcattttacg tttctcgttc   1620
agctttcttg tacaaagtgg tgataattaa ttaagatcag atccggctgc taagcttgga   1680
attgttatcc gctcacaatt cctatagtga gtcgtattac ctaggctgct gccaccgctg   1740
agcaataact agcataaccc cttggggcct ctaaacgggt cttgaggggt ttttgctga    1800
aaggaggaac tatatccgga ttggcgaatg ggacgcgccc tgtagcggcg cattaagcgc   1860
ggcgggtgtg gtggttacgc gcagcgtgac cgctacactt gccagcgccc tagcgcccgc   1920
tcctttcgct ttcttccctt cctttctcgc cacgttcgcc ggctttcccc gtcaagctct   1980
aaatcggggg ctcccttag ggttccgatt tagtgcttta cggcacctcg accccaaaaa    2040
acttgattag ggtgatggtt cacgtagtgg gccatcgccc tgatagacgg ttttcgccc    2100
tttgacgttg gagtccacgt tctttaatag tggactcttg ttccaaactg gaacaacact   2160
caaccctatc tcggtctatt cttttgattt ataagggatt ttgccgattt cggcctattg   2220
gttaaaaaat gagctgattt aacaaaaatt taacgcgaat tttaacaaaa tattaacgtt   2280
tacaatttct ggcggcacga tggcatgaga ttatcaaaaa ggatcttcac ctagatcctt   2340
ttaaattaaa aatgaagttt taaatcaatc taaagtatat atgagtaaac ttggtctgac   2400
agttaccaat gcttaatcag tgaggcacct atctcagcga tctgtctatt tcgttcatcc   2460
atagttgcct gactccccgt cgtgtagata actacgatac gggagggctt accatctggc   2520
cccagtgctg caatgatacc gcgagaccca cgctcaccgg ctccagattt atcagcaata   2580
aaccagccag ccggaagggc cgagcgcaga agtggtcctg caactttatc cgcctccatc   2640
cagtctatta ttgttgccg ggaagctaga gtaagtagtt cgccagttaa tagtttgcgc    2700
aacgttgttg ccattgctac aggcatcgtg gtgtcacgct cgtcgtttgg tatggcttca   2760
ttcagctccg gttcccaacg atcaaggcga gttacatgat cccccatgtt gtgcaaaaaa   2820
gcggttagct ccttcggtcc tccgatcgtt gtcagaagta agttggccgc agtgttatca   2880
ctcatggtta tggcagcact gcataattct cttactgtca tgccatccgt aagatgcttt   2940
tctgtgactg gtgagtactc aaccaagtca ttctgagaat agtgtatgcg gcgaccgagt   3000
tgctcttgcc cggcgtcaat acgggataat accgcgccac atagcagaac tttaaaagtg   3060
ctcatcattg gaaaacgttc ttcggggcga aaactctcaa ggatcttacc gctgttgaga   3120
tccagttcga tgtaacccac tcgtgcaccc aactgatctt cagcatcttt tactttcacc   3180
agcgtttctg ggtgagcaaa aacaggaagg caaaatgccg caaaaaaggg aataagggcg   3240
acacggaaat gttgaatact catactcttc cttttttcaat catgattgaa gcatttatca   3300
```

```
gggttattgt ctcatgagcg gatacatatt tgaatgtatt tagaaaaata aacaaatagg    3360
tcatgaccaa aatcccttaa cgtgagtttt cgttccactg agcgtcagac cccgtagaaa    3420
agatcaaagg atcttcttga gatccttttt ttctgcgcgt aatctgctgc ttgcaaacaa    3480
aaaaaccacc gctaccagcg gtggtttgtt tgccggatca agagctacca actcttttc    3540 cgaaggtaac tggcttcagc agagcgcaga taccaaatac tgtccttcta gtgtagccgt    3600
agttaggcca ccacttcaag aactctgtag caccgcctac atacctcgct ctgctaatcc    3660
tgttaccagt ggctgctgcc agtggcgata gtcgtgtct taccggggttg gactcaagac    3720 gatagttacc ggataaggcg cagcggtcgg gctgaacggg gggttcgtgc acacagccca    3780
gcttggagcg aacgacctac accgaactga gatacctaca gcgtgagcta tgagaaagcg    3840
ccacgcttcc cgaagggaga aaggcggaca ggtatccggt aagcggcagg gtcggaacag    3900
gagagcgcac gagggagctt ccaggggaa acgcctggta tctttatagt cctgtcgggt    3960
ttcgccacct ctgacttgag cgtcgatttt tgtgatgctc gtcaggggggg cggagcctat    4020 ggaaaacgc cagcaacgcg gcctttttac ggttcctggc cttttgctgg ccttttgctc    4080
acatgttctt cctgcgtta tccctgatt ctgtggataa ccgtattacc gcctttgagt    4140
gagctgatac cgctcgccgc agccgaacga ccgagcgcag cgagtcagtg agcgaggaag    4200
cggaagagcg cctgatgcgg tattttctcc ttacgcatct gtgcggtatt tcacaccgca    4260
tatatggtgc actctcagta caatctgctc tgatgccgca tagttaagcc agtatacact    4320
ccgctatcgc tacgtgactg ggtcatggct gcgcccccgac acccgccaac acccgctgac    4380
gcgccctgac gggcttgtct gctcccggca tccgcttaca dacaagctgt gaccgtctcc    4440
gggagctgca tgtgtcagag gttttcaccg tcatcaccga aacgcgcgag gcagctgcgg    4500
taaagctcat cagcgtggtc gtgaagcgat tcacagatgt ctgcctgttc atccgcgtcc    4560
agctcgttga gtttctccag aagcgttaat gtctggcttc tgataaagcg ggccatgtta    4620
agggcggttt ttcctgtttt ggtcactgat gcctccgtgt aagggggatt tctgttcatg    4680
ggggtaatga taccgatgaa acgagagagg atgctcacga tacgggttac tgatgatgaa    4740
catgcccggt tactggaacg ttgtgagggt aaacaactgg cggtatggat gcggcgggac    4800
cagagaaaaa tcactcaggg tcaatgccag cgcttcgtta atacagatgt aggtgttcca    4860
cagggtagcc agcagcatcc tgcgatgcag atccggaaca taatggtgca gggcgctgac    4920
ttccgcgttt ccagacttta cgaaacacgg aaaccgaaga ccattcatgt tgttgctcag    4980
gtcgcagacg ttttgcagca gcagtcgctt cacgttcgct cgcgtatcgg tgattcattc    5040
tgctaaccag taaggcaacc ccgccagcct agccgggtcc tcaacgacag gagcacgatc    5100
atgctagtca tgccccgcgc ccaccggaag gagctgactg ggttgaaggc tctcaagggc    5160
atcggtcgag atcccggtgc ctaatgagtg agctaactta cattaattgc gttgcgctca    5220
ctgcccgctt tccagtcggg aaacctgtcg tgccagctgc attaatgaat cggccaacgc    5280
gcggggagag gcggtttgcg tattgggcgc cagggtggtt tttcttttca ccagtgagac    5340
gggcaacagc tgattgccct tcaccgcctg gccctgagag agttgcagca agcggtccac    5400
gctggtttgc cccagcaggc gaaaatcctg tttgatggtg gttaacggcg ggatataaca    5460
tgagctgtct tcggtatcgt cgtatcccac taccagatg tccgcaccaa cgcgcagccc    5520
ggactcggta atggcgcgca ttgcgcccag cgccatctga tcgttggcaa ccagcatcgc    5580
agtgggaacg atgccctcat tcagcatttg catggtttgt tgaaaaccgg acatggcact    5640
ccagtcgcct tcccgttccg ctatcggctg aatttgattg cgagtgagat atttatgcca    5700
```

-continued

| | |
|---|---|
| gccagccaga cgcagacgcg ccgagacaga acttaatggg cccgctaaca gcgcgatttg | 5760 |
| ctggtgaccc aatgcgacca gatgctccac gcccagtcgc gtaccgtctt catgggagaa | 5820 |
| aataatactg ttgatgggtg tctggtcaga gacatcaaga aataacgccg gaacattagt | 5880 |
| gcaggcagct tccacagcaa tggcatcctg gtcatccagc ggatagttaa tgatcagccc | 5940 |
| actgacgcgt tgcgcgagaa gattgtgcac cgccgcttta caggcttcga cgccgcttcg | 6000 |
| ttctaccatc gacaccacca cgctggcacc cagttgatcg gcgcgagatt taatcgccgc | 6060 |
| gacaatttgc gacggcgcgt gcagggccag actggaggtg gcaacgccaa tcagcaacga | 6120 |
| ctgtttgccc gccagttgtt gtgccacgcg gttgggaatg taattcagct ccgccatcgc | 6180 |
| cgcttccact ttttcccgcg ttttcgcaga acgtggctg gcctggttca ccacgcggga | 6240 |
| aacggtctga taagagacac cggcatactc tgcgacatcg tataacgtta ctggtttcac | 6300 |
| attcaccacc ctgaattgac tctcttccgg gcgctatcat gccataccgc gaaaggtttt | 6360 |
| gcgccattcg atggtgtccg ggatctcgac gctctccctt atgcgactcc tgcattagga | 6420 |
| agcagcccag tagtaggttg aggccgttga gcaccgccgc cgcaaggaat ggtgcatgca | 6480 |
| aggagatggc gcccaacagt cccccggcca cggggcctgc caccataccc acgccgaaac | 6540 |
| aagcgctcat gagcccgaag tggcgagccc gatcttcccc atcggtgatg tcggcgatat | 6600 |
| aggcgccagc aaccgcacct gtggcgccgg tgatgccggc cacgatgcgt ccggcgtaga | 6660 |
| ggatcgagat cgatctcgat cccgcgaaat taatacgact cactata | 6707 |

<210> SEQ ID NO 14
<211> LENGTH: 5325
<212> TYPE: DNA
<213> ORGANISM: Artificial Sequence
<220> FEATURE:
<223> OTHER INFORMATION: Description of Artificial Sequence: Synthetic
    vector nucleotide sequence

<400> SEQUENCE: 14

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggaccat gattacgcca agctatcaac tttgtataga aagttgaac gagaaacgta | 180 |
| aaatgatata aatatcaata tattaaatta gattttgcat aaaaaacaga ctacataata | 240 |
| ctgtaaaaca caacatatcc agtcactatg gtcgacctgc agactggctg tgtataaggg | 300 |
| agcctgacat ttatattccc cagaacatca ggttaatggc gttttgatg tcattttcgc | 360 |
| ggtggctgag atcagccact tcttccccga taacggagac cggcacactg gccatatcgg | 420 |
| tggtcatcat cgccagcttt catcccccga tatgcaccac cgggtaaagt tcacggggga | 480 |
| ctttatctga cagcagacgt gcactggcca gggggatcac catccgtcgc ccgggcgtgt | 540 |
| caataatatc actctgtaca tccacaaaca gacgataacg gctctctctt ttataggtgt | 600 |
| aaaccttaaa ctgcatttca ccagccctg ttctcgtcgg caaagagcc gttcatttca | 660 |
| ataaaccggg cgacctcagc catcccttcc tgattttccg ctttccagcg ttcggcacgc | 720 |
| agacgacggg cttcattctg catggttgtg cttaccgaac cggagatatt gacatcatat | 780 |
| atgccttgag caactgatag ctgtcgctgt caactgtcac tgtaatacgc tgcttcatag | 840 |
| catacctctt tttgacatac ttcgggtata catatcagta tatattctta taccgcaaaa | 900 |
| atcagcgcgc aaatacgcat actgttatct ggcttttagt aagccggatc tctagatta | 960 |
| cgccccgccc tgccactcat cgcagtactg ttgtaattca ttaagcattc tgccgacatg | 1020 |
| gaagccatca caaacggcat gatgaacctg aatcgccagc ggcatcagca ccttgtcgcc | 1080 |

```
ttgcgtataa tatttgccca tggtgaaaac gggggcgaag aagttgtcca tattggccac    1140
gtttaaatca aaactggtga aactcaccca gggattggct gagacgaaaa acatattctc    1200
aataaaccct ttagggaaat aggccaggtt ttcaccgtaa cacgccacat cttgcgaata    1260
tatgtgtaga aactgccgga aatcgtcgtg gtattcactc cagagcgatg aaaacgtttc    1320
agtttgctca tggaaaacgg tgtaacaagg gtgaacacta tcccatatca ccagctcacc    1380
gtctttcatt gccatacgga attccggatg agcattcatc aggcgggcaa gaatgtgaat    1440
aaaggccgga taaaacttgt gcttattttt ctttacggtc tttaaaaagg ccgtaatatc    1500
cagctgaacg gtctggttat aggtacattg agcaactgac tgaaatgcct caaaatgttc    1560
tttacgatgc cattgggata tatcaacggt ggtatatcca gtgattttt  tctccatttt    1620 agcttcctta gctcctgaaa atctcgacgg atcctaactc aaaatccaca cattatacga    1680
gccggaagca taaagtgtaa agcctggggg tgcctaatgc ggccgccata gtgactggat    1740
atgttgtgtt ttacagtatt atgtagtctg tttttatgc  aaaatctaat ttaatatatt    1800
gatatttata tcattttacg tttctcgttc aactttatta tacatagttg ataattcact    1860
ggccgtcgtt ttacaacgtc gtgactggga aaaccctggc gttacccaac ttaatcgcct    1920
tgcagcacaa gcttggaatt gttatccgct cacaattcct atagtgagtc gtattaccta    1980
ggctgctgcc accgctgagc aataactagc ataacccctt ggggcctcta acgggtctt    2040 gagggggtttt ttgctgaaac ctcaggcatt tgagaagcac acggtcacac tgcttccggt    2100
agtcaataaa ccgtaaacc  agcaatagac ataagcggct atttaacgac cctgccctga    2160
accgacgacc gggtcatcgt ggccggatct tgcggcccct cggcttgaac gaattgttag    2220
acattatttg ccgactacct tggtgatctc gcctttcacg tagtggacaa attcttccaa    2280
ctgatctgcg cgcgaggcca agcgatcttc ttcttgtcca agataagcct gtctagcttc    2340
aagtatgacg ggctgatact gggccggcag gcgctccatt gcccagtcgg cagcgacatc    2400
cttcggcgcg attttgccgg ttactgcgct gtaccaaatg cgggacaacg taagcactac    2460
atttcgctca tcgccagccc agtcgggcgg cgagttccat agcgttaagg tttcatttag    2520
cgcctcaaat agatcctgtt caggaaccgg atcaaagagt tcctccgccg ctggacctac    2580
caaggcaacg ctatgttctc ttgcttttgt cagcaagata gccagatcaa tgtcgatcgt    2640
ggctggctcg aagatacctg caagaatgtc attgcgctgc cattctccaa attgcagttc    2700
gcgcttagct ggataacgcc acggaatgat gtcgtcgtgc acaacaatgg tgacttctac    2760
agcgcggaga atctcgctct ctccagggga agccgaagtt tccaaaaggt cgttgatcaa    2820
agctcgccgc gttgtttcat caagccttac ggtcaccgta accagcaaat caatatcact    2880
gtgtggcttc aggccgccat ccactgcgga gccgtacaaa tgtacggcca gcaacgtcgg    2940
ttcgagatgg cgctcgatga cgccaactac ctctgatagt tgagtcgata cttcggcgat    3000
caccgcttcc ctcatactct tcctttttca atattattga agcatttatc agggttattg    3060
tctcatgagc ggatacatat ttgaatgtat ttagaaaaat aaacaaatag ctagctcact    3120
cggtcgctac gctccgggcg tgagactgcg gcgggcgctg cggacacata caaagttacc    3180
cacagattcc gtggataagc agggactaa  catgtgaggc aaaacagcag gccgcgccg     3240 gtggcgtttt tccataggct ccgccctcct gccagagttc acataaacag acgcttttcc    3300
ggtgcatctg tgggagccgt gaggctcaac catgaatctg acagtacggg cgaaacccga    3360
caggacttaa agatcccac  cgtttccggc gggtcgctcc ctcttgcgct ctcctgttcc    3420
gaccctgccg tttaccggat acctgttccg cctttctccc ttacgggaag tgtggcgctt    3480
```

```
tctcatagct cacacactgg tatctcggct cggtgtaggt cgttcgctcc aagctgggct    3540
gtaagcaaga actccccgtt cagcccgact gctgcgcctt atccggtaac tgttcacttg    3600
agtccaaccc ggaaaagcac ggtaaaacgc cactggcagc agccattggt aactgggagt    3660
tcgcagagga tttgtttagc taaacacgcg gttgctcttg aagtgtgcgc caaagtccgg    3720
ctacactgga aggacagatt tggttgctgt gctctgcgaa agccagttac cacggttaag    3780
cagttcccca actgacttaa ccttcgatca aaccacctcc ccaggtggtt ttttcgttta    3840
cagggcaaaa gattacgcgc agaaaaaaag gatctcaaga agatcctttg atcttttcta    3900
ctgaaccgct ctagatttca gtgcaattta tctcttcaaa tgtagcacct gaagtcagcc    3960
ccatacgata taagttgtaa ttctcatgtt agtcatgccc cgcgcccacc ggaaggagct    4020
gactgggttg aaggctctca agggcatcgg tcgagatccc ggtgcctaat gagtgagcta    4080
acttacatta attgcgttgc gctcactgcc cgctttccag tcgggaaacc tgtcgtgcca    4140
gctgcattaa tgaatcggcc aacgcgcggg gagaggcggt ttgcgtattg ggcgccaggg    4200
tggtttttct tttcaccagt gagacgggca acagctgatt gcccttcacc gcctggccct    4260
gagagagttg cagcaagcgg tccacgctgg tttgccccag caggcgaaaa tcctgtttga    4320
tggtggttaa cggcgggata taacatgagc tgtcttcggt atcgtcgtat cccactaccg    4380
agatgtccgc accaacgcgc agcccggact cggtaatggc gcgcattgcg cccagcgcca    4440
tctgatcgtt ggcaaccagc atcgcagtgg gaacgatgcc ctcattcagc atttgcatgg    4500
tttgttgaaa accggacatg gcactccagt cgccttcccg ttccgctatc ggctgaattt    4560
gattgcgagt gagatattta tgccagccag ccagacgcag acgcgccgag acagaactta    4620
atgggcccgc taacagcgcg atttgctggt gacccaatgc gaccagatgc tccacgccca    4680
gtcgcgtacc gtcttcatgg agaaaataa tactgttgat gggtgtctgg tcagagacat    4740
caagaaataa cgccggaaca ttagtgcagg cagcttccac agcaatggca tcctggtcat    4800
ccagcggata gttaatgatc agcccactga cgcgttgcgc gagaagattg tgcaccgccg    4860
ctttacaggc ttcgacgccg cttcgttcta ccatcgacac caccacgctg cacccagtt    4920 gatcggcgcg agatttaatc gccgcgacaa tttgcgacgg cgcgtgcagg gccagactgg    4980
aggtggcaac gccaatcagc aacgactgtt tgcccgccag ttgttgtgcc acgcggttgg    5040
gaatgtaatt cagctccgcc atcgccgctt ccactttttc ccgcgttttc gcagaaacgt    5100
ggctggcctg gttcaccacg cgggaaacgg tctgataaga gacaccggca tactctgcga    5160
catcgtataa cgttactggt ttcacattca ccaccctgaa ttgactctct tccgggcgct    5220
atcatgccat accgcgaaag gttttgcgcc attcgatggt gtccgggatc tcgacgctct    5280
cccttatgcg actcctgcat taggaaatta atacgactca ctata               5325
```

<210> SEQ ID NO 15
<211> LENGTH: 5373
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 15

```
ggggaattgt gagcggataa caattcccct gtagaaataa ttttgtttaa ctttaataag     60
gagatatacc atgggcagca gccatcacca tcatcaccac agccaggatc cgaattcgag    120
ctcggaccat gattacgcca agctatcaac tttgtataga aaagttgaac gagaaacgta    180
```

```
aaatgatata aatatcaata tattaaatta gattttgcat aaaaaacaga ctacataata    240
ctgtaaaaca caacatatcc agtcactatg gtcgacctgc agactggctg tgtataaggg    300
agcctgacat ttatattccc cagaacatca ggttaatggc gttttttgatg tcattttcgc   360 ggtggctgag atcagccact tcttccccga taacggagac cggcacactg gccatatcgg    420
tggtcatcat gcgccagctt tcatccccga tatgcaccac cgggtaaagt tcacggggga    480
ctttatctga cagcagacgt gcactggcca ggggatcca catccgtcgc ccgggcgtgt    540
caataatatc actctgtaca tccacaaaca gacgataacg gctctctctt ttataggtgt    600
aaaccttaaa ctgcatttca ccagcccctg ttctcgtcgg caaagagcc gttcatttca    660 ataaaccggg cgacctcagc catcccttcc tgattttccg ctttccagcg ttcggcacgc    720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc ctctagatta    960
cgccccgccc tgccactcat cgcagtactg ttgtaattca ttaagcattc tgccgacatg   1020
gaagccatca caaacggcat gatgaacctg aatcgccagc ggcatcagca ccttgtcgcc   1080
ttgcgtataa tatttgccca tggtgaaaac ggggcgaag aagttgtcca tattggccac   1140
gtttaaatca aaactggtga aactcaccca gggattggct gagacgaaaa acatattctc   1200
aataaaccct ttagggaaat aggccaggtt tcaccgtaa cacgccacat cttgcgaata   1260
tatgtgtaga aactgccgga atcgtcgtg gtattcactc cagagcgatg aaaacgtttc   1320
agtttgctca tggaaaacgg tgtaacaagg gtgaacacta tcccatatca ccagctcacc   1380
gtctttcatt gccatacgga attccggatg agcattcatc aggcgggcaa gaatgtgaat   1440
aaaggccgga taaaacttgt gcttattttt ctttacggtc tttaaaaagg ccgtaatatc   1500
cagctgaacg gtctggttat aggtacattg agcaactgac tgaaatgcct caaaatgttc   1560
tttacgatgc cattgggata tatcaacggt ggtatatcca gtgattttttt tctccatttt   1620 agcttcctta gctcctgaaa atctcgacgg atcctaactc aaaatccaca cattatacga   1680
gccggaagca taaagtgtaa agcctggggg tgcctaatgc ggccgccata gtgactggat   1740
atgttgtgtt ttacagtatt atgtagtctg ttttttatgc aaaatctaat ttaatatatt   1800
gatatttata tcattttacg tttctcgttc aactttatta tacatagttg ataattcact   1860
ggccgtcgtt ttacaacgtc gtgactggga aaaccctggc gttacccaac ttaatcgcct   1920
tgcagcacaa gcttggaatt gttatccgct cacaattcct atagtgagtc gtattaccta   1980
ggctgctgcc accgctgagc aataactagc ataacccctt ggggcctcta acgggtctt    2040 gaggggtttt ttgctgaaac ctcaggcatt tgagaagcac acggtcacac tgcttccggt   2100
agtcaataaa ccggtaaacc agcaatagac ataagcggct atttaacgac cctgccctga   2160
accgacgaca agctgacgac cgggtctccg caagtggcac ttttcgggga aatgtgcgcg   2220 gaaccctat ttgttatttt ttctaaatac attcaaatat gtatccgctc atgaattaat    2280
tcttagaaaa actcatcgag catcaaatga aactgcaatt tattcatatc aggattatca   2340
ataccatatt tttgaaaaag ccgtttctgt aatgaaggag aaaactcacc gaggcagttc   2400
cataggatgg caagatcctg gtatcggtct gcgattccga ctcgtccaac atcaatacaa   2460
cctattaatt tcccctcgtc aaaaataagg ttatcaagtg agaaatcacc atgagtgacg   2520
actgaatccg gtgagaatgg caaaagttta tgcatttctt ccagacttg ttcaacaggc    2580
```

```
cagccattac gctcgtcatc aaaatcactc gcatcaacca aaccgttatt cattcgtgat    2640
tgcgcctgag cgagacgaaa tacgcggtcg ctgttaaaag gacaattaca aacaggaatc    2700
gaatgcaacc ggcgcaggaa cactgccagc gcatcaacaa tattttcacc tgaatcagga    2760
tattcttcta atacctggaa tgctgttttc ccggggatcg cagtggtgag taaccatgca    2820
tcatcaggag tacggataaa atgcttgatg gtcggaagag gcataaattc cgtcagccag    2880
tttagtctga ccatctcatc tgtaacatca ttggcaacgc tacctttgcc atgtttcaga    2940
aacaactctg gcgcatcggg cttcccatac aatcgataga ttgtcgcacc tgattgcccg    3000
acattatcgc gagcccattt atacccatat aaatcagcat ccatgttgga atttaatcgc    3060
ggcctagagc aagacgtttc ccgttgaata tggctcatac tcttcctttt tcaatattat    3120
tgaagcattt atcagggtta ttgtctcatg agcggataca tatttgaatg tatttagaaa    3180
aataaacaaa taggcatgca gcgctcttcc gcttcctcgc tcactgactc gctacgctcg    3240
gtcgttcgac tgcggcgagc ggtgtcagct cactcaaaag cggtaatacg gttatccaca    3300
gaatcagggg ataaagccgg aaagaacatg tgagcaaaaa gcaaagcacc ggaagaagcc    3360
aacgccgcag cgttttttcc ataggctccg ccccccctgac gagcatcaca aaaatcgacg    3420
ctcaagccag aggtggcgaa acccgacagg actataaaga taccaggcgt ttccccctgg    3480
aagctccctc gtgcgctctc ctgttccgac cctgccgctt accggatacc tgtccgcctt    3540
tctcccttcg ggaagcgtgg cgctttctca tagctcacgc tgttggtatc tcagttcggt    3600
gtaggtcgtt cgctccaagc tgggctgtgt gcacgaaccc cccgttcagc ccgaccgctg    3660
cgccttatcc ggtaactatc gtcttgagtc caacccggta agacacgact tatcgccact    3720
ggcagcagcc attggtaact gatttagagg actttgtctt gaagttatgc acctgttaag    3780
gctaaactga agaacagat tttggtgagt gcggtcctcc aacccactta ccttggttca    3840
aagagttggt agctcagcga accttgagaa aaccaccgtt ggtagcggtg ttttttcttt    3900
atttatgaga tgatgaatca atcggtctat caagtcaacg aacagctatt ccgttactct    3960
agatttcagt gcaatttatc tcttcaaatg tagcacctga agtcagcccc atacgatata    4020
agttgtaatt ctcatgttag tcatgccccg cgccccaccgg aaggagctga ctgggttgaa    4080
ggctctcaag ggcatcggtc gagatcccgg tgcctaatga gtgagctaac ttacattaat    4140
tgcgttgcgc tcactgcccg ctttccagtc gggaaacctg tcgtgccagc tgcattaatg    4200
aatcggccaa cgcgcgggga gaggcggttt gcgtattggg cgccagggtg ttttttcttt    4260
tcaccagtga gacgggcaac agctgattgc ccttcaccgc ctggccctga gagagttgca    4320
gcaagcggtc cacgctggtt tgccccagca ggcgaaaatc ctgtttgatg gtggttaacg    4380
gcgggatata acatgagctg tcttcggtat cgtcgtatcc cactaccgag atgtccgcac    4440
caacgcgcag cccggactcg gtaatggcgc gcattgcgcc cagcgccatc tgatcgttgg    4500
caaccagcat cgcagtggga acgatgccct cattcagcat ttgcatggtt tgttgaaaac    4560
cggacatggc actccagtcg ccttcccgtt ccgctatcgg ctgaatttga ttgcgagtga    4620
gatatttatg ccagccagcc agacgcagac gcgccgagac agaacttaat gggcccgcta    4680
acagcgcgat ttgctggtga cccaatgcga ccagatgctc cacgcccagt cgcgtaccgt    4740
cttcatggga gaaaataata ctgttgatgg gtgtctggtc agagacatca agaaataacg    4800
ccggaacatt agtgcaggca gcttccacag caatggcatc ctggtcatcc agcggatagt    4860
taatgatcag cccactgacg cgttgcgcga agattgtg caccgccgct ttacaggctt    4920
cgacgccgct tcgttctacc atcgacacca ccacgctggc acccagttga tcggcgcgag    4980
```

| | |
|---|---|
| atttaatcgc cgcgacaatt tgcgacggcg cgtgcagggc cagactggag gtggcaacgc | 5040 |
| caatcagcaa cgactgtttg cccgccagtt gttgtgccac gcggttggga atgtaattca | 5100 |
| gctccgccat cgccgcttcc acttttccc gcgttttcgc agaaacgtgg ctggcctggt | 5160 |
| tcaccacgcg ggaaacggtc tgataagaga caccggcata ctctgcgaca tcgtataacg | 5220 |
| ttactggttt cacattcacc accctgaatt gactctcttc cgggcgctat catgccatac | 5280 |
| cgcgaaaggt tttgcgccat cgatggtgt ccgggatctc gacgctctcc cttatgcgac | 5340 |
| tcctgcatta ggaaattaat acgactcact ata | 5373 |

<210> SEQ ID NO 16
<211> LENGTH: 6964
<212> TYPE: DNA
<213> ORGANISM: Artificial Sequence
<220> FEATURE:
<223> OTHER INFORMATION: Description of Artificial Sequence: Synthetic
vector nucleotide sequence

<400> SEQUENCE: 16

| | |
|---|---|
| ggggaattgt gagcggataa caattcccct ctagaaataa ttttgtttaa ctttaagaag | 60 |
| gagatatacc atgggcagca gccatcacca tcatcaccac agccaggatc cgaattcgag | 120 |
| ctcggaccat gattacgcca agctatcaac tttgtataga aaagttgaac gagaaacgta | 180 |
| aaatgatata aatatcaata tattaaatta gattttgcat aaaaaacaga ctacataata | 240 |
| ctgtaaaaca caacatatcc agtcactatg gtcgacctgc agactggctg tgtataaggg | 300 |
| agcctgacat ttatattccc cagaacatca ggttaatggc gttttgatg tcattttcgc | 360 |
| ggtggctgag atcagccact tcttccccga taacggagac cggcacactg gccatatcgg | 420 |
| tggtcatcat gcgccagctt tcatcccga tatgcaccac cgggtaaagt tcacggggga | 480 |
| ctttatctga cagcagacgt gcactggcca ggggatcac catccgtcgc ccgggcgtgt | 540 |
| caataatatc actctgtaca tccacaaaca gacgataacg gctctctctt ttataggtgt | 600 |
| aaaccttaaa ctgcatttca ccagccctg ttctcgtcgg caaagagcc gttcatttca | 660 |
| ataaaccggg cgacctcagc catccttcc tgattttccg cttccagcg ttcggcacgc | 720 |
| agacgacggg cttcattctg catggttgtg cttaccgaac cggagatatt gacatcatat | 780 |
| atgccttgag caactgatag ctgtcgctgt caactgtcac tgtaatacgc tgcttcatag | 840 |
| catacctctt tttgacatac ttcgggtata catatcagta tatattctta taccgcaaaa | 900 |
| atcagcgcgc aaatacgcat actgttatct ggcttttagt aagccggatc tctagatta | 960 |
| cgccccgccc tgccactcat cgcagtactg ttgtaattca ttaagcattc tgccgacatg | 1020 |
| gaagccatca caaacggcat gatgaacctg aatcgccagc ggcatcagca ccttgtcgcc | 1080 |
| ttgcgtataa tatttgccca tggtgaaaac ggggcgaag aagttgtcca tattggccac | 1140 |
| gtttaaatca aaactggtga aactcaccca gggattggct gagacgaaaa acatattctc | 1200 |
| aataaaccct ttagggaaat aggccaggtt ttcaccgtaa cacgccacat cttgcgaata | 1260 |
| tatgtgtaga aactgccgga atcgtcgtg gtattcactc cagagcgatg aaaacgtttc | 1320 |
| agtttgctca tggaaaacgg tgtaacaagg gtgaacacta tcccatatca ccagctcacc | 1380 |
| gtctttcatt gccatacgga attccggatg agcattcatc aggcgggcaa gaatgtgaat | 1440 |
| aaaggccgga taaaacttgt gcttattttt ctttacggtc tttaaaaagg ccgtaatatc | 1500 |
| cagctgaacg gtctggttat aggtacattg agcaactgac tgaaatgcct caaaatgttc | 1560 |
| tttacgatgc cattgggata tatcaacggt ggtatatcca gtgatttttt ctccatttt | 1620 |
| agcttcctta gctcctgaaa atctcgacgg atcctaactc aaaatccaca cattatacga | 1680 |

```
gccggaagca taaagtgtaa agcctgggggg tgcctaatgc ggccgccata gtgactggat   1740
atgttgtgtt ttacagtatt atgtagtctg tttttttatgc aaaatctaat ttaatatatt   1800
gatatttata tcattttacg tttctcgttc aactttatta tacatagttg ataattcact   1860
ggccgtcgtt ttacaacgtc gtgactggga aaaccctggc gttacccaac ttaatcgcct   1920
tgcagcacaa gcttggaatt gttatccgct cacaattcct atagtgagtc gtattaccta   1980
ggctgctgcc accgctgagc aataactagc ataacccctt ggggcctcta acgggtctt    2040
gagggggtttt ttgctgaaag gaggaactat atccggattg gcgaatggga cgcgccctgt   2100
agcggcgcat taagcgcggc gggtgtggtg gttacgcgca gcgtgaccgc tacacttgcc   2160
agcgccctag cgcccgctcc tttcgctttc ttcccttcct ttctcgccac gttcgccggc   2220
tttccccgtc aagctctaaa tcggggggctc cctttagggt tccgatttag tgctttacgg   2280
cacctcgacc ccaaaaaact tgattagggt gatggttcac gtagtgggcc atcgccctga   2340
tagacggttt ttcgcccttt gacgttggag tccacgttct taatagtgg actcttgttc     2400
caaactggaa caacactcaa ccctatctcg gtctattctt ttgatttata agggatttg    2460
ccgattttcgg cctattggtt aaaaaatgag ctgatttaac aaaaatttaa cgcgaatttt   2520
aacaaaatat taacgtttac aatttctggc ggcacgatgg catgagatta tcaaaagga     2580
tcttcaccta gatccttta aattaaaaat gaagttttaa atcaatctaa agtatatatg     2640
agtaaacttg gtctgacagt taccaatgct taatcagtga ggcacctatc tcagcgatct   2700
gtctatttcg ttcatccata gttgcctgac tccccgtcgt gtagataact acgatacggg   2760
agggcttacc atctggcccc agtgctgcaa tgataccgcg agacccacgc tcaccggctc   2820
cagatttatc agcaataaac cagccagccg gaagggccga gcgcagaagt ggtcctgcaa   2880
ctttatccgc ctccatccag tctattaatt gttgccggga agctagagta agtagttcgc   2940
cagttaatag tttgcgcaac gttgttgcca ttgctacagg catcgtggtg tcacgctcgt   3000
cgtttggtat ggcttcattc agctccggtt cccaacgatc aaggcgagtt acatgatccc   3060
ccatgttgtg caaaaagcg gttagctcct tcggtcctcc gatcgttgtc agaagtaagt    3120
tggccgcagt gttatcactc atggttatgg cagcactgca taattctctt actgtcatgc   3180
catccgtaag atgcttttct gtgactggtg agtactcaac caagtcattc tgagaatagt   3240
gtatgcggcg accgagttgc tcttgcccgg cgtcaatacg ggataatacc gcgccacata   3300
gcagaacttt aaaagtgctc atcattggaa aacgttcttc ggggcgaaaa ctctcaagga   3360
tcttaccgct gttgagatcc agttcgatgt aacccactcg tgcacccaac tgatcttcag   3420
catcttttac tttcaccagc gtttctgggt gagcaaaaac aggaaggcaa aatgccgcaa   3480
aaaagggaat aagggcgaca cggaaatgtt gaatactcat actcttcctt tttcaatcat   3540
gattgaagca tttatcaggg ttattgtctc atgagcggat acatatttga atgtatttag   3600
aaaaataaac aaataggtca tgaccaaaat cccttaacgt gagttttcgt tccactgagc   3660
gtcagacccc gtagaaaaga tcaaaggatc ttcttgagat cctttttttc tgcgcgtaat   3720
ctgctgcttg caaacaaaaa aaccaccgct accagcggtg gtttgtttgc cggatcaaga   3780
gctaccaact cttttttcga aggtaactgg cttcagcaga gcgcagatac caaatactgt   3840
ccttctagtg tagccgtagt taggccacca cttcaagaac tctgtagcac cgcctacata   3900
cctcgctctg ctaatcctgt taccagtggc tgctgccagt ggcgataagt cgtgtcttac   3960
cggggttggac tcaagacgat agttaccgga taaggcgcag cggtcgggct gaacggggggg  4020
ttcgtgcaca cagcccagct tggagcgaac gacctacacc gaactgagat acctacagcg   4080
```

```
tgagctatga gaaagcgcca cgcttcccga agggagaaag gcggacaggt atccggtaag    4140
cggcagggtc ggaacaggag agcgcacgag ggagcttcca gggggaaacg cctggtatct    4200
ttatagtcct gtcgggtttc gccacctctg acttgagcgt cgattttgt gatgctcgtc     4260
aggggggcgg agcctatgga aaaacgccag caacgcggcc ttttacggt tcctggcctt     4320
ttgctggcct tttgctcaca tgttctttcc tgcgttatcc cctgattctg tggataaccg    4380
tattaccgcc tttgagtgag ctgataccgc tcgccgcagc cgaacgaccg agcgcagcga    4440
gtcagtgagc gaggaagcgg aagagcgcct gatgcggtat tttctcctta cgcatctgtg    4500
cggtatttca caccgcatat atggtgcact ctcagtacaa tctgctctga tgccgcatag    4560
ttaagccagt atacactccg ctatcgctac gtgactgggt catggctgcg ccccgacacc    4620
cgccaacacc cgctgacgcg ccctgacggg cttgtctgct cccggcatcc gcttacagac    4680
aagctgtgac cgtctccggg agctgcatgt gtcagaggtt ttcaccgtca tcaccgaaac    4740
gcgcgaggca gctgcggtaa agctcatcag cgtggtcgtg aagcgattca cagatgtctg    4800
cctgttcatc cgcgtccagc tcgttgagtt tctccagaag cgttaatgtc tggcttctga    4860
taaagcgggc catgttaagg gcggttttt cctgtttggt cactgatgcc tccgtgtaag    4920
ggggatttct gttcatgggg gtaatgatac cgatgaaacg agagaggatg ctcacgatac    4980
gggttactga tgatgaacat gcccggttac tggaacgttg tgagggtaaa caactggcgg    5040
tatggatgcg gcgggaccag agaaaaatca ctcagggtca atgccagcgc ttcgttaata    5100
cagatgtagg tgttccacag ggtagccagc agcatcctgc gatgcagatc cggaacataa    5160
tggtgcaggg cgctgacttc cgcgtttcca gactttacga aacacggaaa ccgaagacca    5220
ttcatgttgt tgctcaggtc gcagacgttt tgcagcagca gtcgcttcac gttcgctcgc    5280
gtatcggtga ttcattctgc taaccagtaa ggcaaccccg ccagcctagc cgggtcctca    5340
acgacaggag cacgatcatg ctagtcatgc cccgcgccca ccggaaggag ctgactgggt    5400
tgaaggctct caagggcatc ggtcgagatc ccggtgccta atgagtgagc taacttacat    5460
taattgcgtt gcgctcactg cccgctttcc agtcgggaaa cctgtcgtgc cagctgcatt    5520
aatgaatcgg ccaacgcgcg gggagaggcg gtttgcgtat tgggcgccag gtggtttttt    5580
cttttcacca gtgagacggg caacagctga ttgcccttca ccgcctggcc ctgagagagt    5640
tgcagcaagc ggtccacgct ggtttgcccc agcaggcgaa aatcctgttt gatggtggtt    5700
aacggcggga tataacatga gctgtcttcg gtatcgtcgt atcccactac cgagatgtcc    5760
gcaccaacgc gcagcccgga ctcggtaatg gcgcgcattg cgcccagcgc catctgatcg    5820
ttggcaacca gcatcgcagt gggaacgatg ccctcattca gcatttgcat ggtttgttga    5880
aaaccggaca tggcactcca gtcgccttcc cgttccgcta tcggctgaat ttgattgcga    5940
gtgagatatt tatgccagcc agccagacgc agacgcgccg agacagaact taatgggccc    6000
gctaacagcg cgatttgctg gtgacccaat gcgaccagat gctccacgcc cagtcgcgta    6060
ccgtcttcat gggagaaaat aatactgttg atgggtgtct ggtcagagac atcaagaaat    6120
aacgccggaa cattagtgca ggcagcttcc acagcaatgg catcctggtc atccagcgga    6180
tagttaatga tcagcccact gacgcgttgc gcgagaagat tgtgcaccgc cgctttacag    6240
gcttcgacgc cgcttcgttc taccatcgac accaccacgc tggcacccag ttgatcggcg    6300
cgagatttaa tcgccgcgac aatttgcgac ggcgcgtgca gggccagact ggaggtggca    6360
acgccaatca gcaacgactg tttgcccgcc agttgttgtg ccacgcggtt gggaatgtaa    6420
ttcagctccg ccatcgccgc ttccactttt tcccgcgttt tcgcagaaac gtggctggcc    6480
```

-continued

| | |
|---|---|
| tggttcacca cgcgggaaac ggtctgataa gagacaccgg catactctgc gacatcgtat | 6540 |
| aacgttactg gtttcacatt caccaccctg aattgactct cttccgggcg ctatcatgcc | 6600 |
| ataccgcgaa aggttttgcg ccattcgatg gtgtccggga tctcgacgct ctcccttatg | 6660 |
| cgactcctgc attaggaagc agcccagtag taggttgagg ccgttgagca ccgccgccgc | 6720 |
| aaggaatggt gcatgcaagg agatggcgcc caacagtccc ccggccacgg ggcctgccac | 6780 |
| catacccacg ccgaaacaag cgctcatgag cccgaagtgg cgagcccgat cttccccatc | 6840 |
| ggtgatgtcg gcgatatagg cgccagcaac cgcacctgtg gcgccggtga tgccggccac | 6900 |
| gatgcgtccg gcgtagagga tcgagatcga tctcgatccc gcgaattaa tacgactcac | 6960 |
| tata | 6964 |

<210> SEQ ID NO 17
<211> LENGTH: 6902
<212> TYPE: DNA
<213> ORGANISM: Artificial Sequence
<220> FEATURE:
<223> OTHER INFORMATION: Description of Artificial Sequence: Synthetic
vector nucleotide sequence

<400> SEQUENCE: 17

| | |
|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttag | 180 |
| cagccggatc tgatcttaat taattatcac cactttgtac aagaaagctg aacgagaaac | 240 |
| gtaaaatgat ataaatatca atatattaaa ttagattttg cataaaaaac agactacata | 300 |
| atactgtaaa acacaacata tccagtcact atggtcgacc tgcagactgg ctgtgtataa | 360 |
| gggagcctga catttatatt ccccagaaca tcaggttaat ggcgtttttg atgtcatttt | 420 |
| cgcggcggct gagatcagcc acttcttccc cgataacgga gaccggcaca ctggccatat | 480 |
| cggtggtcat catgcgccag cttttcatcc cgatatgcac caccgggtaa agttcacggg | 540 |
| agactttatc tgacagcaga cgtgcactgg ccaggggat caccatccgt cgcccggcg | 600 |
| tgtcaataat atcactctgt acatccacaa acagacgata acggctctct cttttatagg | 660 |
| tgtaaacctt aaactgcatt tcaccagtcc ctgttctcgt cagcaaaaga gccgttcatt | 720 |
| tcaataaacc gggcgaccct agccatccct tcctgatttt ccgctttcca gcgttcggca | 780 |
| cgcagacgac gggcttcatt ctgcatggtt gtgcttacca gaccggagat attgacatca | 840 |
| tatatgcctt gagcaactga tagctgtcgc tgtcaactgt cactgtaata cgctgcttca | 900 |
| tagcacacct ctttttgaca tacttcgggt atacgctagc accggtgttg caacgaacag | 960 |
| gtcactatca gtcaaaataa aatcattatt tgccatccag ctgatatccc ctatagtgag | 1020 |
| tcgtattaca tggtcatagc tgtttcctgg cagctctggc ccgtgtctca aaatctctga | 1080 |
| tgttacattg cacaagataa aataatatca tcatgatcag tcctgctcct cggccacgaa | 1140 |
| gtgcacgcag ttgccggccg ggtcgcgcag ggcgaactcc cgcccccacg gctgctcgcc | 1200 |
| gatctcggtc atggccggcc cggaggcgtc ccggaagttc gtggacacga cctccgacca | 1260 |
| ctcggcgtac agctcgtcca ggccgcgcac ccacacccag gccagggtgt tgtccggcac | 1320 |
| cacctggtcc tggaccgcgc tgatgaacag ggtcacgtcg tcccggacca ccgggcgaa | 1380 |
| gtcgtcctcc acgaagtccc gggagaaccc gagccggtcg gtccagaact cgaccgctcc | 1440 |
| ggcgacgtcg cgcgcggtga gcaccggaac ggcactggtc aacttggcca tggtttagtt | 1500 |

-continued

```
cctcaccttg tcgtattata ctatgccgat atactatgcc gatgattaat tgtcaacacg    1560
tgctgatcat gaccaaaatc ccttaacgtg gcggccgcca tagtgactgg atatgttgtg    1620
ttttacagta ttatgtagtc tgttttttat gcaaaatcta atttaatata ttgatattta    1680
tatcatttta cgtttctcgt tcagcttttt tgtacaaact tgtgatcgag ctcgaattcg    1740
gatccgaatt aattccgata tccatggcca tcgccggctg ggcagcgagg agcagcagac    1800
cagcagcagc ggtcggcagc aggtatttca tatgtatatc tccttcttaa agttaaacaa    1860
aattatttct agaggggaat tgttatccgc tcacaattcc cctatagtga gtcgtattaa    1920
tttcgcggga tcgagatctc gatcctctac gccggacgca tcgtggccgg catcaccggc    1980
gccacaggtg cggttgctgg cgcctatatc gccgacatca ccgatgggga agatcgggct    2040
cgccacttcg ggctcatgag cgcttgtttc ggcgtgggta tggtggcagg ccccgtggcc    2100
gggggactgt tgggcgccat ctccttgcat gcaccattcc ttgcggcggc ggtgctcaac    2160
ggcctcaacc tactactggg ctgcttccta atgcaggagt cgcataaggg agagcgtcga    2220
gatcccggac accatcgaat ggcgcaaaac ctttcgcggt atggcatgat agcgcccgga    2280
agagagtcaa ttcagggtgg tgaatgtgaa accagtaacg ttatacgatg tcgcagagta    2340
tgccggtgtc tcttatcaga ccgtttcccg cgtggtgaac caggccagcc acgtttctgc    2400
gaaaacgcgg gaaaagtgg aagcggcgat ggcggagctg aattacattc ccaaccgcgt    2460
ggcacaacaa ctggcgggca aacagtcgtt gctgattggc gttgccacct ccagtctggc    2520
cctgcacgcg ccgtcgcaaa ttgtcgcggc gattaaatct cgcgccgatc aactgggtgc    2580
cagcgtggtg gtgtcgatgg tagaacgaag cggcgtcgaa gcctgtaaag cggcggtgca    2640
caatcttctc gcgcaacgcg tcagtgggct gatcattaac tatccgctgg atgaccagga    2700
tgccattgct gtggaagctg cctgcactaa tgttccggcg ttatttcttg atgtctctga    2760
ccagacaccc atcaacagta ttattttctc ccatgaagac ggtacgcgac tgggcgtgga    2820
gcatctggtc gcattgggtc accagcaaat cgcgctgtta gcgggcccat taagttctgt    2880
ctcggcgcgt ctgcgtctgg ctggctggca taaatatctc actcgcaatc aaattcagcc    2940
gatagcggaa cgggaaggcg actggagtgc catgtccggt tttcaacaaa ccatgcaaat    3000
gctgaatgag gcatcgttc ccactgcgat gctggttgcc aacgatcaga tggcgctggg    3060
cgcaatgcgc gccattaccg agtccgggct gcgcgttggt gcggatatct cggtagtggg    3120
atacgacgat accgaagaca gctcatgtta tcccgccg ttaaccacca tcaaacagga    3180
ttttcgcctg ctggggcaaa ccagcgtgga ccgcttgctg caactctctc agggccaggc    3240
ggtgaagggc aatcagctgt tgcccgtctc actggtgaaa agaaaaacca ccctggcgcc    3300
caatacgcaa accgcctctc cccgcgcgtt ggccgattca ttaatgcagc tggcacgaca    3360
ggtttcccga ctggaaagcg ggcagtgagc gcaacgcaat taatgtaagt tagctcactc    3420
attaggcacc gggatctcga ccgatgccct tgagagcctt caacccagtc agctccttcc    3480
ggtgggcgcg gggcatgact atcgtcgccg cacttatgac tgtcttcttt atcatgcaac    3540
tcgtaggaca ggtgccggca gcgctctggg tcattttcgg cgaggaccgc tttcgctgga    3600
gcgcgacgat gatcggcctg tcgcttgcgg tattcggaat cttgcacgcc ctcgctcaag    3660
ccttcgtcac tggtccccgcc accaaacgtt tcggcgagaa gcaggccatt atcgccggca    3720
tggcggcccc acgggtgcgc atgatcgtgc tcctgtcgtt gaggacccgg ctaggctggc    3780
ggggttgcct tactggttag cagaatgaat caccgatacg cgagcgaacg tgaagcgact    3840
gctgctgcaa aacgtctgcg acctgagcaa caacatgaat ggtcttcggt ttccgtgttt    3900
```

```
cgtaaagtct ggaaacgcgg aagtcagcgc cctgcaccat tatgttccgg atctgcatcg    3960
caggatgctg ctggctaccc tgtggaacac ctacatctgt attaacgaag cgctggcatt    4020
gaccctgagt gattttctc tggtcccgcc gcatccatac cgccagttgt ttaccctcac     4080
aacgttccag taaccgggca tgttcatcat cagtaacccg tatcgtgagc atcctctctc    4140
gtttcatcgg tatcattacc cccatgaaca gaaatccccc ttacacggag gcatcagtga    4200
ccaaacagga aaaaccgcc cttaacatgg cccgctttat cagaagccag acattaacgc     4260
ttctggagaa actcaacgag ctggacgcgg atgaacaggc agacatctgt gaatcgcttc    4320
acgaccacgc tgatgagctt taccgcagct gcctcgcgcg tttcggtgat gacggtgaaa    4380
acctctgaca catgcagctc ccggagacgg tcacagcttg tctgtaagcg gatgccggga    4440
gcagacaagc ccgtcaggc gcgtcagcgg tgttggcgg tgtcgggc gcagccatga        4500
cccagtcacg tagcgatagc ggagtgtata ctggcttaac tatgcggcat cagagcagat    4560
tgtactgaga gtgcaccata tatgcggtgt gaaataccgc acagatgcgt aaggagaaaa    4620
taccgcatca ggcgctcttc cgcttcctcg ctcactgact cgctgcgctc ggtcgttcgg    4680
ctgcggcgag cggtatcagc tcactcaaag gcggtaatac ggttatccac agaatcaggg    4740
gataacgcag gaaagaacat gtgagcaaaa ggccagcaaa aggccaggaa ccgtaaaaag    4800
gccgcgttgc tggcgttttt ccataggctc cgcccccctg acgagcatca caaaaatcga    4860
cgctcaagtc agaggtggcg aaacccgaca ggactataaa gataccaggc gtttccccct    4920
ggaagctccc tcgtgcgctc tcctgttccg accctgccgc ttaccggata cctgtccgcc    4980
tttctccctt cgggaagcgt ggcgctttct catagctcac gctgtaggta tctcagttcg    5040
gtgtaggtcg ttcgctccaa gctgggctgt gtgcacgaac cccccgttca gcccgaccgc    5100
tgcgccttat ccggtaacta tcgtcttgag tccaacccgg taagacacga cttatcgcca    5160
ctggcagcag ccactggtaa caggattagc agagcgaggt atgtaggcgg tgctacagag    5220
ttcttgaagt ggtggcctaa ctacggctac actagaagga cagtatttgg tatctgcgct    5280
ctgctgaagc cagttacctt cggaaaaaga gttggtagct cttgatccgg caaacaaacc    5340
accgctggta gcggtggttt ttttgtttgc aagcagcaga ttacgcgcag aaaaaaagga    5400
tctcaagaag atcctttgat cttttctacg gggtctgacg ctcagtggaa cgaaaactca    5460
cgttaaggga ttttggtcat gaacaataaa actgtctgct tacataaaca gtaatacaag    5520
gggtgttatg agccatattc aacgggaaac gtcttgctct aggccgcgat taaattccaa    5580
catgatgct gatttatatg gtataaatg ggctcgcgat aatgtcgggc aatcaggtgc      5640
gacaatctat cgattgtatg ggaagcccga tgcgccagag ttgtttctga acatggcaa     5700
aggtagcgtt gccaatgatg ttacagatga atggtcaga ctaaactggc tgacggaatt     5760
tatgcctctt ccgaccatca agcattttat ccgtactcct gatgatgcat ggttactcac    5820
cactgcgatc cccgggaaaa cagcattcca ggtattagaa gaatatcctg attcaggtga    5880
aaatattgtt gatgcgctgg cagtgttcct gcgccggttg cattcgattc ctgtttgtaa    5940
ttgtcctttt aacagcgatc gcgtatttcg tctcgctcag gcgcaatcac gaatgaataa    6000
cggtttggtt gatgcgagtg attttgatga cgagcgtaat ggctggcctg ttgaacaagt    6060
ctggaaagaa atgcataaac ttttgccatt ctcaccggat tcagtcgtca ctcatggtga    6120
tttctcactt gataaccttta ttttgacga ggggaaatta ataggttgta ttgatgttgg    6180
acgagtcgga atcgcagacc gataccagga tcttgccatc ctatggaact gcctcggtga    6240
gttttctcct tcattacaga aacggctttt tcaaaaatat ggtattgata atcctgatat    6300
```

-continued

| | |
|---|---|
| gaataaattg cagtttcatt tgatgctcga tgagtttttc taagaattaa ttcatgagcg | 6360 |
| gatacatatt tgaatgtatt tagaaaaata aacaaatagg ggttccgcgc acatttcccc | 6420 |
| gaaaagtgcc acctgaaatt gtaaacgtta atattttgtt aaaattcgcg ttaaattttt | 6480 |
| gttaaatcag ctcattttt aaccaatagg ccgaaatcgg caaaatccct tataaatcaa | 6540 |
| aagaatagac cgagataggg ttgagtgttg ttccagtttg gaacaagagt ccactattaa | 6600 |
| agaacgtgga ctccaacgtc aaagggcgaa aaaccgtcta tcagggcgat ggcccactac | 6660 |
| gtgaaccatc accctaatca agttttttgg ggtcgaggtg ccgtaaagca ctaaatcgga | 6720 |
| accctaaagg gagcccccga tttagagctt gacggggaaa gccggcgaac gtggcgagaa | 6780 |
| aggaagggaa gaaagcgaaa ggagcgggcg ctagggcgct ggcaagtgta gcggtcacgc | 6840 |
| tgcgcgtaac caccacaccc gccgcgctta atgcgccgct acagggcgcg tcccattcgc | 6900 |
| ca | 6902 |

<210> SEQ ID NO 18
<211> LENGTH: 5626
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 18

| | |
|---|---|
| cctgcattag gaagcagccc agtagtaggt tgaggccgtt gagcaccgcc gccgcaagga | 60 |
| atggtgcatg caaggagatg cgcccaaca gtcccccggc cacggggcct gccaccatac | 120 |
| ccacgccgaa acaagcgctc atgagcccga agtggcgagc ccgatcttcc ccatcggtga | 180 |
| tgtcggcgat ataggcgcca gcaaccgcac ctgtggcgcc ggtgatgccg gccacgatgc | 240 |
| gtccggcgta gaggatcgag atctcgatcc cgcgaaatta atacgactca ctatagggga | 300 |
| attgtgagcg gataacaatt cccctctaga aataattttg tttaacttta agaaggagat | 360 |
| atacatatga ataccctgct gccgaccgct gctgctggtc tgctgctcct cgctgcccag | 420 |
| ccggcgatgg ccatggatat cggaattaat tcggatccga attcgagctc gatcacaagt | 480 |
| ttgtacaaaa aagctgaacg agaaacgtaa aatgatataa atatcaatat attaaattag | 540 |
| attttgcata aaaaacagac tacataatac tgtaaaacac aacatatcca gtcactatgg | 600 |
| cggccgccac gttaagggat tttggtcatg atcagcacgt gttgacaatt aatcatcggc | 660 |
| atagtatatc ggcatagtat aatacgacaa ggtgaggaac taaaccatgg ccaagttgac | 720 |
| cagtgccgtt ccggtgctca ccgcgcgcga cgtcgccgga gcggtcgagt tctggaccga | 780 |
| ccggctcggg ttctcccggg acttcgtgga ggacgacttc gccggtgtgg tccgggacga | 840 |
| cgtgaccctg ttcatcagcg cggtccagga ccaggtggtg ccggacaaca ccctggcctg | 900 |
| ggtgtgggtg cgcggcctgg acgagctgta cgccgagtgg tcggaggtcg tgtccacgaa | 960 |
| cttccgggac gcctccgggc cggccatgac cgagatcggc gagcagccgt gggggcggga | 1020 |
| gttcgccctg cgcgacccgg ccggcaactg cgtgcacttc gtggccgagg agcaggactg | 1080 |
| atcatgatga tattattta tcttgtgcaa tgtaacatca gagattttga cacacggcc | 1140 |
| agagctgcca ggaaacagct atgaccatgt aatacgactc actataggg atatcagctg | 1200 |
| gatggcaaat aatgatttta ttttgactga tagtgacctg ttcgttgcaa caccggtgct | 1260 |
| agcgtatacc cgaagtatgt caaaagagg tgtgctatga agcagcgtat tacagtgaca | 1320 |
| gttgacagcg acagctatca gttgctcaag gcatatgaa tgtcaatatc tccggtctgg | 1380 |
| taagcacaac catgcagaat gaagcccgtc gtctgcgtgc cgaacgctgg aaagcggaaa | 1440 |

```
atcaggaagg gatggctgag gtcgcccggt ttattgaaat gaacggctct tttgctgacg    1500
agaacaggga ctggtgaaat gcagtttaag gtttacacct ataaagaga gagccgttat    1560 cgtctgtttg tggatgtaca gagtgatatt attgacacgc ccgggcgacg gatggtgatc    1620
cccctggcca gtgcacgtct gctgtcagat aaagtctccc gtgaacttta cccggtggtg    1680
catatcgggg atgaaagctg gcgcatgatg accaccgata tggccagtgt gccggtctcc    1740
gttatcgggg aagaagtggc tgatctcagc cgccgcgaaa atgacatcaa aaacgccatt    1800
aacctgatgt tctggggaat ataaatgtca ggctcccttta tacacagcca gtctgcaggt    1860
cgaccatagt gactggatat gttgtgtttt acagtattat gtagtctgtt ttttatgcaa    1920
aatctaattt aatatattga tatttatatc attttacgtt tctcgttcag ctttcttgta    1980
caaagtggtg ataattaatt aagatcagat ccggctgcta agcttgcggc cgcataatgc    2040
ttaagtcgaa cagaaagtaa tcgtattgta cacggccgca taatcgaaat taatacgact    2100
cactataggg gaattgtgag cggataacaa ttccccatct tagtatatta gttaagtata    2160
agaaggagat atacatatgg cagatctcaa ttggatatcg gccggccacg cgatcgctga    2220
cgtcggtacc ctcgagtctg gtaaagaaac cgctgctgcg aaatttgaac gccagcacat    2280
ggactcgtct actagcgcag cttaattaac ctaggctgct gccaccgctg agcaataact    2340
agcataaccc cttggggcct ctaaacgggt cttgagggggt tttttgctga aacctcaggc    2400
atttgagaag cacacggtca cactgcttcc ggtagtcaat aaaccggtaa accagcaata    2460
gacataagcg gctatttaac gaccctgccc tgaaccgacg accgggtcat cgtggccgga    2520
tcttgcggcc cctcggcttg aacgaattgt tagacattat ttgccgacta ccttggtgat    2580
ctcgcctttc acgtagtgga caaattcttc caactgatct gcgcgcgagg ccaagcgatc    2640
ttcttcttgt ccaagataag cctgtctagc ttcaagtatg acgggctgat actgggccgg    2700
caggcgctcc attgcccagt cggcagcgac atccttcggc gcgattttgc cggttactgc    2760
gctgtaccaa atgcgggaca acgtaagcac tacatttcgc tcatcgccag cccagtcggg    2820
cggcgagttc catagcgtta aggtttcatt tagcgcctca aatagatcct gttcaggaac    2880
cggatcaaag agttcctccg ccgctggacc taccaaggca acgctatgtt ctcttgcttt    2940
tgtcagcaag atagccagat caatgtcgat cgtggctggc tcgaagatac ctgcaagaat    3000
gtcattgcgc tgccattctc caaattgcag ttcgcgctta gctggataac gccacggaat    3060
gatgtcgtcg tgcacaacaa tggtgacttc tacagcgcgg agaatctcgc tctctccagg    3120
ggaagccgaa gtttccaaaa ggtcgttgat caaagctcgc cgcgttgttt catcaagcct    3180
tacggtcacc gtaaccagca atcaatatc actgtgtggc ttcaggccgc catccactgc    3240
ggagccgtac aaatgtacgg ccagcaacgt cggttcgaga tggcgctcga tgacgccaac    3300
tacctctgat agttgagtcg atacttcggc gatcaccgct ccctcatac tcttcctttt    3360 tcaatattat tgaagcattt atcagggtta ttgtctcatg agcggataca tatttgaatg    3420
tatttagaaa aataaacaaa tagcagtctc actcggtcgc tacgctccgg gcgtgagact    3480
gcggcgggcg ctgcggacac atacaaagtt acccacagat tccgtggata agcagggac    3540 taacatgtga ggcaaaacag cagggccgcg ccggtggcgt ttttccatag gctccgccct    3600
cctgccagag ttcacataaa cagacgcttt tccggtgcat ctgtgggagc cgtgaggctc    3660
aaccatgaat ctgacagtac gggcgaaacc cgacaggact taaagatccc caccgtttcc    3720
ggcgggtcgc tccctcttgc gctctcctgt tccgaccctg ccgttaccg gatacctgtt    3780 ccgcctttct cccttacggg aagtgtggcg ctttctcata gctcacacac tggtatctcg    3840
```

```
gctcggtgta ggtcgttcgc tccaagctgg gctgtaagca agaactcccc gttcagcccg      3900
actgctgcgc cttatccggt aactgttcac ttgagtccaa cccggaaaag cacggtaaaa      3960
cgccactggc agcagccatt ggtaactggg agttcgcaga ggatttgttt agctaaacac      4020
gcggttgctc ttgaagtgtg cgccaaagtc cggctacact ggaaggacag atttggttgc      4080
tgtgctctgc gaaagccagt taccacggtt aagcagttcc ccaactgact taaccttcga      4140
tcaaaccacc tccccaggtg ttttttcgt ttacagggca aaagattacg cgcagaaaaa       4200
aaggatctca agaagatcct ttgatctttt ctactgaacc gctctagatt tcagtgcaat      4260
ttatctcttc aaatgtagca cctgaagtca gccccatacg atataagttg taattctcat      4320
gttagtcatg ccccgcgccc accggaagga gctgactggg ttgaaggctc tcaagggcat      4380
cggtcgagat cccggtgcct aatgagtgag ctaacttaca ttaattgcgt tgcgctcact      4440
gcccgctttc cagtcgggaa acctgtcgtg ccagctgcat taatgaatcg gccaacgcgc      4500
ggggagaggc ggtttgcgta ttgggcgcca gggtggtttt tcttttcacc agtgagacgg      4560
gcaacagctg attgcccttc accgcctggc cctgagagag ttgcagcaag cggtccacgc      4620
tggtttgccc cagcaggcga aaatcctgtt tgatggtggt taacgcgggg atataacatg      4680
agctgtcttc ggtatcgtcg tatcccacta ccgagatgtc cgcaccaacg cgcagcccgg      4740
actcggtaat ggcgcgcatt gcgcccagcg ccatctgatc gttggcaacc agcatcgcag      4800
tgggaacgat gccctcattc agcatttgca tggtttgttg aaaaccggac atggcactcc      4860
agtcgccttc ccgttccgct atcggctgaa tttgattgcg agtgagatat ttatgccagc      4920
cagccagacg cagacgcgcc gagacagaac ttaatgggcc cgctaacagc gcgatttgct      4980
ggtgacccaa tgcgaccaga tgctccacgc ccagtcgcgt accgtcttca tgggagaaaa      5040
taatactgtt gatgggtgtc tggtcagaga catcaagaaa taacgccgga acattagtgc      5100
aggcagcttc cacagcaatg gcatcctggt catccagcgg atagttaatg atcagcccac      5160
tgacgcgttg cgcgagaaga ttgtgcaccg ccgctttaca ggcttcgacg ccgcttcgtt      5220
ctaccatcga caccaccacg ctggcaccca gttgatcggc gcgagattta atcgccgcga      5280
caatttgcga cggcgcgtgc agggccagac tggaggtggc aacgccaatc agcaacgact      5340
gtttgcccgc cagttgttgt gccacgcggt tgggaatgta attcagctcc gccatcgccg      5400
cttccacttt ttcccgcgtt ttcgcagaaa cgtggctggc ctggttcacc acgcgggaaa      5460
cggtctgata agagacaccg gcatactctg cgacatcgta taacgttact ggtttcacat      5520
tcaccaccct gaattgactc tcttccgggc gctatcatgc cataccgcga aaggttttgc      5580
gccattcgat ggtgtccggg atctcgacgc tctcccttat gcgact                    5626

<210> SEQ ID NO 19
<211> LENGTH: 5674
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 19
cctgcattag gaagcagccc agtagtaggt tgaggccgtt gagcaccgcc gccgcaagga        60
atggtgcatg caaggagatg cgcccaaca gtcccccggc cacggggcct gccaccatac       120
ccacgccgaa acaagcgctc atgagcccga agtggcgagc ccgatcttcc ccatcggtga       180
tgtcggcgat ataggcgcca gcaaccgcac ctgtggcgcc ggtgatgccg gccacgatgc       240
```

```
gtccggcgta gaggatcgag atctcgatcc cgcgaaatta atacgactca ctatagggga    300
attgtgagcg gataacaatt cccctctaga ataattttg tttaacttta agaaggagat    360
atacatatga aatacctgct gccgaccgct gctgctggtc tgctgctcct cgctgcccag    420
ccggcgatgg ccatggatat cggaattaat tcgatccga attcgagctc gatcacaagt     480
ttgtacaaaa aagctgaacg agaaacgtaa aatgatataa atatcaatat attaaattag    540
attttgcata aaaaacagac tacataatac tgtaaaacac aacatatcca gtcactatgg    600
cggccgccac gttaagggat tttggtcatg atcagcacgt gttgacaatt aatcatcggc    660
atagtatatc ggcatagtat aatacgacaa ggtgaggaac taaaccatgg ccaagttgac    720
cagtgccgtt ccggtgctca ccgcgcgcga cgtcgccgga gcggtcgagt tctggaccga    780
ccggctcggg ttctcccggg acttcgtgga ggacgacttc gccggtgtgg tccgggacga    840
cgtgaccctg ttcatcagcg cggtccagga ccaggtggtg ccggacaaca ccctggcctg    900
ggtgtgggtg cgcggcctgg acgagctgta cgccgagtgg tcggaggtcg tgtccacgaa    960
cttccgggac gcctccgggc cggccatgac cgagatcggc gagcagccgt ggggggcggga    1020 gttcgccctg cgcgacccgg ccggcaactg cgtgcacttc gtggccgagg agcaggactg    1080
atcatgatga tattatttta tcttgtgcaa tgtaacatca gagattttga gacacgggcc    1140
agagctgcca ggaaacagct atgaccatgt aatacgactc actataggg atatcagctg    1200 gatggcaaat aatgatttta ttttgactga tagtgacctg ttcgttgcaa caccggtgct    1260
agcgtatacc cgaagtatgt caaaaagagg tgtgctatga agcagcgtat tacagtgaca    1320
gttgacagcg acagctatca gttgctcaag gcatatatga tgtcaatatc tccggtctgg    1380
taagcacaac catgcagaat gaagcccgtc gtctgcgtgc cgaacgctgg aaagcggaaa    1440
atcaggaagg gatggctgag gtcgcccggt ttattgaaat gaacggctct tttgctgacg    1500
agaacaggga ctggtgaaat gcagtttaag gtttacacct ataaaagaga gagccgttat    1560
cgtctgtttg tggatgtaca gagtgatatt attgacacgc ccgggcgacg gatggtgatc    1620
cccctggcca gtgcacgtct gctgtcagat aaagtctccc gtgaactta cccggtggtg    1680 catatcgggg atgaaagctg gcgcatgatg accaccgata tggccagtgt gccggtctcc    1740
gttatcgggg aagaagtggc tgatctcagc cgccgcgaaa atgacatcaa aaacgccatt    1800
aacctgatgt tctggggaat ataaatgtca ggctccctta tacacagcca gtctgcaggt    1860
cgaccatagt gactggatat gttgtgtttt acagtattat gtagtctgtt ttttatgcaa    1920
aatctaattt aatatattga tatttatatc attttacgtt tctcgttcag ctttcttgta    1980
caaagtggtg ataattaatt aagatcagat ccggctgcta agcttgcggc cgcataatgc    2040
ttaagtcgaa cagaaagtaa tcgtattgta cacggccgca taatcgaaat taatacgact    2100
cactataggg gaattgtgag cggataacaa ttccccatct tagtatatta gttaagtata    2160
agaaggagat atacatatgg cagatctcaa ttggatatcg gccggccacg cgatcgctga    2220
cgtcggtacc ctcgagtctg gtaaagaaac cgctgctgcg aaatttgaac gccagcacat    2280
ggactcgtct actagcgcag cttaattaac ctaggctgct gccaccgctg agcaataact    2340
agcataaccc cttggggcct ctaaacgggt cttgaggggt ttttgctga aacctcaggc    2400 atttgagaag cacaccggtca cactgcttcc ggtagtcaat aaaccggtaa accagcaata    2460
gacataagcg gctatttaac gaccctgccc tgaaccgacg acaagctgac gaccgggtct    2520
ccgcaagtgg cacttttcgg ggaaatgtgc gcggaacccc tatttgttta ttttttctaaa    2580 tacattcaaa tatgtatccg ctcatgaatt aattcttaga aaaactcatc gagcatcaaa    2640
```

```
tgaaactgca atttattcat atcaggatta tcaataccat attttttgaaa aagccgtttc    2700
tgtaatgaag gagaaaactc accgaggcag ttccatagga tggcaagatc ctggtatcgg    2760
tctgcgattc cgactcgtcc aacatcaata caacctatta atttcccctc gtcaaaaata    2820
aggttatcaa gtgagaaatc accatgagtg acgactgaat ccggtgagaa tggcaaaagt    2880
ttatgcattt cttttccagac ttgttcaaca ggccagccat tacgctcgtc atcaaaatca   2940
ctcgcatcaa ccaaaccgtt attcattcgt gattgcgcct gagcgagacg aaatacgcgg    3000
tcgctgttaa aaggacaatt acaaacagga atcgaatgca accggcgcag gaacactgcc    3060
agcgcatcaa caatattttc acctgaatca ggatattctt ctaataccctg gaatgctgtt   3120
ttcccgggga tcgcagtggt gagtaaccat gcatcatcag gagtacggat aaaatgcttg    3180
atggtcggaa gaggcataaa ttccgtcagc cagtttagtc tgaccatctc atctgtaaca    3240
tcattggcaa cgctaccttt gccatgtttc agaaacaact ctggcgcatc gggcttccca    3300
tacaatcgat agattgtcgc acctgattgc ccgacattat cgcgagccca tttataccca    3360
tataaatcag catccatgtt ggaatttaat cgcggcctag agcaagacgt ttcccgttga    3420
atatggctca tactcttcct ttttcaatat tattgaagca tttatcaggg ttattgtctc    3480
atgagcggat acatatttga atgtatttag aaaaataaac aaataggcat gcagcgctct    3540
tccgcttcct cgctcactga ctcgctacgc tcggtcgttc gactgcggcg agcggtgtca    3600
gctcactcaa aagcggtaat acggttatcc acagaatcag gggataaagc cggaaagaac    3660
atgtgagcaa aaagcaaagc accggaagaa gccaacgccg caggcgtttt tccataggct    3720
ccgccccccct gacgagcatc acaaaaatcg acgctcaagc cagaggtggc gaaacccgac    3780
aggactataa agataccagg cgtttccccc tggaagctcc ctcgtgcgct ctcctgttcc    3840
gaccctgccg cttaccggat acctgtccgc ctttctccct tcgggaagcg tggcgctttc    3900
tcatagctca cgctgttggt atctcagttc ggtgtaggtc gttcgctcca agctgggctg    3960
tgtgcacgaa ccccccgttc agcccgaccg ctgcgcctta ccggtaact atcgtcttga    4020
gtccaacccg gtaagacacg acttatcgcc actggcagca gccattggta actgatttag    4080
aggactttgt cttgaagtta tgcacctgtt aaggctaaac tgaaagaaca gattttggtg    4140
agtgcggtcc tccaacccac ttaccttggt tcaaagagtt ggtagctcag cgaaccttga    4200
gaaaaccacc gttggtagcg gtggttttt ctttatttatg agatgatgaa tcaatcggtc    4260
tatcaagtca acgaacagct attccgttac tctagatttc agtgcaattt atctcttcaa    4320
atgtagcacc tgaagtcagc cccatacgat ataagttgta attctcatgt tagtcatgcc    4380
ccgcgcccac cggaaggagc tgactgggtt gaaggctctc aagggcatcg gtcgagatcc    4440
cggtgcctaa tgagtgagct aacttacatt aattgcgttg cgctcactgc ccgctttcca    4500
gtcgggaaac ctgtcgtgcc agctgcatta atgaatcggc caacgcgcgg ggagaggcgg    4560
tttgcgtatt gggcgccagg gtggttttc ttttcaccag tgagacgggc aacagctgat    4620
tgcccttcac cgcctggccc tgagagagtt gcagcaagcg gtccacgctg gtttgcccca    4680
gcaggcgaaa atcctgtttg atggtggtta acggcgggat ataacatgag ctgtcttcgg    4740
tatcgtcgta tcccactacc gagatgtccg caccaacgcg cagcccggac tcggtaatgg    4800
cgcgcattgc gcccagcgcc atctgatcgt tggcaaccag catcgcagtg gaacgatgc    4860
cctcattcag catttgcatg gtttgttgaa aaccggacat ggcactccag tcgccttccc    4920
gttccgctat cggctgaatt tgattgcgag tgagatattt atgccagcca gccagacgca    4980
gacgcgccga gacagaactt aatgggcccg ctaacagcgc gatttgctgg tgacccaatg    5040
```

```
cgaccagatg ctccacgccc agtcgcgtac cgtcttcatg ggagaaaata atactgttga    5100
tgggtgtctg gtcagagaca tcaagaaata acgccggaac attagtgcag gcagcttcca    5160
cagcaatggc atcctggtca tccagcggat agttaatgat cagcccactg acgcgttgcg    5220
cgagaagatt gtgcaccgcc gctttacagg cttcgacgcc gcttcgttct accatcgaca    5280
ccaccacgct ggcacccagt tgatcggcgc gagatttaat cgccgcgaca atttgcgacg    5340
gcgcgtgcag ggccagactg gaggtggcaa cgccaatcag caacgactgt tgcccgcca     5400 gttgttgtgc cacgcggttg gaatgtaat tcagctccgc catcgccgct tccactttt     5460 cccgcgtttt cgcagaaacg tggctggcct ggttcaccac gcgggaaacg gtctgataag    5520
agacaccggc atactctgcg acatcgtata acgttactgg tttcacattc accaccctga    5580
attgactctc ttccgggcgc tatcatgcca taccgcgaaa ggttttgcgc cattcgatgg    5640
tgtccgggat ctcgacgctc tcccttatgc gact                                5674

<210> SEQ ID NO 20
<211> LENGTH: 5853
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 20
cctgcattag gaagcagccc agtagtaggt tgaggccgtt gagcaccgcc gccgcaagga      60
atggtgcatg caaggagatg cgcccaaca gtcccccggc cacggggcct gccaccatac      120
ccacgccgaa acaagcgctc atgagcccga agtggcgagc ccgatcttcc ccatcggtga    180
tgtcggcgat ataggcgcca gcaaccgcac ctgtggcgcc ggtgatgccg ccacgatgc     240 gtccggcgta gaggatcgag atctcgatcc cgcgaaatta atacgactca ctatagggga    300
attgtgagcg gataacaatt cccctctaga aataattttg tttaacttta agaaggagat    360
atacatatga aatacctgct gccgaccgct gctgctggtc tgctgctcct cgctgcccag    420
ccggcgatgg ccatggatat cggaattaat tcggatccga attcgagctc gatcacaagt    480
ttgtacaaaa aagctgaacg agaaacgtaa aatgatataa atatcaatat attaaattag    540
attttgcata aaaaacagac tacataatac tgtaaaacac aacatatcca gtcactatgg    600
cggccgccac gttaagggat tttggtcatg atcagcacgt gttgacaatt aatcatcggc    660
atagtatatc ggcatagtat aatacgacaa ggtgaggaac taaaccatgg ccaagttgac    720
cagtgccgtt ccggtgctca ccgcgcgcga cgtcgccgga cggtcgagt tctggaccga    780 ccggctcggg ttctcccggg acttcgtgga ggacgacttc gccggtgtgg tccgggacga    840
cgtgaccctg ttcatcagcg cggtccagga ccaggtggtg ccggacaaca ccctggcctg    900
ggtgtgggtg cgcggcctgg acgagctgta cgccgagtgg tcggaggtcg tgtccacgaa    960
cttccgggac gcctccgggc cggccatgac cgagatcggc gagcagccgt gggggcggga   1020
gttcgccctg cgcgacccgg ccggcaactg cgtgcacttc gtggccgagg agcaggactg   1080
atcatgatga tattatttta tcttgtgcaa tgtaacatca gagattttga gacacggcc    1140 agagctgcca ggaaacagct atgaccatgt aatacgactc actatagggg atatcagctg   1200
gatggcaaat aatgatttta ttttgactga tagtgacctg ttcgttgcaa caccggtgct   1260
agcgtatacc cgaagtatgt caaaagagg tgtgctatga agcagcgtat tacagtgaca   1320
gttgacagcg acagctatca gttgctcaag gcatatatga tgtcaatatc tccggtctgg   1380
taagcacaac catgcagaat gaagcccgtc gtctgcgtgc cgaacgctgg aaagcggaaa   1440
```

```
atcaggaagg gatggctgag gtcgcccggt ttattgaaat gaacggctct tttgctgacg    1500
agaacaggga ctggtgaaat gcagtttaag gtttacacct ataaaagaga gagccgttat    1560
cgtctgtttg tggatgtaca gagtgatatt attgacacgc ccgggcgacg gatggtgatc    1620
cccctggcca gtgcacgtct gctgtcagat aaagtctccc gtgaacttta cccggtggtg    1680
catatcgggg atgaaagctg gcgcatgatg accaccgata tggccagtgt gccggtctcc    1740
gttatcgggg aagaagtggc tgatctcagc cgccgcgaaa atgacatcaa aaacgccatt    1800
aacctgatgt tctggggaat ataaatgtca ggctccctta tacacagcca gtctgcaggt    1860
cgaccatagt gactggatat gttgtgtttt acagtattat gtagtctgtt ttttatgcaa    1920
aatctaattt aatatattga tatttatatc attttacgtt tctcgttcag ctttcttgta    1980
caaagtggtg ataattaatt aagatcagat ccggctgcta agcttgcggc cgcataatgc    2040
ttaagtcgaa cagaaagtaa tcgtattgta cacggccgca taatcgaaat taatacgact    2100
cactataggg gaattgtgag cggataacaa ttccccatct tagtatatta gttaagtata    2160
agaaggagat atacatatgg cagatctcaa ttggatatcg gccggccacg cgatcgctga    2220
cgtcggtacc ctcgagtctg gtaaagaaac cgctgctgcg aaatttgaac gccagcacat    2280
ggactcgtct actagcgcag cttaattaac ctaggctgct gccaccgctg agcaataact    2340
agcataaccc cttggggcct ctaaacgggt cttgaggggt tttttgctga acctcaggc    2400 atttgagaag cacacggtca cactgcttcc ggtagtcaat aaaccggtaa accagcaata    2460
gacataagcg gctatttaac gaccctgccc tgaaccgacg accgggtcga atttgctttc    2520
gaatttctgc cattcatccg cttattatca cttattcagg cgtagcacca ggcgtttaag    2580
ggcaccaata actgccttaa aaaaattacg ccccgccctg ccactcatcg cagtactgtt    2640
gtaattcatt aagcattctg ccgacatgga agccatcaca gacggcatga tgaacctgaa    2700
tcgccagcgg catcagcacc ttgtcgcctt gcgtataata tttgcccata gtgaaaacgg    2760
gggcgaagaa gttgtccata ttggccacgt ttaaatcaaa actggtgaaa ctcacccagg    2820
gattggctga gacgaaaaac atattctcaa taaacccttt agggaaatag gccaggtttt    2880
caccgtaaca cgccacatct tgcgaatata tgtgtagaaa ctgccggaaa tcgtcgtggt    2940
attcactcca gagcgatgaa aacgtttcag tttgctcatg gaaaacggtg taacaagggt    3000
gaacactatc ccatatcacc agctcaccgt ctttcattgc catacggaac tccggatgag    3060
cattcatcag cgggcaagaa atgtgaataa aggccggata aaacttgtgc ttatttttct    3120
ttacggtctt taaaaaggcc gtaatatcca gctgaacggt ctggttatag gtacattgag    3180
caactgactg aaatgcctca aaatgttctt tacgatgcca ttgggatata tcaacggtgg    3240
tatatccagt gatttttttc tccattttag cttccttagc tcctgaaaat ctcgataact    3300
caaaaaatac gcccggtagt gatcttattt cattatggtg aaagttggaa cctcttacgt    3360
gccgatcaac gtctcatttt cgccaaaagt tggcccaggg cttcccggta tcaacaggga    3420
caccaggatt tatttattct gcgaagtgat cttccgtcac aggtatttat tcggcgcaaa    3480
gtgcgtcggg tgatgctgcc aacttactga tttagtgtat gatggtgttt ttgaggtgct    3540
ccagtggctt ctgtttctat cagctgtccc tcctgttcag ctactgacgg ggtggtgcgt    3600
aacggcaaaa gcaccgccgg acatcagcgc tagcggagtg tatactggct tactatgttg    3660
gcactgatga gggtgtcagt gaagtgcttc atgtggcagg agaaaaaagg ctgcaccggt    3720
gcgtcagcag aatatgtgat acaggatata ttccgcttcc tcgctcactg actcgctacg    3780
ctcggtcgtt cgactgcggc gagcggaaat ggcttacgaa cggggcggag atttcctgga    3840
```

| | |
|---|---|
| agatgccagg aagatactta acagggaagt gagagggccg cggcaaagcc gttttccat | 3900 |
| aggctccgcc cccctgacaa gcatcacgaa atctgacgct caaatcagtg gtggcgaaac | 3960 |
| ccgacaggac tataaagata ccaggcgttt cccctggcgg ctccctcgtg cgctctcctg | 4020 |
| ttcctgcctt tcggtttacc ggtgtcattc cgctgttatg gccgcgtttg tctcattcca | 4080 |
| cgcctgacac tcagttccgg gtaggcagtt cgctccaagc tggactgtat gcacgaaccc | 4140 |
| cccgttcagt ccgaccgctg cgccttatcc ggtaactatc gtcttgagtc caacccggaa | 4200 |
| agacatgcaa aagcaccact ggcagcagcc actggtaatt gatttagagg agttagtctt | 4260 |
| gaagtcatgc gccggttaag gctaaactga aggacaagt tttggtgact gcgctcctcc | 4320 |
| aagccagtta cctcggttca aagagttggt agctcagaga accttcgaaa aaccgccctg | 4380 |
| caaggcggtt ttttcgtttt cagagcaaga gattacgcgc agaccaaaac gatctcaaga | 4440 |
| agatcatctt attaatcaga taaatatttt ctagatttca gtgcaattta tctcttcaaa | 4500 |
| tgtagcacct gaagtcagcc ccatacgata taagttgtaa ttctcatgtt agtcatgccc | 4560 |
| cgcgcccacc ggaaggagct gactgggttg aaggctctca agggcatcgg tcgagatccc | 4620 |
| ggtgcctaat gagtgagcta acttacatta attgcgttgc gctcactgcc cgcttttcca | 4680 |
| tcgggaaacc tgtcgtgcca gctgcattaa tgaatcggcc aacgcgcggg gagaggcggt | 4740 |
| ttgcgtattg ggcgccaggg tggttttct tttcaccagt gagacgggca acagctgatt | 4800 |
| gcccttcacc gcctggccct gagagagttg cagcaagcgg tccacgctgg tttgccccag | 4860 |
| caggcgaaaa tcctgtttga tggtggttaa cggcgggata taacatgagc tgtcttcggt | 4920 |
| atcgtcgtat cccactaccg agatgtccgc accaacgcgc agcccggact cggtaatggc | 4980 |
| gcgcattgcg cccagcgcca tctgatcgtt ggcaaccagc atcgcagtgg gaacgatgcc | 5040 |
| ctcattcagc atttgcatgg tttgttgaaa accggacatg gcactccagt cgccttcccg | 5100 |
| ttccgctatc ggctgaattt gattgcgagt gagatattta tgccagccag ccagacgcag | 5160 |
| acgcgccgag acagaactta atgggcccgc taacagcgcg atttgctggt gacccaatgc | 5220 |
| gaccagatgc tccacgccca gtcgcgtacc gtcttcatgg gagaaaataa tactgttgat | 5280 |
| gggtgtctgg tcagagacat caagaaataa cgccggaaca ttagtgcagg cagcttccac | 5340 |
| agcaatggca tcctggtcat ccagcggata gttaatgatc agcccactga cgcgttgcgc | 5400 |
| gagaagattg tgcaccgccg ctttacaggc ttcgacgccg cttcgttcta ccatcgacac | 5460 |
| caccacgctg gcacccagtt gatcggcgcg agatttaatc gccgcgacaa tttgcgacgg | 5520 |
| cgcgtgcagg gccagactgg aggtggcaac gccaatcagc aacgactgtt tgcccgccag | 5580 |
| ttgttgtgcc acgcggttgg gaatgtaatt cagctccgcc atcgccgctt ccactttttc | 5640 |
| ccgcgttttc gcagaaacgt ggctggcctg gttcaccacg cgggaaacgg tctgataaga | 5700 |
| gacaccggca tactctgcga catcgtataa cgttactggt ttcacattca ccaccctgaa | 5760 |
| ttgactctct tccgggcgct atcatgccat accgcgaaag gttttgcgcc attcgatggt | 5820 |
| gtccgggatc tcgacgctct cccttatgcg act | 5853 |

<210> SEQ ID NO 21
<211> LENGTH: 6998
<212> TYPE: DNA
<213> ORGANISM: Artificial Sequence
<220> FEATURE:
<223> OTHER INFORMATION: Description of Artificial Sequence: Synthetic vector nucleotide sequence

<400> SEQUENCE: 21

```
cctgcattag gaagcagccc agtagtaggt tgaggccgtt gagcaccgcc gccgcaagga      60
atggtgcatg caaggagatg gcgcccaaca gtcccccggc cacggggcct gccaccatac     120
ccacgccgaa acaagcgctc atgagcccga agtggcgagc ccgatcttcc ccatcggtga     180
tgtcggcgat ataggcgcca gcaaccgcac ctgtggcgcc ggtgatgccg gccacgatgc     240
gtccggcgta gaggatcgag atctcgatcc cgcgaaatta atacgactca ctatagggga     300
attgtgagcg gataacaatt cccctctaga ataattttgt ttaactttaa gaaggagat     360 atacatatga ataccgtgct gccgaccgct gctgctggtc tgctgctcct cgctgcccag     420
ccggcgatgg ccatggatat cggaattaat tcggatccga attcgagctc gatcacaagt     480
ttgtacaaaa aagctgaacg agaaacgtaa aatgatataa atatcaatat attaaattag     540
attttgcata aaaaacagac tacataatac tgtaaaacac aacatatcca gtcactatgg     600
cggccgccac gttaagggat tttggtcatg atcagcacgt gttgacaatt aatcatcggc     660
atagtatatc ggcatagtat aatacgacaa ggtgaggaac taaaccatgg ccaagttgac     720
cagtgccgtt ccggtgctca ccgcgcgcga cgtcgccgga gcggtcgagt tctggaccga     780
ccggctcggg ttctcccggg acttcgtgga ggacgacttc gccggtgtgg tccgggacga     840
cgtgaccctg ttcatcagcg cggtccagga ccaggtggtg ccggacaaca ccctggcctg     900
ggtgtgggtg cgcggcctgg acgagctgta cgccgagtgg tcggaggtcg tgtccacgaa     960
cttccgggac gcctccgggc cggccatgac cgagatcggc gagcagccgt gggggcggga    1020
gttcgccctg cgcgacccgg ccggcaactg cgtgcacttc gtggccgagg agcaggactg    1080
atcatgatga tattatttta tcttgtgcaa tgtaacatca gagattttga gacacgggcc    1140
agagctgcca ggaaacagct atgaccatgt aatacgactc actatagggg atatcagctg    1200
gatggcaaat aatgatttta ttttgactga tagtgacctt ttcgttgcaa caccggtgct    1260
agcgtatacc cgaagtatgt caaaaagagg tgtgctatga agcagcgtat tacagtgaca    1320
gttgacagcg acagctatca gttgctcaag gcatatatga tgtcaatatc tccggtctgg    1380
taagcacaac catgcagaat gaagcccgtc gtctgcgtgc cgaacgctgg aaagcgaaa     1440 atcaggaagg gatggctgag gtcgcccggt ttattgaaat gaacggctct tttgctgacg    1500
agaacaggga ctggtgaaat gcagtttaag gtttacacct ataaaagaga gagccgttat    1560
cgtctgtttg tggatgtaca gagtgatatt ttgacacgc ccgggcgacg gatggtgatc      1620
cccctggcca gtgcacgtct gctgtcagat aaagtctccc gtgaacttta cccggtggtg    1680
catatcgggg atgaaagctg gcgcatgatg accaccgata tggccagtgt gccggtctcc    1740
gttatcgggg aagaagtggc tgatctcagc cgccgcgaaa atgacatcaa aaacgccatt    1800
aacctgatgt tctggggaat ataaatgtca ggctccctta tacacagcca gtctgcaggt    1860
cgaccatagt gactggatat gttgtgtttt acagtattat gtagtctgtt ttttatgcaa    1920
aatctaattt aatatattga tatttatatc attttacgtt tctcgttcag ctttcttgta    1980
caaagtggtg ataattaatt aagatcagat ccggctgcta agcttgcggc cgcataatgc    2040
ttaagtcgaa cagaaagtaa tcgtattgta cacggccgca taatcgaaat taatacgact    2100
cactataggg gaattgtgag cggataacaa ttcccatct agtatatta gttaagtata     2160 agaaggagat atacatatgg cagatctcaa ttggatatcg gccggccacg cgatcgctga    2220
cgtcggtacc ctcgagtctg gtaaagaaac cgctgctgcg aaatttgaac gccagcacat    2280
ggactcgtct actagcgcag cttaattaac ctaggctgct gccaccgctg agcaataact    2340
agcataaccc cttggggcct ctaaacgggt cttgaggggt ttttgctgaa aggaggaac     2400
```

```
tatatccgga ttggcgaatg ggacgcgccc tgtagcggcg cattaagcgc ggcgggtgtg      2460
gtggttacgc gcagcgtgac cgctacactt gccagcgccc tagcgcccgc tcctttcgct      2520
ttcttccctt cctttctcgc cacgttcgcc ggctttcccc gtcaagctct aaatcggggg      2580 ctcccttttag ggttccgatt tagtgcttta cggcacctcg accccaaaaa acttgattag      2640
ggtgatggtt cacgtagtgg gccatcgccc tgatagacgg ttttcgccc tttgacgttg       2700 gagtccacgt tctttaatag tggactcttg ttccaaactg gaacaacact caaccctatc      2760
tcggtctatt cttttgattt ataagggatt ttgccgattt cggcctattg gttaaaaaat      2820
gagctgattt aacaaaaatt taacgcgaat tttaacaaaa tattaacgtt tacaatttct      2880
ggcggcacga tggcatgaga ttatcaaaaa ggatcttcac ctagatcctt ttaaattaaa      2940
aatgaagttt taaatcaatc taaagtatat atgagtaaac ttggtctgac agttaccaat      3000
gcttaatcag tgaggcacct atctcagcga tctgtctatt tcgttcatcc atagttgcct      3060
gactccccgt cgtgtagata actacgatac gggagggctt accatctggc cccagtgctg      3120
caatgatacc gcgagaccca cgctcaccgg ctccagattt atcagcaata aaccagccag      3180
ccggaagggc cgagcgcaga agtggtcctg caactttatc cgcctccatc cagtctatta      3240
attgttgccg ggaagctaga gtaagtagtt cgccagttaa tagtttgcgc aacgttgttg      3300
ccattgctac aggcatcgtg gtgtcacgct cgtcgtttgg tatggcttca ttcagctccg      3360
gttcccaacg atcaaggcga gttacatgat cccccatgtt gtgcaaaaaa gcggttagct      3420
ccttcggtcc tccgatcgtt gtcagaagta agttggccgc agtgttatca ctcatggtta      3480
tggcagcact gcataattct cttactgtca tgccatccgt aagatgcttt tctgtgactg      3540
gtgagtactc aaccaagtca ttctgagaat agtgtatgcg gcgaccgagt tgctcttgcc      3600
cggcgtcaat acgggataat accgcgccac atagcagaac tttaaaagtg ctcatcattg      3660
gaaaacgttc ttcggggcga aaactctcaa ggatcttacc gctgttgaga tccagttcga      3720
tgtaacccac tcgtgcaccc aactgatctt cagcatcttt tactttcacc agcgtttctg      3780
ggtgagcaaa aacaggaagg caaaatgccg caaaaaaggg aataagggcg acacggaaat      3840
gttgaatact catactcttc cttttcaat catgattgaa gcatttatca gggttattgt       3900
ctcatgagcg gatacatatt tgaatgtatt tagaaaaata aacaaatagg tcatgaccaa      3960
aatcccttaa cgtgagtttt cgttccactg agcgtcagac cccgtagaaa agatcaaagg      4020
atcttcttga gatccttttt ttctgcgcgt aatctgctgc ttgcaaacaa aaaaaccacc      4080
gctaccagcg gtggtttgtt tgccggatca agagctacca actctttttc cgaaggtaac      4140
tggcttcagc agagcgcaga taccaaatac tgtccttcta gtgtagccgt agttaggcca      4200
ccacttcaag aactctgtag caccgcctac atacctcgct ctgctaatcc tgttaccagt      4260
ggctgctgcc agtggcgata agtcgtgtct taccggggtg gactcaagac gatagttacc      4320
ggataaggcg cagcggtcgg gctgaacggg gggttcgtgc acacagccca gcttggagcg      4380
aacgacctac accgaactga gatacctaca gcgtgagcta tgagaaagcg ccacgcttcc      4440
cgaagggaga aaggcggaca ggtatccggt aagcggcagg gtcggaacag gagagcgcac      4500
gagggagctt ccagggggaa acgcctggta tctttatagt cctgtcgggt ttcgccacct      4560
ctgacttgag cgtcgatttt tgtgatgctc gtcaggggggg cggagcctat ggaaaaacgc      4620
cagcaacgcg gccttttttac ggttcctggc cttttgctgg ccttttgctc acatgttctt      4680
tcctgcgtta tcccctgatt ctgtggataa ccgtattacc gcctttgagt gagctgatac      4740
cgctcgccgc agccgaacga ccgagcgcag cgagtcagtg agcgaggaag cggaagagcg      4800
```

```
cctgatgcgg tatttctcc ttacgcatct gtgcggtatt tcacaccgca tatatggtgc    4860
actctcagta caatctgctc tgatgccgca tagttaagcc agtatacact ccgctatcgc    4920
tacgtgactg ggtcatggct gcgccccgac acccgccaac acccgctgac gcgccctgac    4980
gggcttgtct gctcccggca tccgcttaca gacaagctgt gaccgtctcc gggagctgca    5040
tgtgtcagag gttttcaccg tcatcaccga acgcgcgag gcagctgcgg taaagctcat    5100
cagcgtggtc gtgaagcgat tcacagatgt ctgcctgttc atccgcgtcc agctcgttga    5160
gtttctccag aagcgttaat gtctggcttc tgataaagcg ggccatgtta agggcggttt    5220
tttcctgttt ggtcactgat gcctccgtgt aagggggatt tctgttcatg ggggtaatga    5280
taccgatgaa acgagagagg atgctcacga tacgggttac tgatgatgaa catgcccggt    5340
tactggaacg ttgtgagggt aaacaactgg cggtatggat gcggcgggac cagagaaaaa    5400
tcactcaggg tcaatgccag cgcttcgtta atacagatgt aggtgttcca cagggtagcc    5460
agcagcatcc tgcgatgcag atccggaaca taatggtgca gggcgctgac ttccgcgttt    5520
ccagacttta cgaaacacgg aaaccgaaga ccattcatgt tgttgctcag gtcgcagacg    5580
ttttgcagca gcagtcgctt cacgttcgct cgcgtatcgg tgattcattc tgctaaccag    5640
taaggcaacc ccgccagcct agccgggtcc tcaacgacag gagcacgatc atgctagtca    5700
tgccccgcgc ccaccggaag gagctgactg ggttgaaggc tctcaagggc atcggtcgag    5760
atcccggtgc ctaatgagtg agctaactta cattaattgc gttgcgctca ctgcccgctt    5820
tccagtcggg aaacctgtcg tgccagctgc attaatgaat cggccaacgc gcggggagag    5880
gcggtttgcg tattgggcgc cagggtggtt tttcttttca ccagtgagac gggcaacagc    5940
tgattgccct tcaccgcctg gccctgagag agttgcagca agcggtccac gctggtttgc    6000
cccagcaggc gaaaatcctg tttgatggtg gttaacggcg ggatataaca tgagctgtct    6060
tcggtatcgt cgtatcccac taccgagatg tccgcaccaa cgcgcagccc ggactcggta    6120
atggcgcgca ttgcgcccag cgccatctga tcgttggcaa ccagcatcgc agtgggaacg    6180
atgccctcat tcagcatttg catggtttgt tgaaaaccgg acatggcact ccagtcgcct    6240
tcccgttccg ctatcggctg aatttgattg cgagtgagat atttatgcca gccagccaga    6300
cgcagacgcg ccgagacaga acttaatggg cccgctaaca gcgcgatttg ctggtgaccc    6360
aatgcgacca gatgctccac gcccagtcgc gtaccgtctt catgggagaa ataatactg    6420 ttgatgggtg tctggtcaga gacatcaaga aataacgccg gaacattagt gcaggcagct    6480
tccacagcaa tggcatcctg gtcatccagc ggatagttaa tgatcagccc actgacgcgt    6540
tgcgcgagaa gattgtgcac cgccgcttta caggcttcga cgccgcttcg ttctaccatc    6600
gacaccacca cgctggcacc cagttgatcg gcgcgagatt taatcgccgc gacaatttgc    6660
gacggcgcgt gcagggccag actggaggtg gcaacgccaa tcagcaacga ctgtttgccc    6720
gccagttgtt gtgccacgcg gttgggaatg taattcagct ccgccatcgc cgcttccact    6780
ttttcccgcg ttttcgcaga acgtggctg gcctggttca ccacgcggga aacggtctga    6840
taagagacac cggcatactc tgcgacatcg tataacgtta ctggtttcac attcaccacc    6900
ctgaattgac tctcttccgg gcgctatcat gccataccgc gaaaggtttt gcgccattcg    6960
atggtgtccg ggatctcgac gctctcccctt atgcgact                          6998

<210> SEQ ID NO 22
<211> LENGTH: 7071
<212> TYPE: DNA
<213> ORGANISM: Artificial Sequence
<220> FEATURE:
```

<223> OTHER INFORMATION: Description of Artificial Sequence: Synthetic vector nucleotide sequence

<400> SEQUENCE: 22

| | | | | | |
|---|---|---|---|---|---|
| ggggaattgt | gagcggataa | caattcccct | gtagaaataa | ttttgtttaa | ctttaataag | 60 |
| gagatatacc | atgggcagca | gccatcacca | tcatcaccac | agccaggatc | cgaattcgag | 120 |
| ctcggaccat | gattacgcca | agctatcaac | tttgtataga | aaagttgaac | gagaaacgta | 180 |
| aaatgatata | aatatcaata | tattaaatta | gattttgcat | aaaaaacaga | ctacataata | 240 |
| ctgtaaaaca | caacatatcc | agtcactatg | gtcgacctgc | agactggctg | tgtataaggg | 300 |
| agcctgacat | ttatattccc | cagaacatca | ggttaatggc | gttttttgatg | tcattttcgc | 360 |
| ggtggctgag | atcagccact | tcttccccga | taacggagac | cggcacactg | gccatatcgg | 420 |
| tggtcatcat | gcgccagctt | tcatcccga | tatgcaccac | cgggtaaagt | tcacggggga | 480 |
| ctttatctga | cagcagacgt | gcactggcca | ggggatcac | catccgtcgc | ccgggcgtgt | 540 |
| caataatatc | actctgtaca | tccacaaaca | gacgataacg | gctctctctt | ttataggtgt | 600 |
| aaaccttaaa | ctgcatttca | ccagccctg | ttctcgtcgg | caaaagagcc | gttcatttca | 660 |
| ataaaccggg | cgacctcagc | catcccttcc | tgattttccg | ctttcagcg | ttcggcacgc | 720 |
| agacgacggg | cttcattctg | catggttgtg | cttaccgaac | cggagatatt | gacatcatat | 780 |
| atgccttgag | caactgatag | ctgtcgctgt | caactgtcac | tgtaatacgc | tgcttcatag | 840 |
| catacctctt | tttgacatac | ttcgggtata | catatcagta | tatattctta | taccgcaaaa | 900 |
| atcagcgcgc | aaatacgcat | actgttatct | ggcttttagt | aagccggatc | ctctagatta | 960 |
| cgccccgccc | tgccactcat | cgcagtactg | ttgtaattca | ttaagcattc | tgccgacatg | 1020 |
| gaagccatca | caaacggcat | gatgaacctg | aatcgccagc | ggcatcagca | ccttgtcgcc | 1080 |
| ttgcgtataa | tatttgccca | tggtgaaaac | ggggggcgaag | aagttgtcca | tattggccac | 1140 |
| gtttaaatca | aaactggtga | aactcaccca | gggattggct | gagacgaaaa | acatattctc | 1200 |
| aataaaccct | ttagggaaat | aggccaggtt | ttcaccgtaa | cacgccacat | cttgcgaata | 1260 |
| tatgtgtaga | aactgccgga | aatcgtcgtg | gtattcactc | cagagcgatg | aaaacgtttc | 1320 |
| agtttgctca | tggaaaacgg | tgtaacaagg | gtgaacacta | tcccatatca | ccagctcacc | 1380 |
| gtctttcatt | gccatacgga | attccggatg | agcattcatc | aggcgggcaa | gaatgtgaat | 1440 |
| aaaggccgga | taaaacttgt | gcttattttt | ctttacggtc | tttaaaaagg | ccgtaatatc | 1500 |
| cagctgaacg | gtctggttat | aggtacattg | agcaactgac | tgaaatgcct | caaaatgttc | 1560 |
| tttacgatgc | cattgggata | tatcaacggt | ggtatatcca | gtgatttttt | tctccatttt | 1620 |
| agcttcctta | gctcctgaaa | atctcgacgg | atcctaactc | aaaatccaca | cattatacga | 1680 |
| gccggaagca | taaagtgtaa | agcctggggg | tgcctaatgc | ggccgccata | gtgactggat | 1740 |
| atgttgtgtt | ttacagtatt | atgtagtctg | ttttttatgc | aaaatctaat | ttaatatatt | 1800 |
| gatatttata | tcattttacg | tttctcgttc | aactttatta | tacatagttg | ataattcact | 1860 |
| ggccgtcgtt | ttacaacgtc | gtgactggga | aaaccctggc | gttacccaac | ttaatcgcct | 1920 |
| tgcagcacaa | gcttgcggcc | gcataatgct | taagtcgaac | agaaagtaat | cgtattgtac | 1980 |
| acggccgcat | aatcgaaatt | aatacgactc | actatagggg | aattgtgagc | ggataacaat | 2040 |
| tccccatctt | agtatattag | ttaagtataa | gaaggagata | tacatatgga | tcacaagttt | 2100 |
| gtacaaaaaa | gctgaacgag | aaacgtaaaa | tgatataaat | atcaatatat | taaattagat | 2160 |
| tttgcataaa | aaacagacta | cataatactg | taaaacacaa | catatccagt | cactatggcg | 2220 |
| gccgccacgt | taagggattt | tggtcatgat | cagcacgtgt | tgacaattaa | tcatcggcat | 2280 |

```
agtatatcgg catagtataa tacgacaagg tgaggaacta aaccatggcc aagttgacca    2340
gtgccgttcc ggtgctcacc gcgcgcgacg tcgccggagc ggtcgagttc tggaccgacc    2400
ggctcgggtt ctcccgggac ttcgtggagg acgacttcgc cggtgtggtc cgggacgacg    2460
tgaccctgtt catcagcgcg gtccaggacc aggtggtgcc ggacaacacc ctggcctggg    2520
tgtgggtgcg cggcctggac gagctgtacg ccgagtggtc ggaggtcgtg tccacgaact    2580
tccgggacgc ctccgggccg gccatgaccg agatcggcga gcagccgtgg gggcgggagt    2640
tcgccctgcg cgacccggcc ggcaactgcg tgcacttcgt ggccgaggag caggactgat    2700
catgatgata ttattttatc ttgtgcaatg taacatcaga gattttgaga cacgggccag    2760
agctgccagg aaacagctat gaccatgtaa tacgactcac tatagggat atcagctgga    2820
tggcaaataa tgattttatt ttgactgata gtgacctgtt cgttgcaaca ccggtgctag    2880
cgtatacccg aagtatgtca aaaagaggtg tgctatgaag cagcgtatta cagtgacagt    2940
tgacagcgac agctatcagt tgctcaaggc atatatgatg tcaatatctc cggtctggta    3000
agcacaacca tgcagaatga agcccgtcgt ctgcgtgccg aacgctggaa agcggaaaat    3060
caggaaggga tggctgaggt cgcccggttt attgaaatga acggctcttt tgctgacgag    3120
aacagggact ggtgaaatgc agtttaaggt ttacacctat aaaagagaga gccgttatcg    3180
tctgtttgtg gatgtacaga gtgatattat tgacacgccc gggcgacgga tggtgatccc    3240
cctggccagt gcacgtctgc tgtcagataa agtctcccgt gaactttacc cggtggtgca    3300
tatcggggat gaaagctggc gcatgatgac caccgatatg gccagtgtgc cggtctccgt    3360
tatcggggaa gaagtggctg atctcagccg ccgcgaaaat gacatcaaaa acgccattaa    3420
cctgatgttc tggggaatat aaatgtcagg ctcccttata cacagccagt ctgcaggtcg    3480
accatagtga ctggatatgt tgtgttttac agtattatgt agtctgtttt ttatgcaaaa    3540
tctaatttaa tatattgata tttatatcat tttacgtttc tcgttcagct ttcttgtaca    3600
aagtggtgat aattaattaa gatcagatcc ggctgctggt accctcgagt ctggtaaaga    3660
aaccgctgct gcgaaatttg aacgccagca catggactcg tctactagcg cagcttaatt    3720
aacctaggct gctgccaccg ctgagcaata actagcataa ccccttgggg cctctaaacg    3780
ggtcttgagg ggttttttgc tgaaacctca ggcatttgag aagcacacgg tcacactgct    3840
tccggtagtc aataaaccgg taaaccagca atagacataa gcggctattt aacgaccctg    3900
ccctgaaccg acgaccgggt catcgtggcc ggatcttgcg gccccctcggc ttgaacgaat    3960
tgttagacat tatttgccga ctaccttggt gatctcgcct ttcacgtagt ggacaaattc    4020
ttccaactga tctgcgcgcg aggccaagcg atcttcttct tgtccaagat aagcctgtct    4080
agcttcaagt atgacgggct gatactgggc cggcaggcgc tccattgccc agtcggcagc    4140
gacatccttc ggcgcgattt tgccggttac tgcgctgtac caaatgcggg acaacgtaag    4200
cactacattt cgctcatcgc cagcccagtc gggcggcgag ttccatagcg ttaaggtttc    4260
atttagcgcc tcaaatagat cctgttcagg aaccggatca agagttcct ccgccgctgg    4320
acctaccaag gcaacgctat gttctcttgc ttttgtcagc aagatagcca gatcaatgtc    4380
gatcgtggct ggctcgaaga tacctgcaag aatgtcattg cgctgccatt ctccaaattg    4440
cagttcgcgc ttagctggat aacgccacgg aatgatgtc tcgtgcacaa caatggtgac    4500
ttctacagcg cggagaatct cgctctctcc aggggaagcc gaagtttcca aaaggtcgtt    4560
gatcaaagct cgccgcgttg tttcatcaag ccttacggtc accgtaacca gcaaatcaat    4620
atcactgtgt ggcttcaggc cgccatccac tgcggagccg tacaaatgta cggccagcaa    4680
```

```
cgtcggttcg agatggcgct cgatgacgcc aactacctct gatagttgag tcgatacttc   4740
ggcgatcacc gcttccctca tactcttcct ttttcaatat tattgaagca tttatcaggg   4800
ttattgtctc atgagcggat acatatttga atgtatttag aaaaataaac aaatagctag   4860
ctcactcggt cgctacgctc cgggcgtgag actgcggcgg gcgctgcgga cacatacaaa   4920
gttacccaca gattccgtgg ataagcaggg gactaacatg tgaggcaaaa cagcagggcc   4980
gcgccggtgg cgttttttcca taggctccgc cctcctgcca gagttcacat aaacagacgc   5040
ttttccggtg catctgtggg agccgtgagg ctcaaccatg aatctgacag tacgggcgaa   5100
acccgacagg acttaaagat ccccaccgtt tccggcgggt cgctccctct tgcgctctcc   5160
tgttccgacc ctgccgttta ccggatacct gttccgcctt tctcccttac gggaagtgtg   5220
gcgctttctc atagctcaca cactggtatc tcggctcggt gtaggtcgtt cgctccaagc   5280
tgggctgtaa gcaagaactc cccgttcagc ccgactgctg cgccttatcc ggtaactgtt   5340
cacttgagtc caacccggaa aagcacggta aaacgccact ggcagcagcc attggtaact   5400
gggagttcgc agaggatttg tttagctaaa cacgcggttg ctcttgaagt gtgcgccaaa   5460
gtccggctac actggaagga cagatttggt tgctgtgctc tgcgaaagcc agttaccacg   5520
gttaagcagt tccccaactg acttaaccctt cgatcaaacc acctccccag gtggtttttt   5580
cgtttacagg gcaaaagatt acgcgcagaa aaaaggatc tcaagaagat cctttgatct   5640
tttctactga accgctctag atttcagtgc aatttatctc ttcaaatgta gcacctgaag   5700
tcagccccat acgatataag ttgtaattct catgttagtc atgccccgcg cccaccggaa   5760
ggagctgact gggttgaagg ctctcaaggg catcggtcga gatcccggtg cctaatgagt   5820
gagctaactt acattaattg cgttgcgctc actgcccgct ttccagtcgg gaaacctgtc   5880
gtgccagctg cattaatgaa tcggccaacg cgcggggaga ggcggtttgc gtattgggcg   5940
ccagggtggt ttttcttttc accagtgaga cgggcaacag ctgattgccc ttcaccgcct   6000
ggccctgaga gagttgcagc aagcggtcca cgctggtttg cccagcagg cgaaaatcct   6060
gtttgatggt ggttaacggc gggatataac atgagctgtc ttcggtatcg tcgtatccca   6120
ctaccgagat gtccgcacca acgcgcagcc cggactcggt aatggcgcgc attgcgccca   6180
gcgccatctg atcgttggca accagcatcg cagtgggaac gatgccctca ttcagcattt   6240
gcatggtttg ttgaaaaccg gacatggcac tccagtcgcc ttcccgttcc gctatcggct   6300
gaatttgatt gcgagtgaga tatttatgcc agccagccag acgcagacgc gccgagacag   6360
aacttaatgg gcccgctaac agcgcgattt gctggtgacc caatgcgacc agatgctcca   6420
cgcccagtcg cgtaccgtct tcatgggaga aaataatact gttgatgggt gtctggtcag   6480
agacatcaag aaataacgcc ggaacattag tgcaggcagc ttccacagca atggcatcct   6540
ggtcatccag cggatagtta atgatcagcc cactgacgcg ttgcgcgaga agattgtgca   6600
ccgccgcttt acaggcttcg acgccgcttc gttctaccat cgacaccacc acgctggcac   6660
ccagttgatc ggcgcgagat ttaatcgccg cgacaatttg cgacggcgcg tgcagggcca   6720
gactggaggt ggcaacgcca atcagcaacg actgtttgcc cgccagttgt tgtgccacgc   6780
ggttgggaat gtaattcagc tccgccatcg ccgcttccac ttttcccgc gttttcgcag   6840
aaacgtggct ggcctggttc accacgcggg aaacggtctg ataagagaca ccggcatact   6900
ctgcgacatc gtataacgtt actggtttca cattcaccac cctgaattga ctctcttccg   6960
ggcgctatca tgccataccg cgaaaggttt tgcgccattc gatggtgtcc gggatctcga   7020
cgctctccct tatgcgactc ctgcattagg aaattaatac gactcactat a            7071
```

<210> SEQ ID NO 23
<211> LENGTH: 8490
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 23

```
ggggaattgt gagcggataa caattcccct gtagaaataa ttttgtttaa ctttaataag     60
gagatatacc atgggcagca gccatcacca tcatcaccac agccaggatc cgaattcgag    120
ctcggaccat gattacgcca agctatcaac tttgtataga aagttgaac gagaaacgta     180
aaatgatata aatatcaata tattaaatta gattttgcat aaaaaacaga ctacataata    240
ctgtaaaaca caacatatcc agtcactatg gtcgacctgc agactggctg tgtataaggg    300
agcctgacat ttatattccc cagaacatca ggttaatggc gttttttgatg tcattttcgc   360
ggtggctgag atcagccact tcttccccga taacggagac cggcacactg gccatatcgg    420
tggtcatcat gcgccagctt tcatccccga tatgcaccac cgggtaaagt tcacggggga    480
ctttatctga cagcagacgt gcactggcca ggggatcac catccgtcgc ccgggcgtgt     540
caataatatc actctgtaca tccacaaaca gacgataacg gctctctctt ttataggtgt    600
aaaccttaaa ctgcatttca ccagccctg ttctcgtcgg caaagagcc gttcatttca      660
ataaaccggg cgacctcagc catcccttcc tgattttccg cttcagcg ttcggcacgc      720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc tctagatta     960
gcatgcctac aggaacaggt ggtggcggcc ctcggtgcgc tcgtactgct ccacgatggt   1020
gtagtcctcg ttgtgggagg tgatgtccag cttggcgtcc acgtagtagt agccgggcag   1080
ctgcacgggc ttcttggcca gtagatgga cttgaactcc accaggtagt ggccgccgtc    1140
cttcagcttc agggccttgt gggtctcgcc cttcagcacg ccgtcgcggg ggtacaggcg   1200
ctcggtggag gcctcccagc ccatggtctt cttctgcatc acggggccgt cggaggggaa   1260
gttcacgccg atgaacttca ccttgtagat gaagcagccg tcctgcaggg aggagtcctg   1320
ggtcacggtc gccacgccgc cgtcctcgaa gttcatcacg cgctcccact gaagccctc    1380
ggggaaggac agcttcttgt agtcgggat gtcggcgggg tgcttcacgt acaccttgga    1440
gccgtactgg aactgggggg acaggatgtc ccaggcgaag ggcaggggc cgcccttggt    1500
caccttcagc ttcacggtgt tgtggccctc gtaggggcgg ccctcgccct cgccctcgat   1560
ctcgaactcg tggccgttca cggtgccctc catgcgcacc ttgaagcgca tgaactcggt   1620
gatgacgttc tcggaggagg ccatactagt cgccccgccc tgccactcat cgcagtactg   1680
ttgtaattca ttaagcattc tgccgacatg gaagccatca caacggcat gatgaacctg    1740
aatcgccagc ggcatcagca ccttgtcgcc ttgcgtataa tatttgccca tggtgaaaac   1800
gggggcgaag aagttgtcca tattggccac gtttaaatca aaactggtga actcaccca    1860
gggattggct gagacgaaaa acatattctc aataaaccct ttagggaaat aggccaggtt   1920
ttcaccgtaa cacgccacat cttgcgaata tatgtgtaga aactgccgga atcgtcgtg    1980
gtattcactc cagagcgatg aaaacgtttc agtttgctca tggaaaacgg tgtaacaagg   2040
```

```
gtgaacacta tcccatatca ccagctcacc gtctttcatt gccatacgga attccggatg    2100
agcattcatc aggcgggcaa gaatgtgaat aaaggccgga taaaacttgt gcttattttt    2160
ctttacggtc tttaaaaagg ccgtaatatc cagctgaacg gtctggttat aggtacattg    2220
agcaactgac tgaaatgcct caaaatgttc tttacgatgc cattgggata tatcaacggt    2280
ggtatatcca gtgattttt tctccatttt agcttcctta gctcctgaaa atctcgacgg     2340
atcctaactc aaaatccaca cattatacga gccggaagca taaagtgtaa agcctggggg    2400
tgcctaatgc ggccgccata gtgactggat atgttgtgtt ttacagtatt atgtagtctg    2460
ttttttatgc aaaatctaat ttaatatatt gatatttata tcattttacg tttctcgttc    2520
aactttatta tacatagttg ataattcact ggccgtcgtt ttacaacgtc gtgactggga    2580
aaaccctggc gttacccaac ttaatcgcct tgcagcacaa gcttgcggcc gcataatgct    2640
taagtcgaac agaaagtaat cgtattgtac acggccgcat aatcgaaatt aatacgactc    2700
actatagggg aattgtgagc ggataacaat tccccatctt agtatattag ttaagtataa    2760
gaaggagata tacatatgga tcacaagttt gtacaaaaaa gctgaacgag aaacgtaaaa    2820
tgatataaat atcaatatat taaattagat tttgcataaa aaacagacta cataatactg    2880
taaaacacaa catatccagt cactatggcg gccgccacgt taagggattt tggtcatgat    2940
cagcacgtgt tgacaattaa tcatcggcat agtatatcgg catagtataa tacgacaagg    3000
tgaggaacta aaccatggcc aagttgacca gtgccgttcc ggtgctcacc gcgcgcgacg    3060
tcgccggagc ggtcgagttc tggaccgacc ggctcgggtt ctcccgggac ttcgtggagg    3120
acgacttcgc cggtgtggtc cgggacgacg tgaccctgtt catcagcgcg gtccaggacc    3180
aggtggtgcc ggacaacacc ctggcctggg tgtgggtgcg cggcctggac gagctgtacg    3240
ccgagtggtc ggaggtcgtg tccacgaact tccgggacgc ctccgggccg gccatgaccg    3300
agatcggcga gcagccgtgg gggcgggagt tcgccctgcg cgaccgcgcc ggcaactgcg    3360
tgcacttcgt ggccgaggag caggacacta gtatgagtaa aggagaagaa cttttcactg    3420
gagttgtccc aattcttgtt gaattagatg gtgatgttaa tgggcacaaa ttttctgtca    3480
gtggagaggg tgaaggtgat gcaacatacg gaaaacttac ccttaaattt atttgcacta    3540
ctggaaaact acctgttcca tggccaacac ttgtcactac tttctcttat ggtgttcaat    3600
gcttttcccg ttatccggat catatgaaac ggcatgactt tttcaagagt gccatgcccg    3660
aaggttatgt acaggaacgc actatatctt tcaaagatga cgggaactac aagacgcgtg    3720
ctgaagtcaa gtttgaaggt gatacccttg ttaatcgtat cgagttaaaa ggtattgatt    3780
ttaaagaaga tggaaacatt ctcggacaca actcgagta caactataac tcacacaatg    3840
tatacatcac ggcagacaaa caaaagaatg gaatcaaagc taacttcaaa attgccaca    3900 acattgaaga tggatccgtt caactagcag accattatca acaaaatact ccaattggcg    3960
atggccctgt ccttttacca gacaaccatt acctgtcgac acaatctgcc ctttcgaaag    4020
atcccaacga aaagcgtgac cacatggtcc ttcttgagtt tgtaactgct gctgggatta    4080
cacatggcat ggatgagctc tacaaataag catgctgatc atgatgatat tattttatct    4140
tgtgcaatgt aacatcagag attttgagac acggccaga gctgccagga aacagctatg    4200
accatgtaat acgactcact atagggata tcagctggat ggcaaataat gattttattt    4260
tgactgatag tgacctgttc gttgcaacac cggtgctagc gtatacccga agtatgtcaa    4320
aaagaggtgt gctatgaagc agcgtattac agtgacagtt gacagcgaca gctatcagtt    4380
gctcaaggca tatatgatgt caatatctcc ggtctggtaa gcacaaccat gcagaatgaa    4440
```

```
gcccgtcgtc tgcgtgccga acgctggaaa gcggaaaatc aggaagggat ggctgaggtc    4500
gcccggttta ttgaaatgaa cggctctttt gctgacgaga acagggactg gtgaaatgca    4560
gtttaaggtt tacacctata aaagagagag ccgttatcgt ctgtttgtgg atgtacagag    4620
tgatattatt gacacgcccg ggcgacggat ggtgatcccc ctggccagtg cacgtctgct    4680
gtcagataaa gtctcccgtg aactttaccc ggtggtgcat atcggggatg aaagctggcg    4740
catgatgacc accgatatgg ccagtgtgcc ggtctccgtt atcggggaag aagtggctga    4800
tctcagccgc cgcgaaaatg acatcaaaaa cgccattaac ctgatgttct ggggaatata    4860
aatgtcaggc tcccttatac acagccagtc tgcaggtcga ccatagtgac tggatatgtt    4920
gtgttttaca gtattatgta gtctgttttt tatgcaaaat ctaatttaat atattgatat    4980
ttatatcatt ttacgtttct cgttcagctt tcttgtacaa agtggtgata attaattaag    5040
atcagatccg gctgctggta ccctcgagtc tggtaaagaa accgctgctg cgaaatttga    5100
acgccagcac atggactcgt ctactagcgc agcttaatta acctaggctg ctgccaccgc    5160
tgagcaataa ctagcataac cccttggggc ctctaaacgg tcttgaggg gttttttgct    5220 gaaacctcag gcatttgaga agcacacggt cacactgctt ccggtagtca ataaaccggt    5280
aaaccagcaa tagacataag cggctattta acgaccctgc cctgaaccga cgaccgggtc    5340
atcgtggccg gatcttgcgg cccctcggct tgaacgaatt gttagacatt atttgccgac    5400
taccttggtg atctcgcctt tcacgtagtg acaaattct tccaactgat ctgcgcgcga    5460
ggccaagcga tcttcttctt gtccaagata agcctgtcta gcttcaagta tgacgggctg    5520
atactgggcc ggcaggcgct ccattgccca gtcggcagcg acatccttcg gcgcgatttt    5580
gccggttact gcgctgtacc aaatgcggga caacgtaagc actacatttc gctcatcgcc    5640
agcccagtcg gcggcgagt tccatagcgt taaggtttca tttagcgcct caaatagatc    5700
ctgttcagga accggatcaa agagttcctc cgccgctgga cctaccaagg caacgctatg    5760
ttctcttgct tttgtcagca agatagccag atcaatgtcg atcgtggctg gctcgaagat    5820
acctgcaaga atgtcattgc gctgccattc tccaaattgc agttcgcgct tagctggata    5880
acgccacgga atgatgtcgt cgtgcacaac aatggtgact tctacagcgc ggagaatctc    5940
gctctctcca ggggaagccg aagtttccaa aaggtcgttg atcaaagctc gccgcgttgt    6000
ttcatcaagc cttacggtca ccgtaaccag caaatcaata tcactgtgtg gcttcaggcc    6060
gccatccact gcggagccgt acaaatgtac ggccagcaac gtcggttcga atggcgctc     6120 gatgacgcca actacctctg atagttgagt cgatacttcg gcgatcaccg cttccctcat    6180
actcttcctt tttcaatatt attgaagcat ttatcagggt tattgtctca tgagcggata    6240
catatttgaa tgtatttaga aaaataaaca aatagctagc tcactcggtc gctacgctcc    6300
gggcgtgaga ctgcggcggg cgctgcggac acatacaaag ttacccacag attccgtgga    6360
taagcagggg actaacatgt gaggcaaaac agcagggccg cgccggtggc gttttttccat    6420 aggctccgcc ctcctgccag agttcacata aacagacgct tttccggtgc atctgtggga    6480
gccgtgaggc tcaaccatga atctgacagt acgggcgaaa cccgacagga cttaaagatc    6540
cccaccgttt ccggcgggtc gctccctctt gcgctctcct gttccgaccc tgccgtttac    6600
cggatacctg ttccgccttt ctcccttacg ggaagtgtgg cgctttctca tagctcacac    6660
actggtatct cggctcggtg taggtcgttc gctccaagct gggctgtaag caagaactcc    6720
ccgttcagcc cgactgctgc gccttatccg gtaactgttc acttgagtcc aacccggaaa    6780
agcacggtaa aacgccactg gcagcagcca ttggtaactg ggagttcgca gaggatttgt    6840
```

```
ttagctaaac acgcggttgc tcttgaagtg tgcgccaaag tccggctaca ctggaaggac    6900
agatttggtt gctgtgctct gcgaaagcca gttaccacgg ttaagcagtt ccccaactga    6960
cttaaccttc gatcaaacca cctccccagg tggttttttc gtttacaggg caaaagatta    7020
cgcgcagaaa aaaaggatct caagaagatc ctttgatctt ttctactgaa ccgctctaga    7080
tttcagtgca atttatctct tcaaatgtag cacctgaagt cagccccata cgatataagt    7140
tgtaattctc atgttagtca tgccccgcgc ccaccggaag gagctgactg ggttgaaggc    7200
tctcaagggc atcggtcgag atcccggtgc ctaatgagtg agctaactta cattaattgc    7260
gttgcgctca ctgcccgctt tccagtcggg aaacctgtcg tgccagctgc attaatgaat    7320
cggccaacgc gcggggagag gcggtttgcg tattgggcgc cagggtggtt ttctttttca    7380
ccagtgagac gggcaacagc tgattgccct tcaccgcctg gccctgagag agttgcagca    7440
agcggtccac gctggtttgc cccagcaggc gaaaatcctg tttgatggtg gttaacggcg    7500
ggatataaca tgagctgtct tcggtatcgt cgtatcccac taccgagatg tccgcaccaa    7560
cgcgcagccc ggactcggta atggcgcgca ttgcgcccag cgccatctga tcgttggcaa    7620
ccagcatcgc agtgggaacg atgccctcat tcagcatttg catggtttgt tgaaaaccgg    7680
acatggcact ccagtcgcct tcccgttccg ctatcggctg aatttgattg cgagtgagat    7740
atttatgcca gccagccaga cgcagacgcg ccgagacaga acttaatggg cccgctaaca    7800
gcgcgatttg ctggtgaccc aatgcgacca gatgctccac gcccagtcgc gtaccgtctt    7860
catgggagaa aataatactg ttgatgggtg tctggtcaga gacatcaaga aataacgccg    7920
gaacattagt gcaggcagct tccacagcaa tggcatcctg gtcatccagc ggatagttaa    7980
tgatcagccc actgacgcgt tgcgcgagaa gattgtgcac cgccgcttta caggcttcga    8040
cgccgcttcg ttctaccatc gacaccacca cgctggcacc cagttgatcg gcgcgagatt    8100
taatcgccgc gacaatttgc gacggcgcgt gcagggccag actggaggtg caacgccaa    8160 tcagcaacga ctgtttgccc gccagttgtt gtgccacgcg gttgggaatg taattcagct    8220
ccgccatcgc cgcttccact ttttcccgcg ttttcgcaga aacgtggctg gcctggttca    8280
ccacgcggga aacggtctga taagagacac cggcatactc tgcgacatcg tataacgtta    8340
ctggtttcac attcaccacc ctgaattgac tctcttccgg gcgctatcat gccataccgc    8400
gaaaggtttt gcgccattcg atggtgtccg ggatctcgac gctctccctt atgcgactcc    8460
tgcattagga aattaatacg actcactata                                     8490
```

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtttcttgcg gccgccacgt taagggattt tggtca                              36

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gtttcttacc ggtgttgcaa cgaacaggtc act                               33
```

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gtttcttgag ctcgatcaca agtttgtaca aaaaagc                           37
```

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
gtttcttaag cttagcagcc ggatctgatc tta                               33
```

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Met Arg Ser Gly Ser His His His His His His Arg Ser Asp Ile Thr
  1               5                  10                  15

Ser Leu Tyr Lys Lys Ala Glu Arg Glu
             20                  25
```

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Met Ala His His His His His His Val Gly Thr Gly Ser Asn Asp Asp
  1               5                  10                  15

Asp Asp Lys Ser Thr Ser Leu Tyr Lys Lys Ala Glu Arg Glu
             20                  25                  30
```

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gtttcttgcg gccgcttctc atgtttgaca gcttatcat                         39
```

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtttctttct agagacgcga tggatatgtt ctg                               33

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctaggtaata cgactcacta taggaattgt gagcggataa caattcca               48

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agcttggaat tgttatccgc tcacaattcc tatagtgagt cgtattac               48

<210> SEQ ID NO 34
<211> LENGTH: 120
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttacaagtt tgtacaaaaa agcaggctta cttcaggtag tgatgatcta tcaaacaaat    60
tatatgatca attttcagaa aaagtcagca aaagtttggt gaaggtggtg gagagctgca   120

<210> SEQ ID NO 35
<211> LENGTH: 120
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cttaccactt tgtacaagaa agctgggtgg gacggttgag acaaactgga gatggcatag    60
cgtattttac tacttcgagg tattcatctt gcagctctcc accaccttca cccaaacttt   120

<210> SEQ ID NO 36
<211> LENGTH: 120
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cttacaagtt tgtacaaaaa agcaggctta tggttctccg gccttcacac ggaattcctt    60
tccatccaaa tccaaatcga acttcggagc ctcatgcatt ggcttagcag tagcagccgc   120

```
<210> SEQ ID NO 37
<211> LENGTH: 119
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cttaccactt tgtacaagaa agctgggtgt atgaataccg tgtcgttgcc gtcaacaaag      60
ctgggccagg acaaccatca gattcgtctg cggctgctac tgctaagcca atgcatgag    119

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 38 gacnnnngtc                                                             10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gacaagagtc                                                             10

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gacaaatcaa c                                                           11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gttgatgagt c                                                           11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
```

```
gacaagagct c                                                           11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aagcttgagt c                                                           11

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 44

His His His His His His
  1               5

<210> SEQ ID NO 45
<211> LENGTH: 124
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 45

Met Ala Lys Leu Thr Ser Ala Val Pro Val Leu Thr Ala Arg Asp Val
  1               5                  10                  15

Ala Gly Ala Val Glu Phe Trp Thr Asp Arg Leu Gly Phe Ser Arg Asp
             20                  25                  30

Phe Val Glu Asp Asp Phe Ala Gly Val Val Arg Asp Asp Val Thr Leu
         35                  40                  45

Phe Ile Ser Ala Val Gln Asp Gln Val Val Pro Asp Asn Thr Leu Ala
     50                  55                  60

Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Met Thr Glu
                 85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120
```

VECTORS AND METHODS FOR HIGH THROUGHPUT CO-EXPRESSIONS

CONTINUING APPLICATION DATA

This application is a divisional application of U.S. Ser. No. 11/327,200, filed on Jan. 6, 2006, which claims the benefit of U.S. Provisional Application Ser. No. 60/642,309, filed Jan. 7, 2005, U.S. Provisional Application Ser. No. 60/642,310, filed Jan. 7, 2005, and U.S. Provisional Application Ser. No. 60/756,028, titled "Vectors," filed Jan. 4, 2006, each of which is incorporated by reference herein.

GOVERNMENT FUNDING

The present invention was made with government support under Grant No. NIH GM062407, awarded by the National Institutes of Health. The Government may have certain rights in this invention.

BACKGROUND

With the completion of the sequencing of the human genomes and genomes of other organisms including, for example, the genomes of a wide and rapidly expanding number of prokaryotes, yeast, rice, rat, and dog, increasing attention has focused on the characterization and function of proteins, the products of genes. See, for example, Celestino et al., Gen Mol. Res. 3:421-431, 2004; Nature 436:793-800, 2005; Toh et al., Nature 438:803-819, 2005; Collins et al., Nature 422:835-847, 2003; and Cherry et al., Nature 387(6632 Suppl):67-73, 1997. The availability of sequence data and the growing impact of structural biology on biomedical research have prompted international efforts to determine protein structures on a large scale. Structural genomics (also referred to as "SG") is a worldwide initiative aimed at determining a large number of protein structures in a high throughput mode (see, for example, Rost, Structure 6:259-63, 1998; and Stevens et al., Science 294:89-92, 2001). One such effort is the National Institutes of Health's Protein Structure Initiative, a large-scale, high-throughput (also referred to as "HTP") effort to determine the three-dimensional atomic-level structures of a broad range of protein. These structures will be made widely available for clinical and basic studies that will expand the knowledge of the role of proteins both in normal biological processes and in disease. Initiatives, such as the Protein Structure Initiative, focus on an important aspect of proteins: the three-dimensional structures of proteins. While gene sequencing projects identify and arrange all the nucleotide bases in an organism's genetic material, efforts such as the Protein Structure Initiative will harness this genetic information to help identify and group into "families" all the natural shapes that proteins can form. To examine a protein's role in health and disease, and to explore ways to control its action, researchers seek to decipher the protein's shape, or structure. This structure reveals the physical, chemical and electrical properties of the protein and provides clues about its role in the body. See, for example, Norvell and Machalek, Nat Struct Biol 7 Suppl:931, 2000; the worldwide web at nigms.nih.gov/psi/ and rcsb.org/pdb/strucgen.html#Worldwide; and "From Genes to Proteins: NIGMS Catalogs the Shapes of Life," NIH Record, February 2001.

In structural genomics-type high-throughput projects, thousands of genes must be inserted into expression vectors and it has become clear that protein expression and protein purification are limiting steps and a major expense. Traditional technologies of manipulating genes are too cumbersome and inefficient when one is dealing with more than a few genes at a time. See, for example, Rual et al., Curr Opin Chem Biol. 8(1):20-5, 2004.

While success rates for gene cloning are close to one hundred percent, only about twenty percent of targeted genes are successfully expressed and purified and an accurate crystal structure is obtained for only a fraction of those polypeptides that are expressed and purified. See, for example, Adams et al., Acc Chem Res 36:191-8, 2003; Brenner, Nat Struct Biol 7 Suppl:967-9, 2000; Brenner and Levitt, Protein Sci 9:197-200, 2000; Burley, Nat Struct Biol 7 Suppl:932-4, 2000; Chance et al., Biophysical Journal 82:454a-454a, 2002; Chayen, J Struct Funct Genomics 4:115-20, 2003; Lesley et al., Proc Natl Acad Sci USA 99:11664-9, 2002; and Christendat et al., Nat Struct Biol 7:903-9, 2000. Traditional technologies of manipulating genes are too cumbersome and inefficient when one is dealing with more than a few genes at a time. See, for example, Rual et al., Curr Opin Chem Biol. 8(1):20-5, 2004.

Current methodologies for determining protein structures are difficult and time-consuming. Thus, there is a need for products and methods that allow for the determination of protein structures in a low-cost and high-throughput manner.

SUMMARY OF THE INVENTION

The present invention includes expression vectors having a nucleotide sequence operably encoding a ccdB polypeptide flanked by att recombination recognition sequences, wherein the selectable marker for selection of the expression vector within a host cell is not ampicillin resistance.

In another aspect, the invention includes host cells having one or more expression vectors having a nucleotide sequence operably encoding a ccdB polypeptide flanked by att recombination recognition sequences, wherein the selectable marker for selection of the expression vector within a host cell is not ampicillin resistance.

In another aspect, the invention include methods for the expression of one or more polypeptides, the method including expressing at least one polypeptide by an expression vector having a nucleotide sequence operably encoding a ccdB polypeptide flanked by att recombination recognition sequences, wherein the selectable marker for selection of the expression vector within a host cell is not ampicillin resistance.

In another aspect, the invention includes methods for the co-expression of four or more polypeptides, the method including expressing at least one polypeptide by an expression vector having a nucleotide sequence operably encoding a ccdB polypeptide flanked by att recombination recognition sequences, wherein the selectable marker for selection of the expression vector within a host cell is not ampicillin resistance.

In another aspect, the invention includes methods of improving the solubility of one or more expressed polypeptides, the method including expressing at least one polypeptide by an expression vector having a nucleotide sequence operably encoding a ccdB polypeptide flanked by att recombination recognition sequences, wherein the selectable marker for selection of the expression vector within a host cell is not ampicillin resistance.

In another aspect, the invention includes the expression vector pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, or pDEST-CMZc1.

In another aspect, the invention includes host cells having one of more expression vectors selected from pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, and pDEST-CMZc1.

In another aspect, the invention includes methods for the expression of one or more polypeptides, the method including expressing at least one polypeptide by an expression vector selected from pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, and pDEST-CMZc1.

In another aspect, the invention includes methods for the co-expression of four or more polypeptides, the method including expressing at least one polypeptide by an expression vector selected from pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, and pDEST-CMZc1.

In another aspect, the invention includes methods of improving the solubility of one or more expressed polypeptides, the method including expressing at least one polypeptide by an expression vector selected from pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, and pDEST-CMZc1.

In another aspect, the invention includes polynucleotides having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the polynucleotide includes the G144704 cassette. In some embodiments, the G144704 cassette includes SEQ ID NO: 4 as shown in FIG. 9.

In another aspect, the invention includes expression vectors having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes host cells having an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4 as shown in FIG. 9.

In another aspect, the invention includes methods for the expression of one or more polypeptides, the method including expressing at least one polypeptide by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes methods for the co-expression of four or more polypeptides, the method including expressing at least one polypeptide by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4 as shown in FIG. 9.

In another aspect, the invention includes methods of improving the solubility of one or more expressed polypeptides, the method including expressing at least one polypeptide by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes polynucleotides having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes expression vectors including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes a host cell including an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods for the expression of one or more polypeptides, the method including expressing at least one polypeptide by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods for the co-expression of four or more polypeptides, the method including expressing at least one polypeptide by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods of improving the solubility of one or more expressed polypeptides, the method including expressing at least one polypeptide by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes RNA interference (RNAi) vectors including a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the polynucleotide includes a G144704 cassette. In some embodiments, the G144704 cassette includes SEQ ID NO: 4, as shown in FIG. 9.

In another aspect, the invention includes methods of producing one or more interfering RNA products, the method including expressing at least one interfering RNA product by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes RNA interference (RNAi) vectors including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods of producing one or more interfering RNA products, the method including expressing at least one interfering RNA product by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes the RNAi vectors pRIPPER-1, pRIPPER-2, pRIPPER-3, pRIPPER-4, pRIPPER-II, pRIPPER-III, and pRIPPER-IV.

In another aspect, the invention includes methods of producing one or more interfering RNA products, the method including expressing at least one interfering RNA product by an expression vector selected form pRIPPER-1, pRIPPER-2, pRIPPER-3, pRIPPER-4, pRIPPER-II, pRIPPER-III, or pRIPPER-IV.

BRIEF DESCRIPTION OF THE FIGURES

FIG. 3 presents the nucleotide sequence of the pDEST-C1 vector (SEQ ID NO: 1).

FIG. 5 presents the nucleotide sequence of the pDEST-C2 vector (SEQ ID NO: 2).

FIG. 7 presents the nucleotide sequence of the pDEST-C3 vector (SEQ ID NO: 3).

FIG. 8A shows a map of the zeomycin cassette. FIG. 8B shows a map of the Gateway cassette. FIG. 8C shows a map of the G144704 cassette. FIG. 8D is a map of the G144704 cassette, indicating the location of various restriction enzyme sites.

Figure 9:
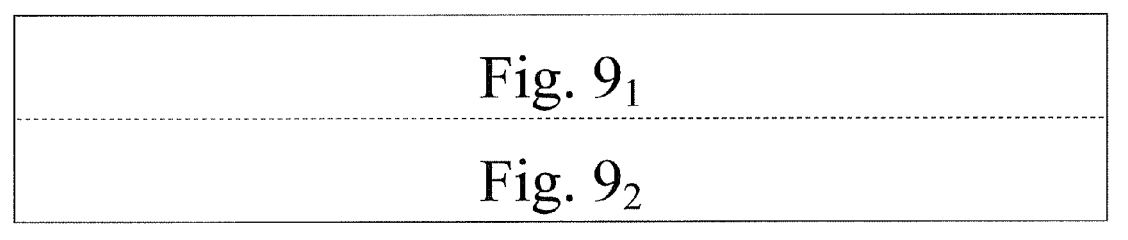

FIG. 9 shows the nucleotide sequence of the G144704 cassette. The nucleotide sequences of the attR1 and attR2 sites are shaded.

In FIG. 14A, lanes 1 and 8 are the molecular weight markers; lanes 2, 4, and 6 are the three soluble fractions that represent calmodulin hPMCA4b and co-expression of the two, respectively; lanes 3, 5 and 7 are the pellet fractions of the same growths, and lane 6 contains the soluble complex and this growth was further pursued to purification. FIG. 14B is the FPLC 280 nm chromatogram and SDS-PAGE of the indicated fraction in lane 9 showing a complex of the two proteins. Lane 10 is the same marker as lanes 1 and 8 in FIG. 14A.

FIG. 17 presents the nucleotide sequence of the pDEST-CM1 vector (SEQ ID NO: 5).

FIG. 19 presents the nucleotide sequence of the pDEST-CM2 vector (SEQ ID NO: 6).

FIG. 21 is the nucleotide sequence of the Multisite TetR cassette (SEQ ID NO: 7).

FIG. 23 show the nucleotide sequence of the pDEST-CM3 vector (SEQ ID NO: 8).

FIG. 25 presents the nucleotide sequence of the pDEST-CM4 vector (SEQ ID NO: 9).

FIG. 26A is the Gateway® cassette. FIG. 26B is the G144704 cassette. FIG. 26C is a Multisite® cassette.

FIG. 28 is the nucleotide sequence of the pRIPPER-3 vector (SEQ ID NO: 10).

FIG. 30 is the nucleotide sequence of the pRIPPER-1 vector.

FIG. 32 is the nucleotide sequence of the pRIPPER-2 vector (SEQ ID NO: 12).

FIG. 34 is the nucleotide sequence of the pRIPPER-4 vector (SEQ ID NO: 13).

FIG. 36 is the nucleotide sequence of the pRIPPER-II vector (SEQ ID NO: 14).

FIG. 38 is the nucleotide sequence of the pRIPPER-III vector (SEQ ID NO: 15).

FIG. 40 is the nucleotide sequence of the pRIPPER-IV vector (SEQ ID NO: 16).

FIG. 42 is the nucleotide sequence of the pDEST-CS vector (SEQ ID NO: 17).

FIG. 44 is the nucleotide sequence of the pDEST-C1 vector (SEQ ID NO: 18).

FIG. 46 is the nucleotide sequence of the pDEST-CS2 vector (SEQ ID NO: 19).

FIG. 48 is the nucleotide sequence of the pDEST-CS3 vector (SEQ ID NO: 20).

FIG. 50 is the nucleotide sequence of the pDEST-CS4 vector (SEQ ID NO: 21).

FIG. 52 is the nucleotide sequence of the pDEST-CMZ1 vector (SEQ ID NO: 22).

FIG. 54 is the nucleotide sequence of the pDEST-CMZc1 vector (SEQ ID NO: 23).

DETAILED DESCRIPTION OF ILLUSTRATIVE EMBODIMENTS OF THE INVENTION

Figure 1:
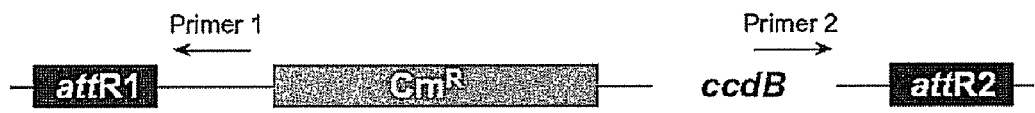
FIG. 1 is a schematic presenting the locations of the attR1 site, the attR2 site, the chloramphenical resistance gene, the ccdB gene and Primer 1 and Primer 2 in the Gateway Conversion Cassette for Reading Frame A, Reading Frame B and Reading Frame C.

The polynucleotides, vectors and methods of the present invention provide for the improved high throughput (HTP) expression of polypeptides and for the improved high throughput (HTP) expression of interfering RNAs.

The present invention includes vectors having a nucleotide sequence operably encoding a ccdB polypeptide flanked by att recombination recognition sequences, wherein the selectable marker for selection of the expression vector within a host cell is not resistance to the antibiotic ampicillin. Selectable markers for the expression vector within the host cell include, but are not limited to, kanamycin resistance, chloramphenicol resistance, streptomycin resistance, spectinomycin resistance, zeomycin resistance, carbenicillin resistance, tetracycline resistance, and rifampicin resistance. See, for example, Novagen 2004/2005 catalog and New England Biolabs 2005-06 Catalog. In some aspects, the present invention includes vectors having a nucleotide sequence operably encoding a ccdB polypeptide and operably encoding chloramphenicol resistance, wherein the nucleotide sequence is flanked by att recombination recognition sequences, and wherein the selectable marker for selection of the expression vector within a host cell is not ampicillin resistance. In some aspects of the present invention, the vector is an expression vector.

As used herein, the terms "polynucleotide" and "nucleotide sequence" refer to polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

As used herein, the terms "polypeptide," "peptide," and "protein" are used interchangeably herein to refer to polymers of amino acids of any length.

As used herein, a "vector" is a polynucleotide which transfers an inserted nucleic acid molecule into and/or between host cells. A vector may provide for the insertion of DNA or RNA into a cell, the replication of DNA or RNA, the transcription of the DNA or RNA, the translation of the DNA or RNA, and/or the processing of the translated polypeptide product. A vector may provide for more than one of the above functions. A vector may include an origin of replication, also referred to as an ori sequence or a replicon, which allows for replication of the polynucleotide in an appropriate host cell. See, for example, Novagen 2004/2005 catalog and New England Biolabs 2005-06 Catalog.

As used herein, an "expression vector" is a vector which, when introduced into an appropriate host cell, can be transcribed and translated into a polypeptide(s). An "expression system" usually connotes a suitable host cell comprised of an expression vector that can function to yield a desired expression product. An expression vector may include an origin of replication, which allows for replication of the polynucleotide in an appropriate host cell. Origins of replication include, but are not limited to the ColE1 replicon, the P15A replicon, the CloDF13 replicon, or the RSD1030 replicon. An expression vector may include a promoter, including, for example, the T7lac promoter, that provides for protein expression in the host cell. See, for example, Novagen 2004/2005 catalog and New England Biolabs 2005-06 Catalog.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product.

The polynucleotides and vectors of the present invention take advantage of Gateway® technology. The Gateway® cloning system is an vitro site-specific recombination technology that takes advantage of the att site-specific recombination properties of bacteriophage lambda (Hartley et al., Genome Res. 10:1788-1795, 2000; (Landy, Annu Rev Biochem 58:913-49, 1989; Sasaki et al., J. Biotechnol. 107, 233-243, 2004; U.S. Pat. Nos. 5,888,732, 6,143,557, 6,171,861, 6,270,969, 6,277,608, and 6,720,140; and the Gateway Technology manual Version E, updated Sep. 22, 2003; available on the worldwide web at invitrogen.com/content/sfs/manuals/gatewayman.pdf) to provide a rapid and efficient way to move a gene of interest between multiple vector systems.

Polynucleotides and vectors of the present invention include one or more att recombination recognition sequences. As used herein, att recombination recognition sequences include, but are not limited to attR1, attR2, attR3, and attR4, the sequences of which are well known, and include, but are not limited to, those described in the examples included herewith and those described in Landy, Annu Rev Biochem 58:913-49, 1989; Sasaki et al., J. Biotechnol. 107, 233-243, 2004; U.S. Pat. Nos. 5,888,732, 6,143,557, 6,171,861, 6,270,969, 6,277,608, and 6,720,140; and the Gateway Technology manual Version E, updated Sep. 22, 2003; available on the worldwide web at invitrogen.com/content/sfs/manuals/gatewayman.pdf. The two recombination recognition sequences, attR1 and attR2 have been employed in the conventional gateway technology (Hartley et al., Genome Res. 10: 1788-1795, 2000; (Landy, Annu Rev Biochem 58:913-49, 1989; Sasaki et al., J. Biotechnol. 107, 233-243, 2004; U.S. Pat. Nos. 5,888,732, 6,143,557, 6,171,861, 6,270,969, 6,277,608, and 6,720,140; and the Gateway Technology manual Version E, updated Sep. 22, 2003; available on the worldwide web at invitrogen.com/content/sfs/manuals/gatewayman.pdf). The recombination recognition sequences, attR3 and attR4, have been recently made available as MultiSite™ Gateway® Three-Fragment Vector Construction Kit from Invitrogen Corp.

Gateway® technology makes gene cloning simpler, more specific and faster than traditional methods of gene cloning based on restriction enzyme digestion and ligation. Gateway® technology allows for the rapid site specific exchange of target DNA between an entry vector (containing the initial clone of the target gene) and multiple expression vectors, via recombination. In order to allow for this versatility, the Gateway® system is characterized by a DNA sequence called the Gateway® cassette. This DNA sequence contains two recombination sites attR1 and attR2 along with genes that encode chloramphenicol resistance and the "control of cell death" polypeptide, also referred to herein as ccdB (Bernard et al., J. Mol. Biol. 234, 534-541, 1993). The ccdB polypeptide is lethal to Escherichia coli (Bernard and Couturier, Mol. Gen. Genet. 226:297-304, 1991). Nucleotide sequences encoding the ccdB polypeptide are well known in the art, and include those described in the examples included herewith. A Gateway cassette allows for the selection of recombinants, as only the desired recombinants will form colonies when transformed into E. coli.

In some aspects, polynucleotides and vectors of the present invention may have a Gateway® cassette, wherein a Gateway® cassette is a polynucleotide sequence containing the two recombination sites attR1 and attR2, along with a nucleotide sequence that operably encodes the gene product responsible for chloramphenicol resistance and the nucleotide sequence operably encoding a ccdB polypeptide. The two recombination sites, attR1 and attR2, may flank the nucleotide sequence encoding chloramphenicol resistance and the nucleotide sequence encoding a ccdB polypeptide. As used herein, a nucleotide sequence that "operably encodes" a polypeptide product with a given function includes all of the appropriate sequences necessary to result in the expression of the polypeptide product with the identified function, including, for example, coding sequences and regulatory sequences.

In some aspects, polynucleotides and vectors of the present invention may have a MultiSite™ Gateway® cassette, wherein a MultiSite™ Gateway® cassette is a polynucleotide sequence containing the two recombination sites attR3 and attR4, along with a nucleotide sequence that operably encodes the gene product responsible for chloramphenicol resistance and the nucleotide sequence operably encoding a ccdB polypeptide. The two recombination sites, attR3 and attR4, may flank the nucleotide sequence encoding chloramphenicol resistance and the nucleotide sequence encoding a ccdB polypeptide.

The present invention includes vectors having a nucleotide sequence operably encoding a ccdB polypeptide flanked by att recombination recognition sequences, wherein the selectable marker for selection of the expression vector within a host cell is not ampicillin resistance. Selectable markers for the expression vector within the host cell include, but are not limited to, kanamycin resistance, chloramphenicol resistance, streptomycin resistance, spectinomycin resistance, zeomycin resistance, carbenicillin resistance, tetracycline resistance, and rifampicin resistance. See, for example, Novagen 2004/2005 catalog and New England Biolabs 2005-06 Catalog. Of the more than fifty Gateway® expression vectors currently available, all encode ampicillin resistance, which is not desirable for an expression vector, due to high background problems when grown for over sixteen.

Vectors of the present invention include vectors in which the chloramphenicol resistance (chlR) gene in the Gateway® recombination cassette has been replaced with the Zeocin® resistance gene as a selective marker. Vectors of the present invention include vectors in which the technologies of the Gateway® site-specific recombination system is fused with the capacities of a multiple vector co-expression system, resulting is vectors that can express multiple proteins in a parallel manner in one *E. coli* strain.

A series of several vectors of the present invention, when compared to one another, may have differing replicons and resistance genes, allowing for the effective propagation, maintenance of the series of vectors in a single host cell.

The vectors of the present invention may be used in concert with any of the many available co-expression vectors, including, for example, the pET family of expression vectors (Novagen, Madison, Wis.). These vectors use a strong phage T7 promoter driven by the presence of lactose or a lactose analog (isopropyl-β-D-galactopyranoside, IPTG) to express the target protein. Other available co-expression vectors include pCDF, pRSF, and pACYC, which are compatible with pET (www.emdbiosciences.com). All four of these have compatible replication origins, and different antibiotic selection markers, so as many as all four can be stably maintained in the same *E. coli* cell. Thus, co-expression of up to four proteins in the same cell became possible. These vectors have been further modified (the pDUET series; see www.emdbiosciences.com) so that each vector contains two multiple cloning site, allowing for expression of up to eight different target genes simultaneously. However, while these vectors are well known, their use is limited due to the necessity of using classical restriction enzymes and ligation for cloning.

The vectors of the present invention combine aspects of co-expression vectors with the power of Gateway® technology. The vectors of the present invention may include one or more of the elements of such co-expression vectors, including, but not limited, one or more elements from a member of the pET family of vectors, the pDUET series of vectors, pCDF, pRSF, and pACYC.

The vectors of the present invention may include one or more additional elements, including, for example, elements encoding various fusion tags, fusion proteins, affinity tags, protease cleavage sites, expression signals, or promoters, including, for example, prokaryotic or eukaryotic promoters. Vectors may include, for example, an N-terminal 6×His tag and/or an enterokinase cleavage site just before the attR1 recombination site. The vectors of the present invention may include any of the various nucleotide sequences that provide for the expression of native proteins, N- or C-terminally tagged proteins, secreted proteins, or proteins that are targeted to a subcellular location. The vectors of the present invention may include any of the various nucleotide sequences that provide a variety of promoters, poly-A addition signals, and/or elements for transient, stable and bicistronic expression.

The vectors of the present invention may include the appropriate promoters and/or origins of replication that allow for the expression of a polypeptide product in a range of host cells, including, but not limited to, bacterial host cells, including, for example, *E. coli*, yeast, insect cells, and mammalian cells.

Figure 2:
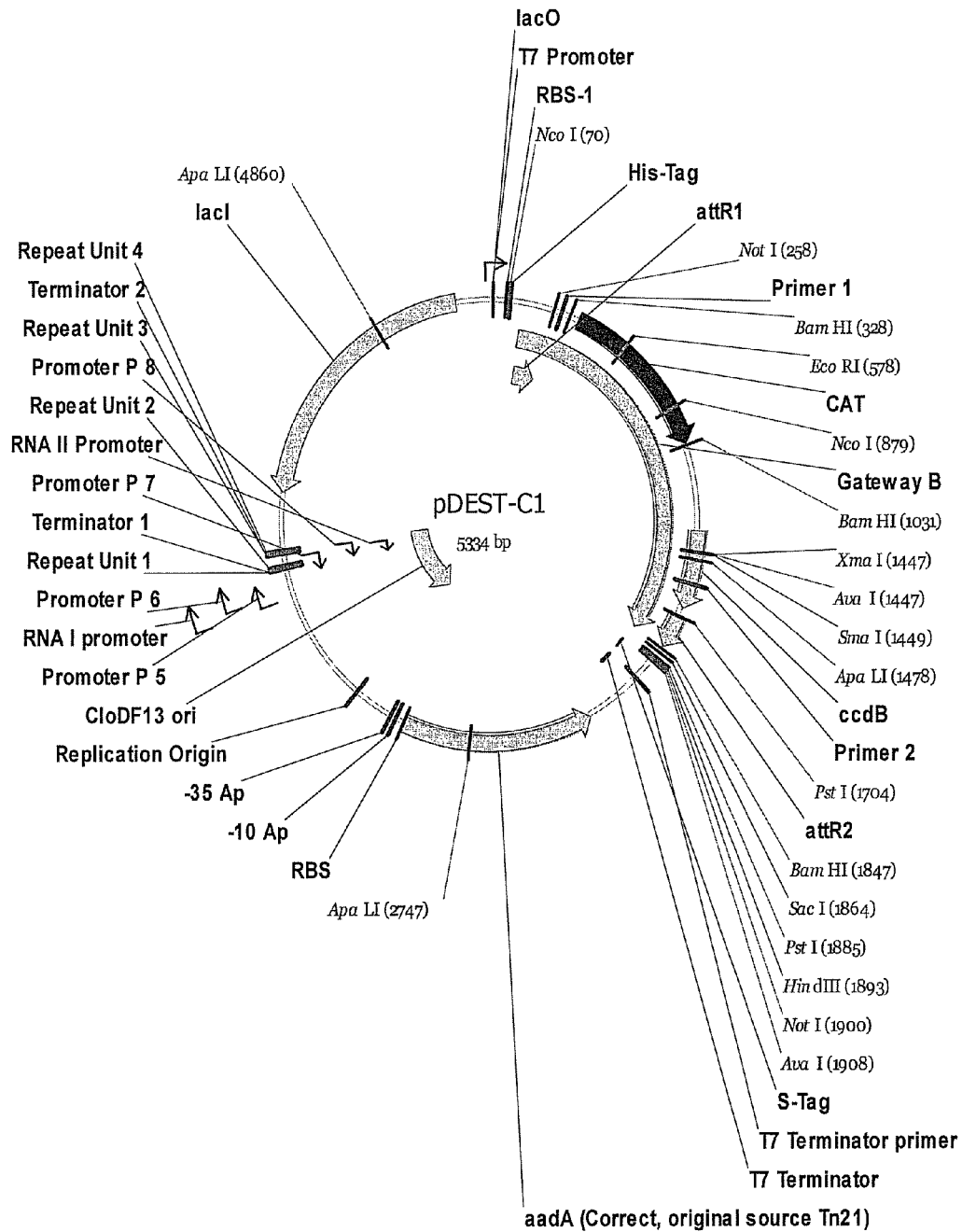
FIG. 2 shows a map of the pDEST-C1 vector.
Figure 3:
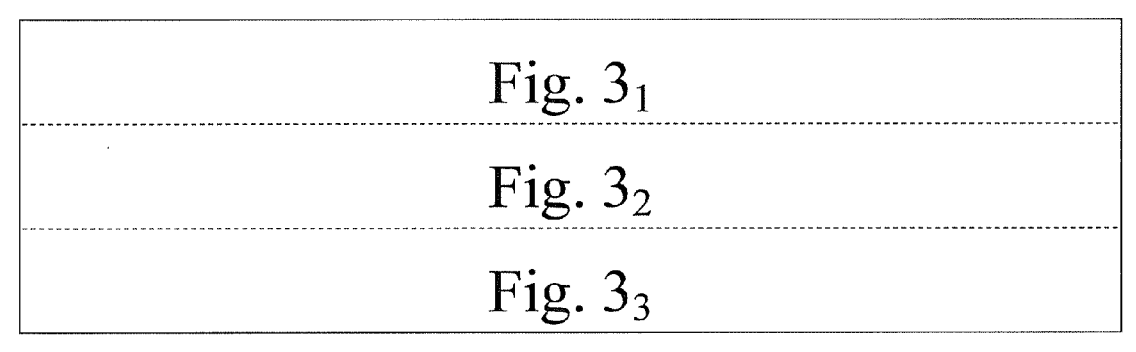

Vectors of the present invention include vectors having one or more of the elements shown in FIG. 2. An example of such a vector is the pDEST-C1 vector, the nucleotide sequence of which is shown in FIG. 3.

Figure 4:
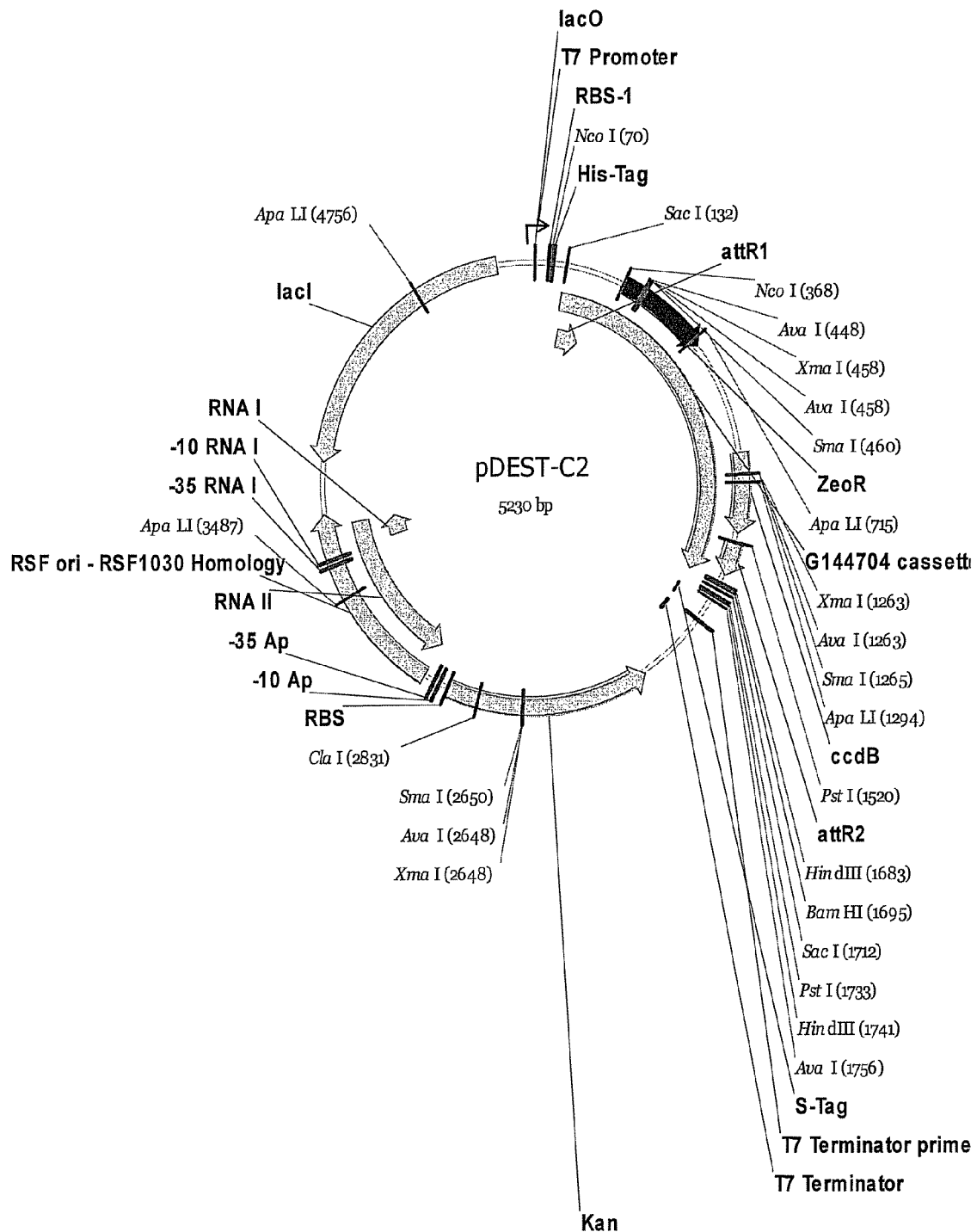
FIG. 4 shows a map of the pDEST-C2 vector.
Figure 5:
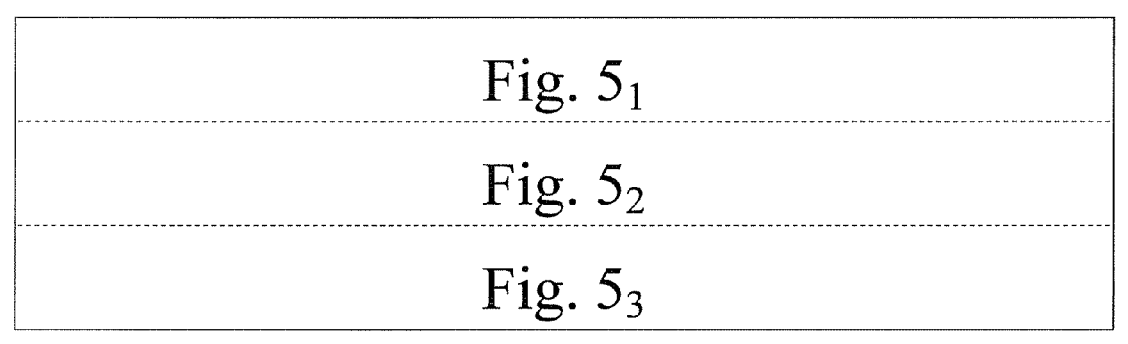

Vectors of the present invention include vectors having one or more of the elements shown in FIG. 4. An example of such a vector is the pDEST-C2 vector, the nucleotide sequence of which is shown in FIG. 5.

Figure 6:
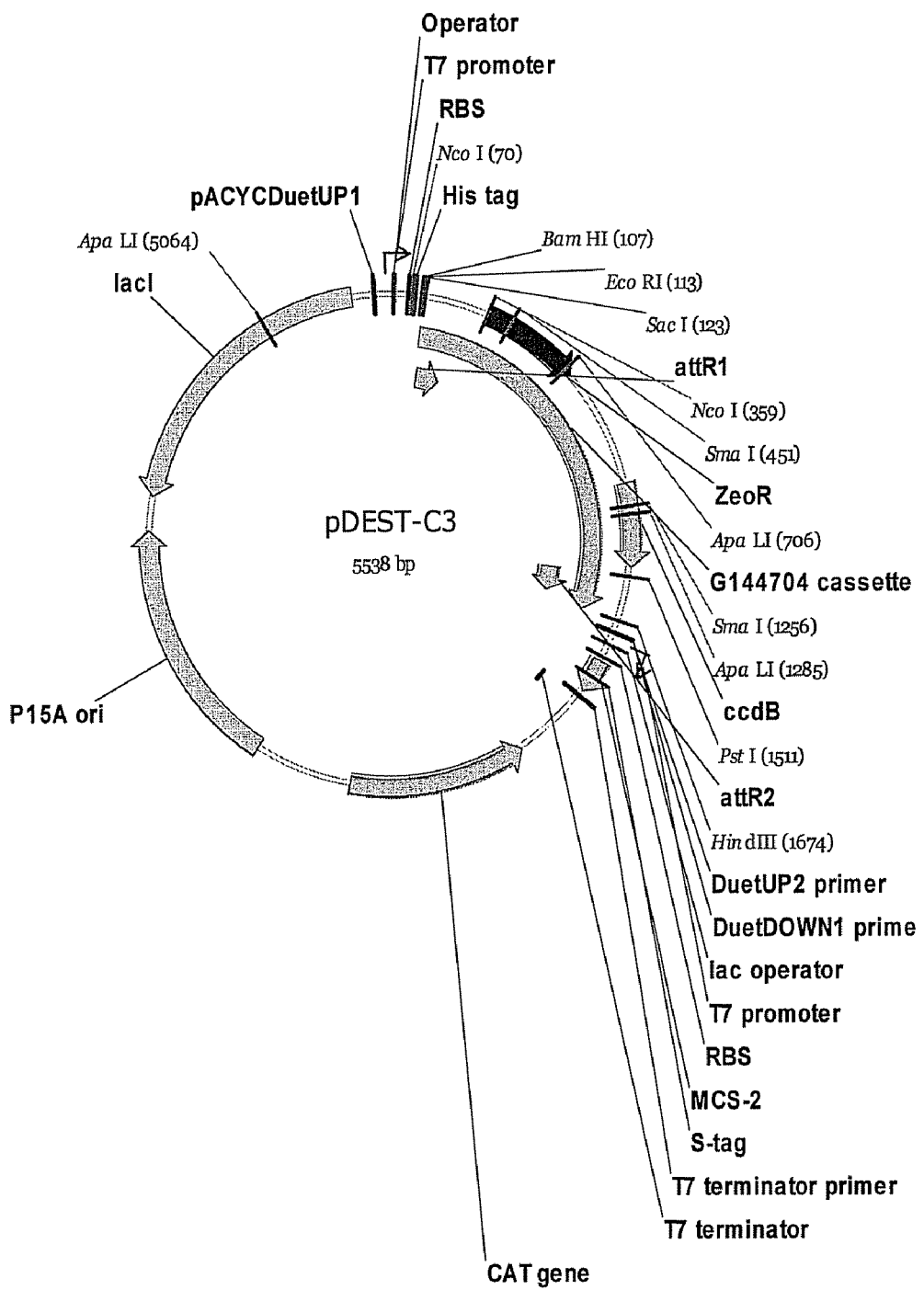
FIG. 6 shows a map of the pDEST-C3 vector.
Figure 7:
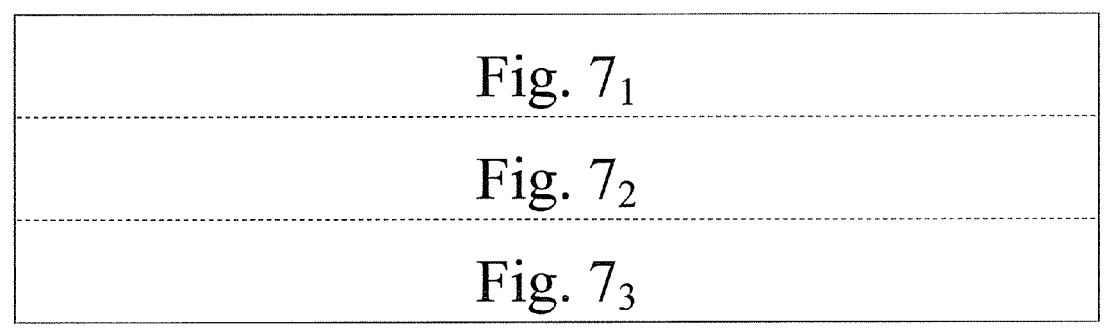

Vectors of the present invention include vectors having one or more of the elements shown in FIG. 6. An example of such a vector is the pDEST-C3 vector, the nucleotide sequence of which is shown in FIG. 7.

Figure 16:
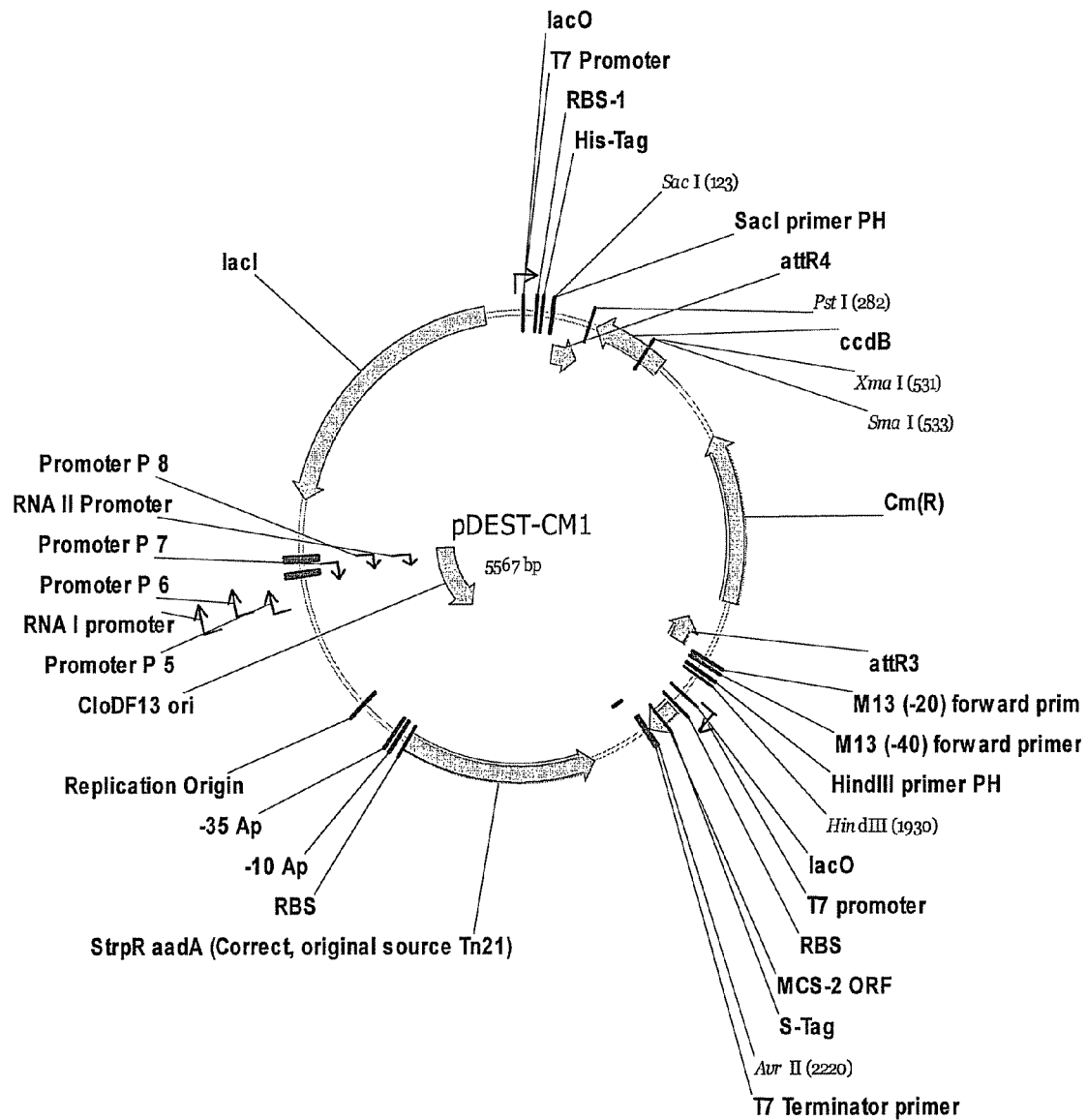
FIG. 16 shows a map of the pDEST-CM1 vector.
Figure 17:
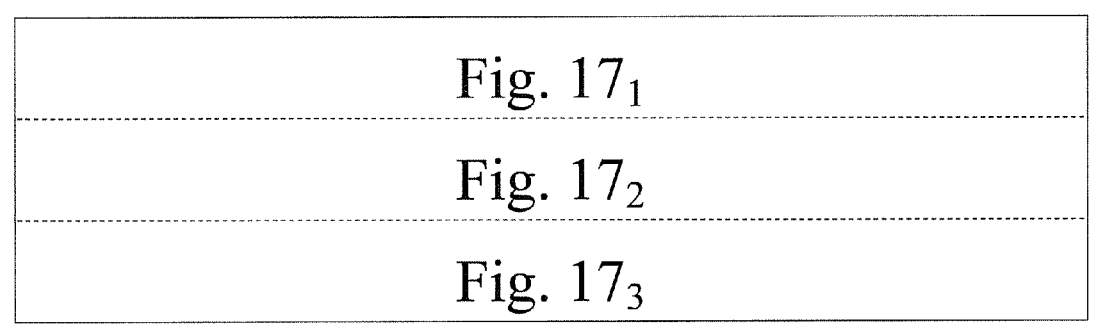

Vectors of the present invention include vectors having one or more of the elements shown in FIG. 16. An example of such a vector is the pDEST-CM1 vector, the nucleotide sequence of which is shown in FIG. 17.

Figure 18:
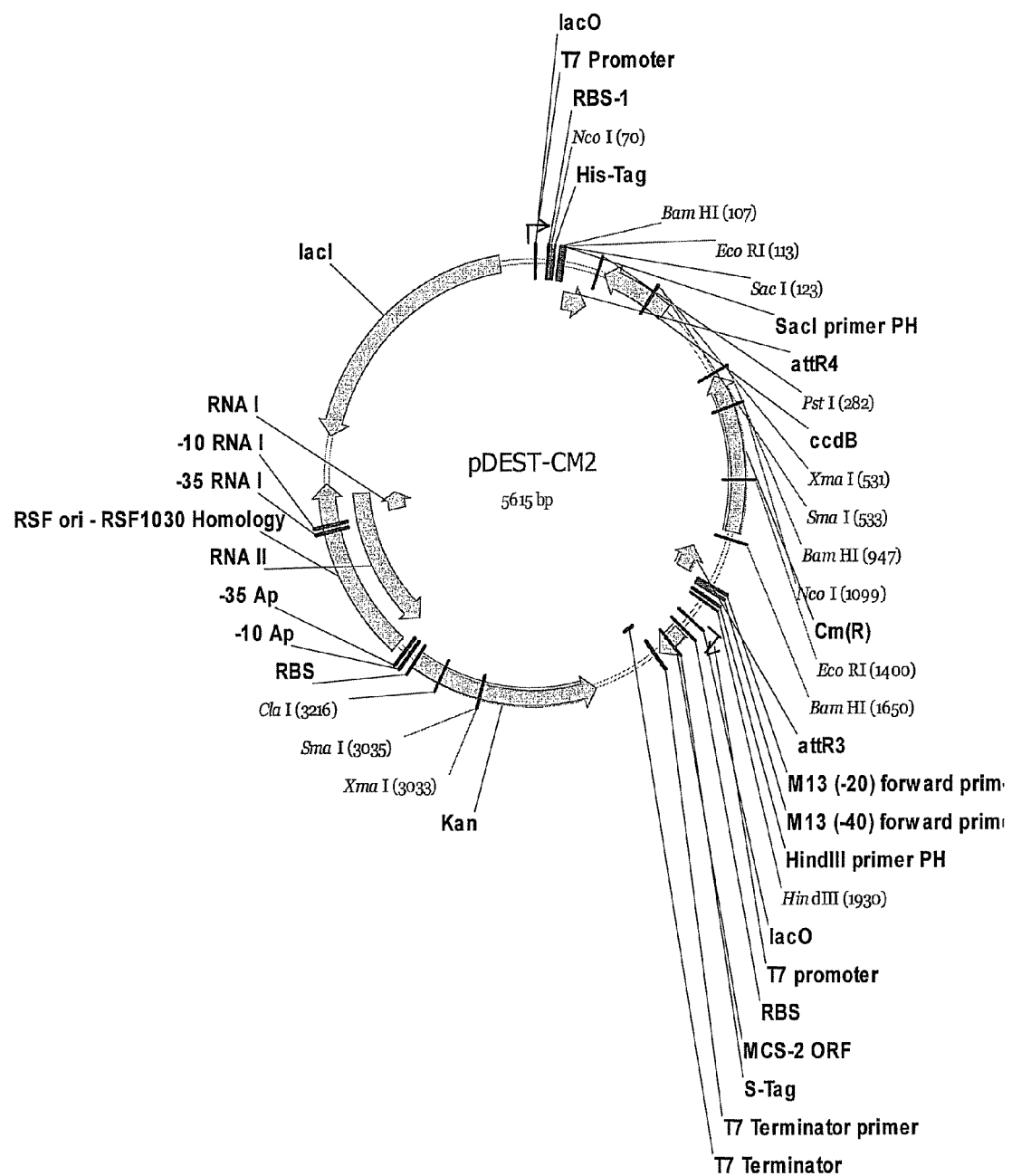
FIG. 18 shows a map of the pDESTCM-2 vector.
Figure 19:
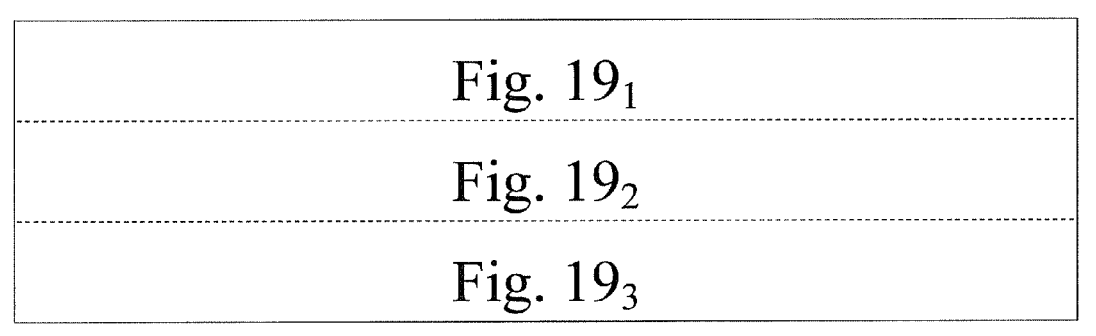

Vectors of the present invention include vectors having one or more of the elements shown in FIG. 18. An example of such a vector is the pDEST-CM2 vector, the nucleotide sequence of which is shown in FIG. 19.

Figure 22:
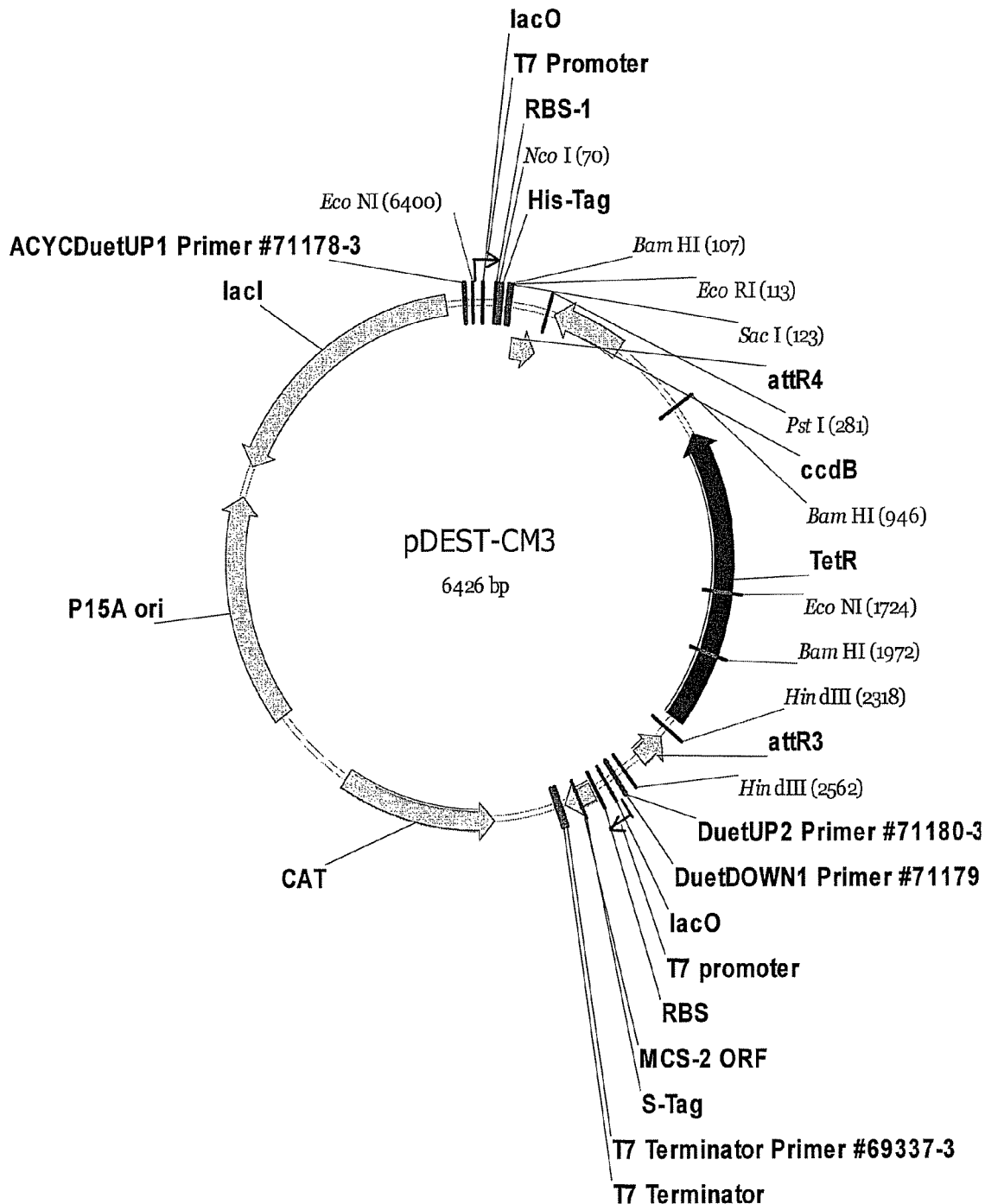
FIG. 22 shows a map of the pDEST-CM3 vector.
Figure 23:
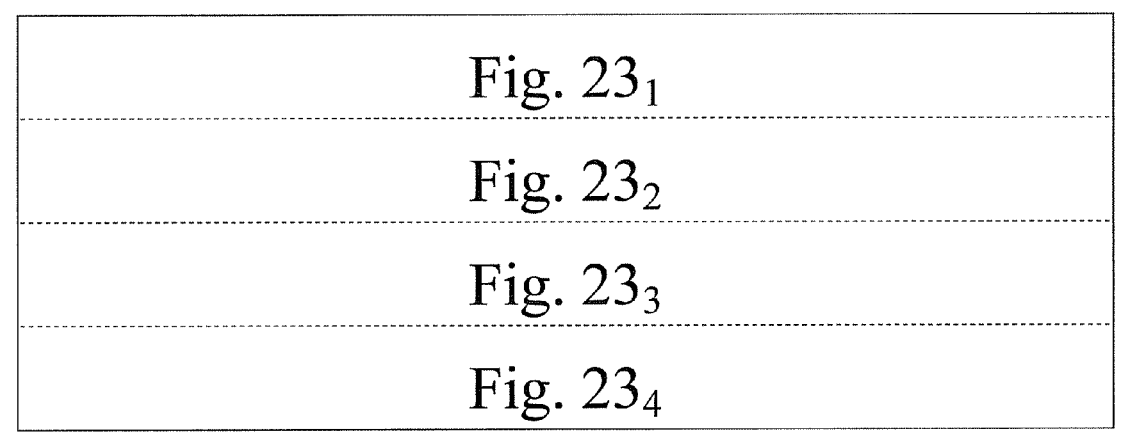

Vectors of the present invention include vectors having one or more of the elements shown in FIG. 22. An example of such a vector is the pDEST-CM3, the nucleotide sequence of which is shown in FIG. 23.

Figure 24:
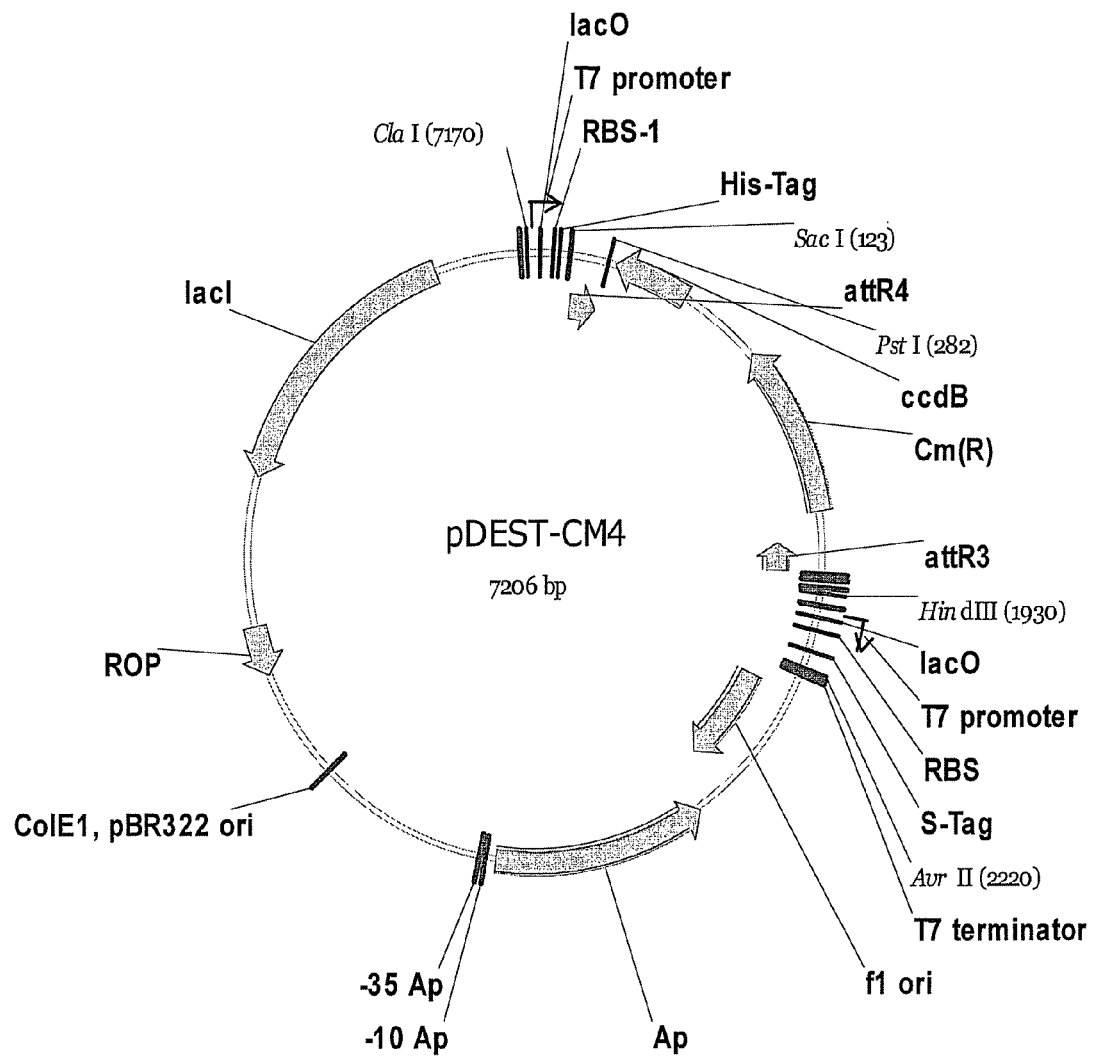
FIG. 24 shows a map of the pDEST-CM4 vector.
Figure 25:
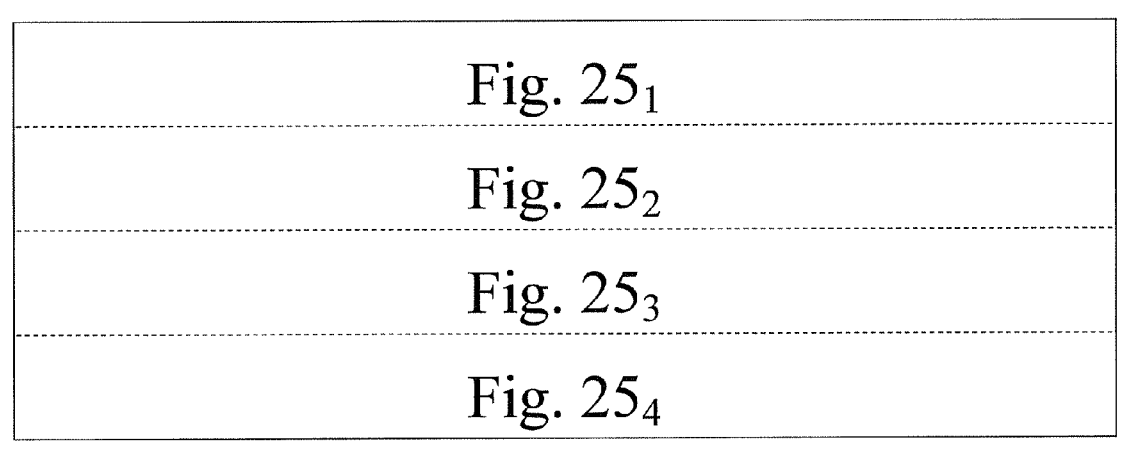

Vectors of the present invention include vectors having one or more of the elements shown in FIG. 24. An example of such a vector is the pDEST-CM4 vector, the nucleotide sequence of which is shown in FIG. 25.

Figure 41:
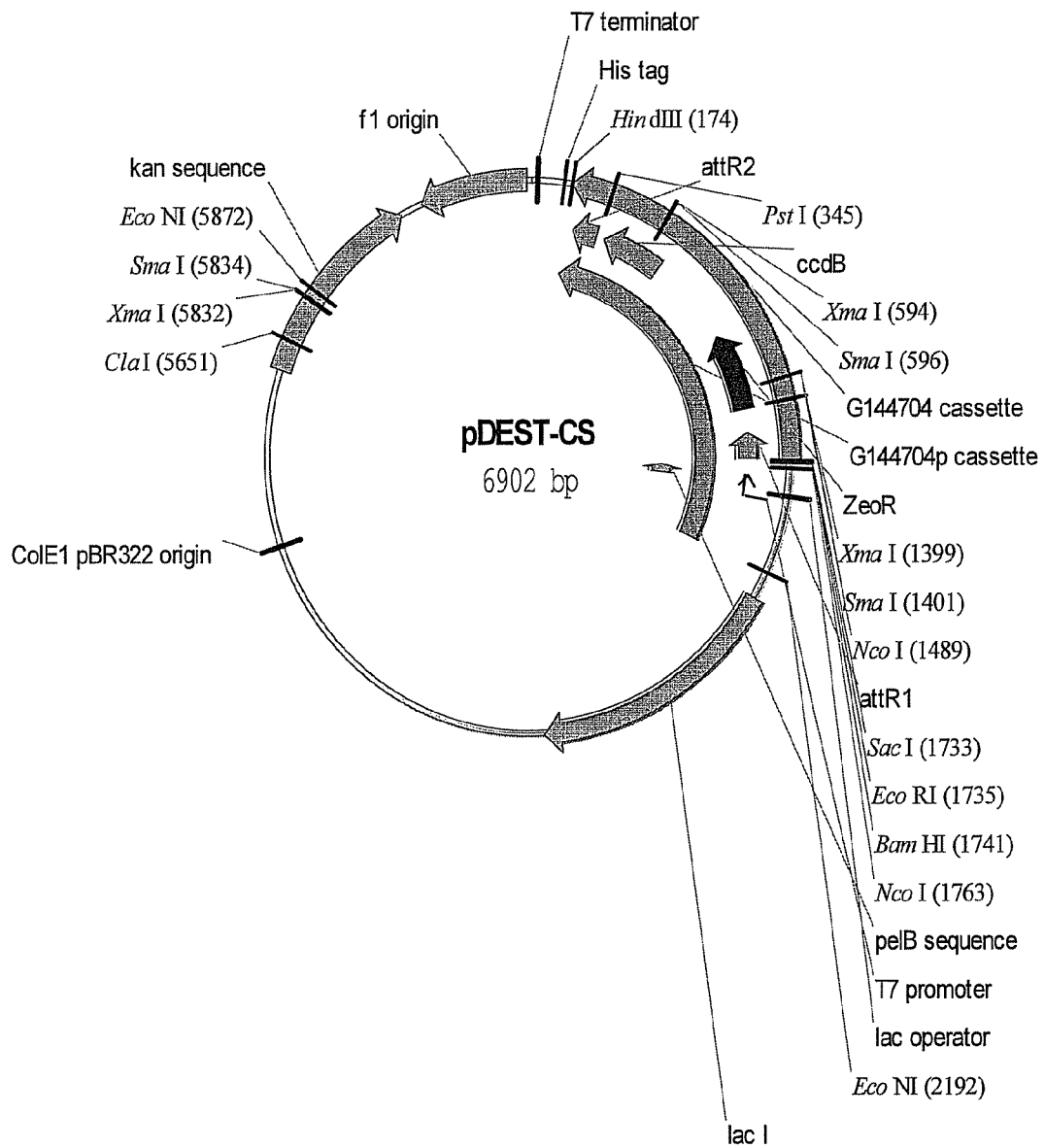
FIG. 41 is a map of the pDEST-CS.
Figure 42:
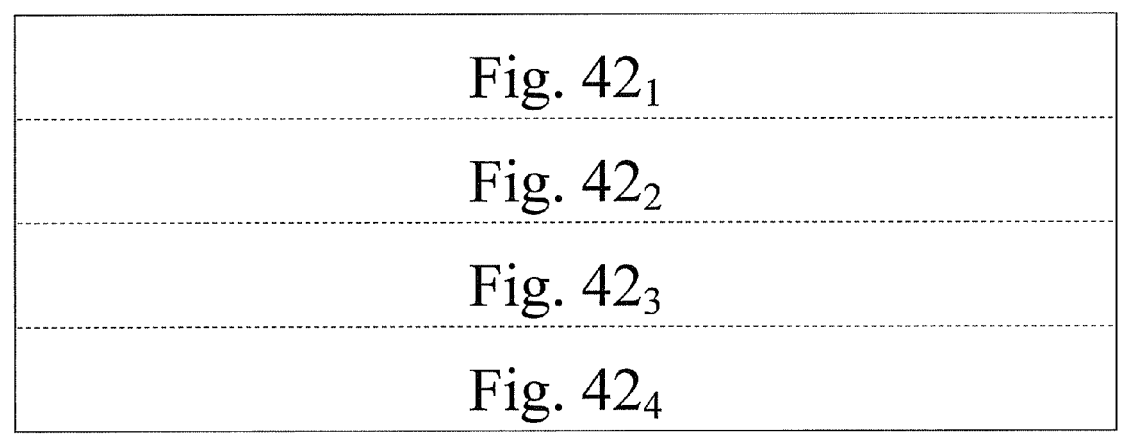

Vectors of the present invention include vectors having one or more of the elements shown in FIG. 41. An example of such a vector is the pDEST-CS vector, the nucleotide sequence of which is shown in FIG. 42.

Figure 43:
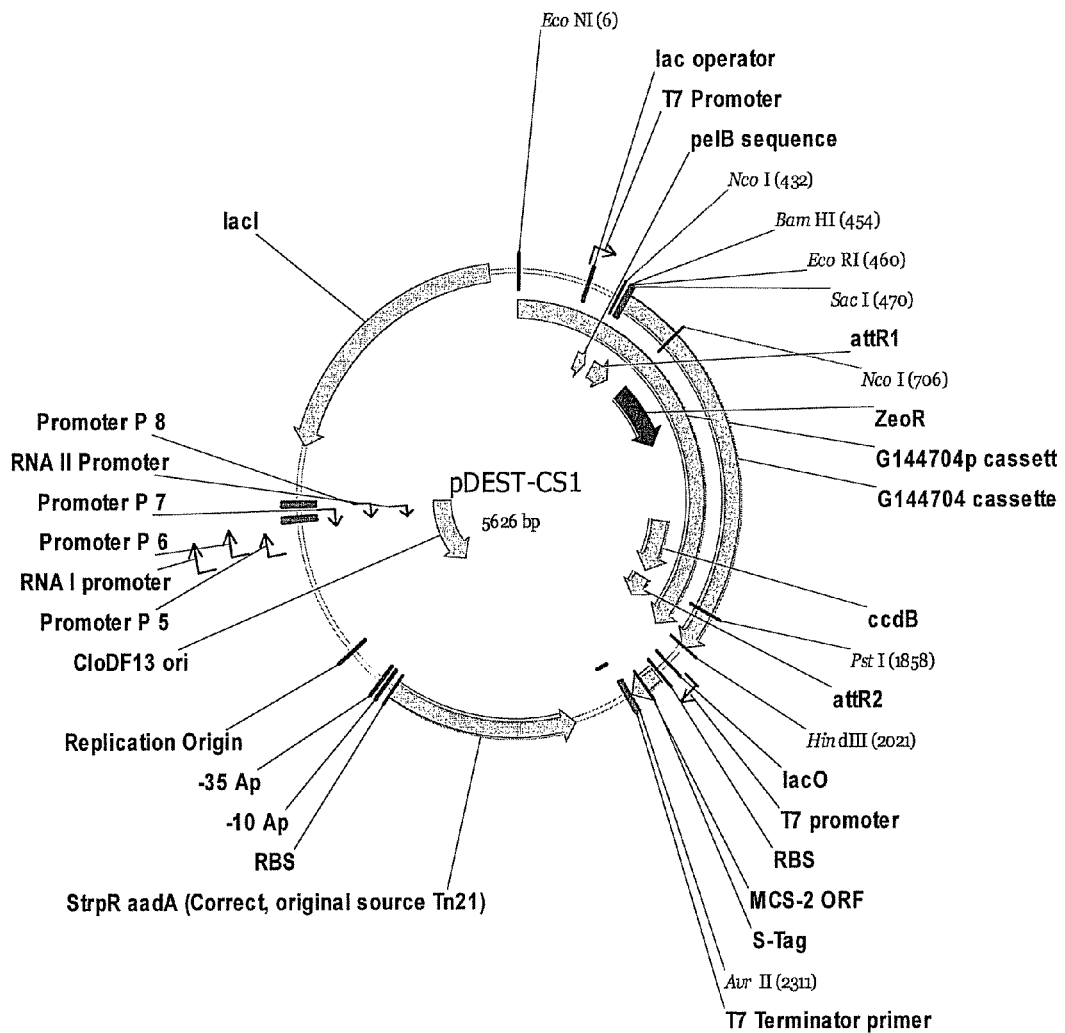
FIG. 43 is a map of the pDEST-CS1 vector.
Figure 44:
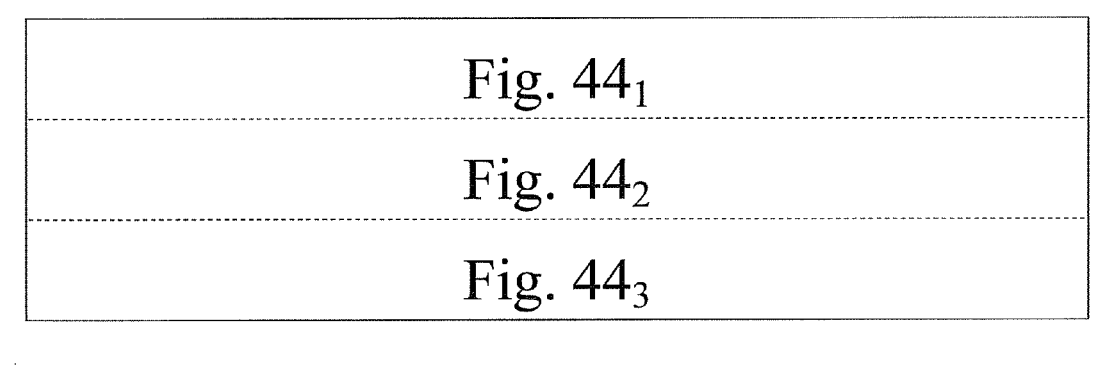

Vectors of the present invention include vectors having one or more of the elements shown in FIG. 43. An example of such a vector is the pDEST-CS1 vector, the nucleotide sequence of which is shown in FIG. 44.

Figure 45:
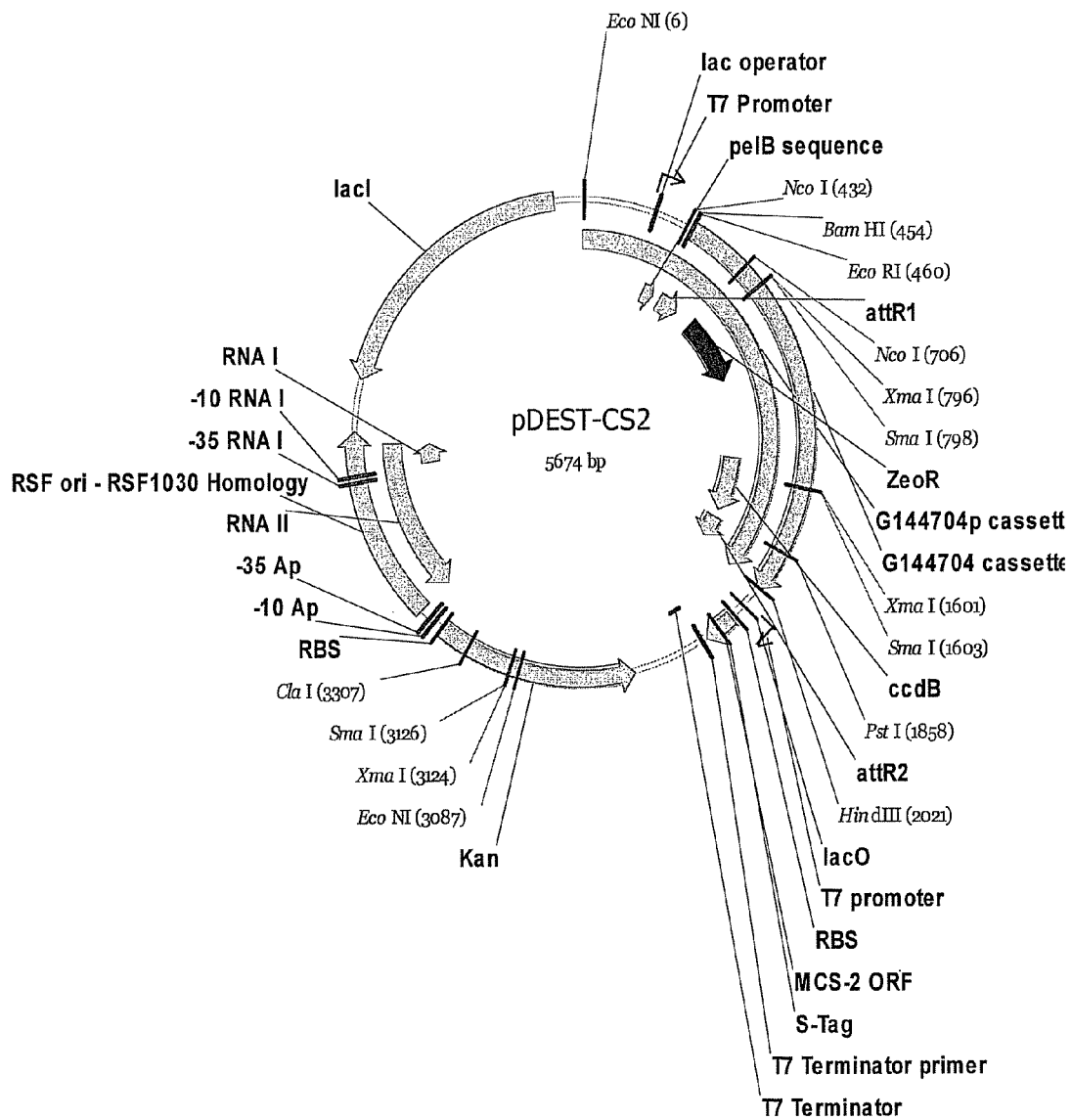
FIG. 45 is a map of the pDEST-CS2 vector.
Figure 46:
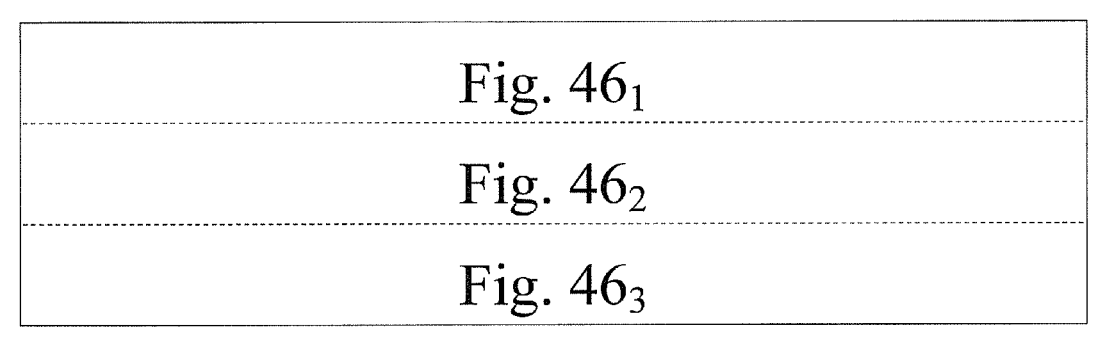

Vectors of the present invention include vectors having one or more of the elements shown in FIG. 45. An example of such a vector is the pDEST-CS2, the nucleotide sequence of which is shown in FIG. 46.

Figure 47:
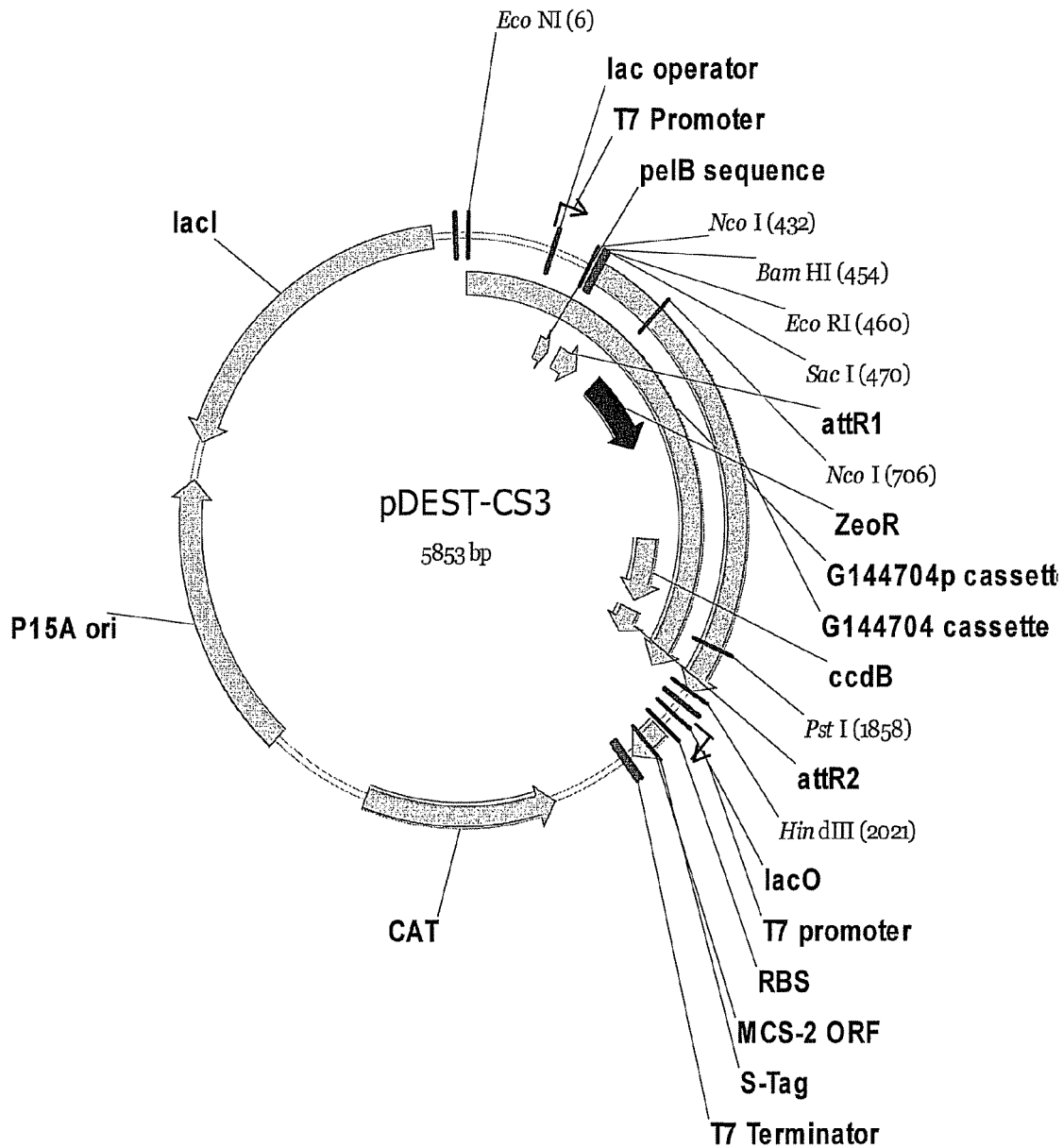
FIG. 47 is a map of the pDEST-CS3 vector.
Figure 48:
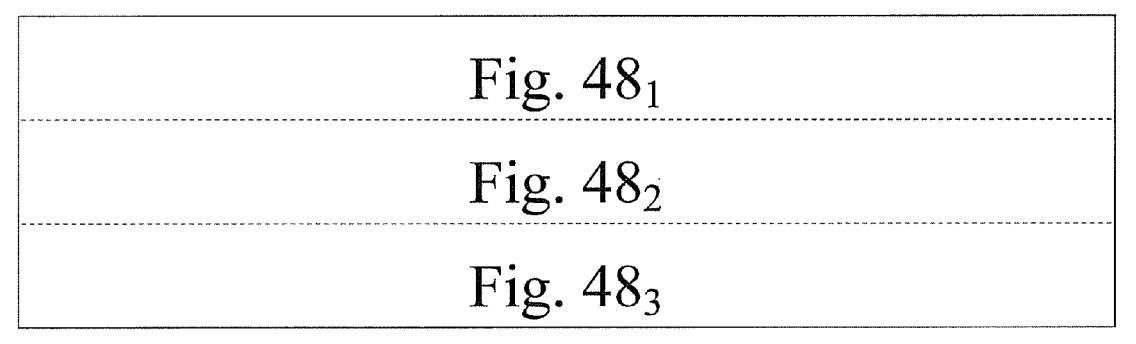

Vectors of the present invention include vectors having one or more of the elements shown in FIG. 47. An example of such a vector is the pDEST-CS3, the nucleotide sequence of which is shown in FIG. 48.

Figure 49:
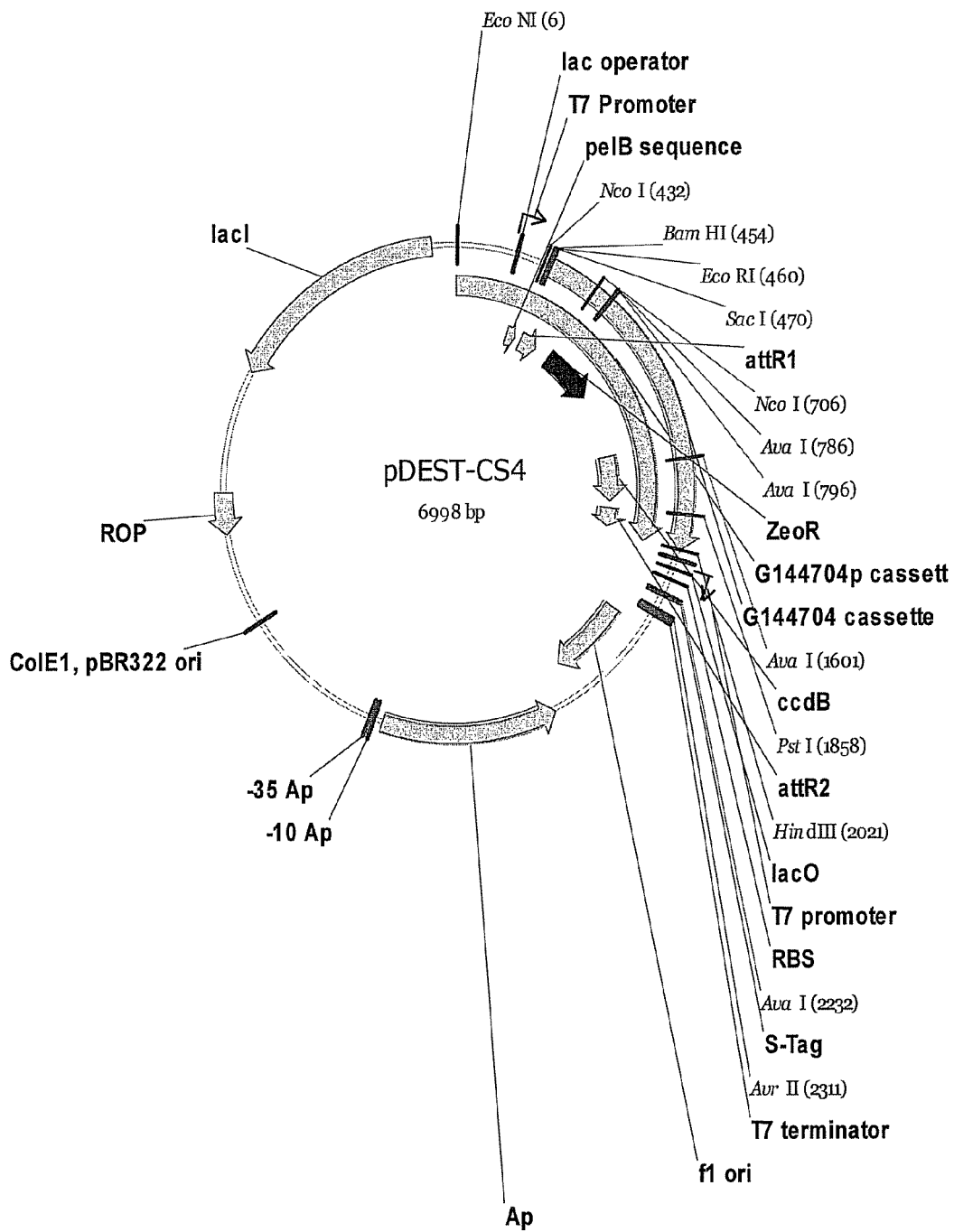
FIG. 49 is a map of the pDEST-CS4 vector.
Figure 50:
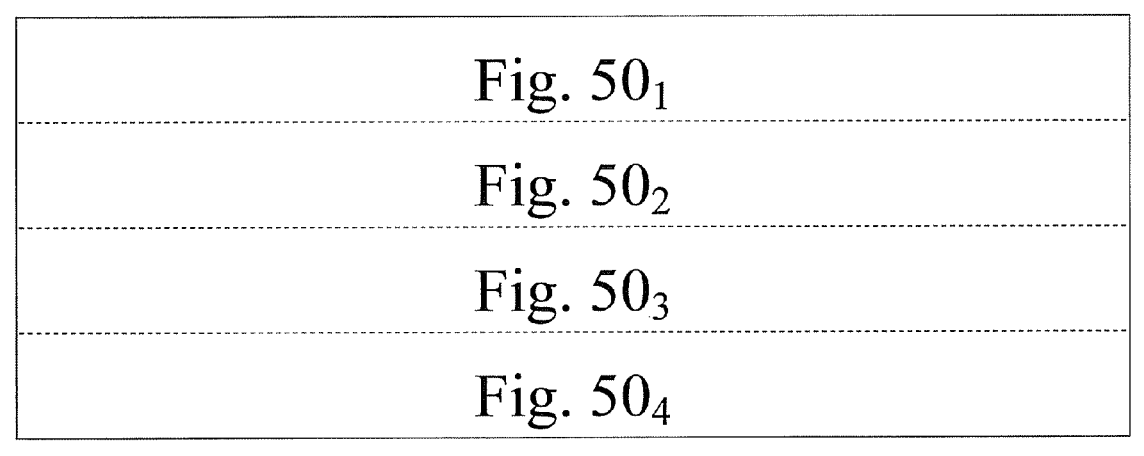

Vectors of the present invention include vectors having one or more of the elements shown in FIG. 49. An example of such a vector is the pDEST-CS4, the nucleotide sequence of which is shown in FIG. 50.

Figure 51:
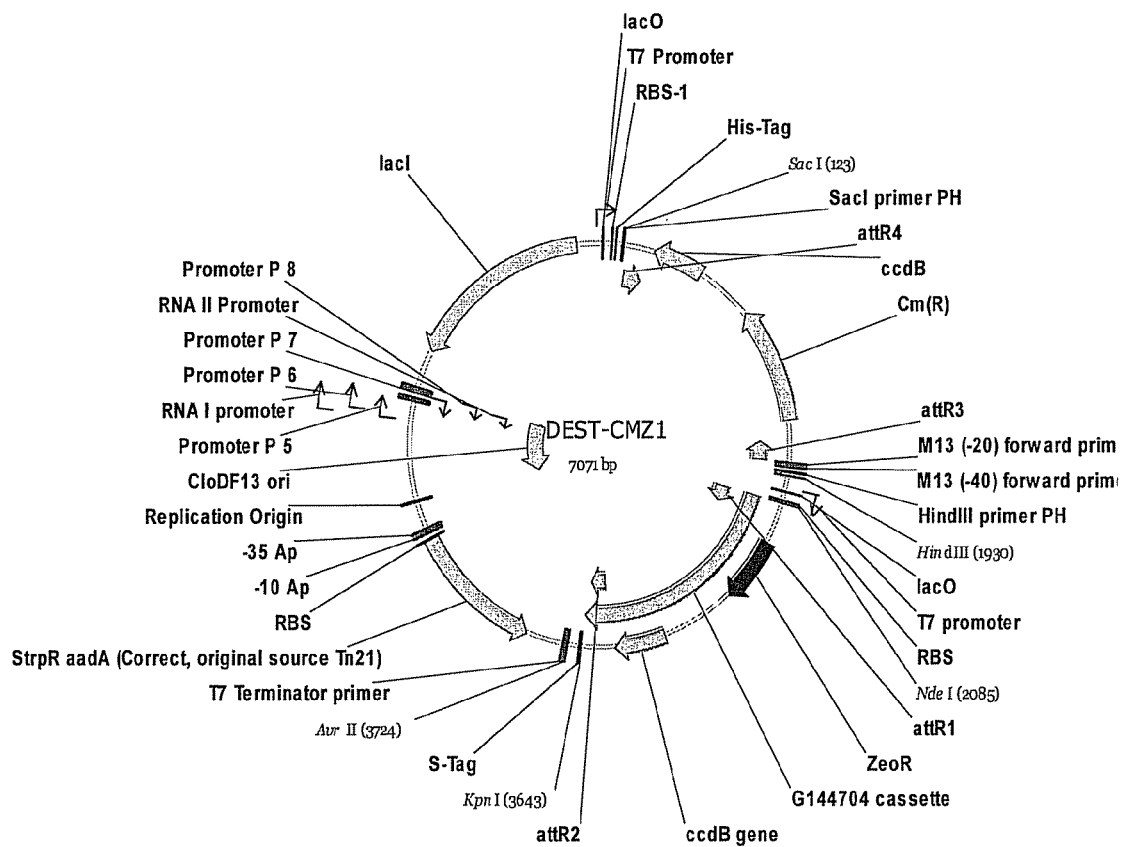
FIG. 51 is a map of the pDEST-CMZ1 vector.
Figure 52:
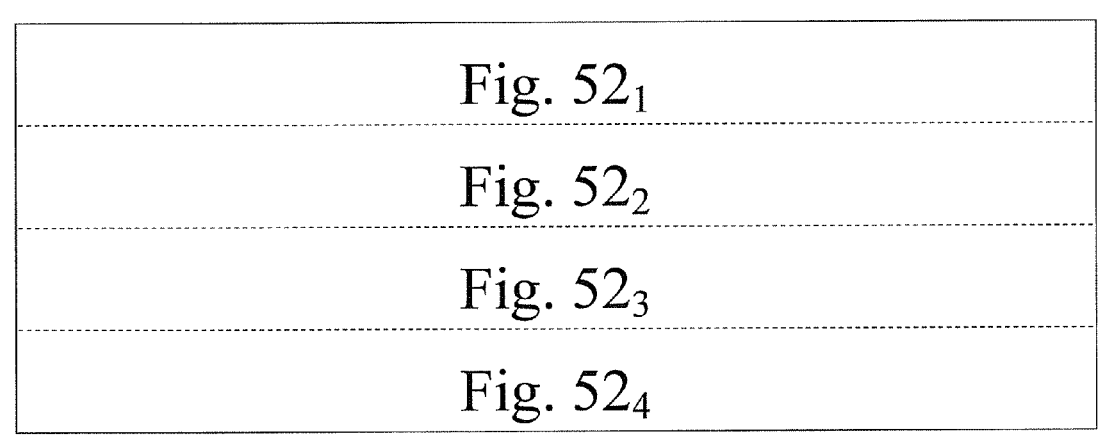

Vectors of the present invention include vectors having one or more of the elements shown in FIG. 51. An example of such a vector is the pDEST-CMZ1, the nucleotide sequence of which is shown in FIG. 52.

Figure 53:
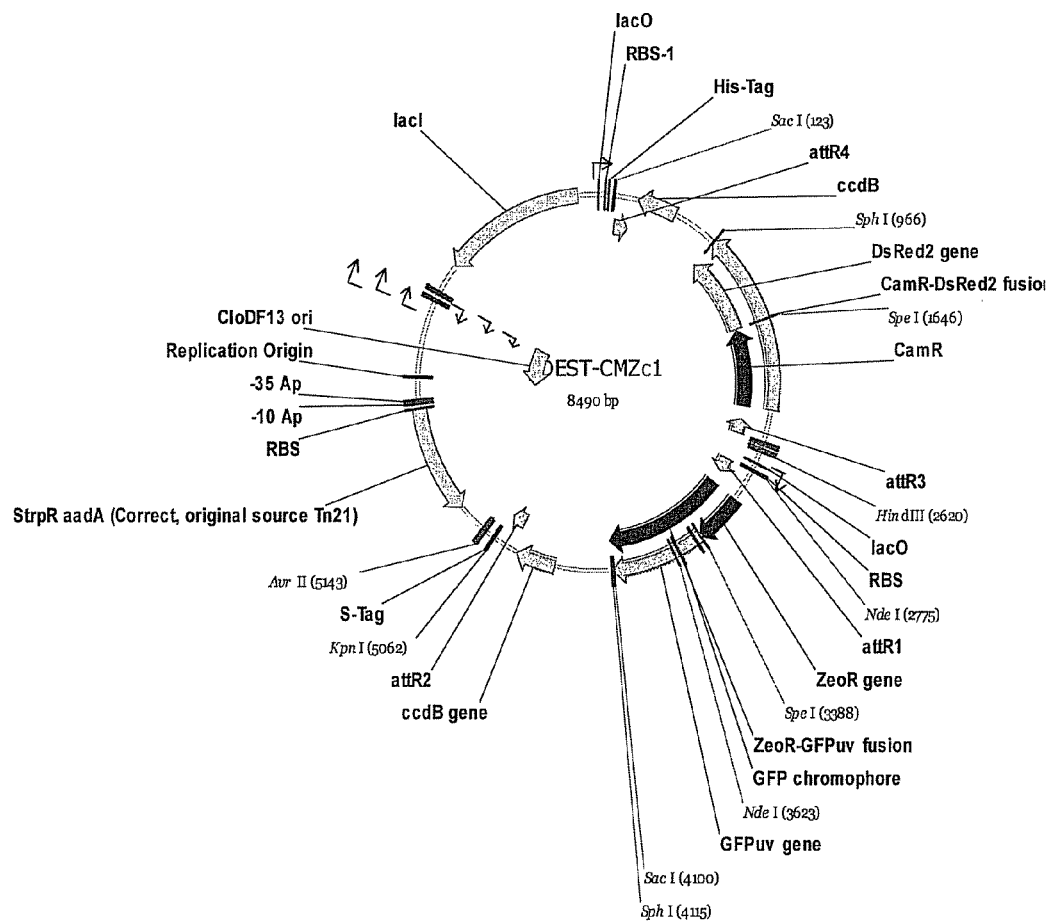
FIG. 53 is a map of the pDEST-CMc1 vector.
Figure 54:
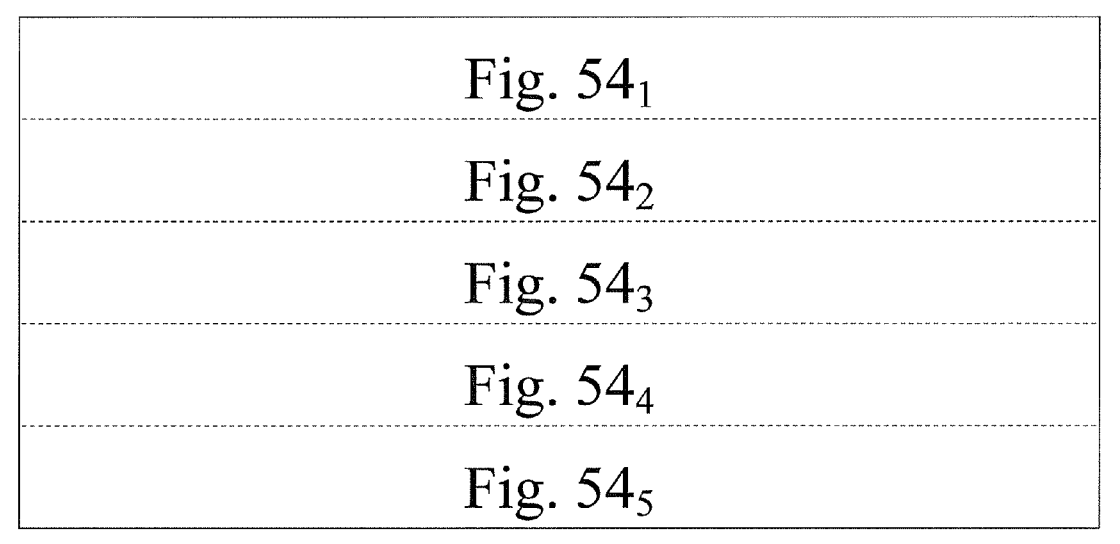

Vectors of the present invention include vectors having one or more of the elements shown in FIG. 53. An example of such a vector is the pDEST-CMc1, the nucleotide sequence of which is shown in FIG. 54.

The vectors of the present invention, when used together in the same cell, can express in a parallel manner multiple open reading frames ("ORFs"). As used herein, an ORF may include, for example, a polypeptide product, mRNA product, and an RNAi product. For example, up to two ORFs, two or more ORFs, up to three ORFs, three or more ORFs, up to four ORFs, four or more ORFs, up to six ORFs, six or more ORFs, up to eight ORFs, eight or more ORFs, up to ten ORFs, ten or more ORFs, up to twelve ORFs, twelve or more ORFs, up to sixteen ORFs, sixteen or more ORFs, up to twenty ORFs, twenty or more ORFs, up to twenty-two ORFs, twenty-two or more ORFs, up to twenty-four ORFs, twenty-four or more ORFs, up to twenty-eight ORFs, twenty-eight or more ORFs, up to thirty ORFs, thirty or more ORFs, up to thirty-two ORFs, thirty-two, or more ORFs may be expressed in a single host cell using a combination of the vectors of the present invention. Any combination of vectors of the present invention may be used in concert with any number of other available expression vectors to express multiple reading frames. The present invention also includes methods of expressing such ORFs using the one or more of the vectors of the present invention. The present invention also includes methods of expressing such ORFs using the one or more of the vectors of the present invention in combination with one or more additional expression vectors.

One, two, three, four, five, six, seven, eight, nine, ten, or more of the vectors described herein may be used in a single co-expression experiment. The vectors of the present invention may be used along with any number of currently available expression vectors and/or newly developed co-expression vectors. Examples of such vectors include, but are not limited to, those reported in the scientific literature and the many commercially available expression vectors, including those marketed, for example, Invitrogen, Novagen (Novagen 2004/2005 Catalog), Promega (Promega 2005 Life Sciences Catalog), Stratagene (Strategene 2005-06 Catalog) and New England Biolabs (2006 NEB catalog).

The expression vectors of the present invention may be used to for the expression of one or more polypeptides. The polypeptide may be homologous to the host cell, which includes, for example, proteins or peptides that are naturally encoded by the host cell, from a native DNA sequence, or a substitution, deletion, and/or insertion variant thereof. The polypeptide may also be heterologous to the host cell, expressed on a heterologous nucleic acid sequence, which includes, for example, proteins and peptides that are not naturally expressed by the host cell, proteins and peptides that are naturally expressed or encoded by the host cell, and substitutions, deletions, and/or insertion variants of proteins and peptides that are naturally expressed or encoded by the host cell. The protein or peptide may be a fusion protein, comprising two or more polypeptides that are synthesized from a nucleic acid molecule encoding both polypeptides under the control of a single set of translational control elements. The fusion protein may include a linker peptide situated between the polypeptides.

A DNA molecule encoding the polypeptide may be prepared using well known recombinant DNA technology methods such as those set forth in Sambrook et al. (Molecular Cloning: A Laboratory Manual, Cold Spring Harbor Laboratory Press, Cold Spring Harbor, N.Y., 2001) and/or Ausubel et al., eds, (Current Protocols in Molecular Biology, Green Publishing Assoc., Inc. John Wiley & Sons, Inc., N.Y., 1994).

Insertion (also referred to as "transformation" or "transfection") of a vector of the present invention into the selected host cell may be accomplished using any of a variety of methods. The method selected will in part be a function of the type of host cell to be used. These methods and other suitable methods are well known to the skilled artisan. Transformation of a bacterial host with the vector of the present invention may be accomplished using any of a variety of methods. For example, any of the methods described in the examples herein, and any of the well known methods such as those set forth, for example, in Sambrook et al., *Molecular Cloning: A Laboratory Manual*, Cold Spring Harbor Laboratory Press, 1989, may be used. Methods that may be used include, for example, such methods as calcium phosphate precipitation or electroporation. Likewise, transfection of the vectors of the present invention into mammalian cells may be accomplished using any of the many known methods. For example, transfection into mammalian cells may be accomplished using Lipofectamine™ (Invitrogen Corp) according to the supplier's instructions.

Any of a variety of host-expression vector systems may be used to express the protein or peptide. These include, but are not limited to, microorganisms such as bacteria, yeast, insect cell systems, plant cell systems, or animal cell systems, including, for example, any of a variety of murine and human cells systems. The co-expression systems of the present invention may be used to express therapeutic proteins, including protein complexes, including, for example antibodies.

The vectors of the present invention provide many innovations, including, but not limited to the following. Constructs may be created in the same reaction and plated on different antibiotic supplemented plates. Each of these vectors can be used by itself, which allows for their use as a conventional expression vector. The throughput of expression screening is increased by testing up to four non-interacting ORFs' expression/solubility in the same cells. The vectors of the present invention can be used in methods of solubilizing proteins through soluble complex expression. The vectors of the present invention may be used in methods of high throughput (HTP) expression of already known protein complexes. And, the vectors of the present invention are compatible with the existing Gateway cloning system via the well-known L/R reaction.

In some aspects, polynucleotides and vectors of the of the present invention may include a cassette, wherein the cassette is a polynucleotide sequence containing the two recombination sites, for example attR1 and attR2 or attR3 and attR4, along with a nucleotide sequence that operably encodes the ccdB polypeptide. The two recombination sites flank the nucleotide sequence encoding a ccdB polypeptide. This cassette may also include a nucleotide sequence that operably encodes a selectable marker other than chloramphenicol resistance, including for example, zeocin resistance. Zeocin™, a registered trademark of Cayla, is the commercial name of a formulation containing Phleomycin D1, an antibiotic of the bleomycin family (also called the phleomycin family). The ble gene encodes zeocin antibiotic resistance, conferring resistance to an antibiotic of the phleomycin family (U.S. Pat. Nos. 5,021,344 and 5,118,620). In the nucleotides and vectors of the present invention, the efficiency of the Gateway® recombination reaction is not affected by the insertion of the Zeocin gene between the att recombination recognition sites.

The present invention includes a polynucleotide, also referred to herein as a "cassette," wherein the cassette has a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide are flanked by attR sites, including, for example, attR1 and attR2 or attR3 and attR4 recombinant recognition sites. An example of such a cassette is a cassette including one or more of the elements shown in FIGS. 8C and 8D. An example of such a cassette is the G144704 cassette, the nucleotide sequence of which is shown in FIG. 9. Another example of such a cassette is a cassette having one or more of the elements shown in FIG. 20. An example of such a cassette is the Multisite TetR cassette, the nucleotide sequence of which is shown in FIG. 21.

Vectors of the present invention allow for the tandem expression of more than one polypeptide product from a single co-expression vector. See, also, Sone et al. (Multi-gene gateway clone design for expression of multiple heterologous genes in living cells: Modular construction of multiple cDNA expression elements using recombinant cloning," J Biotechnol. 2005 Jun. 24 (doi:10,1016/jbiotec.2005.02.021)).

The present invention also includes methods of improving the solubility of expressed polypeptides by co-expressing more than one polypeptide using one or more of the vectors described herein. The vectors described herein may be used in concert with additional, available expression vectors in such methods of improving the solubility of one or more expressed polypeptides. The solubility of an expressed polypeptide can be determined using standard methods known in the art, including any of the methods described in the examples included herewith. For example, host cells may be collected three to twenty hours after induction and the cells are lysed. Cell lysis may be accomplished using physical methods such as homogenization, sonication, French press, microfluidizer, or the like, or by using chemical methods such as treatment of the cells with EDTA and a detergent (see Falconer et al., Biotechnol. Bioengin. 53:453-458 [1997]) or by taking advantage of the lytic activities of some bacteriophage proteins (Crabtree, S. & Cronan, J. E., J. Bact., 1984, 158:354-356). In some cases, it may be advantageous to combine more than one technique.

Expression of and mRNA or polypeptide product by a vector of the present invention may be assayed by any of a wide variety of methods, including any of those described herein.

Additionally, for example, fluorescent proteins with different excitation and emission wavelengths can be used to label a target product of a cDNA or to be expressed solely. Examples of such fluorescent proteins include, for example, EGFP (BD Biosciences Clontech Inc.; GenBank accession no.: U55763) (Cormack et al., Gene 173:33-38, 1996; Zhang et al., Biochem. Biophys. Res. Commun. 227:707-711, 1996), Venus (EYFP-F46L/F64L/M153T/V163A/S175G) (Nagai et al., Nat. Biotechnol. 20:87-90, 2002), SECFP (ECFP-K27R/N165H) (Zhang et al., Proc. Natl. Acad. Sci. U.S.A. 98:14997-15002, 2001), DsRed2 (BD Biosciences Clontech Inc.) (Matz et al., Nat. Biotechnol. 17:969-973, 1999; Terskikh et al., J. Biol. Chem. 277:7633-7636.2002) and mRFP1 (GenBank accession no.: AF506027) (Campbell et al., Proc. Natl. Acad. Sci. U.S.A. 99:7877-7882, 2002).

The present invention includes nucleotides and vectors for use in producing interfering RNA molecules for use in RNA interference (RNAi) studies. RNA is a biological process that involves sequence-specific mRNA degradation that is mediated by short interfering RNA (siRNA) molecules generated from the cleavage of dsRNA homologous to the gene targeted for silencing. The mechanism of RNAi-mediated specific gene silencing was first discovered in *C. elegans* and has also been found in other organisms, including *Drosophila*, hydra, zebrafish, and trypanasomes.

While the exact mechanism behind RNA interference is still not entirely understood, it appears that a dsRNA is processed into 20-25 nucleotide short interfering RNAs (siRNAs) by an Rnase III-like enzyme called Dicer. The siRNAs assemble into endoribonuclease-containing complexes known as RNA-induced silencing complexes (RISCs). The siRNA strands are then unwound to form activated RISCs, and the siRNA strands subsequently guide the RISCs to complementary RNA molecules, where they cleave and destroy the cognate RNA (discussed in Bass, B., Nature 411: 428-429 (2001) and Sharp, P. A., Genes Dev. 15:485-490 (2001)). Although the phenomenon of RNAi was first characterized in *C. elegans* and *Drosophila*, RNAi has also been demonstrated to work in mammalian cells (Wianny, F. and Zernica-Goetz, M., (2000), Nature Cell Biology Vol. 2., 70-75.

Accordingly, the invention includes both novel methods and compositions for reducing nonspecific suppression and novel methods and compositions for performing RNAi to reduce expression of target genes.

Nucleotides and vectors of the present invention for use in RNAi may include any of the various nucleotides, vectors, cassettes and elements described herein.

The RNAi vectors of the present invention may be used in any of the many available RNAi systems. For example, the RNAi vectors of the present invention may used to produce an interfering RNA product in the worm *Cerenohabditis elegans* (*C. elegans*). For example, worms may be fed with bacteria transformed with one or more vectors of the present invention. Currently available methods of RNAi allow for only gene to be studied at a time. The vectors of the present invention provide HTP RNAi vectors and provide for the large scale RNAi investigation of multiple genes at a time, for example, up to four, up to eight, up to ten, up to twelve, up to sixteen, up to twenty, up to twenty-four, up to twenty-eight, or up to thirty-two genes at one time.

Figure 27:
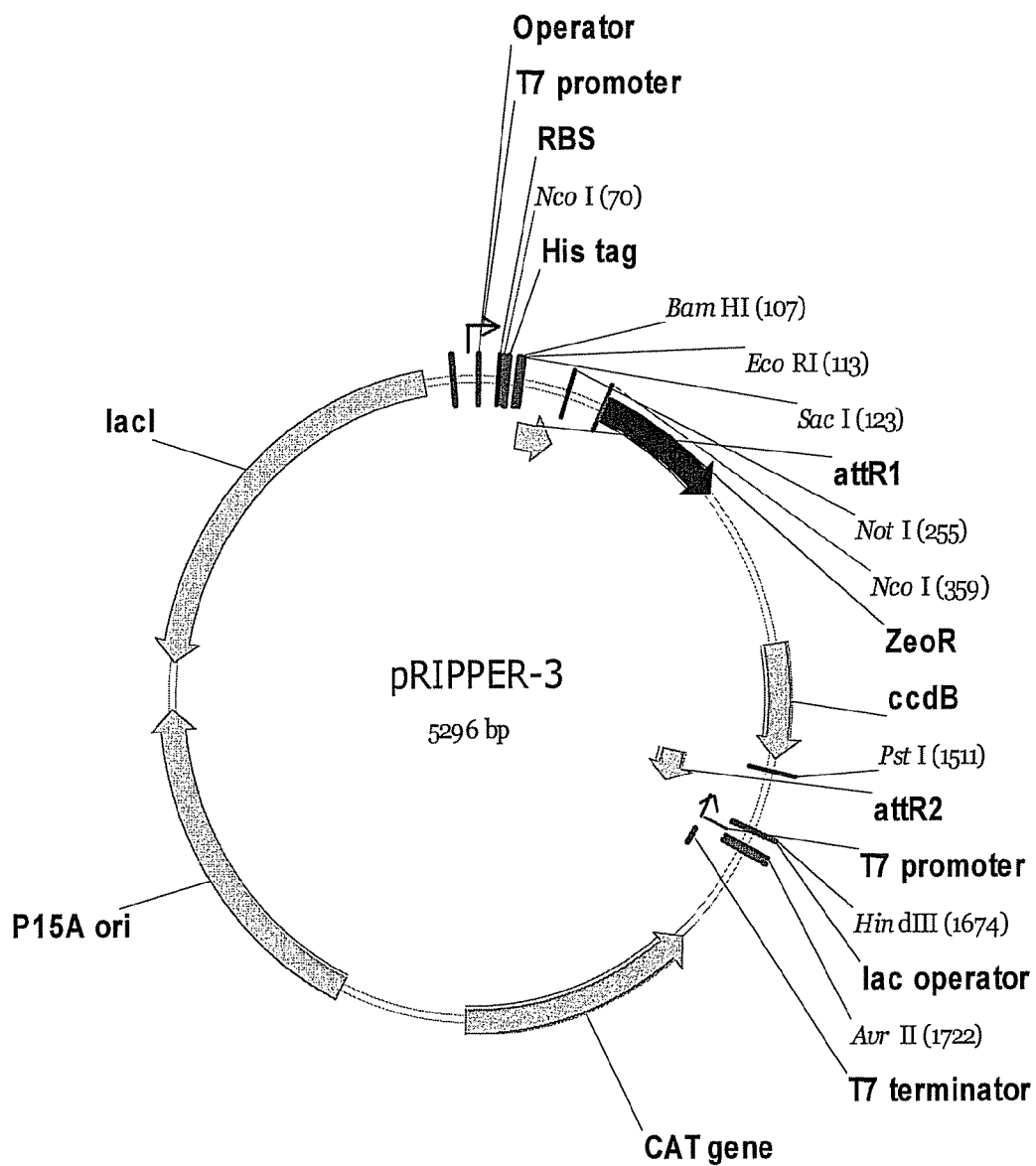
FIG. 27 is a map of the pRIPPER-3 vector.
Figure 28:
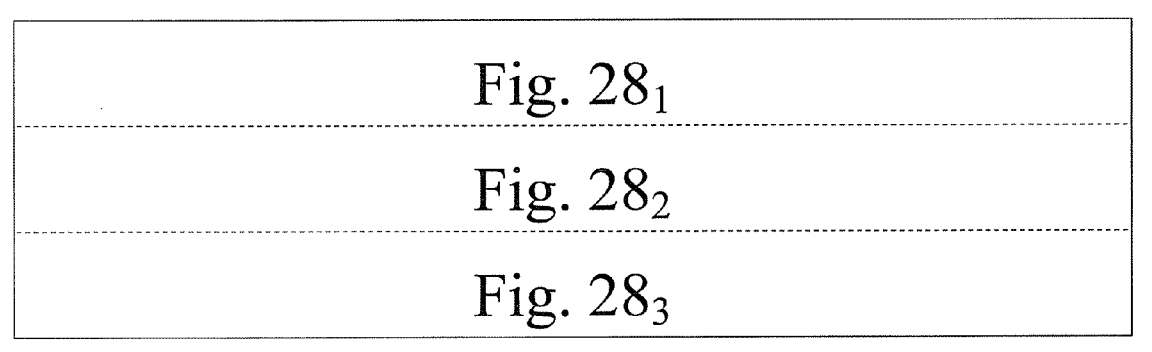

RNAi vectors of the present invention include vectors having one or more of the elements shown in FIG. 27. An example of such a vector is the pRIPPER-3 vector, the nucleotide sequence of which is shown in FIG. 28.

Figure 29:
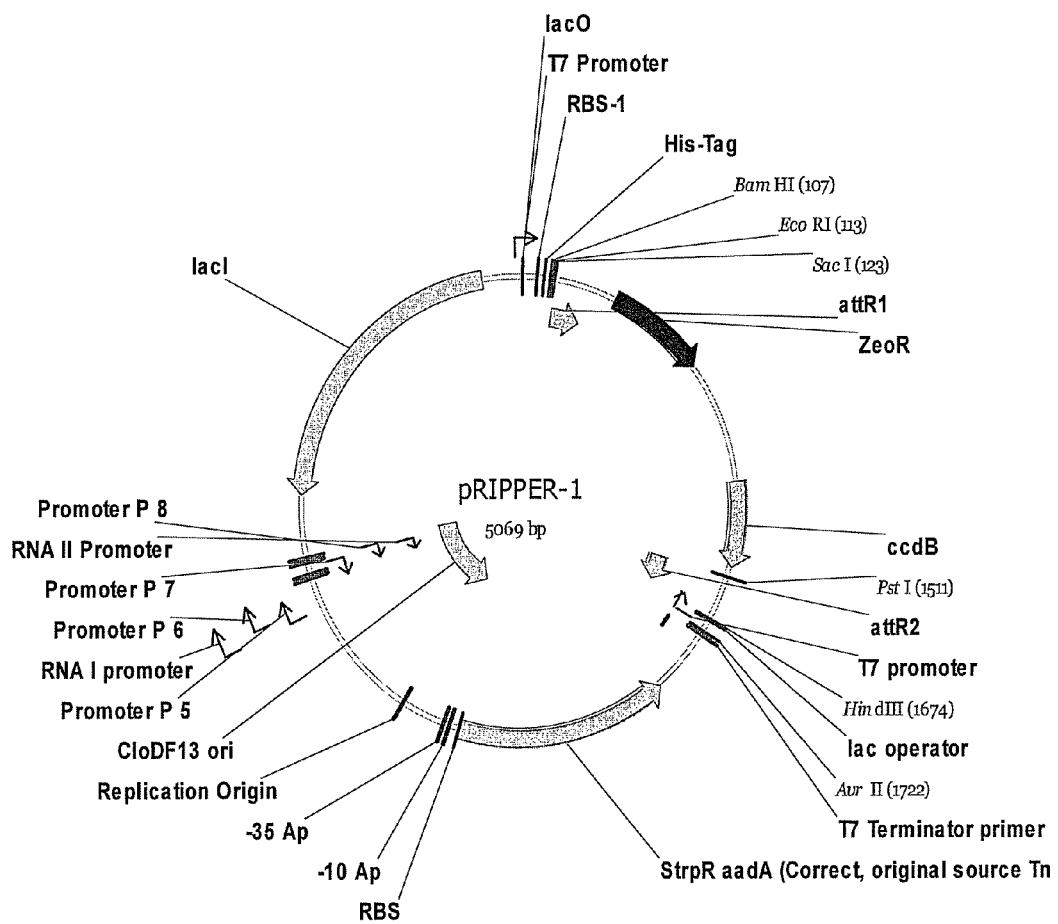
FIG. 29 is a map of the pRIPPER-1 vector.
Figure 30:
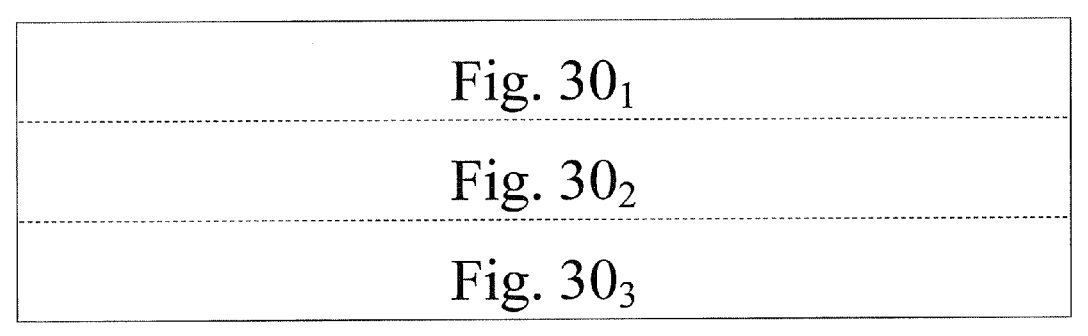

RNAi vectors of the present invention include vectors having one or more of the elements shown in FIG. 29. An example of such a vector is the pRIPPER-1 vector, the nucleotide sequence of which is shown in FIG. 30.

Figure 31:
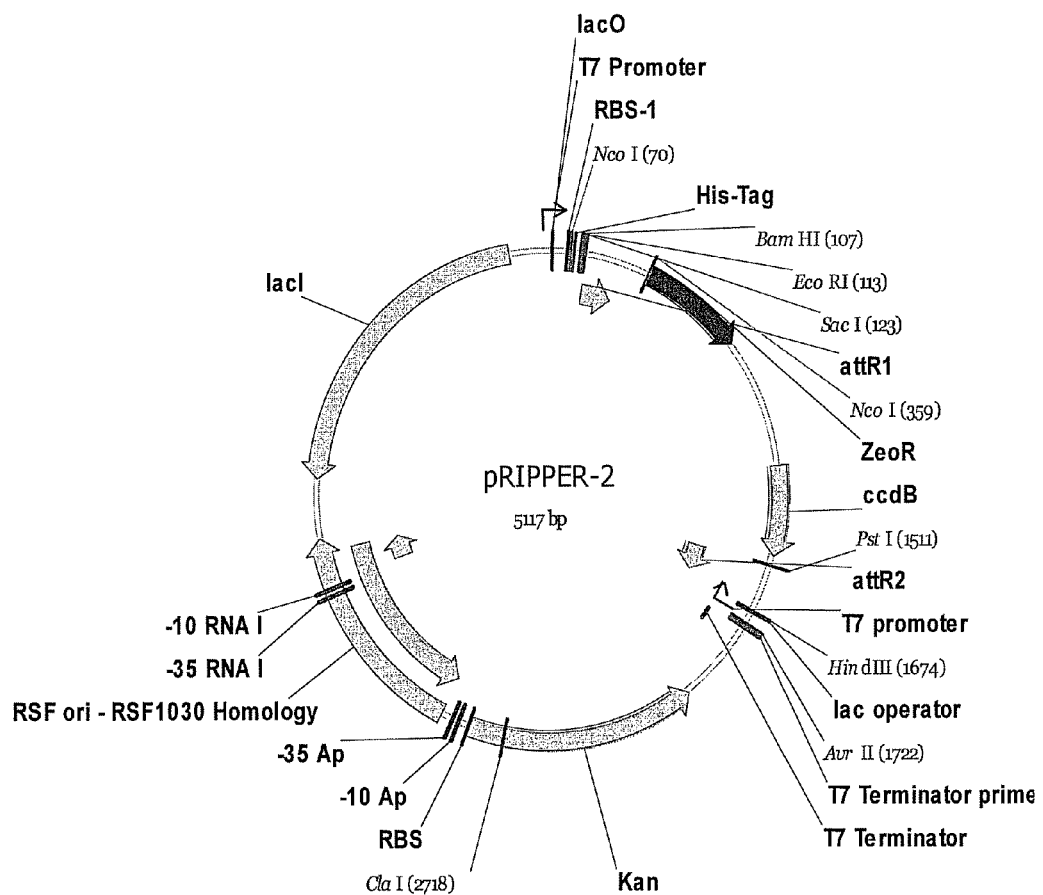
FIG. 31 is the map of the pRIPPER-2 vector.
Figure 32:
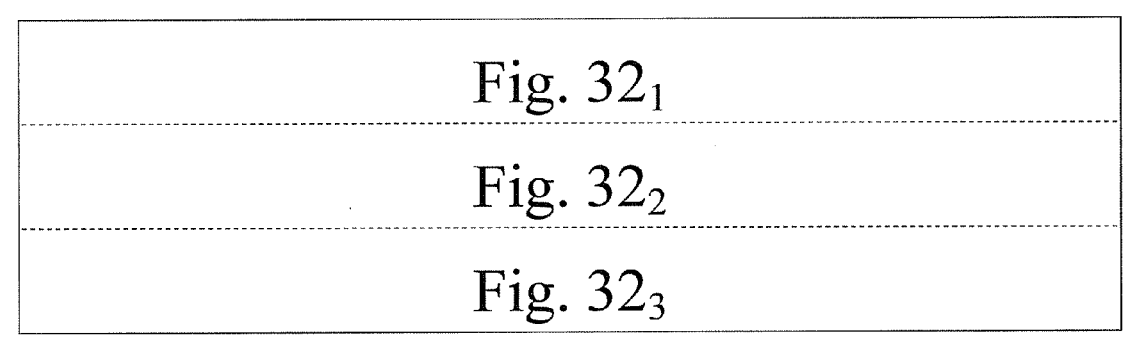

RNAi vectors of the present invention include vectors having one or more of the elements shown in FIG. 31. An example of such a vector is the pRIPPER-2 vector, the nucleotide sequence of which is shown in FIG. 32.

Figure 33:
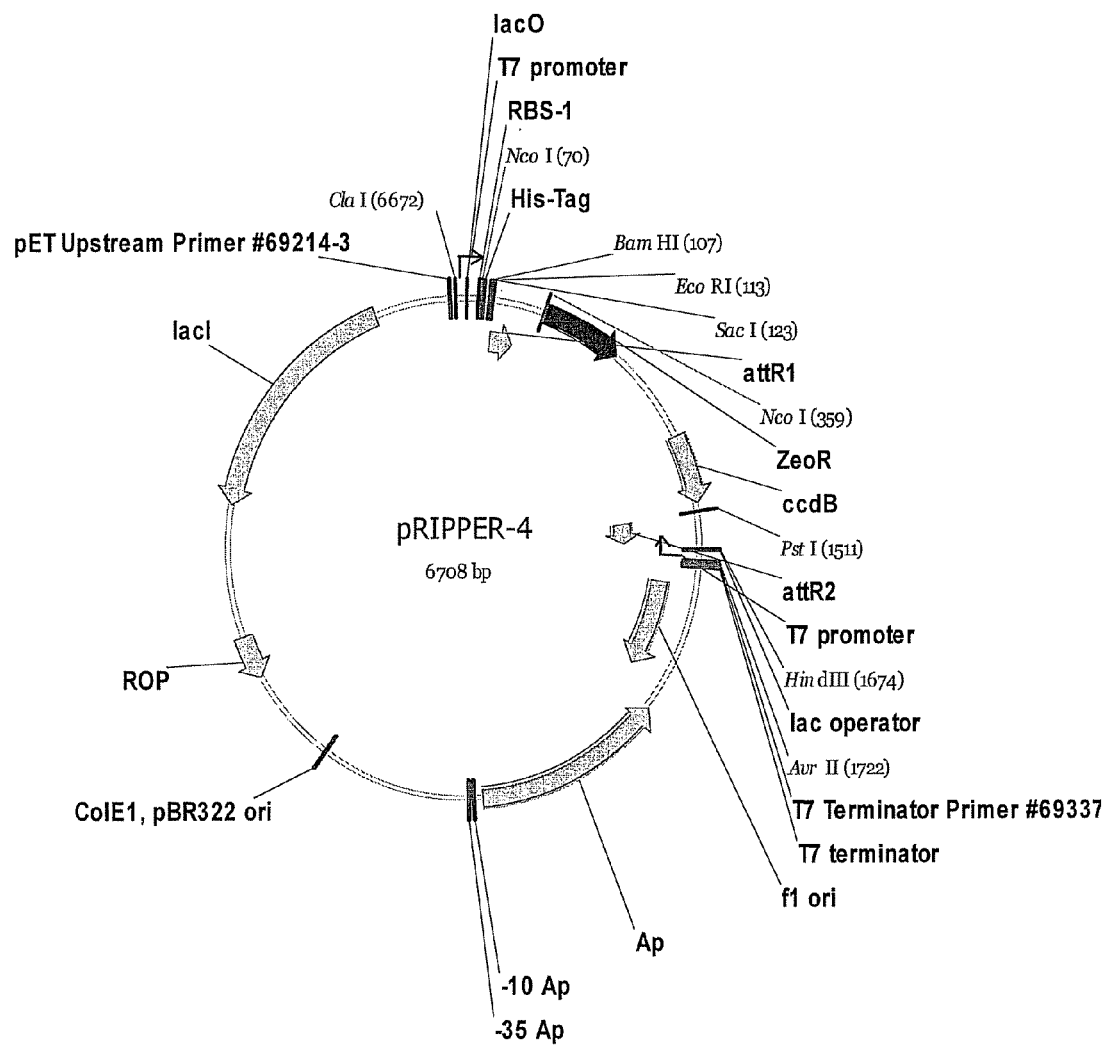
FIG. 33 is the map of the pRIPPER-4 vector.
Figure 34:
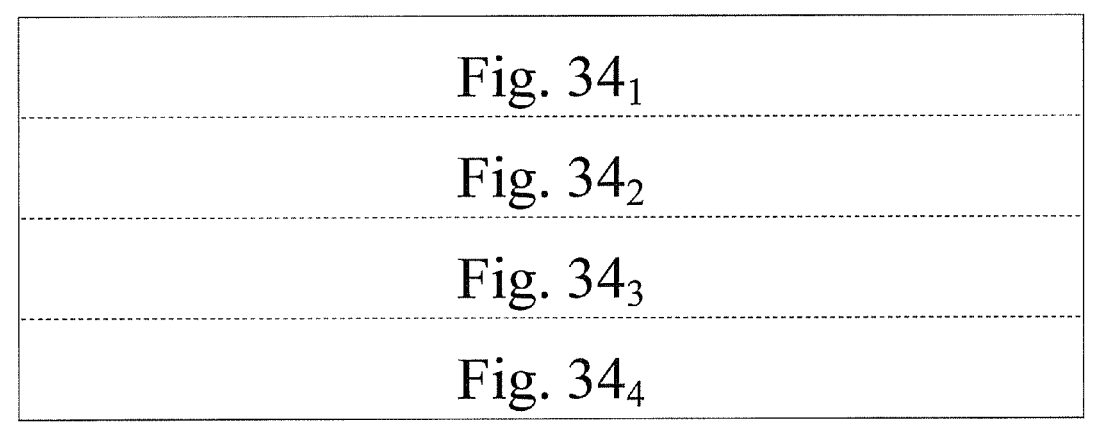

RNAi vectors of the present invention include vectors having one or more of the elements shown in FIG. 33. An example of such a vector is the pRIPPER-4 vector, the nucleotide sequence of which is shown in FIG. 34.

Figure 35:
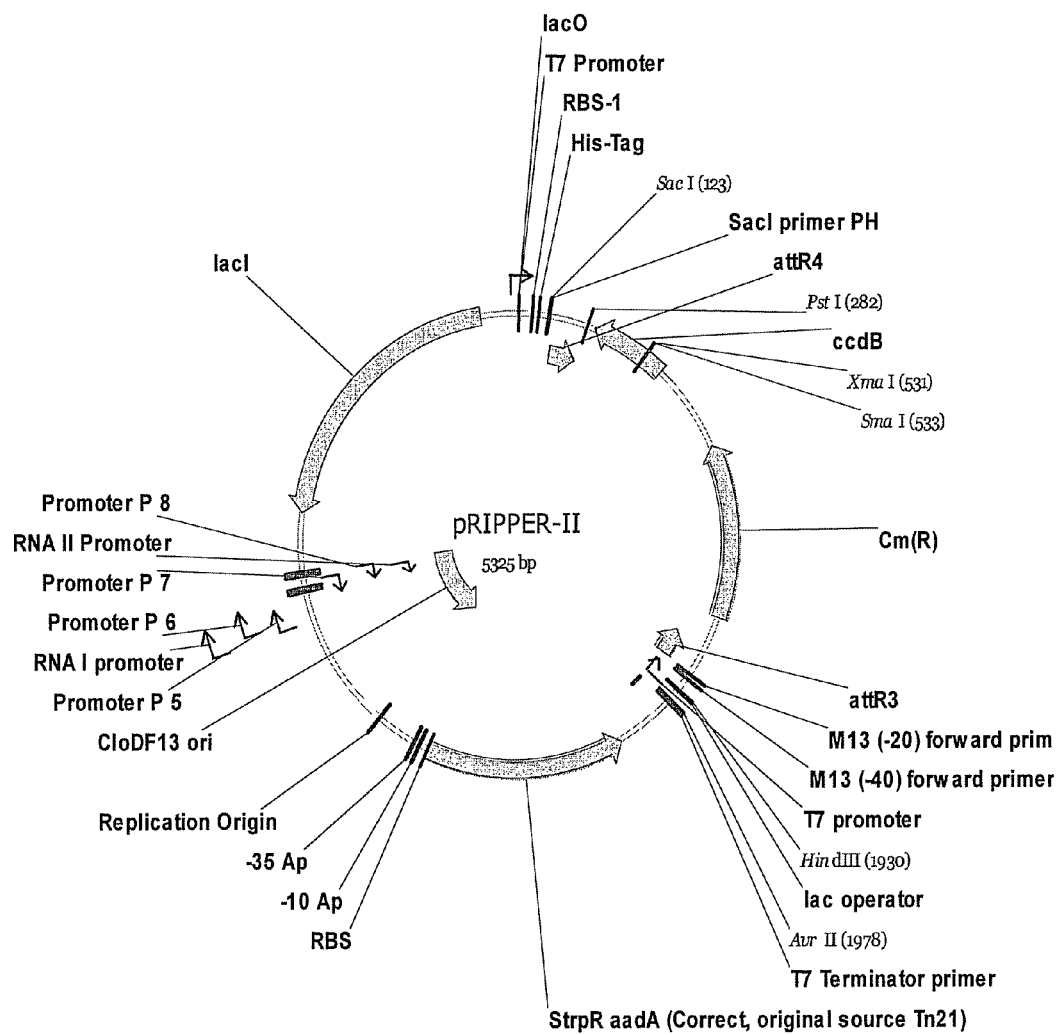
FIG. 35 is a map of the pRIPPER-II vector.
Figure 36:
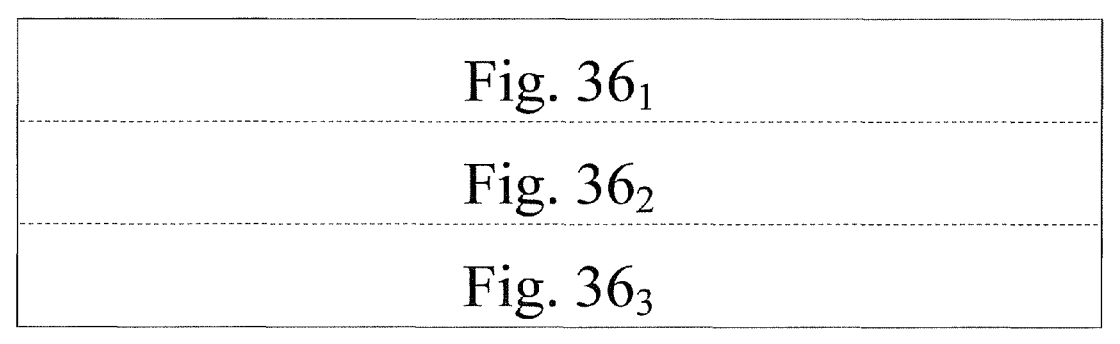

RNAi vectors of the present invention include vectors having one or more of the elements shown in FIG. 35. An example of such a vector is the pRIPPER-II vector, the nucleotide sequence of which is shown in FIG. 36.

Figure 37:
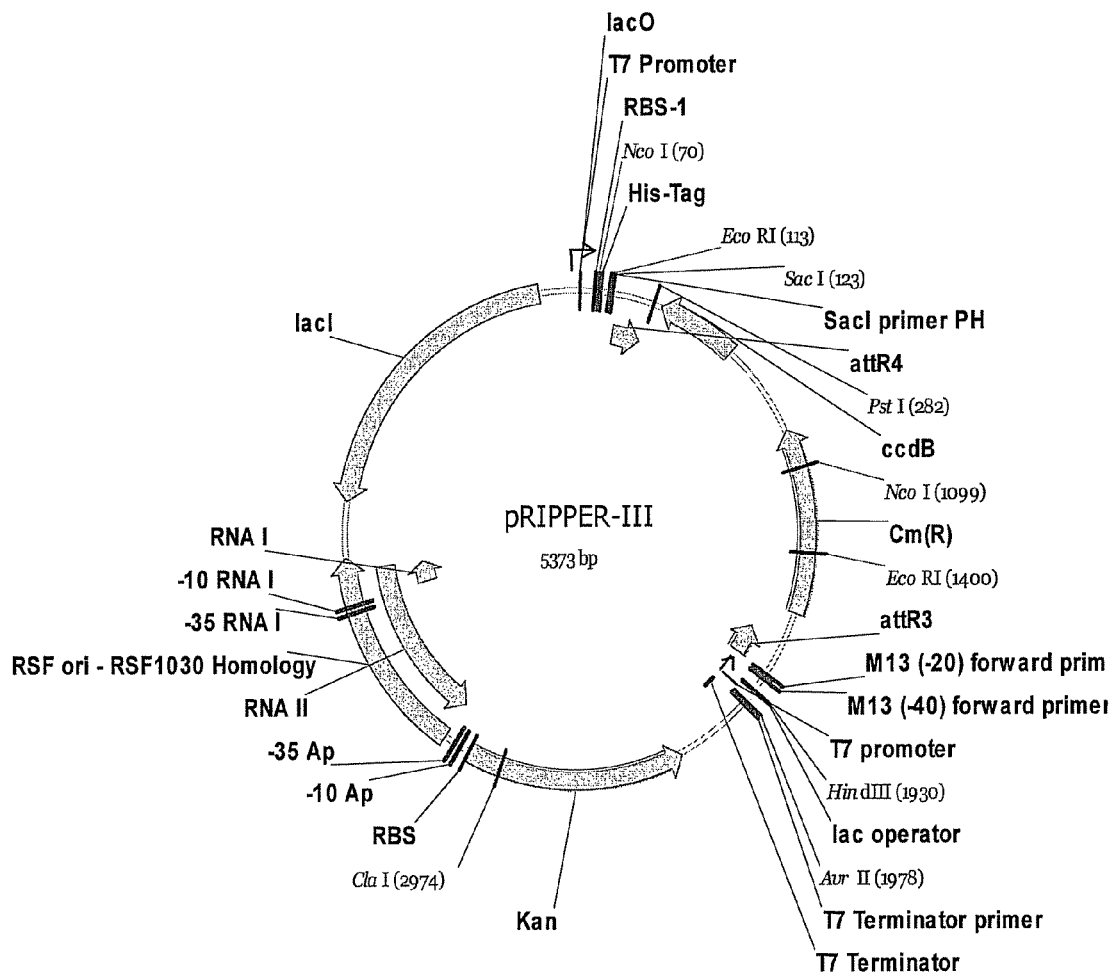
FIG. 37 is a map of the pRIPPER-III vector.
Figure 38:
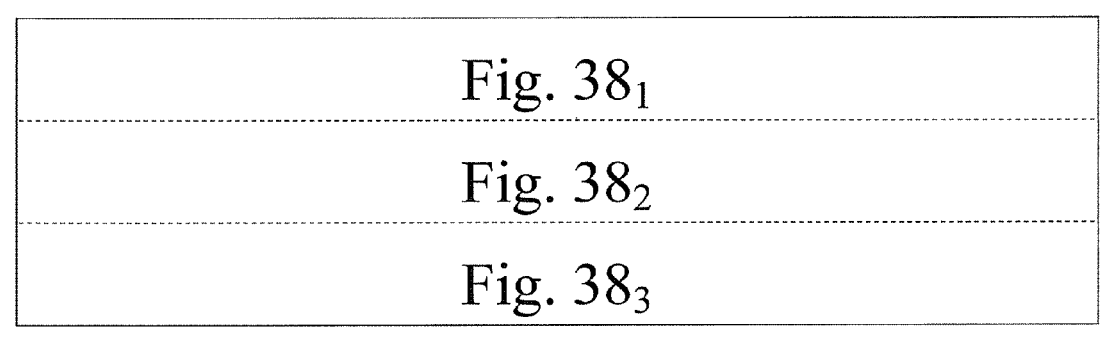

RNAi vectors of the present invention include vectors having one or more of the elements shown in FIG. 37. An example of such a vector is the pRIPPER-III vector, the nucleotide sequence of which is shown in FIG. 38.

Figure 39:
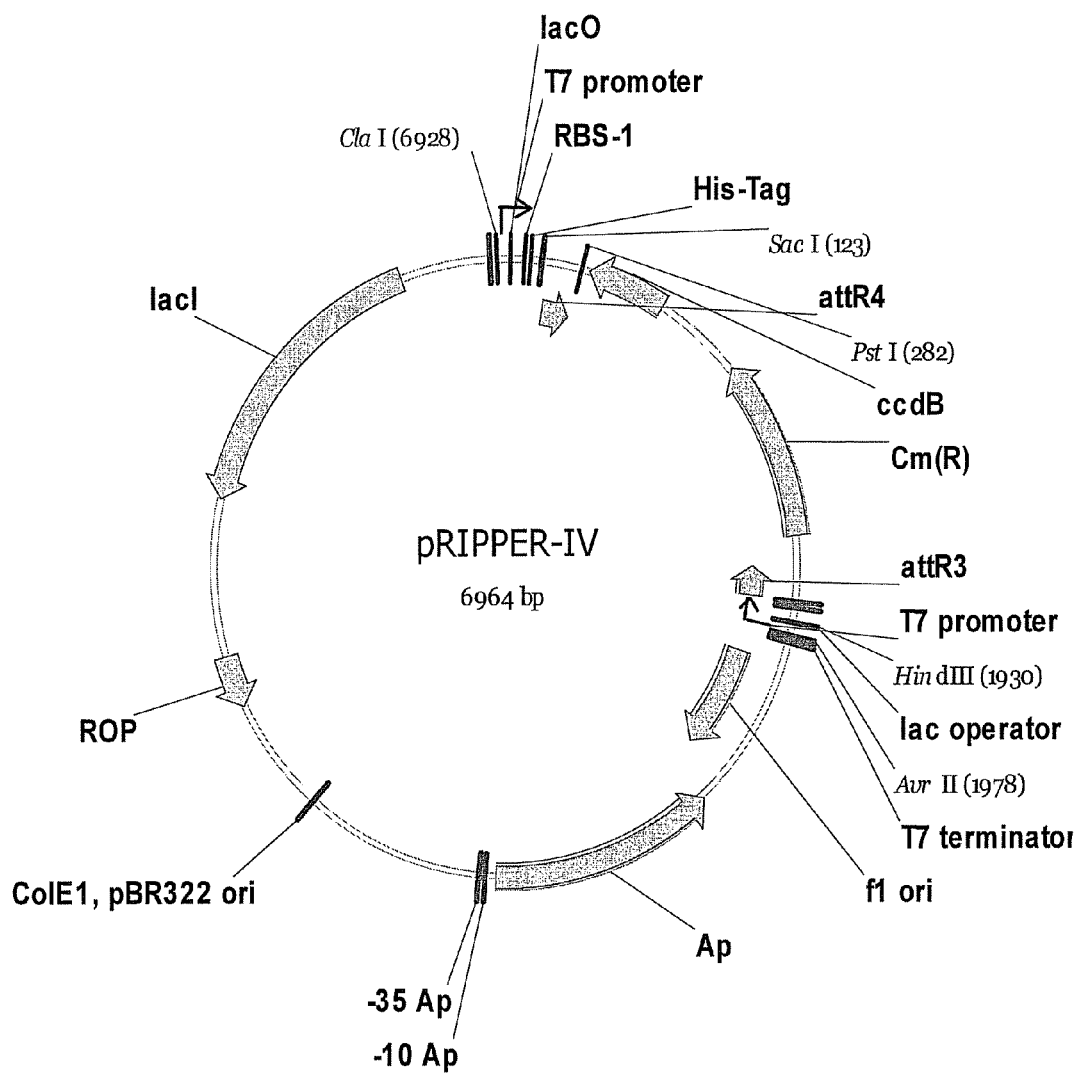
FIG. 39 is a map of the pRIPPER-IV vector.
Figure 40:
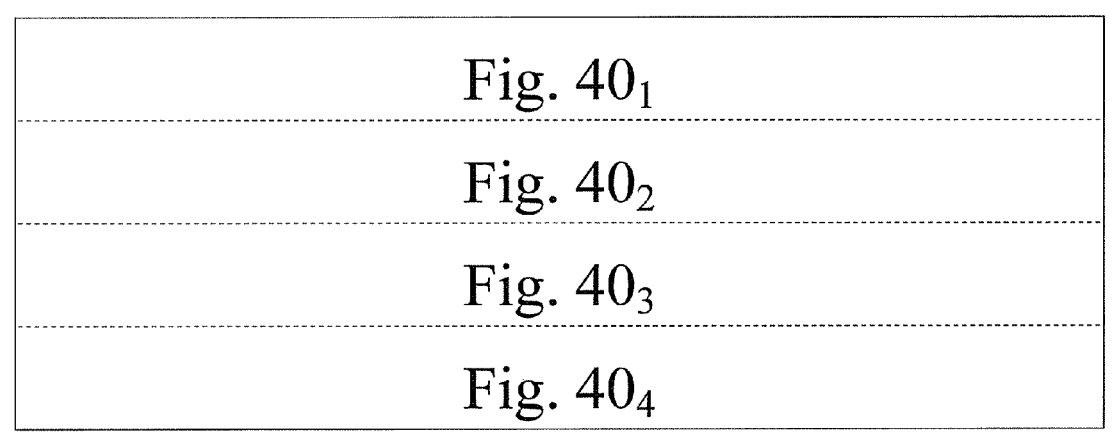

RNAi vectors of the present invention include vectors having one or more of the elements shown in FIG. 39. An example of such a vector is the pRIPPER-IV vector, the nucleotide sequence of which is shown in FIG. 40.

The present invention also includes methods of producing one or more interfering RNAs using one or more of the vectors described herein. The present invention also includes methods of inhibiting the expression of a gene, thereby inhibiting gene function, in a host cell or animal model system, including, for example, *C. elegans* and transgeneic animals, such as transgenic mice, by expressing one or more interfering RNAs in the host cell or animal model system using the vectors described herein. Methods for producing and assaying the effect of interfering RNAs produced by the vectors described herein may be by any of the many available methods. See, for example, materials available on the world wide web at ambion.com/techlib/resources/RNAi/; "RNAi" A "How To" for New Users" TechNotes 11(5), Ambion, 2006; or "RNA Interference and Gene Silencing—History and Overview," Ambion, May 20, 2002.

The vectors and method of the present invention may be used to lower production costs by allowing the use of parallel gene expression, the simultaneous expression of multiple proteins in the same cell. For example, multiple vector constructs, for example, four, sixteen, or thirty-two constructs, may be in a single expression experiment. For example, four constructs, each containing an affinity tag with a varying cleavage site can be used and four different trials can be carried out simultaneously in one experiment and therefore greatly increases protein expression and screening efficiency.

The vectors and methods of the present invention also allow for the use of different antibiotic resistance encoding vectors in addition to the Ampicillin resistance encoding pDEST vectors currently in use. Furthermore, the vectors and methods of the present invention allow for the co-expression of soluble multiple-protein complexes and for RNAi studies of certain organisms where many genes are turned on/off simultaneously. The vectors and method of the present invention will facilitate large scale operations in protein production. The vectors and method of the present invention provide for the co-expression of stable protein complexes. The vectors and method of the present invention may be used for the co-expression of endogenous and/or exogenous proteins. The vectors and method of the present invention may be used for the expression of secreted, intracellular and/or periplasmic polypeptides.

The vectors and methods of the present invention also allow for parallel gene expression and target salvaging at the gene level. Recombinant expression is a technique of choice for the synthesis of proteins of interest for structural genomics ("SG") studies. However, based on the recent structural genomics initiatives' data, less than one half of attempted open reading frames are expressed solubly and a fraction of these actually become structures (Liu et al., Acta Crystallogr D Biol Crystallogr 61(Pt 6):679-84, 2005). The total cost and speed of the structural determinations can be deciding factors in efficiency of SG studies. When a protein does not express, or is expressed, but insoluble, using the standard recombinant protocols, then multiple approaches have to be attempted, including co-expression with potential partners (Shen et al., Proteome Sci, 3(1):3, 2005). Proteins in their native environment exist as part of complexes, bound by other, specific proteins with weak, non-covalent interactions (Sorensen and Mortensen, J Biotechnol 115(2):113-28, 2005). Soluble proteins have been shown to solubilize other, previously insoluble, proteins (Sorensen and Mortensen, J Biotechnol 115(2):113-28, 2005). The vectors and methods of the present invention allow for screening multiple proteins (and their interactions) in the same cell and can be used to facilitate the expression of proteins that are known essential parts of a stable protein-complex and to individual, non-interacting proteins.

Since many proteins are tightly bound subunits of multi-protein complexes in vivo (Wang and Chong, Proc Natl Acad Sci USA 100:478-483, 2003) co-expression of multiple target proteins is a tool for successful heterologous protein expression. It has been shown for genes that are in a stable complex in the native host, that co-expression can improve their solubility and expression yield (Bernard and Couturier, Mol. Gen. Genet. 226:297-304, 1991; Li et al., Proc Natl Acad Sci USA 94:2278-2283, 1997; and Henricksen et al., J Biol Chem, 269:11121-11132 1994). Using the vectors and methods of the present invention, genes may be co-expressed either on the same expression vector from the same promoter, or using multiple, compatible vectors each containing one target gene.

The polynucleotides and vectors of the present invention can be used in methods to perform rapid and convenient construction of many different types of expression clones carrying multiple cDNAs on a single vector for their simultaneous introduction into cells.

The polynucleotides and vectors of the present invention can be used in methods of co-expression that allow for the parallel expression of multiple proteins that are essential subunits of stable protein complexes. In most of these protein partners are difficult to identify, and once they are known, other questions arise, which requires the creation of new constructs and attempting new complexes. Addressing such question using conventional technologies is laborious and time consuming. The vectors and methods of the present invention allow such questions to be addressed in a single reaction. With the vectors and methods of the present invention, one can mix and match any proteins in a potential complex easily in hours not weeks.

Many, if not most proteins in living cells exist as part of complexes, bound by a large number of weak, non-covalent interactions. The expression of a protein in the absence of a partner protein required for it to fold properly, or for stabilization, will in most cases lead to an insoluble (incorrectly folded) product, or degradation of the target protein by the cell's normal recycling systems. The vectors and methods of the present invention provide for parallel expression of multiple proteins that form a soluble and stable complex.

The vectors and methods of the present invention may be used to simultaneously and stoichiometrically introduce multiple heterologous genes into a single living cell and has many applications in proteomic research. For example, the vectors and methods of the present invention may be in used in study of pathways, cascades, multi-unit functional protein complexes, receptor-ligand interactions and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

Vectors for High Throughput (HTP) Recombinant Co-Expression of Genes in *E. coli*

To develop vectors for use in high-throughput co-expression methods, various commercially available co-expression vectors were modified to make them compatible for use in the Gateway® system, marketed by Invitrogen. The nucleic acid sequences encompassing the att recombination sites of the Gateway® system were transferred into each of the commercially available co-expression vectors pCDF-1b (Novagen catalog no. 71330-3), pRSF-1b (Novagen catalog no. 1363-3), and pACYCDuet™-1 (Novagen catalog no. 71147-3). The new vector constructs are called pDEST-C1, pDEST-C2, and pDEST-C3, respectively. The development of the pDEST-C3 vector is discussed in more detail in Example 2. The nucleotide sequence of vectors obtained from Novagen and Invitrogen is available online, for example at invitrogen.com and novagen.com.

Invitrogen's Gateway® technology allows one to quickly shuttle a cloned insert between various vectors systems, such as cloning vectors and expression vectors. The Gateway® system utilizes phage lambda site-specific att recombination sites to make cloning simpler, more specific, and faster in comparison to traditional methods utilizing restriction enzyme digestion and ligation. As marketed, the Gateway® system is suitable for the expression of only single proteins, not the co-expression of multiple proteins. The nucleic acid sequence encompassing the att recombination site is also referred to as the Gateway® cloning cassette and includes the two recombination recognitions sequences, a gene encoding chloramphenicol resistance, and the ccdB gene.

A commercially available Gateway® conversion kit (Invitrogen, catalog #118280) was used for the initial conversion of the pCDF-1b and pRSF-1b vectors to derive the pDEST-C1 and pDEST-C2 vectors. Development of the pDEST-C3 vector required a modification of the commercially available Gateway® cassette, replacing a chloramphenicol resistance gene with a gene encoding zeocin resistance. This modified cassette, called the G144704 cassette, is discussed in more detail in Example 2.

The Gateway® conversion kit includes three different versions of the Gateway® cassette, representing reading frame A, reading frame B, and reading Frame C.1 (see FIG. 1). Gateway® cassette reading frame B was used in the construction of the pDEST-C1, pDEST-C2, and pDEST-C3 vectors. FIG. 1 presents the locations of the attR1 site, attR2 site, chloramphenicol resistance gene, ccdB gene and Prime 1 and Primer 2 for Gateway Conversion Cassettes for Reading Frame A, Reading Frame B and Reading Frame C.1. Procedures were as described in more detail in Invitrogen Life Technologies Instruction Manual Gateway® Vector Conversion System with One Shot® ccdB Survival™ Competent Cells (Catalog no. 11828-029, Version A, 14 Jun. 2004, 25-0748, Invitrogen Life Technologies).

The PshAI restriction site present in both the pCDF-1b and pRSF-1b vectors was used for the insertion of the Gateway® cassette. The restriction enzyme PshA1 recognizes the nucleotide sequence GACNN|NNGTC (SEQ ID NO: 38). For the pDEST-C1 vector, the PshA1 recognition sequence in the pCDF-1b vector is 5'-GACAA|GAGTC-3' (SEQ ID NO: 39) and the resultant sequence after the insertion of the Gateway cassette is 5'-GACAAATCAAC . . . GTTGATGAGTC-3' (SEQ ID NOS 40 and 41). For the pDEST-C2 vector, the PshA1 recognition sequence in the pRSF-1b vector is 5'-GACAA|GAGTC-3' (SEQ ID NO: 39) and the resultant sequence after the insertion of the Gateway cassette is 5'-GACAAGAGCTC . . . AAGCTTGAGTC-3' (SEQ ID NOS 42 and 43).

The pDEST-C1 vector was selected for by growth of on streptomycin and chloramphenicol. The pDEST-C2 vector was selected for by growth on kanamycin and chloramphenicol. The orientation of the insert was verified by digestion with PstI. A proper insert results in a PstI fragment of about 500 basepairs on an agarose gel. Plasmids showing the correct digestion pattern on an agarose gel were sequenced to ensure that the destination vector was created in the proper reading frame.

FIG. 2 is a map of the pDEST-C1 vector. FIG. 3 presents the nucleotide sequence of the pDEST-C1 vector. FIG. 4 is a map of the pDEST-C2 vector. FIG. 5 presents the nucleotide sequence of the pDEST-C2 vector.

Example 2

A Zeocin Resistant Gateway Technology Cassette

Currently available co-expression vectors do not include a vector with resistance to the antibiotic zeocin as a selectable marker. In this example, a co-expression vector containing both the Gateway® cloning cassette and zeocin resistance was created by replacing the chloramphenicol gene within a Gateways cassette with the gene encoding zeocin resistance. The resultant modified Gateway® cassette is called the G144704 Zeocin resistant Gateway® Cassette. The G144704 Zeocin resistant Gateway® Cassette was inserted into Novagen's pACYCDuet™-1 expression vector. The resultant zeomycin resistant co-expression vector was named pDEST-C3. FIG. 6 is a map of the pDEST-C3 vector. FIG. 7 presents the nucleotide sequence of the pDEST-C3 vector.

Figure 8:
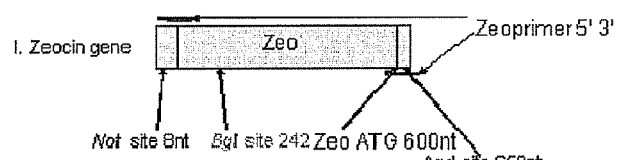
FIGS. 8A-8D show maps of the zeomycin gene, the Gateway cassette, and the G144704 cassette.
Figure 8:
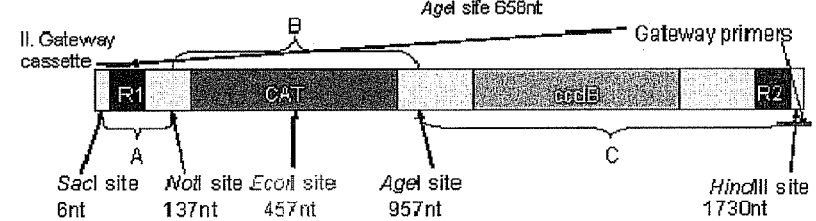
Figure 8:
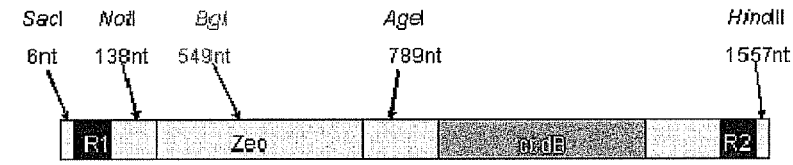
Figure 8:
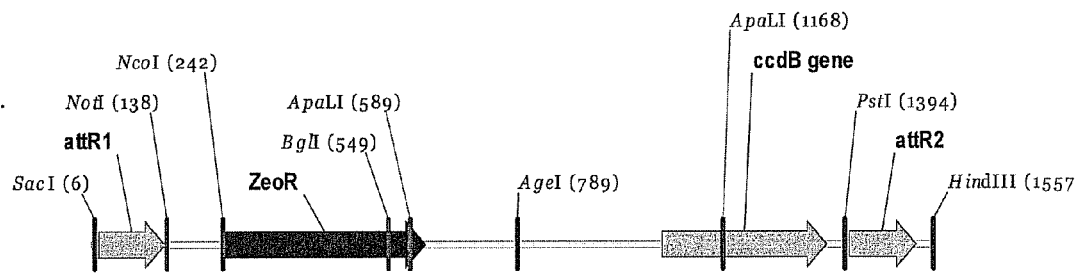

The gene encoding zeocin resistance, shown in FIG. 8A, was obtained from the pDONR-Zeo vector (Invitrogen catalog no. 12535-035). The nucleotide sequence of the pDONOR-Zeo vector is available online at novagen.com.

Zeocin is an antibiotic that is an effective selection reagent in E. coli (Drocourt et al., Nucleic Acids Res. 18:4009, 1990). Analysis of the commercially available pDONOR-Zeo vector sequence with the New England Biolab's NEBcutter software (Vincze et al., Nucleic Acids Res. 31:3688-3691, 2003) identified the 510 nucleotide long zeomycin gene and upstream regulatory sequences of approximately 58 nucleotides (FIG. 8A). This sequence is cut by the restriction enzyme BglI at nucleotide 242. A set of primers was designed for amplification of this region by PCR which also contained a 5' NotI site and a 3' AgeI site (restriction enzymes that flank the CAT gene within a Gateway cassette (see FIG. 8B). The 5' Zeocin gene primer used was 5'-GTT TCT TGC GGC CGC CAC GTT AAG GGA ITT TGG TCA-3' (SEQ ID NO: 24) and the 3' Zeocin gene primer used was 5'-GTT TCT TAC CGG TGT TGC AAC GAA CAG GTC ACT-3' (SEQ ID NO: n.

The expression vector pDEST160 (Invitrogen) was used as the source for the Gateway DNA sequences (FIG. 8B) for amplification by PCR. The sequence was analyzed for restriction enzyme recognition sites. The enzymes SacI and HindIII, on the 5' and 3' ends, respectively, where identified as restriction enzymes that do not cut within the cassette and, thus, allow the cloning of the cassette into the new expression vector pACYC (Novagen, San Diego, Calif.). The restriction enzymes NotI and AgeI were selected as enzymes that cut the cassette at specific locations, allowing for the removal of the CAT gene from the Gateway cassette and replacement with the Zeo gene.

Polymerase chain reaction (PCR) was used to amplify this template. Primers used in the amplification of the Gateway cassette were designed with SacI and HindIII sites on the 5' and 3' ends, respectively. The Gateway cassette 5' primer was 5'-GTT TCT TGA GCT CGAT CAC AAG TTT GTA CAA AAA AGC-3' (SEQ ID NO: 26) and the Gateway cassette 3' primer was 5'-GTT TCT TAA GCT TAG CAG CCG GAT CTG ATC TTA-3' (SEQ ID NO: 27).

After PCR amplification of both the Gateway cassette, the resultant PCR products were digested with the enzymes indicated in FIG. 8B by the enzymes SacI and HindIII. The cassette had to be further digested with the restriction enzyme EcoRI, as fragments B and C in FIG. 8B are indistinguishable on a gel with sizes 820 and 773 nucleotides, respectively. Cutting fragment B with EcoRI, into a 500 nucleotide and a 320 nucleotide fragment, facilitated the accurate identification and isolation of fragments A and C. Fragment A and Fragment C were purified from agarose gels using standard techniques (see, for example, Sambrook et al., *Molecular Cloning: A Laboratory Manual*, Cold Spring Harbor Laboratory Press, 1989).

Fragment A and Fragment C (FIG. 8B) along with the digested Zeo PCR product were purified and mixed with the vector pACYC (digested with SacI and HindIII and gel-purified) and T4 DNA ligase. The ligation reaction was incubated overnight at 13° C. and transformed into a strain of *E. coli* called ccdB survival cells on plates containing both zeocin and chloramphenicol. Colonies were picked and grown up for plasmid DNA isolation. Each of the plasmids were digested with SacI, HindIII and BglI, since BglI cuts the Zeo gene, but it does not cut the commercially available Gateway cassette or pACYC. SacI and HindIII separate the plasmid and the newly inserted fragment. The correct digestion pattern as well, as correct molecular weight, were observed on agarose gel, confirming success of the new construct.

FIG. 8A shows a schematic of the cassette modification. Each site is labeled with the nucleotide number where the respective sites end. FIG. 8A shows the Zeocin gene as amplified for this experiment containing all regulatory regions. FIG. 8B shows the original Gateway cassette as amplified for this experiment. FIGS. 8C and 8D show the G144704 cassette. The G144704 cassette is also referred to herein "GatewayZeoPH." The strategy discussed above will be used to create additional co-expression vectors encoding tetracycline resistance. In FIG. 8B, the capital letters A, B, and C represent the three fragments of the original Gateway cassette when cleaved by enzymes listed in black. Fragments A and C are retained throughout the experiments. R1 and R2 represent the attR1 attR2 sites respectively. Each of the genes are represented by the following abbreviations: Zeo, zeocin resistance gene; CAT, chloramphenicol acetyl transferase (chloramphenicol resistance gene); ccdB, encodes a protein that stabilizes gyrase covalent intermediates and is lethal for E. coli cells not containing the ccdA gene (Bernard and Couturier, Mol. Gen. Genet. 226:297-304, 1991; and Salmon et al., Mol. Gen. Genet. 244:530-538, 1994).

Sequencing of the three plasmid clones confirmed the construct. The sequence of the G144704 cassette is shown in FIG. 9. Both the orientation and DNA sequence of the new cassette has been confirmed by DNA sequencing. This plasmid was designated pDEST-C3. Using the new destination vector pDEST-C3, a number of genes have been tested for expression of the correct molecular weight proteins.

The plasmid pDEST-C3 was then utilized in a L/R recombination reaction to test that the recombination sites were intact and that genes could be cloned into the Gateway R1 R2 cassette. The efficiency of the reaction was not affected by the insertion of the Zeocin gene between the recombination sites. To date, six different genes have been tested for expression of the correct molecular weight proteins using this destination vector.

The pDEST-C3 vector, along with the pDEST-C1 and pDEST-C2 vectors described in Example 1, are three new Gateway® compatible expression/destination vectors that, when used in combination with one of the many currently available co-expression vectors allows for the expression in a parallel manner up to four genes. Each of the pDEST-C1, pDEST-C2, and pDEST-C3 vectors can also be used individually, as a conventional expression vector. Each of the vectors can be maintained individually. Each of these vectors can be further modified to include various fusion tags/proteins, protease cleavage sites, expression signals. The plasmids presently have an N-terminal 6xHis tag and pDEST-C1 and pDEST-C2 have an enterokinase cleavage site just before the attR1 recombination site.

Example 3

Expression of Son Proteins

The vectors of the present invention were used to simultaneously express various Shewanella oneidensis ("Son") polypeptides; Son-3961, Son-0433, Son-1358, Son-1350, and Son-2015. The Son-3961 polypeptide was expressed in the pDEST-15G vector; Son-0433 polypeptide was expressed in the pDEST-C3 vector; Son-1358 polypeptide was expressed in the pDEST-C2 vector; Son-1350 polypeptide was expressed in the pDEST-C1 vector; and Son-2015 was expressed in the pDEST-15 vector.

Figure 10:
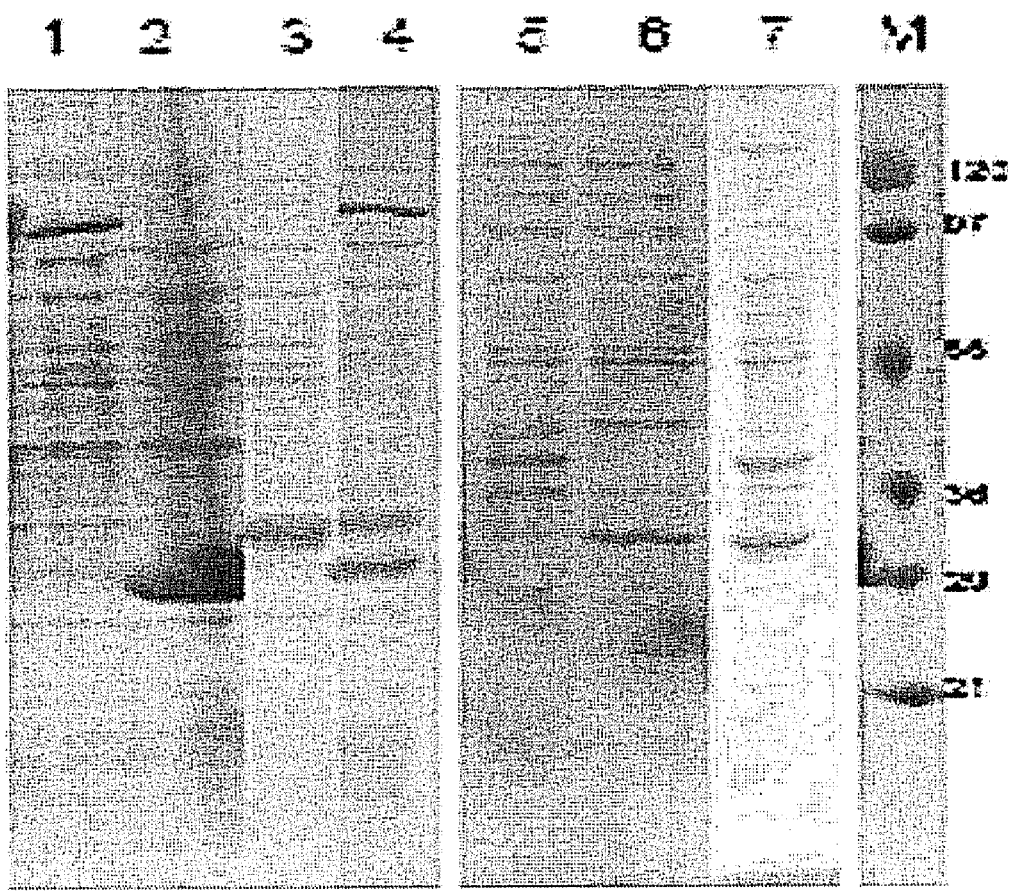
FIG. 10 show a SDS-PAGE demonstrating expression of various *Shewanella oneidensis* ("Son") polypeptides. Lane 1 shows expression of Son-3961. Lane 2 shows expression of Son-0433. Lane 3 shows expression of Son-1358. Lane 4 shows parallel expression of Son-3961, Son-0433 and Son-1358. Lane 5 shows expression of Son-1350. Lane 6 shows expression of Son-2015. Lane 7 shows parallel expression of Son-1350 and Son-2015. Lane "M" is molecular weight markers.

The respective plasmids were transformed into BL21 (DE3) cells (Stratagene, La Jolla, Calif.) and the cells were grown in LB media and induced with 1 mM IPTG at OD of 0.6. The cells were then allowed to grow for four hours. Cells were harvested by spinning at 13,000 RPM for 1 minute and the resulting pellet was then run on an SDS-PAGE gel. The results are shown in FIG. 10. Lane 1 shows the expression of Son-3961. Lane 2 shows the expression of Son-0433. Lane 3 shows the expression of Son-1358. Lane 4 shows the parallel expression of Son-3961, Son-0433 and Son-1358. Lane 5 shows the expression of Son-1350. Lane 6 shows expression of Son-2015. Each of the four constructs created contains an affinity tag with varying cleavage sites. Thus, up to four different trials (see FIG. 10, lanes 4 and 7) can be carried out simultaneously in one experiment and therefore may greatly increase protein expression and screening efficiency.

Example 4

Expression of Clostrodium thermocellum JW-20 Polypeptides

Materials and Methods

For expression studies, genes cloned lab from the organism Clostrodium thermocellum JW-20 were expressed using the pDEST-C1, pDEST-C2, and pDEST-C3 vectors. Entry vectors were created with the use of pDONR-221 (kanamycin resistance) or pDONR-Zeo (Zeocin® resistance). The L/R recombination reaction was used to insert six genes into the R1-R2 sites of each of the vectors. These individual vectors were then transformed into Mach-1 E. coli cells (Invitrogen). After plasmid DNA was purified and the size of the DNA was confirmed by agarose gel electrophoresis, E. coli BL21 (DE3) cells were transformed with each of the vectors at the same time and plated on media supplemented with the appropriate antibiotics. These gene targets were chosen as proteins which had been expressed and purified successfully in earlier experiments. They were grown in one milliliter small scale test cultures overnight in LB medium. The cells were then induced with 2 mM IPTG for 5 five hours and the total cell and soluble fractions, where applicable were run on a gel. Soluble fraction of cells was achieved by incubating the cell pellet with five mg/ml lysozyme for fifteen minutes at room temperature.

Figure 12:
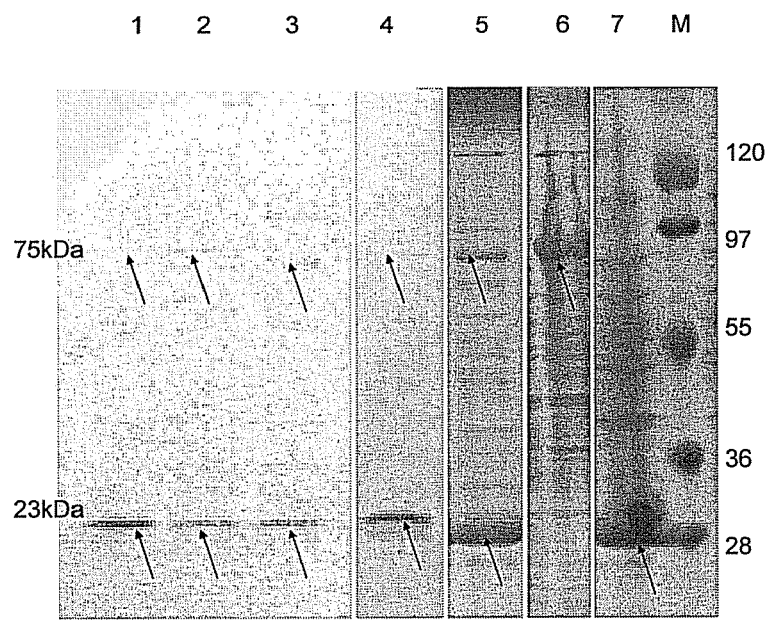
FIG. 12 shows the co-expression of a stable protein complex for Son0433 and Son1284. Lanes 1-3 show consecutive fractions from gel-filtration. Lane 4 shows the elution from the NiNTA, 6×HIS affinity column. Lanes 5-7 show total cell extracts; Lane 5 shows the co-expression of Son0433 and Son1284; Lanes 7 and 6 show the single expression experiments of Son0433 and Son1284, respectively.

For studies on the purification of protein complexes, cloned genes from the organism Shewanella oneidensis (Son) were provided Dr. Jizhong Zhou from Oak Ridge National Labs. The genes Son0433 (also called Regulator of Sigma Factor D) and Son1284 (also called Sigma Factor D) were cloned into pDEST 221. These clones were then inserted into each of the vectors (Son1284 into pDEST-C3 and Son 0433 into DEST C1) and the colonies were grown in defined PA 0.56 media overnight. These two proteins (Son0433 and Son 1284) were identified as a complex by Database of Interacting Proteins. These cultures were then inoculated into 5 L of PASM 5052 media that is self inducing and was labeled with Seleno-Methionine. The cultured were grown at 30 degrees Celsius for sixteen hours. The cells were harvested by centrifugation and the cells were lysed by sonication in 50 mM HEPES buffer pH 7.6/500 mM NaCl. Both of the proteins were purified by their individual 6xHIS tags, in the same solution by one step elution with 400 mM imidazole. The eluted sample was then passed through a Superdex 75 column in 10 mM NaCl, 50 mM HEPES pH 7.6, 1 mM DTT. FIG. 12 shows the fractions from the purification, showing that the proteins formed a complex.

mRNA detection. E. coli BL21(DE3) cells containing the gene Pfu-89099 cloned into the entry clones pDEST-C1, pDEST-C2, pDEST-C3 and pET15G were grown overnight with the appropriate antibiotics and induced with 3 mM IPTG for six hours. Total RNA was isolated with the RNeasy kit from Qiagen (Valencia, Calif.) and was run on a 1.0% agarose gel. The amount of RNA was quantitated with the intensity of the band detected in the gel.

Results

Compatibility with existing system. The new vectors pDEST-C1, pDEST-C2, and pDEST-C3 are compatible with the existing Gateway cloning system via the well-known L/R reaction. The efficiency of the reaction was not affected by the insertion of the zeocin gene between the recombination sites. The proteins expressed are all the correct molecular weight with 2 shown in experiments below. Both the orientation and DNA sequence of the new cassette has been confirmed by DNA sequencing. The most widely used entry vectors used today encode kanamycin resistance. If these vectors are used, they can make the isolation of correct destination vectors from the L/R reaction with pDEST-C2 difficult and not HTP. The use of pDONR-Zeo is recommended for the use of these vectors, since other antibiotic resistance markers can interfere with the cloning into any of the four vectors.

Parallel screening of genes. In the 2×2×2 matrix shown in FIG. 11, all of the genes made their predicted protein product. The expression of two vectors at the same time is cost effective and convenient. With transformation of the third and fourth vectors, a reduced antibiotic concentration resulted in improved DNA quality. There is no apparent difference in growth rate when using any combination of the vectors used. The proteins are expressed in a similar manner in all cases, but the amount of the protein made is different in each case.

Figure 11:
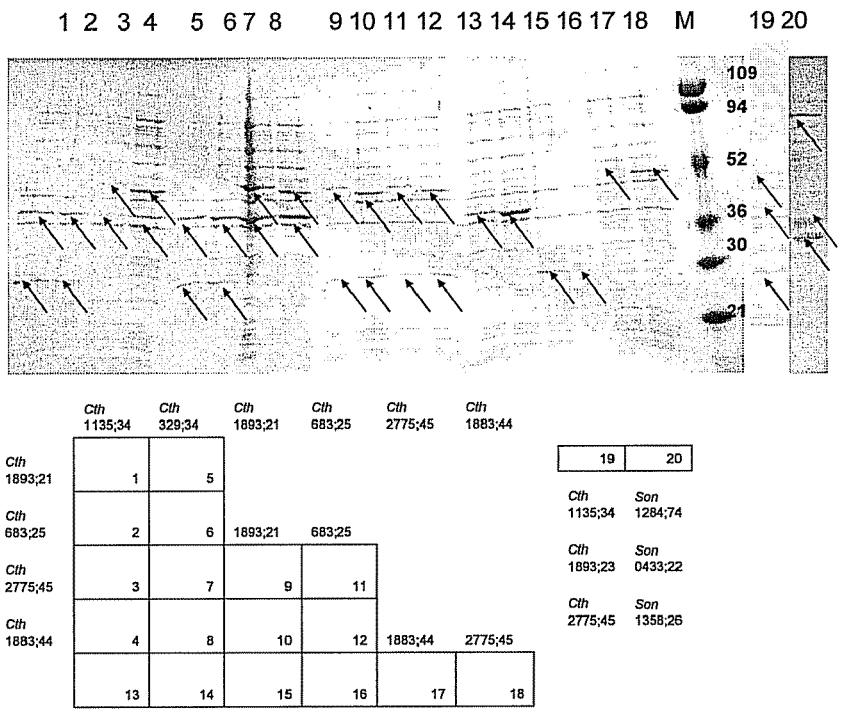
FIG. 11 shows the co-expression of *Clostrodium thermocellum* JW-20 gene construct in pDEST-C1-C3 vectors. The top is an SDS-PAGE of the total cell extract of the recombinant expression experiments for each *Clostrodium thermocellum* JW-20 gene construct. The black arrows point to the bands that correspond to the proteins expressed in the cells. The bottom is a chart identifying each of the lanes. Lanes 1 through 12 are cells with two different, randomly selected, genes expressed. Lanes 13-18 are the expression testing of those cells with only one expression construct, to monitor expression of the individual proteins. Lanes 19 and 20 show expression of three non-interacting proteins.

Each vector/protein construct was also expressed individually (FIG. 11). All individual expression experiments show expression of the proteins in a similar way as the parallel expression studies. This shows that our system is compatible with the previously established Gateway® system.

FIG. 11A is an SDS-PAGE of the total cell extract for each *Clostrodium thermocellum* JW-20 gene construct. The black arrows point to the bands that correspond to the proteins expressed in the cells. FIG. 11B is a chart identifying each of the lanes. Lanes 1 through 12 are cells with two different, randomly selected, genes expressed. Lanes 13-18 are the expression testing of those cells with only one expression construct, to monitor expression of the individual proteins. Lanes 19 and 20 are the two lanes, where three non-interacting proteins are expressed.

Parallel expression for purification. The experiments illustrate that the expression system can produce the desired protein. The data shows that varying combinations of ORFs can be expressed in parallel, in the same cell, without inhibiting each others' expression. Since these proteins are also soluble as observed during single expression experiments, the purification of all of the soluble proteins is possible, especially if the proteins expressed together have large difference in molecular weight, or only three vectors are used together. pDEST-C1 and pDEST-C2 contain an enterokinase cleavage site which can also be used for cleavage of the tag, while pDEST-C3 does not. All Gateway® compatible clones in our collection have a Tobacco Etch Virus (TEV) protease cleavage site between the gene and the recombination sequence for a final processing step. This ensures that the protein attempted for crystallization will have the native sequence, without any extra amino acids. All constructs are optimized for structural biological experiments, so when the protein is fully processed only 2 N-terminal glycines are extra to the native sequence.

Co-expression of a stable protein complex. Gateway® compatible HTP protein complex expression is the power of the present invention. Expressing more than one protein at the same time to form a stable protein complex is shown in this example. When the newly developed co-expression or parallel expression system is used, these experiments now can be carried out in a HTP manner, or with the use of all of the resources available with Gateway® compatible clones. The two genes used in here, Son0433 (Regulator of Sigma Factor D (rsd)) and Son 1284 (Sigma Factor D (rpoD)), were co-expressed in culture and they co-purified in gel filtration, in the same fraction. The proteins expressed separately before the co-expression studies and the total yield of protein during co-expression was comparable, although the expression level of Son0433 was slightly affected (see a comparison of lanes 5, 6, and 7 in FIG. 12). The expression level for Son 1284 seemed to have decreased in this case. The interaction between these two proteins was not investigated. The separation of the two proteins was not possible in this co-expression experiment, due to their seemingly stable interaction with each other. Only the smaller molecular weight protein (Son 0433), due to its excess concentration compared to (Son 1284) could be isolated from the mixture, by filtering the solution through a 50 kDa MW cutoff concentrator.

FIG. 12 shows the co-expression of a stable protein complex. Proteases were a problem with rpoD; the effect of proteolysis on rpoD can be seen in lane 3 of FIG. 12. Lanes 1-3 of FIG. 12 were the consecutive fractions from gel-filtration through a Superdex 75 (Amersham, Piscataway, N.J.). Lane 4 of FIG. 12 is the elution from the NiNTA, 6×HIS affinity column. Lanes 5 through 7 are the total cell gels, with Lane 5 showing the co-expression of Son0433 and Son1284. Lanes 7 and 6 are the single expression experiments of Son0433 and Son1284 respectively. These results for the Son0433 and Son1284 proteins are also shown in lanes 1-4 of FIG. 10.

This example facilitates the parallel expression of proteins that are essential parts of a stable protein complex. In most of these protein partners are difficult to identify, and once they are known, other questions arise, which requires the creation of new constructs and new complexes. These second set of experiments, or sub-cloning, used to be laborious and time consuming. The true power of this system lies here, since with these novel vectors, scientists now can mix and match any proteins in a potential complex easily in hours not weeks. The parallel expression testing or the parallel expression of non-interacting proteins is an added benefit, which was not anticipated. Beyond those benefits already listed, some of the other potentials of this system is that the use of expression vectors that encode for antibiotics other than ampicillin are preferred for protein expression, especially when the cells have to be grown for long times, for increased time of induction. With the vectors of the present invention, a drastic reduction of cell mass is observed, when compared to non-ampicillin resistance encoding vectors in defined media. The effects of defined media on the expression is important, since labeling of each protein with seleno-methionine allows for the HTP structure determination of each protein. Using currently available vectors in concert with the vectors of the present example, the amount of cells has increased.

Example 5

Parallel Gene Expression and Target Salvaging at Gene Level

This example demonstrates that three Gateway® compatible coexpression vectors, pDEST-C1, pDEST-C2, and pDEST-C3, when used together, along with a commercially available expression vector, in the same cell, can express in a parallel manner up to four ORFs.

Materials and Methods

Expression testing. The genes for all ORFs shown were cloned from the organism *Clostrodium thermocellum* JW-20. Entry vectors were created with the use of pDONR-221 (kanamycin resistance) or pDONR-Zeo (Zeocin® resistance). The L/R recombination reaction was used to insert six ORFs into the R1-R2 sites of each of the vectors. These individual vectors were then transformed into Mach-1 *E. coli* cells (Invitrogen). After plasmid DNA was purified the size of the DNA was confirmed by agarose gel electrophoresis and *E. coli* BL21 (DE3) cells were transformed with each of the vectors at the same time and plated on media supplemented with the appropriate antibiotics. These ORFs were chosen randomly from proteins that had been expressed and purified successfully in earlier experiments. They were grown in one milliliter small scale test cultures overnight in LB medium. The cells were then induced with 2 mM IPTG for five hours and the total cell and soluble fractions, where applicable were run on a gel. Soluble fraction of cells was achieved by incubating the cell pellet with five mg/ml lysozyme for fifteen minutes at room temperature.

Solubilization and Purification of a protein complex. The human Plasma Membrane Calcium ATPase C-terminal tail was cloned by Hua Yang. This ninety amino acid 10.5 kDa protein was truncated to amino acid 1055 through 1142. This construct was predicted to have secondary structure by JPRED (Cuff et al., Bioinformatics 14:892-3, 1998). The PCR product was cloned into pDONR-Zeo vector. The hPMCA construct was then inserted into pDEST-C1. The Calmodulin construct was supplied by Dr. Jeffrey Urbauer in a pET 15 plasmid. The two vectors were then co-transformed into BL21-DE3 cells. These cultures were then inoculated into five liters of PASM 5052 media, a self inducing media labeled with seleno-methionine. The cultures were grown at 30° C. for sixteen hours. The cells were harvested by centrifugation at 4000 g and were lysed by sonication in 50 mM HEPES buffer pH 7.6 500 mM NaCl. Both of the proteins were purified by their individual 6×HIS tags, in the same solution by one step elution with 400 mM imidazole. The eluted sample was then passed through a Superdex 75 column in 100 mM NaCl, 50 mM HEPES pH 7.6, 1 mM DTT.

Results

Compatibility with existing system. The new vectors pDEST-Cx described here are compatible with the existing Gateway® cloning system via the well-known L/R reaction. The efficiency of the reaction was not noticeably affected by the insertion of the Zeocin® gene between the recombination sites. The proteins expressed are all the correct molecular weight. Both the orientation and DNA sequence of the new DESTination vectors has been confirmed by DNA sequencing. The most widely used entry vectors encode kanamycin resistance which is not productive when using the pDEST-C1-C3 vectors. The use of pDONR-Zeo is recommended use as a pDONR vector, since other antibiotic resistance markers can interfere with each of the four vectors.

Figure 13:
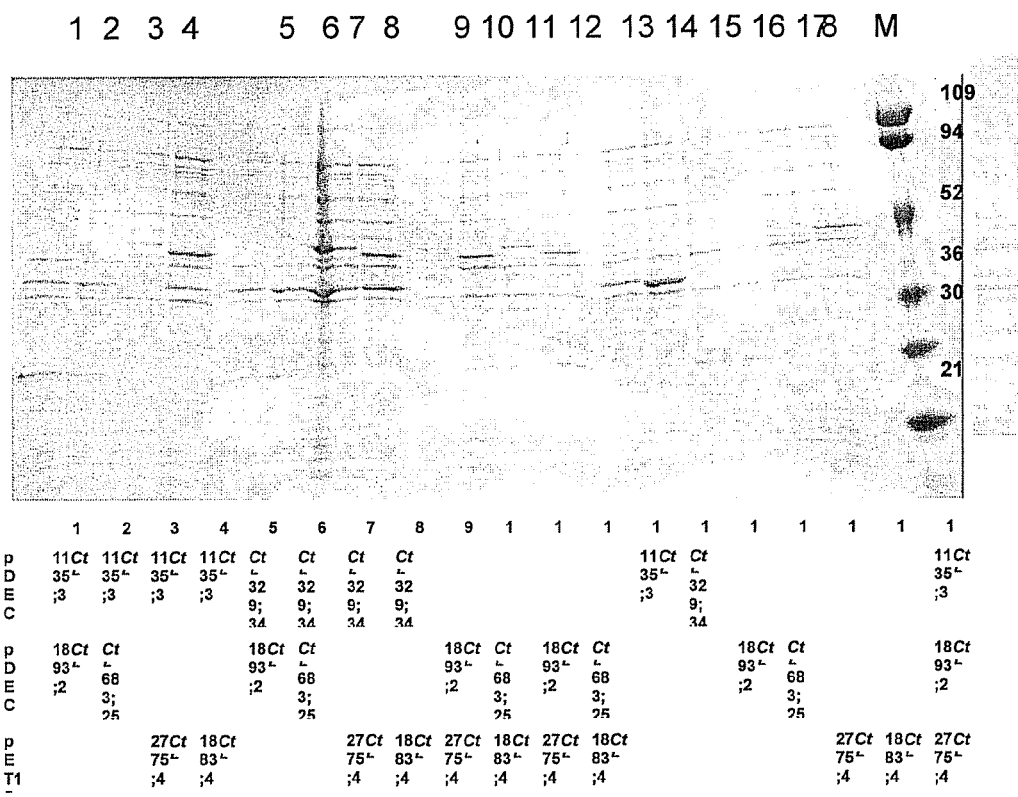
FIG. 13 shows parallel expression of non-interacting proteins in the same cell. Lanes 13-18 are the expression studies of single genes per cell. Lanes 1-12 are the expression tests of two genes per cell. Lane 19 is the parallel expression of three genes.

Parallel screening of genes. In the 2×2×2 matrix shown in FIG. 13, all of the genes made their predicted protein product. The expression of two vectors at the same time is the most cost effective and convenient method used here with cell yields similar as those cells expressing each construct individually. Transformation with the third and fourth vectors demonstrates a reduced success rate, but this can be overcome by reducing the concentration of the antibiotics. Nonetheless each non-interacting, co-expressed protein, was made in this system as they were when expressed individually FIG. 13. The same expression profile are seen for the co-expression of three proteins. The proteins were all known to be soluble prior to expression and the soluble cell fractions were loaded onto the gel in FIG. 13. FIG. 13 shows parallel expression of non-interacting proteins in the same cell. Lanes 13-18 are the expression studies of single genes per cell. Lanes 1-12 are the expression tests of 2 genes per cell. Lane 19 is the parallel expression of three genes. The results from this co-expression experiment are also presented in FIG. 11.

Figure 14:
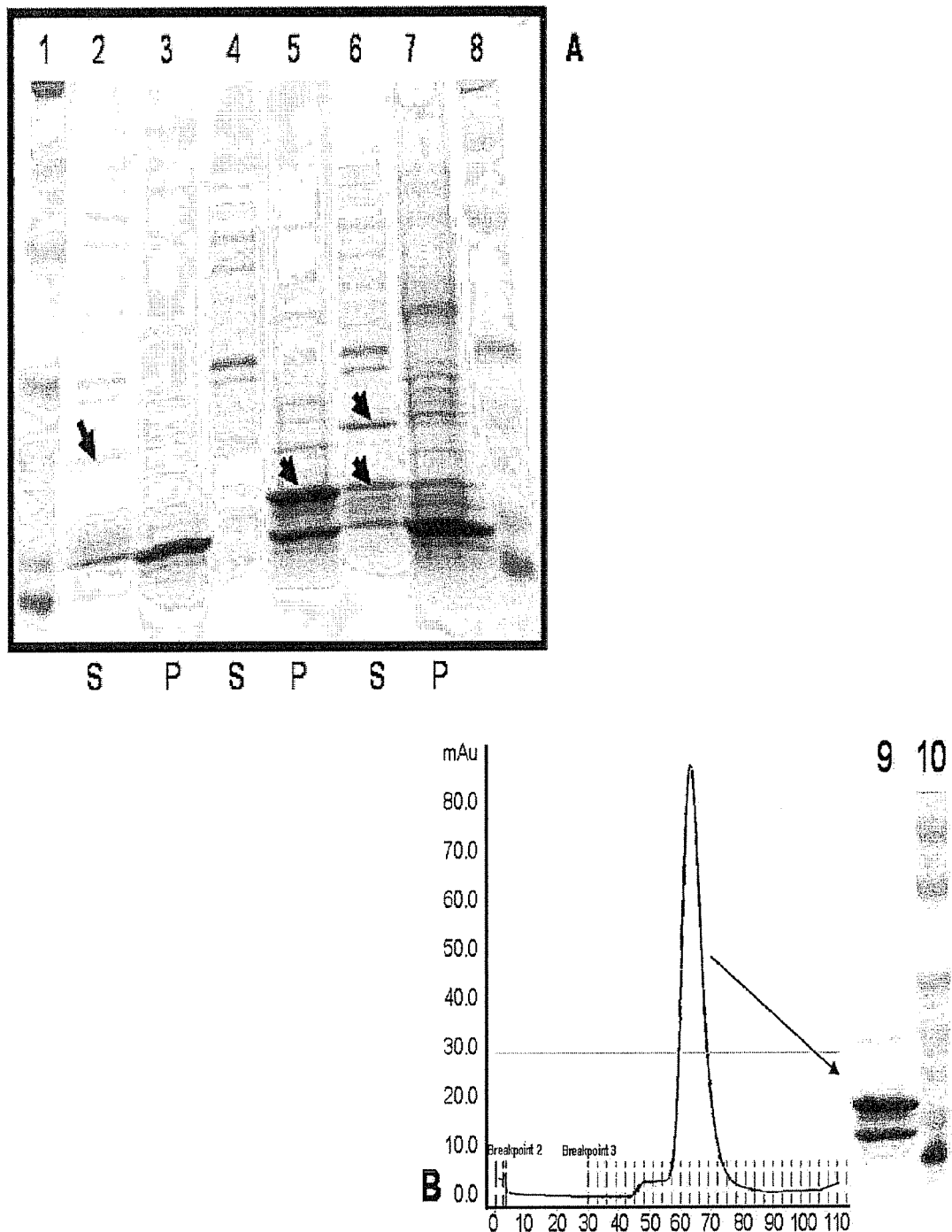
FIGS. 14A and 14B show improved recombinant protein solubility with co-expression of the two individual proteins, calmodulin and the human Plasma Membrane Calcium ATPase C-terminal calmodulin binding domain (hPMCA4b).

Improving protein solubility with co-expression of a protein complex. The protein complexes expressed are of greater use than just co-expression of already soluble proteins. Co-expression of previously insoluble protein with soluble, well expressing partner has been known to improve solubility. In this experiment, the insoluble human Plasma Membrane Calcium ATPase isoform 4b's (hPMCA4b) C-terminal tail was used as the insoluble protein. Previous work has shown that this part of the protein insoluble (see FIG. 13, lane 5) and it has been identified as the Calmodulin Binding Domain of the protein (Kessler et al., Biochemistry 31:11785-92, 1992). This insoluble protein was co-expressed, using our vectors, with Calmodulin, a soluble protein. These two proteins have been known to interact (Elshorst et al., Biochemistry 38:12320-32, 1999). Upon their co-expression, as shown in FIG. 14A, the two proteins are co-expressed and the previously insoluble C-terminal fragment of hPMCA4b is now soluble and in a complex with Calmodulin. This complex can also be purified together as shown by lane 9 of FIG. 14B.

Improving recombinant protein solubility with coexpression. The expression testing of the two individual proteins, calmodulin and the human Plasma Membrane Calcium ATPase C-terminal calmodulin binding domain (hPMCA4b) is shown in FIGS. 14A and 14B. The hPMCA protein was truncated for structural studies. The amino acids used here are from 1055 through 1145. This construct is the JPRED predicted structured part of the hPMCA (Cuff et al., Bioinformatics 14:892-3, 1998. In FIG. 14A, lanes 1 and 8 are the molecular weight markers; lanes 2, 4, and 6 are the three soluble fractions that represent calmodulin hPMCA4b and co-expression of the two, respectively; lanes 3, 5 and 7 are the pellet fractions of the same growths; lane 6 contains the soluble complex and this growth was further pursued to purification. FIG. 14B show the FPLC 280 nm chromatogram and the SDS-PAGE of the indicated fraction in lane 9 showing a complex of the two proteins. Lane 10 is the same marker as lanes 1 and 8 of FIG. 13.

The pDEST-C1, pDEST-C2, and pDEST-C3 coexpression vectors present at least five new innovations. One, all four of these constructs are created with the same reaction and plated on four different antibiotic supplemented plates. Two, each of these vectors can also be used by itself, which allows for their use as just a conventional expression vector. Three, increasing the throughput of expression screening by testing up to four non-interacting ORFs' expression/solubility in the same cells. Four, they are new tools for solubilizing proteins through soluble complex expression. And, five, HTP Expression of already known protein complexes. The use of parallel processing at the screening and expression level enables the structural genomics community to express, in an HTP manner, protein-protein complexes and cut costs by increasing expression efficiency of non-interacting soluble proteins.

Example 6

Copy Number and Increased Protein Solubility

Currently available recombinant protein expression system, based on very efficient and fast RNA polymerases, such as T7 polymerase, used in the DE3 cell lines are very powerful and widely used. However, the benefit of the increased efficiency with this expression system presents problems. The overabundance of the recombinant transcript causes the cells to translate the transcript faster than the protein can be folded. This folding inefficiency then interferes with soluble protein expression.

A solution for this problem with protein expression is to use the vectors of the present invention to manipulate the copy number of the vectors that encode the recombinant proteins. The vectors pDEST-C1, pDEST-C2, and pDEST-C3 have different replicons which results in different numbers of copies in the cell. This characteristic facilitates their use as co-expression vectors.

Previously, the protein PF1955 from the organism *Pyrococcus furiosus* was expressed and its structure determined. This effort took two years to accomplish, since the protein was not soluble. The vector pDEST527 was used to express this protein for refolding studies. The present example demonstrates that the PF1955 protein can be expressed in a complex or by itself, when using a vector with a lower copy number that that of pDEST527. The results are shown in FIG. 15, a SDS-PAGE gel of the expression experiment.

Figure 15:
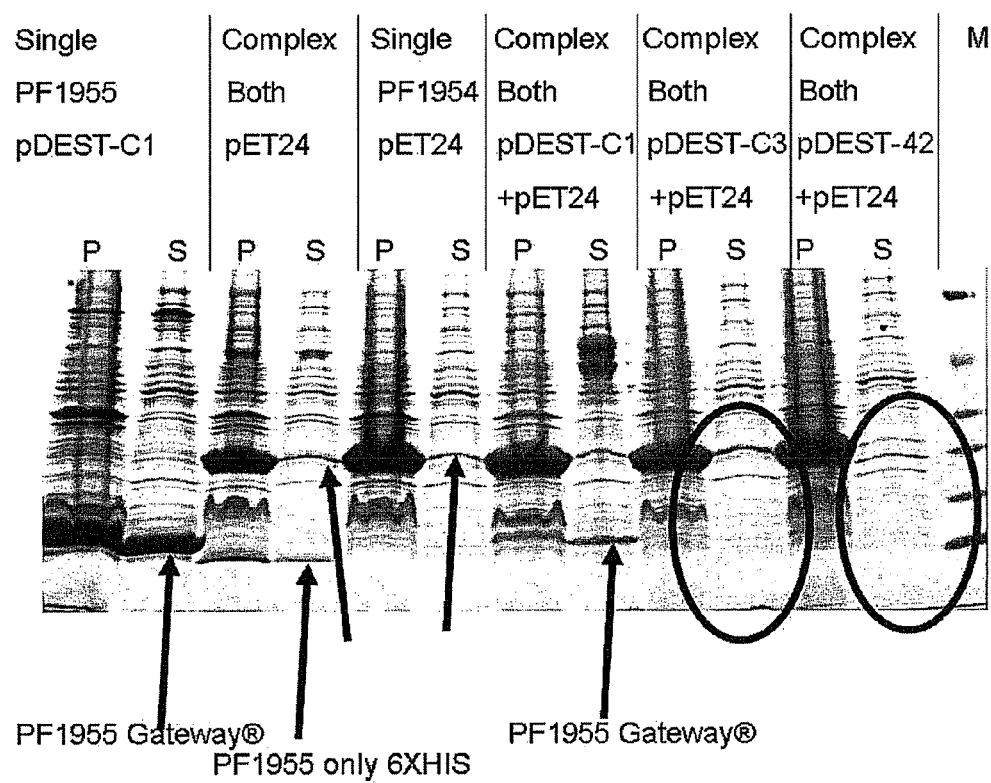
FIG. 15 is an SDS-PAGE gel showing expression of the PF194 and PF1955 proteins. Each pair of lanes shows total cell fraction ("P") and soluble ("S") fraction, side by side. "M" represents molecular size markers.

In FIG. 15, every pair of lanes show total cell fraction ("P") and soluble ("S") fraction side by side. Lanes 1 and 2 show expression of PF1955 protein in the vector pDEST-C1. Lanes 1 and 2 show that in the PF1955 protein is soluble when expressed in the pDEST-C1 vector. Lanes 3 and 4 of FIG. 15 show expression of the PF1955 and PF1954 proteins, each cloned into the pET24 vector. These two genes are structured in the same operon in the genome of *Pyrococcus furiosus*. Lanes 3 and 4 demonstrate expression of the complex using traditional methods of protein complex expression. Lanes 5 and 6 show expressions of the PF1954 protein in the pET24 vector. Lanes 7 and 8 show expression of the PF1955 protein in the pDEST-C1 vector and expression of the PF1954 protein in the pET24 vector. An expression pattern similar to the control was observed. Lanes 9 and 10 show expression of PF1955 protein in the pDEST-C3 vector and expression of the PF1954 protein in the pET24 vector. Little expression was observed. Lanes 11 and 12 show expression of the PF1955 protein in the pDEST42 vector and expression of the PF1954 protein in the pET24 vector. Both the plasmids have the same replicon, but different antibiotics resistances. These lanes show no expression of either protein from the complex, suggesting that plasmid copy number has an effect of recombinant protein expression. Lane "M" represents molecular size markers.

In the experiments of this example, the pDEST-527 vector has the 6HIS tag of Met R S G S H H H H H H R S D I T S L Y K K A E R E (SEQ ID NO: 28) while the pDEST-C1 vector has 6HIS tag of Met A H H H H H H V G T G S N D D D D K S T S L Y K K A E R E (SEQ ID NO: 29). The difference in HIS tags is five amino acids, encoding an enterokinase cleavage site. The pDEST-527 vector has a copy number of 40 copies per cell and the pDEST-C1 vector has a copy number of 20-40 copies per cell.

This example demonstrates that the use of an alternate copy number vector alone can improve solubility. This example also shows that different copy number plasmids, when used together, can efficiently form a complex of two proteins (PF1954 and PF1955) that interact on protein level.

Example 7 pDEST-CM Vectors

The additional vectors pDEST-CM1, pDEST-CM2, pDEST-CM3, and pDEST-CM4 were developed. To develop these vectors, the commercially available Multisite Gateway®. Three-Fragment cassette, pDEST R4-R3 (Invitrogen, catalog #12537-023) was introduced into the commercially available vectors pCDF-Duet1 (Novagen catalog #71340-3), pRSF-Duet1 (Novagen catalog #71341-3), pACYC-Duet1 (Novagen catalog #71147-3), and pET-Duet 1 (EMD Biosciences, catalog #71146-3). The nucleotide sequence of vectors obtained from Novagen and Invitrogen is available online, for example at invitrogen.com and novagen.com.

Modification of the pCDF-Duet1 vector resulted in the pDEST-CM1 vector. FIG. 16 shows a map of the pDEST-CM1 and FIG. 17 presents the nucleotide sequence of the pDEST-CM1 vector. pDEST-CM1 was created by amplifying the Gateway® Multisite cassette from pDESTR4-R3 and adding SacI and HindIII sites to the 5' and 3' ends, respectively. This construct was then ligated to similarly digested pCDF-Duet1, to create pDEST-CM1. The nucleotide sequence of the pCDF-Duet1 vector is available online, for example at novagen.com.

Modification of the pRSF-Duet1 vector resulted in the pDEST-CM2 vector. FIG. 18 shows a map of the pDESTCM-2 vector and FIG. 19 presents the nucleotide sequence of the pDEST-CM2 vector. pDEST-CM2 was created by amplifying the Gateway® Multisite cassette from pDESTR4-R3 and adding SacI and HindIII sites to the 5' and 3' ends, respectively. This construct was then ligated to similarly digested pRSF-Duet1, to create pDEST-CM1. The nucleotide sequence of the pRSF-Duet1 vector is available online, for example at novagen.com.

Modification of the pACYC-Duet1 vector resulted in the pDEST-CM3 vector. To construct the pDEST-CM3 vector, a tetracycline resistance multisite cassette (TetR multisite cassette) was first created by amplifying the multisite cassette from the pDEST R4-R3 vector by PCR with the same primers used for the creation of the pDEST-CM1, pDEST-CM2, and pDEST-CM4 vectors. The tetracycline resistance (TetR) gene was amplified from the plasmid pBR322 (Promega # D1511) using as a 5' primer: GTTTCTTGCGGCCGCTTCTCATGTTTGACAGCTTATCAT (SEQ ID NO: 30) (creating a recognition site for the restriction enzyme NotI) and as a 3' primer: GTTTCTTTCTAGAGACGCGATGGATATGTTCTG (SEQ ID NO: 31) (creating a recognition site for the restriction enzyme XbaI).

The two PCR reactions then were then cleaved with enzymes from New England Biolabs using standard protocols. The Multisite PCR product was digested with HindIII, SacI, NotI and XbaI, creating two fragments of interest; a 834 bp SacI-XbaI fragment and a 208 bp NotI-HindIII fragment. Fragments were gel purified using standard methods. The TetR gene PCR product was digested with NotI and XbaI and ligated to the two remaining fragments of the Multisite cassette, replacing the CamR gene with the TetR gene between the NotI and XbaI sites. This was simultaneously ligated to HindIII, SacI digested pACYCDuet-1 to create pDEST-CM3 (See FIG. 20). Note this cannot be moved out using EcoNI and HindIII as the other Multisite cassette constructs were made due to internal EcoNI and HindIII sites in this construct.

Figure 20:
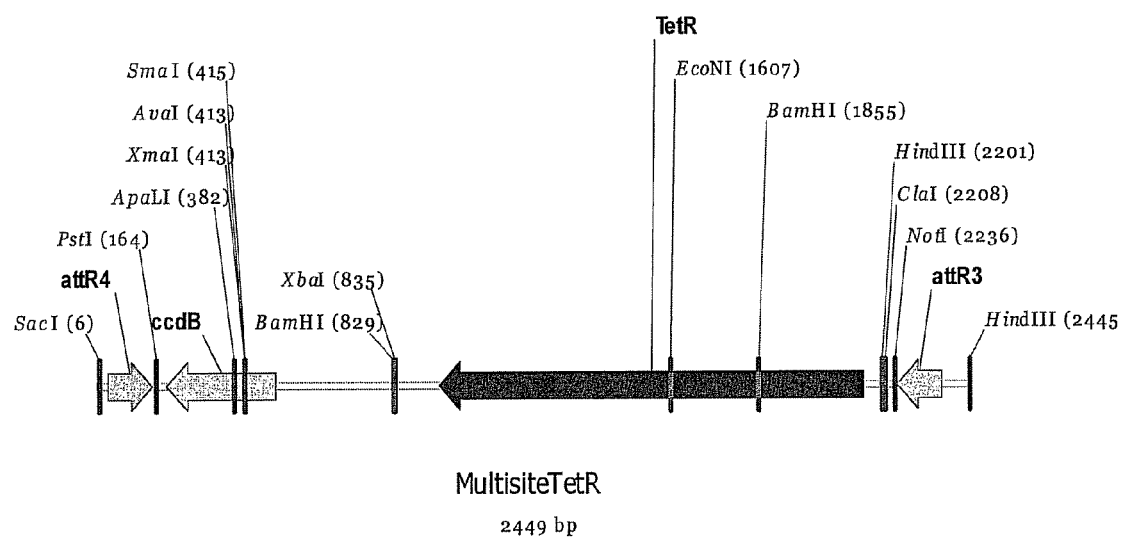
FIG. 20 shows a map of the Multisite TetR cassette.
Figure 21:
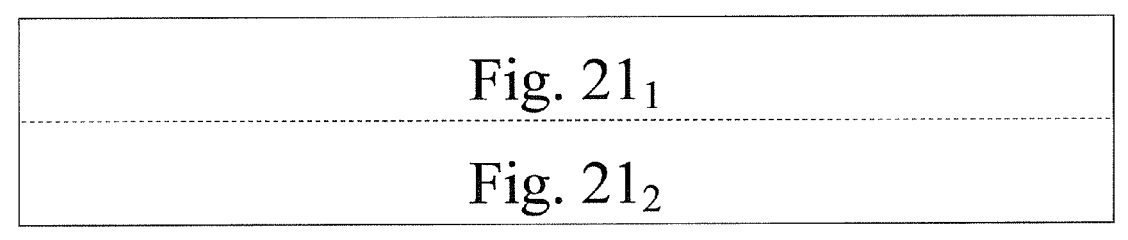

FIG. 20 shows a map of the Multisite TetR cassette. FIG. 21 is the nucleotide sequence of the Multisite TetR cassette (SEQ ID NO: 7).

FIG. 22 shows a map of the pDEST-CM3 vector. FIG. 23 is the nucleotide sequence of the pDEST-C3 vector (SEQ ID NO: 8)

Modification of the pET-Duet 1 vector resulted in the pDEST-CM4 vector. FIG. 24 shows a map of the pDEST-CM4 and FIG. 25 presents the nucleotide sequence of the pDEST-CM4 vector. The pDEST-CM4 vector was created by amplifying the Gateway Multisite cassette from pDESTR4-R3 and adding SacI and HindIII sites to the 5' and 3' ends, respectively. This was then ligated to similarly digested pET-Duet1.

The pDEST-CM1, pDEST-CM2, pDEST-CM3, and pDEST-CM4 vectors were produced following the procedures described in Example 1 for the development of the pDEST-C1, pDEST-C2, and pDEST-C3 vectors. A Multisite Gateway® cassette with SacI and HindIII ends was cloned into the first multicloning site of each pDUET vector.

The pDEST-CM series vectors will allow the simultaneous expression of up to sixteen genes, twelve cloned by recombination into the Multisite, and four cloned by standard techniques into the second multiple cloning site on each vector.

Example 8

High Throughput RNAi Co-Interference

Figure 26:
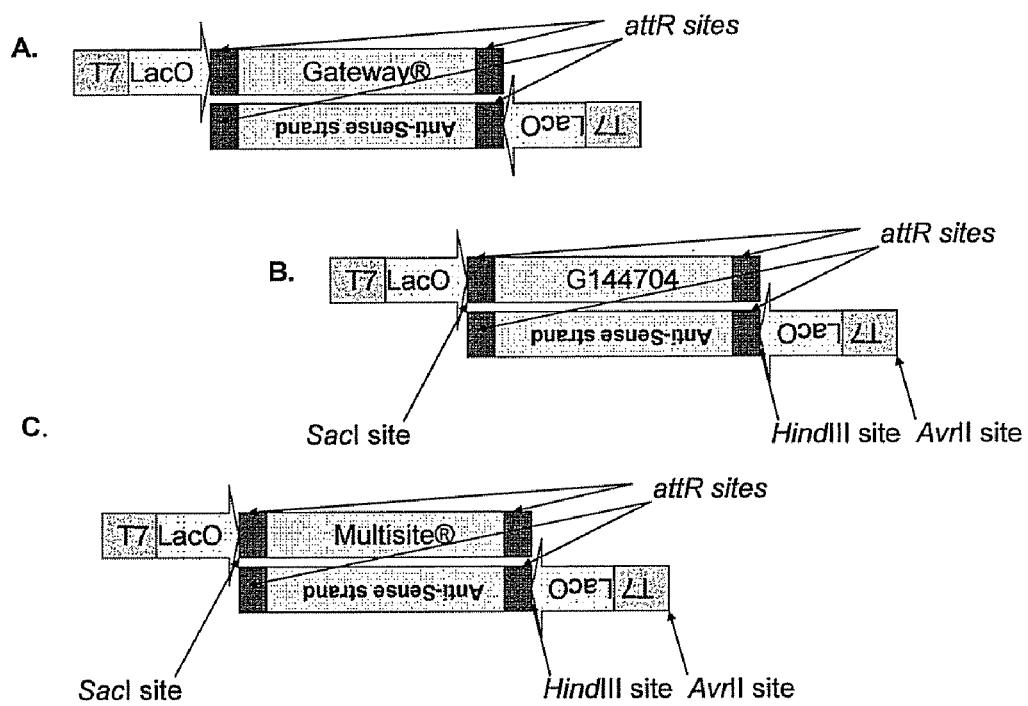
FIGS. 26A-26C show the various cassettes used in the construction of the pRIPPER vectors.

Current RNA-mediated interference (RNAi) assays study one gene at a time. Current RNAi vectors rely on T7 promoters and Lac operator sequences. To allow for the analysis of multiple genes simultaneously, this example presents five new vectors for use in methods of high throughput RNAi co-interference. These five vectors are pRIPPER-1, pRIPPER-2, pRIPPER-3, pRIPPER-II, and pRIPPER-III. Each of these high throughput RNAi vectors contains two T7 promoters ("T7") and two Lac Operator sequences ("LacO") pointing towards the Gateway® cassette from both sides (See FIG. 26A). The vectors also have an antibiotic resistance gene and an origin of replication.

Each of the new vectors pRIPPER-1, pRIPPER-2, and pRIPPER-3 contain a Zeocin-labeled Gateway® cassette G144704 flanked by two T7 promoters and Lac Operator sequences (see FIG. 26B) pointing at the Gateway® sequences. This DNA cassette is from the pC3-DEST vector, described in more detail in Example 2. The 3' end of this Gateway® cassette contains a HindIII restriction site that is the end of the site. This sequence is followed by a second T7 promoter and open reading frame with multiple cloning site and S-Tag™, followed by an AvrII site. All of these sequences are removed in order to reduce background by digestion with the two restriction enzymes AvrII and HindIII. Further downstream, a T7 terminator is retained.

To create the pRIPPER-3 vector, the pDEST-C3 vector (as described in more detail in Example 2) was altered to remove a multiple cloning site, an S-tag™ and an AvrII restriction site by digestion with the two restriction enzymes AvrII and HindIII. Then a second T7 promoter and a second Lac operator were added. The T7 promoter and Lac operator were added by ligating in the short double stranded synthetic oligonucleotide sequence formed by 5' CTAGGTAATACGACTCAC-TATAGGAATTGTGAGCGGATAACAATTCCA 3' (SEQ ID NO: 32) and 3' CATTATGCTGAGTGATATCCTIAA-CACTCGCCTATTGTTAAGGTTCGA 5' (SEQ ID NO: 33). The sequence of the T7 promoter is shown in bold. The underlined sequence is the Lac Operator sequence. The proper sequence overhang needed for the AvrII enzyme recognition sequence to be complete and the sequence of the HindIII enzyme recognition sequence required for ligation are formed by the double stranded product. This sequence was synthetically created at Integrated DNA Technologies (Coralville, Iowa).

The G144704 cassette was modified by inserting a copy of the T7 promoter LacO operator in reverse orientation relative to the upstream promoter into the HindIII-AvrII sites of pDEST-C3, creating pRIPPER-3, and the novel G144704ri cassette (with a reversed-orientation promoter) surrounded by SacI and AvrII sites. This G144704ri cassette was then removed from pRIPPER-3 by digestion with SacI-AvrII, and ligated into similarly digested pCDFDuet-1, pRSFDuet-1, and pETDuet-1 to create pRIPPER-1, pRIPPER-2, and pRIPPER-4 respectively.

A map of the pRIPPER-3 vector is shown in FIG. 27 and the nucleotide sequence of the pRIPPER-3 vector (SEQ ID NO: 10) is shown in FIG. 28.

To create the pRIPPER-1 vector, a large fragment of the pRIPPER-3 vector was inserted into Novagen's pCDF-Duet™-1 vector (catalog no. 71340-3). Specifically, the sequence from between the SacI site (5' site of pC3-DEST Zeo labeled Gateway® cassette) and the AvrII site in vector pRIPPER-3 were moved into the pCDF-DUET, creating pRIPPER-1. Clones with correct digestion pattern with AvrII, HindIII and SacI were sequenced to ensure correct sequence. A map of the pRIPPER-1 vector is shown in FIG. 29 and the nucleotide sequence of the pRIPPER-1 vector (SEQ ID NO: 11) is shown in FIG. 30.

To create the pRIPPER-2 vector, this same fragment of the pRIPPER-3 vector was inserted into Novagen's pRSF-Duet™-1 vector (catalog no. 71341-3). A map of the pRIPPER-2 vector is shown in FIG. 31 and the nucleotide sequence of the pRIPPER-2 vector (SEQ ID NO: 12) is shown in FIG. 32.

To create the pRIPPER-4 vector, this same fragment of the pRIPPER-3 vector was inserted into the pETDuet-1 vector (Novagen). A map of the pRIPPER-4 vector is shown in FIG. 33 and the nucleotide sequence of the pRIPPER-2 vector (SEQ ID NO: 13) is shown in FIG. 34.

To create the pRIPPER-II vector, the Multisite® Gateway® Cassette from Invitrogen's pDEST™ R4-R3 vector (catalog no. 12537-023) was amplified using polymerase chain reaction (PCR) and ligated into the pCDFDuet vector, using SacI and HindIII (yielding the pDEST-CM1 vector described in Example 4) followed by the insertion of an additional T7 promoter and Lac operator. The T7 promotor and lac operator sequences were inserted into the HindIII/AvrII sites of pDEST-CM1, creating pRIPPER II. The pRIPPER-II vector is streptomycin Str(R)) and chloramphenicol resistant (Cm(R)). A map of the pRIPPER-II vector is shown in FIG. 35 and the nucleotide sequence of the pRIPPER-II vector (SEQ ID NO: 14) is shown in FIG. 36.

To create the pRIPPER-III and pRIPPER-IV vectors, the pRIPPER-II vector sequence between the ScaI and AvrII restriction sites was ligated into the pRSFDuet-1 and pET-Duet™-1 (Novagen catalog no. 71146-3) vectors, respectively. A map of the pRIPPER-III vector is shown in FIG. 37 and the nucleotide sequence of the pRIPPER-III vector (SEQ ID NO: 15) is shown in FIG. 38. A map of the pRIPPER-IV vector is shown in FIG. 39 and the nucleotide sequence of the pRIPPER-W vector (SEQ ID NO: 16) is shown in FIG. 40.

Example 9

RNAi Vectors in Functional Assays

The RNAi vectors of the present invention may be utilized in any of the various methods of functional genomic analysis. For example, the RNAi vectors of the present invention may be used in assays utilizing *Caenorhabditis elegans*, including the assays described by Gonczy et al. (Gonczy et al., Nature 408(6810):331-6, 2000). For example, the RNAi vectors of the present invention will be used interfere with the expression of the Eri-1 and Rrf-3 genes in *C. elegans*. The RNAi vectors of the present invention will also be used interfere with the expression of the Lin-1 and Unc-22 proteins in *C. elegans*, genes which give the worms a multi-vulva phenotype and a stumpy phenotype, respectively. These phenotypes are recalcitrant to regular RNAi methods. The RNAi vectors of the present invention will also be used interfere with the expression Green Fluorecent Protein (GFP) and Red Fluorescent Protein in *C. elegans*. With the experiments outlined above, the RNAi vectors of the present invention will also be used interfere with the expression of at least six different proteins in a single *C. elegans* organism. The RNAi vectors of the present invention will also be used interfere with the expression of additional genes and phenotypes in *C. elegans*. These will show that the RNAi vectors of the present invention can be used to interfere with the expression of a large number of genes at the same time. Additional genes may include Lin-15A and lin-35 (which together give a synthetic multi-vulva phenotype), Dpy-10 (giving a dumpy phenotype), Zyg-11 (sterile phenotype) and an ORF called F33H2.8 in wormbase (giving an uncoordinated phenotype).

Example 10

Interference of URF3 and UNC-22 in *C. elegans* with pRIIPER Vector Constructs

*C. elegans* strains used in this example (strain CF1827 with GFP expression in the intestine and strain GR1373, a Eri-1 mutation no phenotype that enables increased RNAi response) were from the Caenorhabditis Genetics Center, University of Minnesota. Worms were incubated with *E. coli* cells that were purchased for feeding the worm, *C. elegans*. This strain of *E. coli*, was acquired from Open biosystems (pn RCE1182-9366364 feeding clone pL4440-DEST for ORF T07A9.5 (Eri-1) in *E. coli* strain HT115 (DE3)). The above strain of bacteria was than made competent and transformed with plasmids pRIPPER 1-Rrf-3, pRIPPER-2 Unc-22. These bacterial strains were then grown with appropriate antibiotics in liquid media and were induced with 2 mM IPTG for two hours and plated on LB plates supplemented with the appropriate antibiotics and 2 mM IPTG. The above listed worms were then plated onto the bacteria and allowed to grow for two days. Observation showed that the twitching phenotype that is associated with the Unc-22 gene's RNAi-mediated induction of the twitching phenotype. Results were observed for four worms in the GR1373 strain of worms and for one worm that does not lay the eggs is the CF1827 strain.

The RNAi constructs were made by PCRing the following primers together in the absence of any template. The primers contain the attB sequences (capitalized) and sequences that are complimentary to each other (underlined). These primers were then cycled in the PCR machine for five cycles to create the constructs used in the subsequent cloning reactions using pDONR Zeo as the DONR vector and pRIPPER 1 and pRIPPER 2 as destination vectors.

The RRF3 primers used were as follows:

```
                                        (SEQ ID NO: 34)
5' CTTACAAGTTTGTACAAAAAAGCAGGCTTA cttcaggtag tgatgatcta tcaaacaaat tatatgatca attttcagaa aaagtcagca aaagtttggt gaaggtggtg gagagctgca 3'
and (SEQ ID NO: 35)
5' CTTACCACTTTGTACAAGAAAGCTGGGTG ggacggttga gacaaactgg agatggcata gcgtatttta ctacttcgag gtattcatct tgcagctctc caccaccttc acccaaacttt 3'.
```

The UNC-22 primers used were as follows:

```
                                        (SEQ ID NO: 36)
5' CTTACAAGTTTGTACAAAAAAGCAGGCTTA tggttctccg gccttcacac ggaattcctt tccatccaaa tccaaatcga acttcggagc ctcatgcatt ggcttagcag tagcagccgc 3'
and (SEQ ID NO: 37)
5' CTTACCACTTTGTACAAGAAAGCTGGGTG tatgaatacc gtgtcgttgc cgtcaacaaa gctgggccag gacaaccatc agattcgtct gcggctgcta ctgctaagcc aatgcatgag 3'.
```

Example 11 pDEST-CS Vectors

The PDEST-CS series of vectors (pDEST-CS, pDEST-CS1, pDEST-CS2, pDEST-CS3, and pDEST-CS4) allows for the co-expression of secreted proteins. The pDEST-SC vector was created by removing the G114704 cassette from pDEST-C3 using SacI and HindIII and ligating it to similarly digested pET-26b(+) (Novagen catalog #70774-3). PDEST-CS contains the G144704p cassette as an EcoNI and HindIII fragment containing the G144704 cassette fused to the pelB sequence of pET-26b(+). This results in a vector which will create a fusion of the pelB sequence to the N-terminal of target proteins, which can target proteins for secretion into the periplasmic space in *Escherichia coli*. This vector is created to provide theG144704 cassette. The pDEST-CS1-4 family of vectors is then created by digestion of pDEST-CS with EcoNI and HindIII, and ligating the fragment containing the G144704p cassette to similarly digested DUET series plasmids. FIG. 41 is a map of the pDEST-CS. FIG. 42 is the nucleotide sequence of the pDEST-CS vector (SEQ ID NO: 17).

The pDEST-CS1 vector was created by removing the G114704p cassette from pDEST-CS using EcoNI and HindIII and ligating it to similarly digested pCDFDuet-1. FIG. 43 is a map of the pDEST-CS1 vector. FIG. 44 is the nucleotide sequence of the pDEST-C1 vector (SEQ ID NO: 18).

The pDEST-CS2 vector will be created by removing the G114704p cassette from pDEST-CS using EcoNI and HindIII and ligating it to similarly digested pRSFDuet-1. There is a second EcoNIsite in the middle of the KanR gene. However, this simply means the construct will be made by a limiting digestion (a standard technique where limiting amounts of enzyme are used to give only partially digested plasmid) using a low concentration of EcoNI. Correct constructs will be selected for by KanR. If the EcoNI in the KanR gene is cut, then no colony will result. FIG. 45 is a map of the pDEST-CS2 vector. FIG. 46 is the expected nucleotide sequence of the pDEST-CS2 vector (SEQ ID NO: 19).

The pDEST-CS3 vector will be created by removing the G114704p cassette from pDEST-CS using EcoNI and HindIII, and ligating it to similarly digested pACYCDuet-1. FIG. 47 is a map of the pDEST-C3 vector. FIG. 48 is the expected nucleotide sequence of the pDEST-C3 vector (SEQ ID NO: 20).

The pDEST-CS4 vector will be created by removing the G114704p cassette from pDEST-CS using EcoNI and HindIII, and ligating it to similarly digested pETDuet-1. FIG. 49 is a map of the pDEST-C4 vector. FIG. 50 is the expected nucleotide sequence of the pDEST-CS4 vector (SEQ ID NO: 21).

Example 12 pDEST-CMZ (pSYZYGY) Family of Vectors Containing Both G144704 and Multisite Cassettes Modification of the pDEST-CM family of vectors to include the G144704 Gateway ZeoR cassette in the second multiple cloning site will be done as follows. The pDEST-CM1, pDEST-CM2, and pDEST-CM4 vectors contain the Gateway Multisite cassette in the first multiple cloning site (MCS) of each of the available Novagen DUET vectors, pCDFDuet-1, pRSFDuet-1, and pETDuet-1, respectively, and the Gateway Multisite TetR cassette in pACYCDuet-1 (CM3). However, each of these vectors has a second multiple cloning site, accessible only by standard restriction enzyme/ligation cloning. The second MCS on each of these vectors will be replaced with the G144704 cassette, allowing Gateway recombination cloning at this site as well. Note that the recombination sites of the G144704 and Multisite differ, so that as long as the recombination reactions are performed separately, both are possible. This will be performed in a manner very similar to that described for the initial construction of the pDEST-C series of vectors. This will create a set of four vectors, pDEST-CMZ1, pDEST-CMZ2, pDEST-CMZ3, and pDEST-CMZ4 also referred to as the 'pSYZYGY' family, each with a total of four possible Gateway recombination sites, for a grand total of sixteen co-expressible proteins. This will be done by amplifying the G144704 cassette using primers that add NdeI and KpnI restriction sites to the 5' and 3' ends respectively. This will be digested with these two enzymes, and then ligated directly to each of the similarly digested pDEST-CM1-4 vectors, creating pDEST-CMZ1-4. An example map of the proposed pDEST-CMZ1 is shown below. The other three vectors will be constructed in precisely the same manner, insertion of the same cassette at the NdeI and KpnI sites on those vectors.

A map of the pDEST-CMZ1 vector is shown in FIG. 51. The expected nucleotide sequence of the pDEST-CMZ1 vector is shown in FIG. 52.

Example 13 pDEST-CMZc (pSYZYGYc) Family Containing Both G144704 and Multisite Cassettes Tagged with GFP and RFP To create the pDEST-CMc series of vectors, the G144704 cassette will be modified to include a green fluorescent protein (GFP) marker and the Gateway Multisite cassette will be modified to include a red fluorescent protein (RFP) marker.

PCR will be used to amplify pDEST-C3 at the 3' end of the ZeoR gene using primers abutting at their 3' ends, which will amplify the entire vector to create a linear plasmid with SpeI and SphI restriction sites artificially added on (SpeI on the 3' end of the ZeoR gene), followed by digestion with these enzymes to create sticky ends. Next, the green fluorescent protein (GFPuv) encoding gene from the commercially available plasmid pGFPuv (BD Biosciences/Clontech #632312) will be amplified with primers that SpeI and SphI restriction sites to the 5' and 3' ends of the PCR product respectively. After digestion with these enzymes, it will be ligated to the similarly digested pDEST-C3 to create pDEST-C3g. The primers will be designed such that the GFPuv encoding gene will be fused in frame with the ZeoR gene, creating a gene fusion. These are all standard molecular biology protocols. This vector will contain the new G144704g cassette, which will have all the same characteristics of the parent G1144704 cassette (ZeoR, ccdB, Gateway R1 and R2 recombination sites), but additionally will express the GFPuv protein as a fusion with the ZeoR protein. This will result in colonies with a green fluorescent color when grown in the appropriate ccdA host strain in the presence of Zeocin.

In a similar manner, the gene (DsRed2) encoding the red fluorescent protein (RFP) will be amplified from the commercially available plasmid pDsRed2 (BD Biosciences/Clontech #632404), and cloned into the Gateway Multisite cassette as a 3' fusion with the CamR gene, to create the MultisiteR cassette, which will result in red colonies.

A third construct will be made in a similar manner, fusing the RFP encoding gene to the 3' end of the TetR gene in the Multisite TetR cassette, the only difference being that the restriction enzymes used will be SpeI and XbaI, due to the presence of an SphI site in the TetR gene, creating the Multisite TetRr cassette.

These constructs will allow for a fluorescent screen for the first step of recombination. The current selection for successful recombination, the loss of the ccdB gene in the cassette, will not work when there are two copies of this lethal gene. In the pDEST-CMZ1-4 family of vectors, which will contain two different Gateway cassettes (G144704 and Multisite), each with a ccdB gene, one can use either the ZeoR or CamR marker on the G144704 or Multisite cassette respectively to screen for recombination at one cassette or the other, but this is a two step process requiring growth of colonies under non-selective conditions, followed by replica plating and screening for colonies which have lost the marker of interest. The utility of this insertion of the GFPuv and RFP markers into the G144704g and MultisiteR cassettes respectively will reduce this selection process to one step. Colonies which have lost the color of interest, and thus contain plasmids which have successfully recombined at the desired position, can be screened directly, and moved on to the next recombination event. The G144704g cassette will be used to replace the G144704 cassettes in the second multiple cloning sites of the four pDEST-CMZ family of vectors, and the MultisiteR will replace the Multisite cassette (Multisite TetRr will replace the Multisite TetR in pDEST-CMZ3) in the other recombination site of these four vectors. This will create the pDEST-CMZc1-4 family of vectors (or 'pSYZYGYc family), with colored markers ('c') for recombination screening.

A representative map of a pDEST-CMZc1 vector is shown in FIG. 53. The expected nucleotide sequence of a pDEST-CMZc1 vector is shown in FIG. 54.

Example 14

Expression of Multiple Genes in a Single Vector

The vectors of the pDEST-C series, the pDEST-CS series, and the pRIPPER series can be further modified to allow the co-expression of up to five unique proteins for each vector, allowing the expression of up to sixteen different genes, when the vectors of the present invention are used in concert with the available vectors (PDEST, pL4440, pET). In turn, the SYZYGY vectors of the present invention can be used for the co-expression of up to thirty-two proteins or, when used in RNAi, to silence thirty-two genes, since these vectors unite the traditional Gateway® and Multisite® methods into one plasmid. See also, Sone et. al. (Multi-gene gateway clone design for expression of multiple heterologous genes in living cells: Modular construction of multiple cDNA expression elements using recombinant cloning," J Biotechnol. 2005 Jun. 24 (doi:10,1016/jbiotec.2005.02.021)) which describes methods for the insertion of up to five unique DNA fragments into the B1 B2 sites of a single Gateway® vector.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method for the expression of a polypeptide, the method comprising expressing said polypeptide by an expression vector, the expression vector comprising a first nucleotide sequence operably encoding zeomycin resistance and a second nucleotide sequence operably encoding a ccdB polypeptide, wherein the first nucleotide sequence and the second nucleotide sequence are flanked within the same attR1 and attR2 sites, and wherein the polynucleotide comprises a G144704 cassette having SEQ ID NO:4, or the expression vector comprising a first nucleotide sequence operably encoding tetracycline resistance and a second nucleotide sequence operably encoding a ccdB polypeptide, wherein the first nucleotide sequence and the second nucleotide sequence are flanked within the same attR3 and attR4 sites, and wherein the polynucleotide comprises a tet Multisite having SEQ ID NO: 7.

2. The method of claim 1, improving the solubility of said polypeptide.

3. The method of claim 1, wherein the expression vector is selected from the group consisting of pDEST-C1 (SEQ ID NO:1), pDEST-C2 (SEQ ID NO:2), pDEST-C3 (SEQ ID NO:3), pDEST-CM1 (SEQ ID NO:5), pDEST-CM2 (SEQ ID NO:6), pDEST-CM3 (SEQ ID NO:8), pDEST-CM4 (SEQ ID NO:9), pDEST-CS (SEQ ID NO:17), pDEST-CS1 (SEQ ID NO:18), pDEST-CS2 (SEQ ID NO:19), pDEST-CS3 (SEQ ID NO:20), pDEST-CS4 (SEQ ID NO:21), pDEST-CMZ1 (SEQ ID NO:22), and pDEST-CMZc1 (SEQ ID NO:23).

4. The method of claim 1, wherein the expression vector comprises a first nucleotide sequence operably encoding zeomycin resistance and a second nucleotide sequence operably encoding a ccdB polypeptide, wherein the first nucleotide sequence and the second nucleotide sequence are flanked within the same attR1 and attR2 sites, and wherein the polynucleotide comprises a G144704 cassette having SEQ ID NO:4.

5. The method of claim 4, wherein the expression vector is selected from the group consisting of pDEST-C1 (SEQ ID NO:1), pDEST-C2 (SEQ ID NO:2), pDEST-C3 (SEQ ID NO:3), pDEST-CS (SEQ ID NO:17), pDEST-CS1 (SEQ ID NO:18), pDEST-CS2 (SEQ ID NO:19), pDEST-CS3 (SEQ ID NO:20), pDEST-CS4 (SEQ ID NO:21), pDEST-CMZ1 (SEQ ID NO:22), and pDEST-CMZcl (SEQ ID NO:23).

6. The method of claim 1, wherein the expression vector comprises a first nucleotide sequence operably encoding tetracycline resistance and a second nucleotide sequence operably encoding a ccdB polypeptide, wherein the first nucleotide sequence and the second nucleotide sequence are flanked within the same attR3 and attR4 sites, and wherein the polynucleotide comprises a tet Multisite having SEQ ID NO:7.

7. The method of claim 6, wherein the expression vector is selected from the group consisting of is selected from the group consisting of pDEST-CM1 (SEQ ID NO:5), pDEST-CM2 (SEQ ID NO:6), pDEST-CM3 (SEQ ID NO:8), pDEST-CM4 (SEQ ID NO:9), pDEST-CMZ1 (SEQ ID NO:22), and pDEST-CMZc1 (SEQ ID NO:23).

* * * * *

UNITED STATES PATENT AND TRADEMARK OFFICE
CERTIFICATE OF CORRECTION

Page 1 of 1

PATENT NO. : 8,008,016 B2
APPLICATION NO. : 12/501666
DATED : August 30, 2011
INVENTOR(S) : Horanyi et al.

It is certified that error appears in the above-identified patent and that said Letters Patent is hereby corrected as shown below:

In the Specification

Column 1, line 13, under GOVERNMENT FUNDING

Please delete
"The present invention was made with government support under Grant No. NIH GM062407, awarded by the National Institutes of Health. The Government may have certain rights in this invention"

And insert
--This invention was made with government support under Grant No. GM062407 awarded by the National Institutes of Health. The government has certain rights in this invention.--

Signed and Sealed this
Twenty-sixth Day of January, 2016

Michelle K. Lee
*Director of the United States Patent and Trademark Office*